United States Patent
Dorrell et al.

(10) Patent No.: US 11,179,456 B2
(45) Date of Patent: Nov. 23, 2021

(54) HPV VACCINE

(71) Applicant: Oxford University Innovation Limited, Oxford (GB)

(72) Inventors: Lucy Dorrell, Oxford (GB); Joshua Blight, Oxford (GB); Arturo Reyes-Sandoval, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 16/639,144

(22) PCT Filed: Aug. 16, 2018

(86) PCT No.: PCT/GB2018/052335
§ 371 (c)(1),
(2) Date: Feb. 14, 2020

(87) PCT Pub. No.: WO2019/034887
PCT Pub. Date: Feb. 21, 2019

(65) Prior Publication Data
US 2020/0306358 A1    Oct. 1, 2020

(30) Foreign Application Priority Data

Aug. 16, 2017 (GB) ..................... 1713163

(51) Int. Cl.
*A61K 39/12*    (2006.01)
*A61K 39/39*    (2006.01)
*C07K 14/005*    (2006.01)
*C12N 7/00*    (2006.01)

(52) U.S. Cl.
CPC .............. *A61K 39/12* (2013.01); *A61K 39/39* (2013.01); *C07K 14/005* (2013.01); *C12N 7/00* (2013.01); *C07K 2319/00* (2013.01); *C12N 2710/20022* (2013.01); *C12N 2710/20034* (2013.01)

(58) Field of Classification Search
None
See application file for complete search history.

(56) References Cited

U.S. PATENT DOCUMENTS

2007/0014810 A1 *   1/2007   Baker ................ A61K 39/0011
                                                    424/186.1

FOREIGN PATENT DOCUMENTS

| WO | 2005/089164 A2 | 9/2005 |
| WO | 2009/059325 A2 | 5/2009 |
| WO | 2010/123561 A1 | 10/2010 |
| WO | 2014/165291 A1 | 10/2014 |
| WO | 2018/060288 A1 | 4/2018 |

OTHER PUBLICATIONS

GenBank: K02718.1. Human papillomavirus type 16 (HPV16), complete genome. Dated Mar. 18, 1994.*
Gan et al. usion of CTLA-4 with HPV16 E7 and E6 Enhanced the Potency of Therapeutic HPV DNA Vaccine. PLoS ONE, 2014, 9(9):e108892.*
Chen et al. Fusion protein linkers: Property, design and functionality. Advanced Drug Delivery Reviews 65 (2013) 1357-1369.*
Qian et al. Prophylactic, therapeutic and anti-metastatic effects of an HPV-16 mE6/mE7/TBhsp70 fusion protein vaccine in an animal model. Immunology Letters 102 (2006) 191-201.*
International Search Report and Written Opinion for PCT/GB2018/052335, dated Nov. 26, 2018, pp. 1-14.
UK Search Report for GB 1713163.2, dated May 14, 2018, pp. 1-4.
Brazilian J. Biol., vol. 73, 2013, Gabriel, J. E. et al., "Revealing highly conserved regions in the E6 protein among distinct human papillomavirus types using comparative analysis of multiple sequence alignments", pp.4549-4550. May 31, 2013.
Krishna P. Singh et al: "Sequence-based approach for rapid identification of cross-clade CD8+ T-cell vaccine candidates from all high-risk HPV strains", 3 Biotech, vol. 6, No. 1, Jan. 27, 2016 (Jan. 27, 2016).
Yan J et al: "Induction of antitumor immunity in vivo following delivery of a novel HPV-16 DNA vaccine encoding an E6/E7 fusion antigen",Vaccine, Elsevier, Amsterdam, NL, vol. 27, No. 3, Jan. 14, 2009 (Jan. 14, 2009), pp. 431-440.

* cited by examiner

*Primary Examiner* — Nianxiang Zou
(74) *Attorney, Agent, or Firm* — Thomas|Horstemeyer, LLP

(57) ABSTRACT

The invention relates to a nucleic acid encoding a polypeptide comprising a plurality of conserved peptide sequences, or variants thereof, wherein the conserved sequences are conserved across one or more HPV genotypes 16, 18, 31, 52, 53, and 58; and wherein the polypeptide comprises a conserved peptide sequence of each of the HPV proteins E1, E2, E4, E5, E6, and E7; and associated vaccines, viral vectors, treatment and prophylaxis.

Figure 1:
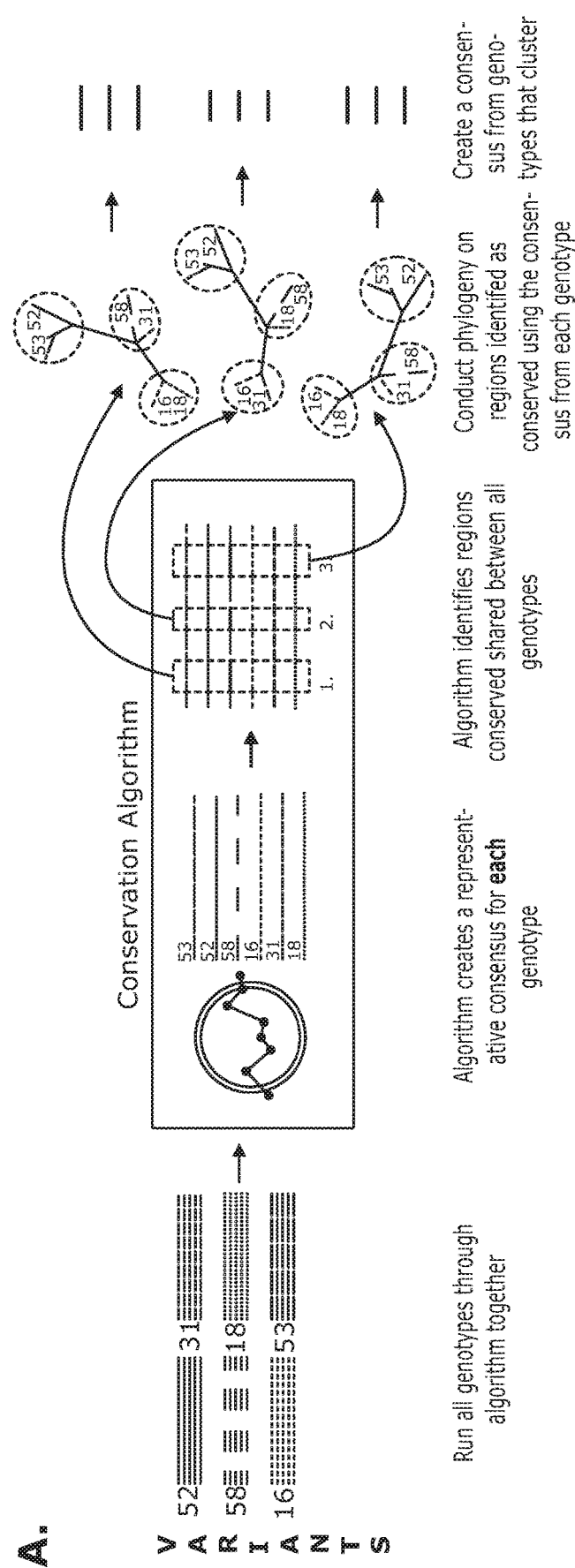
Figure 1:
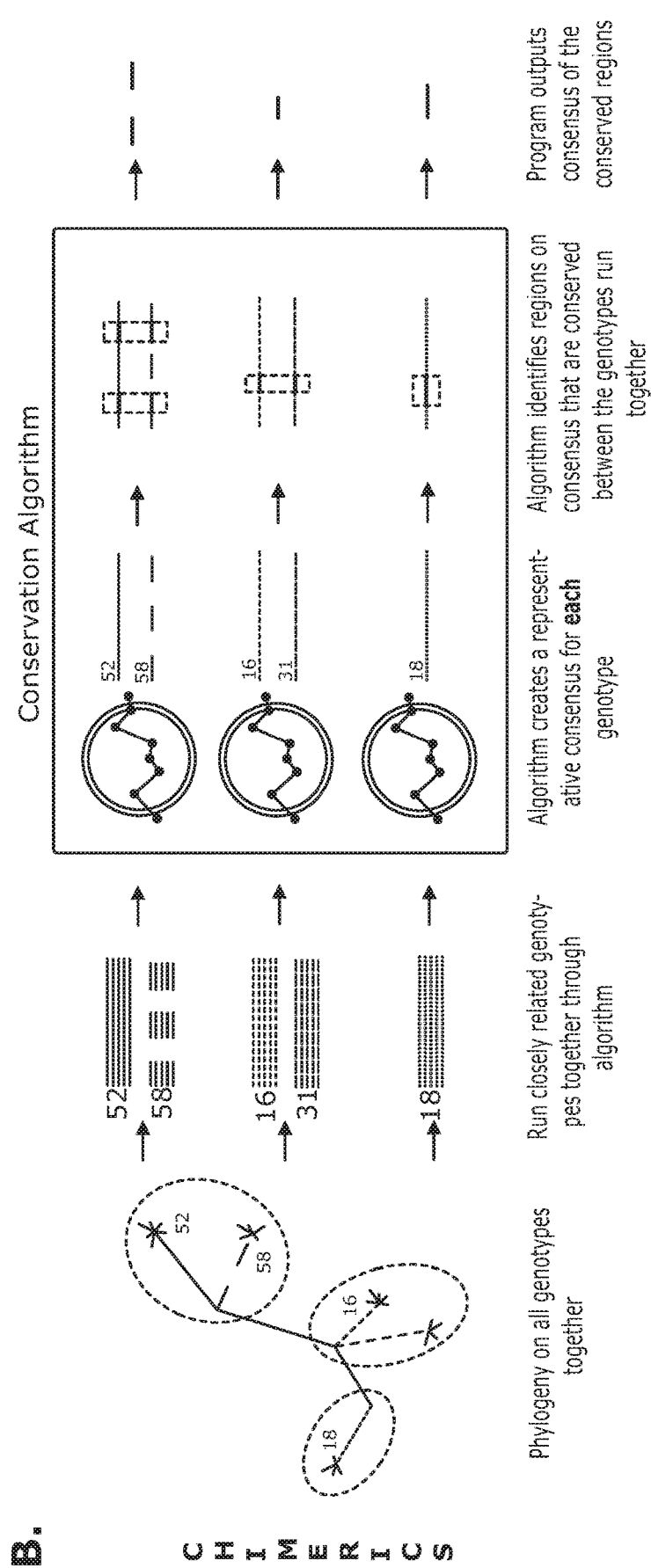

7 Claims, 23 Drawing Sheets
Specification includes a Sequence Listing.

SEQUENCE LISTING

```
<160> NUMBER OF SEQ ID NOS: 159

<210> SEQ ID NO 1
<211> LENGTH: 20
<212> TYPE: PRT
<213> ORGANISM: Artificial Sequence
<220> FEATURE:
<223> OTHER INFORMATION: Consensus sequence

<400> SEQUENCE: 1

Asp Glu Asp Glu Thr Ala Tyr Asp Ser Gly Thr Asp Leu Ile Asp Phe
1               5                   10                  15

Ile Asp Asp Ser
            20

<210> SEQ ID NO 2
<211> LENGTH: 19
<212> TYPE: PRT
<213> ORGANISM: Artificial Sequence
<220> FEATURE:
<223> OTHER INFORMATION: Consensus sequence

<400> SEQUENCE: 2

Asp Glu Asn Glu Asn Asp Ser Asp Thr Gly Glu Asp Met Val Asp Phe
1               5                   10                  15

Ile Asp Asn

<210> SEQ ID NO 3
<211> LENGTH: 19
<212> TYPE: PRT
<213> ORGANISM: Artificial Sequence
<220> FEATURE:
<223> OTHER INFORMATION: Consensus sequence

<400> SEQUENCE: 3

Asp Glu Thr Asp Glu Glu Ser Thr Glu Ser Asp Leu Asp Gly Phe Ile
1               5                   10                  15

Asp Asn Ser

<210> SEQ ID NO 4
<211> LENGTH: 15
<212> TYPE: PRT
<213> ORGANISM: Artificial Sequence
<220> FEATURE:
<223> OTHER INFORMATION: Consensus sequence

<400> SEQUENCE: 4

Ala Gln Leu Ala Asp Ser Asp Ser Asn Ala Cys Ala Phe Leu Lys
1               5                   10                  15
```

```
<210> SEQ ID NO 5
<211> LENGTH: 15
<212> TYPE: PRT
<213> ORGANISM: Artificial Sequence
<220> FEATURE:
<223> OTHER INFORMATION: Consensus sequence

<400> SEQUENCE: 5

Ala Gln Leu Ala Asp Val Asn Ser Asn Ala Ala Ala Phe Leu Lys
1               5                   10                  15

<210> SEQ ID NO 6
<211> LENGTH: 20
<212> TYPE: PRT
<213> ORGANISM: Artificial Sequence
<220> FEATURE:
<223> OTHER INFORMATION: Consensus sequence

<400> SEQUENCE: 6

Asn Cys Ile Leu Leu Tyr Gly Ala Ala Asn Thr Gly Lys Ser Leu Phe
1               5                   10                  15

Gly Met Ser Leu
            20

<210> SEQ ID NO 7
<211> LENGTH: 20
<212> TYPE: PRT
<213> ORGANISM: Artificial Sequence
<220> FEATURE:
<223> OTHER INFORMATION: Consensus sequence

<400> SEQUENCE: 7

Asn Cys Leu Val Leu Cys Gly Pro Ala Asn Thr Gly Lys Ser Tyr Phe
1               5                   10                  15

Gly Met Ser Leu
            20

<210> SEQ ID NO 8
<211> LENGTH: 20
<212> TYPE: PRT
<213> ORGANISM: Artificial Sequence
<220> FEATURE:
<223> OTHER INFORMATION: Consensus sequence

<400> SEQUENCE: 8

Asn Cys Leu Val Ile Tyr Gly Pro Pro Asn Thr Gly Lys Ser Cys Phe
1               5                   10                  15

Ala Met Ser Leu
            20

<210> SEQ ID NO 9
<211> LENGTH: 17
<212> TYPE: PRT
<213> ORGANISM: Artificial Sequence
<220> FEATURE:
<223> OTHER INFORMATION: Consensus sequence

<400> SEQUENCE: 9

Trp Pro Tyr Leu His Ser Arg Leu Val Val Phe Thr Phe Pro Asn Pro
1               5                   10                  15

Phe

<210> SEQ ID NO 10
<211> LENGTH: 17
<212> TYPE: PRT
```

```
<213> ORGANISM: Artificial Sequence
<220> FEATURE:
<223> OTHER INFORMATION: Consensus sequence

<400> SEQUENCE: 10

Trp Pro Tyr Leu Glu Ser Arg Ile Thr Val Phe Glu Phe Pro Asn Ala
1               5                   10                  15

Phe

<210> SEQ ID NO 11
<211> LENGTH: 17
<212> TYPE: PRT
<213> ORGANISM: Artificial Sequence
<220> FEATURE:
<223> OTHER INFORMATION: Consensus sequence

<400> SEQUENCE: 11

Leu Arg Tyr Leu His Ser Arg Ile His Val Leu Gln Phe Leu Asn Pro
1               5                   10                  15

Phe

<210> SEQ ID NO 12
<211> LENGTH: 17
<212> TYPE: PRT
<213> ORGANISM: Artificial Sequence
<220> FEATURE:
<223> OTHER INFORMATION: Consensus sequence

<400> SEQUENCE: 12

Asn Val Cys Gln Asp Lys Ile Leu Glu His Tyr Glu Asn Asp Ser Lys
1               5                   10                  15

Asp

<210> SEQ ID NO 13
<211> LENGTH: 16
<212> TYPE: PRT
<213> ORGANISM: Artificial Sequence
<220> FEATURE:
<223> OTHER INFORMATION: Consensus sequence

<400> SEQUENCE: 13

Ile Leu Glu His Tyr Glu Asn Asp Ser Lys Asp Leu Cys Asp His Ile
1               5                   10                  15

<210> SEQ ID NO 14
<211> LENGTH: 21
<212> TYPE: PRT
<213> ORGANISM: Artificial Sequence
<220> FEATURE:
<223> OTHER INFORMATION: Consensus sequence

<400> SEQUENCE: 14

Cys Asp His Ile Asp Tyr Trp Lys His Ile Arg Leu Glu Cys Ala Ile
1               5                   10                  15

Met Tyr Lys Ala Arg
            20

<210> SEQ ID NO 15
<211> LENGTH: 17
<212> TYPE: PRT
<213> ORGANISM: Artificial Sequence
<220> FEATURE:
<223> OTHER INFORMATION: Consensus sequence

<400> SEQUENCE: 15
```

```
Ile Arg Leu Glu Cys Ala Ile Met Tyr Lys Ala Arg Glu Met Gly Phe
1               5                   10                  15

His

<210> SEQ ID NO 16
<211> LENGTH: 17
<212> TYPE: PRT
<213> ORGANISM: Artificial Sequence
<220> FEATURE:
<223> OTHER INFORMATION: Consensus sequence

<400> SEQUENCE: 16

Ile Arg Leu Glu Cys Ala Ile Met Tyr Lys Ala Arg Glu Met Gly Phe
1               5                   10                  15

His

<210> SEQ ID NO 17
<211> LENGTH: 17
<212> TYPE: PRT
<213> ORGANISM: Artificial Sequence
<220> FEATURE:
<223> OTHER INFORMATION: Consensus sequence

<400> SEQUENCE: 17

Ile Tyr Ile Cys Glu Asp Ala Gln Cys Thr Val Val Glu Gly Gln Val
1               5                   10                  15

Asp

<210> SEQ ID NO 18
<211> LENGTH: 17
<212> TYPE: PRT
<213> ORGANISM: Artificial Sequence
<220> FEATURE:
<223> OTHER INFORMATION: Consensus sequence

<400> SEQUENCE: 18

Lys Lys Trp Glu Val His Ala Gly Gly Gln Val Ile Leu Cys Pro Glu
1               5                   10                  15

Ser

<210> SEQ ID NO 19
<211> LENGTH: 11
<212> TYPE: PRT
<213> ORGANISM: Artificial Sequence
<220> FEATURE:
<223> OTHER INFORMATION: Consensus sequence

<400> SEQUENCE: 19

Gly Gln Arg Arg Ile Lys Arg Pro Arg Ser Glu
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Consensus sequence

<400> SEQUENCE: 20

Asn Cys His Pro Asn Lys Leu Leu
1               5

<210> SEQ ID NO 21
```

```
<211> LENGTH: 15
<212> TYPE: PRT
<213> ORGANISM: Artificial Sequence
<220> FEATURE:
<223> OTHER INFORMATION: Consensus sequence

<400> SEQUENCE: 21

Ile Leu Lys Cys Leu Arg Tyr Arg Phe Lys Lys His Cys Lys Leu
1               5                   10                  15

<210> SEQ ID NO 22
<211> LENGTH: 14
<212> TYPE: PRT
<213> ORGANISM: Artificial Sequence
<220> FEATURE:
<223> OTHER INFORMATION: Consensus sequence

<400> SEQUENCE: 22

Ser Ser Thr Trp His Trp Thr Cys His Asp Gly Lys His Lys
1               5                   10

<210> SEQ ID NO 23
<211> LENGTH: 19
<212> TYPE: PRT
<213> ORGANISM: Artificial Sequence
<220> FEATURE:
<223> OTHER INFORMATION: Consensus sequence

<400> SEQUENCE: 23

Trp His Trp Thr Cys His Asp Gly Lys His Lys Asn Ala Ile Val Thr
1               5                   10                  15
Leu Thr Tyr

<210> SEQ ID NO 24
<211> LENGTH: 34
<212> TYPE: PRT
<213> ORGANISM: Artificial Sequence
<220> FEATURE:
<223> OTHER INFORMATION: Consensus sequence

<400> SEQUENCE: 24

Tyr Glu Ala Asp Lys Asn Asp Leu Asn Ala Gln Ile Glu His Trp Lys
1               5                   10                  15
Leu Ile Arg Met Glu Cys Ala Ile Phe Tyr Lys Ala Lys Glu Leu Gly
                20                  25                  30
Ile Ser

<210> SEQ ID NO 25
<211> LENGTH: 34
<212> TYPE: PRT
<213> ORGANISM: Artificial Sequence
<220> FEATURE:
<223> OTHER INFORMATION: Consensus sequence

<400> SEQUENCE: 25

Ile Cys His Gln Val Val Pro Pro Leu Ala Ala Ser Lys Ala Lys Ala
1               5                   10                  15
Cys Gln Ala Ile Glu Leu Gln Leu Ala Leu Glu Ala Leu Asn Ala Ser
                20                  25                  30
Pro Tyr

<210> SEQ ID NO 26
<211> LENGTH: 18
<212> TYPE: PRT
```

```
<213> ORGANISM: Artificial Sequence
<220> FEATURE:
<223> OTHER INFORMATION: Consensus sequence

<400> SEQUENCE: 26

Asp Glu Trp Thr Leu Gln Gln Thr Ser Leu Glu Met Trp Leu Ala Glu
1               5                   10                  15

Pro Gln

<210> SEQ ID NO 27
<211> LENGTH: 29
<212> TYPE: PRT
<213> ORGANISM: Artificial Sequence
<220> FEATURE:
<223> OTHER INFORMATION: Consensus sequence

<400> SEQUENCE: 27

Phe Lys Lys His Gly Ile Thr Ile Thr Val Gln Tyr Asp Asn Asp Lys
1               5                   10                  15

Ala Asn Thr Met Asp Tyr Thr Asn Trp Lys Glu Ile Tyr
            20                  25

<210> SEQ ID NO 28
<211> LENGTH: 18
<212> TYPE: PRT
<213> ORGANISM: Artificial Sequence
<220> FEATURE:
<223> OTHER INFORMATION: Consensus sequence

<400> SEQUENCE: 28

Val Ile Val Cys Pro Ala Ser Ile Pro Ser Asp Glu Ile Ser Thr Glu
1               5                   10                  15

Glu Ala

<210> SEQ ID NO 29
<211> LENGTH: 20
<212> TYPE: PRT
<213> ORGANISM: Artificial Sequence
<220> FEATURE:
<223> OTHER INFORMATION: Consensus sequence

<400> SEQUENCE: 29

Asp His Ile Asp Tyr Trp Lys Ala Ile Arg Gln Glu Asn Ala Ile Phe
1               5                   10                  15

Phe Ala Ala Arg
            20

<210> SEQ ID NO 30
<211> LENGTH: 19
<212> TYPE: PRT
<213> ORGANISM: Artificial Sequence
<220> FEATURE:
<223> OTHER INFORMATION: Consensus sequence

<400> SEQUENCE: 30

His Gln Val Val Pro Ala Leu Asn Ile Cys Lys Ala Lys Ala Cys Lys
1               5                   10                  15

Ala Ile Glu

<210> SEQ ID NO 31
<211> LENGTH: 21
<212> TYPE: PRT
<213> ORGANISM: Artificial Sequence
<220> FEATURE:
```

<223> OTHER INFORMATION: Consensus sequence

<400> SEQUENCE: 31

Trp Asn Thr Glu Pro Lys His Cys Phe Lys Lys Gly Gly Gln His Ile
1               5                   10                  15

Glu Val Trp Phe Asp
            20

<210> SEQ ID NO 32
<211> LENGTH: 18
<212> TYPE: PRT
<213> ORGANISM: Artificial Sequence
<220> FEATURE:
<223> OTHER INFORMATION: Consensus sequence

<400> SEQUENCE: 32

Tyr Val Ala Trp Asp Ser Val Tyr Tyr Cys Gly Asp Asp Gly Trp Cys
1               5                   10                  15

Lys Thr

<210> SEQ ID NO 33
<211> LENGTH: 16
<212> TYPE: PRT
<213> ORGANISM: Artificial Sequence
<220> FEATURE:
<223> OTHER INFORMATION: Consensus sequence

<400> SEQUENCE: 33

Glu Ala Glu Lys Tyr Gly Cys Lys Gly Thr Trp Glu Val His Phe Gly
1               5                   10                  15

<210> SEQ ID NO 34
<211> LENGTH: 24
<212> TYPE: PRT
<213> ORGANISM: Artificial Sequence
<220> FEATURE:
<223> OTHER INFORMATION: Consensus sequence

<400> SEQUENCE: 34

Asn Ser Ile Asp Cys Asn Asp Ser Met Cys Ser Thr Phe Asp Asp Asn
1               5                   10                  15

Val Ser Ala Thr Glu Leu Val Lys
            20

<210> SEQ ID NO 35
<211> LENGTH: 20
<212> TYPE: PRT
<213> ORGANISM: Artificial Sequence
<220> FEATURE:
<223> OTHER INFORMATION: Consensus sequence

<400> SEQUENCE: 35

Asp His Ile Asp Tyr Trp Lys Leu Ile Arg Leu Glu Cys Ala Ile Phe
1               5                   10                  15

Tyr Lys Ala Arg
            20

<210> SEQ ID NO 36
<211> LENGTH: 11
<212> TYPE: PRT
<213> ORGANISM: Artificial Sequence
<220> FEATURE:
<223> OTHER INFORMATION: Consensus sequence

<400> SEQUENCE: 36

```
Arg Arg Leu Ser Ser Asp Gln Asp Gln Ser Gln
1               5                   10
```

<210> SEQ ID NO 37
<211> LENGTH: 12
<212> TYPE: PRT
<213> ORGANISM: Artificial Sequence
<220> FEATURE:
<223> OTHER INFORMATION: Consensus sequence

<400> SEQUENCE: 37

```
Leu Val Thr Lys Tyr Pro Leu Leu Lys Leu Leu Ser
1               5                   10
```

<210> SEQ ID NO 38
<211> LENGTH: 41
<212> TYPE: PRT
<213> ORGANISM: Artificial Sequence
<220> FEATURE:
<223> OTHER INFORMATION: Consensus sequence

<400> SEQUENCE: 38

```
Arg Pro Pro Asn Met Gly Val Lys Ala His Gly Lys Cys Ile Trp Glu
1               5                   10                  15

Asn Lys Val Phe Ile Val Pro Thr Leu Cys Pro Val Pro Leu Asp Pro
            20                  25                  30

Thr Tyr Pro Leu Leu Lys Leu Leu Thr
        35                  40
```

<210> SEQ ID NO 39
<211> LENGTH: 29
<212> TYPE: PRT
<213> ORGANISM: Artificial Sequence
<220> FEATURE:
<223> OTHER INFORMATION: Consensus sequence

<400> SEQUENCE: 39

```
Thr Gln Thr Thr Thr Pro Glu Asn Thr Ser Leu Val Glu Leu Arg Val
1               5                   10                  15

Thr Thr Pro Lys Ser Thr Val Val Ile Arg Leu His Leu
            20                  25
```

<210> SEQ ID NO 40
<211> LENGTH: 31
<212> TYPE: PRT
<213> ORGANISM: Artificial Sequence
<220> FEATURE:
<223> OTHER INFORMATION: Consensus sequence

<400> SEQUENCE: 40

```
Thr Thr Arg Tyr Pro Leu Leu Ser Leu Leu Asn Ser Tyr Ser Thr Pro
1               5                   10                  15

Pro His Arg Ile Pro Ala Pro Cys Pro Trp Ala Pro Gln Arg Pro
            20                  25                  30
```

<210> SEQ ID NO 41
<211> LENGTH: 10
<212> TYPE: PRT
<213> ORGANISM: Artificial Sequence
<220> FEATURE:
<223> OTHER INFORMATION: Consensus sequence

<400> SEQUENCE: 41

```
Pro Ile Pro Lys Pro Ser Pro Trp Ala Pro
```

```
1               5                   10
```

<210> SEQ ID NO 42
<211> LENGTH: 10
<212> TYPE: PRT
<213> ORGANISM: Artificial Sequence
<220> FEATURE:
<223> OTHER INFORMATION: Consensus sequence

<400> SEQUENCE: 42

```
Pro Ile Pro Lys Pro Ser Pro Trp Ala Pro
1               5                   10
```

<210> SEQ ID NO 43
<211> LENGTH: 10
<212> TYPE: PRT
<213> ORGANISM: Artificial Sequence
<220> FEATURE:
<223> OTHER INFORMATION: Consensus sequence

<400> SEQUENCE: 43

```
Pro Arg Pro Pro His Cys Pro Trp Val Pro
1               5                   10
```

<210> SEQ ID NO 44
<211> LENGTH: 10
<212> TYPE: PRT
<213> ORGANISM: Artificial Sequence
<220> FEATURE:
<223> OTHER INFORMATION: Consensus sequence

<400> SEQUENCE: 44

```
Pro Pro Pro Pro Pro Arg Pro Trp Ala Pro
1               5                   10
```

<210> SEQ ID NO 45
<211> LENGTH: 26
<212> TYPE: PRT
<213> ORGANISM: Artificial Sequence
<220> FEATURE:
<223> OTHER INFORMATION: Consensus sequence

<400> SEQUENCE: 45

```
Cys Phe Leu Leu Cys Phe Cys Val Leu Cys Val Cys Leu Leu Ile
1               5                   10                  15

Arg Pro Leu Leu Leu Ser Val Ser Thr Tyr
                20                  25
```

<210> SEQ ID NO 46
<211> LENGTH: 27
<212> TYPE: PRT
<213> ORGANISM: Artificial Sequence
<220> FEATURE:
<223> OTHER INFORMATION: Consensus sequence

<400> SEQUENCE: 46

```
Leu Arg Pro Leu Leu Leu Ser Ile Ser Val Tyr Ala Gln Val Leu Val
1               5                   10                  15

Leu Val Leu Leu Leu Trp Val Ser Ile Gly Ser
                20                  25
```

<210> SEQ ID NO 47
<211> LENGTH: 28
<212> TYPE: PRT
<213> ORGANISM: Artificial Sequence
<220> FEATURE:

<223> OTHER INFORMATION: Consensus sequence

<400> SEQUENCE: 47

Leu Leu Pro Ser Val Cys Met Cys Ala Tyr Ala Trp Val Leu Val Phe
1               5                   10                  15

Val Tyr Ile Val Val Ile Thr Ser Pro Ala Thr Ala
            20                  25

<210> SEQ ID NO 48
<211> LENGTH: 54
<212> TYPE: PRT
<213> ORGANISM: Artificial Sequence
<220> FEATURE:
<223> OTHER INFORMATION: Consensus sequence

<400> SEQUENCE: 48

Ile Val Tyr Arg Asp Gly Asn Pro Tyr Ala Val Cys Asp Lys Cys Leu
1               5                   10                  15

Lys Phe Tyr Ser Lys Ile Ser Glu Tyr Arg His Tyr Cys Tyr Ser Leu
            20                  25                  30

Tyr Gly Thr Thr Leu Glu Gln Gln Tyr Asn Lys Pro Leu Cys Asp Leu
        35                  40                  45

Leu Ile Arg Cys Ile Asn
    50

<210> SEQ ID NO 49
<211> LENGTH: 54
<212> TYPE: PRT
<213> ORGANISM: Artificial Sequence
<220> FEATURE:
<223> OTHER INFORMATION: Consensus sequence

<400> SEQUENCE: 49

Val Val Tyr Arg Asp Ser Ile Pro His Ala Ala Cys His Lys Cys Ile
1               5                   10                  15

Asp Phe Tyr Ser Arg Ile Arg Glu Leu Arg His Tyr Ser Asp Ser Val
            20                  25                  30

Tyr Gly Asp Thr Leu Glu Lys Leu Thr Asn Thr Gly Leu Tyr Asn Leu
        35                  40                  45

Leu Ile Arg Cys Leu Arg
    50

<210> SEQ ID NO 50
<211> LENGTH: 26
<212> TYPE: PRT
<213> ORGANISM: Artificial Sequence
<220> FEATURE:
<223> OTHER INFORMATION: Consensus sequence

<400> SEQUENCE: 50

Val Phe Cys Lys Lys Ala Leu Thr Ala Ser Glu Val Tyr Asn Phe Ala
1               5                   10                  15

Tyr Thr Asp Leu Arg Val Val Tyr Arg Asp
            20                  25

<210> SEQ ID NO 51
<211> LENGTH: 18
<212> TYPE: PRT
<213> ORGANISM: Artificial Sequence
<220> FEATURE:
<223> OTHER INFORMATION: Consensus sequence

<400> SEQUENCE: 51

```
Ser Lys Val Arg Lys Leu Arg Tyr Tyr Asn Cys Ser Val Tyr Gly Ala
1               5                   10                  15

Ser Leu

<210> SEQ ID NO 52
<211> LENGTH: 26
<212> TYPE: PRT
<213> ORGANISM: Artificial Sequence
<220> FEATURE:
<223> OTHER INFORMATION: Consensus sequence

<400> SEQUENCE: 52

Val Tyr Cys Lys Gly Gln Leu Thr Glu Thr Glu Val Leu Asp Phe Ala
1               5                   10                  15

Phe Thr Asp Leu Thr Ile Val Tyr Arg Asp
            20                  25

<210> SEQ ID NO 53
<211> LENGTH: 18
<212> TYPE: PRT
<213> ORGANISM: Artificial Sequence
<220> FEATURE:
<223> OTHER INFORMATION: Consensus sequence

<400> SEQUENCE: 53

Ser Lys Val Ser Glu Phe Arg Trp Tyr Arg Tyr Ser Val Tyr Gly Thr
1               5                   10                  15

Thr Leu

<210> SEQ ID NO 54
<211> LENGTH: 15
<212> TYPE: PRT
<213> ORGANISM: Artificial Sequence
<220> FEATURE:
<223> OTHER INFORMATION: Consensus sequence

<400> SEQUENCE: 54

Cys Val Glu Cys Lys Lys Thr Leu Gln Arg Ser Glu Val Tyr Asp
1               5                   10                  15

<210> SEQ ID NO 55
<211> LENGTH: 21
<212> TYPE: PRT
<213> ORGANISM: Artificial Sequence
<220> FEATURE:
<223> OTHER INFORMATION: CQRPLCPQEKKRHVDLNKRFH

<400> SEQUENCE: 55

Cys Gln Arg Pro Leu Cys Pro Gln Glu Lys Lys Arg His Val Asp Leu
1               5                   10                  15

Asn Lys Arg Phe His
            20

<210> SEQ ID NO 56
<211> LENGTH: 21
<212> TYPE: PRT
<213> ORGANISM: Artificial Sequence
<220> FEATURE:
<223> OTHER INFORMATION: Consensus sequence

<400> SEQUENCE: 56

Thr Leu His Glu Tyr Met Leu Asp Leu Gln Pro Glu Thr Thr Asp Leu
1               5                   10                  15
```

-continued

Tyr Cys Tyr Glu Gln
         20

<210> SEQ ID NO 57
<211> LENGTH: 26
<212> TYPE: PRT
<213> ORGANISM: Artificial Sequence
<220> FEATURE:
<223> OTHER INFORMATION: Consensus sequence

<400> SEQUENCE: 57

Pro Glu Thr Thr Asp Leu His Cys Tyr Glu Gln Leu Gly Asp Ser Ser
1               5                   10                  15

Asp Glu Glu Asp Thr Gly Gly Leu Asp Gly
            20                  25

<210> SEQ ID NO 58
<211> LENGTH: 39
<212> TYPE: PRT
<213> ORGANISM: Artificial Sequence
<220> FEATURE:
<223> OTHER INFORMATION: Consensus sequence

<400> SEQUENCE: 58

Asp Glu Asp Glu Asp Glu Val Asp His Leu Gln Glu Gln Pro Gln Gln
1               5                   10                  15

Ala Arg Arg Asp Glu Gln His Pro Cys Tyr Leu Ile Glu Thr Gln Cys
            20                  25                  30

Cys Arg Cys Glu Ser Leu Val
        35

<210> SEQ ID NO 59
<211> LENGTH: 37
<212> TYPE: PRT
<213> ORGANISM: Artificial Sequence
<220> FEATURE:
<223> OTHER INFORMATION: Consensus sequence

<400> SEQUENCE: 59

Glu Glu Asn Asp Glu Ile Asp Gly Val Asn His Gln His Leu Pro Ala
1               5                   10                  15

Arg Arg Ala Glu Pro Gln Arg His Thr Met Leu Cys Met Cys Cys Lys
            20                  25                  30

Cys Glu Ala Arg Ile
        35

<210> SEQ ID NO 60
<211> LENGTH: 3960
<212> TYPE: DNA
<213> ORGANISM: Artificial Sequence
<220> FEATURE:
<223> OTHER INFORMATION: vaccine construct

<400> SEQUENCE: 60
atggatgcta tgaagagggg cctgtgctgc gtgctgctgc tgtgtggcgc cgtgtttgtg      60
tcccccagcc aggaaatcca cgcccggttc agaagaggca gcaagctggc cgacgaggac     120
gagacagcct acgacagcgg caccgacctg atcgacttca tcgacgacag cgacgagaat     180
gagaacgact ccgacaccgg cgaggacatg gtggatttca tcgacaacga cgaaaccgac     240
gaagagagca ccgagagcga cctggacggc tttatcgaca actccgccca gctggctgac     300
agcgacagca atgcctgcgc cttcctgaag gctcagctgg cagacgtgaa cagcaacgcc     360

-continued

```
gctgcttttc tgaagaactg catcctgctg tacggcgctg ccaacaccgg caagagcctg        420
ttcggcatga gcctgaactg cctggtgctg tgcggcccag ccataccgg aaagtcctac         480
ttcggcatgt ccctgaattg tctcgtgatc tacgcccac ctaacacagg caagtcctgc         540
tttgccatgt ctctgtggcc ctacctgcac agcagactgg tggtgtttac cttccccaac        600
cccttctggc cttacctgga aagccggatc accgtgttcg agttccccaa tgcctttctg        660
agatacctgc actcccggat ccacgtgctg cagtttctga ccccttcaa cgtgtgccag        720
gacaagatcc tggaacacta cgagaacgac agcaaggaca ttctggaaca ttatgagaat        780
gattccaagg acctgtgcga ccacatctgc gatcacatcg actactggaa gcacatccgg        840
ctggaatgcg ccatcatgta caaggcccgg atcagactgg aatgtgctat tatgtataag        900
gctcgcgaga tgggcttcca ccagttcgac ggcgacatct gcaacaccat gcactacacc        960
aactggatct atatctgcga ggacgcccag tgcaccgtgg tggaaggcca ggtggacaag       1020
aaatgggagg tgcacgctgg cggccaagtg atcctgtgtc ctgagagcgg ccagcggcgg       1080
atcaagaggc cagaagcga gaactgccac cccaacaagc tgctgatcct gaagtgcctg        1140
cggtacagat tcaagaagca ctgcaagctg agcagcacct ggcactggac ctgccacgac       1200
ggcaagcaca agtggcattg acatgtcac gatgggaaac acaagaacgc cattgtgacc        1260
ctgacctact acgaggccga caagaacgac ctgaacgccc agatcgagca ctggaaactg       1320
atccggatgg aatgtgcaat cttctataag gccaaagagc tgggcatcag catctgccac       1380
caggtggtgc ctccactggc cgcctctaaa gccaaagcct gccaggccat cgaactgcag       1440
ctggccctgg aagccctgaa tgccagcccc tacgatgagt ggaccctgca gcagaccagc       1500
ctggaaatgt ggctggccga gccccagttt aagaagcacg gcatcaccat caccgtgcag       1560
tacgacaatg acaaggccaa taccatggat tacacaaatt ggaaagaaat ctacgtgatc       1620
gtgtgccccg ccagcatccc ctccgatgag atcagcaccg aggaagccga ccacattgat       1680
tattggaaag ccatcaggca ggaaaacgcc atcttcttcg ccgccagaca ccaggtggtg       1740
cccgccctga atatctgcaa ggccaaggcc tgtaaagcca tcgagtggaa caccgagccc       1800
aagcactgct tcaagaaggg cggccagcac atcgaagtgt ggttcgacta cgtggcctgg       1860
gacagcgtgt actactgcgg cgacgatggc tggtgcaaga ccgaggccga aagtacggc        1920
tgcaagggca cctgggaagt gcatttcggc aacagcatcg actgcaacga ctccatgtgc       1980
agcaccttcg acgacaacgt gtccgccacc gagctcgtga aggaccatat cgactattgg       2040
aagctgattc gcctggaatg tgccattttt tacaaggcca gacggcggct gtccagcgac       2100
caggatcagt ctcagctcgt gaccaagtac cccctgctga gctgctgtc cagaccccc         2160
aacatgggcg tgaaggccca cggcaagtgc atctgggaga caaggtgtt catcgtgccc        2220
accctgtgcc ccgtgcctct ggatccaaca tatcctctgc tgaaactgct gaccacccag       2280
accaccaccc ccgagaatac ctccctggtg gaactgagag tgaccaccc caagagcaca       2340
gtcgtgatca ggctgcacct gaccaccaga tacccactgc tgtcactgct gaacagctac       2400
agcaccccc ctcaccggat ccctgctcca tgtccttggg ctcctcagag gcccccatc         2460
cctaagcctt tccatgggc ccctagaatc cctgccccct tgcccctggg acctcctaga       2520
cctccacact gtccatgggt gccccctcca cctcctccaa gaccttgggc cccttgcttc      2580
ctgctgtgct tttgtgtgct gctgtgcgtg tgcctgctga tcagacccct gctgctgagt       2640
gtgtccacct acctgaggcc tctgctgctg tctatcagcg tgtacgctca ggtgctggtg       2700
ctggtgctgc tgctgtgggt gtccatcgga agcctgctgc ccagcgtgtg catgtgtgcc       2760
```

```
tatgcctggg tgctggtgtt cgtgtacatc gtcgtgatta ccagcccgc  caccgccatc    2820 gtgtaccggg atggcaatcc ttacgccgtg tgcgacaagt gcctgaagtt ctacagcaag    2880
atcagcgagt accggcacta ctgctacagc ctgtacggca ccaccctgga cagcagtac    2940 aacaagcccc tgtgcgatct gctgattcgg tgcatcaacg tggtgtacag agactccatc    3000
ccccacgccg cctgccacaa gtgtatcgac ttctactcca gaatcagaga gctgcggcac    3060
tacagcgact ccgtgtacgg cgatacctg  gaaaagctga ccaacactgg cctgtacaac    3120
ctgctgatta gatgcctgcg ggtgttctgc aagaaggccc tgacagccag cgaggtgtac    3180
aacttcgcct acaccgatct gcgggtggtg tatcgggaca gcaaagtgcg gaagctgagg    3240
tactacaact gctctgtgta tggcgccagc ctggtgtatt gcaagggaca gctgaccgag    3300
acagaggtgc tggatttcgc cttcacagac ctgacaatcg tgtatcgcga ctccaaggtg    3360
tccgagttcc ggtggtacag atattccgtg tatggcacca cactgtgcgt ggaatgcaag    3420 aaaacctgc  agagatctga ggtgtacgac tgccagcggc cactgtgtcc gcaggaaaag    3480
aaaagacacg tggacctgaa caagcggttc cacaccctgc acgagtacat gctggatctg    3540
cagcccgaga caaccgacct gtactgctac gagcagcctg aaaccactga tctgcactgt    3600
tatgagcagc tgggagacag ctccgatgaa gaggacactg gcggcctgga tggggacgag    3660
gatgaggacg aagtggacca tctgcaggaa cagcccagc aggctagacg ggacgaacag    3720 caccccttgct atctgatcga cacagtgc  tgcagatgcg aatctctggt ggaagagaac    3780
gacgagatcg acggcgtgaa ccaccagcat ctgcccgcta aagggccga gcctcagaga    3840 cacaccatgc tgtgtatgtg ctgcaagtgc gaggccagaa tcgccggctc tggacctggc    3900
gcctctggca agcctatccc caatccactg ctgggcctgg actccacccg gacctgataa    3960

<210> SEQ ID NO 61
<211> LENGTH: 1318
<212> TYPE: PRT
<213> ORGANISM: Artificial Sequence
<220> FEATURE:
<223> OTHER INFORMATION: Vaccine construct

<400> SEQUENCE: 61

Met Asp Ala Met Lys Arg Gly Leu Cys Cys Val Leu Leu Cys Gly
1               5                   10                  15

Ala Val Phe Val Ser Pro Ser Gln Glu Ile His Ala Arg Phe Arg Arg
                20                  25                  30

Gly Ser Lys Leu Ala Asp Glu Asp Glu Thr Ala Tyr Asp Ser Gly Thr
            35                  40                  45

Asp Leu Ile Asp Phe Ile Asp Asp Ser Asp Glu Asn Glu Asn Asp Ser
        50                  55                  60

Asp Thr Gly Glu Asp Met Val Asp Phe Ile Asp Asn Asp Glu Thr Asp
65                  70                  75                  80

Glu Glu Ser Thr Glu Ser Asp Leu Asp Gly Phe Ile Asp Asn Ser Ala
                85                  90                  95

Gln Leu Ala Asp Ser Asp Ser Asn Ala Cys Ala Phe Leu Lys Ala Gln
                100                 105                 110

Leu Ala Asp Val Asn Ser Asn Ala Ala Phe Leu Lys Asn Cys Ile
            115                 120                 125

Leu Leu Tyr Gly Ala Ala Asn Thr Gly Lys Ser Leu Phe Gly Met Ser
        130                 135                 140

Leu Asn Cys Leu Val Leu Cys Gly Pro Ala Asn Thr Gly Lys Ser Tyr
```

-continued

```
                145                 150                 155                 160
        Phe Gly Met Ser Leu Asn Cys Leu Val Ile Tyr Gly Pro Pro Asn Thr
                        165                 170                 175
        Gly Lys Ser Cys Phe Ala Met Ser Leu Trp Pro Tyr Leu His Ser Arg
                        180                 185                 190
        Leu Val Val Phe Thr Phe Pro Asn Pro Phe Trp Pro Tyr Leu Glu Ser
                        195                 200                 205
        Arg Ile Thr Val Phe Glu Phe Pro Asn Ala Phe Leu Arg Tyr Leu His
                        210                 215                 220
        Ser Arg Ile His Val Leu Gln Phe Leu Asn Pro Phe Asn Val Cys Gln
        225                 230                 235                 240
        Asp Lys Ile Leu Glu His Tyr Glu Asn Asp Ser Lys Asp Ile Leu Glu
                        245                 250                 255
        His Tyr Glu Asn Asp Ser Lys Asp Leu Cys Asp His Ile Cys Asp His
                        260                 265                 270
        Ile Asp Tyr Trp Lys His Ile Arg Leu Glu Cys Ala Ile Met Tyr Lys
                        275                 280                 285
        Ala Arg Ile Arg Leu Glu Cys Ala Ile Met Tyr Lys Ala Arg Glu Met
                        290                 295                 300
        Gly Phe His Gln Phe Asp Gly Asp Ile Cys Asn Thr Met His Tyr Thr
        305                 310                 315                 320
        Asn Trp Ile Tyr Ile Cys Glu Asp Ala Gln Cys Thr Val Val Glu Gly
                        325                 330                 335
        Gln Val Asp Lys Lys Trp Glu Val His Ala Gly Gly Gln Val Ile Leu
                        340                 345                 350
        Cys Pro Glu Ser Gly Gln Arg Arg Ile Lys Arg Pro Arg Ser Glu Asn
                        355                 360                 365
        Cys His Pro Asn Lys Leu Leu Ile Leu Lys Cys Leu Arg Tyr Arg Phe
                        370                 375                 380
        Lys Lys His Cys Lys Leu Ser Ser Thr Trp His Trp Thr Cys His Asp
        385                 390                 395                 400
        Gly Lys His Lys Trp His Trp Thr Cys His Asp Gly Lys His Lys Asn
                        405                 410                 415
        Ala Ile Val Thr Leu Thr Tyr Tyr Glu Ala Asp Lys Asn Asp Leu Asn
                        420                 425                 430
        Ala Gln Ile Glu His Trp Lys Leu Ile Arg Met Glu Cys Ala Ile Phe
                        435                 440                 445
        Tyr Lys Ala Lys Glu Leu Gly Ile Ser Ile Cys His Gln Val Val Pro
                        450                 455                 460
        Pro Leu Ala Ala Ser Lys Ala Lys Ala Cys Gln Ala Ile Glu Leu Gln
        465                 470                 475                 480
        Leu Ala Leu Glu Ala Leu Asn Ala Ser Pro Tyr Asp Glu Trp Thr Leu
                        485                 490                 495
        Gln Gln Thr Ser Leu Glu Met Trp Leu Ala Glu Pro Gln Phe Lys Lys
                        500                 505                 510
        His Gly Ile Thr Ile Thr Val Gln Tyr Asp Asn Asp Lys Ala Asn Thr
                        515                 520                 525
        Met Asp Tyr Thr Asn Trp Lys Glu Ile Tyr Val Ile Val Cys Pro Ala
                        530                 535                 540
        Ser Ile Pro Ser Asp Glu Ile Ser Thr Glu Glu Ala Asp His Ile Asp
        545                 550                 555                 560
        Tyr Trp Lys Ala Ile Arg Gln Glu Asn Ala Ile Phe Phe Ala Ala Arg
                        565                 570                 575
```

```
His Gln Val Val Pro Ala Leu Asn Ile Cys Lys Ala Lys Ala Cys Lys
            580                 585                 590

Ala Ile Glu Trp Asn Thr Glu Pro Lys His Cys Phe Lys Gly Gly
        595                 600                 605

Gln His Ile Glu Val Trp Phe Asp Tyr Val Ala Trp Asp Ser Val Tyr
    610                 615                 620

Tyr Cys Gly Asp Asp Gly Trp Cys Lys Thr Glu Ala Glu Lys Tyr Gly
625                 630                 635                 640

Cys Lys Gly Thr Trp Glu Val His Phe Gly Asn Ser Ile Asp Cys Asn
                645                 650                 655

Asp Ser Met Cys Ser Thr Phe Asp Asn Val Ser Ala Thr Glu Leu
            660                 665                 670

Val Lys Asp His Ile Asp Tyr Trp Lys Leu Ile Arg Leu Glu Cys Ala
        675                 680                 685

Ile Phe Tyr Lys Ala Arg Arg Arg Leu Ser Ser Asp Gln Asp Gln Ser
    690                 695                 700

Gln Leu Val Thr Lys Tyr Pro Leu Leu Lys Leu Leu Ser Arg Pro Pro
705                 710                 715                 720

Asn Met Gly Val Lys Ala His Gly Lys Cys Ile Trp Glu Asn Lys Val
                725                 730                 735

Phe Ile Val Pro Thr Leu Cys Pro Val Pro Leu Asp Pro Thr Tyr Pro
            740                 745                 750

Leu Leu Lys Leu Leu Thr Thr Gln Thr Thr Thr Pro Glu Asn Thr Ser
        755                 760                 765

Leu Val Glu Leu Arg Val Thr Thr Pro Lys Ser Thr Val Val Ile Arg
    770                 775                 780

Leu His Leu Thr Thr Arg Tyr Pro Leu Leu Ser Leu Leu Asn Ser Tyr
785                 790                 795                 800

Ser Thr Pro Pro His Arg Ile Pro Ala Pro Cys Pro Trp Ala Pro Gln
                805                 810                 815

Arg Pro Pro Ile Pro Lys Pro Ser Pro Trp Ala Pro Arg Ile Pro Ala
            820                 825                 830

Pro Cys Pro Trp Ala Pro Pro Arg Pro Pro His Cys Pro Trp Val Pro
        835                 840                 845

Pro Pro Pro Pro Pro Arg Pro Trp Ala Pro Cys Phe Leu Leu Cys Phe
    850                 855                 860

Cys Val Leu Leu Cys Val Cys Leu Leu Ile Arg Pro Leu Leu Leu Ser
865                 870                 875                 880

Val Ser Thr Tyr Leu Arg Pro Leu Leu Leu Ser Ile Ser Val Tyr Ala
                885                 890                 895

Gln Val Leu Val Leu Val Leu Leu Leu Trp Val Ser Ile Gly Ser Leu
            900                 905                 910

Leu Pro Ser Val Cys Met Cys Ala Tyr Ala Trp Val Leu Val Phe Val
        915                 920                 925

Tyr Ile Val Val Ile Thr Ser Pro Ala Thr Ala Ile Val Tyr Arg Asp
    930                 935                 940

Gly Asn Pro Tyr Ala Val Cys Asp Lys Cys Leu Lys Phe Tyr Ser Lys
945                 950                 955                 960

Ile Ser Glu Tyr Arg His Tyr Cys Tyr Ser Leu Tyr Gly Thr Thr Leu
                965                 970                 975

Glu Gln Gln Tyr Asn Lys Pro Leu Cys Asp Leu Leu Ile Arg Cys Ile
            980                 985                 990
```

Asn Val Val Tyr Arg Asp Ser Ile Pro His Ala Ala Cys His Lys Cys
            995                 1000                1005

Ile Asp Phe Tyr Ser Arg Ile Arg Glu Leu Arg His Tyr Ser Asp
    1010                1015                1020

Ser Val Tyr Gly Asp Thr Leu Glu Lys Leu Thr Asn Thr Gly Leu
    1025                1030                1035

Tyr Asn Leu Leu Ile Arg Cys Leu Arg Val Phe Cys Lys Lys Ala
    1040                1045                1050

Leu Thr Ala Ser Glu Val Tyr Asn Phe Ala Tyr Thr Asp Leu Arg
    1055                1060                1065

Val Val Tyr Arg Asp Ser Lys Val Arg Lys Leu Arg Tyr Tyr Asn
    1070                1075                1080

Cys Ser Val Tyr Gly Ala Ser Leu Val Tyr Cys Lys Gly Gln Leu
    1085                1090                1095

Thr Glu Thr Glu Val Leu Asp Phe Ala Phe Thr Asp Leu Thr Ile
    1100                1105                1110

Val Tyr Arg Asp Ser Lys Val Ser Glu Phe Arg Trp Tyr Arg Tyr
    1115                1120                1125

Ser Val Tyr Gly Thr Thr Leu Cys Val Glu Cys Lys Lys Thr Leu
    1130                1135                1140

Gln Arg Ser Glu Val Tyr Asp Cys Gln Arg Pro Leu Cys Pro Gln
    1145                1150                1155

Glu Lys Lys Arg His Val Asp Leu Asn Lys Arg Phe His Thr Leu
    1160                1165                1170

His Glu Tyr Met Leu Asp Leu Gln Pro Glu Thr Thr Asp Leu Tyr
    1175                1180                1185

Cys Tyr Glu Gln Pro Glu Thr Thr Asp Leu His Cys Tyr Glu Gln
    1190                1195                1200

Leu Gly Asp Ser Ser Asp Glu Glu Asp Thr Gly Gly Leu Asp Gly
    1205                1210                1215

Asp Glu Asp Glu Asp Glu Val Asp His Leu Gln Glu Gln Pro Gln
    1220                1225                1230

Gln Ala Arg Arg Asp Glu Gln His Pro Cys Tyr Leu Ile Glu Thr
    1235                1240                1245

Gln Cys Cys Arg Cys Glu Ser Leu Val Glu Glu Asn Asp Glu Ile
    1250                1255                1260

Asp Gly Val Asn His Gln His Leu Pro Ala Arg Arg Ala Glu Pro
    1265                1270                1275

Gln Arg His Thr Met Leu Cys Met Cys Cys Lys Cys Glu Ala Arg
    1280                1285                1290

Ile Ala Gly Ser Gly Pro Gly Ala Ser Gly Lys Pro Ile Pro Asn
    1295                1300                1305

Pro Leu Leu Gly Leu Asp Ser Thr Arg Thr
    1310                1315

<210> SEQ ID NO 62
<211> LENGTH: 42783
<212> TYPE: DNA
<213> ORGANISM: Artificial Sequence
<220> FEATURE:
<223> OTHER INFORMATION: Viral vector construct

<400> SEQUENCE: 62
gtttaaacgc ggccgccagg cctacccact agtcaattcg ggaggatcga acggcagat       60 cgcaaaaaac agtacataca gaaggagaca tgaacatgaa catcaaaaaa attgtaaaac     120

```
aagccacagt tctgactttt acgactgcac ttctggcagg aggagcgact caagccttcg      180
cgaaagaaaa taaccaaaaa gcatacaaag aaacgtacgg cgtctctcat attacacgcc      240
atgatatgct gcagatccct aaacagcagc aaaacgaaaa ataccaagtg cctcaattcg      300
atcaatcaac gattaaaaat attgagtctg caaaaggact tgatgtgtgg acagctggc       360 cgctgcaaaa cgctgacgga acagtagctg aatacaacgg ctatcacgtt gtgtttgctc      420
ttgcgggaag cccgaaagac gctgatgaca catcaatcta catgttttat caaaaggtcg      480
gcgacaactc aatcgacagc tggaaaaacg cgggccgtgt ctttaaagac agcgataagt      540
tcgacgccaa cgatccgatc ctgaaagatc agacgcaaga atggtccggt tctgcaacct      600
ttacatctga cggaaaaatc cgtttattct acactgacta ttccggtaaa cattacggca      660
aacaaagcct gacaacagcg caggtaaatg tgtcaaaatc tgatgacaca ctcaaaatca      720
acggagtgga agatcacaaa acgattttg acggagacgg aaaaacatat cagaacgttc       780
agcagtttat cgatgaaggc aattatacat ccggcgacaa ccatacgctg agagaccctc      840
actacgttga agacaaaggc cataaatacc ttgtattcga agccaacacg ggaacagaaa      900
acggatacca aggcgaagaa tctttatttta acaaagcgta ctacggcggc ggcacgaact      960
tcttccgtaa agaaagccag aagcttcagc agagcgctaa aaaacgcgat gctgagttag     1020
cgaacggcgc cctcggtatc atagagttaa ataatgatta cacattgaaa aaagtaatga     1080
agccgctgat cacttcaaac acggtaactg atgaaatcga gcgcgcgaat gttttcaaaa     1140
tgaacggcaa atggtacttg ttcactgatt cacgcggttc aaaaatgacg atcgatggta     1200
ttaactcaaa cgatatttac atgcttggtt atgtatcaaa ctctttaacc ggcccttaca     1260
agccgctgaa caaaacaggg cttgtgctgc aaatgggtct tgatccaaac gatgtgacat     1320
tcacttactc tcacttcgca gtgccgcaag ccaaaggcaa caatgtggtt atcacaagct     1380
acatgacaaa cagaggcttc ttcgaggata aaaaggcaac atttgcgcca agcttcttaa     1440
tgaacatcaa aggcaataaa acatccgttg tcaaaaacag catcctggag caaggacagc     1500
tgacagtcaa ctaataacag caaaaagaaa atgccgatac ttcattggca ttttctttta     1560
tttctcaaca agatggtgaa ttgactagtg ggtagatcca caggacgggt gtggtcgcca     1620
tgatcgcgta gtcgatagtg gctccaagta gcgaagcgag caggactggg cggcggccaa     1680
agcggtcgga cagtgctccg agaacgggtg cgcatagaaa ttgcatcaac gcatatagcg     1740
ctagcagcac gccatagtga ctggcgatgc tgtcggaatg gacgatatcc cgcaagaggc     1800
ccggcagtac cggcataacc aagcctatgc ctacagcatc cagggtgacg gtgccgagga     1860
tgacgatgag cgcattgtta gatttcatac acggtgcctg actgcgttag caatttaact     1920
gtgataaact accgcattaa agcttatcga tgataagctg tcaaacatga aattgatcc       1980 ggaacccta atataacttc gtataatgta tgctatacga agttattagg tccctcgact       2040 ataggtcac cgtcgacagc gacacacttg catcggatgc agcccggtta acgtgccggc       2100
acggcctggg taaccaggta ttttgtccac ataaccgtgc gcaaatgtt gtggataagc       2160 aggacacagc agcaatccac agcaggcata caaccgcaca ccgaggttac tccgttctac     2220
aggttacgac gacatgtcaa tacttgccct tgacaggcat tgatggaatc gtagtctcac     2280
gctgatagtc tgatcgacaa tacaagtggg accgtggtcc cagaccgata atcagaccga     2340
crayacgagt gggaycgtgg tcccagacta ataatcagac cgacgatacg agtgggaccg     2400
tggtcccaga ctaataatca gaccgacgat acgagtggga ccgtggtycc agwctratwa     2460
```

```
tcagaccgac gatacragtg gracmgtggk cccagasaka atawtcagrc cgagwtaygc    2520
wktckggcct gtaacaaagg acattaagta aagacagata mrmgtgrgac taaaacgtgg    2580
tcccagtctg attatcagac cgacgatacg agtgggaccg tggtcccaga ctaataatca    2640
gaccgacgat acgagtggga ccgtggtccc agactaataa tcagaccgac gatacgagtg    2700
ggaccgtggt cccagtctga ttatcagacc gacgatacaa gtggaacagt gggcccagag    2760
agaatattca ggccagttat gctttctggc ctgtaacaaa ggacattaag taaagacaga    2820
taaacgtaga ctaaaacgtg gtcgcatcag ggtgctggct tttcaagttc cttaagaatg    2880
gcctcaattt tctctataca ctcagttgga acacgagacc tgtccaggtt aagcaccatt    2940
ttatcgccct tatacaatac tgtcgctcca ggagcaaact gatgtcgtga gcttaaacta    3000
gttcttgatg cagatgacgt tttaagcaca aagttaaaa gagtgataac ttcttcagct    3060
tcaaatatca ccccagcttt tttctgctca tgaaggttag atgcctgctg cttaagtaat    3120
tcctctttat ctgtaaaggc tttttgaagt gcatcacctg accgggcaga tagttcaccg    3180
gggtgagaaa aaagagcaac aactgattta ggcaatttgg cggtgttgat acagcgggta    3240
ataatcttac gtgaaatatt ttccgcatca gccagcgcag aaatatttcc agcaaattca    3300
ttctgcaatc ggcttgcata acgctgacca cgttcataag cacttgttgg gcgataatcg    3360
ttacccaatc tggataatgc agccatctgc tcatcatcca gctcgccaac cagaacacga    3420
taatcacttt cggtaagtgc agcagcttta cgacggcgac tcccatcggc aatttctatg    3480
acaccagata ctcttcgacc gaacgccggt gtctgttgac cagtcagtag aaaagaaggg    3540
atgagatcat ccagtgcgtc ctcagtaagc agctcctggt cacgttcatt acctgaccat    3600
acccgagagg tcttctcaac actatcaccc cggagcactt caagagtaaa cttcacatcc    3660
cgaccacata caggcaaagt aatggcatta ccgcgagcca ttactcctac gcgcgcaatt    3720
aacgaatcca ccatcggggc agctggtgtc gataacgaag tatcttcaac cggttgagta    3780
ttgagcgtat gttttggaat aacaggcgca cgcttcatta tctaatctcc cagcgtggtt    3840
taatcagacg atcgaaaatt tcattgcaga caggttccca aatagaaaga gcatttctcc    3900
aggcaccagt tgaagagcgt tgatcaatgg cctgttcaaa aacagttctc atccggatct    3960
gacctttacc aacttcatcc gtttcacgta caacattttt tagaaccatg cttccccagg    4020
catcccgaat tgctcctcc atccacgggg actgagagcc attactattg ctgtatttgg    4080
taagcaaaat acgtacatca ggctcgaacc ctttaagatc aacgttcttg agcagatcac    4140
gaagcatatc gaaaaactgc agtgcggagg tgtagtcaaa caactcagca ggcgtgggaa    4200
caatcagcac atcagcagca catacgacat taatcgtgcc gatacccagg ttaggcgcgc    4260
tgtcaataac tatgacatca tagtcatgag caacagtttc aatggccagt cggagcatca    4320
ggtgtggatc ggtgggcagt ttaccttcat caaatttgcc cattaactca gtttcaatac    4380
ggtgcagagc cagacaggaa ggaataatgt caagccccgg ccagcaagtg gctttattg    4440
cataagtgac atcgtccttt tccccaagat agaaaggcag gagagtgtct tctgcatgaa    4500
tatgaagatc tggtacccat ccgtgataca ttgaggctgt tccctggggg tcgttacctt    4560
ccacgagcaa aacacgtagc cccttcagag ccagatcctg agcaagatga acagaaactg    4620
aggttttgta acgccacct ttatgggcag caaccccgat caccggtgga aatacgtctt    4680
cagcacgtcg caatcgcgta ccaaacacat cacgcatatg attaatttgt tcaattgtat    4740
aaccaacacg ttgctcaacc cgtcctcgaa tttccatatc cgggtgcggt agtcgccctg    4800
cttttctcggc atctctgata gcctgagaag aaaccccaac taaatccgct gcttcaccta    4860
```

-continued

| | | | | |
|---|---|---|---|---|
| ttctccagcg | ccgggttatt | ttcctcgctt | ccgggctgtc | atcattaaac | tgtgcaatgg | 4920 |
| cgatagcctt | cgtcatttca | tgaccagcgt | ttatgcactg | gttaagtgtt | tccatgagtt | 4980 |
| tcattctgaa | catcctttaa | tcattgcttt | gcgttttttt | attaaatctt | gcaatttact | 5040 |
| gcaaagcaac | aacaaaatcg | caaagtcatc | aaaaaaccgc | aaagttgttt | aaaataagag | 5100 |
| caacactaca | aaaggagata | agaagagcac | atacctcagt | cacttattat | cactagcgct | 5160 |
| cgccgcagcc | gtgtaaccga | gcatagcgag | cgaactggcg | aggaagcaaa | gaagaactgt | 5220 |
| tctgtcagat | agctcttacg | ctcagcgcaa | gaagaaatat | ccaccgtggg | aaaaactcca | 5280 |
| ggtagaggta | cacacgcgga | tagccaattc | agagtaataa | actgtgataa | tcaaccctca | 5340 |
| tcaatgatga | cgaactaacc | cccgatatca | ggtcacatga | cgaagggaaa | gagaaggaaa | 5400 |
| tcaactgtga | caaactgccc | tcaaatttgg | cttccttaaa | aattacagtt | caaaaagtat | 5460 |
| gagaaaatcc | atgcaggctg | aaggaaacag | caaaactgtg | acaaattacc | ctcagtaggt | 5520 |
| cagaacaaat | gtgacgaacc | accctcaaat | ctgtgacaga | taaccctcag | actatcctgt | 5580 |
| cgtcatggaa | gtgatatcgc | ggaaggaaaa | tacgatatga | gtcgtctggc | ggcctttctt | 5640 |
| tttctcaatg | tatgagaggc | gcattggagt | tctgctgttg | atctcattaa | cacagacctg | 5700 |
| caggaagcgg | cggcggaagt | caggcatacg | ctggtaactt | tgaggcagct | ggtaacgctc | 5760 |
| tatgatccag | tcgattttca | gagagacgat | gcctgagcca | tccggcttac | gatactgaca | 5820 |
| cagggattcg | tataaacgca | tggcatacgg | attggtgatt | tcttttgttt | cactaagccg | 5880 |
| aaactgcgta | aaccggttct | gtaacccgat | aagaaggga | atgagatatg | ggttgatatg | 5940 |
| tacactgtaa | agccctctgg | atggactgtg | cgcacgtttg | ataaaccaag | gaaaagattc | 6000 |
| atagcctttt | tcatcgccgg | catcctcttc | agggcgataa | aaaccacctt | ccttccccgc | 6060 |
| gaaactcttc | aatgcctgcc | gtatatcctt | actggcttcc | gcagaggtca | atccgaatat | 6120 |
| ttcagcatat | ttagcaacat | ggatctcgca | gataccgtca | tgttcctgta | gggtgccatc | 6180 |
| agattttctg | atctggtcaa | cgaacagata | cagcatacgt | ttttgatccc | gggagagact | 6240 |
| atatgccgcc | tcagtgaggt | cgtttgactg | gacgattcgc | gggctatttt | tacgtttctt | 6300 |
| gtgattgata | accgctgttt | ccgccatgac | agatccatgt | gaagtgtgac | aagttttag | 6360 |
| attgtcacac | taaataaaaa | agagtcaata | agcagggata | actttgtgaa | aaaacagctt | 6420 |
| cttctgaggg | caatttgtca | cagggttaag | ggcaatttgt | cacagacagg | actgtcattt | 6480 |
| gagggtgatt | tgtcacactg | aaagggcaat | ttgtcacaac | accttctcta | gaaccagcat | 6540 |
| ggataaaggc | ctacaaggcg | ctctaaaaaa | gaagatctaa | aaactataaa | aaaataatt | 6600 |
| ataaaaatat | ccccgtggat | aagtggataa | ccccaaggga | agttttttca | ggcatcgtgt | 6660 |
| gtaagcagaa | tatataagtg | ctgttccctg | gtgcttcctc | gctcactcga | ggcttcgcc | 6720 |
| ctgtcgctca | actgcggcga | gcactactgg | ctgtaaaagg | acagaccaca | tcatggttct | 6780 |
| gtgttcatta | ggttgttctg | tccattgctg | acataatccg | ctccacttca | acgtaacacc | 6840 |
| gcacgaagat | ttctattgtt | cctgaaggca | tattcaaatc | gttttcgtta | ccgcttgcag | 6900 |
| gcatcatgac | agaacactac | ttcctataaa | cgctacacag | gctcctgaga | ttaataatgc | 6960 |
| ggatctctac | gataatggga | gattttcccg | actgtttcgt | tcgcttctca | gtggataaca | 7020 |
| gccagcttct | ctgtttaaca | gacaaaaaca | gcatatccac | tcagttccac | atttccatat | 7080 |
| aaaggccaag | gcattattc | tcaggataat | gtttcagca | tcgcaaccgc | atcagactcc | 7140 |
| ggcatcgcaa | actgcacccg | gtgccgggca | gccacatcca | gcgcaaaaac | cttcgtgtag | 7200 |

```
acttccgttg aactgatgga cttatgtccc atcaggcttt gcagaacttt cagcggtata    7260
ccggcataca gcatgtgcat cgcataggaa tggcggaacg tatgtggtgt gaccggaaca    7320
gagaacgtca caccgtcagc agcagcggcg gcaaccgcct ccccaatcca ggtcctgacc    7380
gttctgtccg tcacttccca gatccgcgct ttctctgtcc ttcctgtgcg acggttacgc    7440
cgctccatga gcttatcgcg aataaatacc tgtgacggaa gatcacttcg cagaataaat    7500
aaatcctggt gtccctgttg ataccgggaa gccctgggcc aacttttggc gaaaatgaga    7560
cgttgatcgg cacgtaagag gttccaactt tcaccataat gaaataagat cactaccggg    7620 cgtattttt gagttatcga gattttcagg agctaaggaa gctaaaatgg agaaaaaat    7680 cactggatat accaccgttg atatatccca atggcatcgt aaagaacatt ttgaggcatt    7740
tcagtcagtt gctcaatgta cctataacca gaccgttcag ctggatatta cggccttttt    7800
aaagaccgta agaaaaata agcacaagtt ttatccggcc tttattcaca ttcttgcccg    7860
cctgatgaat gctcatccgg agttccgtat ggcaatgaaa gacggtgagc tggtgatatg    7920
ggatagtgtt caccccttgtt acaccgtttt ccatgagcaa actgaaacgt tttcatcgct    7980
ctggagtgaa taccacgacg atttccggca gtttctacac atatattcgc aagatgtggc    8040
gtgttacggt gaaaacctgg cctatttccc taaagggttt attgagaata tgttttcgt    8100 ctcagccaat ccctgggtga gtttcaccag ttttgattta aacgtggcca atatggacaa    8160
cttcttcgcc cccgttttca ccatgggcaa atattatacg caaggcgaca aggtgctgat    8220
gccgctggcg attcaggttc atcatgccgt ttgtgatggc ttccatgtcg gcagaatgct    8280
taatgaatta caacagtact gcgatgagtg gcagggcggg gcgtaatttt tttaaggcag    8340
ttattggtgc ccttaaacgc ctggttgcta cgcctgaata agtgataata agcggatgaa    8400
tggcagaaat tcgatgataa gctgtcaaac atgagaattg gtcgacgcg cgccaaagct    8460 tgcatgcctg cagccgcgta acctggcaaa atcggttacg gttgagtaat aaatggatgc    8520
cctgcgtaag cggggcacat ttcattacct cttttctccgc acccgacata gataataact    8580
tcgtatagta tacattatac gaagttatct agtagactta atcgcgttta aacccatcat    8640
caataatata cctcaaactt tttgtgcgcg ttaatatgca aatgaggcgt ttgaatttgg    8700
gaagggagga aggtgattgg ccgagagaag ggcgaccgtt aggggcgggg cgagtgacgt    8760
tttgatgacg tgaccgcgag gaggagccag tttgcaagtt ctcgtgggaa aagtgacgtc    8820
aaacgaggtg tggtttgaac acggaaatac tcaatttcc cgcgctctct gacaggaaat    8880
gaggtgtttc taggcggatg caagtgaaaa cgggccattt tcgcgcgaaa actgaatgag    8940
gaagtgaaaa tctgagtaat ttcgcgttta tgacagggag gagtatttgc cgagggccga    9000
gtagactttg accgattacg tggggggttc gattaccgtg tttttcacct aaatttccgc    9060
gtacggtgtc aaagtccggt gtttttacgt aggtgtcagc tgatcgccag ggtatttaaa    9120
cctgcgctct ccagtcaaga ggccactctt gagtgccagc gagaagagtt ttctcctccg    9180
cgcgcgagtc agatctacac tttgaaaggc gatcgctagc gacatcgatc acaagtttgt    9240
acaaaaaagc aggctccacc atgggaacca attcagtcga gcctttcact cattagatgc    9300
atgtcgttac ataacttacg gtaaatggcc cgcctggctg accgcccaac gaccccggc    9360 cattgacgtc aataatgacg tatgttccca tagtaacgcc aatagggact ttccattgac    9420
gtcaatgggt ggagtattta cggtaaactg cccacttggc agtacatcaa gtgtatcata    9480
tgccaagtac gccccctatt gacgtcaatg acggtaaatg gcccgcctgg cattatgccc    9540
agtacatgac cttatgggac tttcctactt ggcagtacat ctacgtatta gtcatcgcta    9600
```

```
ttaccatggt gatgcggttt tggcagtaca tcaatgggcg tggatagcgg tttgactcac    9660
ggggatttcc aagtctccac cccattgacg tcaatgggag tttgtttgg caccaaaatc     9720
aacgggactt tccaaaatgt cgtaacaact ccgccccatt gacgcaaatg ggcggtaggc    9780
gtgtacggtg ggaggtctat ataagcagag ctctccctat cagtgataga gatctcccta   9840
tcagtgatag agatcgtcga cgagctcgtt tagtgaaccg tcagatcgcc tggagacgcc    9900
atccacgctg ttttgacctc catagaagac accgggaccg atccagcctc cggttaagct    9960
cggtaccgct agccgcgccg ccaccatgga tgctatgaag aggggcctgt gctgcgtgct   10020
gctgctgtgt ggcgccgtgt tgtgtcccc cagccaggaa atccacgccc ggttcagaag    10080
aggcagcaag ctggccgacg aggacgagac agcctacgac agcggcaccg acctgatcga   10140
cttcatcgac gacagcgacg agaatgagaa cgactccgac accggcgagg acatggtgga   10200
tttcatcgac aacgacgaaa ccgacgaaga gagcaccgag agcgacctgg acggctttat   10260
cgacaactcc gcccagctgg ctgacagcga cagcaatgcc tgcgccttcc tgaaggctca   10320
gctggcagac gtgaacagca cgccgctgc ttttctgaag aactgcatcc tgctgtacgg    10380
cgctgccaac accggcaaga gcctgttcgg catgagcctg aactgcctgg tgctgtgcgg   10440
cccagccaat accggaaagt cctacttcgg catgtccctg aattgtctcg tgatctacgg   10500
cccacctaac acaggcaagt cctgctttgc catgtctctg tggccctacc tgcacagcag   10560
actggtggtg tttaccttcc ccaaccctt ctggcttac ctggaaagcc ggatcaccgt     10620
gttcgagttc cccaatgcct ttctgagata cctgcactcc cggatccacg tgctgcagtt   10680
tctgaaccc ttcaacgtgt gccaggacaa gatcctggaa cactacgaga acgacagcaa    10740
ggacattctg gaacattatg agaatgattc caaggacctg tgcgaccaca tctgcgatca   10800
catcgactac tggaagcaca tccggctgga atgcgccatc atgtacaagg cccggatcag   10860
actggaatgt gctattatgt ataaggctcg cgagatgggc ttccaccagt tcgacggcga   10920
catctgcaac accatgcact acaccaactg gatctatatc tgcgaggacg cccagtgcac   10980
cgtggtggaa ggccaggtgg acaagaaatg ggaggtgcac gctggcggcc aagtgatcct   11040
gtgtcctgag agcggccagc ggcggatcaa gaggcccaga agcgagaact gccacccccaa   11100
caagctgctg atcctgaagt gcctgcggta cagattcaag aagcactgca agctgagcag   11160
cacctggcac tggaccctgcc acgacggcaa gcacaagtgg cattggacat gtcacgatgg   11220
gaaacacaag aacgccattg tgaccctgac ctactacgag gccgacaaga acgacctgaa   11280
cgcccagatc gagcactgga aactgatccg gatggaatgt gcaatcttct ataaggccaa   11340
agagctgggc atcagcatct gccaccaggt ggtgcctcca ctggccgcct ctaaagccaa   11400
agcctgccag gccatcgaac tgcagctggc cctggaagcc ctgaatgcca gcccctacga   11460
tgagtggacc ctgcagcaga ccagcctgga atgtggctg gccgagcccc agtttaagaa    11520
gcacggcatc accatcaccg tgcagtacga caatgacaag gccaatacca tggattacac   11580
aaattggaaa gaaatctacg tgatcgtgtg ccccgccagc atccctccg atgagatcag    11640
caccgaggaa gccgaccaca ttgattattg gaaagccatc aggcaggaaa cgccatctt    11700
cttcgccgcc agacaccagg tggtgcccgc cctgaatatc tgcaaggcca aggcctgtaa   11760
agccatcgag tggaacaccg agcccaagca ctgcttcaag aagggcggcc agcacatcga   11820
agtgtggttc gactacgtgg cctgggacag cgtgtactac tgcggcgacg atggctggtg   11880
caagaccgag gccgagaagt acggctgcaa gggcacctgg gaagtgcatt tcggcaacag   11940
```

```
catcgactgc aacgactcca tgtgcagcac cttcgacgac aacgtgtccg ccaccgagct   12000
cgtgaaggac catatcgact attggaagct gattcgcctg gaatgtgcca tttttttacaa   12060 ggccagacgg cggctgtcca gcgaccagga tcagtctcag ctcgtgacca agtaccccct   12120
gctgaagctg ctgtccagac cccccaacat gggcgtgaag gcccacggca agtgcatctg   12180
ggagaacaag gtgttcatcg tgcccaccct gtgccccgtg cctctggatc aacatatcc   12240 tctgctgaaa ctgctgacca cccagaccac caccccgag aatacctccc tggtggaact   12300
gagagtgacc accccaaga gcacagtcgt gatcaggctg cacctgacca ccagatacc   12360 actgctgtca ctgctgaaca gctacagcac ccccctcac cggatccctg ctccatgtcc   12420
ttgggctcct cagaggcccc ccatccctaa gccttctcca tgggcccta gaatccctgc   12480 cccttgcccc tgggcacctc ctagacctcc acactgtcca tgggtgcccc ctccacctcc   12540
tccaagacct tgggcccctt gcttcctgct gtgcttttgt gtgctgctgt gcgtgtgcct   12600
gctgatcaga cccctgctgc tgagtgtgtc cacctacctg aggcctctgc tgctgtctat   12660
cagcgtgtac gctcaggtgc tggtgctggt gctgctgctg tgggtgtcca tcggaagcct   12720
gctgcccagc gtgtgcatgt gtgcctatgc ctgggtgctg tgttcgtgt acatcgtcgt   12780 gattaccagc cccgccaccg ccatcgtgta ccgggatggc aatccttacg ccgtgtgcga   12840
caagtgcctg aagttctaca gcaagatcag cgagtaccgg cactactgct acagcctgta   12900
cggcaccacc ctggaacagc agtacaacaa gcccctgtgc gatctgctga ttcggtgcat   12960
caacgtggtg tacagagact ccatccccca cgccgcctgc cacaagtgta tcgacttcta   13020
ctccagaatc agagagctgc ggcactacag cgactccgtg tacggcgata ccctggaaaa   13080
gctgaccaac actggcctgt acaacctgct gattagatgc ctgcgggtgt tctgcaagaa   13140
ggccctgaca gccagcgagg tgtacaactt cgcctacacc gatctgcggg tggtgtatcg   13200
ggacagcaaa gtgcggaagc tgaggtacta caactgctct gtgtatggcg ccagcctggt   13260
gtattgcaag gacagctga ccgagacaga ggtgctggat ttcgccttca cagacctgac   13320
aatcgtgtat cgcgactcca aggtgtccga gttccggtgg tacagatatt ccgtgtatgg   13380
caccacactg tgcgtggaat gcaagaaaac cctgcagaga tctgaggtgt acgactgcca   13440
gcggccactg tgtccgcagg aaaagaaaag acacgtggac ctgaacaagc ggttccacac   13500
cctgcacgag tacatgctgg atctgcagcc cgagacaacc gacctgtact gctacgagca   13560
gcctgaaacc actgatctgc actgttatga gcagctggga gacagctccg atgaagagga   13620
cactggcggc ctgatgggga cgaggatga ggacgaagtg gaccatctgc aggaacagcc   13680
ccagcaggct agacgggacg aacagcaccc ttgctatctg atcgagacac agtgctgcag   13740
atgcgaatct ctggtggaag agaacgacga gatcgacggc gtgaaccacc agcatctgcc   13800
cgctagaagg gccgagcctc agagacacac catgctgtgt atgtgctgca agtgcgaggc   13860
cagaatcgcc ggctctggac ctggcgcctc tggcaagcct atccccaatc cactgctggg   13920
cctggactcc acccggacct gataagcggc cgctcgagca tgcatctaga gggccctatt   13980
ctatagtgtc acctaaatgc tagagctcgc tgatcagcct cgactgtgcc ttctagttgc   14040
cagccatctg ttgtttgccc ctcccccgtg ccttccttga ccctggaagg tgccactccc   14100
actgtccttt cctaataaaa tgaggaaatt gcatcgcatt gtctgagtag gtgtcattct   14160
attctggggg gtgggtggg gcaggacagc aagggggagg attgggaaga caatagcagg   14220
catgctgggg atgcggtggg ctctatggct tctgaggcga aaagaaccag ctggggctcg   14280
aggggggatc gatcccgtcg agatatctag acccagcttt cttgtacaaa gtggtgatcg   14340
```

```
attcgacaga tcgcgatcgc agtgagtagt gttctggggc ggggggaggac ctgcatgagg    14400 gccagaatga ctgaaatctg tgcttttctg tgtgttgcag catcatgagc ggaagcggct    14460
cctttgaggg aggggtattc agcccttatc tgacggggcg tctcccctcc tgggcgggag    14520
tgcgtcagaa tgtgatggga tccacggtgg acggccggcc cgtgcagccc gcgaactctt    14580
caaccctgac ctatgcaacc ctgagctctt cgtcggtgga cgcagctgcc gccgcagctg    14640
ctgcatccgc cgccagcgcc gtgcgcggaa tggccatggg cgccggctac tacggcactc    14700
tggtggccaa ctcgagttcc accaataatc ccgccagcct gaacgaggag aagctgctgc    14760
tgctgatggc ccagcttgag gccttgaccc agcgcctggg cgagctgacc cagcaggtgc    14820
ctcagctgca ggagcagacg cgggccgcgg ttgccacggt gaaatccaaa taaaaaatga    14880
atcaataaat aaacggagac ggttgttgat tttaacacag agtctgaatc tttatttgat    14940
ttttcgcgcg cggtaggccc tggaccaccg gtctcgatca ttgagcaccc ggtggatctt    15000
ttccaggacc cggtagaggt gggcttggat gttgaggtac atgggcatga gcccgtcccg    15060
ggggtggagg tagctccatt gcagggcctc gtgctcgggg gtggtgttgt aaatcaccca    15120
gtcatagcag gggcgcaggg cgtggtgttg cacaatatct ttgaggagga gactgatggc    15180
cacgggcagc cctttggtgt aggtgtttac aaatctgttg agctgggagg gatgcatgcg    15240
gggggagatg aggtgcatct tggcctggat cttgagattg gcgatgttac cgcccagatc    15300
ccgcctgggg ttcatgttgt gcaggaccac cagcacggtg tatccggtgc acttggggaa    15360
tttatcatgc aacttggaag ggaaggcgtg aaagaatttg gcgacgccct tgtgtccgcc    15420
caggttttcc atgcactcat ccatgatgat ggcaatgggc ccgtgggcgg cggcctgggc    15480
aaagacgttt cggggtcgg acacatcata gttgtggtcc tgggtgaggt catcataggc    15540
cattttaatg aatttggggc ggagggtgcc ggactggggg acaaaggtac cctcgatccc    15600
gggggcgtag ttcccctcac agatctgcat ctcccaggct ttgagctcag aggggggat    15660 catgtccacc tgcggggcga taaagaacac ggtttccggg cgggggagga tgagctgggc    15720
cgaaagcaag ttccggagca gctgggactt gccgcagccg gtggggccgt aaatgacccc    15780
gatgaccggc tgcaggtggt agttgaggga gagacagctg ccgtcctccc ggaggagggg    15840
ggccacctcg ttcatcatct cgcgcacgtg catgttctcg cgcaccagtt ccgccaggag    15900
gcgctctccc cccagagata ggagctcctg gagcgaggca agttttttca gcggcttgag    15960
tccgtcggcc atgggcattt tggagagggt ctgttgcaag agttccaagc ggtcccagag    16020
ctcggtgatg tgctctacgg catctcgatc cagcagacct cctcgtttcg cgggttggga    16080
cgactgcggg agtagggcac cagacgatgg gcgtccagcg cagccagggt ccggtccttc    16140
cagggccgca gcgtccgcgt cagggtggtc tccgtcacgg tgaagggtg cgcgccggc    16200 tgggcgcttg cgagggtgcg cttcaggctc atccggctgg tcgaaaaccg ctcccgatcg    16260
gcgccctgcg cgtcggccag gtagcaattg accatgagtt cgtagttgag cgcctcggcc    16320
gcgtggcctt tggcgcggag cttacctttg gaagtctgcc cgcaggcggg acagaggagg    16380
gacttgaggg cgtagagctt gggggcgagg aagacggaat cggggcgta ggcgtccgcg    16440 ccgcagtggg cgcagacggt ctcgcactcc acgagccagg tgaggtcggg ctggtcgggg    16500
tcaaaaacca gtttcccgcc gttcttttg atgcgtttct tacctttggt ctccatgagc    16560
tcgtgtcccc gctgggtgac aaagaggctg tccgtgtccc cgtagaccga ctttatgggc    16620
cggtcctcga gcggtgtgcc gcggtcctcc tcgtagagga accccgccca ctccgagacg    16680
```

```
aaagcccggg tccaggccag cacgaaggag gccacgtggg acgggtagcg gtcgttgtcc   16740
accagcgggt ccacttttc cagggtatgc aaacacatgt cccctcgtc cacatccagg    16800 aaggtgattg gcttgtaagt gtaggccacg tgaccggggg tcccggccgg ggggtataa   16860 aagggggcgg gccctgctc gtcctcactg tcttccggat cgctgtccag gagcgccagc   16920
tgttggggta ggtattccct ctcgaaggcg ggcatgacct cggcactcag gttgtcagtt   16980
tctagaaacg aggaggattt gatattgacg gtgccagcgg agatgccttt caagagcccc   17040
tcgtccatct ggtcagaaaa gacgattttt ttgttgtcga gcttggtggc gaaggagccg   17100
tagagggcgt tggaaaggag cttggcgatg gagcgcatgg tctggttttt ttccttgtcg   17160
gcgcgctcct tggccgcgat gttgagctgc acgtactcgc gcgccacgca cttccattcg   17220
gggaagacgg tggtcatctc gtcgggcacg attctgacct gccaacctcg attatgcagg   17280
gtgatgaggt ccacactggt ggccacctcg ccgcgcaggg gctcgttggt ccagcagagg   17340
cggccgccct tgcgcgagca aaggggggc agagggtcca gcatgacctc gtcgggggg    17400 tcggcatcga tggtgaagat gccgggcagg agatcgggt cgaagtagct gatggaagtg    17460
gccagatcgt ccagggaagc ttgccattcg cgcacggcca gcgcgcgctc gtagggactg    17520
aggggcgtgc cccagggcat gggggtggg agcgcgagg cgtacatgcc gcagatgtcg     17580
tagacgtaga ggggctcctc gaggatgccg atgtaggtgg ggtagcagcg ccccccgcgg   17640
atgctggcgc gcacgtagtc atacagctcg tgcgagggcg cgaggagccc cgggcccagg   17700
ttggtgcgac tgggcttttc ggcgcggtag acgatctggc gaaagatggc atgcgagttg   17760
gaggagatgg tgggccttg gaagatgttg aagtgggcgt gggggaggcc gaccgagtcg    17820
cggatgaagt gggcgtagga gtcttgcagt ttggcgacga gctcggcggt gacgaggacg   17880
tccagagcgc agtagtcgag ggtctcctgg atgatgtcat acttgagctg gcccttttgt   17940
ttccacagct cgcggttgag aaggaactct tcgcggtcct tccagtactc ttcgaggggg   18000
aacccgtcct gatctgcacg gtaagagcct agcatgtaga actggttgac ggccttgtag   18060
gcgcagcagc ccttctccac ggggagggcg taggcctggg cggccttgcg cagggaggtg   18120
tgcgtgaggg cgaaggtgtc cctgaccatg accttgagga actggtgctt gaaatcgata   18180
tcgtcgcagc ccccctgctc ccagagctgg aagtccgtgc gcttcttgta ggcggggttg   18240
ggcaaagcga aagtaacatc gttgaaaagg atcttgcccg cgcggggcat aaagttgcga   18300
gtgatgcgga aaggctgggg cacctcggcc cggttgttga tgacctgggc ggcgagcacg   18360
atctcgtcga aaccgttgat gttgtggccc acgatgtaga gttccacgaa tcgcgggcgg   18420
cccttgacgt ggggcagctt cttgagctcc tcgtaggtga gctcgtcggg gtcgctgaga   18480
ccgtgctgct cgagcgccca gtcggcgaga tgggggttgg cgcggaggaa ggaagtccag   18540
agatccacgg ccagggcggt ttgcagacgg tcccggtact gacggaactg ctgcccgacg   18600 gccattttt cgggggtgac gcagtagaag gtgcgggggt ccccgtgcca gcggtcccat   18660
ttgagctgga gggcgagatc gagggcgagc tcgacgaggc ggtcgtcccc tgagagtttc   18720
atgaccagca tgaaggggac gagctgcttg ccgaaggacc ccatccaggt gtaggtttcc   18780
acatcgtagg tgaggaagag cctttcggtg cgaggatgcg agccgatggg gaagaactgg   18840
atctcctgcc accaattgga ggaatggctg ttgatgtgat ggaagtagaa atgccgacgg   18900
cgcgccgaac actcgtgctt gtgtttatac aagcggccac agtgctcgca acgctgcacg   18960
ggatgcacgt gctgcacgag ctgtacctga gttcctttga cgaggaattt cagtgggaag   19020
tggagtcgtg gcgcctgcat ctcgtgctgt actacgtcgt ggtggtcggc ctggccctct   19080
```

```
tctgcctcga tggtggtcat gctgacgagc ccgcgcggga ggcaggtcca gacctcggcg   19140
cgagcgggtc ggagagcgag gacgagggcg cgcaggccgg agctgtccag ggtcctgaga   19200
cgctgcggag tcaggtcagt gggcagcggc ggcgcgcggt tgacttgcag gagttttttcc  19260 agggcgcgcg ggaggtccag atggtacttg atctccaccg cgccgttggt ggcgacgtcg   19320
atggcttgca gggtcccgtg cccctggggt gtgaccaccg tccccgtttt cttcttgggc   19380
ggctggggcg acggggcgg tgcctcttcc atggttagaa gcgcggcga ggacgcgcgc     19440 cgggcggcag aggcggctcg gggcccggag gcaggggcgg caggggcacg tcggcgccgc   19500
gcgcgggtag gttctggtac tgcgcccgga gaagactggc gtgagcgacg acgcgacggt   19560
tgacgtcctg gatctgacgc ctctgggtga aggccacggg acccgtgagt ttgaacctga   19620
aagagagttc gacagaatca atctcggtat cgttgacggc ggcctgccgc aggatctctt   19680
gcacgtcgcc cgagttgtcc tggtaggcga tctcggtcat gaactgctcg atctcctcct   19740
cctgaaggtc tccgcgaccg gcgcgctcca cggtggccgc gaggtcgttg gagatgcggc   19800
ccatgagctg cgagaaggcg ttcatgcccg cctcgttcca gacgcggctg tagaccacga   19860
cgccctcggg atcgcgggcg cgcatgacca cctgggcgag gttgagctcc acgtggcgcg   19920
tgaagaccgc gtagttgcag aggcgctggt agaggtagtt gagcgtggtg gcgatgtgct   19980
cggtgacgaa gaaatacatg atccagcggc ggagcggcat ctcgctgacg tcgcccagcg   20040
cctccaagcg ttccatggcc tcgtaaaagt ccacggcgaa gttgaaaaac tgggagttgc   20100
gcgccgagac ggtcaactcc tcctccagaa gacggatgag ctcggcgatg gtggcgcgca   20160
cctcgcgctc gaaggccccc gggagttcct ccacttcctc ctcttcttcc tcctccacta   20220
acatctcttc tacttcctcc tcaggcggtg gtggtggcgg gggagggggc ctgcgtcgcc   20280
ggcggcgcac gggcagacgg tcgatgaagc gctcgatggt ctcgccgcgc cggcgtcgca   20340
tggtctcggt gacggcgcgc ccgtcctcgc ggggccgcag cgtgaagacg ccgccgcgca   20400
tctccaggtg gccgggggg tccccgttgg gcagggagag ggcgctgacg atgcatctta   20460
tcaattgccc cgtagggact ccgcgcaagg acctgagcgt ctcgagatcc acgggatctg   20520
aaaaccgttg aacgaaggct tcgagccagt cgcagtcgca aggtaggctg agcacggttt   20580
cttctgccgg gtcatgttgg ggagcggggc gggcgatgct gctggtgatg aagttgaaat   20640
aggcggttct gagacggcgg atggtggcga ggagcaccag gtctttgggc ccggcttgct   20700
ggatgcgcag acggtcggcc atgcccagg cgtggtcctg acacctggcc aggtccttgt    20760
agtagtcctg catgagccgc tccacgggca cctcctcctc gcccgcgcgg ccgtgcatgc   20820
gcgtgagccc gaagccgcgc tggggctgga cgagcgccag gtcggcgacg acgcgctcgg   20880
cgaggatggc ctgctggatc tgggtgaggg tggtctggaa gtcgtcaaag tcgacgaagc   20940
ggtggtaggc tccggtgttg atggtgtagg agcagttggc catgacggac cagttgacgg   21000
tctggtggcc cggacgcacg agctcgtggt acttgaggcg cgagtaggcg cgcgtgtcga   21060
agatgtagtc gttgcaggtg cgcaccaggt actggtagcc gatgaggaag tgcggcggcg   21120
gctggcggta gagcggccat cgctcggtgg cgggggcgcc gggcgcgagg tcctcgagca   21180
tggtgcggtg gtagccgtag atgtacctgg acatccaggt gatgccggcg gcggtggtgg   21240
aggcgcgcgg gaactcgcgg acgcggttcc agatgttgcg cagcggcagg aagtagttca   21300
tggtgggcac ggtctggccc gtgaggcgcg cgcagtcgtg gatgctctat acgggcaaaa   21360
acgaaagcgg tcagcggctc gactccgtgg cctggaggct aagcgaacgg gttgggctgc   21420
```

```
gcgtgtaccc cggttcgaat ctcgaatcag gctggagccg cagctaacgt ggtactggca    21480
ctcccgtctc gacccaagcc tgcaccaacc ctccaggata cggaggcggg tcgttttgca    21540 acttttttttg gaggccggaa atgaaactag taagcgcgga aagcggccga ccgcgatggc    21600
tcgctgccgt agtctggaga agaatcgcca gggttgcgtt gcggtgtgcc ccggttcgag    21660
gccggccgga ttccgcggct aacgagggcg tggctgcccc gtcgtttcca agaccccata    21720
gccagccgac ttctccagtt acggagcgag cccctctttt gttttgtttg tttttgccag    21780
atgcatcccg tactgcggca gatgcgcccc caccaccctc caccgcaaca acagccccct    21840
cctccacagc cggcgcttct gccccgcccc cagcagcagc agcaacttcc agccacgacc    21900
gccgcggccg ccgtgagcgg ggctggacag acttctcagt atgatcacct ggccttggaa    21960
gagggcgagg ggctggcgcg cctggggggcg tcgtcgccgg agcggcaccc gcgcgtgcag    22020
atgaaaaggg acgctcgcga ggcctacgtg cccaagcaga acctgttcag agacaggagc    22080
ggcgaggagc ccgaggagat gcgcgcggcc cggttccacg cggggcggga gctgcggcgc    22140
ggcctggacc gaaagagggt gctgagggac gaggatttcg aggcggacga gctgacgggg    22200
atcagccccg cgcgcgcgca cgtggccgcg gccaacctgg tcacggcgta cgagcagacc    22260
gtgaaggagg agagcaactt ccaaaaatcc ttcaacaacc acgtgcgcac cctgatcgcg    22320
cgcgaggagg tgaccctggg cctgatgcac ctgtgggacc tgctggaggc catcgtgcag    22380
aaccccacca gcaagccgct gacgcgcag ctgttcctgg tggtgcagca tagtcggac    22440 aacgaggcgt tcagggaggc gctgctgaat atcaccgagc ccgagggccg ctggctcctg    22500
gacctggtga acattctgca gagcatcgtg gtgcaggagc gcgggctgcc gctgtccgag    22560
aagctggcgg ccatcaactt ctcggtgctg agtctgggca agtactacgc taggaagatc    22620
tacaagaccc cgtacgtgcc catagacaag gaggtgaaga tcgacgggtt ttacatgcgc    22680
atgaccctga aagtgctgac cctgagcgac gatctggggg tgtaccgcaa cgacaggatg    22740
caccgcgcgg tgagcgccag caggcggcgc gagctgagcg accaggagct gatgcacagc    22800
ctgcagcggg ccctgaccgg ggccgggacc gagggggaga gctactttga catgggcgcg    22860
gacctgcact ggcagcccag ccgccggcc ttggaggcgg caggcggtcc cccctacata    22920
gaagaggtgg acgatgaggt ggacgaggag ggcgagtacc tggaagactg atggcgcgac    22980 cgtattttg ctagatgcaa caacagccac ctccctgatcc cgcgatgcgg gcggcgctgc    23040
agagccagcc gtccggcatt aactcctcgg acgattggac ccaggccatg caacgcatca    23100
tggcgctgac gacccgcaac cccgaagcct ttagacagca gccccaggcc aaccggctct    23160
cggccatcct ggaggccgtg gtgccctcgc gctccaaccc cacgcacgag aaggtcctgg    23220
ccatcgtgaa cgcgctggtg gagaacaagg ccatccgcgg cgacgaggcc ggcctggtgt    23280
acaacgcgct gctggagcgc gtggcccgct acaacagcac caacgtgcag accaacctgg    23340
accgcatggt gaccgacgtg cgcgaggccg tgcccagcg cgagcggttc caccgcgagt    23400
ccaacctggg atccatggtg gcgctgaacg ccttcctcag caccccagccc gccaacgtgc    23460 cccggggcca ggaggactac accaacttca tcagcgccct gcgcctgatg gtgaccgagg    23520
tgccccagag cgaggtgtac cagtccggcc cggactactt cttccagacc agtcgccagg    23580
gcttgcagac cgtgaacctg agccaggcgt tcaagaactt gcagggcctg tggggcgtgc    23640
aggccccggt cggggaccgc gcgacggtgt cgagcctgct gacgccgaac tcgcgcctgc    23700
tgctgctgct ggtggccccc ttcacggaca gcggcagcat caaccgcaac tcgtacctgg    23760
gctacctgat taacctgtac cgcgaggcca tcggccaggc gcacgtggac gagcagacct    23820
```

```
accaggagat cacccacgtg agccgcgccc tgggccagga cgacccgggc aatctggaag   23880
ccaccctgaa cttttttgctg accaaccggt cgcagaagat cccgccccag tacacgctca  23940
gcgccgagga ggagcgcatc ctgcgatacg tgcagcagag cgtgggcctg ttcctgatgc   24000
aggaggggc caccccagc gccgcgctcg acatgaccgc gcgcaacatg gagcccagca     24060
tgtacgccag caaccgcccg ttcatcaata aactgatgga ctacttgcat cgggcggccg   24120
ccatgaactc tgactatttc accaacgcca tcctgaatcc ccactggctc ccgccgccgg   24180
ggttctacac gggcgagtac gacatgcccg accccaatga cgggttcctg tgggacgatg   24240
tggacagcag cgtgttctcc ccccgaccgg gtgctaacga gcgcccttg tggaagaagg    24300
aaggcagcga ccgacgcccg tcctcggcgc tgtccggccg cgagggtgct gccgcggcgg   24360
tgcccgagcc cgccagtcct ttcccgagct tgcccttctc gctgaacagt attcgcagca   24420
gcgagctggg caggatcacg cgcccgcgct tgctgggcga ggaggagtac ttgaatgact   24480
cgctgttgag acccgagcgg gagaagaact tccccaataa cgggatagag agcctggtgg   24540
acaagatgag ccgctggaag acgtatgcgc aggagcacag ggacgatccg tcgcaggggg   24600
ccacgagccg gggcagcgcc gcccgtaaac gccggtggca cgacaggcag cggggactga   24660
tgtgggacga tgaggattcc gccgacgaca gcagcgtgtt ggacttgggt gggagtggta   24720
acccgttcgc tcacctgcgc ccccgcatcg ggcgcatgat gtaagagaaa ccgaaaataa   24780
atgatactca ccaaggccat ggcgaccagc gtgcgttcgt ttcttctctg ttgttgtatc   24840
tagtatgatg aggcgtgcgt acccggaggg tcctcctccc tcgtacgaga gcgtgatgca   24900
gcaggcgatg gcggcggcgg cggcgatgca gcccccgctg gaggctcctt acgtgccccc   24960
gcggtacctg gcgcctacgg aggggcggaa cagcattcgt tactcggagc tggcacccct   25020
gtacgatacc acccggttgt acctggtgga caacaagtcg gcggacatcg cctcgctgaa   25080
ctaccagaac gaccacagca acttcctgac caccgtggtg cagaacaatg acttcaccccc 25140
cacggaggcc agcacccaga ccatcaactt tgacgagcgc tcgcggtggg gcggtcagct   25200
gaaaaccatc atgcacacca acatgcccaa cgtgaacgag ttcatgtaca gcaacaagtt   25260
caaggcgcgg gtgatggtct cccgcaagac ccccaacggg gtgacagtga cagatggtag   25320
tcaggatatc ttggagtatg aatgggtgga gtttgagctg cccgaaggca acttctcggt   25380
gaccatgacc atcgacctga tgaacaacgc catcatcgac aattacttgg cggtggggcg   25440
gcagaacggg gtcctggaga gcgatatcgg cgtgaagttc gacactagga acttcaggct   25500
gggctgggac cccgtgaccg agctggtcat gcccgggtg tacaccaacg aggccttcca    25560
ccccgatatt gtcttgctgc ccggctgcgg ggtggacttc accgagagcc gcctcagcaa   25620
cctgctgggc attcgcaaga ggcagccctt ccaggagggc ttccagatca tgtacgagga   25680
tctggagggg gcaacatcc ccgcgctcct ggatgtcgac gcctatgaga aaagcaagga   25740
ggagagcgcc gccgcggcga ctgcagctgt agccaccgcc tctaccgagg tcagggcga   25800
taatttttgcc agccctgcag cagtggcagc ggccgaggcg gctgaaaccg aaagtaagat   25860
agtcattcag ccggtggaga aggatagcaa ggacaggagc tacaacgtgc tgccggacaa   25920
gataaacacc gcctaccgca gctggtacct ggcctacaac tatggcgacc ccgagaaggg   25980
cgtgcgctcc tggacgctgc tcaccacctc ggacgtcacc tgcggcgtgg agcaagtcta   26040
ctggtcgctg cccgacatga tgcaagaccc ggtcaccttc cgctccacgc gtcaagttag   26100
caactacccg gtggtgggcg ccgagctcct gcccgtctac tccaagagct tcttcaacga   26160
```

```
gcaggccgtc tactcgcagc agctgcgcgc cttcacctcg ctcacgcacg tcttcaaccg    26220
cttccccgag aaccagatcc tcgtccgccc gcccgcgccc accattacca ccgtcagtga    26280
aaacgttcct gctctcacag atcacgggac cctgccgctg cgcagcagta tccggggagt    26340
ccagcgcgtg accgttactg acgccagacg ccgcacctgc ccctacgtct acaaggccct    26400
gggcatagtc gcgccgcgcg tcctctcgag ccgcaccttc taaaaaatgt ccattctcat    26460
ctcgcccagt aataacaccg gttggggcct gcgcgcgccc agcaagatgt acggaggcgc    26520
tcgccaacgc tccacgcaac accccgtgcg cgtgcgcggg cacttccgcg ctccctgggg    26580
cgccctcaag ggccgcgtgc ggtcgcgcac caccgtcgac gacgtgatcg accaggtggt    26640
ggccgacgcg cgcaactaca cccccgccgc cgcgcccgtc tccaccgtgg acgccgtcat    26700
cgacagcgtg gtggccgacg cgcgccggta cgcccgcgcc aagagccggc ggcggcgcat    26760
cgcccggcgg caccggagca cccccgccat gcgcgcggcg cgagccttgc tgcgcagggc    26820
caggcgcacg ggacgcaggg ccatgctcag ggcggccaga cgcgcggctt caggcgccag    26880
cgccggcagg acccggagac gcgcggccac ggcgcggca gcgccatcg ccagcatgtc    26940 ccgcccgcgg cgagggaacg tgtactgggt gcgcgacgcc gccaccggtg tgcgcgtgcc    27000
cgtgcgcacc cgccccccctc gcacttgaag atgttcactt cgcgatgttg atgtgtccca    27060
gcggcgagga ggatgtccaa gcgcaaattc aaggaagaga tgctccaggt catcgcgcct    27120
gagatctacg gccccgcggt ggtgaaggag gaaagaaagc cccgcaaaat caagcgggtc    27180
aaaaaggaca aaaaggaaga agatgacgat ctggtggagt ttgtgcgcga gttcgccccc    27240
cggcggcgcg tgcagtggcg cgggcggaaa gtgcacccgg tgctgagacc cggcaccacc    27300
gtggtcttca cgcccggcga gcgctccggc agcgcttcca agcgctccta cgacgaggtg    27360 tacgggacg aggacatcct cgagcaggcg gccgagcgcc tgggcgagtt tgcttacggc    27420
aagcgcagcc gccccgccct gaaggaagag gcggtgtcca tcccgctgga ccacggcaac    27480
cccacgccga gcctcaagcc cgtgaccctg cagcaggtgc tgccgagcgc agcgccgcgc    27540 cggggggttca agcgcgaggg cgaggatctg taccccacca tgcagctgat ggtgcccaag    27600
cgccagaagc tggaagacgt gctggagacc atgaaggtgg accccgacgt gcagcccgag    27660
gtcaaggtgc ggcccatcaa gcaggtggcc ccgggcctgg gcgtgcagac cgtggacatc    27720
aagatcccca cggagcccat ggaaacgcag accgagccca tgatcaagcc cagcaccagc    27780
accatggagg tgcagacgga tccctggatg ccatcggctc ctagccgaag accccggcgc    27840
aagtacggcg cggccagcct gctgatgccc aactacgcgc tgcatccttc catcatcccc    27900
acgccgggct accgcggcac gcgcttctac cgcggtcata caaccagccg ccgccgcaag    27960
accaccaccc gccgccgccg tcgccgcaca gccgctgcat ctaccctgc cgccctggtg    28020 cggagagtgt accgccgcgg ccgcgcgcct ctgacccta cgcgcgcgcg ctaccacccg    28080
agcatcgcca tttaaacttt cgcctgcttt gcagatggcc ctcacatgcc gcctccgcgt    28140
tcccattacg ggctaccgag gaagaaaacc gcgccgtaga aggctggcgg ggaacgggat    28200
gcgtcgccac caccatcggc ggcggcgcgc catcagcaag cggttggggg gaggcttcct    28260
gcccgcgctg atccccatca tcgccgcggc gatcggggcg atccccggca ttgcttccgt    28320
ggcggtgcag gcctctcagc gccactgaga cacttggaaa acatcttgta ataaaccaat    28380
ggactctgac gctcctggtc ctgtgatgtg ttttcgtaga cagatggaag acatcaattt    28440
ttcgtccctg gctccgcgac acggcacgcg gccgttcatg ggcacctgga gcgacatcgg    28500
caccagccaa ctgaacgggg gcgccttcaa ttggagcagt ctctggagcg ggcttaagaa    28560
```

```
tttcgggtcc acgcttaaaa cctatggcag caaggcgtgg aacagcacca cagggcaggc   28620
gctgagggat aagctgaaag agcagaactt ccagcagaag gtggtcgatg ggctcgcctc   28680
gggcatcaac ggggtggtgg acctggccaa ccaggccgtg cagcggcaga tcaacagccg   28740
cctggacccg gtgccgcccg ccggctccgt ggagatgccg caggtggagg aggagctgcc   28800 tccccctggac aagcggggcg agaagcgacc ccgccccgac gcggaggaga cgctgctgac   28860
gcacacggac gagccgcccc cgtacgagga ggcggtgaaa ctgggtctgc ccaccacgcg   28920
gcccatcgcg cccctggcca ccggggtgct gaaacccgaa agtaataagc ccgcgaccct   28980
ggacttgcct cctcccgctt cccgcccctc tacagtggct aagcccctgc cgccggtggc   29040
cgtggcccgc gcgcgacccg ggggctccgc ccgccctcat gcgaactggc agagcactct   29100
gaacagcatc gtgggtctgg gagtgcagag tgtgaagcgc cgccgctgct attaaaccta   29160
ccgtagcgct taacttgctt gtctgtgtgt gtatgtatta tgtcgccgct gtccgccaga   29220
aggaggagtg aagaggcgcg tcgccgagtt gcaagatggc cacccatcg atgctgcccc   29280 agtgggcgta catgcacatc gccggacagg acgcttcgga gtacctgagt ccgggtctgg   29340
tgcagttcgc ccgcgccaca gacacctact tcagtctggg gaacaagttt aggaacccca   29400
cggtggcgcc cacgcacgat gtgaccaccg accgcagcca gcggctgacg ctgcgcttcg   29460
tgcccgtgga ccgcgaggac aacacctact cgtacaaagt gcgctacacg ctggccgtgg   29520
gcgacaaccg cgtgctggac atggccagca cctactttga catccgcggc gtgctggatc   29580
ggggccctag cttcaaaccc tactccggca ccgcctacaa cagcctggct cccaaggggag  29640 cgcccaattc cagccagtgg gagcaaaaaa aggcaggcaa tggtgacact atggaaacac   29700
acacatttgg tgtggcccca atgggcggtg agaatattac aatcgacgga ttacaaattg   29760
gaactgacgc tacagctgat caggataaac caatttatgc tgacaaaaca ttccagcctg   29820
aacctcaagt aggagaagaa aattggcaag aaactgaaag cttttatggc ggtagggctc   29880
ttaaaaaaga cacaagcatg aaaccttgct atggctccta tgctagaccc accaatgtaa   29940
agggaggtca agctaaactt aaagttggag ctgatggagt tcctaccaaa gaatttgaca   30000
tagacctggc tttctttgat actcccggtg gcacagtgaa tggacaagat gagtataaag   30060
cagacattgt catgtatacc gaaaacacgt atctggaaac tccagacacg catgtggtat   30120
acaaaccagg caaggatgat gcaagttctg aaattaacct ggttcagcag tccatgccca   30180
atagacccaa ctatattggg ttcagagaca actttattgg gctcatgtat tacaacagta   30240
ctggcaatat gggggtgctg gctggtcagg cctcacagct gaatgctgtg gtcgacttgc   30300
aagacagaaa caccgagctg tcataccagc tcttgcttga ctctttgggt gacagaaccc   30360
ggtatttcag tatgtggaat caggcggtgg acagttatga tcctgatgtg cgcattattg   30420
aaaaccatgg tgtggaagac gaacttccca actattgctt ccccctggat gggtctggca   30480
ctaatgccgc ttaccaaggt gtgaaagtaa aaaatggtaa cgatggtgat gttgagagcc   30540
aatgggaaaa tgatgatact gtcgcagctc gaaatcaatt atgcaagggc aacattttg    30600 ccatggaaat taacctccaa gccaacctgt ggagaagttt cctctactcg aacgtggccc   30660
tgtacctgcc cgactcttac aagtacacgc cagccaacat caccctgccc accaacacca   30720
acacttatga ttcatgaac gggagagtgg tgcctccctc gctggtggac gcctacatca   30780
acatcggggc gcgctggtcg ctggacccca tggacaacgt caatcccttc aaccaccacc   30840
gcaacgcggg cctgcgctac cgctccatgc tcctgggcaa cgggcgctac gtgcccttcc   30900
```

```
acatccaggt gccccagaaa tttttcgcca tcaagagcct cctgctcctg cccgggtcct  30960
acacctacga gtggaacttc cgcaaggacg tcaacatgat cctgcagagc tccctcggca  31020
acgacctgcg cacggacggg gcctccatct ccttcaccag catcaacctc tacgccacct  31080
tcttccccat ggcgcacaac acggcctcca cgctcgaggc catgctgcgc aacgacacca  31140
acgaccagtc cttcaacgac tacctctcgg cggccaacat gctctacccc atcccggcca  31200
acgccaccaa cgtgcccatc tccatcccct cgcgcaactg gccgccttc cgcggctggt  31260
ccttcacgcg cctcaagacc aaggagacgc cctcgctggg ctccgggttc gaccectact  31320
tcgtctactc gggctccatc ccctacctcg acggcacctt ctacctcaac cacaccttca  31380
agaaggtctc catcaccttc gactcctccg tcagctggcc cggcaacgac cggctcctga  31440
cgcccaacga gttcgaaatc aagcgcaccg tcgacggcga gggatacaac gtggcccagt  31500
gcaacatgac caaggactgg ttcctggtcc agatgctggc ccactacaac atcggctacc  31560
agggcttcta cgtgcccgag ggctacaagg accgcatgta ctccttcttc cgcaacttcc  31620
agcccatgag ccgccaggtg gtggacgagg tcaactacaa ggactaccag gccgtcaccc  31680
tggcctacca gcacaacaac tcgggcttcg tcggctacct cgcgcccacc atgcgccagg  31740
gccagcccta ccccgccaac tacccgtacc cgctcatcgg caagagcgcc gtcaccagcg  31800
tcacccagaa aaagttcctc tgcgacaggg tcatgtggcg catccccttc tccagcaact  31860
tcatgtccat gggcgcgctc accgacctcg gccagaacat gctctatgcc aactccgccc  31920
acgcgctaga catgaatttc gaagtcgacc ccatggatga gtccacccct ctctatgttg  31980
tcttcgaagt cttcgacgtc gtccgagtgc accagcccca ccgcggcgtc atcgaggccg  32040
tctacctgcg cacccccttc tcggccggta acgccaccac ctaaattgct acttgcatga  32100
tggctgagcc cacaggctcc ggcgagcagg agctcagggc catcatccgc gacctgggct  32160
gcgggcccta cttcctgggc accttcgata agcgcttccc gggattcatg gccccgcaca  32220
agctggcctg cgccatcgtc aacacggccg gccgcgagac cgggggcgag cactggctgg  32280
ccttcgcctg gaacccgcgc tcgaacacct gctacctctt cgacccccttc gggttctcgg  32340
acgagcgcct caagcagatc taccagttcg agtacgaggg cctgctgcgc cgtagcgccc  32400
tggccaccga ggaccgctgc gtcaccctgg aaaagtccac ccagaccgtg cagggtccgc  32460
gctcggccgc ctgcgggctc ttctgctgca tgttcctgca cgccttcgtg cactggcccg  32520
accgcccat ggacaagaac cccaccatga acttgctgac ggggggtgccc aacggcatgc  32580
tccagtcgcc ccaggtggaa cccacccctgc gccgcaacca ggaggcgctc taccgcttcc  32640
tcaactccca ctccgcctac tttcgctccc accgcgcgcg catcgagaag gccaccgcct  32700
tcgaccgcat gaacaatcaa gacatgtaaa ccgtgtgtgt atgtttaaaa tatctttttaa  32760
taaacagcac tttaatgtta cacatgcatc tgagatgatt ttattttaga aatcgaaagg  32820
gttctgccgg gtctcggcat ggccgcggg caggacacg ttgcggaact ggtacttggc  32880
cagccacttg aactcgggga tcagcagttt gggcagcggg gtgtcgggga aggagtcggt  32940
ccacagcttc cgcgtcagct gcagggcgcc cagcaggtcg ggcgcggaga tcttgaaatc  33000
gcagttggga cccgcgttct gcgcgcgaga gttgcggtac acggggttgc agcactggaa  33060
caccatcagg gccgggtgct tcacgctcgc cagcaccgcc gcgtcggtga tgctctccac  33120
gtcgaggtcc tcggcgttgg ccatcccgaa gggggtcatc ttgcaggtct gccttcccat  33180
ggtgggcacg cacccgggct tgtggttgca atcgcagtgc agggggatca gcatcatctg  33240
ggcctggtcg gcgttcatcc ccgggtacat ggccttcatg aaagcctcca attgcctgaa  33300
```

```
cgcctgctgg gccttggctc cctcggtgaa gaagacccccg caggacttgc tagagaactg  33360
gttggtggca cagccggcat cgtgcacgca gcagcgcgcg tcgttgttgg ccagctgcac  33420
cacgctgcgc ccccagcggt tctgggtgat cttggcccgg tcggggttct ccttcagcgc  33480
gcgctgcccg ttctcgctcg ccacatccat ctcgatcatg tgctccttct ggatcatggt  33540
ggtcccgtgc aggcaccgca gtttgccctc ggcctcggtg cacccgtgca gccacagcgc  33600
gcacccggtg cactcccagt tcttgtgggc gatctgggaa tgcgcgtgca cgaacccttg  33660
caggaagcgg cccatcatgg tcgtcagggt cttgttgcta gtgaaggtca acgggatgcc  33720
gcggtgctcc tcgttgatgt acaggtggca gatgcggcgg tacacctcgc cctgctcggg  33780
catcagttgg aagttggctt tcaggtcggt ctccacgcgg tagcggtcca tcagcatagt  33840
catgatttcc atgcccttct cccaggccga gacgatgggc aggctcatag ggttcttcac  33900
catcatctta gcactagcag ccgcggccag ggggtcgctc tcatccaggg tctcaaagct  33960
ccgcttgccg tccttctcgg tgatccgcac cgggggggtag ctgaagccca cggccgccag  34020
ctcctcctcg gcctgtcttt cgtcctcgct gtcctggctg acgtcctgca tgaccacatg  34080
cttggtcttg cggggtttct tcttgggcgg cagtggcggc ggagatgctt gtggcgaggg  34140
ggagcgcgag ttctcgctca ccactactat ctcttcctct tcttggtccg aggccacgcg  34200
gcggtaggta tgtctcttcg ggggcagagg cggaggcgac gggctctcgc cgccgcgact  34260
tggcggatgg ctggcagagc cccttccgcg ttcgggggtg cgctcccggc ggcgctctga  34320
ctgacttcct ccgcggccgg ccattgtgtt tcctaggga ggaacaacaa gcatggagac  34380
tcagccatcg ccaacctcgc catctgcccc caccgccggc gacgagaagc agcagcagca  34440
gaatgaaagc ttaaccgccc cgccgccag ccccgcctcc gacgcagccg cggtcccaga  34500
catgcaagag atggaggaat ccatcgagat tgacctgggc tatgtgacgc ccgcggagca  34560
tgaggaggag ctggcagtgc gctttcaatc gtcaagccag gaagataaag aacagccaga  34620
gcaggaagca gagaacgagc agagtcaggc tgggctcgag catggcgact acctccacct  34680
gagcggggag gaggacgcgc tcatcaagca tctggcccgg caggccacca tcgtcaagga  34740
cgcgctgctc gaccgcaccg aggtgcccct cagcgtggag gagctcagcc gcgcctacga  34800
gctcaacctc ttctcgccgc gcgtgccccc caagcgccag cccaacggca cctgcgagcc  34860
caacccccgc ctcaacttct acccggtctt cgcggtgccc gaggccctgg ccacctacca  34920
catctttttc aagaaccaaa agatccccgt ctcctgccgc gccaaccgca cccgcgccga  34980
cgccctcttc aacctgggtc ccggcgcccg cctacctgat atcgcctcct tggaagaggt  35040
tcccaagatc ttcgagggtc tgggcagcga cgagactcgg gccgcgaacg ctctgcaagg  35100
agaaggagga ggagagcatg agcaccacag cgccctggtc gagttggaag cgacaacgc  35160 gcggctggcg gtgctcaaac gcacggtcga gctgacccat ttcgcctacc cggctctgaa  35220
cctgcccccg aaagtcatga gcgcggtcat ggaccaggtg ctcatcaagc gcgcgtcgcc  35280
catctccgag gacgagggca tgcaagactc cgaggagggc aagcccgtgg tcagcgacga  35340
gcagctggcc cggtggctgg gtcctaatgc taccccctcaa agtttggaag agcggcgcaa  35400
gctcatgatg gccgtggtcc tggtgaccgt ggagctggag tgcctgcgcc gcttcttcgc  35460
cgacgcggag accctgcgca aggtcgagga gaacctgcac tacctcttca ggcacgggtt  35520
cgtgcgccag gcctgcaaga tctccaacgt ggagctgacc aacctggtct cctacatggg  35580
catcttgcac gagaaccgcc tggggcagaa cgtgctgcac accaccctgc gcggggaggc  35640
```

```
ccgccgcgac tacatccgcg actgcgtcta cctctacctc tgccacacct ggcagacggg    35700
catgggcgtg tggcagcagt gtctggagga gcagaacctg aaagagctct gcaagctcct    35760
gcaaaagaac ctcaagggtc tgtggaccgg gttcgacgag cggaccaccg cctcggacct    35820
ggccgacctc atcttccccg agcgcctcag gctgacgctg cgcaacggcc tgcccgactt    35880
tatgagccaa agcatgttgc aaaactttcg ctctttcatc ctcgaacgct ccggaatcct    35940
gcccgccacc tgctccgcgc tgccctcgga cttcgtgccg ctgaccttcc gcgagtgccc    36000 ccgccgctg tggagccact gctacctgct gcgcctggcc aactacctgg cctaccactc    36060
ggacgtgatc gaggacgtca gcggcgaggg cctgctcgag tgccactgcc gctgcaacct    36120
ctgcacgccg caccgctccc tggcctgcaa ccccagctg ctgagcgaga cccagatcat    36180
cggcaccttc gagttgcaag ggcccagcga gggcgaggga gccaaggggg gtctgaaact    36240
caccccgggg ctgtggacct cggcctactt gcgcaagttc gtgcccgagg attaccatcc    36300
cttcgagatc aggttctacg aggaccaatc ccagccgccc aaggccgagc tgtcggcctg    36360
cgtcatcacc caggggcga tcctggccca attgcaagcc atccagaaat cccgccaaga    36420
attcttgctg aaaaagggcc gcggggtcta cctcgacccc cagaccggtg aggagctcaa    36480
ccccggcttc ccccaggatg ccccgaggaa acaagaagct gaaagtggag ctgccgcccg    36540
tggaggattt ggaggaagac tgggagaaca gcagtcaggc agaggagatg gaggaagact    36600
gggacagcac tcaggcagag gaggacagcc tgcaagacag tctggaggaa gacgaggagg    36660
aggcagagga ggaggtggaa gaagcagccg ccgccagacc gtcgtcctcg gcgggggaga    36720
aagcaagcag cacggatacc atctccgctc cgggtcgggg tccgctcgg ccccacagta    36780 gatgggacga gaccgggcga ttcccgaacc ccaccaccca gaccggtaag aaggagcggc    36840
agggatacaa gtcctggcgg gggcacaaaa acgccatcgt ctcctgcttg caggcctgcg    36900
ggggcaacat ctccttcacc cggcgctacc tgctcttcca ccgcggggtg aacttccccc    36960
gcaacatctt gcattactac cgtcacctcc acagccccta ctacttccaa gaagaggcag    37020
cagcagcaga aaaagaccag aaaaccagct agaaaatcca cagcggcggc agcggcaggt    37080
ggactgagga tcgcggcgaa cgagccggcg cagacccggg agctgaggaa ccggatcttt    37140 cccacccctct atgccatctt ccagcagagt cgggggcagg agcaggaact gaaagtcaag    37200
aaccgttctc tgcgctcgct caccccgcagt tgtctgtatc acaagagcga agaccaactt    37260
cagcgcactc tcgaggacgc cgaggctctc ttcaacaagt actgcgcgct cactcttaaa    37320
gagtagcccg cgcccgccca gtcgcagaaa aaggcgggaa ttacgtcacc tgtgcccttc    37380
gccctagccg cctccaccca gcaccgccat gagcaaagag attcccacgc cttacatgtg    37440
gagctaccag ccccagatgg gcctggccgc cggcgccgcc caggactact ccacccgcat    37500
gaattggctc agcgccgggc ccgcgatgat ctcacgggtg aatgacatcc gcgcccaccg    37560
aaaccagata ctcctagaac agtcagcgct caccgccacg ccccgcaatc acctcaatcc    37620
gcgtaattgg cccgccgccc tggtgtacca ggaaattccc cagcccacga ccgtactact    37680
tccgcgagac gcccaggccg aagtccagct gactaactca ggtgtccagc tggcgggcgg    37740
cgccaccctg tgtcgtcacc gccccgctca gggtataaag cggctggtga tccggggcag    37800
aggcacacag ctcaacgacg aggtggtgag ctcttcgctg gtctgcgac ctgacggagt    37860 cttccaactc gccggatcgg ggagatcttc cttcacgcct cgtcaggcgg tcctgacttt    37920
ggagagttcg tcctcgcagc cccgctcggg cggcatcggg actctccagt tcgtggagga    37980
gttcactccc tcggtctact tcaaccccett ctccggctcc cccggccact acccggacga    38040
```

```
gttcatcccg aactttgacg ccatcagcga gtcggtggac ggctacgatt gattaattaa    38100
tcaactaacc ccttacccct ttaccctcca gtaaaaataa agattaaaaa tgattgaatt    38160
gatcaataaa gaatcactta cttgaaatct gaaaccaggt ctctgtccat gttttctgtc    38220
agcagcactt cactcccctc ttcccaactc tggtactgca ggccccggcg ggctgcaaac    38280
ttcctccaca ctctgaaggg gatgtcaaat tcctcctgtc cctcaatctt catttttatc    38340
ttctatcaga tgtccaaaaa gcgcgcgcgg gtggatgatg gcttcgaccc cgtgtacccc    38400
tacgatgcag acaacgcacc gactgtgccc ttcatcaacc ctcccttcgt ctcttcagat    38460
ggattccaag aaaagcccct gggggtgttg tccctgcgac tggccgaccc cgtcaccacc    38520
aagaatgggg ctgtcaccct caagctgggg gaggggtgg acctcgacga ctcgggaaaa     38580
ctcatctcca aaaatgccac caaggccact gcccctctca gtatttccaa cggcaccatt    38640
tcccttaaca tggctgcccc ttttacaac aacaatggaa cgttaagtct caatgtttct     38700
acaccattag cagtatttcc cacttttaac actttaggta tcagtcttgg aaacggtctt    38760
caaacttcta ataagttgct gactgtacag ttaactcatc ctcttacatt cagctcaaat    38820
agcatcacag taaaaacaga caaaggactc tatattaatt ctagtggaaa cagagggctt    38880
gaggctaaca taagcctaaa aagaggactg attttgatg gtaatgctat tgcaacatac      38940
cttggaagtg gttagactta tggatcctat gatagcgatg ggaaaacaag acccatcatc    39000
accaaaattg gagcaggttt gaattttgat gctaataatg ccatggctgt gaagctaggc    39060
acaggtttaa gttttgactc tgccggtgcc ttaacagctg gaaacaaaga ggatgacaag    39120
ctaacacttt ggactacacc tgacccaagc cctaattgtc aattactttc agacagagat    39180
gccaaattta ccctatgtct tacaaaatgc ggtagtcaaa tactaggcac tgttgcagta    39240
gctgctgtta ctgtaggttc agcactaaat ccaattaatg acacagtaaa aagcgccata    39300
gtattcctta gatttgactc tgacggtgtg ctcatgtcaa actcatcaat ggtaggtgat    39360
tactggaact ttagggaagg acagaccacc caaagtgtgg cctatacaaa tgctgtggga    39420
ttcatgccca atctaggtgc atatcctaaa acccaaagca aaacaccaaa aaatagtata    39480
gtaagtcagg tatatttaaa tggagaaact actatgccaa tgacactgac aataactttc    39540
aatggcactg atgaaaaaga cacaacacct gtgagcactt actccatgac ttttacatgg    39600
cagtggactg gagactataa ggacaagaat attacctttg ctaccaactc ctttactttc    39660
tcctacatgg cccaagaata aaccctgcat gccaacccca ttgttccac cactatggaa      39720
aactctgaag cagaaaaaaa taagttcaa gtgttttatt gattcaacag ttttctcaca      39780
gaaccctagt attcaacctg ccacctccct cccaacacac agagtacaca gtcctttctc    39840
cccggctggc cttaaaaagc atcatatcat gggtaacaga catattctta ggtgttatat    39900
tccacacggt ttcctgtcga gccaaacgct catcagtgat attaataaac tccccgggca    39960
gctcacttaa gttcatgtcg ctgtccagct gctgagccac aggctgctgt ccaacttgcg    40020
gttgcttaac gggcggcgaa ggagaagtcc acgcctacat gggggtagag tcataatcgt    40080
gcatcaggat agggcggtgg tgctgcagca gcgcgcgaat aaactgctgc cgccgccgct    40140
ccgtcctgca ggaatacaac atggcagtgg tctcctcagc gatgattcgc accgccgca     40200
gcataaggcg ccttgtcctc cgggcacagc agcgcaccct gatctcactt aaatcagcac    40260
agtaactgca gcacagcacc acaatattgt tcaaaatccc acagtgcaag gcgctgtatc    40320
caaagctcat ggcggggacc acagaaccca cgtggccatc ataccacaag cgcaggtaga    40380
```

```
ttaagtggcg accccctcata aacacgctgg acataaacat tacctctttt ggcatgttgt   40440
aattcaccac ctcccggtac catataaacc tctgattaaa catggcgcca tccaccacca   40500
tcctaaacca gctggccaaa acctgcccgc cggctataca ctgcagggaa ccgggactgg   40560
aacaatgaca gtggagagcc caggactcgt aaccatggat catcatgctc gtcatgatat   40620
caatgttggc acaacacagg cacacgtgca tacacttcct caggattaca agctcctccc   40680
gcgttagaac catatcccag ggaacaaccc attcctgaat cagcgtaaat cccacactgc   40740
agggaagacc tcgcacgtaa ctcacgttgt gcattgtcaa agtgttacat tcgggcagca   40800
gcggatgatc ctccagtatg gtagcgcggg tttctgtctc aaaaggaggt agacgatccc   40860
tactgtacgg agtgcgccga gacaaccgag atcgtgttgg tcgtagtgtc atgccaaatg   40920
gaacgccgga cgtagtcata tttcctgaag caaaaccagg tgcgggcgtg acaaacagat   40980
ctgcgtctcc ggtctcgccg cttagatcgc tctgtgtagt agttgtagta tatccactct   41040
ctcaaagcat ccaggcgccc cctggcttcg ggttctatgt aaactccttc atgcgccgct   41100
gccctgataa catccaccac cgcagaataa gccacaccca gccaacctac acattcgttc   41160
tgcgagtcac acacgggagg agcgggaaga gctggaagaa ccatgattaa ctttattcca   41220
aacggtctcg gagcacttca aaatgcaggt cccggaggtg gcacctctcg cccccactgt   41280
gttggtggaa ataacagcc aggtcaaagg tgacacggtt ctcgagatgt tccacggtgg   41340
cttccagcaa agcctccacg cgcacatcca gaaacaagag gacagcgaaa gcgggagcgt   41400
tttctaattc ctcaatcatc atattacact cctgcaccat ccccagataa tttttcatttt   41460
tccagccttg aatgattcgt attagttcct gaggtaaatc caagccagcc atgataaaaa   41520
gctcgcgcag agcgccctcc accggcattc ttaagcacac cctcataatt ccaagagatt   41580
ctgctcctgg ttcacctgca gcagattaac aatgggaata tcaaaatctc tgccgcgatc   41640
cctaagctcc tccctcaaca ataactgtat gtaatctttc atatcatctc gaaattttt   41700
agccataggg ccgccaggaa taagagcagg gcaagccaca ttacagataa agcgaagtcc   41760
tccccagtgw gcattgccaa atgtaagatt gaaataagca tgctggctag accctgtgat   41820
atcttccaga taactggaca gaaaatcagg caagcaattt ttaagaaaat caacaaaaga   41880
aaagtcgtcc aggtgcaggt ttagagcctc aggaacaacg atggaataag tgcaaggagt   41940
gcgttccagc atggttagtg ttttttttggt gatctgtaga acaaaaaata aacatgcaat   42000
attaaaccat gctagcctgg cgaacaggtg ggtaaatcac tctttccagc accaggcagg   42060
ctacggggtc tccggcgcga ccctcgtaga agctgtcgcc atgattgaaa agcatcaccg   42120
agagaccttc ccggtggccg gcatggatga ttcgagaaga agcatacact ccgggaacat   42180
tggcatccgt gagtgaaaaa aagcgaccta taaagcctcg gggcactaca atgctcaatc   42240
tcaattccag caaagccacc ccatgcggat ggagcacaaa attggcaggt gcgtaaaaaa   42300
tgtaattact cccctcctgc acaggcagca agcccccgc tccctccaga aacacataca   42360
aagcctcagc gtccatagct taccgagcac ggcaggcgca agagtcagag aaaaggctga   42420
gctctaacct gactgcccgc tcctgtgctc aatatatagc cctaacctac actgacgtaa   42480
aggccaaagt ctaaaaatac ccgccaaaat gacacacacg cccagcacac gcccagaaac   42540
cggtgacaca ctcaaaaaaa tacgtgcgct tcctcaaacg cccaaaccgg cgtcatttcc   42600
gggttcccac gctacgtcac cgctcagcga ctttcaaatt ccgtcgaccg ttaaaaacgt   42660
cactcgcccc gcccctaacg gtcgcccttc tctcggccaa tcaccttcct cccttcccaa   42720
attcaaacgc ctcatttgca tattaacgcg cacaaaaagt ttgaggtata tatttgaatg   42780
```

```
atg                                                            42783
```

<210> SEQ ID NO 63
<211> LENGTH: 32
<212> TYPE: PRT
<213> ORGANISM: Artificial Sequence
<220> FEATURE:
<223> OTHER INFORMATION: peptide adjuvant

<400> SEQUENCE: 63

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

<210> SEQ ID NO 64
<211> LENGTH: 27
<212> TYPE: PRT
<213> ORGANISM: Artificial Sequence
<220> FEATURE:
<223> OTHER INFORMATION: peptide adjuvant

<400> SEQUENCE: 64

Ser Leu Leu Trp Gly Gly Val Thr Val Leu Ala Ala Met Leu Ile Ala
1               5                   10                  15

Gly Gln Val Ala Ser Ser Val Val Phe Leu Val
            20                  25

<210> SEQ ID NO 65
<211> LENGTH: 3849
<212> TYPE: DNA
<213> ORGANISM: Artificial Sequence
<220> FEATURE:
<223> OTHER INFORMATION: vaccine construct

<400> SEQUENCE: 65

```
gacgaggacg agacagccta cgacagcggc accgacctga tcgacttcat cgacgacagc      60
gacgagaatg agaacgactc cgacaccggc gaggacatgg tggatttcat cgacaacgac     120
gaaaccgacg aagagagcac cgagagcgac ctggacggct ttatcgacaa ctccgcccag     180
ctggctgaca cgacagcaa tgcctgcgcc ttcctgaagg ctcagctggc agacgtgaac     240
agcaacgccg ctgcttttct gaagaactgc atcctgctgt acggcgctgc caacaccggc     300
aagagcctgt tcggcatgag cctgaactgc ctggtgctgt cggcccagc caataccgga     360 aagtcctact tcggcatgtc cctgaattgt tcgtgatct acggcccacc taacacaggc     420
aagtcctgct ttgccatgtc tctgtggccc tacctgcaca gcagactggt ggtgtttacc     480
ttccccaacc ccttctggcc ttacctggaa agccggatca ccgtgttcga gttccccaat     540
gcctttctga gatacctgca ctcccggatc cacgtgctgc agtttctgaa ccccttcaac     600
gtgtgccagg acaagatcct ggaacactac gagaacgaca gcaaggacat tctggaacat     660
tatgagaatg attccaagga cctgtgcgac cacatctgcg atcacatcga ctactggaag     720
cacatccggc tggaatgcgc catcatgtac aaggcccgga tcagactgga atgtgctatt     780
atgtataagg ctcgcgagat gggcttccac cagttcgacg cgacatctg caacaccatg     840 cactacacca actggatcta tatctgcgag gacgcccagt gcaccgtggt ggaaggccag     900
gtggacaaga atgggaggt gcacgctggc ggccaagtga tcctgtgtcc tgagagcggc     960
cagcggcgga tcaagaggcc cagaagcgag aactgccacc ccaacaagct gctgatcctg    1020
```

```
aagtgcctgc ggtacagatt caagaagcac tgcaagctga gcagcacctg gcactggacc    1080
tgccacgacg gcaagcacaa gtggcattgg acatgtcacg atgggaaaca caagaacgcc    1140
attgtgaccc tgacctacta cgaggccgac aagaacgacc tgaacgccca gatcgagcac    1200
tggaaactga tccggatgga atgtgcaatc ttctataagg ccaaagagct gggcatcagc    1260
atctgccacc aggtggtgcc tccactggcc gcctctaaag ccaaagcctg ccaggccatc    1320
gaactgcagc tggccctgga agccctgaat gccagcccct acgatgagtg gaccctgcag    1380
cagaccagcc tggaaatgtg gctggccgag ccccagttta gaagcacgg catcaccatc     1440 accgtgcagt acgacaatga caaggccaat accatggatt acacaaattg aaagaaatc     1500 tacgtgatcg tgtgccccgc cagcatcccc tccgatgaga tcagcaccga ggaagccgac    1560
cacattgatt attggaaagc catcaggcag gaaaacgcca tcttcttcgc cgccagacac    1620
caggtggtgc ccgccctgaa tatctgcaag gccaaggcct gtaaagccat cgagtggaac    1680
accgagccca agcactgctt caagaagggc ggccagcaca tcgaagtgtg gttcgactac    1740
gtggcctggg acagcgtgta ctactgcggc gacgatggc ggtgcaagac cgaggccgag     1800
aagtacggct gcaagggcac ctgggaagtg catttcggca acagcatcga ctgcaacgac    1860
tccatgtgca gcaccttcga cgacaacgtg tccgccaccg agctcgtgaa ggaccatatc    1920
gactattgga agctgattcg cctggaatgt gccatttttt acaaggccag acggcggctg    1980
tccagcgacc aggatcagtc tcagctcgtg accaagtacc ccctgctgaa gctgctgtcc    2040
agacccccca acatgggcgt gaaggcccac ggcaagtgca tctgggagaa caaggtgttc    2100
atcgtgccca ccctgtgccc cgtgcctctg gatccaacat atcctctgct gaaactgctg    2160
accacccaga ccaccacccc cgagaatacc tccctggtgg aactgagagt gaccaccccc    2220
aagagcacag tcgtgatcag gctgcacctg accaccagat acccactgct gtcactgctg    2280
aacagctaca gcacccccc tcaccggatc cctgctccat gtccttgggc tcctcagagg     2340
ccccccatcc ctaagccttc tccatggggc cctagaatcc ctgccccttg cccctgggca    2400
cctcctagac ctccacactg tccatgggtg ccccctccac ctcctccaag accttgggcc    2460
ccttgcttcc tgctgtgctt ttgtgtgctg ctgtgcgtgt gcctgctgat cagacccctg    2520
ctgctgagtg tgtccaccta cctgaggcct ctgctgctgt ctatcagcgt gtacgctcag    2580
gtgctggtgc tggtgctgct gctgtgggtg tccatcggaa gcctgctgcc cagcgtgtgc    2640
atgtgtgcct atgcctgggt gctggtgttc gtgtacatcg tcgtgattac cagccccgcc    2700
accgccatcg tgtaccggga tgcaatcct tacgccgtgt gcgacaagtg cctgaagttc     2760
tacagcaaga tcagcgagta ccggcactac tgctacagcc tgtacggcac caccctggaa    2820
cagcagtaca acaagcccct gtgcgatctg ctgattcggt gcatcaacgt ggtgtacaga    2880
gactccatcc cccacgccgc ctgccacaag tgtatcgact tctactccag aatcagagag    2940
ctgcggcact acagcgactc cgtgtacggc gatacccctgg aaaagctgac caacactggc    3000
ctgtacaacc tgctgattag atgcctgcgg gtgttctgca agaaggccct gacagccagc    3060
gaggtgtaca acttcgccta caccgatctg cgggtggtgt atcgggacag caaagtgcgg    3120
aagctgaggt actacaactg ctctgtgtat ggcgccagcc tggtgtattg caagggacag    3180
ctgaccgaga cagaggtgct ggatttcgcc ttcacagacc tgacaatcgt gtatcgcgac    3240
tccaaggtgt ccgagttccg gtggtacaga tattccgtgt atggcaccac actgtgcgtg    3300
gaatgcaaga aaaccctgca gagatctgag gtgtacgact gccagcggcc actgtgtccg    3360
caggaaaaga aaagacacgt ggacctgaac aagcggttcc acaccctgca cgagtacatg    3420
```

-continued

```
ctggatctgc agcccgagac aaccgacctg tactgctacg agcagcctga aaccactgat    3480
ctgcactgtt atgagcagct gggagacagc tccgatgaag aggacactgg cggcctggat    3540
ggggacgagg atgaggacga agtggaccat ctgcaggaac agccccagca ggctagacgg    3600
gacgaacagc accccttgcta tctgatcgag acacagtgct gcagatgcga atctctggtg    3660
gaagagaacg acgagatcga cggcgtgaac caccagcatc tgcccgctag aagggccgag    3720
cctcagagac acaccatgct gtgtatgtgc tgcaagtgcg aggccagaat cgccggctct    3780
ggacctggcg cctctggcaa gcctatcccc aatccactgc tgggcctgga ctccacccgg    3840
acctgataa                                                              3849
```

<210> SEQ ID NO 66
<211> LENGTH: 1281
<212> TYPE: PRT
<213> ORGANISM: Artificial Sequence
<220> FEATURE:
<223> OTHER INFORMATION: vaccine construct

<400> SEQUENCE: 66

```
Asp Glu Asp Glu Thr Ala Tyr Asp Ser Gly Thr Asp Leu Ile Asp Phe
1               5                   10                  15

Ile Asp Asp Ser Asp Glu Asn Glu Asn Asp Ser Asp Thr Gly Glu Asp
            20                  25                  30

Met Val Asp Phe Ile Asp Asn Asp Glu Thr Asp Glu Glu Ser Thr Glu
        35                  40                  45

Ser Asp Leu Asp Gly Phe Ile Asp Asn Ser Ala Gln Leu Ala Asp Ser
    50                  55                  60

Asp Ser Asn Ala Cys Ala Phe Leu Lys Ala Gln Leu Ala Asp Val Asn
65                  70                  75                  80

Ser Asn Ala Ala Ala Phe Leu Lys Asn Cys Ile Leu Leu Tyr Gly Ala
                85                  90                  95

Ala Asn Thr Gly Lys Ser Leu Phe Gly Met Ser Leu Asn Cys Leu Val
            100                 105                 110

Leu Cys Gly Pro Ala Asn Thr Gly Lys Ser Tyr Phe Gly Met Ser Leu
        115                 120                 125

Asn Cys Leu Val Ile Tyr Gly Pro Asn Thr Gly Lys Ser Cys Phe
    130                 135                 140

Ala Met Ser Leu Trp Pro Tyr Leu His Ser Arg Leu Val Val Phe Thr
145                 150                 155                 160

Phe Pro Asn Pro Phe Trp Pro Tyr Leu Glu Ser Arg Ile Thr Val Phe
                165                 170                 175

Glu Phe Pro Asn Ala Phe Leu Arg Tyr Leu His Ser Arg Ile His Val
            180                 185                 190

Leu Gln Phe Leu Asn Pro Phe Asn Val Cys Gln Asp Lys Ile Leu Glu
        195                 200                 205

His Tyr Glu Asn Asp Ser Lys Asp Ile Leu Glu His Tyr Glu Asn Asp
    210                 215                 220

Ser Lys Asp Leu Cys Asp His Ile Cys Asp His Ile Asp Tyr Trp Lys
225                 230                 235                 240

His Ile Arg Leu Glu Cys Ala Ile Met Tyr Lys Ala Arg Ile Arg Leu
                245                 250                 255

Glu Cys Ala Ile Met Tyr Lys Ala Arg Glu Met Gly Phe His Gln Phe
            260                 265                 270

Asp Gly Asp Ile Cys Asn Thr Met His Tyr Thr Asn Trp Ile Tyr Ile
```

-continued

```
              275                 280                 285
Cys Glu Asp Ala Gln Cys Thr Val Val Glu Gly Gln Val Asp Lys Lys
    290                 295                 300

Trp Glu Val His Ala Gly Gly Gln Val Ile Leu Cys Pro Glu Ser Gly
305                 310                 315                 320

Gln Arg Arg Ile Lys Arg Pro Arg Ser Glu Asn Cys His Pro Asn Lys
                    325                 330                 335

Leu Leu Ile Leu Lys Cys Leu Arg Tyr Arg Phe Lys Lys His Cys Lys
                340                 345                 350

Leu Ser Ser Thr Trp His Trp Thr Cys His Asp Gly Lys His Lys Trp
            355                 360                 365

His Trp Thr Cys His Asp Gly Lys His Lys Asn Ala Ile Val Thr Leu
        370                 375                 380

Thr Tyr Tyr Glu Ala Asp Lys Asn Asp Leu Asn Ala Gln Ile Glu His
385                 390                 395                 400

Trp Lys Leu Ile Arg Met Glu Cys Ala Ile Phe Tyr Lys Ala Lys Glu
                    405                 410                 415

Leu Gly Ile Ser Ile Cys His Gln Val Val Pro Pro Leu Ala Ala Ser
                420                 425                 430

Lys Ala Lys Ala Cys Gln Ala Ile Glu Leu Gln Leu Ala Leu Glu Ala
            435                 440                 445

Leu Asn Ala Ser Pro Tyr Asp Glu Trp Thr Leu Gln Gln Thr Ser Leu
        450                 455                 460

Glu Met Trp Leu Ala Glu Pro Gln Phe Lys Lys His Gly Ile Thr Ile
465                 470                 475                 480

Thr Val Gln Tyr Asp Asn Asp Lys Ala Asn Thr Met Asp Tyr Thr Asn
                    485                 490                 495

Trp Lys Glu Ile Tyr Val Ile Val Cys Pro Ala Ser Ile Pro Ser Asp
                500                 505                 510

Glu Ile Ser Thr Glu Glu Ala Asp His Ile Asp Tyr Trp Lys Ala Ile
            515                 520                 525

Arg Gln Glu Asn Ala Ile Phe Phe Ala Ala Arg His Gln Val Val Pro
        530                 535                 540

Ala Leu Asn Ile Cys Lys Ala Lys Ala Cys Lys Ala Ile Glu Trp Asn
545                 550                 555                 560

Thr Glu Pro Lys His Cys Phe Lys Lys Gly Gly Gln His Ile Glu Val
                    565                 570                 575

Trp Phe Asp Tyr Val Ala Trp Asp Ser Val Tyr Tyr Cys Gly Asp Asp
                580                 585                 590

Gly Trp Cys Lys Thr Glu Ala Glu Lys Tyr Gly Cys Lys Gly Thr Trp
            595                 600                 605

Glu Val His Phe Gly Asn Ser Ile Asp Cys Asn Asp Ser Met Cys Ser
        610                 615                 620

Thr Phe Asp Asp Asn Val Ser Ala Thr Glu Leu Val Lys Asp His Ile
625                 630                 635                 640

Asp Tyr Trp Lys Leu Ile Arg Leu Glu Cys Ala Ile Phe Tyr Lys Ala
                    645                 650                 655

Arg Arg Arg Leu Ser Ser Asp Gln Asp Gln Ser Gln Leu Val Thr Lys
                660                 665                 670

Tyr Pro Leu Leu Lys Leu Leu Ser Arg Pro Pro Asn Met Gly Val Lys
            675                 680                 685

Ala His Gly Lys Cys Ile Trp Glu Asn Lys Val Phe Ile Val Pro Thr
        690                 695                 700
```

-continued

Leu Cys Pro Val Pro Leu Asp Pro Thr Tyr Pro Leu Lys Leu Leu
705                 710                 715                 720

Thr Thr Gln Thr Thr Thr Pro Glu Asn Thr Ser Leu Val Glu Leu Arg
            725                 730                 735

Val Thr Thr Pro Lys Ser Thr Val Val Ile Arg Leu His Leu Thr Thr
                740                 745                 750

Arg Tyr Pro Leu Leu Ser Leu Leu Asn Ser Tyr Ser Thr Pro Pro His
            755                 760                 765

Arg Ile Pro Ala Pro Cys Pro Trp Ala Pro Gln Arg Pro Pro Ile Pro
            770                 775                 780

Lys Pro Ser Pro Trp Ala Pro Arg Ile Pro Ala Pro Cys Pro Trp Ala
785                 790                 795                 800

Pro Pro Arg Pro Pro His Cys Pro Trp Val Pro Pro Pro Pro Pro Pro
                805                 810                 815

Arg Pro Trp Ala Pro Cys Phe Leu Leu Cys Phe Cys Val Leu Leu Cys
                820                 825                 830

Val Cys Leu Leu Ile Arg Pro Leu Leu Leu Ser Val Ser Thr Tyr Leu
                835                 840                 845

Arg Pro Leu Leu Leu Ser Ile Ser Val Tyr Ala Gln Val Leu Val Leu
850                 855                 860

Val Leu Leu Leu Trp Val Ser Ile Gly Ser Leu Leu Pro Ser Val Cys
865                 870                 875                 880

Met Cys Ala Tyr Ala Trp Val Leu Val Phe Val Tyr Ile Val Val Ile
                885                 890                 895

Thr Ser Pro Ala Thr Ala Ile Val Tyr Arg Asp Gly Asn Pro Tyr Ala
                900                 905                 910

Val Cys Asp Lys Cys Leu Lys Phe Tyr Ser Lys Ile Ser Glu Tyr Arg
                915                 920                 925

His Tyr Cys Tyr Ser Leu Tyr Gly Thr Thr Leu Glu Gln Gln Tyr Asn
930                 935                 940

Lys Pro Leu Cys Asp Leu Leu Ile Arg Cys Ile Asn Val Val Tyr Arg
945                 950                 955                 960

Asp Ser Ile Pro His Ala Ala Cys His Lys Cys Ile Asp Phe Tyr Ser
                965                 970                 975

Arg Ile Arg Glu Leu Arg His Tyr Ser Asp Ser Val Tyr Gly Asp Thr
            980                 985                 990

Leu Glu Lys Leu Thr Asn Thr Gly Leu Tyr Asn Leu Leu Ile Arg Cys
            995                 1000                1005

Leu Arg Val Phe Cys Lys Lys Ala Leu Thr Ala Ser Glu Val Tyr
    1010                1015                1020

Asn Phe Ala Tyr Thr Asp Leu Arg Val Val Tyr Arg Asp Ser Lys
    1025                1030                1035

Val Arg Lys Leu Arg Tyr Tyr Asn Cys Ser Val Tyr Gly Ala Ser
    1040                1045                1050

Leu Val Tyr Cys Lys Gly Gln Leu Thr Glu Thr Glu Val Leu Asp
    1055                1060                1065

Phe Ala Phe Thr Asp Leu Thr Ile Val Tyr Arg Asp Ser Lys Val
    1070                1075                1080

Ser Glu Phe Arg Trp Tyr Arg Tyr Ser Val Tyr Gly Thr Thr Leu
    1085                1090                1095

Cys Val Glu Cys Lys Lys Thr Leu Gln Arg Ser Glu Val Tyr Asp
    1100                1105                1110

| Cys | Gln | Arg | Pro | Leu | Cys | Pro | Gln | Glu | Lys | Lys | Arg | His | Val | Asp |
|-----|-----|-----|-----|-----|-----|-----|-----|-----|-----|-----|-----|-----|-----|-----|
| 1115 | | | | | 1120 | | | | | 1125 | | | | |

| Leu | Asn | Lys | Arg | Phe | His | Thr | Leu | His | Glu | Tyr | Met | Leu | Asp | Leu |
|-----|-----|-----|-----|-----|-----|-----|-----|-----|-----|-----|-----|-----|-----|-----|
| 1130 | | | | | 1135 | | | | | 1140 | | | | |

| Gln | Pro | Glu | Thr | Thr | Asp | Leu | Tyr | Cys | Tyr | Gln | Pro | Glu | Thr |
|-----|-----|-----|-----|-----|-----|-----|-----|-----|-----|-----|-----|-----|-----|
| 1145 | | | | | 1150 | | | | | 1155 | | | |

| Thr | Asp | Leu | His | Cys | Tyr | Glu | Gln | Leu | Gly | Asp | Ser | Ser | Asp | Glu |
|-----|-----|-----|-----|-----|-----|-----|-----|-----|-----|-----|-----|-----|-----|-----|
| 1160 | | | | | 1165 | | | | | 1170 | | | | |

| Glu | Asp | Thr | Gly | Gly | Leu | Asp | Gly | Asp | Glu | Asp | Glu | Asp | Glu | Val |
|-----|-----|-----|-----|-----|-----|-----|-----|-----|-----|-----|-----|-----|-----|-----|
| 1175 | | | | | 1180 | | | | | 1185 | | | | |

| Asp | His | Leu | Gln | Glu | Gln | Pro | Gln | Gln | Ala | Arg | Arg | Asp | Glu | Gln |
|-----|-----|-----|-----|-----|-----|-----|-----|-----|-----|-----|-----|-----|-----|-----|
| 1190 | | | | | 1195 | | | | | 1200 | | | | |

| His | Pro | Cys | Tyr | Leu | Ile | Glu | Thr | Gln | Cys | Cys | Arg | Cys | Glu | Ser |
|-----|-----|-----|-----|-----|-----|-----|-----|-----|-----|-----|-----|-----|-----|-----|
| 1205 | | | | | 1210 | | | | | 1215 | | | | |

| Leu | Val | Glu | Glu | Asn | Asp | Glu | Ile | Asp | Gly | Val | Asn | His | Gln | His |
|-----|-----|-----|-----|-----|-----|-----|-----|-----|-----|-----|-----|-----|-----|-----|
| 1220 | | | | | 1225 | | | | | 1230 | | | | |

| Leu | Pro | Ala | Arg | Arg | Ala | Glu | Pro | Gln | Arg | His | Thr | Met | Leu | Cys |
|-----|-----|-----|-----|-----|-----|-----|-----|-----|-----|-----|-----|-----|-----|-----|
| 1235 | | | | | 1240 | | | | | 1245 | | | | |

| Met | Cys | Cys | Lys | Cys | Glu | Ala | Arg | Ile | Ala | Gly | Ser | Gly | Pro | Gly |
|-----|-----|-----|-----|-----|-----|-----|-----|-----|-----|-----|-----|-----|-----|-----|
| 1250 | | | | | 1255 | | | | | 1260 | | | | |

| Ala | Ser | Gly | Lys | Pro | Ile | Pro | Asn | Pro | Leu | Leu | Gly | Leu | Asp | Ser |
|-----|-----|-----|-----|-----|-----|-----|-----|-----|-----|-----|-----|-----|-----|-----|
| 1265 | | | | | 1270 | | | | | 1275 | | | | |

| Thr | Arg | Thr |
|-----|-----|-----|
| 1280 | | |

<210> SEQ ID NO 67
<211> LENGTH: 2661
<212> TYPE: DNA
<213> ORGANISM: Artificial Sequence
<220> FEATURE:
<223> OTHER INFORMATION: viral construct

<400> SEQUENCE: 67

```
ttaattaacc atcttcaata atatacctca aacttttgt gcgcgttaat atgcaaatga      60
ggcgtttgaa tttggggagg aagggcggtg attggtcgag ggatgagcga ccgttagggg     120
cggggcgagt gacgttttga tgacgtggtt gcgaggagga gccagtttgc aagttctcgt     180
gggaaaagtg acgtcaaacg aggtgtggtt tgaacacgga aatactcaat tttcccgcgc     240
tctctgacag gaaatgaggt gtttctgggc ggatgcaagt gaaaacgggc cattttcgcg     300
cgaaaactga atgaggaagt gaaaatctga gtaatttcgc gtttatggca gggaggagta     360
tttgccgagg gccgagtaga cttgaccga ttacgtgggg gtttcgatta ccgtgttttt     420
cacctaaatt tccgcgtacg gtgtcaaagt ccggtgtttt tacgcgatcg ctagcgacat     480
cgatcacaag tttgtacaaa aaagcaggct ccaccatggg aacccgcgtt ttgagatttc     540
tgtcgccgac taaattcatg tcgcgcgata tggtgtttta tcgccgatag agatggcgat     600
attggaaaaa tcgatatttg aaaatatggc atattgaaaa tgtcgccgat gtgagtttct     660
gtgtaactga tatcgccatt tttccaaaag tgattttgg gcatacgcga tatctggcga     720
tagcgcttat atcgtttacg ggggatggcg atagacgact ttggtgactt gggcgattct     780
gtgtgtcgca aatatcgcag tttcgatata ggtgacagac gatatgaggc tatatcgccg     840
atagaggcga catcaagctg gcacatggcc aatgcatatc gatctataca ttgaatcaat     900
attggccatt agccatatta ttcattggtt atatagcata aatcaatatt ggctattggc     960
cattgcatac gttgtatcca tatcataata tgtacattta tattggctca gtccaacat    1020
```

```
taccgccatg ttgacattga ttattgacta gttattaata gtaatcaatt acggggtcat    1080
tagttcatag cccatatatg gagttccgcg ttacataact tacggtaaat ggcccgcctg    1140
gctgaccgcc caacgacccc cgcccattga cgtcaataat gacgtatgtt cccatagtaa    1200
cgccaatagg gactttccat tgacgtcaat gggtggagta tttacggtaa actgcccact    1260
tggcagtaca tcaagtgtat catatgccaa gtacgccccc tattgacgtc aatgacggta    1320
aatggcccgc ctggcattat gcccagtaca tgaccttatg ggactttcct acttggcagt    1380
acatctacgt attagtcatc gctattacca tggtgatgcg gttttggcag tacatcaatg    1440
ggcgtggata gcggtttgac tcacggggat ttccaagtct ccaccccatt gacgtcaatg    1500
ggagtttgtt ttggcaccaa aatcaacggg actttccaaa atgtcgtaac aactccgccc    1560
cattgacgca aatgggcggt aggcgtgtac ggtgggaggt ctatataagc agagctctcc    1620
ctatcagtga tagagatctc cctatcagtg atagagatcg tcgacgagct cgtttagtga    1680
accgtcagat cgcctggaga cgccatccac gctgttttga cctccataga agacaccggg    1740
accgatccag cctccgcggc cgggaacggt gcattggaac gcggattccc cgtgccaaga    1800
gtgacgtaag taccgcctat agagtctata ggcccacccc cttggcttct tatgcatgct    1860
atactgtttt tggcttgggg tctatacacc cccgcttcct catgttatag gtgatggtat    1920
agcttagcct ataggtgtgg gttattgacc attattgacc actcccctat tggtgacgat    1980
actttccatt actaatccat aacatggctc tttgccacaa ctctctttat tggctatatg    2040
ccaatacact gtccttcaga gactgacacg gactctgtat ttttacagga tggggtctca    2100
tttattattt acaaattcac atatacaaca ccaccgtccc cagtgcccgc agttttttatt    2160 aaacataacg tgggatctcc acgcgaatct cgggtacgtg ttccggacat gggctcttct    2220
ccggtagcgg cggagcttct acatccgagc cctgctccca tgcctccagc gactcatggt    2280
cgctcggcag ctccttgctc ctaacagtgg aggccagact taggcacagc acgatgccca    2340
ccaccaccag tgtgccgcac aaggccgtgg cggtagggta tgtgtctgaa aatgagctcg    2400
gggagcgggc ttgcaccgct gacgcatttg gaagacttaa ggcagcggca gaagaagatg    2460
caggcagctg agttgttgtg ttctgataag agtcagaggt aactcccgtt gcggtgctgt    2520
taacggtgga gggcagtgta gtctgagcag tactcgttgc tgccgcgcgc gccaccagac    2580
ataatagctc acagactaac agactgttcc tttccatggg tctttctgc agtcaccgtc    2640 cttgacacga agcttggtac c                                             2661

<210> SEQ ID NO 68
<211> LENGTH: 37490
<212> TYPE: DNA
<213> ORGANISM: Artificial Sequence
<220> FEATURE:
<223> OTHER INFORMATION: viral construct

<400> SEQUENCE: 68
gcggccgctc gagcatgcat ctagagggcc ctattctata gtgtcaccta aatgctagag     60
ctcgctgatc agcctcgact gtgccttcta gttgccagcc atctgttgtt tgcccctccc    120
ccgtgccttc cttgaccctg gaaggtgcca ctcccactgt cctttcctaa taaaatgagg    180
aaattgcatc gcattgtctg agtaggtgtc attctattct ggggggtggg gtggggcagg    240
acagcaaggg ggaggattgg gaagacaata gcaggcatgc tggggatgcg gtgggctcta    300
tggcttctga ggcggaaaga accagctggg gctcgagggg ggatcgatcc cgtcgagata    360
```

```
tctagaccca gctttcttgt acaaagtggt gatcgattcg acagatcgcg atcgcaagtg    420
agtagtgttc tggggcgggg gaggacctgc atgagggcca gaataactga aatctgtgct    480
tttctgtgtg ttgcagcagc atgagcggaa gcggctcctt tgagggaggg gtattcagcc    540
cttatctgac ggggcgtctc ccctcctggg cgggagtgcg tcagaatgtg atgggatcca    600
cggtggacgg ccggcccgtg cagcccgcga actcttcaac cctgacctat gcaaccctga    660
gctcttcgtc gttggacgca gctgccgccg cagctgctgc atctgccgcc agcgccgtgc    720
gcggaatggc catgggcgcc ggctactacg gcactctggt ggccaactcg agttccacca    780
ataatcccgc cagcctgaac gaggagaagc tgttgctgct gatggcccag ctcgaggcct    840
tgacccagcg cctgggcgag ctgacccagc aggtggctca gctgcaggag cagacgcggg    900
ccgcggttgc cacggtgaaa tccaaataaa aatgaatca ataaataaac ggagacggtt    960
gttgatttta acacagagtc tgaatcttta tttgattttt cgcgcgcggt aggccctgga   1020
ccaccggtct cgatcattga gcacccggtg gatcttttcc aggacccggt agaggtgggc   1080
ttggatgttg aggtacatgg gcatgagccc gtcccggggg tggaggtagc tccattgcag   1140
ggcctcgtgc tcgggggtgg tgttgtaaat cacccagtca tagcaggggc gcagggcatg   1200
gtgttgcaca atatctttga ggaggagact gatggccacg gcagcccctt tggtgtaggt   1260
gtttacaaat ctgttgagct gggagggatg catgcggggg gagatgaggt gcatcttggc   1320
ctggatcttg agattggcga tgttaccgcc cagatcccgc ctggggttca tgttgtgcag   1380
gaccaccagc acggtgtatc cggtgcactt ggggaattta tcatgcaact tggaagggaa   1440
ggcgtgaaag aatttggcga cgcctttgtg cccgcccagg ttttccatgc actcatccat   1500
gatgatggcg atgggcccgt gggcggcggc ctgggcaaag acgtttcggg ggtcggacac   1560
atcatagttg tggtcctggg tgaggtcatc ataggccatt ttaatgaatt tggggcggag   1620
ggtgccggac tgggggacaa aggtaccctc gatcccgggg gcgtagttcc cctcacagat   1680
ctgcatctcc caggctttga gctcggaggg ggggatcatg tccacctgcg gggcgataaa   1740
gaacacggtt tccggggcgg gggagatgag ctgggccgaa agcaagttcc ggagcagctg   1800
ggacttgccg cagccggtgg ggccgtagat gaccccgatg accggctgca ggtggtagtt   1860
gagggagaga cagctgccgt cctcccggag gagggggggcc acctcgttca tcatctcgcg   1920
cacgtgcatg ttctcgcgca ccagttccgc caggaggcgc tctcccccca gggataggag   1980
ctcctggagc gaggcgaagt ttttcagcgg cttgagtccg tcggccatgg gcattttgga   2040
gagggtttgt tgcaagagtt ccaggcggtc ccagagctcg gtgatgtgct ctacggcatc   2100
tcgatccagc agacctcctc gtttcgcggg ttgggacggc tgcgggagta gggcaccaga   2160
cgatgggcgt ccagcgcagc cagggtccgg tccttccagg gtcgcagcgt ccgcgtcagg   2220
gtggtctccg tcacggtgaa ggggtgcgcg ccgggctggg cgcttgcgag ggtgcgcttc   2280
aggctcatcc ggctggtcga aaaccgctcc cgatcggcgc cctgcgcgtc ggccaggtag   2340
caattgacca tgagttcgta gttgagcgcc tcggccgcgt ggcctttggc gcggagctta   2400
cctttggaag tctgcccgca ggcgggacag aggagggact tgagggcgta gagcttgggg   2460
gcgaggaaga cggactcggg ggcgtaggcg tccgcgccgc agtgggcgca gacggtctcg   2520
cactccacga gccaggtgag gtcgggctgg tcggggtcaa aaaccagttt cccgccgttc   2580
tttttgatgc gtttcttacc tttggtctcc atgagctcgt gtcccgctg ggtgacaaag   2640 aggctgtccg tgtccccgta gaccgacttt atggccggt cctcgagcgg tgtgccgcgg   2700
tcctcctcgt agaggaaccc cgcccactcc gagacgaaag cccgggtcca ggccagcacg   2760
```

```
aaggaggcca cgtgggacgg gtagcggtcg ttgtccacca gcgggtccac cttttccagg    2820
gtatgcaaac acatgtcccc ctcgtccaca tccaggaagg tgattggctt gtaagtgtag    2880
gccacgtgac cgggggtccc ggccgggggg gtataaaagg gtgcgggtcc ctgctcgtcc    2940
tcactgtctt ccggatcgct gtccaggagc gccagctgtt ggggtaggta ttccctctcg    3000
aaggcgggca tgacctcggc actcaggttg tcagtttcta gaaacgagga ggatttgata    3060
ttgacggtgc cggcggagat gccttttcaag agcccctcgt ccatctggtc agaaaagacg    3120
atctttttgt tgtcgagctt ggtggcgaag gagccgtaga gggcgttgga gaggagcttg    3180
gcgatggagc gcatggtctg gttttttttcc ttgtcggcgc gctccttggc ggcgatgttg    3240
agctgcacgt actcgcgcgc cacgcacttc cattcgggga agacggtggt cagctcgtcg    3300
ggcacgattc tgacctgcca gccccgatta tgcaggggtga tgaggtccac actggtggcc    3360
acctcgccgc gcagggggctc attagtccag cagaggcgtc cgcccttgcg cgagcagaag    3420
gggggcaggg ggtccagcat gacctcgtcg ggggggtcgg catcgatggt gaagatgccg    3480
ggcaggaggt cggggtcaaa gtagctgatg gaagtggcca gatcgtccag ggcagcttgc    3540
cattcgcgca cggccagcgc gcgctcgtag ggactgaggg gcgtgcccca gggcatggga    3600
tgggtaagcg cggaggcgta catgccgcag atgtcgtaga cgtagagggg ctcctcgagg    3660
atgccgatgt aggtggggta gcagcgcccc ccgcggatgc tggcgcgcac gtagtcatac    3720
agctcgtgcg aggggggcgag gagccccggg cccaggttgg tgcgactggg cttttcggcg    3780
cggtagacga tctggcggaa aatggcatgc gagttggagg agatggtggg cctttggaag    3840
atgttgaagt gggcgtgggg cagtccgacc gagtcgcgga tgaagtgggc gtaggagtct    3900
tgcagcttgg cgacgagctc ggcggtgact aggacgtcca gagcgcagta gtcgagggtc    3960
tcctggatga tgtcatactt gagctgtccc ttttgtttcc acagctcgcg gttgagaagg    4020
aactcttcgc ggtccttcca gtactcttcg agggggaacc cgtcctgatc tgcacggtaa    4080
gagcctagca tgtagaactg gttgacggcc ttgtaggcgc agcagcccctt ctccacgggg    4140
agggcgtagg cctgggcggc cttgcgcagg gaggtgtgcg tgagggcgaa agtgtccctg    4200
accatgacct tgaggaactg gtgcttgaag tcgatatcgt cgcagccccc ctgctcccag    4260
agctggaagt ccgtgcgctt cttgtaggcg gggttgggca aagcgaaagt aacatcgttg    4320
aagaggatct tgcccgcgcg gggcataaag ttgcgagtga tgcggaaagg ttggggcacc    4380
tcggcccggt tgttgatgac ctgggcggcg agcacgatct cgtcgaagcc gttgatgttg    4440
tggcccacga tgtagagttc cacgaatcgc ggacggccct tgacgtgggg cagtttcttg    4500
agctcctcgt aggtgagctc gtcggggtcg ctgagcccgt gctgctcgag cgcccagtcg    4560
gcgagatggg ggttggcgcg gaggaaggaa gtccagagat ccacggccag ggcggtttgc    4620
agacggtccc ggtactgacg gaactgctgc ccgacggcca tttttttcggg ggtgacgcag    4680
tagaaggtgc gggggtcccc gtgccagcga tcccatttga gctggagggc gagatcgagg    4740
gcgagctcga cgagccggtc gtccccggag agtttcatga ccagcatgaa ggggacgagc    4800
tgcttgccga aggaccccat ccaggtgtag gtttccacat cgtaggtgag gaagagcctt    4860
tcggtgcgag gatgcgagcc gatggggaag aactggatct cctgccacca attggaggaa    4920
tggctgttga tgtgatggaa gtagaaatgc cgacggcgcg ccgaacactc gtgcttgtgt    4980
ttatacaagc ggccacagtg ctcgcaacgc tgcacgggat gcacgtgctg cacgagctgt    5040
acctgagttc ctttgacgag gaatttcagt gggaagtgga gtcgtggcgc ctgcatctcg    5100
```

```
tgctgtacta cgtcgtggtg gtcggcctgg ccctcttctg cctcgatggt ggtcatgctg    5160
acgagcccgc gcgggaggca ggtccagacc tcggcgcgag cgggtcggag agcgaggacg    5220
agggcgcgca ggccggagct gtccagggtc ctgagacgct gcggagtcag gtcagtgggc    5280
agcggcggcg cgcggttgac ttgcaggagt ttttccaggg cgcgcgggag gtccagatgg    5340
tacttgatct ccaccgcgcc attggtggcg acgtcgatgg cttgcagggt cccgtgcccc    5400
tggggtgtga ccaccgtccc ccgtttcttc ttgggcggct ggggcgacgg gggcggtgcc    5460
tcttccatgg ttagaagcgg cggcgaggac gcgcgccggg cggcaggggc ggctcggggc    5520
ccggaggcag gggcggcagg ggcacgtcgg cgccgcgcgc gggtaggttc tggtactgcg    5580
cccggagaag actggcgtga gcgacgacgc gacggttgac gtcctggatc tgacgcctct    5640
gggtgaaggc cacgggaccc gtgagtttga acctgaaaga gagttcgaca gaatcaatct    5700
cggtatcgtt gacggcggcc tgccgcagga tctcttgcac gtcgcccgag ttgtcctggt    5760
aggcgatctc ggtcatgaac tgctcgatct cctcctcttg aaggtctccg cggccggcgc    5820
gctccacggt ggccgcgagg tcgttggaga tgcggcccat gagctgcgag aaggcgttca    5880
tgcccgcctc gttccagacg cggctgtaga ccacgacgcc ctcgggatcg ccggcgcgca    5940
tgaccacctg ggcgaggttg agctccacgt ggcgcgtgaa gaccgcgtag ttgcagaggc    6000
gctggtagag gtagttgagc gtggtggcga tgtgctcggt gacgaagaaa tacatgatcc    6060
agcggcggag cggcatctcg ctgacgtcgc ccagcgcctc caaacgttcc atggcctcgt    6120
aaaagtccac ggcgaagttg aaaaactggg agttgcgcgc cgagacggtc aactcctcct    6180
ccagaagacg gatgagctcg gcgatggtgg cgcgcacctc gcgctcgaag gcccccggga    6240
gttcctccac ttcctcttct tcctcctcca ctaacatctc ttctacttcc tcctcaggcg    6300
gcagtggtgg cggggagggg ggcctgcgtc gccggcggcg cacgggcaga cggtcgatga    6360
agcgctcgat ggtctcgccg cgccggcgtc gcatggtctc ggtgacggcg cgcccgtcct    6420
cgcggggccg cagcgtgaag acgccgccgc gcatctccag gtggccgggg gggtccccgt    6480
tgggcaggga gagggcgctg acgatgcatc ttatcaattg ccccgtaggg actccgcgca    6540
aggacctgag cgtctcgaga tccacgggat ctgaaaaccg ctgaacgaag gcttcgagcc    6600
agtcgcagtc gcaaggtagg ctgagcacgg tttcttctgg cgggtcatgt tggttgggag    6660
cggggcgggc gatgctgctg gtgatgaagt tgaaataggc ggttctgaga cggcggatgg    6720
tggcgaggag caccaggtct ttgggcccgg cttgctggat gcgcagacgg tcggccatgc    6780
cccaggcgtg gtcctgacac ctggccaggt ccttgtagta gtcctgcatg agccgctcca    6840
cgggcacctc ctcctcgccc gcgcggccgt gcatgcgcgt gagcccgaag ccgcgctggg    6900
gctggacgag cgccaggtcg gcgacgacgc gctcggcgag gatggcttgc tggatctggg    6960
tgagggtggt ctggaagtca tcaaagtcga cgaagcggtg gtaggctccg gtgttgatgg    7020
tgtaggagca gttggccatg acggaccagt tgacggtctg gtggcccgga cgcacgagct    7080
cgtggtactt gaggcgcgag taggcgcgcg tgtcgaagat gtagtcgttg caggtgcgca    7140
ccaggtactg gtagccgatg aggaagtgcg gcggcggctg gcggtagagc ggccatcgct    7200
cggtggcggg ggcgccgggc gcgaggtcct cgagcatggt gcggtggtag ccgtagatgt    7260
acctggacat ccaggtgatg ccggcggcgg tggtggaggc gcgcgggaac tcgcggacgc    7320
ggttccagat gttgcgcagc ggcaggaagt agttcatggt gggcacggtc tggcccgtga    7380
ggcgcgcgca gtcgtggatg ctctatacgg gcaaaaacga aagcggtcag cggctcgact    7440
ccgtggcctg gaggctaagc gaacgggttg ggctgcgcgt gtaccccggt tcgaatctcg    7500
```

```
aatcaggctg gagccgcagc taacgtggta ttggcactcc cgtctcgacc caagcctgca   7560
ccaaccctcc aggatacgga ggcgggtcgt tttgcaactt ttttttggag gccggatgag   7620
actagtaagc gcggaaagcg gccgaccgcg atggctcgct gccgtagtct ggagaagaat   7680
cgccagggtt gcgttgcggt gtgccccggt tcgaggccgg ccggattccg cggctaacga   7740
gggcgtggct gccccgtcgt ttccaagacc ccatagccag ccgacttctc cagttacgga   7800
gcgagcccct cttttgtttt gtttgttttt gccagatgca tcccgtactg cggcagatgc   7860 gccccccacca ccctccaccg caacaacagc cccctccaca gccggcgctt ctgccccgc   7920 cccagcagca acttccagcc acgaccgccg cggccgccgt gagcggggct ggacagagtt   7980
atgatcacca gctggccttg aagagggcg aggggctggc gcgcctgggg gcgtcgtcgc   8040
cggagcggca cccgcgcgtg cagatgaaaa gggacgctcg cgaggcctac gtgcccaagc   8100
agaacctgtt cagagacagg agcggcgagg agcccgagga gatgcgcgcg gcccggttcc   8160
acgcggggcg ggagctgcgg cgcggcctgg accgaaagag ggtgctgagg gacgaggatt   8220
tcgaggcgga cgagctgacg gggatcagcc ccgcgcgcgc gcacgtggcc gcggccaacc   8280
tggtcacggc gtacgagcag accgtgaagg aggagagcaa cttccaaaaa tccttcaaca   8340
accacgtgcg caccctgatc gcgcgcgagg aggtgaccct gggcctgatg cacctgtggg   8400
acctgctgga ggccatcgtg cagaacccca ccagcaagcc gctgacggcg cagctgttcc   8460
tggtggtgca gcatagtcgg gacaacgaag cgttcaggga ggcgctgctg aatatcaccg   8520
agcccgaggg ccgctggctc ctggacctgg tgaacattct gcagagcatc gtggtgcagg   8580
agcgcgggct gccgctgtcc gagaagctgg cggccatcaa cttctcggtg ctgagtttgg   8640
gcaagtacta cgctaggaag atctacaaga ccccgtacgt gcccatagac aaggaggtga   8700
agatcgacgg gttttacatg cgcatgaccc tgaaagtgct gaccctgagc gacgatctgg   8760
gggtgtaccg caacgacagg atgcaccgtg cggtgagcgc cagcaggcgg cgcgagctga   8820
gcgaccagga gctgatgcat agtctgcagc gggccctgac cggggccggg accgaggggg   8880
agagctactt tgacatgggc gcggacctgc actggcagcc cagccgccgg gccttggagg   8940
cggcggcagg accctacgta gaagaggtgg acgatgaggt ggacgaggag ggcgagtacc   9000
tggaagactg atggcgcgac cgtattttg ctagatgcaa caacaacagc cacctcctga   9060
tcccgcgatg cgggcggcgc tgcagagcca gccgtccggc attaactcct cggacgattg   9120
gacccaggcc atgcaacgca tcatggcgct gacgacccgc aaccccgaag cctttagaca   9180
gcagccccag gccaaccggc tctcggccat cctggaggcc gtggtgccct cgcgctccaa   9240
ccccacgcac gagaaggtcc tggccatcgt gaacgcgctg gtggagaaca aggccatccg   9300
cggcgacgag gccggcctgg tgtacaacgc gctgctggag cgcgtggccc gctacaacag   9360
caccaacgtg cagaccaacc tggaccgcat ggtgaccgac gtgcgcgagg ccgtggccca   9420
gcgcgagcgg ttccaccgcg agtccaacct gggatccatg gtggcgctga acgccttcct   9480
cagcacccag cccgccaacg tgccccgggg ccaggaggac tacaccaact tcatcagcgc   9540
cctgcgcctg atggtgaccg aggtgcccca gagcgaggtg taccagtccg ggccggacta   9600
cttcttccag accagtcgcc agggcttgca gaccgtgaac ctgagccagg ctttcaagaa   9660
cttgcagggc ctgtggggcg tgcaggcccc ggtcggggac cgcgcgacgg tgtcgagcct   9720
gctgacgccg aactcgcgcc tgctgctgct gctggtggcc cccttcacgg acagcggcag   9780
catcaaccgc aactcgtacc tgggctacct gattaacctg taccgcgagg ccatcggcca   9840
```

-continued

```
ggcgcacgtg gacgagcaga cctaccagga gatcacccac gtgagccgcg ccctgggcca    9900
ggacgacccg ggcaacctgg aagccaccct gaacttttg ctgaccaacc ggtcgcagaa     9960
gatcccgccc cagtacgcgc tcagcaccga ggaggagcgc atcctgcgtt acgtgcagca   10020
gagcgtgggc ctgttcctga tgcaggaggg ggccaccccc agcgccgcgc tcgacatgac   10080
cgcgcgcaac atggagccca gcatgtacgc cagcaaccgc ccgttcatca ataaactgat   10140
ggactacttg catcgggcgg ccgccatgaa ctctgactat ttcaccaacg ccatcctgaa   10200
tccccactgg ctcccgccgc cggggttcta cacgggcgag tacgacatgc ccgaccccaa   10260
tgacgggttc ctgtgggacg atgtggacag cagcgtgttc tcccccgac cgggtgctaa    10320
cgagcgcccc ttgtggaaga aggaaggcag cgaccgacgc ccgtcctcgg cgctgtccgg   10380
ccgcgagggt gctgccgcgg cggtgcccga ggccgccagt cctttcccga gcttgccctt   10440
ctcgctgaac agtatccgca gcagcgagct gggcaggatc acgcgcccgc gcttgctggg   10500
cgaagaggag tacttgaatg actcgctgtt gagacccgag cgggagaaga acttccccaa   10560
taacgggata gaaagcctgg tggacaagat gagccgctgg aagacgtatg cgcaggagca   10620
cagggacgat ccccgggcgt cgcagggggc cacgagccgg ggcagcgccg cccgtaaacg   10680
ccggtggcac gacaggcagc ggggacagat gtgggacgat gaggactccg ccgacgcag    10740
cagcgtgttg gacttgggtg ggagtggtaa cccgttcgct cacctgcgcc ccgtatcgg    10800
gcgcatgatg taagagaaac cgaaaataaa tgatactcac caaggccatg cgaccagcg   10860
tgcgttcgtt tcttctctgt tgttgttgta tctagtatga tgaggcgtgc gtacccggag   10920
ggtcctcctc cctcgtacga gagcgtgatg cagcaggcga tggcggcggc ggcgatgcag   10980
ccccgctgg aggctcctta cgtgccccg cggtacctgg cgcctacgga ggggcggaac    11040
agcattcgtt actcggagct ggcacccttg tacgatacca cccggttgta cctggtggac   11100
aacaagtcgg cggacatcgc ctcgctgaac taccagaacg accacagcaa cttcctgacc   11160
accgtggtgc agaacaatga cttcacccc acgaggccaa gcacccagac catcaacttt    11220
gacgagcgct cgcggtgggg cggccagctg aaaaccatca tgcacaccaa catgcccaac   11280
gtgaacgagt tcatgtacag caacaagttc aaggcgcggg tgatggtctc ccgcaagacc   11340
cccaatgggg tgacagtgac agaggattat gatggtagtc aggatgagct gaagtatgaa   11400
tgggtggaat ttgagctgcc cgaaggcaac ttctcggtga ccatgaccat cgacctgatg   11460
aacaacgcca tcatcgacaa ttacttggcg gtggggcggc agaacggggt gctggagagc   11520
gacatcggcg tgaagttcga cactaggaac ttcaggctgg gctgggaccc cgtgaccgag   11580
ctggtcatgc ccggggtgta caccaacgag gctttccatc ccgatattgt cttgctgccc   11640
ggctgcgggg tggacttcac cgagagccgc ctcagcaacc tgctgggcat tcgcaagagg   11700
cagcccttcc aggaaggctt ccagatcatg tacgaggatc tggaggggggg caacatcccc   11760
gcgctcctgg atgtcgacgc ctatgagaaa agcaaggagg atgcagcagc tgaagcaact   11820
gcagccgtag ctaccgcctc taccgaggtc aggggcgata attttgcaag cgccgcagca   11880
gtggcagcgg ccgaggcggc tgaaaccgaa agtaagatag tcattcagcc ggtggagaag   11940
gatagcaaga acaggagcta caacgtacta ccggacaaga taaacaccgc ctaccgcagc   12000
tggtacctag cctacaacta tggcgacccc gagaagggcg tgcgctcctg gacgctgctc   12060
accacctcgg acgtcacctg cggcgtggag caagtctact ggtcgctgcc cgacatgatg   12120
caagacccgg tcaccttccg ctccacgcgt caagttagca actacccggt ggtgggcgcc   12180
gagctcctgc ccgtctactc caagagcttc ttcaacgagc aggccgtcta ctcgcagcag   12240
```

```
ctgcgcgcct tcacctcgct tacgcacgtc ttcaaccgct tccccgagaa ccagatcctc   12300
gtccgcccgc ccgcgcccac cattaccacc gtcagtgaaa acgttcctgc tctcacagat   12360
cacgggaccc tgccgctgcg cagcagtatc cggggagtcc agcgcgtgac cgttactgac   12420
gccagacgcc gcacctgccc ctacgtctac aaggccctgg gcatagtcgc gccgcgcgtc   12480
ctctcgagcc gcaccttcta aatgtccatt ctcatctcgc ccagtaataa caccggttgg   12540
ggcctgcgcg cgcccagcaa gatgtacgga ggcgctcgcc aacgtccac gcaacacccc    12600 gtgcgcgtgc gcgggcactt ccgcgctccc tggggcgccc tcaagggccg cgtgcggtcg   12660
cgcaccaccg tcgacgacgt gatcgaccag gtggtggccg acgcgcgcaa ctacaccccc   12720
gccgccgcgc ccgtctccac cgtggacgcc gtcatcgaca gcgtggtggc ggacgcgcgc   12780
cggtacgccc gcgccaagag ccggcggcgg cgcatcgccc ggcggcaccg gagcacccccc   12840 gccatgcgcg cggcgcgagc cttgctgcgc agggccaggc gcacgggacg cagggccatg   12900
ctcagggcgg ccagacgcgc ggcttcaggc gccagcgccg gcaggacccg gagacgcgcg   12960
gccacggcgg cggcagcggc catcgccagc atgtcccgcc cgcggcgagg gaacgtgtac   13020
tgggtgcgcg acgccgccac cggtgtgcgc gtgcccgtgc gcacccgccc ccctcgcact   13080
tgaagatgtt cacttcgcga tgttgatgtg tcccagcggc gaggaggatg tccaagcgca   13140
aattcaagga agagatgctc caggtcatcg cgcctgagat ctacgccct gcggtggtga    13200 aggaggaaag aaagccccgc aaaatcaagc gggtcaaaaa ggacaaaaag gaagaagaaa   13260
gtgatgtgga cggattggtg gagtttgtgc gcgagttcgc ccccggcgg cgcgtgcagt     13320 ggcgcgggcg gaaggtgcaa ccggtgctga gacccggcac caccgtggtc ttcacgcccg   13380
gcgagcgctc cggcaccgct tccaagcgct cctacgacga ggtgtacggg gatgatgata   13440
ttctggagca ggcggccgag cgcctggggcg agtttgctta cggcaagcgc agccgttccg   13500
caccgaagga agaggcggtg tccatcccgc tggaccacgg caaccccacg ccgagcctca   13560
agcccgtgac cttgcagcag gtgctgccga ccgcggcgcc gcgccggggg ttcaagcgcg   13620
agggcgagga tctgtacccc accatgcagc tgatggtgcc caagcgccag aagctggaag   13680
acgtgctgga gaccatgaag gtggacccgg acgtgcagcc cgaggtcaag gtgcggccca   13740
tcaagcaggt ggccccgggc ctgggcgtgc agaccgtgga catcaagatt cccacggagc   13800
ccatggaaac gcagaccgag cccatgatca agcccagcac cagcaccatg gaggtgcaga   13860
cggatccctg gatgccatcg gctcctagtc gaagaccccg gcgcaagtac ggcgcggcca   13920
gcctgctgat gcccaactac gcgctgcatc cttccatcat ccccacgccg ggctaccgcg   13980
gcacgcgctt ctaccgcggt cataccagca gccgccgccg caagaccacc actcgccgcc   14040
gccgtcgccg caccgccgct gcaaccaccc ctgccgccct ggtgcggaga gtgtaccgcc   14100
gcggccgcgc acctctgacc ctgccgcgcg cgcgctacca cccgagcatc gccatttaaa   14160 cttttcgccag ctttgcagat caatggccct cacatgccgc cttcgcgttc ccattacggg   14220
ctaccgagga agaaaaccgc gccgtagaag gctggcgggg aacgggatgc gtcgccacca   14280
ccaccggcgg cggcgcgcca tcagcaagcg gttgggggga ggcttcctgc ccgcgctgat   14340
ccccatcatc gccgcggcga tcgggcgat ccccggcatt gcttccgtgg cggtgcaggc    14400
ctctcagcgc cactgagaca cacttggaaa catcttgtaa taaacccatg gactctgacg   14460
ctcctggtcc tgtgatgtgt tttcgtagac agatggaaga catcaatttt tcgtccctgg   14520
ctccgcgaca cggcacgcgg ccgttcatgg gcacctggag cgacatcggc accagccaac   14580
```

```
tgaacggggg cgccttcaat tggagcagtc tctggagcgg gcttaagaat ttcgggtcca    14640
cgcttaaaac ctatggcagc aaggcgtgga acagcaccac agggcaggcg ctgagggata    14700
agctgaaaga gcagaacttc agcagaagg tggtcgatgg gctcgcctcg ggcatcaacg     14760
gggtggtgga cctggccaac caggccgtgc agcggcagat caacagccgc ctggaccccgg  14820 tgccgcccgc cggctccgtg gagatgccgc aggtggagga ggagctgcct cccctggaca   14880
agcggggcga gaagcgaccc cgccccgatg cggaggagac gctgctgacg cacacggacg   14940
agccgccccc gtacgaggag gcggtgaaac tgggtctgcc caccacgcgg cccatcgcgc   15000
ccctggccac cggggtgctg aaacccgaaa agcccgcgac cctggacttg cctcctcccc   15060
agccttcccg cccctctaca gtggctaagc ccctgccgcc ggtggccgtg gcccgcgcgc   15120
gacccggggg caccgcccgc cctcatgcga actggcagag cactctgaac agcatcgtgg   15180
gtctgggagt gcagagtgtg aagcgccgcc gctgctatta aacctaccgt agcgcttaac   15240
ttgcttgtct gtgtgtgtat gtattatgtc gccgccgccg ctgtccacca gaaggaggag   15300
tgaagaggcg cgtcgccgag ttgcaagatg gccaccccat cgatgctgcc ccagtgggcg   15360
tacatgcaca tcgccggaca ggacgcttcg gagtacctga gtccgggtct ggtgcagttt   15420
gcccgcgcca cagacaccta cttcagtctg gggaacaagt ttaggaaccc cacggtggcg   15480
cccacgcacg atgtgaccac cgaccgcagc cagcggctga cgctgcgctt cgtgcccgtg   15540
gaccgcgagg acaacaccta ctcgtacaaa gtgcgctaca cgctggccgt gggcgacaac   15600
cgcgtgctgg acatggccag cacctacttt gacatccgcg gcgtgctgga tcggggccct   15660
agcttcaaac cctactccgg caccgcctac aacagtctgg cccccaaggg agcacccaac   15720
acttgtcagt ggacatataa agccgatggt gaaactgcca cagaaaaaac ctatacatat   15780
ggaaatgcac ccgtgcaggg cattaacatc acaaaagatg gtattcaact tggaactgac   15840
accgatgatc agccaatcta cgcagataaa acctatcagc ctgaacctca gtgggtgat    15900 gctgaatggc atgacatcac tggtactgat gaaaagtatg gaggcagagc tcttaagcct   15960
gataccaaaa tgaagccttg ttatggttct tttgccaagc ctactaataa agaaggaggt   16020
caggcaaatg tgaaaacagg aacaggcact actaaagaat atgacataga catggctttc   16080
tttgacaaca gaagtgcggc tgctgctggc ctagctccag aaattgtttt gtatactgaa   16140
aatgtggatt tggaaactcc agatacccat attgtataca aagcaggcac agatgacagc   16200
agctcttcta ttaatttggg tcagcaagcc atgcccaaca gacctaacta cattggtttc   16260
agagacaact ttatcgggct catgtactac aacagcactg gcaatatggg ggtgctggcc   16320
ggtcaggctt ctcagctgaa tgctgtggtt gacttgcaag acagaaacac cgagctgtcc   16380
taccagctct tgcttgactc tctgggtgac agaacccggt atttcagtat gtggaatcag   16440
gcggtggaca gctatgatcc tgatgtgcgc attattgaaa atcatggtgt ggaggatgaa   16500
cttcccaact attgttttccc tctggatgct gttggcagaa cagatactta tcagggaatt   16560
aaggctaatg gaactgatca aaccacatgg accaaagatg acagtgtcaa tgatgctaat   16620
gagataggca agggtaatcc attcgccatg gaaatcaaca tccaagccaa cctgtggagg   16680
aacttcctct acgccaacgt ggccctgtac ctgcccgact cttacaagta cacgccggcc   16740
aatgttaccc tgcccaccaa caccaacacc tacgattaca tgaacggccg ggtggtggcg   16800
ccctcgctgg tggactccta catcaacatc ggggcgcgct ggtcgctgga tccatggac    16860 aacgtgaacc ccttcaacca ccaccgcaat gcggggctgc gctaccgctc catgctcctg   16920
ggcaacgggc gctacgtgcc cttccacatc caggtgcccc agaaattttt cgccatcaag   16980
```

```
agcctcctgc tcctgcccgg gtcctacacc tacgagtgga acttccgcaa ggacgtcaac   17040
atgatcctgc agagctccct cggcaacgac ctgcgcacgg acggggcctc catctccttc   17100
accagcatca acctctacgc caccttcttc cccatggcgc acaacacggc ctccacgctc   17160
gaggccatgc tgcgcaacga caccaacgac cagtccttca cgactacct ctcggcggc    17220 aacatgctct accccatccc ggccaacgcc accaacgtgc ccatctccat ccctcgcgc    17280 aactgggccg ccttccgcgg ctggtccttc acgcgtctca agaccaagga gacgccctcg   17340
ctgggctccg ggttcgaccc ctacttcgtc tactcgggct ccatccccta cctcgacggc   17400
accttctacc tcaaccacac cttcaagaag gtctccatca ccttcgactc ctccgtcagc   17460
tggcccggca acgaccggct cctgacgccc aacgagttcg aaatcaagcg caccgtcgac   17520
ggcgagggct acaacgtggc ccagtgcaac atgaccaagg actggttcct ggtccagatg   17580
ctggcccact acaacatcgg ctaccagggc ttctacgtgc ccgagggcta caaggaccgc   17640
atgtactcct tcttccgcaa cttccagccc atgagccgcc aggtggtgga cgaggtcaac   17700
tacaaggact accaggccgt caccctggcc taccagcaca caactcgggg cttcgtcggc   17760
tacctcgcgc ccaccatgcg ccagggccag ccctaccccg ccaactaccc ctacccgctc   17820
atcggcaaga gcgccgtcac cagcgtcacc cagaaaaagt tcctctgcga cagggtcatg   17880
tggcgcatcc ccttctccag caacttcatg tccatgggcg cgctcaccga cctcggccag   17940
aacatgctct atgccaactc cgcccacgcg ctagacatga atttcgaagt cgaccccatg   18000
gatgagtcca cccttctcta tgttgtcttc gaagtcttcg acgtcgtccg agtgcaccag   18060
ccccaccgcg gcgtcatcga ggccgtctac ctgcgcaccc ccttctcggc cggtaacgcc   18120
accacctaag ctcttgcttc ttgcaagcca tggccgcggg ctccggcgag caggagctca   18180
gggccatcat ccgcgacctg gctgcgggc cctacttcct gggcaccttc gataagcgct    18240
tcccgggatt catggccccg cacaagctgg cctgcgccat cgtcaacacg gccggccgcg   18300
agaccggggg cgagcactgg ctggccttcg cctggaaccc gcgctcgaac acctgctacc   18360
tcttcgaccc cttcggggttc tcggacgagc gcctcaagca gatctaccag ttcgagtacg   18420
agggcctgct gcgccgcagc gccctggcca ccgaggaccc ctgcgtcacc ctggaaaagt   18480
ccacccagac cgtgcagggt ccgcgctcgg ccgcctgcgg gctcttctgc tgcatgttcc   18540
tgcacgcctt cgtgcactgg cccgaccgcc ccatggacaa gaaccccacc atgaacttgc   18600 tgacggggt gcccaacggc atgctccagt cgccccaggt ggaacccacc ctgcgccgca    18660
accaggaggc gctctaccgc ttcctcaact cccactccgc ctactttcgc tcccaccgcg   18720
cgcgcatcga gaaggccacc gccttcgacc gcatgaatca agacatgtaa accgtgtgtg   18780
tatgttaaat gtctttaata aacagcactt tcatgttaca catgcatctg agatgattta   18840
tttagaaatc gaaagggttc tgccgggtct cggcatggcc cgcgggcagg gacacgttgc   18900
ggaactggta cttggccagc cacttgaact cggggatcag cagtttgggc agcggggtgt   18960
cggggaagga gtcggtccac agcttccgcg tcagttgcag ggcgcccagc aggtcgggcg   19020
cggagatctt gaaatcgcag ttgggacccg cgttctgcgc gcgggagttg cggtacacgg   19080
ggttgcagca ctggaacacc atcagggccg ggtgcttcac gctcgccagc accgtcgcgt   19140
cggtgatgct ctccacgtcg aggtcctcgg cgttggccat cccgaagggg gtcatcttgc   19200
aggtctgcct tccatggtg ggcacgcacc cgggcttgtg gttgcaatcg cagtgcaggg   19260
ggatcagcat catctgggcc tggtcggcgt tcatccccgg gtacatggcc ttcatgaaag   19320
```

```
cctccaattg cctgaacgcc tgctgggcct tggctccctc ggtgaagaag accccgcagg    19380
acttgctaga gaactggttg gtggcgcacc cggcgtcgtg cacgcagcag cgcgcgtcgt    19440
tgttggccag ctgcaccacg ctgcgccccc agcggttctg ggtgatcttg gcccggtcgg    19500
ggttctcctt cagcgcgcgc tgcccgttct cgctcgccac atccatctcg atcatgtgct    19560
ccttctggat catggtggtc ccgtgcaggc accgcagctt gccctcggcc tcggtgcacc    19620
cgtgcagcca cagcgcgcac ccggtgcact cccagttctt gtgggcgatc tgggaatgcg    19680
cgtgcacgaa gccctgcagg aagcggccca tcatggtggt cagggtcttg ttgctagtga    19740
aggtcagcgg aatgccgcgg tgctcctcgt tgatgtacag gtggcagatg cggcggtaca    19800
cctcgccctg ctcgggcatc agctggaagt tggctttcag gtcggtctcc acgcggtagc    19860
ggtccatcag catagtcatg atttccatac ccttctccca ggccgagacg atgggcaggc    19920
tcatagggtt cttcaccatc atcttagcgc tagcagccgc ggccaggggg tcgctctcgt    19980
ccagggtctc aaagctccgc ttgccgtcct tctcggtgat ccgcaccggg ggtagctga    20040 agcccacggc cgccagctcc tcctcggcct gtctttcgtc ctcgctgtcc tggctgacgt    20100
cctgcaggac cacatgcttg gtcttgcggg gtttcttctt gggcggcagc ggcggcggag    20160
atgttggaga tggcgagggg gagcgcgagt tctcgctcac cactactatc tcttcctctt    20220
cttggtccga ggccacgcgg cggtaggtat gtctcttcgg gggcagaggc ggaggcgacg    20280
ggctctcgcc gccgcgactt ggcggatggc tggcagagcc ccttccgcgt tcgggggtgc    20340
gctcccggcg gcgctctgac tgacttcctc cgcggccggc cattgtgttc tcctagggag    20400
gaacaacaag catggagact cagccatcgc caacctcgcc atctgccccc accgccgacg    20460
agaagcagca gcagcagaat gaaagcttaa ccgccccgcc gcccagcccc gccacctccg    20520
acgcggccgt cccagacatg caagagatgg aggaatccat cgagattgac ctgggctatg    20580
tgacgcccgc ggagcacgag gaggagctgg cagtgcgctt ttcacaagaa gagatacacc    20640
aagaacagcc agagcaggaa gcagagaatg agcagagtca ggctgggctc gagcatgacg    20700
gcgactacct ccacctgagc ggggggggagg acgcgctcat caagcatctg gcccggcagg    20760
ccaccatcgt caaggatgcg ctgctcgacc gcaccgaggt gccctcagc gtggaggagc    20820 tcagccgcgc ctacgagttg aacctcttct cgccgcgcgt gccccccaag cgccagccca    20880
atggcacctg cgagcccaac ccgcgcctca acttctaccc ggtcttcgcg gtgcccgagg    20940
ccctggccac ctaccacatc ttttttcaaga accaaaagat ccccgtctcc tgccgcgcca    21000
accgcacccg cgccgacgcc ctttttcaacc tgggtcccgg cgcccgccta cctgatatcg    21060
cctccttgga agaggttccc aagatcttcg agggtctggg cagcgacgag actcgggccg    21120
cgaacgctct gcaaggagaa ggaggagagc atgagcacca cagcgccctg gtcgagttgg    21180
aaggcgacaa cgcgcggctg gcggtgctca aacgcacggt cgagctgacc catttcgcct    21240
acccggctct gaacctgccc cccaaagtca tgagcgcggt catggaccag gtgctcatca    21300
agcgcgcgtc gcccatctcc gaggacgagg gcatgcaaga ctccgaggag ggcaagcccg    21360
tggtcagcga cgagcagctg gcccggtggc tgggtcctaa tgctagtccc cagagtttgg    21420
aagagcggcg caaactcatg atggccgtgg tcctggtgac cgtggagctg gagtgcctgc    21480
gccgcttctt cgccgacgcg gagaccctgc gcaaggtcga ggagaacctg cactacctct    21540
tcaggcacgg gttcgtgcgc caggcctgca agatctccaa cgtggagctg accaacctgg    21600
tctcctacat gggcatcttg cacgagaacc gcctggggca gaacgtgctg cacaccaccg    21660
tgcgcgggga ggcccggcgc gactacatcc gcgactgcgt ctacctctac ctctgccaca    21720
```

```
cctggcagac gggcatgggc gtgtggcagc agtgtctgga ggagcagaac ctgaaagagc   21780
tctgcaagct cctgcagaag aacctcaagg gtctgtggac cgggttcgac gagcgcacca   21840
ccgcctcgga cctggccgac ctcatttttcc ccgagcgcct caggctgacg ctgcgcaacg   21900
gcctgcccga ctttatgagc caaagcatgt tgcaaaactt tcgctctttc atcctcgaac   21960
gctccggaat cctgcccgcc acctgctccg cgctgccctc ggacttcgtg ccgctgacct   22020
tccgcgagtg cccccccgccg ctgtggagcc actgctacct gctgcgcctg gccaactacc   22080
tggcctacca ctcggacgtg atcgaggacg tcagcggcga gggcctgctc gagtgccact   22140
gccgctgcaa cctctgcacg ccgcaccgct ccctggcctg caaccccag ctgctgagcg   22200 agacccagat catcggcacc ttcgagttgc aagggcccag cgaaggcgag ggttcagccg   22260
ccaagggggg tctgaaactc accccggggc tgtggacctc ggcctacttg cgcaagttcg   22320
tgcccgagga ctaccatccc ttcgagatca ggttctacga ggaccaatcc catccgccca   22380
aggccgagct gtcggcctgc gtcatcaccc agggggcgat cctggcccaa ttgcaagcca   22440
tccagaaatc ccgccaagaa ttcttgctga aaaagggccg cggggtctac ctcgaccccc   22500
agaccggtga ggagctcaac cccggcttcc cccaggatgc cccgaggaaa caagaagctg   22560
aaagtggagc tgccgcccgt ggaggatttg gaggaagact gggagaacag cagtcaggca   22620
gaggaggagg agatggagga agactgggac agcactcagg cagaggagga cagcctgcaa   22680
gacagtctgg aggaagacga ggaggaggca gaggaggagg tggaagaagc agccgccgcc   22740
agaccgtcgt cctcggcggg ggagaaagca agcagcacgg ataccatctc cgctccgggt   22800
cggggtcccg ctcgaccaca cagtagatgg gacgagaccg gacgattccc gaaccccacc   22860
acccagaccg gtaagaagga gcggcaggga tacaagtcct ggcggggggca caaaaacgcc   22920 atcgtctcct gcttgcaggc ctgcggggggc aacatctcct tcacccggcg ctacctgctc   22980
ttccaccgcg gggtgaactt tccccgcaac atcttgcatt actaccgtca cctccacagc   23040
ccctactact tccaagaaga ggcagcagca gcagaaaaag accagcagaa aaccagcagc   23100
tagaaaatcc acagcggcgg cagcaggtgg actgaggatc gcggcgaacg agccggcgca   23160
aacccgggag ctgaggaacc ggatcttttcc caccctctat gccatcttcc agcagagtcg   23220
ggggcaggag caggaactga aagtcaagaa ccgttctctg cgctcgctca cccgcagttg   23280
tctgtatcac aagagcgaag accaacttca gcgcactctc gaggacgccg aggctctctt   23340
caacaagtac tgcgcgctca ctcttaaaga gtagcccgcg cccgcccagt cgcagaaaaa   23400
ggcgggaatt acgtcacctg tgcccttcgc cctagccgcc tccacccatc atcatgagca   23460
aagagattcc cacgccttac atgtggagct accagcccca gatgggcctg ccgccggtg   23520 ccgcccagga ctactccacc cgcatgaatt ggctcagcgc cgggcccgcg atgatctcac   23580
gggtgaatga catccgcgcc caccgaaacc agatactcct agaacagtca gcgctcaccg   23640
ccacgccccg caatcacctc aatccgcgta attggcccgc cgcccggtg taccaggaaa   23700 ttccccagcc cacgaccgta ctacttccgc gagacgccca ggccgaagtc cagctgacta   23760
actcaggtgt ccagctggcg ggcggcgcca cctgtgtcg tcaccgcccc gctcagggta   23820
taaagcggct ggtgatccgg ggcagaggca cacagctcaa cgacgaggtg gtgagctctt   23880
cgctgggtct gcgacctgac ggagtcttcc aactcgccgg atcgggggaga tcttccttca   23940 cgcctcgtca ggccgtcctg actttggaga gttcgtcctc gcagcccgc tcgggtggca   24000 tcggcactct ccagttcgtg gaggagttca ctccctcggt ctacttcaac cccttctccg   24060
```

| | |
|---|---|
| gctcccccgg ccactacccg gacgagttca tcccgaactt cgacgccatc agcgagtcgg | 24120 |
| tggacggcta cgattgagtt taaactcacc cccttatcca gtgaaataaa gatcatattg | 24180 |
| atgatgattt tacagaaata aaaaataatc atttgatttg aaataaagat acaatcatat | 24240 |
| tgatgatttg agtttaacaa aaaaataaag aatcacttac ttgaaatctg ataccaggtc | 24300 |
| tctgtccatg ttttctgcca acaccacttc actcccctct tcccagctct ggtactgcag | 24360 |
| gccccggcgg gctgcaaact tcctccacac gctgaagggg atgtcaaatt cctcctgtcc | 24420 |
| ctcaatcttc attttatctt ctatcagatg tccaaaaagc gcgtccgggt ggatgatgac | 24480 |
| ttcgaccccg tctaccccta cgatgcagac aacgcaccga ccgtgcccct catcaacccc | 24540 |
| cccttcgtct cttcagatgg attccaagag aagcccctgg gggtgttgtc cctgcgactg | 24600 |
| gccgaccccg tcaccaccaa gaacggggaa atcaccctca agctgggaga gggggtggac | 24660 |
| ctcgattcct cgggaaaact catctccaac acggccacca aggccgccgc ccctctcagt | 24720 |
| ttttccaaca acaccatttc ccttaacatg gatcaccect tttacactaa agatggaaaa | 24780 |
| ttatccttac aagtttctcc accattaaat atactgagaa caagcattct aaacacacta | 24840 |
| gctttaggtt ttggatcagg tttaggactc cgtggctctg ccttggcagt acagttagtc | 24900 |
| tctccactta catttgatac tgatggaaac ataaagctta ccttagacag aggtttgcat | 24960 |
| gttacaacag gagatgcaat tgaaagcaac ataagctggg ctaaaggttt aaaatttgaa | 25020 |
| gatggagcca tagcaaccaa cattggaaat gggttagagt ttggaagcag tagtacagaa | 25080 |
| acaggtgttg atgatgctta cccaatccaa gttaaacttg gatctggcct tagctttgac | 25140 |
| agtacaggag ccataatggc tggtaacaaa gaagacgata aactcacttt gtggacaaca | 25200 |
| cctgatccat caccaaactg tcaaatactc gcagaaaatg atgcaaaact aacactttgc | 25260 |
| ttgactaaat gtggtagtca aatactggcc actgtgtcag tcttagttgt aggaagtgga | 25320 |
| aacctaaacc ccattactgg caccgtaagc agtgctcagg tgtttctacg ttttgatgca | 25380 |
| aacggtgttc ttttaacaga acattctaca ctaaaaaaat actgggggta taggcaggga | 25440 |
| gatagcatag atggcactcc atataccaat gctgtaggat tcatgcccaa tttaaaagct | 25500 |
| tatccaaagt cacaaagttc tactactaaa aataatatag tagggcaagt atacatgaat | 25560 |
| ggagatgttt caaaacctat gcttctcact ataaccctca atggtactga tgacagcaac | 25620 |
| agtacatatt caatgtcatt ttcatacacc tggactaatg gaagctatgt tggagcaaca | 25680 |
| tttgggggcta actcttatac cttctcatac atcgcccaag aatgaacact gtatcccacc | 25740 |
| ctgcatgcca acccttccca ccccactctg tggaacaaac tctgaaacac aaaataaaat | 25800 |
| aaagttcaag tgttttattg attcaacagt ttcacagaac cctagtattc aacctgccac | 25860 |
| ctccctccca acacacagag tacacagtcc tttctccccg gctggcctta aaaagcatca | 25920 |
| tatcatgggt aacagacata ttcttaggtg ttatattcca cacggtttcc tgtcgagcca | 25980 |
| aacgctcatc agtgatatta ataaactccc cgggcagctc acttaagttc atgtcgctgt | 26040 |
| ccagctgctg agccacaggc tgctgtccaa cttgcggttg cttaacgggc ggcgaaggag | 26100 |
| aagtccacgc ctacatgggg gtagagtcat aatcgtgcat caggataggg cggtggtgct | 26160 |
| gcagcagcgc gcgaataaac tgctgccgcc gccgctccgt cctgcaggaa tacaacatgg | 26220 |
| cagtggtctc ctcagcgatg attcgcaccg cccgcagcat aaggcgcctt gtcctccggg | 26280 |
| cacagcagcg cacccctgatc tcacttaaat cagcacagta actgcagcac agcaccacaa | 26340 |
| tattgttcaa aatcccacag tgcaaggcgc tgtatccaaa gctcatggcg gggaccacag | 26400 |
| aacccacgtg gccatcatac cacaagcgca ggtagattaa gtggcgaccc ctcataaaca | 26460 |

```
cgctggacat aaacattacc tcttttggca tgttgtaatt caccacctcc cggtaccata   26520
taaacctctg attaaacatg gcgccatcca ccaccatcct aaaccagctg gccaaaacct   26580
gcccgccggc tatacactgc agggaaccgg gactggaaca atgacagtgg agagcccagg   26640
actcgtaacc atggatcatc atgctcgtca tgatatcaat gttggcacaa cacaggcaca   26700
cgtgcataca cttcctcagg attacaagct cctcccgcgt tagaaccata tcccagggaa   26760
caacccattc ctgaatcagc gtaaatccca cactgcaggg aagacctcgc acgtaactca   26820
cgttgtgcat tgtcaaagtg ttacattcgg gcagcagcgg atgatcctcc agtatggtag   26880
cgcgggtttc tgtctcaaaa ggaggtagac gatccctact gtacggagtg cgccgagaca   26940
accgagatcg tgttggtcgt agtgtcatgc caaatggaac gccggacgta gtcatatttc   27000
ctgaagcaaa accaggtgcg ggcgtgacaa acagatctgc gtctccggtc tcgccgctta   27060
gatcgctctg tgtagtagtt gtagtatatc cactctctca aagcatccag gcgccccctg   27120
gcttcgggtt ctatgtaaac tccttcatgc gccgctgccc tgataacatc caccaccgca   27180
gaataagcca cacccagcca acctacacat tcgttctgcg agtcacacac gggaggagcg   27240
ggaagagctg gaagaaccat gattaacttt attccaaacg gtctcggagc acttcaaaat   27300
gcaggtcccg gaggtggcac ctctcgcccc cactgtgttg gtggaaaata acagccaggt   27360
caaaggtgac acggttctcg agatgttcca cggtggcttc cagcaaagcc tccacgcgca   27420
catccagaaa caagaggaca gcgaaagcgg gagcgttttc taattcctca atcatcatat   27480
tacactcctg caccatcccc agataatttt cattttttcca gccttgaatg attcgtatta   27540
gttcctgagg taaatccaag ccagccatga taaaaagctc gcgcagagcg ccctccaccg   27600
gcattcttaa gcacaccctc ataattccaa gagattctgc tcctggttca cctgcagcag   27660
attaacaatg ggaatatcaa aatctctgcc gcgatcccta agctcctccc tcaacaataa   27720
ctgtatgtaa tctttcatat catctccgaa atttttagcc ataggccgc caggaataag   27780
agcagggcaa gccacattac agataaagcg aagtcctccc cagtgwgcat tgccaaatgt   27840
aagattgaaa taagcatgct ggctagaccc tgtgatatct tccagataac tggacagaaa   27900
atcaggcaag caatttttaa gaaaatcaac aaaagaaaag tcgtccaggt gcaggtttag   27960
agcctcagga acaacgatgg aataagtgca aggagtgcgt tccagcatgg ttagtgtttt   28020
tttggtgatc tgtagaacaa aaaataaaca tgcaatatta aaccatgcta gcctggcgaa   28080
caggtgggta aatcactctt tccagcacca ggcaggctac ggggtctccg gcgcgaccct   28140
cgtagaagct gtcgccatga ttgaaaagca tcaccgagag accttcccgg tggccggcat   28200
ggatgattcg agaagaagca tacactccgg gaacattggc atccgtgagt gaaaaaaagc   28260
gacctataaa gcctcgggc actacaatgc tcaatctcaa ttccagcaaa gccacccat   28320
gcggatggag cacaaaattg gcaggtgcgt aaaaaatgta attactcccc tcctgcacag   28380
gcagcaaagc ccccgctccc tccagaaaca catacaaagc ctcagcgtcc atagcttacc   28440
gagcacggca ggcgcaagag tcagagaaaa ggctgagctc taacctgact gcccgctcct   28500
gtgctcaata tatagcccta acctacactg acgtaaaggc caaagtctaa aaatacccgc   28560
caaataatca cacacgccca gcacacgccc agaaaccggt gacacactca aaaaaatacg   28620
cgcacttcct caaacgccca aaactgccgt catttccggg ttcccacgct acgtcatcaa   28680
aacacgactt tcaaattccg tcgaccgtta aaaacgtcac ccgccccgcc cctaacggtc   28740
gcccgtctct cagccaatca gcgccccgca tccccaaatt caaacacctc atttgcatat   28800
```

```
taacgcgcac aaaaagtttg aggtatatta ttgatgatgg ttaattaagg atccttctat    28860
agtgtcacct aaatgtcgac ggccaggcgg ccgccaggcc tacccactag tcaattcggg    28920
aggatcgaaa cggcagatcg caaaaaacag tacatacaga aggagacatg aacatgaaca    28980
tcaaaaaaat tgtaaaacaa gccacagttc tgacttttac gactgcactt ctggcaggag    29040
gagcgactca agccttcgcg aaagaaaata accaaaaagc atacaaagaa acgtacggcg    29100
tctctcatat tacacgccat gatatgctgc agatccctaa acagcagcaa aacgaaaaat    29160
accaagtgcc tcaattcgat caatcaacga ttaaaaatat tgagtctgca aaaggacttg    29220
atgtgtggga cagctggccg ctgcaaaacg ctgacggaac agtagctgaa tacaacggct    29280
atcacgttgt gtttgctctt gcgggaagcc cgaaagacgc tgatgacaca tcaatctaca    29340
tgttttatca aaaggtcggc gacaactcaa tcgacagctg gaaaaacgcg ggccgtgtct    29400
ttaaagacag cgataagttc gacgccaacg atccgatcct gaaagatcag acgcaagaat    29460
ggtccggttc tgcaaccttt acatctgacg gaaaaatccg tttattctac actgactatt    29520
ccggtaaaca ttacggcaaa caaagcctga acagcgcga gtaaatgtg tcaaaatctg      29580
atgacacact caaaatcaac ggagtggaag atcacaaaac gattttgac ggagacggaa      29640
aaacatatca gaacgttcag cagttatcg atgaaggcaa ttatacatcc ggcgacaacc    29700
atacgctgag agaccctcac tacgttgaag acaaaggcca taaataccctt gtattcgaag   29760
ccaacacggg aacagaaaac ggataccaag gcgaagaatc tttatttaac aaagcgtact    29820
acggcggcgg cacgaacttc ttccgtaaag aaagccagaa gcttcagcag agcgctaaaa    29880
aacgcgatgc tgagttagcg aacggcgccc tcggtatcat agagttaaat aatgattaca    29940
cattgaaaaa agtaatgaag ccgctgatca cttcaaacac ggtaactgat gaaatcgagc    30000
gcgcgaatgt tttcaaaatg aacggcaaat ggtacttgtt cactgattca cgcggttcaa    30060
aaatgacgat cgatggtatt aactcaaacg atatttacat gcttggttat gtatcaaact    30120
ctttaaccgg cccttacaag ccgctgaaca aaacagggct tgtgctgcaa atgggtcttg    30180
atccaaacga tgtgacattc acttactctc acttcgcagt gccgcaagcc aaaggcaaca    30240
atgtggttat cacaagctac atgacaaaca gaggcttctt cgaggataaa aaggcaacat    30300
ttgcgccaag cttcttaatg aacatcaaag gcaataaaac atccgttgtc aaaaacagca    30360
tcctggagca aggacagctg acagtcaact aataacagca aaaagaaaat gccgatactt    30420
cattggcatt ttctttatt tctcaacaag atggtgaatt gactagtggg tagatccaca    30480
ggacgggtgt ggtcgccatg atcgcgtagt cgatagtggc tccaagtagc gaagcgagca    30540
ggactgggcg gcggccaaag cggtcggaca gtgctccgag aacgggtgcg catagaaatt    30600
gcatcaacgc atatagcgct agcagcacgc catagtgact ggcgatgctg tcggaatgga    30660
cgatatcccg caagaggccc ggcagtaccg gcataaccaa gcctatgcct acagcatcca    30720
gggtgacggt gccgaggatg acgatgagcg cattgttaga tttcatacac ggtgcctgac    30780
tgcgttagca atttaactgt gataaactac cgcattaaag cttatcgatg ataagctgtc    30840
aaacatgaga attgatccgg aacccttaat ataacttcgt ataatgtatg ctatacgaag    30900
ttattaggtc cctcgactat agggtcaccg tcgacagcga cacacttgca tcggatgcag    30960
cccggttaac gtgccggcac ggcctgggta accaggtatt ttgtccacat aaccgtgcgc    31020
aaaatgttgt ggataagcag gacacagcag caatccacag caggcataca accgcacacc    31080
gaggttactc cgttctacag gttacgacga catgtcaata cttgcccttg acaggcattg    31140
atggaatcgt agtctcacgc tgatagtctg atcgacaata caagtgggac cgtggtccca    31200
```

```
gaccgataat cagaccgaca acacgagtgg gatcgtggtc ccagactaat aatcagaccg    31260
acgatacgag tgggaccgtg gtcccagact aataatcaga ccgacgatac gagtgggacc    31320
gtggttccag actaataatc agaccgacga tacgagtggg accgtggtcc cagactaata    31380
atcagaccga cgatacgagt gggaccatgg tcccagacta ataatcagac cgacgatacg    31440
agtgggaccg tggtcccagt ctgattatca gaccgacgat acgagtggga ccgtggtccc    31500
agactaataa tcagaccgac gatacgagtg gaccgtggt cccagactaa taatcagacc    31560
gacgatacga gtgggaccgt ggtcccagtc tgattatcag accgacgata caagtggaac    31620
agtgggccca gagagaatat tcaggccagt tatgctttct ggcctgtaac aaaggacatt    31680
aagtaaagac agataaacgt agactaaaac gtggtcgcat cagggtgctg gcttttcaag    31740
ttccttaaga atggcctcaa tttttctctat acactcagtt ggaacacgag acctgtccag    31800
gttaagcacc attttatcgc ccttatacaa tactgtcgct ccaggagcaa actgatgtcg    31860
tgagcttaaa ctagttcttg atgcagatga cgttttaagc acagaagtta aaagagtgat    31920
aacttcttca gcttcaaata tcaccccagc ttttttctgc tcatgaaggt tagatgcctg    31980
ctgcttaagt aattcctctt tatctgtaaa ggcttttga agtgcatcac ctgaccgggc    32040
agatagttca ccggggtgag aaaaaagagc aacaactgat ttaggcaatt tggcggtgtt    32100
gatacagcgg gtaataatct tacgtgaaat attttccgca tcagccagcg cagaaatatt    32160
tccagcaaat tcattctgca atcggcttgc ataacgctga ccacgttcat aagcacttgt    32220
tgggcgataa tcgttaccca atctggataa tgcagccatc tgctcatcat ccagctcgcc    32280
aaccagaaca cgataatcac tttcggtaag tgcagcagct ttacgacggc gactcccatc    32340
ggcaatttct atgacaccag atactcttcg accgaacgcc ggtgtctgtt gaccagtcag    32400
tagaaaagaa gggatgagat catccagtgc gtcctcagta agcagctcct ggtcacgttc    32460
attacctgac catacccgag aggtcttctc aacactatca ccccggagca cttcaagagt    32520
aaacttcaca tcccgaccac atacaggcaa agtaatggca ttaccgcgag ccattactcc    32580
tacgcgcgca attaacgaat ccaccatcgg ggcagctggt gtcgataacg aagtatcttc    32640
aaccggttga gtattgagcg tatgttttgg aataacaggc gcacgcttca ttatctaatc    32700
tcccagcgtg gtttaatcag acgatcgaaa atttcattgc agacaggttc ccaaatagaa    32760
agagcatttc tccaggcacc agttgaagag cgttgatcaa tggcctgttc aaaaacagtt    32820
ctcatccgga tctgaccttt accaacttca tccgtttcac gtacaacatt ttttagaacc    32880
atgcttcccc aggcatcccg aatttgctcc tccatccacg gggactgaga gccattacta    32940
ttgctgtatt tggtaagcaa aatacgtaca tcaggctcga accctttaag atcaacgttc    33000
ttgagcagat cacgaagcat atcgaaaaac tgcagtgcgg aggtgtagtc aaacaactca    33060
gcaggcgtgg gaacaatcag cacatcagca gcacatacga cattaatcgt gccgataccc    33120
aggttaggcg cgctgtcaat aactatgaca tcatagtcat gagcaacagt ttcaatggcc    33180
agtcggagca tcaggtgtgg atcggtgggc agtttaccttcatcaaattt gcccattaac    33240 tcagtttcaa tacggtgcag agccagacag gaaggaataa tgtcaagccc cggccagcaa    33300
gtgggcttta ttgcataagt gacatcgtcc ttttccccaa gatagaaagg caggagagtg    33360
tcttctgcat gaatatgaag atctggtacc catccgtgat acattgaggc tgttccctgg    33420
gggtcgttac cttccacgag caaaacacgt agccccttca gagccagatc ctgagcaaga    33480
tgaacagaaa ctgaggtttt gtaaacgcca cctttatggg cagcaacccc gatcaccggt    33540
```

```
ggaaatacgt cttcagcacg tcgcaatcgc gtaccaaaca catcacgcat atgattaatt   33600
tgttcaattg tataaccaac acgttgctca acccgtcctc gaatttccat atccgggtgc   33660
ggtagtcgcc ctgctttctc ggcatctctg atagcctgag aagaaacccc aactaaatcc   33720
gctgcttcac ctattctcca gcgccgggtt attttcctcg cttccgggct gtcatcatta   33780
aactgtgcaa tggcgatagc cttcgtcatt tcatgaccag cgtttatgca ctggttaagt   33840
gtttccatga gtttcattct gaacatcctt taatcattgc tttgcgtttt tttattaaat   33900
cttgcaattt actgcaaagc aacaacaaaa tcgcaaagtc atcaaaaaac cgcaaagttg   33960
tttaaaataa gagcaacact acaaaaggag ataagaagag cacatacctc agtcacttat   34020
tatcactagc gctcgccgca gccgtgtaac cgagcatagc gagcgaactg gcgaggaagc   34080
aaagaagaac tgttctgtca gatagctctt acgctcagcg caagaagaaa tatccaccgt   34140
gggaaaaact ccaggtagag gtacacacgc ggatagccaa ttcagagtaa taaactgtga   34200
taatcaaccc tcatcaatga tgacgaacta acccccgata tcaggtcaca tgacgaaggg   34260
aaagagaagg aaatcaactg tgacaaactg ccctcaaatt tggcttcctt aaaaattaca   34320
gttcaaaaag tatgagaaaa tccatgcagg ctgaaggaaa cagcaaaact gtgacaaatt   34380
accctcagta ggtcagaaca aatgtgacga accacccctca aatctgtgac agataaccct   34440
cagactatcc tgtcgtcatg gaagtgatat cgcggaagga aaatacgata tgagtcgtct   34500
ggcggccttt ctttttctca atgtatgaga ggcgcattgg agttctgctg ttgatctcat   34560
taacacagac ctgcaggaag cggcggcgga agtcaggcat acgctggtaa ctttgaggca   34620
gctggtaacg ctctatgatc cagtcgattt tcagagagac gatgcctgag ccatccggct   34680
tacgatactg acacagggat tcgtataaac gcatggcata cggattggtg atttcttttg   34740
tttcactaag ccgaaactgc gtaaaccggt tctgtaaccc gataaagaag ggaatgagat   34800
atgggttgat atgtacactg taaagccctc tggatggact gtgcgcacgt ttgataaacc   34860
aaggaaaaga ttcatagcct ttttcatcgc cggcatcctc ttcagggcga taaaaaacca   34920
cttccttccc cgcgaaactc ttcaatgcct gccgtatatc cttactggct tccgcagagg   34980
tcaatccgaa tatttcagca tatttagcaa catggatctc gcagataccg tcatgttcct   35040
gtagggtgcc atcagatttt ctgatctggt caacgaacag atacagcata cgttttgat   35100 cccgggagag actatatgcc gcctcagtga ggtcgtttga ctggacgatt cgcgggctat   35160
ttttacgttt cttgtgattg ataaccgctg tttccgccat gacagatcca tgtgaagtgt   35220
gacaagtttt tagattgtca cactaaataa aaaagagtca ataagcaggg ataactttgt   35280
gaaaaaacag cttcttctga gggcaatttg tcacagggtt aagggcaatt tgtcacagac   35340
aggactgtca tttgagggtg atttgtcaca ctgaaagggc aatttgtcac aacaccttct   35400
ctagaaccag catggataaa ggcctacaag gcgctctaaa aagaagatc taaaaactat   35460 aaaaaaaata attataaaaa tatccccgtg gataagtgga taaccccaag ggaagttttt   35520
tcaggcatcg tgtgtaagca gaatatataa gtgctgttcc ctggtgcttc ctcgctcact   35580
cgagggcttc gccctgtcgc tcaactgcgg cgagcactac tggctgtaaa aggacagacc   35640
acatcatggt tctgtgttca ttaggttgtt ctgtccattg ctgacataat ccgctccact   35700
tcaacgtaac accgcacgaa gatttctatt gttcctgaag gcatattcaa atcgttttcg   35760
ttaccgcttg caggcatcat gacagaacac tacttcctat aaacgctaca caggctcctg   35820
agattaataa tgcggatctc tacgatatg ggagattttc ccgactgttt cgttcgcttc   35880
tcagtggata acagccagct tctctgttta acagacaaaa acagcatatc cactcagttc   35940
```

```
cacatttcca tataaaggcc aaggcattta ttctcaggat aattgtttca gcatcgcaac   36000
cgcatcagac tccggcatcg caaactgcac ccggtgccgg gcagccacat ccagcgcaaa   36060
aaccttcgtg tagacttccg ttgaactgat ggacttatgt cccatcaggc tttgcagaac   36120
tttcagcggt ataccggcat acagcatgtg catcgcatag gaatggcgga acgtatgtgg   36180
tgtgaccgga acagagaacg tcacaccgtc agcagcagcg gcggcaaccg cctccccaat   36240
ccaggtcctg accgttctgt ccgtcacttc ccagatccgc gctttctctg tccttcctgt   36300
gcgacggtta cgccgctcca tgagcttatc gcgaataaat acctgtgacg gaagatcact   36360
tcgcagaata aataaatcct ggtgtccctg ttgataccgg gaagccctgg gccaactttt   36420
ggcgaaaatg agacgttgat cggcacgtaa gaggttccaa ctttcaccat aatgaaataa   36480
gatcactacc gggcgtattt tttgagttat cgagattttc aggagctaag gaagctaaaa   36540
tggagaaaaa aatcactgga tataccaccg ttgatatatc ccaatggcat cgtaaagaac   36600
attttgaggc atttcagtca gttgctcaat gtacctataa ccagaccgtt cagctggata   36660
ttacggcctt tttaaagacc gtaaagaaaa ataagcacaa gttttatccg gcctttattc   36720
acattcttgc ccgcctgatg aatgctcatc cggagttccg tatggcaatg aaagacggtg   36780
agctggtgat atgggatagt gttcacccct tgttacaccg ttttccatga gcaaactgaaa  36840 cgttttcatc gctctggagt gaataccacg acgatttccg gcagtttcta cacatatatt   36900
cgcaagatgt ggcgtgttac ggtgaaaacc tggcctattt ccctaaaggg tttattgaga   36960
atatgttttt cgtctcagcc aatccctggg tgagtttcac cagttttgat ttaaacgtgg   37020
ccaatatgga caacttcttc gcccccgttt tcaccatggg caaatattat acgcaaggcg   37080
acaaggtgct gatgccgctg gcgattcagg ttcatcatgc cgtttgtgat ggcttccatg   37140
tcggcagaat gcttaatgaa ttacaacagt actgcgatga gtggcagggc ggggcgtaat   37200
ttttttaagg cagttattgg tgcccttaaa cgcctggttg ctacgcctga taagtgata   37260 ataagcggat gaatggcaga aattcgatga taagctgtca acatgagaa ttggtcgacg   37320 gcgcgccaaa gcttgcatgc ctgcagccgc gtaacctggc aaaatcggtt acggttgagt   37380
aataaatgga tgccctgcgt aagcggggca catttcatta cctctttctc cgcacccgac   37440
atagataata acttcgtata gtatacatta tacgaagtta tctagtagac                37490
```

<210> SEQ ID NO 69
<211> LENGTH: 143055
<212> TYPE: DNA
<213> ORGANISM: Artificial Sequence
<220> FEATURE:
<223> OTHER INFORMATION: viral construct

<400> SEQUENCE: 69

```
tatttattta gtgtctagaa aaaatgtgt gaccaacgac cgtaggaaac tctagagggt     60
aagaaaaatc aatcgcttta tagagaccat cagaaagagg tttaatatttt ttgtgagacc    120 atcgaaggag aaagagataa aacttttttta cgactccatc agaaagaggt ttaatatttt    180
tgtgagacca tcgaagagag aaagagataa aacttttttta cgactccatc agaaagaggt    240
ttaatatttt tgtgagacca tcgaagagag aaagagataa aacttttttta cgactccatc    300 agaaagaggt ttaatatttt tgtgagacca tcgaaggaga aagagataaa acttttttac    360
gactccatca gaaagaggtt taatatttt tgtgagaccat cgaaggagaa agagataaaa    420
cttttttacg actccatcag aaagaggttt aatatttttg tgagaccatc gaaggagaaa    480
```

```
gagataaaac ttttttacga ctccatcaga aagaggttta atattttgt gagaccatcg    540
aagagagaaa gagataaaac ttttttacga ctccatcaga aagaggttta atattttgt    600
gagaccatcg aaggagaaag agataaaact ttttacgac tccatcagaa agaggtttaa    660
tattttgtg agaccatcga agagagaaag agaataaaaa tattttagtg acaccatcag    720
aaagaggttt aatattttg tgagaccatc gaagagagaa agagataaaa cttttttacg    780
actccatcag aaagaggttt aatattttg tgagaccatc gaaggagaaa gagataaaac    840
ttttttacga ctccatcaga aagaggttta atattttgt gagaccatcg aagagagaaa    900
gagataaaac ttttttacga ctccatcaga aagaggttta atattttgt gagaccatcg    960
aagagagaaa gagataaaac ttttttacga ctccatcaga aagaccatcg aagagagaaa   1020
gagaaagaga tagttagtct agatatttt cttagtacaa aagtcaatgt tttaaaatat   1080
atggacaaga atttgtctgt ataaaaactt gtgtgaaatt ttgtaccaaa gaaaaaatgt   1140
gagcagtatc ccctacatgg attttactag atcatttata taccaaaaaa tattatacga   1200
tctacgtttt attatatgat tttaacgtgt aaattataaa cattattta tgatatacaa   1260
ttgtctggta acctagatgg gcatagggga tgagtatatg ttgttggacg ttattgttta   1320
agaaatagtt gatgcatcag aaagaggttt aatattttg tgagaccatc gaagagagaa   1380
agagataaaa cttttttacg actccatcag aaagaggttt aatattttg tgagaccatc   1440
gaagagagaa agagataaaa cttttttatg actccattga agagagaatg agaataaaaa   1500
tattttagtg acaccatcag aaagaggttt aatatttttt atgagaccat caaagagaga   1560
aagagaataa aaatattta tgactccatt gaagagagaa agagaaaatg agaataaaaa   1620
tattttagtg acaccatcag aaagaggttt aatatttttt atgagaccat caaagagaga   1680
aagagaataa aaatatttt gtaaaacttt ttttatgaga ccatcaaaga gagaaagaga   1740
ataaaaatat ttttgtaaaa ctttttttat gagaccatca agagagaaa gagaataaaa   1800
atattttgt aaaacttttt ttatgagacc atcaaagaga gaaagagaat aaaaatattt   1860
ttgtaaaact ttttttatga ccatcaaaa gagagaaaga gaataaaaat attttgtaa   1920
aacttttttt atgagaccat caaagagaga aagagaataa aaatatttt gtaaaacttt   1980
ttttatgaga ccatcaaaga gagaaagaga ataaaaatat ttttgtaaaa ctttttttat   2040
gagaccatca aagagagaaa gagaataaaa atattttatg actccattga agagagaaag   2100
agaataaaaa tattttagtg acaccatcag aaagaggttt aatattttg tgagaccatc   2160
gaagagagaa agagaataaa aatatttat gactccattg aagagagaaa gagaataaaa   2220
atattttagt gacaccatca gaaagaggtt taatattttt tatgagacca tcaaagagag   2280
aaagagaata aaaatatttt tgtaaaactt ttttatgag accatcaaag agagaaagag   2340
aataaaaata ttttgtaaa acttttttta tgagaccatc aaagagagaa agagaataaa   2400
aatattttg taaaacttt tttatgagac catcaaagag agaaagagaa taaaaatatt   2460
tttgtaaaac tttttttatg agaccatcaa agagagaaag agaataaaaa tattttgta   2520
aactttttt tatgagacca tcaaagagag aaagagaata aaaatatttt atgactccat   2580
tgaagagaga atgagaataa aaatatttta gtgacaccat cagaaagagg tttaatattt   2640
ttgtgagacc atcgaagaga gaaagagaat aaaaatattt tatgactcca ttgaagagag   2700
aaagagaata aaaatatttt agtgacacca tcagaaagag gtttaatatt ttttatgaga   2760
ccatcaaaga gagaaagaga ataaaaatat ttttgtaaaa ctttttttat gagaccatca   2820
aagagagaaa gagaataaaa atattttgt aaaacttttt ttatgagacc atcaaagaga   2880
```

```
gaaagagaat aaaaatattt ttgtaaaact ttttttatga gaccatcaaa gagagaaaga    2940
gaataaaaat attttttgtaa aacttttttt atgagaccat caaagagaga aagagaataa    3000
aaatatttt  gtaaaacttt tttttatgaga ccatcaaaga gagaaagaga ataaaaatat   3060
ttttgtaaaa cttttttat  gagaccatca aagagagaaa gagaataaaa atattttgt    3120
aaaactttt  ttatgagacc atcaaagaga gaaagagaat aaaaatattt tatgactcca    3180
ttgaagagag aatgagaata aaaatattt  agtgacacca tcagaaagag gtttaatatt    3240
tttgtgagac catcgaagag agaaagagaa taaaaatatt ttatgactcc attgaagaga    3300
gaatgagaat aaaaatattt tagtgacacc atcagaaaga ggtttaatat ttttttatgag    3360
accatcaaag agagaaagag aataaaaata ttttgtaaaa cttttttta  tgagaccatc    3420
aaagagagaa agagaataaa aatattttg  taaaattat  aaacattatt ttatgatata    3480
caattgtctg gtaacctaga tgggcatagg ggatgttgat aagctcgacg agtatatgtt    3540
gttggacgtt attgtttaag aaatagttga tgcatcagaa agagaataaa aaatattttta   3600
gtgagaccat cgaagagaga aagagataaa actttttttac gactccatca gaaagaggtt   3660
taatatttt  gtgagaccat cgaagagaga aagagataaa acttttttac gactccatca    3720
gaaagaggtt taatatttt  gtgagaccat cgaaggagaa agagataaaa ctttttttacg   3780
actccatcag aaagaggttt aatatttttg tgagaccatc aaagagagaa agagaataaa    3840
aatattttg  taaaacttt  tttatgagac catcaaagag agaaagagaa taaaaatatt    3900
tttgtaaaac tttttttatg agaccatcaa agagagaaag agaataaaaa tattttgta    3960
aaactttttt tatgagacca tcaaagagag aaagagaata aaaatatttt tgtaaaactt    4020
ttttatgag  accatcaaag agagaaagag aataaaaata ttttatgact ccattgaaga    4080
gagaatgaga ataaaaatat tttagtgaca ccatcagaaa gaggtttaat attttttgtga   4140
gaccatcgaa gagagaaaga gaataaaaat attttatgac tccattgaag agagaatgag    4200
aataaaaata ttttagtgac accatcagaa agaggtttaa attttttat gagaccatca    4260
aagagagaaa gagaataaaa atattttgt  aaaacttttt ttatgagacc atcaaagaga    4320
gaaagagaat aaaaatattt ttgtaaaact ttttttatga gaccatcaaa gagagaaaga    4380
gaataaaaat attttttgtaa aacttttttt atgagaccat caaagagaga aagagaataa    4440
aaatattttt gtaaaacttt tttatgagac catcaaaga  gagaaagaga ataaaaatat    4500
tttatgactc cattgaagag agaatgagaa taaaaatatt ttagtgacac catcagaaag    4560
aggtttaata tttttgtgag accatcgaag agagaaagag aataaaaata ttttatgact    4620
ccattgaaga gagaaagaga ataaaaatat tttagtgaca ccatcagaaa gaggtttaat    4680
attttttatg agaccatcaa agagagaaag agaataaaaa tattttgta  aaactttttt    4740
tatgagacca tcaaagagag aaagagaata aaaatatttt atgactccat tgaagagaga    4800
atgagaataa aaatatttta gtgacaccat cagaaagagg tttaatattt ttgtgagacc    4860
atcgaagaga gaaagagaat aaaaatattt tatgactcca ttgaagagag aatgagaata    4920
aaaatatttt agtgacacca tcagaaagag gtttaatatt tttgtgagac catcgaagag    4980
agaaagagaa taaaaatatt ttatgactcc attgaagaga gaatgagaat aaaaatattt    5040
tagtgacacc atcagaaaga ggtttaatat tttttatgag accatcaaag agagaaagag    5100
aataaaaata ttttgtaaa  actttttta  tgagaccatc aaagagagaa agagaataaa    5160
aatattttg  taaaacttt  tttatgagac catcaaagag agaaagagaa taaaaatatt    5220
```

```
tttgtaaaac tttttttatg agaccatcaa agagagaaag agaataaaaa tattttttgtg    5280
agaccatcaa agagagaaag agaataaaaa tattttttgtg agaccatcaa agagagaaag    5340
agaataaaaa tattttttgtg agaccatcaa agagagaaag agaataaaaa tatttttatga   5400
ctccattgaa gagagaaaga gaataaaaat attttagtga caccatcaga aagaggttta    5460
atattttttgt gagaccatcg aagagagaaa gagaataaaa atattttatg actccattga   5520
agagagaaag agaataaaaa tattttagtg acaccatcag aaagaggttt aatattttt    5580
atgagaccat caaagagaga aagagaataa aaatatttttt tatgagacca tcaaagagag   5640
aaagagaata aaaatatttt atgagaccat caaagagaga aagagaataa aaatatttttt   5700
tatgagacca tcaaagagag aaagagaata aaaatatttt atgagaccat caaagagaga   5760
aagagaataa aaatatttttt tatgagacca tcaaagagag aaagagaata aaaatatttt   5820
tgtatgagac catcagaaag aggtttaata ttttttgtgat accctgaaag gaaataggaa   5880
tagtgtcata atcgtatcac actattgaga cagaaaaga agaagtcgcg agaggtaact    5940
ttttgttttg caaaccggaa tatagtgtcc ggtacacttt tttaattcgt ggtgtgcctg    6000
aatcgttcga ttaaccctac tcatccaatt tcagatgaat agagttatcg attcagacac    6060
acgctttgag ttttgttgaa tcgatgagtg aagtatcatc ggttgcacct tcagatgccg    6120
atccgtcgac atacttgacc tcaagttcag atgattcctt gcacatgtct ccgatacgaa    6180
cgctaaactc tagattcttg acacattttg tatcgacgat cgttgaaccg atgatatctt   6240
cgtaactcac tttcttatga gagatgttag acccgagtac tggatgggtc ttgatgtcgc    6300
tgtctttctc ttcttcgcta catctgatgt cgatagacac ctcacagtct ttccatcagc    6360
ggattctgag atggatttaa tctgaggaca tttggtgaat ccaaagttca ttctcagacc    6420
tccaccgatg atgagtaat aagtggtagg aggatctaca tcctcgactg attccacctc    6480
gggatctgga tctgactcgg actctgtaat ttccgttacg gattggcaaa tcttatcatc    6540
ggtcggtgtt tggtcttgct ttgtgacttt gataataaca tcgattccca tatgatgttt    6600
gttttcttct tccgtacacg atgaggatga ttgctgaaga ctggcaggca catgcatgcc    6660
agtacgatat attgtttcat gattgctatt gattgagtac tgttctttat gattctactt    6720
ccttaccgtg caataaatta gaatatattt tctactttta cgagaaatta attattgtat    6780
ttatgggtga aaaacttact ataaaaagcg ggtgggtttg gaattagtga tcagtttatg   6840
tatatcgcaa ctaccgggca tatggctaca ttacccacat gataagagat tgtatcagtt   6900
tcgtagtctt gagtattggt attactatat agtatataga tgtcgacgct agagttactg    6960
tctccgaatg cggcatgata gtatcattct ttgctttcgt taactgtttg gaggaagaat    7020
ctttgttatt gcatttaatc tcgaaattca gagtgcacac ctttctcctg taaagaaacc    7080
tgaagtcgct accttattaa gaagacggga tcgcagtctt tatgattcat agtaatagtt    7140
agttccgacg ttgagatgga ttcgctgaga ccggtagtgg tcgtccgagt acacgatgtg    7200
tcgttaactg gatacaggtt aatttccaca tcgatatagt taaaggtatt tctgggtacg   7260
ggttcgcatt tatctgcgga agagacggtg tgagaatatg ttccgagacc acacggagaa    7320
cagatgacgt ctccggatac tccgtatcct attccacatt ttgtttggga aacacatgcc    7380
ttgcatccat gatcgggaga gcattcacag attctattgt gagtcgtgtt acacgatcgc    7440
gtcgacattg ttgacagaaa cgtgaccttc attcttaccg tcgtccataa atacgttagg    7500
tatgtaccac atactgtcgc gaacgatgcg tccatctcat aatgatttac tttttcataa    7560
ttaaagatgt gaaagaaaac cgaacaatat attttttttag taatgtttat gcgagacata    7620
```

-continued

```
taaaataaac tccgtgttta tgatgccggt aaatgttttt atcatcttgg acggaatcga    7680
ttttgtaata tgccatggaa acaggacatt atcactccat gataaattat ttaatggagt    7740
cgatcctctc attgttcttt gcgtatctca atctgtggcg tttgcttcgt ttaaataata    7800
tatcaaacat ggagacgcct gatatgtagg cattcttcat tctattaatg tctgctctat    7860
agcgctttag ttccttatga cgaccggcga tatcatactt actttagaag gaaaatcatc    7920
atctaggatt aaggcgtatc tgatacaggc gaataatggt tcaggatata gatagcgtat    7980
atctctatta aatgcgtcaa tcatagtctc tagagtggga tggtaactca gtaataaatc    8040
aactagcttc tctttggtaa ctgcttttct ggatggccgt attgattatc gagcgtgaca    8100
ctcgctccat attccaataa ccgctttgca aattgtatat tattgacatc gaccgcgtaa    8160
tatagtagag ttatcgatca tatctatatc atccatgtac ttgcttagta tatcaaatac    8220
atcttcataa cagtgatacc cgcaattatt aaatctcgat aatatcagac cgtacataca    8280
tagacggcca ttgttagata tgtgatttac agccgcgtgt ccatattttc cacgataaac    8340
cttacgacgt ttacatcgac gagattatta ttaacaaagt tgttgtccgt cgtcttatcc    8400
aacatgcatt gaatgatagg tatacttacc atatcgccgt aatgtaagta gtttatcagt    8460
atggcttgta cgatggattc atcctgttgt ctaaatctct ttagaatgtt atcgatgatg    8520
tagtggttat attctctgga atcgtacgaa gtaatactac gcattacgtc gacaagagta    8580
tgacgtctct caataagaag attaacgatt ccatgtccta cattatatgg ggttactcta    8640
aatcgcttgt ttagataata cgcctctaat atagggctga cgtcgtatac tctacacgtg    8700
tccacatcct ttattaataa tctctatatc tatggttgag caagaccagt agtattggat    8760
ggaaacattg ttatcgatca aacatttaat tacatccttg gatagagatt ctctatgaga    8820
cgatatatag taatgaagag agttcttaca catatcactg ttgtacatac aggtacgaaa    8880
tacgtaaccg gtgctgtaac attctgattt aagaagccat agcaaatact ctggtctcgg    8940
attaggcgtc gttacgtata tatccaccaa tccgagacca ttgattgcat aattcgtatt    9000
cttggacgga cgtatccgtt tatccacaat taggtattt agcagacgta agtcgaaatc    9060
atttatattc gacttgagtt cgttagagga attcgaatag ctggatatca gtagatgcac    9120
aatctgagat tttacgtatc tatgcttact gtatgctcct agcggagtta atccttcgtt    9180
gtttctacaa agtctctcga ctccgcgaga gagtaacagt cgaacaatct taatgtctgt    9240
atcgcattta ttggagacgt aacaatgtag cgcattgttt cctcgtctat ctatatgttt    9300
tgataagttg tgcacacgttt caatttctag ttttattttt ttgtacgtca catcttcatc    9360
cagtagacga catagaatac atgtgcaatc catagctatt ctggtgctaa ttattcctca    9420
taagatgata aaaagtgtag tgagagagca tgaaggagat ttagtattta gcagtgcgga    9480
tatgatccaa gagggtgaga tagtcgttct cgttcagaat ctttcgcagc ataagtagta    9540
tgtcgatata cttatcgttg aagactcttc cagagacgat agctgattga gtacaaagtc    9600
caatgattgc acgaagttct tcggcggttt tcatggagtc atttaatgat ctccacggaa    9660
gtgaatcctt caactcacca ccaaagagct ccgttgcatc agttctgaaa gagatgagaa    9720
gcctgtagag agaccctgcg ctttctctat gggtccatct atgagaaacc cacaggatgt    9780
attcagtcag acaatgtctg acgtcggcca cggtattcag ggagtcctta gtagcgtggc    9840
aatgacaggg tctgaactgg gcacaaggaa aggccattgt aaaggtagac ctgtagccgt    9900
ttatgctaat agagggcttt aatttccatt ttttaatggg ttgtggatga ggaatgagag    9960
```

```
tgatatcata ttgagatacg tagttatgta gaggtgtatt tcctatatta tttactttcg    10020
gtttcatatt ttaccaactc tttaataaat ttcttttcac gatgcatctt attaaatgac    10080
gttttctcat aagtggacat atagatgcag aagtattacc tctatcatct acataattag    10140
ggtctgctcc taacttatac agtacgtagt agtagtttat cggttttaaa tcaagtctag    10200
aatatatagt ggattaatat attttttatat tagctaaagc atatcattct caacttcatc    10260
atgagttaaa tatttgtgtc tactagtttg tttatatcac agcattctac aaacagtcta    10320
aacaatagag aagacggaca gactttaacg tataaatgac acatgttatc gatattcgtt    10380
gataaatgat tctaacgaca tctctcgcta gagataaaat ctagtatcgt atcatactcg    10440
catagcatag ttttttcataa ttaatacaat attttaaaga cttattcgga aagtatttta    10500
atacatgtat catcgatgga gatccatatg aggagtcact tgtagttctt cagtagtgct    10560
atcatcgata gtataattat atgttgttgt aattggagta actgttggta gttcttccgt    10620
ggaatcaata attatactaa cagcaatagt ataattatat aaatatgttc cgttgatatc    10680
acatatttta atgaactcat ttctaaagcc gtacatccac atctattagg atctgatatt    10740
ttacacaact gtttaataga gtctacattt atatgttctc tatcggtgag atacaaatac    10800
ctagatagtc gcgttatagc acaaatacga tataaataat aataataatt attcagtaat    10860
gtatataaaa atgcattgtg tatttactcc aatactactg tagttgtaag ggtttttttca    10920 aaataatagt tgtgtccacg acatttatat gtattaccta tatattcttc agtaacattt    10980
tcaaagtaca aggtcgcctc ggtgataccg cctctactag ttaaaacaga gtatacatca    11040
aaatcgaatc ctataagcca tccggatgga ttttcccatt caatcagtac atcgtcaatc    11100
aataatgacg ttgacacagc agtgcatgtt atattggcag gttctcctat cgttacgttg    11160 attttttggat ctagtattag tttaaacctg tggtcttgcg acggtataac cgtaagtatt    11220
ttacatcttg attctaacgt cgtcgtaatg aacgtaacag ttgtatcttc cactatcttc    11280
taactctgga ttatgaataa ttaatttctt tcccgtttgt gaatacttaa tatcgtcgat    11340
attaatttcc ttattatctt tataccaagt tatattatta taatgttttg cgtaaagaat    11400
tccacagtat aagtctatgc catacttatc atgagtacct agttcatatg ttttttggaat    11460 gcatgaagga ggttttttaa tatgagatct aactataccc tgaacacagt caccattctt    11520
tgtagttacg gtacacaaat acctacggtt actgaaattta gatgtatagt tggctatcca    11580
taaatcacca tgtttaacac gtttattaga aacctgtcgc cgtctatttt tttctagcct    11640
ctcccattta accacatagt ctttatatct gtgcgataaa agactgtctt caataggagg    11700
acactttgcg ctgaatggct ctcctagagc ggctatatca ttcattgtgc ctccgaacat    11760
acatgctgga ttcaaccatt tagagtcttt agctggtaga gtatctctca ttttattgaa    11820
gaattctgtg atttcatttt cgatgtctat ggcgtaactg tggaatagca ataacaataa    11880
tgatacgaaa tatatatgta ccatcatttt catcgtcatc ttcattatac ggcactaaaa    11940
tatttatata atatcagttt ttttacacac atcgcatgag aaaaatacaa ctatactttg    12000
gtaggtggat acgatatatt ataaagatcg ttaattgtca gcatgtataa tatttcgtat    12060
ataatttctg aaggtagtaa tgttagtaga caatttttat ctgtgaaaac aggaaatagt    12120
ttatcatata cctttgacac gtacatatct ttataatata cattaaggta tctctcattc    12180
ataatattag aatatatttt aaaggactta tcgttattat attttttttaa ctcgttgagg    12240 tatcttctta acttttttcga attatggcat cttaaaactg catatagtgt agtgtctaga    12300
acagtggata gtttgagcaa tattgtttct ttatgacatt tagttattat accatcgtat    12360
```

-continued

```
ttatcaaacg acatgtattt tgaaaatgcg tatcgatacg ttttagaatt gcgattccta    12420
acgtgtctat tgtaaaatgt gtcatctaaa agtatacagt aggatatgaa tttctcaaat    12480
gattttatat cgaagatagg tagagatgga agttgatcca ccaacgatct tatcacattc    12540
ttatctacaa tatatctaag tatatacagt aaacaattaa tggtatatgg ggaattttct    12600
ttgttatcta taatgagttg tgtagcgtgt ttgttattgt cggttaacgc atttatatct    12660
ccgttgatac gtataagata atctattacg tgtgtattat tatattcaca tgctacgtgt    12720
aataatgtct ttccttcata gcgggtataa atatctatat ttttaaacct attcatcaaa    12780
taagttatcg aatctgccgg acgtgtagaa tatgttttga taaactcgaa tacgattata    12840
cgacgctcat ctatcggcat ttctccaaca tttgtttcat agtgatgtat taacataaca    12900
agaatatcgt gttgtatgta gtcggaagtt atataacata gtataggcgt taatccatga    12960
ttattacata ttttgaaatt cggattaaaa gtcaacagca ttttagtcat atgaatatta    13020
ttacacattt caatactaag atacaaatgg aatggtgtat taccacaatt atctaacgcg    13080
tttagattag ctccatgttg tataaacaaa gaaataattc gcttggcctt ttttatcgtt    13140
atcggttttc tacactcacc tggtttataa acgtgtgcga gacacaaata ataataatgt    13200
aacgctgtat atccgtcttg tttaaagtta ggatcgattc ccttatctaa taaagtggat    13260
actatgttct catcgatatc ctcttccttc aataacatgt aacgagattt tatatactct    13320
agtagtaggt tggaatagtc tctatgcgat aagtggtttt tatctttgtc tatcatatct    13380
atcactacat catgtgaaat attacaacat ctagtaagca atatataaac aggcatacgt    13440
ccgctactgg ttttcatcgt tacatccact ccatgattta ataatatctt cagtacatcg    13500
tttgtaaagt aattattata caaatagcag tgtagtgcag tatacccagt tacaggttgt    13560
cgtctgttta gatcatagtt tttaactaca aaatcaagtt ctgtagaagt atggtctata    13620
ttgcaatgac taaaatatgt atatatttca ttctcttgta ttttatgagt tgattcgcgg    13680
ttgatattta aaacataaat cagacgacga ctcatttta tgatgctttg tggtaaaagt    13740
cctcatataa ttgtttaata ttcattatta tagacgattc ccattaacta atctaacatc    13800
tttgatatac ccgtaaatat gtaaatatga tcctaaaata acacggattg taagatgtct    13860
agaaagttta tgcaggtgta tgaatatgac agagagcaat atctcgatga gttcattgaa    13920
gacagatata acgatagttt tatcactagt ccagaatact atagtgcgga aaaatacatg    13980
tgtagatata ctacactaaa tcacaattgt ataaacgtac gacgatgcgc gttagactcc    14040
aagttattac atgatatcat aaccaattgt aaaatatata acaatataga attagttagg    14100
gcgacaaaat ttgtttatta tctggatctg ataaaatgta attgggtatc taaggtaggt    14160
gattcagttc tatatcccgt tatatttata acacatacaa gcactagaaa tttagataaa    14220
gtctctgtaa aaacatacaa gggcgttaaa gtaaaaaaac ttaatagatg cgcggatcat    14280
gctattgtaa ttaatccatt cgtcaagttt aaactaacgt tgccgaacaa acaagtcat    14340 gcaaaggtat tggttacatt ttgtaagtta agaacggata taacgcagat agaggcaccg    14400
ctttcgggca atgttttagt ttatacattt cctgacatta ataaaagaat tcctggatat    14460
atacatgtca acatagaagg atgtatcgat ggaatgattt atataaattc ttcaaagttc    14520
gcgtgtgttt taaaactaca tagatcaatg tatcgcattc cacccttttcc tatagatatc    14580 tgctcttgtt gttcacaata tattaacgat gacatagaaa ttcccattca tgatttaata    14640
aaggatgtgg cattttttaa aaataaggag acggtatatt atctaaaatt aaataataaa    14700
```

```
actatagcta gatttacgta ctttaataat atagataccg caattacaca agaacatgag    14760
tatgtcaaaa tagcactagg tatagtctgc aagttaatga ttaataatat gcatagtatc    14820
gtgggagtta atcatagcaa tacgttcgtc aattgtttgt tggaagataa tgtataaaaa    14880
ttcttataaa ctcaattgac atggaaatgt aacaacatac attcacgtta tactaacagt    14940
aactgttttg ctgatgctag gaatagtaaa cgccatacac gtaaacgttg tagcatcttc    15000
ttccttgaca ggattaatgt ttaaccggga tgtaataaca cgtctcttat cggtcatata    15060
gattttattt gctacactta ttctaccgtc tccgtcccca tcatcttctt cgtaatacat    15120
accattactt atccaaaaga cgtctgcatc cgttgtggga ggtctcaacg atactctaca    15180
cgcaatagtc aaattactac ctattgaagt tacaacacct tctggtaatt gcatagtaga    15240
aggtattatt ttatcccgta cctctaattt tacaattctg gttacgttat atgttttgcc    15300
accgtatata tattctaaaa cacatgtata ataaccagca tcatttttc  taacatcttc    15360
tatggtaata attccaggtg tccgttgttt aagtctctta tttctaaggc gtcgatgccc    15420
gctccatata atatctgcgt ttacgttact agcaataaat gcattaatat tgggacatac    15480
catttcgcca gtagatctct catttactat ttgtggatac gagataagat ctatatttga    15540
ttctgagaca gacacgattg tcaaatttaa cgacatcatg tcacagtagg tttcgttcgt    15600
ggtaatgcat ataaaatac  cagagtctga ttgtgtcggg ttcagaatta gcatattgct    15660
accattatct atcggtataa ttctatcatt atccgctcct cgttttccc  ataaaatatc    15720
taatatatta tatccggatg atagcgtatt tatttgagga catggtaaga ttactggctc    15780
gttttctaac tccatgaatg atgcaaaata ttgccctttg tcgatacatt caggcgcgtt    15840
aaaagtctga acgaatgaag aataaaaaaa tatagaaaga aatataacag gtagtatact    15900
catttttattt tatagtgggt aaaaaagtt  tgtttctggg aaagggagaa gagaagaaag    15960
aagaaaatgt caagatgtac aactcatcaa ttcatacgcc ggaatatgat gttataatcc    16020
acgtaaattta gcatctcaag catcacaaac aatgcgttca gactgttact agtgggatgg    16080
tcttcacctc cccagtaagt agcagcatat gcacaaagtc cgatgatggt ttttgctca    16140
tccggtatat aacaacggat gatttctaca caatcttga  catcatccca cggcatattt    16200
tttaccagct cgcgaatgtc gatgaacact aattccgcat catctctaaa agagaggagt    16260
gtggaataca attgtccagc gcattgcctg ttgcggtatg cataggacga ccaataaata    16320
tattcagtca acattgttt  gacgtcatca atactggtca gtctgtcaca tccacagtgc    16380
tgtggtgaaa agacgtgggt actaaagttg gccgtcatct taccaattgc aattggaaga    16440
ataacgacct gcactaatac cacatgtttt ttctattttt ttaaaaaaaa tggttaacaa    16500
ttagttgtcg gagagcaata tctaccaacg aaaaaaattt ttccatcaac atgcctaatc    16560
acatagatga acggatgatc tacacagaac tcatttgtaa ttgttgatgc acagtctgac    16620
accagtgcac aagttgctgc agctgcttct gtatactctt cattgacatc tatatacgtt    16680
ttgtggatca tagcgtcgac actcacatct aaattacaca tattgctata atctccagtt    16740
gaaccgaaca cctctgtcag tcctgacttt actagagtat ccaccagatt atacgagcct    16800
gttaccttaa acttgggaat gtgaacatcg ataaacgtag cttccagaga gttacaccat    16860
ttcttaaaat ttgtatctgt tagattttgt tctatggatt ctaatccatc aatcttgtct    16920
ggaagaatga ccatcatact agtatctcca acatatggca gttctatgat tgaaaagtta    16980
ccgaatgatt cttttacaga tgcgtgatta aatagctcgc cgtacataga catcatactt    17040
acgtctacca tttccgttgg tgatacgtaa aagggataat cactggtaaa ttccttttcg    17100
```

```
aatggcgtca accatttgc tttaaagtat acggcactaa ttgctaggag acaattgttc    17160
atccaatagt ggattgattt tcccctcagt aaagatatct acacacttgt tgattgcatc    17220
tatagtgcga caatcagtga agtcaacagt ttgaaactta tcgccaattt ttctcaaaaa    17280
ggaatcttta aacacggcag aatatcgccc atatacttta ttcatggatt tgaatgagat    17340
attctgagcg ctaaccttat ccgtgttctc ctccttttct acatattttg atagctgttc    17400
agcagtggat ccattagctc cataatacag tattgtcaat actgacgaga ttgacgctgg    17460
agaaatgaat acattctctc ctttcataga agatatccat agtaatcgat attggtcgtg    17520
tagcgcgata gagatagtct aatattaata ttagatatcc gtaacactac cacactctat    17580
aaaaaaagaa tatttcaatc ttgtataaac agtctacgta gtctgtcata attaggagtt    17640
tgagaataat ctaacgtgta tactaattct atatatctaa ctaattccag aggttcattt    17700
ccttcaggaa aacagtcctc aaagaaagta gctataaatt ttttatattc tttttttgt    17760 tttattactt ttatactact ttcgttttc catggaagtt tgccaccgaa ccattctatc    17820
atgcaatatc ccaacatttc taaatctcct cgttttgaaa ctgttgctcc aagatgattg    17880
tctacacaca tataattgat atttcctgaa gttatcatgt cctcgttgta atctatatgt    17940
gagtttccac tcttgtatag tttgttagtt ctagaatagt caattagtga aagacgttta    18000
tttctaatca gtatattcct cggttctatt tttccatggg taaatcctcg agagtgtata    18060
aactctaacg tgtttatcat agtgacgcat gcttcgaaga ctgattcagt atcctttggg    18120
gcgaatactc ttcccaaatt ctttataacg aagaacatat aatcatcggt ttctccaatt    18180
ccatacagat ctggaatagc caaatacttt ataccacgtt cccgtgtcca gttgtcgata    18240
gtcaaaggat ccaatacaga tatatagaat cgtatttcag acaacaatgg cttgtgtgat    18300
ttgtgatcta tcttcattac gtaattgtag aacgaactag tgaaatttt tctgaccta    18360 tagagtattg aattaccaga atataaagta tttccgataa tccatttctt gccatcgtta    18420
tcaaaacaat acttgaagga ttccatgcct gctatgtaat aacgagttgt ttttatgtt    18480 ttgtattgat tataaaaatt agtagatatg atctatattc ctacatcgtg actgatacat    18540
tctataactt ctttatcaat ggaatcacta ttactacttg tattaataac gagtgcttct    18600
ctaatatatt cattgggatg attcttgtta atgtttttat tattttcaat ttctacattt    18660
tttagtattt cttctttctc tctatctatt tcattcatga tatcttctac atttgtaaca    18720
tctgtatctg tatccatgtt agtagtaagc aataaaacta tagggtaata ctgctataca    18780
taaaaactat ttatattttc atttcaatc aataaggaga agttgataat gcctttatag    18840
cggggagacc atcatacttt tccacatatc caatgtcctt actaaataca tagaagacgt    18900
tatttagttt acacaatgat gatatggata tcttataaat agtatatgaa atatcaaacc    18960
acttattcgt tctaggattg taacaagata tctcgttgtt tttctctaaa ttaccatatt    19020
gttcggtaac ggatagacct ccggcaaaat ataacattcc aaatgtcgag tcgatgccgt    19080
gatatcccct agccataggc atttctataa tcgaccattg tttgtcttta taaatgtcaa    19140 gttttttccat attgttaacc acgatcgtgc tattagagtt atttatgaat aatccgccag    19200
ttacgaaaat agtattatta acggaaacag cggacacatt gcttttttta taatttatcg    19260
gtgtttcgta tatccctgaa tccattgcct tcacttgcag ttgggagatg aacactgcaa    19320
tcagttcttt cggatagaa atctttggca attatacaca accctatttt caatccccat    19380
gtttcctctt cagtcttctc acatcgtcta atagacatgg agtagatgat agaggggaac    19440
```

```
agaaggacta taatcaggga cctcatcttg aaaatggtta gagcctataa gggcgttaac   19500
cagtgtataa tatgcagttt tatttcgttt ttgtatcatt aataaaaatt agttatgaat   19560
atttagtcaa gttaagcatg ctaagaaaag tggtaacatc atttgatgtg ctaccgagaa   19620
atttagttaa attttctctt gataactctg gccattttgt ccttgaaatt gggaacatct   19680
tctttggatc taattgcgca tgtatataca ctcttttag gtgtcagaca tactttcgaa    19740
ctccatggag taatttttc gagaaaccct tctgtggctc cctgtgctgt cacgcacact    19800
ttttctgttg tgacaaagtc tatgctgcaa cctgtagacg tgcaatcgta gtcatcgata   19860
tcatatggta ctggttcttt agaatctccg aatgtgaagt tagccgtata caacaagtag   19920
atatcacaca tgtcaccgcg tttgtaaata ggaatctttt tgctacctct agtagcatac   19980
ggatggtcgt cgtattcagt taatgttaca gtcggtggtc ccgtacaata ctcttccact   20040
ttataatcgc cttgttcaaa tttaacccag aaagatacga aatcattctt tggaaatgcg   20100
gatatgtcgt atgttccttc tggtacattt gtatacattg tttgccacgt cttgatgcca   20160
taatttttaa gggatatatt gtatagacca tccccagtcc attcaatttt ggaatcaaaa   20220
ttgacggatt caaacttata actagttatt ttagcgtgta tactattaat gaacaaaact   20280
gcgagaatta taatatatct catggtgttg tttgttattt gactactgtc actgaagtga   20340
taatatattt taaattttta aaatcatat tttgaataat atgtattact atgtccatga     20400
cgatcaaata tataagtaga tccaatttta agagtatgtt ttctcaatag agtatcatcg   20460
ttgatcatac ttatttcata ttttattcct ttatagcatt ttccctctgc agtaatagaa   20520
tattgtcgct catcaccatc atatttgtga atataagggt acttatcata atggcatgat   20580
aatttggtag atattctaca cgtgtgacct ctgcgttgaa tagtagacat atcaataatt   20640
ttatagtcgt ttataacatc tatatctatg gaatcaaatc cgacgtcgca tgactctgta   20700
ataatagaaa ttgtgtactc tttaaaattt aacaccaatt cattattatc atcagtatat   20760
gaattttcta tattatctac tccatctata tagagtttta cactcagttt attaaacgga   20820
gtgtactcat tattcgaata ggatgctaat gcacctatta caaataaaaa cgttattagt   20880
tttttataca tttaaaatct taaaatttta actagtatat tgaaataatt atttatacaa   20940
actaactaga tgcatcaaca gataataaca aacacctcca gcgatcgtgc caatagtagt   21000
tagagatgcg tatccgtaca acttgttaat catatttcta cggatgtata taccatcgtc   21060
gttaaaagcg cttctatatc tctcattagc tagaattata gatacgctat taattatatc   21120
atacattagt tgattgttga tactattttt attgtaatcg aaaaacattt ccatgaatag   21180
tattccggtg ccaacgctta cagaaacatc gcgttcattc atcattatac cattaagtgt   21240
atccatcacc cattgtttaa cacgtgattc atttggcata gtacgtacta tatcatcgaa   21300
cggtataacg gcgcatcttg taaatagcct gtatatatta tgtaatatgg cgttacttct   21360
tccatacaca ataaatctct tgttataata gtgcctgagt aaaaatgctc taacggcatc   21420
gtagatatca acatccactg aagaagacat ctcaattgat tctagctata agtctttaat   21480
cttttgatac ttgtttgtta ttaaattatt aattattaat tattcattat tttaacggat   21540
ttatattcac ggtagcaatt tatggaactt atattggtca ttattttgt cacaggaaca     21600 aactaatact ataacggaga ttaaaaatat gacgcccata attgttaacg ccactatgat   21660
tatatgataa gttgcttcta acgattctat ttcttgttca tattgtacaa cgtctttcga   21720
gagtttgctc aaatctgtct catcgtcggg accatcatcc actggatcaa attttcgtt     21780 agatcgtaca catgttggga gtatgggatt ccatttaccg tcgatacatg tggatgatgg   21840
```

```
agatcccgtt agtataaaac cacttttaca actaagatgt ataacgccac cgatagaaaa    21900
tgtagatccg gaaattaatc cattagatag agacggtata tcacattttt gttgacatga    21960
tggaataaca ttccaagaat tagctgtaca acttatgtac gaagcaccaa taacctcata    22020
tccaacatca cagttgatag ttatatattc cccaaatgag tattttttctt taactggttg    22080 acacgatccg tgttctaatt gaagaggttg acattccgca ttaggacacg taacagtatc    22140
attccaagaa gtatttccat ttttttcttc gcaacgaaaa tattttgttt cgccgttgca    22200
acttagtgtc atggtggaat tcacttcgta tagcggttta ttatatagtt cagagatgta    22260
atcagaaact gtgcacattt ttttgcatgg attttcgtat ttccatttat ctgtttcgca    22320
gacagcattt ggatccgaag aatgatatcc ctgatcacat gtaaacgtaa ctttctggtt    22380
attattaaac gatgtttcgg tagacgttaa tttagcgtta ttcatagtgg gtacagtaca    22440
tgttgaataa acaacagcag gtagtacgca taacaacgta acaacggaaa tcgttttcat    22500
ttttatttat gagcgttaaa aatagtatac actgtcgagc actaaaagga aacaatgatg    22560
tagtgtgatt ttatattttta atagtgttta taagattttt agatatgtgg acagttcgtt    22620
atcgttatat tttatttcgt taggaaaaca cgaccattta tctccaggat ccagcttctt    22680
ggataataga ctaattaatc tctgacgata tctaatagat gctatgatat tacgtacacg    22740
acttccgtat acgtcgagac tagtgcactt cacgaaagaa ggatgtttac cgtatctcat    22800
taaagtatta atgtctttga tacaaaaaac taattggaat acagttttat tttttatata    22860
acatctcttc atgatatcta tttcatcgaa acatcttaaa atataccatt tatattgctg    22920
tagtgattgt acatctataa gagtatcata atcggtcata cacgcagtat attttataca    22980
cattttcaat aaatctgcat tatgctgttt atgtttagta attgctatca tagactgtat    23040
cataattttc aaagatggtc gtttagacaa tagtacttcc attattattt tgttgttgtt    23100
tgcgactgct tccgaaatac atgtacatcc actagtagta atcgtctcaa aatcaccatt    23160
tctgtttaat agatagacca acgtattata cgcattataa ctgacagcgt cgtaaatagt    23220
acgatagtta atatcaataa ctcctctgga taatagataa tctaaagatt caacagcatc    23280
aaaaattatt aaatgacgaa ctatatgttc attatctatt tctaactctg tgtctgattc    23340
caaatatagt tttataagcg agataccgtg tataattcca caataaaatg gagtagttcc    23400
gaatttatta cgcgcattaa catttgctcc tttagaaatt aataacttta caaaatcata    23460
tttattacga catgagacat aatgaagagg tgtatatcta ttaaagtcta cagagtctat    23520
attagcattc tctaaacata tctcaaacaa ttccacgttg ttgatatcgt gtttacataa    23580
taggataaaa ggtgtgtttc cgtacgtatc ttttttatct acatctgatc cattatttaa    23640
caatatctta attaattcat tgtatgattc tgattctgat tctgatttct tatagtgata    23700
tatacatcta tgtaataatg tacaaccgta actgtcttcg gcatctatat aaaatacata    23760
tatagatatt aactgtatct gatatatagg acaaaaaatg tcttgttcta cgtccatttt    23820
caagcattag tcttatccta ttatctggat gatcattatt aactaattga tatacatatt    23880
cttttatatt aatggatgat gataacctga gattgtgtat aaatgacccg ttcttattaa    23940
tatttaatac tctatctaga aaaaaaatta taatattcgt attagcatca tccatagaat    24000
aaatatgtag aatattttcc ccatattcta aaatatggaa taaatttggc aacctagata    24060
aaaaatcaac tattgtttta tccacttttct cgtatgttcg aacgagatta taatcctgta    24120
ttatatggga tgtggaaaaa ttggaaaaca cgcgtgctat ataatgaaga gataaatata    24180
```

```
cactccagtc aagtatttcc ttttaaaaa aaatccatat ataatttata ttctgtaaca    24240
tgttatccct tttcaattaa caatgttggt ttataaaaaa ttaaagaagc gaatcaatga    24300
ttaatagatg ttaagaacta taattacgat gtattaatag gtatagttag ttagttaaaa    24360
agagataaca gttactaatt aattgttagt tattgtctat atgatattac aacctattat    24420
ttgttctcta tagttacatt aattaaaatt ttatatgtga cacctattca tctggagaat    24480
acttcttgat accatgattc tggccaatct gcaaacacag cacaacagca tctttccact    24540
ttgatagcgc acacgtatgt cgaggtagcc tcatccccag gtttatatac cttgatgaat    24600
cgacacgtgt acttgatgtc ctctttcttc tcacagaaat acacaacaca aagtcttttg    24660
atatgctttt ctatatcatt ctctatcagt ctgaggtagt cgtaacccac cgtgaatcca    24720
aatactttgt gtgtattatt atcaactcca atgaacaaat atccaccctc tgtgttggca    24780
aaagatgaga gtatacgtgt tcttagttgc ttagctgaaa cagatgtatg tttaacatta    24840
atagatttac cagcctgaag ttctgatcta ttgaagaact cctctaccaa tctctcaatt    24900
gattcagtgt cttccactcc atctggatat tcaaattcct gcatttctgg tctgggactc    24960
catccacctg attccttcag ttcgctaaga tactcatttg aatgcatgat cccatagtct    25020
tcatgtacaa atttgttttt acagtactcg gtataagatt ttgattagac aaatgcgtat    25080
gcacataaca gcattcttta ccattcacaa tatcaaaatg atcatataca acagaccaca    25140
tatgcgtat agattccaaa cgtttcatga gtacatgatt cacactgtct tccagagagg    25200
tggttacctc gatggtgccg ccgatatagt agaagaaaga ttttctgtat cattctcccc    25260
aagtttaact tttaccagat ttgggatcgg aagcaccgca ccctttttga atctcattct    25320
cataatttcc tttccatgta cgtccacagc agtaacttga cagatacaat ctcctatcca    25380
gacgtggtaa tcgatgatag gtcctgaact gagtgcattc atttctttgg ccttctcttt    25440
gatagtagaa taatcatgtt gaacttttcc atatacagcg ttttctgttt caagtacgtg    25500
atgatgaatc cctactcctt ccaaacacaa gtctagactc tcgtacccga ttccgcttag    25560
agcatagtag tttttgtggc gatatgtgat ttccttcttg atcatggatc ggatctccaa    25620
tttgtagata ttcattgcac tcaaacatag gcagcagtgc tccaatatat ctcttgttca    25680
cctgactgta acaccacata tatttgtctt ttacaatgtc atacttgtta ttataaactg    25740
acatcattgg caacagtcga tgatattcca ggaaaggcat gaagattctc gtcgtaccca    25800
ccgagagcgt gtgcgtaaaa catcgccatg atttcggttg tacacacgag atcaataata    25860
aattaagtta ttttttaatt tttatcgaca aaaattttac atcaaccaaa caccacactt    25920
aataatatac accctgcatt aatatgtgcc gaaacttgtc gtaattgggt tcctcaaaat    25980
atgtcaaaga gttaccatg gtaatatatt gcagcaattc tctaggtgca tattgcaaac    26040
tggtcattaa caaagtcgca gtattgttaa catatttctg ttttgtggca cttactaatg    26100
cacaattctt tgtttcagat atcttagtcc atggcaagat acctcccaac catctaatca    26160
tacaatatcc aagtgtttct agatctccac gtctagatac aacgtatcct ttatgcgaat    26220
ctataggtgt aaattctaga gtaccgttat ccatttatt tggatttctt ataaatggaa    26280
catgttcgcc attagacatg aatttagaaa ccaatccgta atccactaga tataatttat    26340
tcttatctat ttgatccaag actatattac tcgctttaat atctccgtga gaatatcctt    26400
gctcgtgcat aaattgtatg gtatttaaga tttcgattcc gatcaacatc accgaccttt    26460
ttggtaatct attattattg gctctgatca ccgcatctag atctgcacct aatctattaa    26520
ttaccaagaa tcgatattcc acattaatgg atttgtatag accaaatgcc ttgcacgtga    26580
```

```
taagacctac gtgctttata ttgtgagatt ttttccattc ttcgataacg gatggtttaa  26640
gtactctagt ataaaatgcc tgttcggtaa ataatgatcc gttagctttg ggctctattt  26700
ttactacata attattgtca ttagtagtat aaatactacc aaatccacct tttcctatta  26760
atggtccaac gacccattga tttttgcaat tgtcagttaa cacaagtcct tgaaagttca  26820
taatgtgtga tctatctgtc aatgaaatat cattttaaat tttaagtttt acgtggtaag  26880
ttttaatatt taactaatac attagacgtt gaaatagcca catataaaaa cgagttatat  26940
tattaattat caagttttaa gtcttaagtc tctaattagt gttaaaatac attctaatac  27000
ggtcctgtag tatctgaatt aacttactat atgctaaatt cacatcatct tcaatgataa  27060
tagtgtcgaa tagaccggct tcacctgcct catccatgtc agtttttgcc aacatcacac  27120
gacgatgaat ctcatcatcc gcttcagtgt ttctacaacg aagcttggtc tcaaccattt  27180
taagagaggt aggtcttata tacaccgagt aaggcattag gtaagtattt ttaaaacttc  27240
taacaccgtc gatgtttaga tccatcacac aaatacgatt attaatagcc gctgtattca  27300
cagcagtttt agaagttccg taaatatttc ctaaaaactc agtatgttcc ggcggctatt  27360
cccttccaga tggcctctct gttaacgtaa tggtaatcga caccttctcg ttccatagga  27420
cgaggaaatc tagtggtatg ggacaccaca aatccaaata tattcccata gtcttttggc  27480
tatggctgtc tttcctaaac cagatggccc gctcaatatg atagatttta ctatcccaga  27540
catttatgta agtcaaaaat ctagactttg ttctctgttt tgtatttacg tgaacgttta  27600
ttatatatat aatatgtaat acagaatatt gccacggccg acaatataat taatgcggta  27660
ataccaaata tttctacaaa gtccttggtt ttataattgc taatagaggt tgtactaccg  27720
cctacagtag ttgatggtac tgtatcatta tcattgtacg tatcataaag atccgcatca  27780
tcggtggttg atttagtagt gacaattcca gatgatgtac ttactgtagt gtatgagaca  27840
gtgtctgtaa ctgtatgatc ttcttcttta tcagtaattg gttccggagt ctcgtctgtt  27900
gtggattctc cagatgatgc acttactgta ttaatgctat cactagtgta tgtgacggtg  27960
tctgtatgat cttctacatt atcagtaatt ggttccggag tcgcgatttc gaataccgac  28020
gagcaattag aattatctat ataatcaggt ttctcagaac tagtttccgg tgaatgtgta  28080
gatccagata gtattatgtc tatagtcgat tcactatctg tatttacaat caactctgtg  28140
gagtattctt cataatctac tttatcagtg tcatttgtag gcgatgtcat aaagaatgca  28200
catacataag taccggcatc tctagcagtc aatgatttaa ttgtgatagt tgtaactaga  28260
tcatcgtatg gagagtcgta agatattta tccttggtat aattatcaaa atacaagacg  28320
tcgcttttag cagctaaaag aataatggaa ttgggctcct tataccaagc actcataaca  28380
acgtagtcat ttgtattatt tcgattacat gataaagttg catcatcacc tattttttta  28440
gatgtctgag gaaaaggtgt agcgtatact aatgatatta gtaacaaaag tattggtaat  28500
cgtgtcatat tagtataaaa agtgatttat ttttacaaaa ttatgtattt tgttctatca  28560
actacctata aaactttcca aataccagcc accgaaagag caatcttaat catgtcaggt  28620
tcatatttcc ccaacatact agatccaaat tcgcctacat caggtaaatt catcataata  28680
caatgtctgt tcatatcaca cgatgatcca ttgagcatct catctctatc aagaatccta  28740
atctgtggtt caaaataaca gcatctacac tcatcgttaa ttgtagtatt gtctaatata  28800
tttttgctaa tatttgcgta agttctatta tcagctattg catgcatcac agatccatca  28860
acaaccatat ataatataga acaatagtcg gactttatac ttatgtaaaa cttgaaccaa  28920
```

```
ttggaactcg gaagctcgtc atgtagacgc tggtgtctag atataataac attattatcg   28980
gttacacttc ttaagagagg tgccgcatcg atagagaaat caaacaggag aataatcaat   29040
gatgcatttc ctttggtaaa aaggaaaca tccatgggaa gaatggctac tttatatgaa   29100
tttaactcta tacacgcaca cgctttatca gatgagatta atagttcaca aacatctcta   29160
tcctttccta tggatataat aacaggaatg gcatctttag gtttaaaata attatataca   29220
ccagtaggag tcttgtcatc gtcatctatc tttatcaaat tagcaaatct ggatattctt   29280
gatacattct ttttatacag tgaattgcat acatcggata ccgcattatc catatatggc   29340
aaatctgcaa tcactgtatt gttttttagat tgtccgccaa tgtgaacgtt cttgactttt   29400
tcacaacatg gtttaatcat gaaatcatt tttatatgat ttatttcctc gccatgtttt   29460
actaacgcgt ttagacagta tacaataaca ccatccatgg cgaccaccaa ctaaatagtg   29520
ttattttaat ttgtatgtaa ctattaagat ttagtcaagt ttactaaatc gtttagatga   29580
gtagattctt tccacgtttt atcctctctt atcctagtaa atctaggaaa tctaatggat   29640
attccatttg cggtatggga cttggaagat gtaaactctg ctcctgaaat ttcccatatc   29700
tgagattgtt ttggatcctc tactacaaaa tcgggaatat agattttatt aactactaac   29760
cactctggaa tttttttggg atccttgtta attttaatca tctttaattg gtcttgcaac   29820
tcccttaacg tattatcatc gtgtcctgaa cacttggtaa ccgtcttcca tttaccggat   29880
tcatcgtcgt aacaacccat tagaaagact gccatgatac cacccttgc tcctttacca   29940
tagtaagcac ctagtactac taaatcggca gaatctgcca tggaaccctc gttcaaatag   30000
tctcgcttta tttttaacca tcttctcttt cccggttcgt atactccatt aatatctttt   30060
aagaccaatc cttctaattt tctcgttagt gcatcatcca atacgtcagt taactgagac   30120
tcgttactaa tattcgtcaa ctctgagaat actattctat tgggtatttc aaccataaca   30180
tctttgagaa aagatcttcg ttcgtacaat ggaatgtccg tcatatcgaa tccatcaaag   30240
tacaaacagt caaacacgaa caaacacatg ttagagtttt tatattcttt ctttttgtgt   30300
atacctaaac ttccaaacgg gagcggtaca ttatgttcgt ctacaagaac aatttcagaa   30360
tccaatacga tagacgtagc ttttttaaat gctttcggta tgtattcttt gagataatcc   30420
actttatgag agagtactgg tttcatgttt ctactaaaga aggcaaactc gttattattt   30480
ttatgaactt gtactctttc accatcgtat ttgacttccg caaacattcc tgatggaaat   30540
tttttaaacg ccttattgac agaatcacac gattccgcta acatgggatt aattggagtc   30600
ataacagaaa tagatataga gtctagattt tgtttagatg catttctat tatctctttc   30660
aagttattag attttctaaa cacatcatag gcatgaggac taatagcgtt aagtacgtac   30720
cgagggcccg ctttaatttt tagatcttta tcaataagca tgactacaca ttttaaatca   30780
ttacatgtac aaacggatgc gatatcagtc aataatttta tttgatgcga ttctttagtt   30840
acggatgata acgtagttaa aaaactatcc acttcttcta aagttaaaat gcttttatct   30900
cgtggacgga tttctgtgtt ctctttgaag aaagtcctaa tagtgtctcc tatatatccg   30960
tatcctaaat cttgtagcat atcttcctga gattgtttaa atattatact ataaattttt   31020
ataaattgtt tatcgttcat gttataaatt ctatcgtcta atccgggaag caatagctta   31080
atgatcaaat atttatcatc cctatctgtt ataaagtctc taattaattt agatttttct   31140
ttatatcctg atgcgtgata tatatcacag cataattttc taaattcgcg aagcgacgtc   31200
atttaataaa aaaagtattt tttttaata ttttcacaaa tatcgttcgc ggatattatt   31260
agacaattgt agtatattct cacgtatcac ttgtttaata tctatatccg ctattctgga   31320
```

```
accgagtact tcggcatacg tagttttaaa atctggatta ttcattatat attttagagt    31380
aatgatagca tctactatat tttctaggtt atccttataa aagctcataa acttgttaac    31440
tatacaatcg ataatttcat tgtcgtctaa tgaattaatc aattcggtct gatagatctc    31500
ttgatctata atagtatata cagtatctag gaaagagata aatggattat ccaagtttga    31560
tctacacatg ataaaattta caatgtcctt gtttaatata tcattatcta tagtttctat    31620
cttggcaata actaattgag atattgatgc gagttcggta tgcatatcgg acacgtatcc    31680
gagtactgat tccaagttgc cagagtaata tgcttcatcc atttataaaa aatgtaattt    31740
cactattaca tccacagttg ccccactggt ccagtaaccg tgtgtatagc ctctataact    31800
atattcttaa tcaactcctt ctttacatct tcctcgaatt cagaagaaat aatttgccaa    31860
tgaatatctc cttcttcaat catttttta tattcttgta atacctttg ttggaatgta    31920
acatcttcat aaatttcctc gccgacgttt ctattaattt ctttgctacc agattccaag    31980
aatataacta gtcgggttt aggcaatcca gattcataac tcttactgag agtcattgac    32040
gcgcctttag cggcggcata cgctactcca gagaatgcgt atctatcaac tattaaagta    32100
attccctgtt ctagttgttc ttgtataaaa gatgcaaact cccatctatt tgcacaaaat    32160
aatagattaa ctatatgatc attataggtt tttttacgag ttagatagtc atctatcatc    32220
tttccagtga cagtggatct ctgaggaaag ttaagatatt ttatcgtgtt tgccggtata    32280
gattccatga tgttcataca ttgtgttgtt tttccagatt tgtccaatcc ttcaaaaacg    32340
attaatgccc cacgagacat ttttgtaaac ctaacatatt ttttacaatt tatgcgtata    32400
ataaaactga aaataaatat atggtcatcc gagacgatta ggtctacctt tatagatcat    32460
gggtaacaaa aatattaaac catctaagga aaatagactg tccatcttgt ccaaggataa    32520
gatggattca tttaagagag gatcctttag agaaaagtcg cgtgcaacca tccaaagatt    32580
ttcatctctt agacgagaac atattaaagt agaccatcct gacaagttcc tggagttaaa    32640
gagagggata tatgaaataa ttcagaaatc gtcgtctata gatgtggaca aacggactaa    32700
gctcatgtcc aacataaaaa cgatgatgat aaatccattc atgatcgagg gtttaatgac    32760
atctttagaa aacttggatc ccgataacaa gatgagctac tcatcggtga tgatattggg    32820
agaattcgac atcatcaata taagcgacaa tgaggcggca ttcgagttca taaacagtct    32880
gttgaaatct cttctcttgg aatactccat tagtaatgac ttgttgtatg cccacataaa    32940
tgcgttggag tatatcataa aaaatacatt taatgttcca gaacggcaac tgattctgag    33000
aggtcaatac ctaactccaa ttttcagtga tttgttaaag tatgcgggtc taaccataaa    33060
gtcaaacata cttatgtgga ataaacagtt tatcaaacca gtatctgacc tctatacatc    33120
tataagactc cttcattgtg ttacagaatc atataaggtg attggaatgg gataaataca    33180
acaattatat tttttatcat atccttcacg ctataaaaaa aattatacat ccgtttccct    33240
gtcggttacg gcagaacatg tagacgaatc atcgtcttca aaataatcaa attcatcctc    33300
tatgctctca gtgtgcccgc gtagatactt acatagattg tatcgtagtc tagatagctc    33360
agatattgga atactatcag atatatgttc ggctaatgcc atacacctat attttttatt    33420
tgtcaattcc caatgtttag atactagact agatagagct actactattc tagaatcaca    33480
acatatcata tcctttacaa agttgacaaa gtcaaatagt cccgaatcgg agtctacttt    33540
aagtttctca ttaaataata gatcaatgtc tccatactgt ttaatagcca aatcatctag    33600
tgtcatcaat gccgaataaa tattgccgga tatagtattt ctgtgtctta tatattctgc    33660
```

```
taaaatcagt ttaaaactat acttattata caagtaagtc atactaaccg gcgtattaac    33720
cgcgcaacca atattagttt cctctggaag caccccctctt atctctatgg agtcattatg   33780
tctattatat gaaataaacg tgtcaactac tttgtcccta tcaaattcga cagtgtagtg    33840
tgtatcatta acttcattac gtatgactaa tttattttgc tgagtagaaa agtaaactaa    33900
tgcatttatt gttttagacg cattaactga tatatcaaac gccattctcg ttaattgtaa    33960
gaaaatgtat tatcttttca tttatgtaag aaataccaat aactccacac gctaatctct    34020
gatcattttt tgaaatagat aacgcctttc caataattgt agatatattt acatctgtat    34080
ctaaataaac atatgctaca ccatatctgt ttacaaagat gttaccgata aatatttctg    34140
gactgcctat ggaatcacat ccttgactaa tatctccgta acgatgaatt atcaaactat    34200
acgttccgga ttttaatcca ataactttat cttttccatg gactggttca agtaaataa    34260
ctcctctgat attatcgtgg tctattatac aaacagccat tatttagtaa aatagaataa    34320
gtagtctgat attatgagtg gcagcaatgg ccgtgtacgc ggttactggt ggtgccggat    34380
ttctaggcag gtatatagta aaactgttaa ttagtgcaga tgatgttcaa gaaatcagag    34440
tcatagatat tgtagaagat ccacaaccaa taacctcgaa agttaaggtt ataaactata    34500
tacaatgtga tataaacgac tttgataagg taagagaagc gctagatggg gtaaatctga    34560
ttattcatac agctgctcta gtggatgtat ttggaaaata caccgataat gaaatcatga    34620
aagtaaacta ttatggaaca cagactatat ggcagcttg tgtggaccta ggaatcaagt    34680
atttgatcta tactagtagc atggaagcaa taggacccaa taaacacggt gatccattca    34740
tcggccatga gcataccctt tatgatatat caccaggaca tgtatacgca aaaagtaaac    34800
gtatggccga gcaactggtt atgaaagcca ataattccgt aatcatgaat ggagcaaaat    34860
tgtatacttg ttgcctaaga cccactggaa tttacggaga aggagacaaa ttgatgaaag    34920
tcttttacga gcaatgtaag caacacggta acattatgta tcgtacagtc gatgataacg    34980
cggtacatag ccgggtatat gtaggaaatg ctgcatggat gcacgtgttg gctgcaaaat    35040
atatccagta tccgggatct gagattaaag gaaatgctta cttttgctac gattactctc    35100
catcgtgttc gtacgatatg tttaatcttc tattgatgaa accattggga atagaacaag    35160
gatctaggat tccaagatgg atgctaaaaa tgtacgcgtg caagaatgat atgaagagaa    35220
ttctatttag aaaaccatca ctactcaaca actatacgtt gaagatatcc aacactacat    35280
ttgaggtgcg taccaacaat gcagaactag atttcaacta ctcccctatc tttaacgtcg    35340
atgtggcatt cgaacgaaca cggaaatggc tagaagaatc agaataagta tttttttta    35400
aaaaataat cgagtagggt atcaccacta cacagtaaga gtacagtaaa taaaagtat    35460
ttatatactt attttatag atcgtattat gcgctttcta catccatatc atcgtcatct    35520
tcaatatcga taatattttt tcttctacc ttgacatctt ttgcctcttc gacagcaact    35580
gattgcgcta ataatacatc cttttctttt ttctttttag gtgtgacatc aatagttatc    35640
ttttccaagt tatacgatat ggtaacaaca ttaccaattt ttgaatcaac cgtaattttg    35700
attttatcca tttctaatag catagcataa ttaagagttc attttattt ttttaaacac    35760
gtatatggtc actatcaatg tagacgctat tagcatacat attgcagtaa aatcatgat    35820
gtcatttata tctttatacc atataataga atcgtatcct attatagtaa tacacgtgga    35880
ccgatgtaga gaataagtct tatgtttaga tgttaatata gtagatgtac tcgttgccaa    35940
atttttaatg agacacgata catttactga gcattgtata tcattatatt ttaagtttcc    36000
tgataatgag acaatcaaac taggattaag tgaaccatat ttgtgttta aaaaataacc    36060
```

```
atgtgtaaaa aagacattat cgtctagttc atctacggtt aacgtgcgat taataaaatt   36120
atatctatat ggaatatgcg gattatattt tatatttact acattataga tcctatcaaa   36180
atacaaatgc ccataacata attccacatc ctctgaatga aatctaaaaa tcgatgaact   36240
gtatgccaat accggcatta ttgacatcgt caatatggat attatccatt tcatcatcat   36300
catttaaaat tgacactaca tatgaatatt acttttatt ttaattacca gttgcacgta    36360
cacgggtagc gtgatctcta cacgttctat acacgtcacg tctggatgtt gttggcttac   36420
ccatcaaaaa tataagtgcg gtatgagttc tcgctataac gatcggagat acaggggcgt   36480
acccagtaag caactccata gcatacgtgt tctcatccat tagagagtta gtatatacaa   36540
tacaatattt ctgaccaata agaggtttta gaatattacg attagtgatg agaggattaa   36600
tcttggcaaa tgttctgtta ggaatagcag ctagaacatt ctttgtagtc ttgtaatcaa   36660
cgatggcggc atcctcgaac ttattatttt ttgagatatc ctcgataatt ttatgccatt   36720
cagccattgt tatttattat atatgttttt taataagaca tctattggaa taaacttgac   36780
attagcattc tattcttact acaaaatata aaatataaaa taaaatatac aatccaatac   36840
tcacataatc caactcactc gaacactatt tttccaatta cgataacaat attgcagaat   36900
gtactcgtta ttatttatta ttttgatgtg tataccattt agttttcaaa cagtgtatga   36960
tgataaatcg gtatgcgatt ctgacaataa agaatatatg ggaatcgaag tttacgtaga   37020
agcaacacta gacgaacacc tcagacaaac aacgtgtgaa tccgaaatcc ataaatatgg   37080
cgcatctgta tcaaacggag gattaaatat ttctgttgat ttattaaact gttttcttaa   37140
ttttcataca gttggtgtat acactaatcg cgataccgta tacgcgaagt ttgctagttt   37200
ggatccatgg actacggaac ctataaattc tatgacccat gacgatctag taaaattaac   37260
agaagaatgt atagtggaca tttatttaaa atgtgaagtg gataaaacaa aggatttcat   37320
gaaaactaat ggcaatagat taaaaccaag agactttaaa actgttcctc cttctgatgt   37380
aggaagcatg atagaactac agtctgacta ttgcgtaaac gatgtgactg catacgtcaa   37440
aatatacgat gagtgcggaa acattaaaca gcattccatt ccaacactaa gagattattt   37500
taccaccaag aatggtcaac cacgtaaaat attaaagaaa aaatttgata attgttaatt   37560
gttattttta taaaaacaag aacggtacgg cgatatttat ttttttctaa aacatctaac   37620
cgaagtagtg gtatgataaa aatgtagttt gggagtattc gttgtactac aaatatattt   37680 ccgttttta gttccattct tcgtggcatt tttagctata aaattatatg gggttgtctg    37740
gtttaatatt tcggattctc ctacccaata tccgcgtcta atgcttctta aaaaacttaa   37800
ctcgtttgga gtctctatct taattagatc cgaatttgga tttagagctt tgcatgcatt   37860
acgtccttcc tcccaggttt ttcgatcagt agataaatgg atacatttat tattatagct   37920
tatccagtca gtaggacaat cttctctaat atatgcatct tttatcgttt tatctattga   37980
tggtgtatga actaatttac gttctacaac ttttaatagt gtcgctgtaa aaataattcc   38040
aacaattaga ccgcatatta cgcagcaagc ataaccagca taatctgtct tatgtttgtt   38100
cattgtcgtg cggtgtactc gattaagatt acattttaag tatttttttc atttgtggca   38160
ttcctactcc tatccctata tctgctataa ataacggttt cgaagttacc attactgaaa   38220
atagtcgcgc atcgacttgc gagctacgag tttgtttaga ttttgtatcg aacgaatata   38280
tagaattttc ttttatgaag tatattctat attcccgatg ttcattttcc ttctcctta    38340 tatcgaacca tttaacacca gacggtcctt cgaagatagg ttggttagat aaaggcttta   38400
```

```
taatatcatc tagtacatta tattttcta tgacttcaaa cgtggtatgt ggaacaactt    38460
ttccagctgg taaacatata ccaggagctg gagacggcaa ttgctttgta tatccttcca    38520
attttgacgt agaaaaagat tgtttaatgg tattcataga ataggtacat aatgcggact    38580
tggaataagg actatcgaag aatacatata gtatcgtatc attatctgtt tttatagttc    38640
tagaatgaat aatttgtcta taacttcttc cgtcgatatc acattctaat tcgactttga    38700
gaaacgtcga ccatctatga ctagacaatg atgatggacc accttcgtcg tttaggcaca    38760
tttgtgctat atacggaatt tgacaattc tctttgagcc gatagtatca gtgaaaagaa    38820
tgtaaacttt gtcataagta ccatctttat cgacgaatgc tcctcgtaaa ccatcttttg    38880
gaattacgtt atccgccgtg tataaatcat aaccacatgg tccgtcaaat cttctccatc    38940
gtttaattcc ttcttttgat atgtttatgt cagatagtac acatccgttg tgactgatta    39000
tcgttacttt gctatttga taaggagcgt atcctctacc tctatgtttt gggtcgtctg    39060
aaccgtctat tttccaacat ttgggatttc cgttattggt tccgcatcct ctacttttat    39120
agatgttgtt atataattat tattagttaa accagttttg tttagtttat tatttgaaaa    39180
tgtgtatacc gccccattaa cacccgtgta taatacgtcg tctaataagt aagtagaaat    39240
tatttcttca ctcgtttcaa acttatgcca ttcaataccg ttagcaaaat agaataaaat    39300
aaataacaaa ggtatcattt taaataaata aaaatgtca agagttagaa tatcgttgat    39360
atacctctat acgttggttg ttataacaac tacaaagacc atagagtata cagcatgtaa    39420
tgataccatc attattccgt gtactataga taatccgaca aagtatatta gatggaaatt    39480
ggataaccat gatatttaa cttataataa aacttccaag acgacaatat taagtaaatg    39540
gcatactagt gctagacttc attcgttatc agatagtgat gtctcattga ttatggaata    39600
taaagatatc ttaccaggta cttatacatg cggggataat actggaataa aatctactgt    39660
gaaattagtt caacttcata ctaattggtt taatgattac caaacaatgt tgatgtttat    39720
ctttacgggc attactttat tcttattatt tctcgagatc acttatacat cgatatccgt    39780 tgtatttct actaatttag gaatcttaca agtatttggt tgtgttattg ccatgataga    39840
gttatgcgga gcattttgt tttatccgtc aatgtttact ctccggcata ttattggatt    39900
gttgatgatg acgttaccat ctatatttct tataattact aaagtatttt cattttggtt    39960
actgtgtaaa tcatcatgcg ctgtacacct cattatctac tatcaattgg ccggatacat    40020
tttaacggtt ttgggtttgg gattgagttt aaaggaatgt gttgatggta ctctgttatt    40080
atctgggttg ggaactatta tggtgtctga acattttagc ctgttatttc tagtctgctt    40140
tccgtcaacg caaagagact attactaggc atgtgtataa taccacgagc tagtagacgt    40200
ggaagaggaa ccaggaacta ttgttatttt ataataatcc ttgatcttat tcttattctt    40260
tttatcagat ttttgcttc cagttttatc agtagatata caacagagtt tcataaaaag    40320
agaagagaat gaatccattc cgtacagtat ttgataatag cttttttttc gttttatgag    40380
gtatttagag attagagatg attaatgatc cccatactag aaatctatta atccacagaa    40440
atactaatgc tcatatttat attatcaatt ctaccgtaca atatttgttc cttgataggt    40500
acagaattgt acgactgcat ttttttgtat actaagtcga atggatgctc gaggttacaa    40560
acatgtatta aagtatcttg ctcgatgcta gaatttatgt acttggcaga ggacatacct    40620
atacagtttg atggaatagg aaactgctta ttgtcgatgg ttataatgga ataccactta    40680
ttattcgcaa atatctgatc gcatatgtgt ctatccaaat agtcggtaac tcgtctaata    40740
atgaatacag acaacggcga ataattaatc agtgatagat tgtttacata cagtatgtcg    40800
```

```
tttgtaaacg atgttaccaa tcgtttgcta ggtatatccg ctttaacaac caatatggtt    40860
gtaggaccct tgctaactac gacacatttta ctcagtgggg atatgattac agcatgatca   40920
atgggaaagg ttagaatatt tttgccattg acgtcattat ctatagagat aacacatcct   40980
ccgacagaac taatacagag tataatcgtc gataatctat gaggaataag atggtacatc   41040
tcattgtcat ttacaacttc tacgcttaag atgttggtaa aagtaccgt ttcatccatc    41100 tgtctattga tctcatcaga tataattttt tgatgttctg tatctatata atatctacag   41160
tcattattag caataaaatt gctaatttta gaaatgccga atacagggaa tatctccatt   41220
tgtacaacgt gacggcagca ataatactaa atattacttc aattttataa aaaggaaact   41280
aatcacacca atgattctat atcatcgtgt tcatgatctt gttcttgctt attaagataa   41340
tcatcgctat gtgctcgtct aaacggatta ttctcactaa atttattgtt gagttctgta   41400
atgaacggat ttgacttgct acaaatactg gttttattat aatttacgaa aggattggat   41460
gaatagttag gattctgttt ggtatcttca ttaagtacta ctgtagtgtt ctgataaata   41520
gtctgttcat tacgatcatt atttattagc agcgtgcttc cagcaacact atcgtaaatg   41580
tgttctgtgc taggcgccat aacattggat tcgttatccc atattaaact accagcgaag   41640
ctatcatcgt ccaatatctc attcctagaa atattatcta cgtcattgtt ttgttccata   41700
gcactacagt gatcctccca gtctgattcg ctatcagttg atttactaga tttgctggaa   41760
ttagaactct ttatcttttt taattttgtc atgataattt tattgtcatt atagacagta   41820
cgtatctttt tcctacaaat atataatata taacatacta atattgttcc cgcaactacg   41880
gtcaccgtga taagaggtac cagcatcatt tctgattgct caatatacgt actactagtt   41940
caatatttat tgttttatta tttactttac aactttatg ataaaaaatt actattgcat    42000
ttcccatcaa ttatgatcca tccattgccg tctgatatgc agaatgaaga attaaacgac   42060
aatttcattt tcagattatc tgaaggattg atgattagat gataatctcc agctgtatac   42120
aggttatacg cttctatgat tgtagcgtta aaaacatcaa tagatgggaa tagataaaat   42180
ggctgatgtt tatcttctat atctaacatg atatcatagt cgcatgctat gatgatggta   42240 tttttgatc tgtatgcggc acaaatgcta taaatgttga atctagccaa atcattagaa    42300
tcctgaggaa ctatttttacc cttatagcta aagtagcatt tttgcatgtc ggaatatttt   42360
atatcccgta catctatttg gacagttttt atgttaccta taatgtatgg tcctataaag   42420
tccatgattg agatatcgag atcatcatac aatgtatctg ttatagtcaa cacacccatt   42480
ggagtaataa caaacgcggc gtccatggcg gcgtacgtta acgacttatt attaattcat   42540
tttttgttgt cacttgtaga attttttaac acatagtaca gattgagtac ttttacatac   42600
tgttttaacc agttttccag acttgtatat ataacacgct tcagcatccg tcgtactgtt   42660
tagttgttta aaatttgtta atttactaat atctatatct ttatcattat taatatctaa   42720
ccatttatca ttggtctttt ttaaacttac ccaataatct ttataaaaaa tactaaacaa   42780
tactctcaga tgtctagtat ccggtctagg caatctggct cgtaatttac gacactgata   42840
aaccgcatta tctgtagaca tttttaatgtt agtatctaaa taacaatgtt tatcgtattg   42900
tatccatcca ttggcgcaag cactaggcat cagttcttct ttgtaatgca gaaatgttcc   42960
tatgccacta ataatggttg agagtatcat cattatagcg accggcaccg acaacttctt   43020
aaacctactt acagtttgtc tattaagcga tttcatttat taatgtacaa aaataaaatat   43080 tagttcattg tttttaacaca aaaatacttt ctaacttctt gtgatacatc agaatcttga   43140
```

```
taatcggatg tagttttgt aattggatta ccatcagatc cccatgtatc cttaacataa    43200
tcaatgagcc aggtagtcaa gacatcggat ttattgggta gtgttgatga ttccgcagtg    43260
caatttgctt tagcatccga gaataactgg tagtctgaat gtaatatata acaagaaccc    43320
tggtaatata aaccattaca gctttctttg tgatcatatt gcgtagtgct agacgcaacc    43380
tttctatgag tagatgatgc agcagcaacg gcaacagcgg cgtcagtaat agcagcctcg    43440
ttagcagaca tgcattgatt taggcgcact atgagaaacg cggacatggt aatcatagat    43500
agtagtgaaa taaccataga tattctaata catagaccaa tcacgcgttt gcgtttattc    43560
tttccctgaa ttttgtctct gtaaacagta gcggagaaca cagatgtctg ctcttcgtcg    43620
ttttctggtg tcatcatgat aataaatgtt atttatgtca cgatgtgcct tctttgttct    43680
cctccctact aacgaccta gttttccata ttttgattta ttatcaaatt aatttagtaa    43740
ctgtaaatat aattatgaat tgtttccaag aaaaacaatt ttcaagagaa aatttattaa    43800
aaatgccgtt tagaatggtt ttaacgggag gatctggatc tggaaaaact atctatttac    43860
tatctctgtt ttctacacta gttaaaaaat ataaacatgt attcttgttt acaccgttt    43920 ataatccaga ttatgatgga tacatttggc caaatcatat taatttcgtt agtagtcagg    43980
aatctctaga atataatctg atacgaacta aaagtaacat agaaaaatgt attgctgtcg    44040
cacaaaatca taaaaaatca gcacactttt tacttatttt tgatgatgta ggcgataaac    44100
tatcaaaatg caatactcta atagaattct taaactttgg aaggcattta aacacgtcta    44160
ttattctact atgccaaact tatagacacg taccaatatt aggacgggct aacattacgc    44220
atttttgtag ttttaacatt tccatctcag acgcggaaaa tatgctacga tcgatgcctg    44280 taaagggaa acgaaaggat atattaaaca tgttgaatat gatacagaca gctagatcca    44340
ataatcgatt ggctattatt atcgaagact ccgtattttg tgaaggtgaa ttacgtatat    44400
gtaccgatac cgccgataag gacgttatag aacaaaagtt aaacatagat attttagtaa    44460
atcaatattc gcacatgaaa aagaatctaa acgctatatt agaaagtaaa aaaacaaaat    44520
tgtgcaatag cgatcaatca tcatcgtcaa aaaatgtatc ataattataa ttattaactt    44580
ttgtaacaat agtcctattt agagaaagtc tatcgataga cgatcccaat ttgtaaattg    44640
ttccactact tgtcactcca tgatatgata aatccatgta aaatagcatc atctttagat    44700
cattaattgt taccttcccc aatacaacca aatcatcatg atatatacct cctccagaca    44760
agtatttaac aacggtagaa tgctttggct tataaaatac aaatgacatt cccttatgtt    44820
taatcttaat cttttcttta gttattgaat cgttacaatt ataaaatgat gttttttcca    44880
aaaacctaag tgtatttaaa atagatgcca tgttaaaaat gtccgccgtc gacttttgg    44940 aacgattgat aaaagctggt gtttatattt atgttttacg gacaaagtgt gtaattgcag    45000
ctttactagt aaaaaactat tccataaaag acgaataaga tacaaacaca aatgttata    45060 taatatttaa atggaagacc ttaacgaggc aaacttctca catttattga taaatttatc    45120
taataataaa gatatcgatg cgcaatacgc gtctacatta tccgtggtac atgaattgct    45180
atccgctata aattttaaaa tatttaatat aaacaaaaag tcgaaaaaga attccaaatc    45240
aatcgaacaa catcccgtcg ttcatcatgc agcatccgcg ggaagagaat tcaatcgtcg    45300
ttgaactcga accctcattg gctacattta tcaaacaagg atttaataat ctcgtaaaat    45360
ggcccttgtt aaacattgga atagtttgt ctaatacatc taccgctgtc aatgaggaat    45420
ggctaactgc ggtagagcat attcccacca tgaagatatt ttacaaacat atacataaga    45480
tacttactag agaaatgggg ttttagtct atttgaaaag atcccaatct gaacgcgata    45540
```

```
attatataac tttatacgat tttgattatt atattataga taaggataca aattctgtaa   45600
ctatggtaga taaaccgacc gagttaaagg aaactttgtt acatgtattt caagaatatc   45660
gtttaaagag ttctcaaaca atagagctta tagcgtttag ttcaggtacg gtaataaacg   45720
aagcatagt  ttcaaaatta acatttttag atgtggaggt atttaataga gaatataata   45780
atgttaaaac tatcatagat ccggattttg tatttagatc tccatttata gttatttctc   45840
ctatgggtaa actaactttc ttcgtagaag tatattcgtg gtttgatttt aaatcgtgtt   45900
tcaaagatat tatagatttc ttagaaggtg ctctaatagc caatattcat aatcacatga   45960
ttaaggtagg taattgtgac gaaacagtat cgtcttataa tccagagtct ggaatgttgt   46020
ttgttaatga cttaatgact atgaacatag tcaacttttt cggatgtaat tctaggttag   46080
aatcatacca tcggttcgat atgacaaaag tagatgttga actatttatt aaagcattgt   46140
ctgatgcgtg taaaaaaatt ttgtcagctt ctaatagatt ataaatgaac tctctatcaa   46200
ttttttttat tgtggtagct acggctgcgg tgtgtttact ttttatccag ggttactcaa   46260
tatatgaaaa ttatggcaat attaaggaat ttaatgctac tcatgcagca ttcgaatatt   46320
caaaatctat aggtggaaca ccggcattag ataggagagt tcaagatgtc aacgacacaa   46380
tttctgatgt aaagcaaaag tggagatgtg tggtttatcc aggaaacggt tttgtatccg   46440
cttccatatt tggatttcag gcagaagttg gacccaataa tactagatcc attagaaaat   46500
ttaacacgat gcaacaatgt atagacttta cattttctga tgttattaac atcaatattt   46560
ataatccatg tgttgtacca aatataaata acgcagagtg tcagtttcta aaatctgtac   46620
tttaaatgga cggaactctt ttccccggag atgacgatct tgcaattcca gcaactgaat   46680
tttttctac  aacggctgct aaaaagccag aggctaaacg cgaagcaatt gttaaagccg   46740
atgaagacga caatgaggaa actctcaaac aacggctaac taatttggaa aaaaagatta   46800
ctaatgtaac aacaaagttt gaacaaatag aaaagtgttg taaacgcaac gatgaagttc   46860
tatttaggtt ggaaaatcac gctgaaactc taagagcggc tatgatatct ctggctaaaa   46920
agattgatgt tcagactgga cggcgtccat atgagtaact taactctttt gttaattaaa   46980
agtatattca aaaaatgagt tatataaatg gcgaacatta taaatttatg gaacggaatt   47040
gtaccaacgg ttcaagatgt taatgttgcg agcattactg cgtttaaatc tatgatagat   47100
gaaacatggg ataaaaaaat cgaagcaaat acatgcatca gtagaaaaca tagaaacatt   47160
attcacgaag ttattaggga ctttatgaaa gcctatccta aaatggatga gaataaaaaa   47220
tctccattag gagcccccaat gcaatggcta acacaatatt atattttaaa gaatgaatat   47280
cataagacca tgctagcgta tgataatgga tcattgaata caaaatttaa aacgttaaac   47340
atttacatga ttactaacgt gggtcaatat attttatata tagtattttg tataatatct   47400
ggtaagaatc acgatggtac tccttatata tacgattctg aaataacgag caatgataaa   47460
aatcttatta atgatcgtat caagtatgca tgtaagcaaa tattcacggg tcaattaact   47520
atagctctga gaattagaaa taaattcatg tttataggat cacccatgta tttatggttt   47580
aacgtaaacg gatcacaggt atatcacgac atatatgatc gtaatgccgg ttttcataat   47640
aaagagatag gtagactact atacgcattt atgtactatc tatctatcta taagtggtag   47700
atttttgaat gatttcgcac tattaaagtt tacgtattta ggagaatcct ggacatttag   47760
tttgagtgtt cctgaatata tattatatgg tttaggatat tctgtttccg atactattga   47820
aaaatttagc aatgatgcta tactcgttta tattagaaca aacaatagaa atggatatga   47880
```

```
ttatgtagag tttaataaaa aaggaattgc taaggtgaca gaagctaaac ccgataacga    47940
taagcgaatt catgctataa gacgcatgaa ggctgaacgt gaaatcgctc gtaaaaactg    48000
cggaggtaac ccatgcgaac gtgaagaggt tggaatatca actagatgcg gagaaagaaa    48060
aagttaagtt ctacaaaaga gaactagaac gtgatcggta tctttctagt agatatctta    48120
cctcttcttc agatccacat gagaaaccat taccaaatta tacatttcct cgcattgaag    48180
tagctccgtt gatgactgag gataaagaac cagaacctgt agaagtggtg cctccatcgt    48240
ccacagacgt taccgaaccg attagtgatg tgacaccatc ggtggatgtc gaaccagaac    48300
atcccccagc tttctgaata tcagacttca gtatcccaag tagcagttac acctccacca    48360
aaacctaaaa ctccacagat tttcgaatat cagacgtccg attctatagt taacaatcca    48420
cgcccatttt ataattcgga tctcgaattt gatgatattg atatgtatct actaccaaac    48480
tagaatatta caccagaaaa gacggtttga gatcaacttt atctaatggt ttataaaacg    48540
aaggaggcct tcgttcgaaa tctaatttaa cttttacgcc tctggcgttc atttgagtaa    48600
gaaatacttt agatacgtgc gtggtatcaa ttttttgttaa gagaggagag agattaagtt    48660
ttgaacatct aagacatgta ttaatacccct tgatttgtgc tgctatgtct ccacaatttt    48720
cacaaacata cacatcttga taatcttctt ccgaatcttt caaaacttct gtaatagtat    48780
tggctgcacc atgcgctatt aaacagtctc tctccatttc tccgaacttg atacctcctc    48840
cacgttttcg tccctcattc gcctgtctaa tgagcttcgt ctttttacct ctacatctaa    48900
cggttgcctt gtcctgagtt aaatgcctca gacgcaagta ataaattggt ccaaaaaata    48960
ctttggatgc ataaggctta tccgtttcag gatcatagag aatctttcca caaaagattt    49020
tatccgataa ttcttcatca gacaatttcg gatttgaatg ctcataacat tgtttagcga    49080
attgcatata tgtatcgatg gatgtttcgt tactactagg aaaacagaca ggtcggtttt    49140
ctcccttatt gttgtacggc ttagcagaat atgcggctgt taaaataacc tctatcaaca    49200
tagatatagt ttttctagag aagatggatg tagaattaat aatgacatct ggtgtgatac    49260
cattttcatc gtatggaagt tccgtttcat ccgcgatata cgcgactgtt cccttttgac    49320
tcgttctagt ggtaaatttg tctcctagaa tgggtcttct ttctttcatg gttaatactc    49380
gtaccttaac tttgtcagta agttctactt gtactcgttc aacgcgagat ttgtacatat    49440
cggtatattt ttcggaaaca tcaaagctaa tctgattatc tctagcaaaa tcatcttcaa    49500
gagttcttga tgagatattt cgtgctatag cgtctccgga ttccaagaaa gcattcagtc    49560
taactaatcc attactttct aatttttgaat aggcgttaga cctatctctt tctttgttat    49620
taaagttttc caacggaatt tctacttgat gtttcttggc tgtaacaata tcgagaccgc    49680
ctctctgaat aaattgtttt ttgatgataa ttccatcctc ttgattgata cctttgtacg    49740
acattaatgc tatagtaaca tgttggccga agcaattagc cgcaatcttt gaagtttcta    49800
aagccttact aatcacgatt ggcctctctg gatacatcaa atgaattcca ttgtctattt    49860
tatttcgtat atccgagctc agacaagaga tagcttgttt agcttgagca catccaagaa    49920
tagctctggg tccagaattg tgattgattc ccactagtga agatgctaca tatccatctc    49980
taaattcggc aggaaagtca cataaatcgt attgctttct ttcatccttt gacatcattc    50040 taaattttg aaccgattca catacgttac taaaagtaaa ttgttctata tctaccattt    50100
cgatgacatg cggaaactct ttctgaatgt cagagaatgt catgtcgtct aatctgcttt    50160
ctaactccgg acacacatcc atcatgagct ctccgttatc cacaaccaag aatggtctga    50220
ctaatcttcc cgctccaata ttaatgcgaa tttcattcat gtgatcccta actaaagtaa    50280
```

```
tacctacctc caagttaccg aagaatccca tccgttttct acgtctaaag tcagttacaa   50340
aatcacatat catatttgga ttaagagatg cgactagagc attttctata gtgattggaa   50400
atcctgtttc aaagtaactt atatcatctt tataatatga tctgatatac tcacaaattt   50460
tcttttccaa atccaaatac tcagacgtta gtatatttgt aatggaactc aagacagaca   50520
attgagatac taaacctacc tgaggacctc tttccggaac gtccgatgaa caaaagtaaa   50580
gatattgact tggatggtat tttctgacag aaaacatctt tgaaatcttt acttgatccg   50640
gataaaatcc aacactccta ggaatagaaa tattctgcat ccatgaatag tgaggatgtg   50700
ttcgataact accgtctgac ttttttgaact ttccactcaa tagactagaa aatgcatgat   50760
taagtccagg agttgttagt acatgaatgt ttaccgcgta agtgcctctg ttcttgtgat   50820
tgttcatgat atcgtttcgg atgttgccta tgtaattctc taattcatca tgtgccaacg   50880
tctcaaaata tttgccgtac gttaggatgc gatgacaaac catcgaatct ctatctggat   50940
atctagaagt gtggtagata cagtagagaa actttcttag taaagatatc atataaaatc   51000
cctttagttg atcgggtgta tagttcatat gaggtaaaaa gttatgcagc atttcatatt   51060
tgaactcgtt gatcgttaac tgagattttt gtttaatgtg ttcagcttcc accaggtcat   51120
taatgtatgt atcaatatta aagtcagtaa tagattcagt aattcgttta gcactatcta   51180
ttatcgcgtt tactagatag acaacttctg gaggcatatc gtatgataaa ctacgtctaa   51240
tgaattctag actcactcta gataaatatt gagacagcaa aacaatattg accgttataa   51300
atgtctttgt cgatgatata ttcaacgctt ccaattgtga tatatccaga gatatcttgt   51360
aatggcgata tcttgtcggt aatacattag gaggggatac ggaggaaaac gagaaagtga   51420
atgagtttgg cttaacaacc ctaaattttg gccatgttgt aatcttttct actagattaa   51480
ttcctacttt ttcgacagat tgtttattga taaagactcc acctatgaca ttaggaacaa   51540
gatacttggc tgtatcaagt ggatttttat tcccgtatcc tattagtagc ggaattttta   51600
tcaaatgaga atcttttccc tcataactac ttattttagt gatggatata ccctctttgg   51660
tcattacctc tttaaagata tttacagtga acgtggctaa tgcgtcataa ctcttacctt   51720
taatactcgc gattataggt gagtaatctg gaggagtcac tttaacattg ctaatttcta   51780
tcataattcg ttctgtatta ttcttaaacg ataagagtgg ccgcttgacg gtcaagattt   51840
catgcaatcg atgcaatata aaattagaat acgatacata ttggaaatgt aacggtctat   51900
aaaaaactcc ggctttagga tcaggcacca aaaacttata tccgagtcgt tgatccattt   51960
ctgaattagt gttttttttt catttttagaa gcaattcttt tagacgatct accgattccg   52020
tttctatatc tatgctattt aaaatagtcg atctttcctt catcatttct atcatattct   52080
cggatttagt cacgtaattt atacaatcct ccagagatcg taatgctaca atattgagct   52140
ttttcccctt aaaaaacttt attttgctat cctcatctaa cagagagggg aaaacggtat   52200
gatccaacga cttaataaat gtcaggttaa acatccctat tttgaaattg ctaactccat   52260
aaacatcgtg ttcagccatt tcttaatta ggaataattt ctcatctaat gccgtagccg   52320
tgagtacgtg gttacaaaca ttagctactt ctttaaagta ctcgtttggg atgatatcct   52380
cgaacaacag aaataaatta taatagacat agaataattt gtcaatcatg tgtatacacc   52440
ccttttcatc cttgtccttg gatagaataa tgtgcatagt agaatccttg aatatttttca   52500
cacatgttct attagtaaaa ataatttcta tagtttgtaa tatagagctt tttccacgcg   52560
ttactataga gtgattaatg atatctactc tcattctctt agaaatggtt ttgatccaag   52620
```

```
gttgattaat gttggacctg actgtagtgc tcagatactc atcagacttt ttaccggaaa    52680
agtaatttgc attagtgcct ccatgtacag ttttctttat ttccccataa ttgacctttc    52740
tcttcttatt ggtagtttta atatatgata caagagatga cttttccctc tcaaatatct    52800
ctactgtacg agagctaata ttgctattat ctgagtttat atcgaaataa tgacaacatt    52860
tcacttgtga agaatcgtta aataccggat acgtattctg attaataatg tgtttagtaa    52920
gttggatgtc gcaatacact agtttcttaa tggcatgatg tatatcttta ttatacacta    52980
tattatcaaa catatcctct gaggaaatgc gttctttcat aagaccatat atatctccta    53040
tttcatcgca acttattaga tgaaagttaa aaatagttct ggcatatcta tcttctattt    53100
catgtagaaa ggtaaataga ttatccataa tggcgttact aacgttatta cattttttt     53160 atgtaatttc tagatttaca cctattataa ggtgtataat tagtattcca tttatctaat    53220
acgtatctca tagccaaatt gaaactatcc gctacatcgt ctaatttgcg tctatccgga    53280
acggagtctc gcaatccgaa tgtgtccatc caatcaagaa atgcttcgac cgatctcttt    53340
tttcgatctc tatatgaatt accagacatg acaggcgaga cgcaaataac tttggcagcc    53400
gatgtatgat ataaaaagcc tttaataaaa tagataaatt tgacgtacgg cgaccttcta    53460
ggctgacgtt ctagaagaac tgtagtgtat tcatattgtg acaaatcttt agctatgtgc    53520
cttccccaat cagaactcca gtctaatttt gatatatcca ataccctaac ggagttatcc    53580
ttgacttcta aaacagttct ggcaggattt tttgcaccta tcaaaggc gcatattatt       53640 tcactcgaat aatctttttt tgacatcggt gacgatatta agattgaga cgaactggtt     53700 aaagttttcca tatatagtct caatactcgg gttatttaaa caattagtat tttcaatatt   53760
gaaatttaca accttacaat tttctatttt gaaccgcatg ttattaacta acgttataaa    53820
atccgcttct ggatatccca acattctct gcttaaatca aatgctgatt ggttttttat     53880
ttttcgtttt acagttccgg atttattaat ctcatcaact aactcatcga cagttgcgca    53940
ctcattaata tctaatttat tagtcaattg ctttaagcct gcactaccaa ccttagaaga    54000
atactttccg ttaacataat agtctcgtcc tatagtgtct ataattcgtt ttattacttc    54060
tcctctagtt tctgttccgt ttccatcata gtcgtataaa atggaaaatg tgttttttctt   54120 ttttactttt acaaatgtat gttctctaac cttggatcgt attaaatggt ctacatcttt    54180
tactaatatc tttttttcctg attttgttat aacgctagga ataaaaatat tatctcctat   54240
acgatctacc ttgatggact caatatacat gaatgagaat ttgaaaaagt ctacaacttg    54300
ccgcctaagt tctcccaact taatatacga tatggatatt tttggaaatt tatcatcgaa    54360
agagcgttct ataatagagt ataactcgtc gtcaaataat gtgtcttcct ctatttcaat    54420 ttctaaaatat ttgggtatgt ttaatccgta ctcactagct agtttaaata tattaactgg   54480
agactgatat tttgatatag catcttccat tatccatcta ttgtttaaca aaacaaatct    54540
cagaaagtct attccgttat cgctgtctaa tactttgtta cacgcacttc gcatatcatc    54600
tggtatttga aaagagtttc cagatccaag ttctaccata ttttaccct tcgaataaat     54660 aaagacgctc ccaaaatata ccggtaagaa aatgtaatag cccggatcaa tattaaacgg    54720 tttattttt acctcatcat aataatcaga tattgacgtc tcgacattag ctacctttg      54780 cacgcctatt ttccagtaag tagatgttcc ccattctacc aaagaattat acttttctat    54840
agccgcagaa tctgaaaatt tcaaacttt gtacagacta agtaattctt ttaagttagt     54900
taaatcagcg ctagaagtca tgataacttt attttaatc ctatgttatt tcattcttat     54960
ttttaatatt atagtacctg caatatctga aaaaatgaga cgcgaacgag ccgcatacgt    55020
```

```
aaactacaaa cgtctaaaca agaatttcat ttgtgtcgat gatagactgt ttagttataa   55080
ttttacaaca tctggaatta aggcaaaggt ggccgttgat aacaaaaatg ttcccattcc   55140
atgttccaag ataaacgagg tcaataataa taaagatgtc gatacactat attgtgataa   55200
agatagagac gatataccag gttttgcacg atcgtgctat agggcatatt ctgacttatt   55260
ttttactacc taaatggata gcaccaatgt gcgttccgga atgaagagcc gcaaaagaa    55320 gcccaagact acagttatcg atgacgatga tgattgcatg acgtgttctg cctgtcagtc   55380
taaattggtt aagatttccg acatcacaaa agtatcattg gattatatta atactatgag   55440
gggtaataca ctggcctgcg cagcatgcgg atcgtcgctt aaacttctta acgattttgc   55500
gagttaaata ttctatttaa tacacgttct tctctggagg atgttgtaca tacagaagtg   55560
ggatcggatt cttgatgttt ccgataactt ttttgtttaa atcctagttt atctacagac   55620
agactaataa ttcgttgaac gaaatttcct atcatgtact ttatttcttt gatggatgtg   55680
ctaggaaata catataccgt cctatctaat agttctgttt ctcgacatac cctccctagt   55740
aattgctcta tttgcatatt gttgattact gccgagcaaa tgaacaaaga atccaaacta   55800
ggaatatcta aaccagtacc ggaataaaat aaggtggata cgaatataaa tctatttagt   55860
tccttgattg atttgaccat atctggagta cgtctatttt gggcgtctcc tataaataca   55920
acctctgatc cgaaaaaatc taataatcgt ttgtagaaga ataccatatg ttcacgtagt   55980
ttagtaataa ctaaaatgcg attaatagtt cctgacttga attcttctac cagggtatta   56040
agaataagtt gatttctagg ctcgtctaca gataataact tctcggtata tatatgatat   56100
ttattagatg gtccatctaa tcgttttatc atatgtctaa tattatctgt ggaatatggc   56160
tcaaaaaaac tatctactgc atagatagtt tttttttagat cggataactt ggcaatatta   56220
ataatactgt tacaataaat tctgttagat ggtctaggtg tagcagttaa aaaataacac   56280
atcatcggag gataatacgc taaaaatctt gtaactgctg tattgttcat cagattatac   56340
gtatgtgatt catccaagat gaacaaatca taatgcttat tgatatattt acaaaaggca   56400
tcgtttgtca gatgtctact gactactatt aatacatccg gactttgagt ctttagttcc   56460
tttaatagac tacttactcc atctatggat atcttatgtt ccaatccgac tgcctctacc   56520
tgtgtcttcc attgatgtat taacatttta ttgggtacgc aaatgacggt ttttctaccg   56580
tgtgtagcca taagataaca cgtggtaata gtcttaccaa atccacacgc caagtgaaga   56640
gtgatgtata gaggacgttt tgattcgatc attttcctca tattagaaac tacttcagat   56700
acgactttgc gttgaagagg ataaacttt ggcgcatttg ttggattgat actagtaatt   56760
ttattatcgg tcgttgttaa tgtttcaaat actagactcg tctttacgga aggagaggcg   56820
taaaatccct taggtatcag aaacttaaag gatgatcccg gttcaacttc tacgaaatcc   56880
ccgtcttcgt taaaaagact tagggggttga ccacaagtca ttttttttag ttcggcataa   56940
agattatact ccatctttaa tagtgacatt ttttaatata taaatgagtt atttaagata   57000
ttacaatatg cttgacgact tctctgcggg tgctggagtg cttgataaag atttatttac   57060
agaggaacag cagcaatcgt ttatgcctaa agatggaggt atgatgcaaa acgattatgg   57120
aggaatgaat gattatttgg gaatcttcaa aaataatgat gttagaacgt tactcggttt   57180
gattttgttc gtcttggctc tatatagccc tcctctaatc tctatattga tgatatttat   57240
ctcatctttt ctattgcctc ttactagctt agtattacc tattgcttag taactcaaat    57300
gtatcgtgga ggtaatggca acactgtggg aatgtctatt gtatgtattg tagctgctgt   57360
```

```
aattattatg gcaatcaatg tatttacgaa ttcacagata tttaatatta tttcttacat    57420
tattttgttt attctgttct ttgcatatgt gatgaacatc gaaagacagg actatagaaa    57480
aagtataaat gtaaccattc ctgaacagta tacctgcaac aaaccttata ctgcgggaaa    57540
taaggtaaat gttgatatac caacatttaa cagtttaaat actgacgatt attaaaaatg    57600
ggggcagccg ttactcttaa tagaatcaaa atagcaccag gaatagcaga tatacgagac    57660
aaatatatgg aattaggttt taattatcct gaatataata gagctgttaa gtttgcagaa    57720
gaaagttata cgtactatta tgaaacatct ccgggagaaa ttaaacccaa gttttgtttg    57780
atagatggta tgtcgataga tcattgtagt agttttatag ttcctgaatt tgctaaacaa    57840
tatgtattaa ttcatggaga accatgtagt tctttcaaat ttcgtcctgg atcattaatc    57900
tattatcaga acgaggtaac tcctgaatat attaaggatt taaacacgc tactgattat     57960 atagcatccg ggcaacgatg tcattttata aaaaggatt atctcctggg cgatagtgat     58020
agcgtggcaa aatgttgttc taagacaaat accaaacact gtccaaaaat atttaataat    58080
aattacaaga cagaacattg tgatgatttc atgactggat tttgtagaaa cgatcctgga    58140
aaccccaatt gtttagaatg gttacgtgca aaacggaaac cggctatgtc tacttattcc    58200
gatatttgct ccaaacatat ggatgcgaga tattgttctg agtttattag aattattcgt    58260
cctgattatt ttacttttgg ggatacggca ttatacgtct tttgtaacga tcataaagga    58320
aatagaaatt gttggtgcgc gaattatcca aaatctaatt ccggagataa atatttagga    58380
cctagggtat gttggttaca tgagtgcacc gacgaatcta gagatagaaa atggttatat    58440
tataatcaag atgttcaaag aactagatgt aaatacgttg ggtgcacgat taacgttaac    58500
tctttagcgt taaaaaattc ccaagcggaa cttacgtcta attgtactag aactacgtcc    58560
gccgttggtg acgtacatcc aggagaacct gtagtaaaag ataaaataaa actgcctacc    58620
tggttgggcg cggccataac attggttgta atatctgtta ttttctattt tatatctatt    58680
tattcgcgta ctaaaattaa aacaaatgat ataaatgttc gtagacgata attcgttgat    58740
aatttattct acatggccca gtacattgtc cgattcatcg ggtagagtca tcgttatgcc    58800
agataataga tcattcacgt ttaaggaagg gtttaaatta tgatgaatcga taaaatctat    58860 attgttggta aacccgtcgt ctatagatct attaaagatt agagtatata aacatcgcat    58920
aaaatggatg ggtgatatat tcgtattatt tgagcaagaa aatatcccac cacctttcg    58980 tctagtaaat gataagtaat tacgagccgt tgctgctgtt agttataaca tgctgtgtac    59040
tactatttaa ttttaccata tcttcgaaaa caaaaataga tattattttt gcagtacaaa    59100
ctattgtttt tatatggttt atattccact ttgttcattc ggcgatttaa aattttatt     59160 agttaaatgg atatgatgct tatgattgga aattatttt ccggcgtgct aatcgctgga     59220
atcattcttt tgattctttc gtgtatcttc gcctttattg actttagtaa gtctaccagt    59280
cccactcgta catggaaagt attgagtatt atggcgttta tacttggtat tattatcaca    59340
gtcggaatgc taatttattc tatgtgggga aagcactgcg cgccccacag agttagcgga    59400
gtcattcata ccaatcatag cgatatttcc atgaactaaa ttattatcgt ccatatatct    59460
cgacattgtt gaatcattat tactacttat ttagtgaaaa gatgatatat tgcatacttg    59520
atcaatagtg aagttattgt caataaatga ttggtattct tttgttgatc ggtatttgcg    59580
tagcagttac cgtcgccatc ctatatgcgc tgtataataa gatcaagaac ccacaaaatc    59640
caaatccaag tccgaattta aattcgcctc ctccagaacc aaaaaatacc aagtttgtaa    59700
ataatctgga aaaggatcat attagttcat tgtataatct agttaaatct tctgcataaa    59760
```

```
taaaaatatt tttagcttct aaatggcgga taaaaaaat ttagccgtta gaagcagtta      59820
cgatgattat atcgaaacag ttaataagat tacaccacag cttaaaaatc tactagcgca    59880
aatcggtgga gatgcagccg tcaaaggagg caacaataat cttaattctc aaacagatgt    59940
gactgccggc gcatgtgata caaaatgtat tacatgtaaa ccaaaatcaa aatcctcgtc    60000
ttcttctaca tcaacatcca agggctccaa aaatacttct ggtgctccta gacgtagaac    60060
aacagttact actacatcgt acaatgcgat ggatggtcag attgtccaag ctgttactaa    60120
tgctggtaaa atagtttatg gtaccgtcag agacggccaa ttagaagttc gtggaatggt    60180
cggagagatc aatcacgatc ttctaggtat cgactcagtt aatgctggga aaagaaacc     60240 atctaaaaag atgcctacta ataaaaagat taatatgtcg tccggtatga gacgacagga    60300
acagattaat ccagacgatt gttgtctgga tatgggaatg tattaaatta aataatttta    60360
attcgtttaa cgaatatctt gagtataaac aatacaatat taagaaccgg actgttaccg    60420
attcctagtt tgatgctac agcatcgcag tcatctccga tctccacatc gataatttct     60480
gaagtgatat cggtactcag tcctttgatt tcttcaaatc cgagttttag caatgcttgc    60540
tcgataatat ttatgacaat aataatcacg ttagtgacga taattttcg ttttctactt     60600 tcgtgatatt gtttaatcgt tttatagatt ctatctattt catcctctga acaaacatcc    60660
aagtcctcga ctgataaggg agacccgttc aaatttgcat aattaacgat ggctatacgc    60720
ttattaactt ctgttgattt atacggagtc ttaccaaata gtattctggt aaaattatct    60780
aaattatcag atgattttgt attagatcgt tgatttctaa gattaaccac ttcatcctcc    60840
aacatctgaa ttcttttatc tttatcataa actactccca aggatggtgt ttgtgttggc    60900
atagaagata tcatagatct agattccatt attgcttcag cattttcga tactgtaata     60960 ttaaatcttt tttctcgttg ttgacgttgt tccgatatca ataactctct acgaaacgta    61020
ggaggtggag tatcgtcaat aatagtagta tgaggttgta ctcgttcgat aatagtggcc    61080
ggagaatcat catctggaaa tagatcttca ttaagttgtg aggatatttc ctctggagat    61140
gacactacgg cggcattatg ttctctatct accacgttgt taacgtgagt tagaatagac    61200
atttgacgaa gagttatttc ataattttg ttagatggat aattatcttc tgaaaactct     61260
gtaattaaat cgttttgtat atccgtcact ggtacggtcg tcatttaata ctaaataaat    61320
gatgcctatt aagtcaatag ttactcttga tcaattagag gactctgaat atttatttcg    61380
tatagtttct accgttcttc cgcatctatg tctagattac aaagtatgtg accaacttaa    61440
aacaaccttc gttcatccgt tcgatatatt gcttaataac tcattaggat ccgtaactaa    61500
acaagatgag cttcaggctg ctatatccaa attgggcatt aattatttaa ttgataccac    61560
gtcacgtgaa ttaaaactgt ttaatgttac acttaacgct ggaaatatag atattattaa    61620
taccccaatt aacattagtt cggaaactaa tcctatcatt aatactcaca gcttttacga    61680
tcttccacct ttcactcaac accttcttaa tattagattg acggatacag aatacagagc    61740
tagatttatc ggtggttata ttaaaccaga tggctccgac tcaatggatg ttctagcaga    61800
aaagaaatat ccagatctta actttgataa cacttatttg tttaacatcc tctataagga    61860
tgttattaat gcaccaataa aagaattcaa ggcaaaaatt gttaacggtg tattaagcag    61920
acaagatttt gataatctta taggtgttag acaatatata acagcacaag atcgaccccg    61980
ctttgacaac gcttataaca tcgcagatgc tgctagacat tatggagtta atcttaatac    62040
attgccatta ccaaacgtag atctcactac tatgccaaca tataaacatc tcatcatgtt    62100
```

```
tgaacagtac ttcatttata catatgacag agtggatatt tattacaatg gtaacaaaat   62160
gctcttagat gatgagatta tgaacttttg tatttctatg cgatatcaat ctcttattcc   62220
tagactggta gaattctttc cagatatacc agtaaacaat aacatcgtac ttcatactcg   62280
cgatcctcaa aatgctgcag tgaatgtaac cgtggcgctt ccaaacgtgc aatttgtaga   62340
cataggtaga aaccacaaat tctttattaa tttctttaac ctgttggcga aggaacaaag   62400
atctacggct atcaaagtta ccaaatccat gttttgggac ggtatggatt acgaggaata   62460
caagtctaaa aaccttcagg acatgatgtt tataaattct acctgttatg tattcggtct   62520
ttataatcac aataatacta cttattgctc tatcctttct gatattatct ccgcagagaa   62580
aacacctatt agagtttgtt tgttacctag agtagtcgga ggtaagactg ttactaatct   62640
tatttcagaa actttgaaga gtatttcatc tatgactata cgagagtttc ccaggaaaga   62700
taaatctatc atgcatatag actttctga  dacaggattc atgagattct tccaactact   62760
caggctcatg gctgataaac ctcatgaaac ggctattaaa gaggttgtta tggcttatgt   62820
gggtataaag ttgggtgaca aaggtagtcc gtactatatt agaaaggagt cataccaaga   62880
ctttatctat ctgctatttg catcaatggg ctttaaggtg actactagaa gatccattat   62940
gggaagtaat aatatctcta tcatcagtat tagaccaaga gtaactaaac aatacatcgt   63000
cactacattg atgaaaacta gttgtagtaa aaacgaggca gaaaattaa ttacttcagc   63060 gtttgatctt ctcaatttca tggtatcagt tagtgacttt agagattatc agagttacag   63120
acagtataga aactattgtc ctagatattt ctatgcagga tctcccgaag gagaggaaac   63180
cattatctgt gactcggaac cgataagtat cttggataga attgatactc gtggtatctt   63240
ttctgcgtat actattaatg aaatgatgga cactgatatc ttttctccag agaataaggc   63300
atttaagaat aatctgagta gatttatcga gagtggaaat attacaggag aagatatttt   63360
ctgcgcaatg ccatacaaca tcttagatag gattattaca aatgctggta cgtgtaccgt   63420
atccataggt gatatgttgg ataacattac aacccagtca gactgtaata tgactaacga   63480
aatcacagat atgataaacg cctcattgaa gaatacaatt tctaaagata ataatatgct   63540
agtcagccaa gcattggact ctgtagctaa tcgttctaaa caaacgattg gagacttgag   63600
gcaatcatcg tgtaaaatgg cattgttgtt taaaaatctt gctacatcca tctacacaat   63660
agaacgtatt tcaatgcta aagtaggcga tgatgttaag gcatcgatgt tggagaagta   63720
taaagtattc acagatattt ccatgtcatt gtataaagac ttgatagcta tggagaatct   63780
caaagcgatg ctatacatta ttcgacgaag cggatgcaga atagacgatg cacaaattac   63840
tactgacgat ctagtcaagt cttactcatt gatccgtcct aaaattctaa gtatgataaa   63900
ctattataat gaaatgagta gaggatactt tgaacacatg aaaaaaaatc taaatatgac   63960
agatggtgac tctgtctctt ttgatgatga ataaatgtca tgttatacag ctatattaaa   64020
atctgtagga ggactggcgc tatttcaagt agccaatggc gccatagatt tatgtagaca   64080 tttcttatg tatttttgtg aacaaaagct acgaccaaat tcattttggt tcgtcgttgt   64140
tagagccatt gcaagcatga taatgtattt agtattaggc atagcattgc tgtatatttc   64200
tgaacaagat aacaagaaga atactaataa tgataaacga aatgagtcgt ctataaattc   64260
taactccagt cctaagtaaa atattttagt agcgtatcct tatcgcgttt gcttatcttg   64320
aatgaactgg tctttttaa ctcgttgatg aattttgtaa ataattcatt tctatcttta   64380
agtaatttta ttggaagttt tgattccaca gccaatgaac atgtaaattg tgaatcattt   64440
tctatgacca gttgtaactt ttcatacact gtaatcaata cagtatttac catttgatta   64500
```

```
attacagcgc ccgtactagc actccattga acaagatcag attttagatt aattagataa   64560
aatctatatg ttatttcaga taatgaactt accagataac tctcttgacg gatattaaaa   64620
atgccagatg aatgttcatc tcgaatagcc agagctactg tagagtaata cggttcaaaa   64680
tcataaacgt gatagtttcc aaactggtat ccgagttttt cttggatgat ggatacttga   64740
gagttgaatt taaatttctt actatgttca ttatatagtt ctggaaagaa tgcttcaatc   64800
attgtttctg taagtttgca tccttttgat gcgatagtta aaagtgctat ataaggcgcc   64860
acgataatgt tatttttttt ggtaatagtg acgtctttta cagcgtcaac gcatctgaac   64920
aaataatgaa tctctctatg atctaaaaaa taaagtcttt gtaaaaagaa tcgtagtgct   64980
agttttctct catcatcctt agatctatgg gcgaatagac gtctactacg ggatataaaa   65040
ccgctatttt cctttatcat aggtgttgtt tgatctatat ttacctcccc tagttctacg   65100
gaggcctcca aattaagatc tggtactggt tcgaacattg taagacttac atcatcggta   65160
gtagattttc actttacccc acgatataaa tatgcgatat atagtaagtc cgcaattggt   65220
attacaggtg ggtaaggggc aggaggtaga acgagcccta tatctcactc catatgatta   65280
catagatgag aagtcgccca tatattattt tttacgaagt catttaaata tacaacagcc   65340
ggaaatagtt aagagacata ttctattgac gcttcgaatg actcaattaa agggatattt   65400
aggaaatttg ttagatatta aggacgatat tattatctat tctcataaga ataatttgga   65460
atatagttac gttgataata ctattttta tcccttcgta tatactcaga aaaaaacact   65520
actaaaaaac gatagctttt tatacaatgt atatcctgga gcgtgtgact ttttggttat   65580
ctgggtggcc agagcgtgcg atacatctat tccggaattt ggatcgtatg aagatgtaga   65640
taataatatt atcaagtttg aaacaatgtt gatggaagta tttccacaac tagatttgga   65700
cattactgta gaatcaaagt ttaacaatat atttcgtacc aatctaaaac taactgggtt   65760
aaaaaagatc attcagcgag ttcaagactt ggacattaat tataagtcgt tgttatctag   65820
atacgatgaa cactttatta atatgaccgg taatcatttt attctaaacg atgaacagtt   65880
aaatctctcc atttgggact tggatggtac attagcgtta tctagcgacg gcgataccgt   65940
gatgattaat aacgtaaaac tatttacaga tcttgtgtcc gatatagata cacaaatgga   66000
acgcatcaag ggagatataa cgtataaggt acatttggcg actcctatca attctagaat   66060
aaaattggat atcgagacta gcttcatttt tatagagacg gcgactaata atattttact   66120
atcctcggat aaaaaaatat ctatcatttt ggccaaaaac catatatcta ttaaagtgaa   66180
aaaccatatt cctaacatag aaaaatattt tacattttta gttattgcca ttaatgccat   66240
gtttaatagc gttcaaaagt ctgctgattt taccaaagtg gaaactgttt actggtctag   66300
gatatgccaa aatacaaaga ataagaatag aaaacccatc attattaatt atctagatcc   66360
tggaatgaaa aaaatcagta acaactttta cagatccgat gagaaagaag tctttattaa   66420
tgataacggc ataatgttta catgcatgga tcctttgggg aaatataata aggtgggatt   66480
tcttaatata tttcatgata tgtggaaata ttgtatccct tgttgttttc tacatgatca   66540
atctcatcga agtacatttt catcgtgtgt tcatcaaatc gacgttgaga aaaagatagt   66600
aagtccgtat atccttaatt ttggtaaagt tgtaacagaa tccaaaatgt catttctccc   66660
tattatcttt gacgccttct taaatgatgg aatgactgct aatatggaac aagataataa   66720
acgactaaag gaaactagtg gatatcatat agttagatgt tgtgctggtg atgatatagt   66780
tcgtttacga actacatctg atattattca gtttgtaaac gaggataaaa atattcttat   66840
```

```
agttaacgac atggtatatt ttccaatgaa cgcgtccgat ataggaaaga aaatacatat   66900
actcattcaa gaaatagttc atgaggtaat gatagtaaaa aagaaagagt ctagtgataa   66960
aatcgatttt ttcccaccca actataagtt attgaaggat ctatttccaa aacaaactat   67020
tcaaactcct attcaatctg acgcgggaat ggtgttaaca accgatggat tctacataga   67080
tggaaaactt tttaacgaag atctgtcgtc taaatacgtt acatttacaa aaaatgttat   67140
tgcgtctgat gccgtagcta aatatttttc tcctttgttt aaatacgtta tttcagaagc   67200
taaagataga tttatcaaaa cgtggatgat taatattatg atacatatga acgtagatcc   67260
taataatata ataccgacgt tagaaaaata ctatcccaac tctggaagag cacaaataaa   67320
ttaaacaact aaatctgtaa ataaataatg gacaaactta gagttctata cgatgagttc   67380
gtcaccatta gtaaagataa tcttgaacgc gagactggtc ttagcgcatc agatgttgat   67440
atggattttg atttaaacat ttttatgacg ttggttccag tcttggagaa aaaggtatgc   67500
gctattacac caactataga agatgataaa atcgtaacta tgatgaaata ttgtagttat   67560
cagagttttt cattctggtt ccttaaatct ggtgccgttg tgaaatcggt atataataaa   67620
ctagatgatg tggaaaagga aaagtttgca gccacattta gagacatgtt gcttaatgta   67680
caaactctaa tttctcttaa ctctatgtat actagattgc gtcaagatac cgaagatatt   67740
gtatccgatt ccaaaaaaat aatggagatt gtttcccatt tgagagcgtc gactacagag   67800
aacgcggcgt atcaagttct ccaacaaaac aatagtttta tcatatctac actaaataaa   67860
atcttatctg atgaaaacta tctcttgaaa attattgcag tattcgactc taaactaatt   67920
tctgaaaaag agacattgaa tgaatacaaa caattgtaca ccatttcttc tgaaagtttg   67980
gtatatggaa tcagatgcgt tagtaatctg gatatatcat ctgttcaact gagtaacaat   68040
aaatacgttc tctttgttaa gaaatgctac cctaaaatca tactgtttca gaataacgac   68100
atcaatgcac aacaattcgc taatgttatt tctaaaattt atacgttgat ttatagacaa   68160
ttgacgtcga atgtcgatgt tggatgtcta ttgacagata cgatagaatc tgccaaaact   68220
aaaatatctg tagaaaaaat taaacagacg ggtatcaata atgttcaaag tcttatcaaa   68280
ttcatatctg ataacaagaa agaatataag acaataatct ctgaagaata tctatcgaag   68340
gaagatagaa tcattactat tttgcaagat atcgttaatg aacacgatat aaagtacgac   68400
aataaattgc tgaacatgcg agacttgatt gtgacattta gagaacgata ttcgtataaa   68460
ttctaatatc gttttgaag tttccaaatt ttgataatat agtctagatg gaattttaga   68520
ccatctttgt caaaatcgtt taccgacaac aattctccgt tcttttcgat gactatagga   68580
caagaaccct cctctatctc ttgtataatt acatgtagca tattttgctt catcgtttcg   68640
tcagaaaatt ctgaaactag aggtaatctt cctcgttgaa gcaagttata gctttctgct   68700
attatacccg ctatttcaaa tagacttata cgtctagtat agcgtcgttt aagagcagat   68760
atatgattcc ctatatgttt aagattggaa tgcgcatctt ctatatgagt ggatgctgat   68820
tctacaatct tataagaaga tttgggatct atatcactag tttctagtga ctctccatct   68880
tcttcctctt cttcatcatc ctcgtattcg gtgagatcat cggattcata gtcgataata   68940
tcgtctgtgt ctgccattta atcttataat cgcaattcaa ttttaaagcc ttaaatggac   69000
ttctttaaca agttctcaca ggggctggca gaatcctcta caccaaagtc gtcaatctat   69060
tattctgaag aaaaggatcc ggatacgaaa aaggatgaag cgattgaaat aggactaaag   69120
tctcaagagt cgtattatca aagacagttg cgagaacaac tagctagaga taatatgatg   69180
gccgccagca gacagcctat ccaaccgcta caaccaacta ttcatataac tccacagccg   69240
```

```
gttccaacag ctacaccggc tcctacacca aaaccacgac aacaaactaa tacatcatct   69300
gatatgtcta atcttttga ttggctgtct gcagatactg atgcgccggc gagttcactc   69360
cttccagcgt tgacgccgag caatgctgtt caggatatta tctctaaatt taataaagat   69420
caaaagacga cgacgccgcc atctacccaa ccttctcaga cgttaccaac aactacatgt   69480
acacaacaat cggatggaag tatttcttgt actactccaa cggttacacc tcctcaacct   69540
cctattgtgg ccactgtatg tactcctaca cctactggtg gtacagtatg tacaacagca   69600
caacaaaatc caaatccagg agcagcatct caacaaaatc tagacgatat ggcccttaag   69660
gatctcatgt cgaatgttga agagatatg caccaacttc aggccgaaac aaacgatctg   69720
gtgacgaacg tatatgatgc aagggagtat acgcgtaggg caatagatca aattctacaa   69780
ttagtcaaag gttttgaacg attccaaaag taataagatt gaatattaaa atcacgcttt   69840
cgagtaaaaa ctacgaatat aaataatgga agccgtggtc aatagcgatg ttttttaac   69900 atctaacgca ggactaaaat ctagttatac taatcaaact ctttctttgg tagatgaaga   69960
tcatattcac acttctgata aatctttgtc ttgtagtgta tgcaattcat tatccaaaat   70020
tgtagacgat gactttatat ccgcaggggc tagaaatcaa cgtaccaaac ctaaacgtgc   70080
aggaaataat caatctcaac agcctatcaa aaaggattgt atggtttcca tcgacgaagt   70140
agcatccacg catgattgga gtacgagatt gagaaatgat gggaatgcaa ttgctaaata   70200
tctaactact aacaagtatg acacatctaa ctttactatt caggatatgc ttaacattat   70260
gaataaacta atattgtca gaacaaatag aaacgagcta tttcaactcc ttacccatgt   70320
aaagagcaca ttgaacaatg ctagtgtttc tgtgaaatgt actcatcctt tagtacttat   70380
tcattctcga gctagtccta gaatcggtga ccaactcaaa gagttagata aaatatactc   70440
tccatctaat catcatattc ttctgtcgac tacacgattc caatccatgc attttaccga   70500
tatgtctagt tcacaagatt tgtcttttat ttatagaaaa ccagaaacta attactatat   70560
tcatcctatt ctgatggcac tattcggtat taaacttcct gcgctcgaga acgcgtatgt   70620
acatggagac acctatagcc taatccagca actttatgaa tttagaaaag taaagtctta   70680
taattatatg ttgttggtta atcgtcttac ggaggataat ccgatagtga ttacaggtgt   70740
atcagatcta atttccacag agattcagag agcaaacatg cataccatga ttagaaaagc   70800
aattatgaac attagaatgg gaattttta ttgtaacgat gatgatgcgg tagatcccca   70860
tctaatgaag attattcata ctggatgctc tcaagttatg acagatgaag aacagatatt   70920
ggcttctatt ttgtctatag ttggatttag acctacgttg gtttctgtgg ctagacctat   70980
aaacggcatc agttacgata tgaaacttca ggcggcacca tacatagttg ttaatcctat   71040
gaagatgatc acaacatccg acagtccgat ttctatcaat tccaaggata tttattctat   71100
ggcattcgat ggcaatagtg aagagtggt gttcgctcct cctaacatag gatatggaag   71160
atgttctgga gttacacaca ttgatccatt gggaactaat gtgatgggta gtgctgttca   71220
ttcccctgtt atcgttaatg gagcaatgat gttttatgta gaacgacgtc agaataagaa   71280
tatgtttggt ggagaatgtt acaccggctt tagatctcta atagatgata ctccgattga   71340
cgtatcacca gaaatcatgc taaacggtat catgtatagg ttaaagtccg cagttttgtta   71400 caaactcgga gaccaattct ttgattgtgg atcgtctgat atcttcttga agggacatta   71460
tacgattcta tttacagaaa atggaccctg gatgtacgat cctctttctg ttttcaatcc   71520
gggagctaga aatgctagat tgatgcgagc tctcaaaaac cagtacaaga aattatcaat   71580
```

```
ggattcagac gatggttttt atgaatggtt gaatggcgac ggttcagtat ttgctgcctc    71640
aaaacagcaa atgttgatga atcacgttgc taactttgac gacgatcttc taactatgga    71700
agaagccatg tcgatgattt cgagacattg ttgtatctta atttatgcac aggattatga    71760
tcaatatatt agcgctagac atattacaga actattttag attatgatat ttaaatgagt    71820
tggtacgaaa aatataacat tgtactgaat ccgcctaagc ggtgttcttc tgcatgtgcg    71880
gataatttaa ctactatatt ggcggaggac ggtaaccata ttagggcgat actttattca    71940
cagcccaaaa aactaaaaat attacaggat tttctggcaa cgtctagaaa taaaatgttt    72000
ttatataaaa tattggacga cgagatacgt agagtgttaa catgaatcta cgattatgta    72060
gcggttgtag acacaacggt atagtatctg aacaaggata tgaatattgt atttttttgcg   72120 agtctgtatt tcaaaaatgt acaaaggtac aaaaaaagtc aaacttccat gtgtctaata    72180
aacttattca tttgagaaat gtattgcgga gattattgtc tcatcaatgt tctggagaaa    72240
ttatctcgga actcttggat atcatggaaa aaaatcaaat atccacggat gatgtagatg    72300
caaattttgt atctagtttt cttaaggcta acgagagaat aaataaaaag gattataagt    72360
tagtctttga aataatcaat caagtaaaag atgagaaact gaatctgagt acagaaaaga    72420
ttaatgaagt agtagaaata tttaagcact tggtattctt ttgccaagaa aacactcctt    72480
ctaagacaat taattattca ttcttttttgg ataaaatatt cgatatcact tctgtaacta   72540
aaaatctaaa acctcaaact gttaaaaatt atacgaaaaa taatagtaac caattagtat    72600
gggaaaactt tttagcacat atgagatcta aaaaacgtgt aactatggta gaggattatg    72660
gacacgagta tgttttttgta gatgagaggt tttctacttg ctcattagaa gtataaaaaa   72720
atagttccgt aattaaatgg ctaagcgagt aagccttcca gatgtggtta tttcagcacc    72780
taaagcagtc tttaagcccg ctaaagaaga agcactcgct tgtatactac caaagtatta    72840
taaatctatg gcagatgtgt ctattaagac aaatagtgta attgataagt gttggttttg    72900
taatcaagat ttggttttta gacctattag tattgagaca ttcaagggtg gtgaagttgg    72960
gtatttctgt tctaaaatat gtagggattc gttggcttct atggttaagt ctcacgtagc    73020
tcttagagaa gaaccaaaaa tttctttgtt gcctttagta ttctatgaag ataaggaaaa    73080
ggtcataaat acaataaacc tactaagaga taaagacggc gtttacggaa gctgttactt    73140
taaggaaaac tcacaaatta tagatatttc tctacggagt ttattgtaag cttttttccat   73200 tttaaataga aaatgaataa tactatcatt aattctttga tcggtgggga tgactctatt    73260
aaacggtcta atgtcttcgc agtcgatagt caaattccaa cttttgtatat gccgcaatat   73320 atttctctat ccggagttat gacaaacgat ggtccagaca atcaggctat cgctagcttc    73380
gaaattaggg atcagtatat tactgcgctt aatcatttgg ttctgagttt ggaacttcca    73440
gaagttaaag gtatgggaag attcggttac gtaccatatg ttggatataa atgtattaat    73500
cacgtatcta tctcttcgtg taacggtgtt atttgggaaa ttgagggcga agaattatat    73560
aataattgta tcaataatac aattgctttg aaacactctg atattctag tgaacttaat     73620 gatatttcta ttggcctaac tcctaatgac actattaaag aaccatctac agtatacgtt    73680
tatattaaaa ctccgtttga tgtggaagat acattcagca gtcttaaact atccgattca    73740
aaaattaccg taacggtaac cttcaatcca gtatccgata tcgttattcg tgactcttcg    73800
ttcgactttg aaacgttcaa caaagaattt gtttatgttc ctgaattgag ctttattgga    73860
tatatggtta agaatgtaca aattaaacca tcgtttatag agaaacctag gagagtaata    73920
ggtcaaataa accaaccaac ggcgactgta actgaagttc atgcggcaac atcgctctct    73980
```

```
gtttatacta aaccttatta tggaaatacg gataataaat ttatttcgta tccagggtac   74040
tcacaagatg aaaaagatta tatagatgca tatgtgagta gattgttgga tgatctagtt   74100
attgttagtg atggcccacc gactggttat ccggagtctg ccgagattgt tgaggttcca   74160
gaagatggta tcgtttctat tcaagatgct gatgtgtatg taaaaattga taatgttcct   74220
gataatatga gtgtttatct tcatactaat ctgctaatgt ttggaacacg aaaaaattct   74280
tttatatata acatttctaa aaagttttcc gccattactg gaacatatag tgatgccact   74340
aagagaacaa tctttgctca catatcacat agtatcaaca tcatcgatac atctattcct   74400
gtaagtcttt ggactagtca acgtaacgtc tataacggag ataatagatc agccgaatca   74460
aaggccaagg atttgttcat taacgatccc ttcatcaagg gaatagattt taagaataag   74520
accgatatta tttctagact agaagttaga tttggaaatg atgttctata ttcagagaac   74580
ggacccatct cgagaattta taatgaacta ctgacaaaaa gcaataatgg aacaagaacc   74640 ctaacttta actttacacc aaagatattc tttaggccga caactattac ggccaatgta   74700
tctaggggga aagataaact atctgttcga gtagtttatt ccaccatgga tgtcaaccat   74760
ccaatctatt atgtacaaaa acaattggta gttgtatgta atgacctgta taaggtatct   74820
tacgatcaag gggtaagtat taccaagatt atgggagata ataactaata ataatgaaaa   74880
caaactatag agttgtaaat ggatgaaatt gtaaaaaata tccgggaggg aacgcatgtc   74940
cttcttccat tttatgaaac attgccagaa cttaacttgt ctttaggtaa aagcccatta   75000
cctagtctgg aatacggagc taattacttt cttcagattt ctagagttaa tgatctaaat   75060
agaatgccga ccgacatgtt aaaactttt acacatgata tcatgttacc agaaagcgat   75120
ctagataaag tctatgaaat tttaaagatt aatagcgtaa agtattatgg gaggagtact   75180
aaagcggacg ccgtagttgc cgacctcagc gcacacaata aactgttcaa acgtgaacga   75240
gatgctatta aatctaataa tcatctcact gaaaacaatc tatacattag cgattataag   75300
atgttaacct tcgacgtgtt tcgaccatta tttgattttg taaacgaaaa atattgtatt   75360
attaaacttc caactttatt cggtagaggt gtaatcgata ctatgagaat atattgtagt   75420
ctctttaaaa atgttagact gctaaaatgc gtaagcgata gctggttgaa agatagcgcc   75480
attatggtgg ctagtgatgt ttgtaaaaaa aatttggatt tatttatgtc tcatgttaag   75540
tccgtcacta agtcttcttc ttggaaggat gtgaacagtg ttcaatttag tattttaaac   75600
aatccagtgg atacggaatt cattaataag ttcttagagt tttcgaatag agtatacgaa   75660
gctctctatt acgttcactc gttgctttat tctagtatga cttctgattc aaaaagtatc   75720
gaaaacaaac atcagagaag actagttaaa ctactgctgt gatttttaaa acatagttat   75780
tacttatcac tcataaatga gtaaatcaca cgcggcctat atcgattatg cattgcgcag   75840
aactactaat atgcctgttg aaatgatggg aacagacgta gtacgcctca aggattatca   75900
acattttgta gcaagagttt tcttaggatt agacagtatg cattctcttt tattgttcca   75960
tgaaacgggt gttggtaaaa caatgactac tgtatatatt ctcaaacatc ttaaggatat   76020
ttatacgaat tgggctatta tcttattggt gaaaaaggct ttgatagaag atccttggat   76080
gaacactata ctcagatacg ctccagagat aacgaaggat tgtatttta ttaattcga   76140 tgatcaaaat tttagaaata aattttttac taatatcaaa actattaatt ccaagagtag   76200
aatatgcgtc attattgatg aatgtcataa cttcatttct aaatcattaa tcaaagaaga   76260
tggtaagatc cgtcctactc gttcagtata taatttttta tctaagacca tcgcattaaa   76320
```

```
aaaccataag atgatttgtt tatcggctac acctatcgtt aatagtgtgc aagaattcac   76380
catgttggtt aacttactac gaccaggatc cttacaacac caatcgctat ttgagaataa   76440
acgtctagtt gatgagaaag aattagtctc caaactagga ggcctatgtt cgtacatagt   76500
taataacgag ttttctattt ttgatgacgt agaagggtct gcatcattcg ctaagaaaac   76560
agtattaatg cgatacgtta atatgtcgaa aaagcaagaa gaaatttatc aaaaggctaa   76620
actcgctgaa ataaaaacag gtatatcatc atttagaatt ctgagacgta tggctactac   76680
gtttacgttc gatagctttc ctgaaagaca aaatcgtgat ccgggcgaat acgcgcaaga   76740
gatagcaaca ctatataatg attttaaaaa ttcattaaga gatagagagt tttctaaatc   76800
cgcattagat acctttaaaa agggagaact attgaaaggg gatgctagtg cggctgatat   76860
ctctctattt actgaattaa aagagaaaag cgtcaaattt atagatgtat gtttgggaat   76920
attagcatcc catggtaaat gtctagtctt tgaaccattt gttaatcagt caggaataga   76980
aatcttatta ctatatttca aagtctttgg tatctctaat atagagttct catctagaac   77040
aaaagatact agaatcaagg cggtggctga gtttaaccaa gaatcaaaca ctaacggaga   77100
atgcattaaa acatgcgtat tctcttctag tggaggcgag ggtattagtt ttttctcaat   77160
taatgatatc ttcattttag atatgacatg gaacgaggcg tctcttcgtc agatagtagg   77220
aagagccatt cgtctcaata gtcacgttct tactcctcca gaacgtagat atgtaaacgt   77280
gcactttata atggctagat tatctaatgg tatgcctact gtagacgaag acctatttga   77340
aatcattcaa agcaaatcaa aagaatttgt ccaattgttt agagtgttta aacatacatc   77400
attagaatgg attcatgcta atgaaaaaga cttctcaccg atcgacaatg agtccggttg   77460
gaaaaccttg gtttcaagag ccatcgatct atcgtctaaa aaaaatatta ccaataaact   77520
aattgagggt actaatattt ggtattccaa ttctaataga ttaatgtcaa taaatagagg   77580
atttaaaggc gtagatggtc gagtatacga tgtagacggt aactatctac atgatatgcc   77640
ggacaatccc gttataaaaa tacacgatgg taaattaatt tatattttct aatcaatcat   77700
cctcagttaa ttttttttaat gattcgtaat aacatcctct atggccataa catttgagtt   77760
ttgcagtatc tagagcatat tttgcaattt cgtattggag tccattacct gaattcggat   77820
ctaaaaatat tagatccttg atttcatgat tactttttaaa tgtatcaatg atttgatcac   77880
tcgttaaaga tattcttccg acaaagaaga ttacctcaaa aaatttatta ataatggtat   77940
cttctatgat gccatgaata aaaaaccgag tgtctatgaa tacaaaagaa ttgtctatat   78000
taacttcttc tttaatttcc ctggataaac actctggaac attctcaccc cttttgggta   78060
tgccacccgg ataaatagca tctattctat cattatcagt agtagctgga tctagagaaa   78120
aaaatgacga tagtatactt ctttcctgtt tggacaaata attggaataa ttcagaaata   78180
atcgtttctt tctagacatg tttctagttc taattatttc agaatagaga aaactatctc   78240
gtctgttaca tactaatatt ttgttatcag tagttaataa aatagcggac acggatactc   78300
gtttatgaca ccataggcat tggttaacga atgccgtgag tgtaataatt tgagagtcat   78360
cctcgcaaat aatagactta gctagtcgtc tattatactt aataatctga ctaattatac   78420
tagatctgta aaagttcatt tactattaac tagcatatta taaatataag acagatattc   78480
gtatttatcg tcgttaatac aatcatttaa tgatttaatc tttctaatttt ctacattgta   78540 aatactagta tgcgataaat cctccaacga ttgattaata aaacacgcca tgcaataact   78600
tatatatact ttattaaaata atttatcccg tgttgtaagt tttagaatta catttccaaa   78660
ttcttttact gttatacgtt catcactttc ctctttttaat tctcttctta aacaatcttt   78720
```

```
aatagattcc tttttatcta gtttaccacc caataatatt aactcttcaa agtgaggatc   78780
gatatcgttg atagaacctt ttctcaaccg tctaaagatt tctcttagtt cattgtagta   78840
cataaaccgt aatagtttag tggatactct aaagatagaa tctgaatttt gttgagataa   78900
tatcgcttgg aatgcgaatg aagttcttct agctcctatt aacggatatc cgtcacttgt   78960
tatacacgca gcaaacacat gcgtgtcttt tgatcttgga atatctttta ttcgtttaat   79020
agatattaat tctctaggag tttcaaatat cacttcctca tccattgtaa ttcccatact   79080
aagagctatt tttaaacagt tatcatttca tttttactat gccgcaacaa ctatctccta   79140
ttaatataga aactaaaaaa gcaatttcta acgcgcgatt gaagccgtta gacatacatt   79200
ataatgagtc gaaaccaacc actatccaga acactggaaa actagtaagg attaatttta   79260
aaggaggata tataagtgga gggtttctcc ccaatgaata tgtgttatca tcactacgta   79320
tatattgggg aaaggaagac gattatggat ccaatcactt gatagatgtg tacaaatact   79380
ctggagagat taatcttgtt cattggaata agaaaaaata tagttcttat gaagaggcaa   79440
aaaaacacga tgatggactt atcattattt ctatattctt acaagtatcg gatcataaaa   79500
atgtatattt tcaaaagata gttaatcaat tggattccat tagatccacc aatacgtctg   79560
caccgtttga ttcagtattt tatctagaca atttgctgcc tagtaagttg gattatttta   79620
catatctagg aacaactatc aaccactctg cagacgctgt atggataatt tttccaacgc   79680
caataaacat tcattctgat caactatcta aatttagaac actattgtcg tcgtctaatc   79740
atgatggaaa accgcattat ataacagaga actatagaaa tccgtataaa ttgaacgacg   79800
acacgcaagt atattattct ggggagatta tacgagcagc aactacctct ccagcgcgcg   79860
agaactattt tatgagatgg ttgtccgatt tgagagagac atgtttttca tattatcaaa   79920
aatatatcga agggaataaa acattcgcaa ttattgccat agtattcgtg tttatactta   79980
ccgctattct ctttttatg agtcaacgat attcgcgaga aaaacaaaac tagattcgat   80040
accttgttga gcctccatta gaacggcagt gacttcgctg ccattgtcat acgcattacc   80100
atttcgaaaa aagcagtact ttgaatcgct aaatgataca gtacccgaat ctctacttag   80160
tttacagatt aaatctccac attgaatagt tacatttgat tcatcttcga tgtttaatgt   80220
tcctctgact atatccccaa cgtgataata cgcgtaggtt attacacacg gaacgtttat   80280
aactacagaa ttattaacta tttcgccgag aggtaattcc acgtcttcac gaatttctat   80340
tttcttggcc attttaccac taatttctct atggagatac gtcttatata cggcattcct   80400
aatattagtt tttatgtcta acgtcagctc gtgtggctcc aatgtaactg gaaggtatcc   80460
attggtaaca aagctcgaca tttatttctt tatatatctc atcagtttta tggagaagat   80520
accacgttat attctttacg aaagttaact ccccaaacaa atggttcgta ggaaagtcta   80580
aacggtactg taataatatc gttttcgtat ttgtataaaa gagatttatc aaatacttta   80640
ttcgatacaa agaagtgacc gtttacaata tcatctatgt aattcctagc gtcttcttta   80700 tttttataa ctgatgtaac catttaagt aacttggtat cgttatactt aatacgagaa   80760
ttattataaa aaaattgtct gaccaattct cccaataaaa cttttacaat tgatggatgt   80820
ggtggaagag aatacgtttc agacatctct tgaagaatag agtatattct attcgtttct   80880
ttagtcttaa attttagata caacagcttt ttgatgtcaa atggtaaaac attaattaat   80940
tcatcctgtg tgtaatcgtt taatgacgtc acttcgtcat tgaaatcgga atatacggcg   81000
gctaaaagat atacattaac tggttcagaa atatcggcgt aagagaattt tctaatagat   81060
```

```
cgtccaagaa tttggttgta ttgagaaaaa gtatctggga tagtcataaa ccaaatatgc    81120
cttacctctt tcagagtata ggattcggac ataatgtttg acgaaaacaa aaacatcaat    81180
tgactgccat catcgttttc aggagaatta tacacatcta atagatcctc taaagacgat    81240
ttcattttac tagtaacgat agcaaatgtt tttggtttgc cgtttatcat atgtggatta    81300
gttccctgag aaccattata ttcagaatat ccattactga gcatgatata tttaattacc    81360
aatccgccat atgtagaatt agaaaagtat ataaaatgtt ttccgttgag tgtctgtatc    81420
cgattaataa agtatttaaa tttggaacta atgtttaacg ttaccaattc ttctccgtat    81480
aacacgccat tatttatttt cagatttggg tacaattcct tatcctgttc ctgaaataaa    81540
gtatctaaat tattcatcag attaagttgt cccaatactg ccattgacac gttatacata    81600
tttttatcaa acatttcatg ataacatagc tgtcgtctag taatcatata atctctctct    81660
tgaagtttag acatgtgaca atatactact ctagtatcta gaaacttacg tccgtgatat    81720
cttatcgttg gtagatcttt atcaggcatt tcgtaatatg atattcttcc tttaagcaaa    81780
tccttaagta cattcacacc tcgttcgtta agaagtgtct gaattacttt cttaccacga    81840
ctaataattt caccaaaatc tatcgtctct tcggacatta aatctataat atgacccaga    81900
gtattaggtg tgttagtaat gggagatcca gacaatagta aaaaggaat cttgttttta     81960 tttttatca cggtcataag ttctccagta ttattcccaa agatattatg tgcctcatca    82020
acgataaaaa tagagttatt gtagcgagat aatccgttat aattaatgac gttatcgtta    82080
taattaagag aataaaaact tgttgtggaa tgaataaaga tattctcagc tatgaattcg    82140
tcattaaaca agttcatagc tacacccata ttataattaa aaattttcaa aatgttaata    82200
ttaggcacta gaatgtaaac cttttttaaat ctggaagcta ccaaggcgaa caacaaagcg    82260
attattgttt tacctgatcc cataaatatgg aacaataaca cgcttctgtt ctcatctatg    82320
atagttctaa ctagataatc tagagtagct aactgatgag gtaatatagt tggtatacta    82380
tcaacatgat tatcaaataa atctatgatt ccggtattca tttagatatg tgatatcttc    82440 tataaaatata tgagcatata tttacggaga tgaaatatcc tctatgaata tatattgcag    82500
atattcatca ctaacattgg caaatttctt atgtctattg atgaagctct ctatatcgtg    82560
tccaaatagt ctagaattaa aatacttgga tattttctgt tggaaagtag tcaacggaag    82620
agtaaccaca ttatcgtaca atatatatcc ctttttggag aggtccgtca ttaatggaat    82680
atgctttaca gagctagata ctaacagagt acctattttg agatagaatg caaagtccgg    82740
aatctcttcc ggtgtaggat atagtttcat aataggaaca tgatatttt tgtaccattt     82800 caccaacaag tatagaaatg cgaatctata tctattattt tgtatttac catctaaccc     82860 ctcgtctaat agtttgactt tatcgtacgc gtcattattt tcagcagcct ctctaccaga    82920
aggttgagaa aagtgtgttc tgaatcgcac gacggcaatt cttctcatta atgcgttatc    82980
tatcctatca aagacaggtt tgtaattagt atcgataatg attgtcgcat ggtttctatt    83040
attaatttta ttggagaaac acggtcttcc aatgacacaa ggttctgtca acttttaat    83100 attgtcagat ctaattttct ttgatccact acaggcaaaa tcaggtagtt cgctacagaa    83160
tacagatctt ttcaaatgca tgttagcgat aaatggatta ggtcctttat ccaatacatc    83220
tgttaaaatt gtttgacccg tctcaacaaa caggtcaccg atagcagact ttaacaaacg    83280
tttggttgtc gactttccag ttgcagtttc tccaaaaaag aatgttaaac atcctttggt    83340
agcaccgcat aaacaactag ataaagtttt ttcgtacaac tctctatttt tcttattttc    83400
atccgttaat ggttggatat cgttaatgat attcattaac tcttccattt ctggactgtc    83460
```

```
ttcgacgaac tttgtatcgt caaatttaaa tccggttgat acagtacacg tatatttttt  83520
agcatcatct ccagagtaaa acattccgtc taccaggtcc aatacaccat ttttaaacgg  83580
aagtttatcc ggataggtat cggtctccac tgaatctatt aacatgtctc gtatgttagc  83640
ttctacagtc tttcgtttcc tcggacagag taattcgctt gaatattcct taggtagttg  83700
atgtcttatt gacagaatta gttttgttat caagggttct tcgctgttaa atttccatga  83760
attattaatc caaactatat ggtctcctcg ttcggttaat aaaacagagt tagtgtctaa  83820
aattctttgt gcaatattaa acagtttatt accatccaac ggaacaattt taactttaca  83880
actatgtgga ttaccagttt tgtaaattct aatagcacca ttttccaacg atagttgatg  83940
cggatgttta tgcgatcgtt ttttacataa tgcacaaggt gttacgtaat ctatgaccag  84000
tggtaccgtt gtaaaattat tttcatcgag atcattaaag tttattatag aattaatgaa  84060
tattttgaa actctttta tagcgtcttc gaatgaaata accctggtt cccataactt    84120
atcaggaact aaatcctcca atcgtcgttg tagagaaaag taataactat tgttgttcat  84180
atccacgtaa gtgaataggt aatcttctat attatcatgc ggtggttgca ttacatgaat  84240
agtgtcgcaa tttggatttt tcctagtacc tacaacccga agagttgttt ttctcctata  84300
tacggcagtg tctatcgatc tggttagtgg attttcagat gatctactta attctaatag  84360
tgttcgtttc atagctatca atgtatccat agtggtatac gtgtctaaaa agataaatatg 84420
aaaacttgtt ttatctctat ttgtagactt agtcaatgaa aaattagatc tcatggattt  84480
tattacattt tcatgaatgg caccgcattc tgtaaacgcg aatctagcta cacagtttga  84540
cacctcgata ataaaatctt gaatagccgt taaataatct atttcgtcta gacacgcgtc  84600
taaatctaca tccatgaaaa ttctgactat agagtatgct tcctcatccc taagactttc  84660
gaatagtgta cattctggat tattctcaat atatctttct aactcgtcgc atttaaatgc  84720
ttctacaaat cttggatctt cattttgtct gcacgctgac gggacaccta tagtcttaag  84780
aacaaagata acatcattac ctctaatagt tgcatccatt tagaacacaa gttaaaattt  84840
cactaaagca ttaataaata aacccttgag cccaatttat aggtgccttg ttgtctaatt  84900
ccagtaaaac gttgataatt tcaaatgatc tatcttctc gaattggcgg tctctagccg   84960
ctggatgata tccgactatg gtagttaccg gggattctaa cttttgcccgt atattcgaga  85020
aatctgtttt acccaaacaa taagaacac taacgtgttt agttatatgc tgcagcagta    85080
acttggaaat cttatcccag tagatcgcgt gactttttgt ttctcctaat ttacaactta  85140
agtaataatt ccagggtata accccgtcta ttatattaag gttataacct ttataatcaa  85200
ttactccggt taatctagat atagatgaag ctatctcctt aattgatttt tttgtaaaat  85260
ttggtgattc gaacggtaca ccagttccat ctttcggata cggatctata ccacacacac  85320
atactcgttt atttctaagc ggttgtttca actgtataaa gaacttatca ggataggcg    85380
acgtctcgtc tcgtagcagc caactggcta cttcgttata aaactctacc aattgactca  85440
ttactggttc ccaatcatcg tgataagtaa tagtatatgg cgcgtgtgat acagtcactg  85500
aattcattat atcaaattag ataccttttt atacgtatct agtaccttt catttttccga  85560
aacgccgtta aaccaagcga atacaaacgc cttaaactta tctctattat aacatattct  85620
cgttagattt aattcttcgg tatccttgta tctaactatt gttatatgtt tagaaactct  85680
atagtggctt ctaatcagat gttctaataa atatttaaa aatgaatctt gattaaaaat   85740
catatcattg accatttgtc tggctactga attacgataa tacggagaca ataacggatt  85800
```

| | | | | | |
|---|---|---|---|---|---|
| agtcaaatag | ctatcatctc | ctaatgatgg | aggcacctgt | acaaatacca | atcgtttatt | 85860 |
| cttgaacgaa | tcaaacgtat | aaatatcata | aatgacaaat | ttatcagtgt | gcatatcttc | 85920 |
| agatatatga | ttggatgtag | aacaccatct | aacttgtctt | ccagcatcta | taaattcctc | 85980 |
| cacctctata | tatctaccac | cgtgctgaaa | actagaccca | tttaattcga | cgcataaaga | 86040 |
| tccatatgta | tctggagtca | caatatattc | agaaaaaaat | acatgctcct | ttaattttgt | 86100 |
| taattttgat | ctgataaagt | cattgtgatt | tcctaaaagt | ataaatactt | cgttatcgtc | 86160 |
| gttatcgact | ttgggatact | tattatcctt | aactataaaa | atgtccatca | atatcgatat | 86220 |
| aaaaaaaata | actgatttac | tcaacagtag | tattttattc | ccagatgatg | tgcaagaact | 86280 |
| tcttcgagag | aaatatatag | tattagaaag | aaaatcaaat | ggtacaccta | cagtagctca | 86340 |
| catctataag | acaatggcta | gatttgataa | taagagtata | tatagaatcg | ccaagttttt | 86400 |
| atttatgaac | aggccagatg | ttatcaaact | tttatttta | gaagacgtag | aacctctgtt | 86460 |
| acccgacaaa | agtattaata | tatctattaa | caatacagag | tatccacagt | tggaaggtcc | 86520 |
| tataggaaca | aaaatcgctc | tattggaatt | atttaatgca | tttagaacgg | ggatatcaga | 86580 |
| acccatacca | tattattatt | taccgcttag | aaaagacata | aacaacatag | taactaagta | 86640 |
| agtcttcgac | atctaaacct | tcacatttaa | tggctcctct | atttagttcg | aaaaagtttt | 86700 |
| ttgtagacgg | tctatcttcc | attgtagatg | cgccattaat | aaacttttta | cttcgttcta | 86760 |
| taattgtagc | gaaatcaacg | ttatctacaa | gaacaaatcc | gtattcgtta | aacactctga | 86820 |
| ctatatcgtt | cttttgata | atgtattcag | tcattggagt | agacattgtt | gatggattat | 86880 |
| ataccactat | tctatcatca | gctattttt | ctacagacat | atagttttcg | ctactaggta | 86940 |
| aattcttatg | aattataaaa | gtctttttat | ctgttaattt | tgataatttg | tctccgtcca | 87000 |
| tggtagtgat | taatacccttg | cctccagaag | cagttagttc | ggataagtta | ttcatgacgg | 87060 |
| tagcataatg | tctcggatga | aaagaataat | ggatagcaaa | ctgccagtcg | atgatattaa | 87120 |
| actttccaaa | atagaatact | tctctgacac | tagagacaaa | tgtatcggat | cgaatagttt | 87180 |
| cctgaatgta | gtcaaatttg | tagtacttgg | ttttaattcc | agagtttaat | ttgttgtatc | 87240 |
| tttcattttcc | tctagctata | gcatcagcat | ccggatccgt | cgctaccaat | aacgcaatct | 87300 |
| ctccataaaa | gtattttcc | aggtccgcac | cgtttccaaa | atcaatcgcc | aatacctttc | 87360 |
| gtttgttgga | atcgtctaaa | aatgttttgg | aacaatacat | agaaataaga | agagtcttga | 87420 |
| cgtagtttga | taaaattccc | aacggtcctc | tagttcgttt | attcgtaaaa | taactaactt | 87480 |
| ctggatttaa | tctaaattta | tcattattgg | cgtattgatg | tcccacatcc | gatagtttat | 87540 |
| cctcgttaaa | gatatctcct | attttgatgc | tttgatctct | taaatgttcg | actatgatat | 87600 |
| tatgttgatt | tccataataa | tcttctgagt | taatatattt | catggtttta | tcaattctag | 87660 |
| gtttaagtat | ttctccatta | actaagaatt | ctgctataaa | cttaataggt | acaaccacgg | 87720 |
| acttaatacc | cacttcatta | tgtgtattaa | tatattccaa | acaatagata | ttatttagat | 87780 |
| aattaacgcc | gttatataac | acaatcttac | cagaaccata | ttctttagga | aagcctttat | 87840 |
| cgttgctaaa | tttcttatac | tctacaaaga | tagacgattc | tccaaagata | attggttcac | 87900 |
| tggacatgta | cctaaatact | acatttgcag | tttggtctat | agtattttcc | tttttaattt | 87960 |
| taaaatcaat | gttagattta | ggtcccttg | aatagaacag | aataacacct | tctggttgct | 88020 |
| ttggtaaata | tgtagataac | atatcgacga | cttcactagt | tgtagtaaac | ggaccttcgt | 88080 |
| atttctttga | cttgaatact | atccgatcac | aaatatccac | tagtttagat | tcaacatact | 88140 |
| tactttcttc | tagtctatca | ttgattgcat | tcacaggctc | tattagctta | atgagatata | 88200 |

```
cggtccagtt cttatcctta actgcctcac caaagactac tacttcggaa tctattattc    88260
tcttaacagg atatctaata atataaccaa gatgtgtaaa ataacaatac aacccttttg    88320
atgtaactct gatagttata ggaattccgt cagtcttagt tacggcatat agattttcca    88380
gatccaaacc tactatatct tgtttaggca acataaaggt ttttataggc gcgttaatag    88440
gcggagaaag aattacattc tctggagaag ccataaatat atgacgtgat agagtcgtca    88500
attcctttat tagttcatca tatggaactt tttcattgtc tctaggtgtg aattctattt    88560
ccagagatgt attaggcctt gactttggat gattaatagc gtgtaataaa gaacttttag    88620
actgggcacc ggatcctaga aaatatttta gcttaaagtc tatcgtaaag ttttttgttt    88680
ttgcttgaat aagattgact aattctagtc ggatagagga tccatatttc ttgtaatcca    88740
aaaatatatg acgttcctct gtcgatagtc tcaacaagca ttctttgtga agacgatttt    88800
ccgtcactaa tgatttcttt tcccaaacta tgttatctat agcatctact aactgtacat    88860
tttttacatc tagaccatgt acctagata atggaatctt agttctaatt ttaacacctt    88920
ccttattagt aacggtaaat cgaataaacg attcctgaat cgtagagata ttcactacat    88980
ttgtcaaagt aattaatggc ggcttaataa atactagttc caattcatta tttatttcgt    89040
atgcggtaga cctctgttct aattctgaag cattcttcgc taaagcgtct atatacgttg    89100
caatagtaga agatgatact atgttggcat ccatattgtg ttttattata aacgactagt    89160 ttttttttcat ttacttatta acaagcgtct tttatatatt cgtaatctat gcctttagct    89220 agagctatttt taagcttttc tgtatctcga ctgatacgag tatctgatct attgcggtat    89280 tttttttataa atcgtttaag acggggagta gttttgatat attcgctaat atcctcttta    89340
ataatatcca cacacgccaa ttgttcggct atactcgatg cgtgagtctt gcattcatct    89400
ccagatatcg gagtgagggt cagatccaaa tattgagaag ccttataatt atcgtattcg    89460
aaatcaatca taaactgacc atccttatcc actgaaaaaa tggtattgtt tggatggcgt    89520
ttaaatatag acattatcaa tgccataata tctaatgtgt ttagctctcc gaagaaagct    89580
gtcattgcga gagatttcat acgcttatcc atttccattt atcggtcttg taattatttg    89640
tgtaaagatc tatatcatcc atccgtagat gatttaacgt gatctacgac tatagatagg    89700
aattcatcga acgtagtttt agatactaca tctaaaaaat ttttatcctt taccatttct    89760
aaaatagtcg ttgccatata agctcttttt gaaattgatg gagtatgacc taccacttca    89820
gcagtttgtt tgatagttaa cgctattaac ttttttggtg acggaagagg agatatggac    89880
tttacatttg tccaaaaatt atataaaaac gtataattga ctccatacgt tcggagatcc    89940
ttgattctaa taccaaactg tttgatacat tcgtatacct ttcgttcact tagtttgttg    90000
aacagaaatt cttcgggact agaatcatcc gtcagtttca atagcggttt atatagtcta    90060
ttagacttat gaacaacaaa ttcatgtgaa actttgtcct ttcctacaaa cttgataact    90120
atttcatcgg gacttatttc tatgtgttta ttttttagtg ttaataaccc tactgtttca    90180
ttctccttaa gatatttcat tttaccaaat ctaataaaaa acatagtttc cattaacata    90240
aaaaccgcca actgataatt ggaatctgtg gacgatttct ttatattttt gtttataaaa    90300
caattaattc gtttcataac gttatatact ctaacaaaaa tacgatctct tttagcgttg    90360
cgattctgta catgcatttt tccgtaaaag tattgtctac gtccttttga atcacttccc    90420
acaaaaatta atctagttaa cgcctcctcc cacgtttgtt catatactac tacatctgtt    90480
aaatgagtag gaatttttaac atgttgcaaa acctcatacg ctggattatc gtctgataca    90540
```

```
ggatttaaaa aattattatc ggtaaagagt ttaccatctt tataaaaaag tgcacgcatt   90600
tacttcttac aagttttaac ttttttacga acaactttag attttccctc ggtgactaga   90660
tcagatagtg ttgtaatagc tttagtcata gaagtaaatt gtctagagat accagctgct   90720
tgaacatcct ctagaaccgt cgatactgca gagattctag taataatttt cttaagatct   90780
ttaacgatat tgtcggtagc cacctttagg tcagaaagat cgcttctagc actatgattt   90840
actttaccag cttcaacttg taccataggt tcatcatccc cgtcgctatc atcgagctct   90900
acagcagcca cgctttctac aatgtcgctg actccaggag atggagaatt tttttcagtt   90960
gtttgatgat attcctctat aactacttct tcttccactt cctcctttt ggttgatctt    91020 ttagtagccg ctggtttacg aggagtagtg gctcgtttgg ttttgggctt agtagatgga   91080
attattacat cttccgggaa aatatcctcg tttttatctt tattttcagc gctatttttt   91140
agatgagctc tgatttcagc catctttgtg aagctactag tatccgcttt atttgtaatt   91200
gaccacgcca ttacgataca aacttaacgg atatcgcgat aatgaaataa tttatgatta   91260
tttctcgctt tcaatttaac acaaccctca agaacctttg tatttatttt catttttaa    91320 gtatagaata aagaatctat aaaaactaaa aaaattatac atcataaacc aatttcctag   91380
ttgtttgtaa ctttaaatgg actctaaaga gactattcta attgagatca ttccaaaaat   91440
aaaagcatat ctactagacg cgaatataag tccaaaatcc tacgatgact ttatctcacg   91500
aaataaaaat attttcgtta tcaacctttta taacgtatcg actatcacag aagaagatat   91560
acgattgtta tacactacga tagaacagaa tattgacgcg gatgatcaaa cactggttgc   91620 tatttttcg tatataggat ataaatttga acaggctgtt aaagaagaga ttagtacgag    91680
tttatccttc aatgacaaga ataccacaga tgaaatgacg tataacttgt atgatctttt   91740
ttttaacaca ttagacatgt atttacgaca aaagaagatc agtattctgg taaatgatga   91800
tgttagaggt gatgtaatcg ttagttataa aaatagtgac ttagtttcat catttaatgc   91860
ggaactagaa ccagagatta agaagatacc gttcaatatg aaaaatctat taccgtactt   91920
ggaaaagaat ttggaccaac taagattctc taaaaaatat ttagactttg catatttatg   91980
tagacacatc ggtattccca tttccaaaaa aaagtataat gtgcgatatg tatttcttta   92040
taaaatagac ggattatcca ttcctattat cattaaggat ttttagatg ttaagtacgt    92100 atatttggaa aatactggaa aaatttataa aaattctttt tccgaagacc ataacaacag   92160
tctatctgat tggggtaaag tcatcatacc tctcttaaag gatcgtcatc tatatagcta   92220 catcttttcta tctagttatc atttacatag ttactataca gatctcatcg cgagagacga   92280
gcctgtgttt gtgaaacgca aaaaactaga tattatagag atcgatgaac ctgaggcatg   92340
gaaaagggat gttagagtgg aattcgcacc gtgtgagcat caaattagat tgaaggaagc   92400
tatgaaagtt gacgctaact atttcactaa aattaataat tttgctaacg aatttattta   92460
ttatgaagat ggtgtggcat attgtagagt gtgtggaata aatataccta tatttaattt   92520
agatgccgct gacgtgatta aaaatacagt tatcgtttcc acgtttaaca agactatatt   92580
cttgagcgaa ccatatagct atttcgttca tagtcagcgc tttatcttta atattatcat   92640 gtctttgat aatattatga atctcaaac ttgggtaatg aaatacaaca ttaaccgact     92700
aattcttaac tttcttattg atataaactc tagacgtcag gaatacgaaa aaagttttc    92760 ttctgaaatt aagagaggtc tgttctttct tcgtttgtct gcaaacttat tcgaaagtca   92820
agtatcgtct acagagttat tttatgtttc caagatgctt aatttaaact atatagttgc   92880
gttagtaatc attcttaaca gtagtgcgga ctttatagtt tcttatatga aatccaagaa   92940
```

```
caaaacggta gaagaatcca ctcttaaata cgccatctcc gtggttatat acgattttttt    93000 ggttaagact agaatttgcg agaagggatc gttggatact atagttttat ttaccgatgt    93060
atacacatct ataatgccgg aggaattgga tttacatttt cagagaatca cattagaact    93120
tagaaaacta gtatccattc agagatcggc gttagaaccc aattacgatg tagaaagtcg    93180
cggcgaagag cttccattat ctgcattaaa gttttccgat acaagcacca ttatagttaa    93240
gacaatggct ccagtacata catacatcga acaaaaaatt gttgcaccta ctccatcggt    93300
cgaaccaact gatgcatctc ttaaaaactt caaagaacta acgtgtgacg aagatattaa    93360
gatctcgatt agagttcatg atactaatgc tacaaaatta gtcattttttc catcacatct    93420 aaaaatagaa atcgagagaa aaaaactaat tataccgcta aagagtttat atattaccaa    93480
tactctcaaa tattattatt ctaactccta tttatacgtt ttcagattcg gagatcctat    93540
gccattcgaa gaagaactca tagatcacga acatgtgcaa tacaaaataa attgttacaa    93600
tattctaaga tatcatttat tgccagacag tgacgtgttt gtatatttta gtaattcatt    93660
aaacagagaa gcattggaat acgcatttta tatctttttg tcgaaatatg taaatgtgaa    93720
acaatggata gacgaaaata taactcgtat taaagagttg tatatgatta atttcaataa    93780
ctaaatggcg gcggtgaaaa ctcctgttat tgttgtgcca gttattgata gacctccatc    93840
agaaacattt cctaatgttc atgagcatat taatgatcag aagttcgatg atgtaaagga    93900
caatgaagtt atgccagaaa aagaaatgt tgtggtagtc aaggatgatc cagatcatta    93960
caaggattat gcgtttatac agtggactgg aggaaacatt agaaatgatg acaagtatac    94020
tcacttcttt tcagggtttt gtaacactat gtgtacagag gaaacgaaaa gaaatatcgc    94080 tagacatttta gccctatggg attctaattt ttttaccgag ttagaaaata aaaaggtaga    94140
atatgtagtt attgtagaaa acgataacgt tattgaggat attacgtttc ttcgtcccgt    94200
cttgaaggca atgcatgaca aaaaaataga tatcctacag atgagagaaa ttattacagg    94260
caataaagtt aaaaccgagc ttgtaatgga caaaaatcat gccatattca catatacagg    94320
agggtatgat gttagcttat cagcctatat tattagagtt actacggcgc tgaacatcgt    94380 agatgaaaatt ataaagtctg gaggtctatc atcgggattt tattttgaaa tagccagaat    94440
cgaaaacgaa atgaagatca ataggcagat actggataac gccgccaaat atgtagaaca    94500
cgatcctcga cttgttgcag aataccgttt cgaaaacatg aaaccgaatt tttggtctag    94560
aataggaacg gcagctgcta aacgttatcc aggagttatg tacgcgttta ctactccact    94620
gatttcattt tttggattgt tgatattaa tgttataggt ttgattgtaa ttttgtttat    94680
tatgtttatg ctcatctttat acgttaaatc taagctgtta tggttcccta caggaacatt    94740
cgttaccgca tttatctaac actattccat attactaaaa tcggaacacc aatgcggtga    94800
cataaaataa ccgctataac ctaattcatt taacatctca ttaccacaag taataacatt    94860
attagacttg tgtttatca aatactgaca aaattgttga gcagatggat cgacctttgc    94920 cgcctttttta accatccacg cgtctccagt acctcgccta atagcttgcg gcagatatgt    94980
tttcttatcc aatcgcatag ctataaaata ggcgccgaaa tccacacatt tgaattcgaa    95040
tatatcatcc ttaccagcgg ctagaagtct acctctatca ctttctaatt ttgttttgct    95100
atccgttaat gatttccaat cgttaaccgt attttttaatt cgcatatatc tcgttaattc    95160
attaaagact ggattatcag acgtctgaaa ccagagtaat agcgcactaa ttgccaatat    95220
aataacaaag aatataagtg ttgatgtttt ggctgcttgt acgcctacta tagccttttc    95280
```

```
tctaacgtat tctaaattac acgcgtttac cgataaagta gttttatcca tttgtacgtt    95340
ataaatggat aagaaaagtt tgtataaata cttactacta cgttcaactg gagatatgca    95400
caaagccaaa tctcccacta taatgacaag agtaaccaat aatgtgtatt tgggaaatta    95460
taaaaatgct atggatgcac catcatctga agttaagttc aaatatgttt taaatttgac    95520
gatggataaa tatacattac ctaactctaa tattaatatt attcatatac cgttggtaga    95580
tgatacaact accgatatta gtaaatattt tgacgacgta accgcctttt tatctaaatg    95640
tgatcaacga aacgagcccg tgttggttca ttgtgctgcg ggagtaaata gaagcggggc    95700
tatgattttg gcatatctaa tgtctaaaaa taaggagtca ttgcctatgc tatattttt    95760 atacgtgtat cattctatga gggacttgag aggcgcattt gtggaaaatc catcgtttaa    95820
aagacagatc atagaaaaat atgttattga taagaattaa aagtcttctg tttcttccat    95880
ttccttgatc ttttgagaag atatcttatc agatagtttc ctttccattc tcatgagaag    95940
acccaagtcg ataaagtatt tgtaatatcc agttcctata ttagggacct tgctaaaaaa    96000
gtggcagcta ctattatcgt taataggttc tgactttta tgaagagccg cgtttaacaa    96060
tgctttattg tctccgaacg tagctctctt aagagtacta gctgcgccga acttgaattt    96120
attcactgat tctggttcgt aactagcaca tagtaaacta gcgagaagat cacaaggctg    96180
atacagataa tcgaacccct ctccataggt gtttaacatg gcttcgcaca agtattcacg    96240
agcggcctcg ataccgaaga tatcgtatgt attccatact ccaggataca cgttgacgtt    96300
ttccaaatcg aaagaaccca attcttttag attcatgagt tctacagtca tcttattgag    96360 ctttttgtt tgattgaagt cgtcatatcc cgtataatca gagataggaa tcttgaattt    96420
actaatcttg cccttgttgg cggcacccgg aagaaccatc ataaacttac taagattcaa    96480
ttcttccggt tcaacgaaat ttaggtagac agtaaatcta atattatcct catcctcaat    96540
gaatgtttcc atacccccatt cctttacaat gacgctaaag gagatgaatc gttcaatcat    96600
atattcgacg actaattcgg taatttctgc tctcttgatg tataatctat tgactattat    96660
atctactaca tacctatctg tttctttttcg aagagtgatg tttggattta attctcccaa    96720
acatacaaat tcgaaattaa tcttaacaga ttgaagttta gagatatcat cggataccag    96780
agtgataatt tcggtcttat tcttactcaa attagtcaag ttattaaact cgttgaaacc    96840 aagttttgt ttgacggcac cacttttttc agtagtgtga aaactggaca gggcttgttg    96900
tgtaaacttc tcagacaata cctgtgcaga aataattcca ataggagttc caccacctag    96960
agtataattg agttttttcat agaacttttc aaagatagtg atagccgttt cttttgtaat    97020
tctaattcta gaaggattaa gatgcgtcaa gaatatatac tccataaaat ctatattaga    97080
taccgtaaag aagtatttct ctctcacatc atcaatgacg ttatgaatca tatcgtacag    97140
atccttaacc ttaatagcat tatcctcagt ggtgggtttg acgaatacta ggaaattaaa    97200
cggcgccaat gtcttttttg caagtttctg ttctgagag taaacgaatc cctgttttat    97260
tttattccac agagcactaa tttccaaata ccaagtcatg gactcatctg gatagataag    97320
atctacaggt ttacatactg agcctagaat tttggtataa ttggcggcgt acttgatgag    97380
cgtattacct ataactactt gtccgtatcc gtcgaccacc atatcctcca tcttttaat    97440 gattttcta gccagtgttc cggtacgtga tgtttcacag acgatatcag tagattgaga    97500
tcttgcaacc agcatcgaaa agtaatattg agaacccgtt aatcctttg ttaaagaatt    97560 aagaatgtaa cctcttcctt ctggatcctt agagtctgga agatagtaag gtaagactct    97620
acccaatact cgagtctctg ctggttcacc atcaatcctc tgttgtccat aagtacctag    97680
```

```
aatatacatt agttctgtgg gatttacttt ataacccgct ttggccattt tcaggaggtt    97740
attatctgga tcatctatca gcgtttgtct catatgttct tctatctctc ggatattaag    97800
atttgtcaag ttggataaca tggattccac atagtccgcc tctaaagctt tagataatgg    97860
aactattttc ccgtctctta catcgttgag atatttggcg tatgcttctt tgataagttc    97920
tattttttct acgttgatgg cctccaattt attagtgaac gtcgaatttg gtctcagatc    97980
tttgaatgtc accccaaaac cgtaaataga tagatatctc ttaaaaacat aagatgactt    98040
gataataaag ttgataccct ccacgttcga cttatgatcg gataagagtc cagccaatga    98100
cagatgcctc atagccacaa caaaattact atctacgtcg tttgcaataa tttcaccatc    98160
ctttaagaga cccggataat taatcttttc acctatcaag taagtataga tatctttacc    98220
gctgaattta catttacctt taggatcgaa ctctcttcca tatttcccca agatgttcaa    98280
tacttcatct aaacaaagat cttgtatcct aaacaatgaa tacgctgcta cgatttcatc    98340
ttgaatagat ccataaacgg gggctccatg aatatcgtgt ttgagtaacg tcgtcggata    98400
cataagaata ctttgttcaa ttacggcttt aggattttgc tccaatatca tccattcttc    98460
atctccgtcg aaatcagcat tttgagagtt gacaattccg ggagatattt tgatagtatc    98520
tccttcggta gctctgatag atgaagcgat gacgttgtat ctatgtagag acggctgtct    98580
tccaaaaata atacttgtat attcttgaac agctacttct acccaatcac caggcaataa    98640
atgtatttta ttttttgataa actttccttg gcgtattctt gttaattggt ttaatcgttt    98700
attaaagtaa aatttaactt ggtttgacgc taatagttgt ttaactttat ccactgtaaa    98760
ggcattaaca aatatctttt ctgtaagtgt atttctaata tatgcgggca ttcctacctc    98820
attaacggtg atagatgtac tgggaccaat tacagatcta gcggtctgat cttttcgccg    98880
ggcgacgata taacttctaa tcatattatt tttgccggat gtgatatatg ataaattgat    98940
actggaagtg ttattagaaa taattttaat atcatcgtat tctattaccg ccttctggat    99000
aacctgttca tcagcattca agttacaatt cttaacgatc atacctaata agtaagttaa    99060
ttcattggtt tctttgggta tactatctat ccaaaaacta atagccggtc taataatcaa    99120
cggagggatg ggaaagtagt ctgtataaaa taagttagct ggatattgat gaatttctaa    99180
taatggccaa aacttttcat gaatagaaat taactttga tagatgagag aattaggaac    99240
gttaatatca tccaacttgt tgacgaaaca aaccttttc tttgaaaaag taattttttg    99300
atacggttgc atacattcac tgttccaaca tgacttttc ttggataata ttttatcctt    99360
taatctccta agagcgtgtc ccgataactc ttttaggtta atatcgtcgg aatacggttc    99420
tcgtgaacgc aataatccgc agtgaataca tatataattc agtaaacgaa taatttctga    99480
aataaattca ggcttaacta tatgagtttt ataaatactt actttacccc agtgaccgaa    99540
acattccaat tccgttttcc cacaagtttt acataatgcc ccatccatag cacctagtct    99600 accatctta acggtaccga tatcgtcgtc attttaaca tgactaatga taatatctgt    99660
agcattaatc tctttttgat catatagact atacgtaacc ttagagatta cagccatttt    99720
tatcaagtca gtttctttta aagaaccgaa agtatacaat caaatttccc tttttattac    99780
aactataaaa taatagttat atttacactt taaattttta tcatgacgga cgaacaaatt    99840
tatgcattct gtgatgctaa caaagacgat atacgatgta aatgtattta tcctgataaa    99900
agcatagtac ggataggaat agatacaaga ttaccctatt attgttggta cgagccatgt    99960
aaacgaagcg atgcgttgtt accagcctct ttaaaaaaaa atataacaaa atgcaatgta   100020
```

```
tcggattgta ccatttcatt gggaaacgtt tccattacag atagtaaatt agatgtaaat 100080
aatgtttgtg attccaaacg agtagctacc gagaatatag ctgtccgcta tctgaatcag 100140
gaaattagat accctattat agatatcaaa tggcttccga ttggattact agcgttagct 100200
attttaatat tagcattttt ctaaacaaga tataagatat aaaatatatt attgattatt 100260
ataatgttct tatctcatct ctactaattg attaatcagc gactgaaata acagatctat 100320
cggctatctc tactccagtt accatgttat tgcggaaaaa tctaacaatt tttaatggta 100380
tattaggacg gtagagaatc ttgacaacta tttccgtctc taacattttg ggaagacgaa 100440
gagtcttttt accatcgcct gtttgtagta cactattaac tatattagtt tctgtagtat 100500
ctagtctaac aaagctagga aataagtcag atattaccac atctatgtat agaaaattta 100560
caggaaactt gttatgacct ttttgaagat acgatgttat aatgattggt tctccataat 100620
catcatcaac cggagtataa tttatggatg attcgttaaa tacctgaaac acagttttca 100680
tagaatcaat tttatgtcta acggttatta aagtaactaa atcattatac tctatatcgg 100740
tagtatatct cagtagtacg tttctattta ttactgcgta cggatctctt gctatttctg 100800
tttttagaca tagaattttt gctagatatt ttacgttgta ttggttcatg actaactttt 100860
tcagttgatg ttgttggaat atttaagaaa cgaaatatag attgttgtag aaatagtacc 100920
tttgctttag tagtaggaaa tgttttattg cagtacacgg tcctcagcat aaagtacatg 100980
tgaaaatagt catattcctg attaggataa tcaaagttaa caactacttt gttacgacg 101040 atcttattaa ggtagtacat cttttttca taatttacag cgtctgattt ggtaactcga 101100
gtcagtctca tgttctcacc ggtataaata cttaataatc tcatttcagc tgaatatgaa 101160
ggagcaaaag gttgtaacat tttattaccg tgtgggatat aaaagtcctt gatccattga 101220
tctggaaacg ggcatctcca tttaagacta dacgccacgg ggtttaaaat actaatcatg 101280
acattttgta gagcgtaatt acttagtaaa tccgccgtac taggttcatt tcctcctcgt 101340
ttggatctca catcagaaat taaaataatc ttagaaggat gcagttgttt tttgatggat 101400
cgtagatatt cctcatcaac gaaccgagtc actagagtca catcacgcaa tccatttaaa 101460
ataggatcat gatggcggcc gtcaattagc atccatttga tgatcactcc taaattatag 101520
aaatgatctc tcaaataacg tatatgtgta ccgggagcag atcctatata cactacggtg 101580
gcaccatcta atataccgtg tcgctgtaac ttactaagaa aaaataattc tcctagtaat 101640
agttttaact gtccttgata cggcagtttt tttgcgacct catttgcact ttctggttcg 101700
taatctaact cattatcaat ttcctcaaaa tacataaacg gtttatctaa cgacacaaca 101760 tccatttta agtattatat taaaatttaa tcaatgttta tttttagttt tttagataaa 101820
aaatataata ttatgagccg acgtaacact ttctacacac cgattgatac atatcattac 101880
ctcctattat ctctatctcg gtttcctcac ccaatcgttt agaaaggaa gcctccttaa 101940 agcatttcat acacacagca gttagtttta ccaccatttc agataatgga ataagattca 102000 aaatatt aaacggtta cgttgaaatg tcccatcgag tgcggctact ataactattt 102060
ttccttcgtt tgccatacgc tcacagaatt caacaatgtc tggaaagaac tgtccttcat 102120
cgatacctat cacggagaaa tctgtaattg attccaagac atcacatagt ttagttgctt 102180
ccaatgcttc aaaattattc ttatcatgcg tccatagtcc cgttccgtat ctattatcgt 102240
tagaatattt tatagtcacg catttatatt gagctatttg ataacgtcta actcgtctaa 102300
ttaattctgt acttttacct gaaaacatgg ggccgattat caactgaata tgtccgccgt 102360
tcatgatgac aataaagaat taattattgt tcactttatt cgactttaat atatccatca 102420
```

```
cgttagaaaa tgcgatatcg cgacgaggat ctatgtatct aataggatct attgcggtgg    102480
tagctagaga ggattctttt ttgaatcgca tcaaactaat cacaaagtcg aacaaatatc    102540
ctttattaag tttgaccctt ccatctgtaa caatagggac cttgttaaac agttttttaa    102600
aatcttgaaa gtctgtgaat tttgtcaatt gtctgtattc ctctgaaaga gattcataac    102660
aatgacccac ggcttctaat ttatttttg attggatcaa taataataac agaaagtcta    102720
gatattgagt gatttgcaat atatcagata atgaagattc atcatcttga ctagccaaat    102780
acttaaaaaa tgaatcatca tctgcgaaga acatcgttaa gagatactgg ttgtgatcca    102840
tttattgatc gcaaaagctt tgcacaatct ttatacacta tcggtttact atttattgat    102900
aacgcagatg tttgagttgt catccatggt aatccataga tcattaattt atcgtcttca    102960
cacgctagat tagcacgtcg taatctatca ataggatcgg gtattttttcg tttaggcatg    103020 aagaacatat ttaattcaga tctaaaaaat acatatatta gaatgaatac aatgaatact    103080
tcaaataaaa ctattaatct gtgtttataa acacttaata aagaatgttt aaacgtgggc    103140
tctataaaca caggattaaa gtatacatta ggaacattct ccatttatag taatcaatcc    103200
tttgtcggaa tatctgttag aggaatattc ttttttaacac attccaatag tcccagaaaa    103260
tcatttaacc taatgggttc ttgaagaggg ctagaactat acgattctag ttccttatta    103320
gtactaagtt tctctagttt attttttattg gtgaatccgt aaatggcatt caatctcatg    103380
gatgtggaag gagaatacac attcaggaca ttaattcccg catatttaga tatcaaagcc    103440
ttgttgtctc cgataggtgt atactcagtc gacgcggatt ccatattttc tttataaata    103500
ttaatctttt tacgagtttc gaaaatacac aagataggtg atgatccttg acggaaaata    103560
accatgttct tattctttct cctaccactt ttttaggaa tgacggcagt catatccgta    103620
ttattaatga taagaggcat aacctcattg ttaggatcca agaaatagtt ttcaatggct    103680
tcaatagtta gtttatcatc tcctagaccc aaattgtttc ttatattata cattgtggta    103740
aacattgccc ctgtgatatt ctcgttatga atcaactcca actcatattt tgacatcgtt    103800
ctaggtacta tattaaaaat agaaagcata gatcttggaa atttggattt tgcgccggca    103860
ataaccattt gtaaatcatc atactcagat atacttcctg caaaaaatat ggtatcttct    103920
tcgatgaggt tttctagcag tagactcatt tagagaagtt ttttttgtga taaatgaata    103980
cccgtaccga tgttacaaac gataatatag acaaaaatcc aaccaaacga ggtgatagaa    104040
atataccagg aagaaatgaa agatttaatg accaaaatag attcaacaac gatataccaa    104100
agcctaaacc aagactacag cctaatcagc caccgaaaca agataataaa tgcagagaag    104160
agaatggaga ttttatcaat attagattgt gtgcctacga aaaggaatat tgcaatgacg    104220
gatatctatc tcctgcctat tatatgttaa acaggtgga tgatgaagaa ataagttgct    104280
ggtcagaact atcgtcgttg gtgagatcca gaaaggcggt gggatttcct ctattaaagg    104340
cggctaaacg tatttctcat ggatcgatgc tatattttga acagtttaaa aacagtaaag    104400
ttgtgaaatt aaccccgcaa gttaaatgtt taaatgatac tgttattttt caaactgtag    104460 ttatttata ttccatgtat aaacgtggca tatattctaa cgaattttgt tttgatctgg    104520
tttctattcc cagaacgaac attgtttttt ctgttaatca attaatgttt aacatttgta    104580
cagacatatt ggtagttcta tctatttgcg gcaaccggct ctatagaaca aatctaccac    104640
agtcgtgtta cttaaatttc atacacggcc atgagacaat agcccgtaga ggatatgaac    104700
actccaatta ctttttttgag tggttgataa aaaatcacat atcgctattg accaagcaaa    104760
```

```
cgatggatat tctcaaggta aagaaaaagt atgctacagg agcaccagta aataggttgt   104820
tagaacctgg tacactggta tatgtgccca aagaagatta ttactttata ggcatatcac   104880
tcaccgatgt gtcaattagc gataatgtca gagtattatt ttccacagat ggaatagtgt   104940
tagaaataga agactttaat atcaagcatt tatttatggc aggtgagatg tttgttagaa   105000
gtcagtctag tactattata gtataaagta ataaaaaata gttaatgtga tgactagcgc   105060
caccaacgcc aacaacattt gataatttct acttactaga cgtaccgtaa aaatataaat   105120
tactataaca aataatagta tatcaataaa caacctaatt aatggtcgaa gtatagcagg   105180
acattgatgc tctagaccgt gtataacaaa atctacaaat ttttcatccg ctatattttg   105240
tttcactata tcgtctagac gatcagcgat aacttccatg ttaatctatt aaaatattat   105300
caatatattt tcagttttgc atatccgtgg tagcaataac catcggagaa gttctaaaga   105360
atgtgtccat gtaagtagtc caatggacgt tttccttatt ggctaaaata agtttgattt   105420
tatcattggt ggatgtgaac aacatacgct tggcatagta cataaacaac gctgccaata   105480
ttataacacc gataacaatc atataaaact gaactcctgt accagcaact tgtctaggtg   105540
ctatttgagt agtggcctta gtcgtcaatt gcatcaacgc tttaatggca caatttcctt   105600
tgctagatcc tgtattaata aattccaaat ttgttggaga tcctggggct ccgtaacatt   105660
catctatgat tacgttttgt atctttaatt tgttatcgac gaccgcgcta gaattacaag   105720
tctgtttcac ataattttca aaatctctaa caacagtgtt tacactcgtc tgaatgttta   105780
acgcagcagt aaacatagct ggtacgtatg cttttgttc cggtgttaat ccactatatg   105840
tttctgtagc ggctgataac acagcatcca actgagcatc cgcgtccgca gagcacatat   105900
ttttaacagt gaggttacat ccatggtttt gtcggatata aaaatttccg atttctatat   105960
cacattttgt ttgagcacta gcgttcgctt cttgttctaa tttagacgag atacgttcgc   106020
tgagtgtatt caccgtcgtc tgtatgcttg ccgcggcacc catttaaata gctacaatta   106080
gtatccatat taccaagaga gataataaac tgatcaaatg caattttagg tcgaacgaat   106140
gtttaatatt atgttgaact acttttgctc tattgacggg aacagtagaa aatctatcac   106200
tattgcttaa tccacatgac aatcttaatg aggaagtttt atccatctgt aagttgttca   106260
cgctagtatt acatcgtaca atattgcaaa gtcctaaatt attataatta cgtgttagta   106320
agaaattaac attggcattc gaacactctg gatcccaaca ttctcgaggt tccgcatatt   106380
ttaatgactc ttctaactta tctctagtgg gataactaca tctcatatat ttctgtttaa   106440
agtccgcaga ctgttgtctt agaatataat cgatcatctc tttgctatct tctgtattgt   106500
gtgcgcgtaa atgatgcaaa aatgattcac atattggtac actagcatct ttactacata   106560
atgtttgcat cttattatac agatttatta acgattgttg accctctaca gttctatcac   106620
tcctattaaa ggctgaaccg atccactgat ggcatatgtt tctatcgaac gtatcccct   106680 gacaccagtc gaataaatca acatcgcatt ttccagtgtc gtgaacgtct ggccaacacg   106740
attctaatac tgcaccctct tcatacttat ctgatatctt tccatccttt ttccaataat   106800
gagtacgatt aaaagtgcga cagcaattgg gtgcggttcc attatacgat tgtcttaaca   106860
atgccgaaag accaccgggt cctgtgttga ctaatctaaa ctctggatat cttttctta   106920 ctttatcctc tttatctttt gctagtggtc ctatatgcac atattctaaa agcttagcgg   106980
gagctatcac gtcatgcatt ttatccacgt ttaataacat ctcatcagtg ggtactcccg   107040
gaggcggatc ccgtttaggg agctcaacac ttactctgcc acccatattt atctcattga   107100
aagtattaat ctaaaaacgt cataaagatg ttgatcttaa aggattgaac tctatccgaa   107160
```

```
aacaacattc ctagaatgtt atcgtcatta tccattacga ttctagtttc aaaaacattg    107220
actctctttt tgaatcctcg tagtttgttg agagacgaga tagctatttt gaaagaaaac    107280
ttttgtagtt cttgagaaca ttcagtcata gaatattccc tggaaaacgc atcagtatta    107340
ccaggagtct tcataataat attgtcatct ttaaacataa tagccaaatg ctgatgctga    107400
ctaatacact tgataaagcc caacaaccat tctaaatgaa tgacggttct accacaacat    107460
ttttcttcat acttgtgaaa attaaacacg taagatttct tttgatctat acttagacaa    107520
atagtagtat ctgtcctaat aggcatcagt tccttgttac aatcgacact tactacatga    107580
taactagaaa gttttactag attatttttcc agatcaggtt ctatatctat gatggcatca    107640
ttgtgaaaac tacacaaaca cgattttacc ttggacacag gaagattaaa cacaatgttt    107700
tcggctccgc ggtagaacac tgatgcactg agaggtataa tggcccaaat gtttacagat    107760
ccgcccaagg cggcaaaaat atacattaac tcatccgtcg agtctacatt tatagatact    107820
tcttcactga actctgaaaa atatgccaca atttggcgca gtttatcgat ttttatacgg    107880 atgctcalttt taaattttttg taaattattt aaagttaaat ggctgcagaa cagcgtcgtt    107940
ctacaatttt tgcatagtt tcaaaatgta tagtgcaatc tgtattgaga gatatatcta    108000
ttaattctga atacatagag tccaaagcta aacaattgtg ctattgtccg gcatcgaaaa    108060
aggaatcagt gattaatggt atctacaatt gttgcgagtc aaatatagaa ataatggaca    108120
aagagcagct attaaaaata ttggacaatc ttcgatgtca ttcggctcat gtatgtaacg    108180
ccacagattt ctggagacta tataattcgt taaaacggtt tactcatact accgcattct    108240
ttaatacatg caagcccact attctagcca cgctaaacac tttgataacc ctgattttat    108300
ctaacaagtt attgtatgcg gcagaaatgg tagagtatct agagaaccaa ctagattcat    108360
caaataaatc aatgtctcaa gaactagcag aattattgga aatgaaatat gctctcatta    108420
atctggtaca atataggatt ttgccaatga tcatcggtga gcctattata gtagctggat    108480
tttctggtaa agaaccaatt tctgattatt ctgcagaagt ggaaaggcta atggaactac    108540
cagttaaaac tgatatagtg aataccacat atgacttctt agccagaaaa ggtattgata    108600
ctagcaacaa tatagcagaa tatatagccg gcttgaaaat agaagagatt gaaaaggtag    108660
aaaaatattt accagaagtt atatctacaa ttgccaatag taatataata aaaaataaaa    108720
aatctatctt tccggccaat atcaacgata aacagatcat ggaatgctct agaatgttag    108780
acacgagtga gaaatactct aaaggatata aaactgatgg agctgtgact agtccattga    108840
cgggaaataa tacaattaca acatttatac caattctctgc gtccgatatg caaaagttta    108900
ccattttaga atatctttac attatgagag tgatggcaaa caacgttaag aaaaagaacg    108960
agggaaaaaa caacgaggga gtagttatgc atattaactc acccttttaag gtaatcaatt    109020 tgccaaaatg ttaaattatt agaatcatat atctttatcc atctattatc atctgtgaag    109080
ttttggctca gaaaaatatc tttacctaat attcgtttag acgatgtatc aataccggca    109140
tttttataac attcagctac caatttaaaa caatacattc tattatgacc aaatccatac    109200 ggaatacccca ataaagttaa tgacgtatca gctgctattt tcataacttg aatattctct    109260
aacatgtata cttttgcact aagatatcct tcaaaaaaac tatccaatgg gactattcga    109320
actccttttc tataggtaga ttcaactacc aagtgttccg ataataacgt accataataa    109380
atacccacat gttttctat cgatggattc aaatgacttg ttaatgacat ggtataatta    109440
ataaaaataa tagaacctct aggcgcatat gtcttgataa aattaaccgg atccatatta    109500
```

```
gtttatatcc aatagaggtt gcactgttaa gttacgttga ggttctattt gtgtagataa 109560
ttttaaccta caacattcgt tctttacact gacgagtaca tcctttaatg attttttcg  109620 tataatcaat ttatatcgtt cgtgagaaat atctttgccg cacgtagagc acacgagttg 109680
gaacaccatt tttaatctag taacctatat ttattatatt atcacttttta gtattggtta 109740 ttaacagact atcgttaaag taaaatgaac tatttatact cagtagtaaa ttatccttat 109800
agatgccgaa cactatagtg ttacagtttt cgttagaata tccgaagatc gaagatatag 109860
attttataac atcgatatct gatttagtat tttcgaaatc tatataagat gataaagttt 109920
taacttctga aacatcaatc tccttgcgtg gttctaatgc atacattaat tggcagggta 109980
acggaacggt ctctaaataa gatgatttaa aattgttcca ttttcatct  aatgcggaaa 110040 atataaattc ttgaacagtg cattgacaag gaggaacata cgagtagaca tcgtctaaat 110100
tagcgtaatc gtttataaac gtaacaatat tacgcacgtc tacggtagag ttagtctttc 110160
tataataatt tttaattgcc aaactagtga ctatattatc gattgtaaaa tcactaaaca 110220
attgtatttt gtttaagttg gtgggtgtta tagatgcccc atagagtcca ggaaagaaat 110280
cacatccatt cactaacgcc gttaattttg ctaaatagtt atcctctgcc gagggaacaa 110340
atttaaacag ttgagttaag ttttttatca tcttaggatg attatcagta gatgcaaata 110400
gcatagtatc ctgatcggta cttattatca acggccattc tcctgtggta gagaaatgtg 110460
ttttagcctc gagacacata acgaattctg cgtctcgttc atcacaataa aataatgtaa 110520
cattctcatt attgttgaaa tgtgttagta tctcattcaa tgatattttt atgttatcag 110580
aatcagataa atatatttga aatgtgagtt tatcgatttt taattgcatt tctgccttta 110640
tttcttcttc cataaatccg gtaacatttt gtatttcgga tgtacacttt tctaattcta 110700
gcatttttct gtccttggtt aatttagaat atttacgtct cttgtctcta acgtcttgtt 110760
taatttttat acttcctcta tcgataaaaa gggttacatg ccctcccttt tttacccatc 110820
cgtttacgta ttttatgaat accgtagtta actcttctaa gtttctgaca caattggcga 110880
cggctatata aatactcatt gtatccacaa atattccatt gtatactttg tataaattat 110940
catctaatat cgtcagtgat ttattttcca gcagtaacga ttttaagttt ttgatacccc 111000
taaatgaaga acgtactgat tattttcggt aaaccgtatt gtagtatttg tgaaaatgtc 111060
agtgatgcag tagaagaatt aaaatccgag tatgatatac tccatgttga tatcttatca 111120 tttttttttaa aggatggtga ttcaagtatg ctgggtgacg taaagcgcgg aaccctaata 111180
ggaaactttg cagcgcatct atctaactac atcgtttcca ttttcaaata caatccacag 111240 acaaacaaa tggcatttgt ggacattaat aaatccttgg atttcaccaa aaccgataaa 111300
tcgctggtga atttggaaat tctaaaatcc gaaatagaaa aagcaaatta tggagtttgg 111360
ccaccggtta ccgaataaaa tatcttcctg agtatttgt ttattgttcc gcttccttta 111420
tcaaataaat tttgaagtat ttgataattt attggatcga ctagttcatc tatacatttt 111480
ttggaaacga gaacatctac ctttttattt gttgttatat gcgacgttgt atacgccata 111540
aatgtaactt gagaaaatcc acaaagaatt aattttgaac cagttatggg gacgcgctca 111600
ttagaatatg tataaatctg aggagtgtat tccttgagga gatattctat caagtcatca 111660
tttgcttctc taatataaat attcctgtcc tttataacaa ctatgccttt tagattatct 111720
cctaatttat aacacggccg tatacacttg gaatacttgt acaatctaag atagactaaa 111780
tctctcagag ttgtatcatg gaattccata cttaattcct ccgataaatc tacatgttca 111840
aatactttag aaatatattt atggtatttc ctatctggaa agtaagttat caagtcatca 111900
```

```
taagatattt caaatcctct acataaggaa gacactatct ccaacgattc ctcatcttct    111960
gtaagtagga atttggacaa gttaaacaaa attagatctc taaatggcat ctttattata    112020
tcttatttta tttttgttat tcgtatgtat ttcttattat tttacatatt atccgaccaa    112080
taaacttcag gcagctgtaa tggaaacaga tagagaaaac gctattatta gacagcgaaa    112140
tgatgaaata ccgactagaa cattagatac agctatattt accgatgcat caaccgtcgc    112200
gagtgcgcaa atacacctat attataattc caatattggt aaaattataa tgtcacttaa    112260
tggtaaaaaa cacacccttta atttatacga tgataacgac atacgaacat tacttcctat    112320
tttactcctt agtaaatgat tgtcttaccg aataaagttc gtattttcat caacgatcgg    112380
atgaaaaagg atatctactt gggaatttct aatttcggat tcgagaatga tatagatgaa    112440
atcttgggaa ttgctcactt gttggaacat ctacttatat cctttgattc tactaatttt    112500
ttagcgaatg cttctacatc tagaagttat atgagttttt ggtgtaaatc cattaattca    112560
gcaacggaat cggacgcaat cagaacatta gtttcgtggt tcttttctaa cggaaaactc    112620
aaagataatt tttcccttttc tagtatacga tttcacatta aagaattaga aaacgaatac    112680
tattttagaa atgaagtatt ccattgtatg gatatactaa cgtttcttag cggaggcgat    112740
ttatataacg gtgggagaat agacatgata gataatctta atatagttcg tgatatgctg    112800
gtaaatagaa tgcaaaggat atcgggatcg aaatatcgtaa ttttgttaa gagattagga    112860 cctggaacat tggatttctt caaacagaca tttgggtctt taccagcatg tccggagatt    112920
attccttcgt ctattccagt aagtacaaac ggtaaaatag ttatgactcc gtctccattt    112980
tatacagtta tggtaaagat taatccaaca ttagataata ttttagggat tctgtatttg    113040
tacgaaactt accacttaat agactatgag actatcggca accagttata tttaacggta    113100
tcctttatcg atgaaactga atacgagagc tttcttcgtg gcgaggctat attacaaatt    113160
agtcaatgtc aacgtattaa tatgaattat agcgacgatt atatgatgaa catctatttta    113220 aattttcctt ggctatcgca tgatttatat gattacatta cacgtattaa tgacgatagc    113280
aagtcgatac taatatcctt gacaaatgaa atatatgcat ctataattaa tagagatatc    113340
atagttattt acccaaactt tagtaaggcc atgtgtaaca ctagagatac ccaacaacat    113400
ccgatagtag ttcttgacgc aaccaatgat ggactgatta agaaaccttta tagaagtata    113460 cccctaatga agcgtctaac atctaatgaa atatttatac gatacggaga cgcgtctctc    113520
atggacatga taactttatc attgtctaaa caagatatat cattaaaaag aaatgccgaa    113580
ggaatacgtg taaaacatag ttttttcagct gatgatatac aggcaattat ggaatctgat    113640 tcgttttttaa agtatagtag atcaaaacca gctgcgatgt atcaatatat atttctatca    113700
ttttttgcta gtggtaattc catagatgac atattggcaa atagagattc taccttagaa    113760
ttttctaaaa gaactaaaag taaaattttg tttggtagga ataccagata cgacgtcact    113820
gcaaaatcta gttttgtatg tggtatagta cgaggtaaat cattggataa aacgtctctg    113880
gttgaaatga tgtgggatct caagaagaaa ggattaatat attctatgga atttaccaat    113940
ctattgagca agaatacctt ttatctgttc acatttacta tctacactga tgaagtatac    114000
gattatctaa acactaataa acttttttct gcaaaatgtt tagtcgtgtc tacaaaagga    114060
gatgtggaaa atttttcatc tctaaaaaaa gatgtggtca ttagagtttg atttttagtt    114120
attatctaca ggaacaaaata tagtatctga aatcatattc atatatcccg ttagaggtct    114180
atgataatat atagtagcgt ttgttccgtt atagacaccg aataatattt tacaaaagtg    114240
```

```
tatatacgta tcatcatctt tatgtttaaa atttaaaatc ttaattcgta aatttagaga   114300
taaaatggct tcttgtacaa tactagttaa ttctcccgtc ctctcaaaat tatccaactc   114360
ctcagcgaga ataggactta gtacataaag tttagcatac tctatcatct tcatataata   114420
attggataat aatttattcc atgtttctgt actaatatcg aacgagtcta tatattcctt   114480
tgtacgccat agaatatcca aatttgtagg gattataaac aaatcttcgg ggagtgttag   114540
attaaactta ttagcgtaca atatataatt atgtagaaat tctgaatcta ttcgctgtat   114600
agacttcata taagacagat catagaaata tacgtatgtc ccaggattaa ctcttcctac   114660 tcttccttt cgttgatctc tcatagattt agaaataaat tcttgcgatc tccaaaagg    114720 agcggggaca aaaactctac ccatatcata aatgtgtgta acattgcgta tagtaacgct   114780
ggattccaaa taaggagtag aaataattat cgatacatta ggtgatgaat acacttttc    114840 taatatttcg tctatatcta agaccttacc atgaataata tacatatcat acggtaatct   114900
tttttctaaa tatgatttat attcgtgaca ctgtgcaacg gatgccacaa agactatacc   114960
ggatgatcca tcaggaggag tatacatctg tatagcagta actaaatttc tcttttcttc   115020
ttctatgtat gccattctgg aagatggatt tatcttatta tgaataaata cctcgctaat   115080
tttaaacagt gtatctccag gaatatgtat aaatgcggga ttaggtaaaa atactttag    115140 ccgttccctg tcatcctcta acgtggcagt cattaaaaac atagaatcta ttttcgtatg   115200
atgctttctc gctactgcta taataatatc tcctatttga tcatgctcat gaacttcgtc   115260
tataataaga gtgccataac taaatagttt tgttagagat aacttatggg tagaaaatac   115320
aattccatat ttttttggtt gtttgtttat taattcttcc ggtatagatc cgtaccgtaa   115380
agaaatagga gatccatcta gtaccttaaa tcccaatgat tttaaaatgg tattgctatg   115440
caatctaact aaaagctatcc taggaagaga tagaatgact ggtctttcgt gaaagtcagt   115500
gattttatct agagtagaga atccaccaaa taaataatta aaccaaagca ataacttggg   115560
tacctgtgac gtcttaccca ctccagttcc tccagttaaa actacaggtc tatgagaaat   115620
ccacgctgaa aatatctctc gttgtgcttt aggagttaat gaggccaatg gaattttgct   115680
aaatggatac ttattcccta gtacacctat agtatctgtt cgtttaccta cggaattgga   115740
aaatatctgt aaactattac cagcttctaa tagtcctctt aatatatact catcgaacga   115800
attgatttct gtatttgtta tacattttag aaaactataa cattcaaagc ttattgtgtg   115860
ttcactgtat atatattgct tcgcggttag gtttatgtgt gcgggttttc ctagtgatgg   115920
aggagatact tttttccac gtgcttctgt actaactttg tatattcctt tatgttttac    115980
aacgtgtgcg ttatgccatc tatgttttat aactggaaac accgccaatg agaaactatc   116040
acgttccgtt ttactcatat tactgaattc atcttgtgaa tatttgtaag agaatacatt   116100
aacgcagttt ggaaaaaaga agatatctgg taaattcttt tccatgataa atggaaagat   116160
atacagattt agtaattagt aaaataccag aactaggatt taccaattta ttatgtcata   116220
tatattcact agctggatta tgtagcaata tagatgtatc taaattttta acaaattgta   116280
acggatatgt agtggagaaa tatgataaat ctacaaccgc cggcaaagtg tcttgtattc   116340
ctatcggtat gatgttggaa ctagtagagt cggggcacct gagcagaccc aatagtagcg   116400
acgaactcga tcaaaagaaa gagttaaccg acgagttaaa gacgcgttac cattctatat   116460
atgatgtctt tgagttacct actagtatac cgttagcgta tttctttaaa cctcgactac   116520
gggaaaaagt atctaaggcg atagacttct cacaaatgga tttgaaaatc gatgattat    116580 cacgtaaagg aatacatact ggtgaaaatc caaaggtcgt caagatgaaa atagagcctg   116640
```

```
agagaggagc ctggatgagc aatcgaagta ttaagaactt agtctctcag tttgcttatg    116700
gatccgaagt ggattatata ggacaatttg acatgagatt cttaaactcc ttagcgattc    116760
atgaaaaatt tgacgcgttt atgaataaac atatcttatc gtatatactt aaagacaaaa    116820
ttaaaagttc tacctctaga tttgtaatgt ttggattttg ttatttgtct cattggaaat    116880
gtgtaattta tgataaaaaa caatgtttag tatccttta tgactccgga ggcaatattc    116940
caactgaatt ccaccactat aataattttt attttattc cttctccgat ggttttaaca    117000
cgaatcacaa acattctgta ttggataata caaattgtga catcgatgtt ttattcagat    117060
ttttcgaatg tacatttgga gcgaaaatag gctgtattaa tgtagaagtt aatcagctgt    117120
tggaatctga atgtggaatg tttattagtt tgtttatgat attgtgtact aggacaccac    117180
ctaagagttt caaatctctg aaaaaggttt atacattctt taaattttta gcggataaga    117240
aaatgacatt atttaagagc attctattta acttgcaaga tctatccctg gatataacgg    117300
aaacggataa cgcaggatta aaagaatata acgtatgga aaaatggacc aaaaagtcaa    117360
ttaatgtgat atgtgataaa ttaactacaa aattaaatag aatagtaaac gacgatgaat    117420
aactttgtta aacaagtagc ttcaaagtct ctaaaaccta ccaaaaaatt gtctccgtca    117480
gatgaggtga tatctttaaa cgaatgcata atatccttta acttggataa cttttattat    117540
tgcaacgatg gactgtttac taagcccatt aatactccgg aggatgttct taaatcactc    117600
ttgatcatgg aatcattcgc ctacgagaag atgataatca aaggattgat aaaaatacta    117660
atatctagag catatattaa tgatatttat tttactccat tcggttggtt gacgggcgtc    117720
gacgatgatc ctgaaacaca cgtggtgata aaaataattt tcaattcatc actaatatct    117780
atcaagtctc aagttataga atatttaaaa ccatacaatg tcaataaccct atcggtactt    117840 accacagaaa aagaattaag tattaatacg ttcaatgttc cagattctat acctatgtcg    117900
ataatttcgt ttttcccatt cgatacagat tttatactag ttattttgtt ttttggagta    117960
tataatgact cgtattgtgg aataagctat ataagtccga agagagact accgtatatc    118020 atcgaaatat taaaaccgtt ggtgtcggaa attaacatgt tatcggatga aataggtaga    118080
acatcatcca ttagaatctt caattccact agcgtcaaaa aatttcctac taatacatta    118140
acatccattt gtgaaattgt ttattcgttt gatgaatcat cctttccgac gcctaagacg    118200
ttcactcctc taaacgcgag tccatacatt cctaaaaaga tagtttcact attggattta    118260
ccatctaatg tggaaataaa agcgatatct agaggcggtg tggatttcat cactcatatt    118320
aataataagc gtctaaacac aatcttggta atagcaaaag ataactttt aaaaaattct    118380 acattttctg gaactttat caaagagaat attatttgga agggtatcta tacttataga    118440
ataatcaagt ctagttttcc agttcctact attaagtcgg ttactaataa aaaaaaaata    118500
tgtaagaaac attgtttcgt caattctcag tatacaacta ggactttgtc acatattctt    118560
tgatctaatt tttagatata aatggtggat gctataaccg ttctaactgc gatcggcata    118620
actgtattaa tgcttttgat ggtaatttct ggcgccgcca tgatagtcaa ggagttaaat    118680
cctaatgata tattcactat gcaatcatta agtttaatc gagccgtaac gattttcaaa    118740
tatataggac tctttatcta tataccagga acgataattt gtacgctac atacgtcaaa    118800 tccctattaa tgaaaagtta ataatttttt tttattacac caacaaaaat gtttgtcatt    118860
aaacgaaatg gatacaagga aaatgtcatg tttgataaaa tcacgtctcg tattagaaaa    118920
ttatgttatg gcttaaacac ggatcatata gatcctatta aaatagctat gaaggttatt    118980
```

```
caaggaatat ataatggagt aacaacggta gaattggaca ctctggcagc cgaaatagca   119040
gccacttgta ctacacaaca tccggattat gccattctag ccgccagaat agccgtatca   119100
aatctacaca aggaaacaaa aaaactattt agtgaagtga tggaggattt attcaactat   119160
gttaatccta aaaatgggaa acattctccg attatttcaa gtatcaccat ggatatagtt   119220
aacaaatata aggataaact caactcggtt attatttacg aacgagactt ttcatacaac   119280
tattttggtt ttaaaacttt ggaaaaatcc tacttgttga aaataaacaa caagatcgtt   119340
gaaagacctc agcacatgtt aatgcgtgtc gcagtaggaa ttcatcaatg ggatatagac   119400
tcagctattg agacgtacaa tctactttct gaaaaatggt ttacgcacgc ttctcctacc   119460
ttatttaatg cgggaactag tcgtcaccaa atgtctagct gttttctact taacatgatc   119520
gatgatagca tagagggtat ctatgacacg ttaaaacgat gcgcattaat ctctaaaatg   119580
gcaggggggaa taggtctatc aattagtaat attcgtgcca gtggaagcta tatctccggt   119640
accaatggta tatcaaacgg tattattcca atgttgagag tttataataa caccgctaga   119700
tacatagatc agggaggaaa caaacggcct ggagttatgg ccatatactt ggaaccgtgg   119760
cattctgata ttatggcgtt cctcgatctt aaaaagaata caggaaacga gaacataga   119820
accagagatc tatttatagc tctttggatt cctgatctct ttatgaaacg agtgaaggat   119880
gacggagagt ggtcgttgat gtgtccggat gaatgtcctg gattggacaa tgtttgggga   119940
gacgagttcg aacgattgta tacactatac gaaagagaaa ggagatacaa atctataata   120000
aaggctcgag tcgtctggaa agcgattata gaatctcaga ttgaaactgg tactccattc   120060
attctttata aggatgcgtg taacaaaaag agtaatcaac aaaatttagg aactatcaag   120120
tgtagtaatc tttgcactga gataatacaa tatgcggatg ctaatgaggt agccgtttgt   120180
aatctggcat ctgttgcctt gaacatgttt gtaatagatg ggcgatttga ttttctcaaa   120240
ctgaaggatg tggtcaaagt aattgtcaga atctcaata aaattataga tattaattat   120300
tatcctattc cagaagctga aatctctaat aagagacata gacctatcgg tattggtgtt   120360
caaggattag cggacgcgtt tattctctta aattatccat ttgatagcct ggaagcacaa   120420
gatctaaata agaagatctt cgaaaccatt tattacggtg cattagaggc gagttgtgaa   120480
ctagctgaga aggaaggacc atacgataca tatgtaggat cgtacgccag taacggtatt   120540
ctacaatatg atctttggaa tgttgtaccg tcggatcttt ggaattggga acctctaaaa   120600
gataaaatca gaacatacgg tcttagaaat agtttattgg tggcacctat gccgactgca   120660
tcaactgctc aaattttggg aaataatgag tcggtggaac cgtataccag taatatttac   120720
actcggagag tattgtctgg agaatttcaa gtagttaatc cgcatctcct tagagtttta   120780
accgagagaa aattatggaa tgatgagatc aagaatagga ttatggcaga tggtggatcc   120840
attcagaata caaaccttcc agaagatatt aagcgagttt ataaaactat ttgggaaatt   120900
ccacaaaaga cgatcataaa aatggctgca gacaggggag ccttcatcga tcaaagtcaa   120960
tctatgaata tccatatagc agatccgagt tattccaaac taacgagtat gcatttttac   121020
ggatggagtc tcggtctaaa aacgggaatg tactatctac gtacgaaacc cgcatccgct   121080
cccattcaat tcacattgga caaggataaa ataaaaccac tggtggtttg cgattccgaa   121140
atctgtacat catgcagtgg ttaaacaaaa acattttat tctcaaatga gataaagtga   121200
aaatatatat cattatatta caagtacaa ttatttaggt ttaatcatga gtaaggtaat   121260
caagaagaga gttgaaactt caccaagacc tactgcatct agcgattctc tacagacttg   121320
tgcgggtgtt atagagtatg caaaatcgat tagtaaatct aatgcaaaat gtatcgaata   121380
```

```
cgttacacta aatgcttctc aatacgctaa ttgttcgtct atctctataa aacttactga 121440
tagtttatct agtcaaatga cttccacttt tattatgttg aaggagaga ctaaacttta 121500 taaaaataaa tctaaacaag atagaagcga tggatacttt ctaaaaataa aagttaccgc 121560
ggctagtcct atgttgtatc aacttctaga agccgtctat ggaaacatta agcacaagga 121620
acgcattcca aattctttgc atagtctttc ggtggaaact attacagaga aaacatttaa 121680
ggatgaatcc atcttcatca acaaattaaa cggatccatg gtagaatatg tttcgactgg 121740
agaatcatcc attctcagat ctatagaagg tgaactagaa tcactcagta aaagagaaag 121800
acaattggcc aaggcaatta tcacacctat cgtcttctat agatccggaa cggaaacaaa 121860
aattacattc gcactcaaga aactaatcat tgatagagaa gtggtggcta acgttatcgg 121920
actctctgga gatagtgaac gtgtatcaat gactgaaaat gtagaagaag atctggctcg 121980
taatctggga cttgttgata ttgatgatga atatgatgaa gatagcgata agaaaaagcc 122040
aatattcaat gtataaatgg ataagttgta cgccgctata tttggtgtat ttatggggtc 122100
tccggaagat gatttgacag actttataga aattgttaaa tctgttctaa gtgatgagaa 122160
aacagtcaca tcaactaata ataccggttg ttggggttgg tattggttaa ttattatttt 122220
ttttatagtt cttattctac tactattgat atatttgtat ttaaaagttg tttggtgaac 122280
ttaaatggcg gaatttgaag atcaactcgt tttcaatagt atcagtgccc gtgcattgaa 122340
agcttatttc actgctaaaa tcaatgaaat ggtagatgag ttggtcacaa gaaaatgtcc 122400
acaaaagaaa aaatcacaag ctaagaaacc tgaattacgc attcctgtag atcttgtaaa 122460
gtctagtttt gttaaaaagt ttggattgtg caattatgga ggaatcctta tcagtcttat 122520
taatagtcta gtagaaaata atttctttac aaaggatgga aaactggatg atacaggcaa 122580
aaaggaattg gttttgacag atgtcgaaaa acgaattctt aataccatag ataaatcatc 122640
tcctttgtat atcgatatta gtgatgttaa agtattggct gctagactaa aaagaagcgc 122700
tacacaattt aactttaatg gacatacata tcatctggaa aatgataaaa tagaagatct 122760
cattaatcag ttggttaagg acgaatccat tcaactggat gaaaagagtt ctattaaaga 122820
tagtatgtat gtcattcccg atgaacttat cgatgttctc aaaactagat tgtttagatc 122880
tcctcaagtc aaggataata ttatttcgcg tactagattg tatgattatt ttactagagt 122940
tactaagaga gacgaatcgt caatctatgt gattctaaag gatcctagga tcgctagcat 123000
tttgtcacta gaaactgtta aaatgggcgc ctttatgtat acaaaacata gtatgttgac 123060
gaacgctatt tcatctagag tcgatagata ttctaaaaag tttcaagaat cttttttacga 123120 agatattgta gaatttgtta aagaaaatga gagagttaat gtatcgagag tggttgaatg 123180
tttgactgtg cctaatatta ctatatcaag taatgctgaa taaaaatatt tataaatatg 123240
ctcgtcgtaa ttatgttttt tatagcgttt gccttctgta gttggctatc atatagctat 123300
ctgcgtccat atatctcgac taaagagtta aataagtcga gatagtttta tatcacttaa 123360
atattaaaat ggccgaggaa tttgtacaac aaaggttggc caataacaaa gtgacaattt 123420
ttgtcaagta tacatgtcct tttttgtagaa atgcactgga tattctaaat aagtttagtt 123480
tcaaaagagg agcgtatgaa attgtcgata ttaaagaatt taaacccgaa aatgaattgc 123540
gtgactattt tgaacaaatt actggtggta gaactgttcc tagaatcttt tttggaaaaa 123600
cttctattgg tggatatagc gacctgttgg aaatagacaa catggacgca ttgggtgata 123660
ttctatcatc tattggggta ttgagaactt gttgagaaaa taatgaaaaa acaatactta 123720
```

```
atcatgtcgc cgacatgttc atgtatccgg aatttgcgag gaaggcttta tcaaagctta  123780
tttcaaaaaa attaaacatt gaaaaggtgt ctagcaagca ccagctcgtg ttactggatt  123840
atggattaca cggactattg ccaaaatcac tgtatctgga agctattaat tccgatattc  123900
tcaatgttag attctttcct cctgaaataa taaacgtcac tgatatcgtt aaggctctcc  123960
aaaattcttg tagagtagat gagtacctaa atctgtttc cttatatcat aagaattctt  124020
taatggtatc gggaccaaat gtagtcaagc ttatgataga atataatctt cttacacaca  124080
gtgacttgga atggttaatt aatgagaatg tagtcaaggc tacatacctt ttaaaaatca  124140
atgcctatat gattaacttt aaaatagatc taacggttga tgaaatcatt gacttagtta  124200
aagatattcc tgtaggagct acgctacatc tatataatat attaaacaat atagatttgg  124260
acattgttct tcgtatatct gatgaatata atataccacc tgttcacgat attctgtcta  124320
aacttaccga tgaagagatg tgtataaaac tagttacaaa gtatcctatg acaatgttta  124380
taaattttat taatcaagat gttagatata gtcccacctt catcaagaca attaaagatt  124440
ttgtcaacaa gcatcttcca accatgtacg atggattaaa tgattatcta cattctgtta  124500
ttatcgacga ggacttaata gaggaatata aaattaaatc cgttgccatg tttaatttgg  124560
aatacaaaac tgatgtagat actctaacat tggacgaaca gatatttgta gaggtaaaca  124620
tctcatatta tgatttttaga tatagacaat ttgccgatga atttagagat tacattatga  124680
taaaagaaag aagacaaatc accatgcaat ctggtgatag aataagaagg tttagacgtc  124740
ccatgtcatt gagatccact atcatcaaaa aggatactga ttctctagag gatattctcg  124800
cacatataga taatgccaga aaaaatagca aggtatccat tgaagatgtt gagagaatca  124860
tttcatcttt ccgtcttaat ccttgtgttg tcagacgcac catgctgtct gatatagata  124920
tcaaaacaaa gattggaaat cttgtgctct gacactatca gccatcaaag gaattatggt  124980
aacagatacc atcaataccg tgttatccaa aattctgcat catcatagga atgtcttcaa  125040
gtatcttaca tctgtagaga ataaagaaat tgctgtctgt cgctcttcta tagaattaa   125100 aaaagtgtac gatgtgatct acgcacagat gatggattat tggataggct atacgatctg  125160
actagatacg cctacacgg aaaaatcaat caaaacttaa tcggtcaacg atgttggggt   125220
ccgttgacag aaatgctgtt taacgagaat aaaagaaaa aactaaataa tttaatggaa   125280
tacatcaaaa tatcagacat gttggtatac ggacactcta tcgagaagac gcttattcca  125340
attactgatt ctctttcatt caagctatct gttgatacca tgtctgtgtt aaatgatcaa  125400
tatgccaaga ttgtcatctt cttcaatacc atcatagaat atattatagc tactatctat  125460
tatagattga cagtcttgga caattatact aatgtcaaac attttgtatc caaagtgtta  125520
cacactgtca tggaagcatg tggcgtactg ttttcataca ttaaagttaa tgacaaaata  125580
gagcatgaat tggaggagat ggtggacaaa ggtaccgtac cttcttattt gtatcatctg  125640
tccatcaacg tcatttcaat aatattggat gatataaatg gaactcgtta atattttttt  125700
agaaacggat gctggaagag taaagtttgc cataaaaaat accgacgatg tatgtgcctc  125760
ggagttaata aataaatttg tggaactgtt aagtgaatac attcacattg accaatcaga  125820
attttatttg gtggtaaagg ataaggtat ttttattt aagtgtgata gggggtctat     125880
ttcgattgta acaatgagt tttatgtctt tgacgaaccc ttgctgtttg ttaaagattt    125940
cactaatgta acgggggttg aattcatagt tacagaaacc atgccgtgta gaattatacc  126000
aaaaaataat cacgcggtta tttcagtcgt gactaatcat aagttttata atgggttaag  126060
tttataaagg gttaacctt gtcacatcga tcgcgtattt gggatcagat gccaaattgt    126120
```

```
taaataatct gatgaaaaaa taataaatat aattcagatc atcgctagac atgacattat   126180
tgtcctctat agcgatagtc gcgtgccgtc tacatgcagg acatggaaga gtgctgacta   126240
tagtatatag ttttcgttta cacgcttcta tgttgccgtc taaacccgct tgcgaaagta   126300
ctataaaaat aatggtccat acggctcttc cccaatgttt gggattcatt taaatgaaaa   126360
tatatttcta aattctataa atggatgttc ggtgcattaa ttggtttgaa agtcacggtg   126420
aaaacagatt tttatatctg aaatccagat gtcgaaatgg cgagaccgta tttatacgat   126480
ttcctcatta cttttattac gtagttacgg acgaaatata tcagtcattg tctcctcctc   126540
catttaatgc gaggccgttg ggaaagatga gaactataga cattgacgag acaataagtt   126600
ataatctaga tattaaagat agaaaatgct ccgtcgcaga tatgtggttg atagaagagc   126660
caaagaaacg cagcatacaa aatgccacca tggatgaatt tctcaatatt agttggtttt   126720
atatttctaa cgggatatct ccagacggat gttactcgtt ggacgagcaa tatttgacaa   126780
agattaacaa tggatgttat cattgtgacg atccacgtaa ctgtttcgct aaaaaaatac   126840
ctagattcga tatcccaaga tcgtacttat ttctagatat agagtgtcac ttcgataaga   126900
agtttccttc tgtatttatt aacccaatct cgcatacaag ttactgttat atcgatttaa   126960
gtggtaaacg attattgttt acgctcatta atgaagagat gttaacggaa caggaaatac   127020
aagaagccgt cgatagagga tgtttgagga tacagtcact aatggaaatg gattacgaac   127080
gagaactagt tctatgttct gaaatagttt tgttacgaat agctaaacaa ttgttggaac   127140
taacgttcga ctacgtcgtt accttttaacg gacataactt tgatctgaga tatattacta   127200
atcgtctaga gttattaaca ggagagaaga ttatctttag atctccggac aaaaaggaag   127260
ctgtacatct ctgtatttat gagagaaatc agtctagtca taagggagta ggcggcatgg   127320
ccaatactac gtttcacgtt aataacaata atggaactat atttttcgat ctatattcat   127380
tcattcaaaa atctgaaaaa ttggattcgt acaaattgga ttctatatcc aagaacgcgt   127440
tcagttgcat gggtaaagta ttaaatagag gagttagaga aatgacgttc atcggtgacg   127500
atactacgga cgcgaaaggc aaagccgctg catttgcaaa ggttttaacc acaggtaatt   127560
atgtgactgt tgatgaggat attatatgta aagtaattcg taaagatatt tgggaaaatg   127620
gatttaaagt cgtactatca tgtcctactt tacctaatga tacatataaa ttatctttcg   127680
gaaaggatga cgttgattta gctcagatgt ataaggatta taatctaaac atagcttag   127740 atatggctag atactgtatt catgatgctt gtttgtgtca gtatttgtgg gagtattatg   127800
gagtagaaac aaaaacagac gcgggtgcgt caacatatgt gcttcctcaa tccatggtat   127860
tcgaatatag agcgagtaca gtcatcaagg gtccactgtt aaagctattg ttggaaacta   127920
aaactatctt agttagatca gaaacaaaac aaaagtttcc ttatgaaggc ggtaaggtat   127980
ttgctccaaa acaaaaaatg tttagtaata atgtattaat ctttgattat aacagtctgt   128040
atcctaatgt gtgtatcttt ggaaatctat ctccggaaac attagtcggt gtcgttgtta   128100
gtaccaatag attggaagaa gaaataaata atcagctctt gcttcagaaa tatccacctc   128160
ctagatatat tacggttcat tgtgaaccta gactaccgaa cctcatctct gaaatagcaa   128220
ttttcgatag atcgatagaa ggaaccattc ctagactatt aagaacattt ttggcagaga   128280
gagccagata taaaaagatg ctaaaacagg ctaccagttc aactgaaaag gccatctatg   128340
attccatgca atatacgtac aagatagtag ccaactcagt atatggtctg atgggatta   128400 gaaatagtgc tctatactca tacgcttcgg ctaagagttg cacatccata ggacgtagaa   128460
```

```
tgatcttgta tctagaatcg gtactaaatg gagcagagtt atctaacggt atgttacggt    128520
ttgccaatcc attaagtaat ccattttata tggacgatag agatattaat ccgattgtga    128580
aaacatcgtt gcctatagat tacagatttc gttttcgtag cgtgtatgga gataccgact    128640
ccgtgtttac agagatagac agtcaagatg tcgataagtc tatagaaata gcgaaagagt    128700
tagaacgact gattaataat agagtattgt ttaataattt taaaatagag tttgaggcgg    128760
tatataagaa tctgattatg caatcgaaga agaaatatac aacgatgaaa tactcagcat    128820
cgtcgaattc aaaatctgta cctgagagaa ttaataaagg tactagtgaa actagaagag    128880
atgtttccaa gtttcataag aatatgatta agacatacaa gaccagactg tctgagatgt    128940
tgtctgaagg acggatgaat tctaatcagg tatgtataga tattctccgt tctttagaaa    129000
cagatttacg atccgaattt gatagtagat cgtctcctct agaattattt atgttgagtc    129060
gaatgcatca ctcaaattat aaatccgcag ataaccctaa tatgtatttg gttactgaat    129120
ataataaaaa taatccagaa actatagaac ttggagaacg atattatttt gcatatattt    129180
gtccggctaa tgtaccatgg accaaaaaac ttgtaaatat taaaacatat gaaacaatta    129240
tcgatagaag ttttaaactc ggcagtgatc aaagaatatt ttacgaagtt tactttaaac    129300
gattgacgtc cgaaatagtc aatctattgg ataataaagt tttatgcatc tcattctttg    129360
aaagaatgtt tggttcaaaa cctacatttt acgaagcata aataattta caacagttgt    129420 acgtcgctct ttgttagatt cagtttatcc attagatatt ctacggctgg agtaattttt    129480
gtagtaattg aatacccagg tacgtaaaac aataaaaaca ttaataccgg atcatacttg    129540
gtaaagtaca atatagtact aatattagct aatgtctcat aatcggatgg acttcttgct    129600
ctactaagat tagggtgatc tatatctttg atacttattg gaacgggacc ggtaaatata    129660
taattctctt tgagacgact aaacaaaggc ttatagtctc ctgtttgatg catataccta    129720
gccaacgcca ggtgtttggc attatctgta tagacgtatc tgaataatgt gtgtttagta    129780
atatcaaact gagtattttt aaaccagaac aagatattat agattggaat ggaagtcagt    129840
aacaaaaaac taataaaactc gtttgttgga agggcagaaa actttcgaag atatgatacg    129900
tatctaccag agaacgatcc attagcaatg aattcagtat ttacttttc ttcatatacg    129960 ggaataggac ctttatatag agacatgaga aactcgaact ttttaagtaa tcccaacgaa    130020
atgggataat agtcacttgc atctaagttt gcgtatctac tactccaaat tgcagtttct    130080
ggtatccatc catacgcgta attatcaaat agatatgtgt ttttcattaa cggtctactt    130140
agacctctac taaaaaatgt ttcttgatct agaattcttc tttgtgcatt tttgtacacg    130200
tcgtcaaaac gcggaacggt ggcagccata atatttatat cctaccgctt tttatcaact    130260
atgttatgtc ttttagttag gttaatattc taataagatg caggtaatac atcaggttaa    130320
agtattagaa tgggattata cttatatatt tagtttatct ttcatcagat aactaaaaaa    130380
tgtataaaac agacgcgtta cattgcctat gctacatgag ttccatgtgc ggagattgtt    130440
aaagtttagg gtagagagtt gttctagcat ccattcattg tctttacatc cgttatatgt    130500
aattatgtca cccatggaca ttataggttt taatagtact tcagatactg gaataagata    130560
ttgttcgtat atgtgtttga taatcatttg ttgcgtttct ggagaacttt tctctgcatg    130620 attttacat agctttacaa actcgtgatc acttttata atgagagatc tatagtcttc    130680
gtatctgtta cgaaaatcaa tatattcagg attattttct gaatcacttg attcgtcact    130740
aatatacata actatatgat caacaatttt ttccaaaatc atttctgcat tttctttatt    130800
cattaatttg gtgggagtct gaattgttgc agcagttccc atttatcaaa aatgtgtgat    130860
```

```
aattatatct atgtatatac aaattattaa taatatattt ggtctgttct atgatctacc  130920
gtgtcttatc aattgaagta tatatttctt atccgtcttg gttagatgga tgcttttatc  130980
caagaattct tctacatgat atagattatc tctcaaaaac ctttgaaata agacgatgat  131040
ggaaatatta taactagcta aaatagtttt gattagcgat ggaagaatac tagggttttt  131100
atctgtagaa aatcgaacga atgcggatac atcctccaca gacttaagat ggtttatcat  131160
tttaactaac aagtctcctt tataatcatc taacacaaga cctagacgag ccaattgtcc  131220
gtctaaataa tattttaaaa tgttttgct aaacaagttc agccgtctac tcttggattt  131280
tatagatgac agtttcttta gtattccgtt ctctatgacc atgggatccg actcgtgcaa  131340
aaacaggtat gtattgtatt ccttaacata atacgacgta tcctcgttaa agatttgaca  131400
cttcttcata tcatccattg tatctaatgt gatatcgttc acctcataaa ttatattaga  131460
tatataactg ttattaatat ctaactcatc aaatcgttta atgtccgcag cactcgtaga  131520
gaataaagac ataattcgtt cattatcgaa atattcggga tctatttgaa caacaactct  131580
gaataagtcc tcgttaaacg ttctatcact aataaatgta ttaccgttaa taaaattagc  131640
tttataaaaa ctaataaaat atttttttcca atcgtcgttt tttgcatcaa taatagatag  131700
gatatctcca ggaatatcat atatgatttc tagcagaagt tctctgatat ctttttcagg  131760
ctcaaagata taaactaact taagcatgtt tttattaacg cgtccttgtt ttatctcaga  131820
gtatatataa ctaagaattt tatcatacat ggtaatggcg tgtctattaa gaacaatatc  131880
cgcatcatta gctatacttt cgtttaacca cacccaatag ctagtcttat ctccgggaaa  131940
gatataatct ctaaacgttt ctgttagatt gctatggact attctaccag tttgttgaaa  132000
tagagtgtat atatcttgtc tatcattatc cgcaaactct atgcctgtat ctttcttgct  132060
taggtaagcc caaataagta atcttataac acttaattt ttaacaactt tgaagtctgt  132120
tttcttaaac agttttaaaa aaatgatttc catatctttg atgggttccc ctccgtgaaa  132180
taatggatta agaactaagt cataatttac gcctataagt tctcctaatt cgtccatgta  132240
ttcggcaacc tctaaaaatt tttcatcttg tgttagttta tgcacggttt ccttgtacga  132300
ttgtattgcg ttactaaacg ataaataatt cttagtcaat gctttaacgt acaacgtggg  132360
tgcatcaaat gcgtgtcgta aaaccgcttc gtacactta caacatcgta ccatatgtat  132420
gaaaacaaaa aaattggtat tagctaatac atccttagta ataacgtgtt gaggaaaatt  132480
gctaactaga tacttgagag ctagtacatg attgagggta aaattgttta ctttacttaa  132540
tgtatcatcc tttaaaaaat ctatattatt ttctactgtg tatataagat actttctacg  132600
aataaaatcc atttttatag aagagagtta tctatgatac tacactctta ttctaataat  132660 tattttttact attttatcac taataactat ttatactatc cattattaat ttaacaattt  132720
gaattagtat tggagaaaga tgaaatgcct attcactaac aaagtcaatg cactcttgaa  132780
gatttttacc aataatatgt agcggattct caaagtattt atttaccatt tctttacaca  132840
gtatcttagc cactggccta cgaacaggca tacatggttc aactatatca tgaacaatgt  132900
ttaattttag tgtatccaat ccaataaatc cattttctac atcatcatcg tatctgtacg  132960
ctttgtattc tccactcttg aacaaatctc taaacagtat cttcaacact ttttccacca  133020
attcctggga tgtcacacat tgttctacca tctgtttgat aaagagggta tcttcttcag  133080 attttcctt gattctatac atgggttta ggttataccct tgcatctatt gtatatttat  133140
cagattcagc tatcaacatt ttatcaactt gtgttccaat tattctccat ttattagatc  133200
```

```
tgcattcatt attatagaat ctttcttcca ctaatattct aataagatta agtttgaaag    133260
gagagaagat cttgtgtttg attttactca ttggatgcat tctataacga atgaatctat    133320
gatcatctcc aaacaaattg ggaaacatgt aaagcagcag agcatatacc atcttactcg    133380
gattctgtga tgctttgccg atggctgaaa tgtccgagaa tagtttataa gttttctgat    133440
tatttggaat agatggtgct atatcttcta gagtagtagt cctaatcatt ctcttaaatt    133500
ttatgtatcc tagtttcaat gtctcgtaat gagtttgtgc tgctcttatt gtctgattta    133560
tttcttttac cattttggct ctattctgaa actttatcct cttcttatcc atttttattg    133620
ttgactccgc actatcgatt tgatactttc ttttcagagt aaagctatcg tcattgatca    133680
tcggacactg acttccactc attatgaaat tgtagccgta taaccacaat acaattatta    133740
acatatatat tcacttttgt taatatcaac ataataatga aaaatataaa atgaacaaag    133800
ttaatacata agtgttataa atggaaaatg tatacattag tagttactca tccaatgaac    133860
aaacatcaat ggcggtagcc gctactgata tccgagaatt actatcacaa tatgtggatg    133920
atgccaactt ggaagactta atagaatggg ccatggaaaa atcatcaaag tactacatca    133980
agaatatagg taatacaaaa tctaatatcg aagaaactaa attcgaatca agaataata    134040 ttggtataga atactcaaag gattccagaa acaaactatc gtatagaaat aaaccgtcta    134100
ttgccacaaa tttggaatat aaaacactat gtgatatgat taagggtact agcggcaccg    134160
aaaaagaatt ccttcgctat ctcttattcg gtataaaatg cattaagaaa ggagtagaat    134220
acaatataga taaaataaag gatgtgagtt acaacgatta ttttaacgtt ctcgacgaga    134280
aatacaatac accgtgtcct aactgtaaaa gtaggaatac tacgccgatg atgattcaaa    134340
ctagagccgc tgacgaacct ccactagtta gacatgcgtg tagagattgc aaacaacact    134400
ttaagcctcc caaatttaga gcatttcgca atcttaatgt tacaacgcaa tcgtatacatg    134460 aaaacaagga aataacagag attcttccag ataataatcc atctcctcca gaatctccag    134520
aaccagcatc acctatagat gacgggttaa tcagatccac attcgataga aacgacgaac    134580
caccagagga tgatgaataa aaaaatgata aaataaatta gttttattgc tggttgtgtt    134640
agttctctct aaaaatgtct aagatctata ttgacgagcg ttctgacgca gagattgtgt    134700
gtgcggctat taaaaacatt ggaatcgaag gagctactgc tgcacaacta actagacaac    134760
ttaatatgga gaagcgagaa gttaataaag ctctgtacga tcttcaacgt agtgctatgg    134820
tgtacagctc cgacgatatt cctcctcgtt ggtttatgac aacggaggcg gataagccgg    134880
atgctgatgt tatggctgac gccataatag atgatgtatc ccgcgaaaaa tcaatgagag    134940
aggatcataa gtcttttgat gatgttattc cggctaaaaa aattattgat tggaaagatg    135000
ctaaccctgt caccattatt aatgagtact gccaaataac taagagagat tggtcttttc    135060
gtattgaatc agtggggcct agtaactctc ctacatttta tgcctgtgta gatatcgacg    135120
gaagagtatt cgataaggca gatggaaaat ctaaacgaga tgctaaaaat aatgcagcta    135180
aattggcagt agataaactt cttggttacg tcatcattag attctgattc tagttatcaa    135240
taacagttag tagtttagtt atacattgaa tcatacatat taatttttt attgagatag    135300 attaaaaaat acaaattgta gtactattaa cgcgactagt atattctcta aagatgtatat    135360 ctgtcacaga tattcgtaga gcgtttctag acaatgaatg ccatactatc acaaaagcgt    135420
ttggatatct gcacgaggac aaggctatcg cattaattaa aataggattt catcccactt    135480
atctacccaa agtcctttat aataatgttg tagaattcgt tccagaaaaa ctatatctgt    135540
ttaagccaag aactgtagct ccattggatt tgatatctac tataacaaaa ttaaagaacg    135600
```

```
tggacaaatt tgcctcacac ataaattatc acaagaatag tatattgata acaggagaca   135660
agtctctaat tgttaaatgt atgccttaca tgattatttc agatgatgat atacgattca   135720
taagagaaca gtttgttggt acaaattcta ttgagtatat tctatccttc atcaacaagg   135780
aaagcatata tagaatgagt taccaatttt cagagaatga aatagtcact atcatcaata   135840
gagatcattt catgtatgaa ccaatatatg aacatcaggt cttagattct gactttctta   135900
aaactatgtt agatagatac ggaatagttc ccattaattc tggtataata gatgaattat   135960
gtccagaagc tataatagag atattaatgg cagtagttcg tcctagggac gctatccgtt   136020
tcttagatat agtgaataag aatcaattga cagaagatag tgtcaaaaac tatatcatta   136080
atgatatcag aagaggtaaa atagattatt atattccata cgttgaagat ttttttagaag   136140 atagaactga agacttggga atatatgcga atatatttt tgaggatgct atagatatta   136200
cgaaactaga catcacaaag acagagttgg aacatatatc gaaatacatg aattattaca   136260
ctacttatat agatcacata gttaacatca tcttacaaaa taattatata gatatcttgg   136320
catctataat agattacgtg caagacgtat taacagaaga attatgtatt agaatagttt   136380
gcgaatcaac aaaccctgtt cccgttacat ctcttcctat acattctacg ttagtaatgg   136440
ttatgtgtat acaaatgaaa tatgtcgata tagttgaatt cttagacgag atcgacatcg   136500
atactttaat agaaaaagga gcagatccga taaccgaata cacatttaca acaagatggt   136560
acaataaaca caatgatttg atcactcttt acattaagaa atatggattc tgtccaatga   136620
tgatgaaacg gttaatgttc gaatatccat tgactaaaga agccagtgat catttactta   136680
aaaccatgga tgaaaacagg ggagctatta tgttttttcc gcgtactatt tgcacacttc   136740
cttatctatt atgttgtaat tataaactaa ttcaaaaacc tattccattc aaagaagaaa   136800
atcgtaacat cgtatataag aaaaccaaca gagtattatg ctttgactcg ttggagaact   136860
ctgcgtttaa aagcctcatt aaaatagatt ctattccagg attaaaaact tataacatga   136920
aagacattac atacgaaaag tctaataata taatttgtgt taggtttata cctcaagaat   136980
caattcataa tgaagagcga agaataaaat tacagttatt cgacattgct agattggcat   137040
cctatggact atattatatt ccctctagat atttatcatc gtggcacaca gtagtgaaca   137100
tgatagaggg aagagagtac actaatccac aaaaaataga atgtctagtt attttggatt   137160
tattttcaga ggaattcata gaatatcaaa atctgggcaa tgcggtatct aataaatatg   137220
aactggaata tactatatct aattatcaag ctgccataaa ctgcctaatg agcacgttat   137280
taatatatct agttctagga tcaatcagat cgatatcaaa aactgaagat tttgtattat   137340
ctatattaaa tatcttctat aaaggactga aaattaatga attactttct gaaccagtat   137400
caggagtttg tatcgaatta aataaaataa agatagagc gagctctgga gacagtagtt   137460
ttatatttct taagaaaaac gagttatcaa aaactctatc gctctgtgaa aaagtttgtg   137520
ttgagaccat attagacaat aatcagagtt ttaaatcctc aaaatgaata ggaatcctga   137580
tcagaatact tttcctaata ttacattaaa gattatagaa acctatttag gcagagtacc   137640
tagtgtgaac gaatatcata tgttaaaatt acaagctaga atattcaga aataactgt   137700 ttttaacaaa gacatatttg tatctttagt aaaaaagaat aaaaaaagat tttttccga   137760 tgttgataca tctgcatcag aaataaaaga tcgtatactt agctacttt ctaaacagac   137820 tcaaacatat aatataggta aattatttac gattatagaa ctacaatctg tattagtgac   137880
cacatacacg gacatattag gagttcttac tattaaagct ccaaatgtaa tttcatctaa   137940
```

```
aatttcttat aatgtaacat caatggaaga attggcaaga gatatgctaa attctatgaa   138000
cgtcgcagta atagacaagg caaaagtaat gggacgtcat aatgtatctt ccctagtcaa   138060
aaatgttaat aagttgatgg aagaatatct tagacgccat aataaaagtt gtatatgtta   138120
cggatcatat tctctatatc taattaatcc aaatatacgg tacggcgata tagatattct   138180
tcaaactaat tcgaggactt ttcttataga tttggcattt ctaataaaat ttattacggg   138240
aaataatatt atattaagta aaatcccata tcttagaaac tatatggtga taaaagatga   138300
aaacgataat catatcattg atagttttaa tattcgccag gataccatga acgtagttcc   138360
taaaatcttt atagataata tctatatagt ggatccgacg tttcaactat tgaacatgat   138420
aaaaatgttt tctcaaatag atagattgga agatctatcc aaagatcctg aaaagtttaa   138480
tgcgcgtatg gcaaccatgc tagaatacgt tagatataca catggtatag tctttgatgg   138540
taagcgtaat aatatgccga tgaaatgtat catcgatgaa aataatcgca tagttactgt   138600
tactactaaa gactatttta gctttaaaaa atgtctagtg tatctagatg aaaatgtgtt   138660
atcgagtgat atattagatc ttaacgccga cacatcgtgt gatttcgaga gtgttacaaa   138720
ttctgtatat ctaattcatg ataatatcat gtatacatat ttctcaaata ctattctcct   138780
tagtgataag gggaaggtac atgaaataag tgccagaggt ttatgtgcac atatattgtt   138840
gtatcagatg ctgacatctg gagaatacaa acaatgttta tcggatctct taaattcgat   138900
gatgaataga gataaaatac ctatctattc acatactgaa agagataaaa aacctggacg   138960
acacggattt attaatatcg aaaaggatat aattgtattt taggacaaaa gtctagaagc   139020
tacattatcg cgattagccg cgaacatatt ttgtagcatg tccgtcctca taaacggaac   139080 ttgtttttcct gggttattca ttctctcgca tctggaaggg gacgaaggtc ttctctcaca   139140
cgcgggtgat gagggtttat ctactttgag tacgcaggaa gctttacttc cttcgcattc   139200
tacagttcta acatcgcata ctttaacggc ttttagaacc agatatcttc cttctttggt   139260
attgatataa aacggagtat gagcagatgc aaaatgagaa ttcatttata gcatagaaaa   139320
aaaacaaaat gaaattctac tatatttta catatatata ttctaaatat gaaagtggtg   139380
attgtgacta gcgtagcatc gcttctagac gcatctattc agtttcaaaa aacggcatgt   139440
aggcatcact gtaattacct atctatgcaa gtagttaaag agatagaaga atttggtact   139500
atcaatgaaa aaaatttgga atttgacact tggaaagacg ttatacaaaa cgatgaaata   139560
gatgcattag tattttatag agtaaaacaa attagtattt ctacgggtgt tctatataaa   139620
tctatgatgc gcaatagaac aaaacctatt tccatgtact ttgtacgtga ttgtctggca   139680
tttgatggag atcctccgtc ttttagaatg acgtcttgca atatcaacgc atacaatcgt   139740
agtaagatta aagatttaat aatcctaatg aaatatgaaaa catgtaataa aaaaattatc   139800
ggtgagttta taatagacaa ttttggaagc gtcgatgcat tactatcgat agttaattcc   139860
aatgttacgt ggattacatc agttataaat aatagtaacg gcaggggtat taatatcagg   139920
gtatcaaata ataaaatgtt aactataact agttttcgac gattcgtcaa taaacttaaa   139980
atgtacaaaa ctactaaatg cgcttctcaa ttggataatc tatgtaccga gatgaacaaa   140040
atggatatta tagacaaaaa atgaaacgta atgaggagta ttgcggggct acataaatta   140100
aaaatggaaa tttttaatgt agaagaattg ataaatatga aaccttttaa gaatatgaat   140160
aaaataacaa ttaatcaaaa tgataattgt atattagcaa atcgatgctt tgttaaaata   140220
gatactccta gatacatacc atcgacatcc attagcagtt ctaatatcat cagaatacgg   140280
aatcatgatt ttacattatc tgaattattg tattcaccgt ttcattttca acagcctcag   140340
```

```
tttcaatatc tccttcctgg gtttgtatta acgtgtattg ataaagtttc gaaacagcaa   140400
aaaaaatgta aatattgtat ctctaatcgt ggagatgatg atagtttaag cattaatcta   140460
tttattccga ctattaacaa gtctatatat attattatcg gtttacggat gaaaaatttt   140520
tggaagccta aattcgaaat agaataatgt ttttatatta tacatgttct aaaagaataa   140580
tcgatacagt ttaagtgaaa gctagagagg ggttttaaa tggtcatcgg tttagtcata    140640
ttcgtgtctg tggcggccgc catcgtcggt gtgttgtcta acgtattgga catgtttatg   140700
tacgtagaag aaaataatga agaggatgct agaatcaagg aggagcaaga actactgttg   140760
ctatattgat acataattga aaatctacca acttaaatac accgcctata aatttacaat   140820
gaaacacaga ttgtattctg aaggattgag tattagtaat gatttaaact cgataatcgg   140880
tcaacaatct acaatggata cggatataga aatagacgaa gatgacatca tggaacttct   140940
taatatattg actgagttag gttgtgatgt cgactttgat gaaaatttta gcgatatagc   141000
cgatgatatt ctagaatcgt tgatagaaca ggatgtataa gttttatgt taactaaatg    141060 tggccatttg caccggtacc tgcgggagca aaatgtaggc tggtagaaac actaccagaa   141120
aatatggatt ttagatccga tcatttaaca acatttgaat gttttaacga aattatcact   141180
ctagctaaga aatatatata catagcatct ttttgttgta atcctctgag tacgactagg   141240
ggagcgctta tttttgataa actaaaagag gcatctgaaa aagggattaa aataatagtt   141300
ttgctagatg aacgagggaa aagaaatctg ggagagctac aaagtcactg cccggatata   141360
aattttataa ccgttaatat agataaaaaa aataatgtgg gactactact cggttgtttt   141420
tgggtgtcag ataatgaaag atgttatgta ggaaacgcgt catttactgg aggatctata   141480
catacgatta aaacgttagg tgtatattct gattatcccc cgctggccac agatcttcgt   141540
agaagatttg atacttttaa agcctttaat agcgcaaaaa attcatggtt gaatttatgc   141600
tctgcggctt gttgtctgcc agttagcact gcgtatcata ttaagaatcc tataggtgga   141660 gtgttctta ctgattctcc ggaacaccta ttgggatatt ctagagatct agacactgat    141720
gtagttattg ataaactcaa gtcggctaag actagtatag atattgaaca tttggccata   141780
gttcccacta cacgtgtcga cggtaatagc tactattggc ccgacattta caactccatt   141840
atagaagcag ccattaatag aggagttaag atcagacttc tagttggtaa ttgggataag   141900
aacgacgtat attctatggc aaccgccaga agtctagacg cgttgtgtgt tcaaaatgat   141960
ctatctgtga aggttttcac tattcagaat aatacaaaat tgttgatagt cgacgacgaa   142020
tatgttcata tcacttcggc aaatttcgac ggaaacccatt accaaaatca cggattcgtc   142080
agttttaata gtatagataa acagcttgta agcgaggcta aaaaaatatt tgagagagat   142140
tgggtatcta gccacagtaa atcgttaaaa atttaaaaaa tagaaacgta tagaacgcca   142200
tcatgttaaa caggatacaa accttgatga aaacagctaa caattatgaa actattgaga   142260
tattgcgtaa ctatttaaga ctgtatatca ttttggcacg aaatgaagaa ggtcatggta   142320
tactaatata cgatgataac atagatagtg ttatgtcgat gatgaatatt acaatattag   142380
aagttatagg attgacgact cattgcacaa aattaagatc atcgcctcca attcctatgt   142440
ctagattgtt tatggacgaa atagatcatg agtcatatta ttctccaaaa acttcagatt   142500
atccgttgat cgatattata cgaaagcgtt ctcacgaaca gggagatata gcactggctt   142560
tagaacgata cggtattgag aatacagatt ccatatcaga aattaatgaa tggttgtcgt   142620
caaaaggttt agcatgttat agatttgtaa aatttaacga ttataggaaa cagatgtatc   142680
```

-continued

```
gtaagttctc taggtgtact atagttgaca gtatgataat agggcatata ggtcatcatt    142740
atatttggat taaaaattta gaaacatata cgcgtcccga aattgatgtg ttaccgtttg    142800
atattaaata catatctaga gatgaattgt gggcgcgaat tcttcctcg ttagatcaaa     142860 cacatataaa aaccatcgcc gtatcagttt atggagctat tactgataat ggaccaatac   142920
catatatgat atccacgtat ccgggtaata cctttgttaa ctttaacagt gtaaaaaatc   142980
taattttaaa tttcttagat tggattaaag atattatgac tagtacacga actatcattc   143040
tagtaggtta catga                                                     143055

<210> SEQ ID NO 70
<211> LENGTH: 31690
<212> TYPE: DNA
<213> ORGANISM: Artificial Sequence
<220> FEATURE:
<223> OTHER INFORMATION: viral construct

<400> SEQUENCE: 70
tggctggaat cattaacaag aaataaaaa acaatttcaa agttaaacat aactggtatt      60
acgatttcca tttctttgtt catactttat taaaaacata tccagaaatc gaaaagata    120 tcgaatttag tacggcattg gaagaattca tcatgtgtac caaaacagac tgtgataaat    180
atagattaaa ggtttccatt cttcacccaa ttagtttctt ggaaaaattt attatgagag    240
acattttctc agactggata aatggcggaa actaaagagt ttaaaacttt gtataatctt    300
tttatagata gttatttaca aaaattagct caacattcta tccctactaa tgtcacttgt    360
gctattcata taggagaggt tataggacag tttaaaaatt gcgcgctccg aataactaac    420
aaatgcatga gtaattctcg acttagtttc acactcatgg ttgaatcatt tattgaagtg    480
atttcattgc ttccggaaaa ggatagaaga gctatcgctg aggaaatagg aatagatcta    540
gacgatgtac ctagtgcggt atccaagcta gaaaagaact gtaatgcgta tgcggaggtt    600
aataatatta tagatataca gaaattggat atcggagaat gttcggctcc gcccggtcaa    660
catatgcttt tacagatagt taatacagga tccgcggaag caaattgtgg tttacagaca    720
attgttaagt ccttaaataa aatatacgtt ccacctatta tcgaaaaccg attgccgtat    780
tacgatccgt ggtttctagt gggtgtagca attattctag ttatttttac tgtagctatt    840
tgttctatta gacgaaatct ggctcttaaa tacagatacg gaacgttttt atacgtttaa    900
ttaataaaaa aatttaatta caaggtataa aatagtactc catctacgca atcgcgataa    960
tggagggatc taaacgcaga cacgacagtc ggcgactaca acaagaacag gagcagcctc   1020
gtccacgtac accgccatca tatgaagaaa ttgcaaaata tggacactca tttaacgtga   1080
aaagatttac gaatgaagaa atgtgtctta agaatgatta tccacgaatt atatcatata   1140
atcctccacc aaaatagagt atatatatat catcatttca tgatgtatac tactgacata   1200
gtttcaatgt gaactttca ctttcttgcc ggttatgaag aatattttta ttttaatggt    1260
cattactaat cgtatattat aattgaaaat ggattagttt aatatgacgc tcgtcatggg   1320
atcctgctgt ggtagattct gtgacgctaa gaataagaat aagaaggaag atgtagaaga   1380
gggaagagaa ggatgttaca attataagaa ccttaatgat ctggatgaat ccgaagcacg   1440
tgtagaattt ggaccattat atatgataaa tgaagaaaaa tcagacataa atacattgga   1500
tataaaaaga agatatagac acacgataga gtctgtatat ttctaaaagt ttttataaaa   1560
aatgagtaaa atactcacgt ttgttaaaaa taagataatt gacttgatta ataatgacca   1620
aattaaatat tctagagtta taatgataga agagtccgat agtctttac cggttgatga   1680
```

```
ggtgcatgct aaccacggat ttgactgtgt ggagatgata gatgaaaata taagcaatga    1740
gaatatcgaa cagtataaaa ccgaatcttt ttttacaata aattgaaatc aaaacattta    1800
ttaaaccgca tcaagatggg tacgaacggc gttagagtat ttgtcatttt atatttgttg    1860
gctgtatgcg gatgtatcga atacgacgta gacgataatg tacatatttg tacccacact    1920
aacgtgtcac atattaatca cactagttgg tattataatg ataaggttat agcgctagcc    1980
accgaggata aaacttctgg ttatatatca tcattcataa aacgcgttaa tatctcatta    2040
acttgtttaa atatatcgag tttgaggtac gaagattctg gtacatacaa aggagtatcg    2100
catctaaaag atggagtcat cgttacgact actatgaata tatctgtaaa ggctaatatc    2160
attgacttga ctggtagagt gcgttatcta accagaaatt attgcgaagt taaaatacga    2220
tgcgaaataa catcttttcg gcttaatggt tctactacac caccacatat gatattagga    2280
acagtagata aatggaaata tcttccatttt cctacagatg attatagata cgtaggggaa    2340
ctgaaaagat atatatctgg aaacccatat ccaacagagt cgctagcgtt agaaattagc    2400
tcgacgttta atcggtttac tatcgttaaa aatttgaacg atgacgagtt ttcttgttat    2460
ctgtttccat aaaatgttga acgcgcgcca tatttgtgaa tccgaatggg aggctttaaa    2520
taataataac gataattcat cctccatgcc cgcttccac aacaatctcg caaacgattt    2580
atctagtatg atgtcacaat tacaaaatga taataacgat aatttaatta tgatagtact    2640
aataacaatg ctatcaataa tacttgtaat tattgtagtg attgcggcga tatcgatgta    2700
caaaagatcc aagtacaggc atatagataa ctgaaaaaaa atttattgtt attgttaatt    2760
tagttatgga acccatcctt gcaccaaatc caaatagatt tgttattttc ccaatccaat    2820
atcatgacat ctggaacatg tataaaaagg cagaggcatc attttggaca gtggaagaag    2880
tagatatatc taaagatatc aatgattgga ataaactaac accagacgaa aaatatttta    2940
taaaacatgt attggcgttt tttgcagcca gtgacggaat agtgaatgaa atttggcgg    3000 aacgattttg tacagaagta cagattaccg aggctagatg tttctacgga tttcagatgg    3060
ccattgaaaa cattcattcg gaaatgtata gtcttttgat cgatacttat gttaaagata    3120
gtaatgaaaa aaactatctc tttaatgcca tagaaacgat gccttgtgta aaaagaagg    3180 ccgattgggc tcaaaagtgg atacatgaca gcgccggtta tggagagaga cttattgcct    3240
ttgctgcagt agaaggaatc ttcttttccg gatcattcgc ttccataitt tggcttaaaa    3300 agcgtggcct aatgcccgga ctcacgtttt ccaacgaatt gattagtaga gacgagggtc    3360
tacactgcga cttcgcatgt ttgatgttta aacattatt gcatccaccg agtgaagaaa    3420
ccgttagatc tattataaca gatgcggtat ccattgaaca agaatttctt actgcggctc    3480
ttccagttaa acttatagga atgaattgtg aaatgatgaa aacatatata gaattcgtcg    3540
cggatagatt gatttctgaa ttgggattta aaaaaattta taatgttacc aatccgtttg    3600
atttcatgga aaatatatca ttagaaggta aaactaattt tttcgaaaaa cgtgtgggtg    3660
aataccaaaa aatgggagtt atgtctcaag aagataatca tttttcttta gatgttgact    3720
tttaaagaaa cataaatgcc gatatttgtc aatactgtgt actgtaagaa tatattagca    3780
ttgtctatga ctaagaaatt caaaacaatt attgatgcca taggaggcaa tataaagtc    3840 aattctacga tattgaaaaa gttatctcct tactttcgca cacatttacg tcaaaaatac    3900
acgaaaaata aagatccagt tacgagggtt tgtctagacc ttgacattca cagtctaact    3960
tctatagtta tttactcata tactggaaag gtatatatag atagtcataa cgtcgtcaat    4020
```

-continued

```
ttattacgtg cttctatatt aacctctgta gaatttatca tctacacttg tataaacttt    4080
atcctacgag atttagaaa ggaatattgt gtcgagtgtt acatgatggg tatagaatac    4140
ggactatcca atctcttatg tcatactaaa aactttattg ccaaacactt tttggaactg    4200
gaagatgaca tcatagacaa ttttgattat ctatctatga aacttattct agaaagcgat    4260
gaactaaatg ttccagatga ggattttgtc attaagtggt atataaagcg aagaaataaa    4320
ttaggaaatc tgctactcct tatcaaaaat gtaatcaggt caaattatct ttctcccaga    4380
ggtataaata atgtaaaatg gatactagac tgtaccaaaa tatttcattg tgataaacaa    4440
ccacgcaaat catacaagta tccattcata gagtatccta tgaacatgga tcaaattata    4500
gatatattcc atatgtgtac aagtactcat gttggagaag tagtatatct catcggtgga    4560
tggatgaaca atgaaataca taacaatgct atagctgtaa attatatatc aaacaattgg    4620
attccaattc ctccgatgaa tagccccaga ctgtatgcta gcgggatacc cgctaacaat    4680
aaattatacg tagtaggagg tctaccaaat cccacatctg ttgagcgttg gttccacggg    4740
gatgctgctt gggttaatat gccgagtctt ctgaaaccta gatgtaatcc agcagtggca    4800
tccataaaca atgttatata cgtaatggga ggacattctg aaactgatac aactacagaa    4860
tatttgctac ccaatcatga tcagtggcag tttggaccat ccacttatta tcctcattat    4920
aaatcatgcg cgttagtgtt cggtagaagg ttattcttgg ttggtagaaa tgcggaattt    4980
tattgtgaat ccagcaatac atggactctg atagatgatc ctatttatcc gagggataat    5040
ccagaattga tcatagtgga taataaactg ctattgatag aggattttta tcgtgaatcg    5100
tatatagata ctatagaagt gtacaatcat cacacttatt catggaatat atgggatggt    5160
aaataatttt gaaataaaat attagtttta tgttcaacat gaatattaac tcaccagtta    5220
gatttgttaa ggaaactaac agagctaaat ctcctactag gcaatcgccg ggtgctgccg    5280
gatatgattt gtatagcgct tacgattata ctatccctcc aggagaaaga cagttaatta    5340
agacagatat tagtatgtcc atgcctaaga tttgctatgg tagaatagct cctaggtctg    5400
gtctgtcact aaaaggcatt gatataggag gtggtgtaat agacgaagat tataggggaa    5460
acataggagt cattcttatt aataatggaa aatgtacgtt taatgtaaat actggagata    5520
gaatagctca gctaatctat caacgtatat attatccaga actggaagaa gtacaatctc    5580
tagatagtac aaatagagga gatcaagggt ttggatcaac aggacttaga taataaacaa    5640
tagtatgttg tcgatgttta tgtgtaataa tatcgtagat tatgtagatg gtatagtaca    5700
ggatatagaa gatgaggcta gcaataatgt tgatcacgac tatgtatatc cacttccaga    5760
aaatatggta tatagatttg acaagtccac taacatactc gattatctat caacggaacg    5820
ggaccatgta atgatggctg ttcgatacta tatgagtaaa caacgtttag acgacttgta    5880
tagacagttg cccacaaaga ctagatcata tatagatatt atcaacatat attgtgataa    5940
agttagtaat gattataata gggacatgaa tatcatgtat gatatggcat ctacaaaatc    6000
atttacagtt tatgacataa ataacgaagt taatactata ctaatggata caagggggtt    6060
gggtgtaaga ttggcgacaa tttcattcat aaccgaattg ggtagacgat gtatgaatcc    6120
agtaaaaact ataaaaatgt ttactctact atcgcatact atatgcgatg attgttttgt    6180
agattatata acggacattt caccaccaga taataccatc cctaacacta gcacgcgtga    6240
atatctaaag cttattggca tcacagctat catgtttgct acatataaaa ctctcaaata    6300
catgatagga taatttttt taacacggat atagaatgct aacgtaataa ttatgcgtta    6360
tgaagacccc tatatcatca attcaatttt ttttctagaa aaagtatcaa gatgttata    6420
```

```
ttatcgtcgg tcatcagatc tgtaatgttt cccaatgatt ggaatctaga ttctgaaatc    6480
tttttgtatc cccaatgttc agtgatttta gcacatattc ctatggtagc gaataaactt    6540
tcctgatcat ggacttttgt aaaattgatg tagtggtctc cttcgctcat agcttcgaca    6600
atctcattaa ttttatcaat accatagtac cgtatagcga catcatcgaa cttcatcaat    6660
tccttgtaca gtcttccaca actggtaata tctttgttaa acactataac atgatttctc    6720
cacgtaatat attcatctat tagatcgatg atggagtcgc gactacatat tttatcatca    6780
tccacaaagt aaaaaacagc atcctcataa tctaatttag tcgccatgac tatctcacaa    6840
aagacagtag ccgtctcctt cctctatatt gatttaattg tatgttttta caattatcaa    6900
taaaacataa aaataatatg atcatcaaac gaactgttaa tattgatagt tatataacgt    6960
gaatcatgag tgcaaactgt atgttcaatc tggacaatga ttacatatcc taaggcatta    7020
gtattcataa gtcatggagc tggtaaacat tctggacgtt atgacgaact agctgaaaac    7080
atatcatcgt taggaatttt agtattctca catgatcata ttggacatgg aagaagtaat    7140
ggtgaaaaaa tgatgattga tgactttggt acagcacgtg gtaactatta aatctactta    7200
ttgggtcatt ccatgggagc aacaatttct atactagcct cttacgataa tccaaacttg    7260
tttacagcaa tgattctaat gtctcctcta gttaatgcag atgctgtttc aagactgaat    7320
ctgctagctg ccaaacttat gggaaccatc acaccaaatg cgccagtcgg aaagctatgt    7380
ccagaatcag tatctagaga tatggataaa gtttataaat accaatacga cccattaatc    7440
aatcatgaaa aaattaaggc tggatttgct agtcaggtct tgaaggctac caacaaggtt    7500
agaaaaataa tttccaagat taacaccccg actctcatac tccagggaac aaacaatgag    7560
attagcgatg ttttaggtgc atattatttc atgcaacatg caaattgtaa tagagaaata    7620
aaaatttatg aaggtgccaa acatcatctt cataaggaaa cggatgaagt taaaaaatca    7680
gtcatgaaag aaatagaaac ttggattttt aatagagtga agtgatatag gattattctt    7740
ttaacaaata aaatgaatcc ggataataca atcgcagtga ttacagagac tattcctata    7800
ggtatgcaat ttgataaagt atatttgtct acatttaaca tgtggaggga aattctatcc    7860
aataccacaa aaacactaga tatatcatct ttttattgga gtttatcgga tgaagtgggt    7920
acgaatttcg gcacgataat attaaacgag attgtacaat tacccaaaag aggagtacga    7980
gttagagtag ccgtcaataa atctaacaaa ccattaaagg atgttgaaag actacaaatg    8040
gccggagttg aagtacgata catagatatt acaaatatcc taggaggagt tcttcataca    8100
aaattttgga tatctgataa tacacatatt tatttaggaa gcgctaacat ggattggaga    8160
tcactaactc aggtcaaaga attgggtatt gcgatcttca ataataggaa cttggcagcg    8220
gatctcactc aaatttttga ggtatactgg tatcttggag ttaacaatct accatataat    8280
tggaaaaact tttatccgtc gtattataat acagatcatc ctcttagtat taacgtaagt    8340
ggtgttccac actctgtatt tattgcttct gcaccgcaac aactatgtac tatggaaaga    8400
accaatgatt taaccgcttt attgtcatgt attagaaatg cgagtaaatt cgtttatgta    8460
tctgttatga actttatccc tattatttat tcgaaggcgg gtaaaatttt gttttggcct    8520
tatatagaag atgaattaag aagatccgct atagacagac aagtatccgt taagctattg    8580
attagttgct ggcaacgatc ttcgtttatc atgagaaact ttttaagatc tatcgctatg    8640
ctaaaatcta aaaacataaa tatagaagta aagctattta ttgtaccaga tgctgatcct    8700
cccattccgt attctagggt aaaccatgcc aaatatatgg taaccgataa aacggcctat    8760
```

```
ataggtacct caaattggac aggaaattac tttacggata catgtggagc atctattaat    8820
attacaccgg atgatggatt aggtcttcgt caacaattag aagatatttt tatgcgtgat    8880
tggaattcaa aatacagcta tgaattgtac gatactagtc ctactaaaag gtgtaaacta    8940
ttaaaaaata tgaaacaatg tacaaatgat atatactgcg atgagataca accggaaaaa    9000
gaaattcctg aatattctct tgaataaaat agatataaaa acataatttt tatcccaatt    9060
tacgagcccg ttaacaagat gcttgcattt tgttattcgt tgcccaatgc gggcgatgta    9120
ataaagggca gagtatacga gaatgattat gctctatata tttatctttt tgactatcct    9180
cactctgaag ctatcttggc agagagtgtt aagatgcata tggatagata tgttgaatat    9240
agggataaac tggtagggaa aactgtaaaa gttaaagtga ttagagttga ttatacaaaa    9300
ggatatatag atgtcaatta caaaaggatg tgtagacatc aataatttt ataccgaaca    9360
taaaaataag gttaattatt aataccataa aatcatgatt gcgttattga tactatcgtt    9420
aacgtgttca gcgtctacct atcgtctaca aggatttacc aatgccggta tagtagcgta    9480
taaaaatatt caagatgata atattgtctt ctcaccgttt ggttattcgt tttctatgtt    9540
tatgtcgcta ttgcctgcat caggtaatac tagaatagaa ttattgaaga ctatggattt    9600
gagaaaaaga gatctgggtc cagcatttac agaattaata tcaggattag ctaagctgaa    9660
aacatctaaa tatacgtaca ctgatctaac ttatcaaagt ttcgtagata atactgtgtg    9720
tattaaaccg tcgtattatc aacaatatca tagattcggc ctatatagat taaactttag    9780
acgagatgcg gttaataaaa ttaattctat agtagaacgt agatccggta tgtctaatgt    9840
agtagattct aatatgctcg acaataatac tctatgggca atcattaata ctatatattt    9900
taaaggtata tggcaatatc cgtttgatat cactaaaaca cgcaatgcta gttttactaa    9960
taagtacggt acgaaaacgg ttcccatgat gaacgtagtt actaaattgc aaggaaatac   10020
aatcacaatc gatgacaaag aatatgacat ggtacgcctt ccgtataagg atgctaatat   10080
tagtatgtac ctggcaatag gtgataatat gacccatttc acagattcta ttacggctgc   10140
aaaattagac tattggtcgt ttcaattagg gaataaagtg tacaatctta aactccctaa   10200
attttctatc gaaaataaga gggatattaa gtcgatagcc gaaatgatgg ctcctagtat   10260
gtttaatcca gataatgcgt cgtttaaaca tatgactagg gacccattat atatttataa   10320
aatgtttcag aatgcaaaga tagatgtcga cgaacaagga actgtagcag aggcatctac   10380
tattatggta gctacggcga gatcatctcc tgaaaaactg gaatttaata caccatttgt   10440
gttcatcatc agacatgata ttactggatt tatattgttt atgggtaagg tagaatctcc   10500
ttaatatggg tacggtgtaa ggaatcatta ttttatttat attgatgggt acgtgaaatc   10560
tgaattttct taataaatat tatttttatt aaatgtgtat atgttgtttt gcgatagcca   10620
tgtatctact aatcagatct attagagata ttattaattc tggtgcaata tgacaaaaat   10680
tatacactaa ttagcgtctc gtttcagaca tggatctgtc acgaattaat acttggaagt   10740
ctaagcagct gaaaagcttt ctctctagca aagatgcatt taaggcggat gtccatggac   10800
atagtgcctt gtattatgca atagctgata ataacgtgcg tctagtatgt acgttgttga   10860
acgctggagc attgaaaaat cttctagaga atgaatttcc attacatcag gcagccacat   10920
tggaagatac caaaatagta aagattttgc tattcagtgg actggatgat tcgtattcga   10980
tgattatttt taacaaaata acataaaaat aatatatttt tttaggatgc gatcatgacg   11040
tcctctgcaa tggataacaa tgaacctaaa gtactagaaa tggtatatga tgctacaatt   11100
ttacccgaag gtagtagcat ggattgtata aacagacaca tcaatatgtg tatacaacgc   11160
```

```
acctatagtt ctagtataat tgccatattg gatagattcc taatgatgaa caaggatgaa    11220
ctaaataata cacagtgtca tataattaaa gaatttatga catacgaaca aatggcgatt    11280
gaccattatg gagaatatgt aaacgctatt ctatatcaaa ttcgtaaaag acctaatcaa    11340
catcacacca ttaatctgtt taaaaaaata aaaagaaccc ggtatgacac ttttaaagtg    11400
gatcccgtag aattcgtaaa aaagttatc ggatttgtat ctatcttgaa caaatataaa    11460
ccggtttata gttacgtcct gtacgagaac gtcctgtacg atgagttcaa atgtttcatt    11520
gactacgtgg aaactaagta tttctaaaat taatgatgca ttaattttg tattgattct    11580 caatcctaaa aactaaaata tgaataagta ttaaacatag cggtgtacta attgatttaa    11640
cataaaaaat agttgttaac taatcatgag gactctactt attagatata ttctttggag    11700
aaatgacaac gatcaaacct attataatga tgattttaaa aagcttatgt tgttggatga    11760
attggtagat gacggcgatg tatgtacatt gattaagaac atgagaatga cgctgtccga    11820
cggtccattg ctagatagat tgaatcaacc agttaataaa atagaagacg ctaagcgaat    11880
gatcgctatt agtgccaaag tggctagaga cattggtgaa cgttcagaaa ttagatatag    11940
agaaaatagc tccagaatac agacaatgct tacaggatct ataccatatg aaaattacgc    12000
gtcctagaca ctttgataac tagttatgtc attctcgttt ttatagagtg tactcgttac    12060
taaatattaa ttaatgaaat aataacaatt attaagacat actattcatc caacttaaac    12120
aacgaaaaac attttcatt aagtttatca tgaatgcgta taataaagcc gattcgtttt    12180
ctttagagtc tgattctatc aaagatgtta tacacgatta tatttgttgg ctcagtatga    12240
ctgatgaaat gagaccatct atcggaaacg tctttaaagc gatggaaacg tttaagatag    12300
acgcggttag atattacgat ggtaacatat acgatttagc taaagatata aatgcgatgt    12360
cattcgacag ttttataaga tctctacaaa atatctcttc aaagaaagat aaactcactg    12420
tttatggaac catgggactg ctgtctattg tcgtagatat taacaaaggt tgtgatatat    12480
ccaatatcaa gttcgctgcc ggaataatca ttttaatgga gtatattttt gatgacacgg    12540
atatgtctca tcttaaagta gcactctatc gtagaataca gagacgtgat gatgtagata    12600 gatattttt tttcctaaac tgatttctct gtttaaattc gtagcgatat ataaaacaac    12660
atgtaattaa ttaataaact ttaagacatg tgtgttatac taagatggtt ggcttattcc    12720
atagtagctt gtggaattta taaacttatg atagtaaaac tagtacccaa tatgtaaaga    12780
tgaaaaagta aattactatt aacgccgtcg gtattcgttc atccattcag tatgggtata    12840
cagcacgaat tcgacatcat tattaatgga gatatcgcgt tgagaaattt acagttacat    12900
aaaggggata actacggatg caaactaaaa attatttcga atgattacaa gaaattaaag    12960
tttagattca ttatacgccc agattggtcg gaaatcgacg aggtcaaagg attaaccgta    13020
tttgcaaaca actatgcggt gaaagttaat aaggtagatg acacgttcta ttacgtaata    13080
tatgaggctg taatacatct gtataacaaa aaaacagaga tattgattta ttctgatgat    13140
gagaacgaac tctttaaaca ctattaccca tacatcagtc taaatatgat tagtaaaaag    13200
tataaagtta aagaagaaaa ctactcatcc ccgtatatag aacatccgtt aatcccgtat    13260
agagattatg agtccatgga ttaatatgag tatagtgtta aatgacactt actaaatagc    13320
caaggtgatt attcgtattt ttttaaggag taaccatgtc cgcaattaga tttattgcat    13380
gtctatatct catttccatc ttcggaaatt gtcatgagga tccatattat caaccatttg    13440
ataaattaaa cattactcta gatatataca cttatgagga tctagtacca tacaccgtag    13500
```

```
acaatgacac aacttctttc gttaagatat actttaaaaa tttttggatt acggttatga   13560
ctaaatggtg tgctccgttt attgataccg ttagcgtata cacatctcat gataatctga   13620
atatacaatt ttatagtagg gacgaatatg atacacaaag cgaggataaa atttgtacca   13680
ttgatgttaa agcacgatgc aaacatctaa caaaacgaga agttacagta caacaagaag   13740
cctacagata ttcattatct tctgacctat cgtgttttga ttctatagat ctagagattg   13800
atcttattga aactaatagt actgacacta cagtactgaa atcatatgag ctcatgcttc   13860
ccaaacgtgc taaatccata cataactgaa atgaaagaaa ccaaaaaatg cgatagcatc   13920
aacaaccaat catggttaac gataagatac tctatgatag ttgtaaaaca tttaacatcg   13980
atgccagcag tgcacaatca ttgatagaaa gtggtgcaaa tccattatat gagtatgatg   14040
gtgaaactcc attaaaggca tacgttacca agaaaaataa taatatcaaa aacgatgttg   14100
tgattttgtt attgtcgtca gtcgactata aaaatatcaa tgattttgat atactcgaat   14160
atctatgttc tgataacatc gatatagact tattgaaatt actaatttcg aaaggtatag   14220
aaataaatag tatcaaaaat ggtattaata ttgtagaaaa atacgctaca acatcaaatc   14280
ccaatgtaga tgtgtttaaa ctattattgg ataaggaat acctacatgt agcaacatac   14340
agtatggata caagatcaaa atagaacaga ttagacgtgc tggtgaatat tataattggg   14400
atgatgaatt agacaattac gattacgact acaccactga ttatgatgat agaatgggta   14460
aaacagttct ctattattat attattacta ggtcacaaga tggttatgct acatctttgg   14520
acgtaataaa ctatttaatt tcacacgaaa aagagatgcg ttattatact tatcgtgaac   14580
ataccacact ctattattat cttgacaaat gcgatattaa acgggaaata tttgacgcgt   14640
tattcgatag taactatagt ggtcatgaac taatgaatat tctatctaac tatttacgta   14700
aacagtttag gaagaaaaat cacaaaatcg ataattatat agttgatcaa ctattattcg   14760
accgtgatac gttttatatt ttagaattgt gtaatagttt acgtaataat atccacaatt   14820
cttaaaagat atacagattc tatacaagat ctattgttag aatatgtatc ttatcataca   14880
gtatacatca atgttattaa atgtatgatt gatgaaggag ctacattata tagatttaag   14940
catataaata aatattttca aaaatttggc aatagagatc ctaaagttgt cgagtatatt   15000
ttaaaaaatg gaaacttagt tgtagataat gacaatgatg ataacctaat aaatattatg   15060
ccattattcc ctaccttctc tatgcgtgag ttggatgtgt tatcgatact aaaactttgt   15120
aagccgtata ttgatgatat aaacatggat gtagtatact ttatcattgt attaagtcgc   15180
atagtgtcag cctagtagaa tggttaatag ataatggcgc agacattaat ataataacaa   15240
aatatgggtt tacatgtatt actatttgtg ttatactggc agataaatat atcccagaaa   15300
tagcagaatt atatattaag atattggaaa ttattctgag taaattacca accatcgaat   15360
gtattaagaa aacagttgat tacctagacg atcacaggta cttattcata ggtggtaata   15420
ataaatcgtt actgaaaata tgtatcaagt acttcatatt agtcgattat aagtacacat   15480
gtagcatgta tccatcatat atagaattta taaccgactg cgaaaaagaa attgcggata   15540
tgcgtcaaat taaaataaat ggtacggaca tgcttacagt gatgtacatg ttaaataaac   15600
ctacaaagaa acgatatgtt aataatccga tatttacaga ttgggctaat aagcaatata   15660
agttttataa tcaaataata tataatgcta ataagttaat agaacaaagt aagaaaatag   15720
acgacatgat agaggaggta tccattgacg ataatcgttt atcaacacta ccgttagaaa   15780
ttagacattt gattttctcg tacgcgttcc tataaaaata gaaactataa tcatataata   15840
gtgtaggttg gtagtattgc tcttgtgact agagacttta gttaaggtac tgtaaaaata   15900
```

```
gaaactataa tcatataata gtgtaggttg gtagtagggt actcgtgatt aattttattg    15960
ttaaacttgt ccttaagtct tattaatatg tcttctaaag ggggtagtgg cggcatgtgg    16020
agtgtcttta tccatggaca tgatggtagt aataaaggat ctaaaactta tacatctggt    16080
ggcggtggaa tgtggggagg aggatcgtcc agtggtgtaa aaagtggggt taacggaggt    16140
gtaaaatctg gaactggtaa aatttaaaca ctaaattatt tttattaata attgtacaag    16200
tttttgacat gatatttaat gacattagtt gtgtgggtgt atagagttca cagtagctca    16260
ttcagtcaaa atgtttgact atttggaaaa tgaggaggtg gctctcgatg aacttaaaca    16320
gatgttgaga gacagagatc ctaatgatac caggaaccaa ttcaagaata atgctttaca    16380
cgcatacctt tttaatgagc attgtaataa tgtcgaggtc gtcaaactac tactagacag    16440
tggcactaat ccattacgca aaaattggag acagctaccc cattagaaga atacacaaat    16500
agtagacatg ttaaagttaa aggatatagc gatggctcta ctagaagcca ctggatttag    16560
caacataaat gactttaata tattcagcta tatgaaatcc aaaaatgtag acgttgactt    16620
gataaaggtg ttggtagaac atggatttga cttgagtgtt aaatgtgaaa accatcgttc    16680
agttatagaa aattatgtaa tgacagatga tcctgttcct gaaattattg atttgttcat    16740
agaaaatggc tgcagtgttc tttatgagga cgagtactga tacgcgtatg atgattatca    16800
actacgaaat tgcggtaccg tattgcatct gtatatcatc tctcatctgt attcagagtc    16860
ggatacgaga gcatatgtgc gtccggaagt tgttaaatgt ctaattaatc acggaatcaa    16920 gccgtcttt atagataaaa actattgtac agctcttcaa tattatatta agtcatctca    16980
tatagatata gacatcgtta aattgttaat gaaaggaata gataacacgg cttattcata    17040
tatagacgat ctaacatgtt gcactcgagt aattatggct gattatctaa atagtgatta    17100
tagatacaat aaagatgtag atttggtcaa attgtttttg gaaaatggaa agccgcacgg    17160
aataatgtgt agtattgtac cactatggag aaatgataag gaaaccatct ttttgatatt    17220
gaaaacaatg aactcggatg tcctccaaca tatactaatt gagtatatga cattcggcga    17280
tatccctcta gtggaatatg gaactgtggt aaataaagag gctatacacg gatactttag    17340
aaatattaat attgattctt acacgatgaa atatctacta aaaaaggaag ggagatgcca    17400
tcaattatct cgatgatgga gagatcccga ttggacacct atgtaaatcc aactatgaat    17460
gttataattt ttacacttat acatacaaaa agggtctttg tgacatgtct tatgcttgcc    17520
caattcttag tactataaac atttgcctac cttatcttaa agacattaac atgattgaca    17580
aacgaggaga aacacttctt cacaaggctg ttagatataa taaacaatct ctagtatctt    17640
tactgctaga atccggttca gatgtcaaca ttagatcaaa taacggatat acatgtatag    17700
ccattgccat caacgaatct aaaaacattg aactgctgaa aatgctatta tgtcataaac    17760
ctacattaga ttgtgtgatt gattcattga gagaaatatc taacatcgta gataacgact    17820
atgctataaa acaatgtatt aaatatgcca tgattataga tgactgtaca tcgtctaaga    17880
ttccagagtc cataagtcaa cgctataatg attatataga tctttgcaat taagaattga    17940
atgagatgaa aaaataatg gtaggtggta atactatgtt ctcattaata tttactgatc    18000
atggagctaa aattattcat agatatgtca ataatccaga attacgtgag tattatgagt    18060
taaaacaaaa taaaatatat gtggaagcat atgatattat ttccaacgca atagtgaaac    18120
atgatagaat acataaaacc atagaatcag ttgatgataa tacctacatt tctaatcttc    18180
cgtataccat caaatacaaa atattcgagc aacaataagt attttttata cctttaaaat    18240
```

```
tgataaataa attttttcta gtgatatttt ggcaagatga aaatcctatt tctcatcgct    18300
ttcatgtatg ggtgtgttca ctcatatgtt aacgcggttg aaaccaaatg tccaaatcta    18360
gacattgtaa catcttctgg agaatttcat tgttcaggat gtgtggaaca tatgcctgag    18420
tttagctata tgtattggtt ggcaaaggat accaagttta tagaacatct gggtgatggc    18480
atcaaagaag atgaaaccgt tcgtaccaca gatagtggaa tcaccactct acgtaaagtc    18540
cttcatgtaa ccgatactaa taaatttgct cattataggt tcacttgtgt cctcactacg    18600
atagatggcg tttcaaaaaa gaatatttgg ctgaagtagt gcgtgctact attttttattt   18660 atgatataat ctaatggaat taatttgaat tgatatttat ccaatactaa agattatatt    18720
agaatcaaat taatctttta tacgagaaaa aataacgaca tacgtcgtca acaaattaaa    18780 cttttttattt attagttaac ttgctcattg ttatgtttct aaaacgggta cgacatatag    18840
gacaattatc cgacgcaccg gtttctcttc gtgttctatg ccatatattg atgcatgtta    18900
tgcaaaatat atgattacac gaatccaata aaccaaagta tctatcgttt tgagtaaaca    18960
acttcatagc aaatttcaca ttcttttttct ttacttactc tatacacgtc ctcgtatttta   19020 tccagtattt tgatgatatc caactcagaa atggttgttg tattattggg tgtataggta    19080
ttattagcta tgtaccaatt taccaacctt cttaatattt attgataatc acatcggtta    19140
tccaattaat aactaaattg tagtgtatat atagaccata tatgtttcta ttttttttgac   19200 agtttcagta agttttgatt gttgtattcc tgtatctcta gataagttag tcatatagtc    19260
ccttccggcg atacgttttt tccaagcccg aaattgatta gccaaatgtg gatttatttt    19320
tgtgataatg catactgtta gtcttatatc atttggttca tctatgtatt gtaatatttgt   19380 tacatgatct atagatgatg tattgatttt ggcaggatcg aattccatat ccgcgactaa    19440
acagtgaaaa aaatgtaaat aattttaaat tagtaaaact ttttttttatt tttttatgatt  19500 ccaaaaaaac tgaatacaaa gtcctaaatt ataaatatgg agatcatact accacaactt    19560
attattatgt atacaaggcc ggtgtaatag atagatatat ataattctat tacaccggca    19620
gacaattacc gatcggtatt tgtcgttacc aacataccgt ataatatgta atatacaatt    19680
ccataaccca ttgacagttg ttatacatca aaattgcaat tctttgatt acgatgttat     19740 aagaatgtag ttaattgatg tatgatgtta atgtgtcctc tttcctctta taacatcgta    19800
atcaaaaact tttttataat atatacctaa taatgtgtct taatagttct cgtgattcgt    19860
caaacaatca ttcttataaa atataataaa gcaacgtaaa aacacataaa aataagcgta    19920
actaataaga caatggatat ttacgacgat aaaggtctac agactattaa actgtttaat    19980
aatgaatttg attgtataag gaatgacatc agagaattat ttaaacatgt aactgattcc    20040
gatagtatac aacttccgat ggaagacaat tctgatatta tagaaaatat cagaaaaata    20100
ctatatagac gattaaaaaa tgtagaatgt gttgacatcg atagtacaat aactttatg    20160 aaatacgatc caaatgatga taataagcgt acgtgttcta attgggtacc cttaactaat    20220
aactatatgg aatattgtct agtaatatat ttggaaacac cgatatgtgg aggcaaaata    20280
aaattatacc accctacagg aaatataaag tcggataagg atattatgtt tgcaaagact    20340
ctagacttta atcaacgaa agtgttaact ggacgtaaaa caattgccgt tctagacata     20400
tccgtttcat ataatagatc aatgactact attcactaca acgacgacgt tgatatagat    20460
atacatactg ataaaaacgg aaaagagtta tgttattgtt ataacaat agatgatcat      20520 tacttggttg atgtggaaac tataggagtt atagtcaata gatctggaaa atgtctgtta    20580
gtaaataacc atctaggtat aggtatcgtt aaagataaac gtataagcga tagttttgga    20640
```

```
gatgtatgta tggatacaat atttgacttt tctgaagcac gagagttatt ttcattaact    20700
aatgatgata acaggaatat agcatgggac gatgatacag atatatggac tcccgtcaca    20760
gaagatgatt acaaatttct ttctagacta gtattgtatg caaaatctca atcggatact    20820
gtattcgact attatgttct tactggtgat acggaaccac ccactgtatt cattttcaag    20880
gtaactagat tttactttaa tatgccgaaa taaaaaattt ttgtataata tctagaggta    20940
gaggtattgt ttagataaat acaaataaca tagatacatc gcatatttag cattttata     21000
aatatacata agacatacac tttatacatt tttgtaaaaa tactcataaa aaaaatttat    21060
aaaaattatg gcacaaccat atcttgtata ggtagtttag ttcgtcgagt gaacctataa    21120
acagataata gacaacacgt aataataata atgcctacta atacaagcat aataccggga    21180
gatgggatat atgacgttgt agtgtttggt ttttctgaac gttgatagtc tactaatact    21240
acatgctgac atctaatgcc tgtataacca tgagagcatc tacaatacat accgtcgata    21300
tctctagcgt ggatacagtc accgtgtaaa caatatccat ctccctctgg accgcataat    21360
ctgatagctg aatatctgt tgtagcgttt gtaatttctg gcgatgtcgt ttcgatagcg     21420
ttaccactat cggcgaatga tctgattatc atagcagcga acaacaacat cagataattt    21480
atcaacattt ttgatggatt ttgtgtttat gctgtttctc agtgtgtgtt tatgacaaga    21540
ttgggaattt tatattatta attcagtaat ataaactaat aatatattgt taattgtgta    21600
aataatataa aaataacaat acaatattga atgtgttgct gttaaaaatg tatgtgttaa    21660
tataatagaa taaataaat gagtatgatc attttagata acgattgatt ttatcattac     21720
cgcttcattc ttatattctt tgcttacgga acctatattt agaaacatct actaacgatt    21780
ttttatgctt gcattattaa tggtatgtaa taccaatttg ttaagtatga atacggggta    21840
caaacataaa ctgaaattta gatcattaaa tgtttcatca gaaatgactc catgaaaacc    21900
gccgaagaac ttcgtgcaat cattggactt tgtactcaat cagctatcgt ctctggaaga    21960
gtcttcaacg ataagtatat cgacatacta cttatgctgc gaaagattct gaacgagaac    22020
gactatctca ccctcttgga tcatatccgc actgctaaat actaaatctc cttcatgctc    22080
tctcactaca cttttatca tcttatgagg aataattagc accagaatag ctatggattg     22140
cacatgtatt ctatgtcgtc tactggatga agatgtgacg tacaaaaaaa taaaactaga    22200
aattgaaacg tgtcacaact tatcaaaaca tatagataga cgaggaaaca atgcgctaca    22260
ttgttacgtc tccaataaat gcgatacaga cattaagatt gttcgactgt tactctctcg    22320
cggagtcgag agactttgta gaaacaacga aggattaact ccgctaggag catacagtaa    22380
gcatagatac gtaaaatctc agattgtgca tctactgata tccagctatt cgaattcctc    22440
taacgaactc aagtcgaata taaatgattt cgacttacgt ctgctaaaat acctaattgt    22500
ggataaacgg atacgtccgt ccaagaatac gaattatgca atcaatggtc tcggattggt    22560
ggatatatac gtaacgacgc ctaatccgag accagaagta ttgctatggc ttcttaaatc    22620
agaatgttac agcaccggtt acgtatttcg tacctgtatg tacaacagtg atatgtgtaa    22680
gaactctctt cattactata tatcgtctca tagagaatct ctatccaagg atgtaattaa    22740
atgtttgatc gataacaatg tttccatcca atactactgg tcttgctcaa ccatagatat    22800
agagattatt aataaggat gtggacacgt gtagagtata cgacgtcagc cctatattag     22860
aggcgtatta tctaaacaag cgatttagag taaccccata taatgtagac atggaaatcg    22920
ttaatcttct tattgagaga cgtcatactc ttgtcgacgt aatgcgtagt attacttcgt    22980
```

```
acgattccag agaatataac cactacatca tcgataacat tctaaagaga tttagacaac    23040
aggatgaatc catcgtacaa gccatactga taaactactt acattacggc gatatggtaa    23100
gtatacctat cattcaatgc atgttggata agacgacgga caacaacttt gttaataata    23160
atctcgtcga tgtaaacgtc gtaaggttta tcgtggaaaa tatggacacg cggctgtaaa    23220
tcacatatct aacaatggcc gtctatgtat gtacggtctg atattatcga gatttaataa    23280
ttgcgggtat cactgttatg aagatgtatt tgatatacta agcaagtaca tggatgatat    23340
agatatgatc gataactcta ctatattacg cggtcgatgt caataatata caatttgcaa    23400
agcggttatt ggaatatgga gcgagtgtca cgctcgataa tcaatacggc catccagaaa    23460
agcagttacc aaagagaagc tagttgattt attactgagt taccatccca ctctagagac    23520
tatgattgac gcatttaata gagatatacg ctatctatat cctgaaccat tattcgcctg    23580
tatcagatac gccttaatcc tagatgatga ttttccttct aaagtaagta tgatatcgcc    23640
ggtcgtcata aggaactaaa gcgctataga gcagacatta atagaatgaa gaatgcctac    23700
atatcaggcg tctccatgtt tgatatatta tttaaacgaa gcaaacgcca cagattgaga    23760
tacgcaaaga acaatgagag gatcgactcc attaaataat ttatcatgga gtgataatgt    23820 cctgttttcca tggcatatta caaaatcgat tccgtccaag atgataaaaa catttaccgg    23880
catcataaac acggagttta ttttatatgt ctcgcataaa cattactaaa aaatatatt    23940 gttcggtttt ctttcacatc tttaattatg aaaaagtaaa tcattatgag atggacgcat    24000
cgttcgcgac agtatgtggt acataccta cgtatttatg gacgacggta agaatgaagg    24060
tcacgtttct gtcaacaatg tcgacgcgat cgtgtaacac gactcacaat agaatctgtg    24120
aatgctctcc cgatcatgga tgcaaggcat gtgtttccca acaaaatgt ggaataggat    24180 acggagtatc cggagacgtc atctgttctc cgtgtggtct cggaacatat tctcacaccg    24240
tctcttccgc agataaatgc gaacccgtac ccagaaatac ctttaactat atcgatgtgg    24300
aaattaacct gtatccagtt aacgacacat cgtgtactcg gacgaccact accggtctca    24360
gcgaatccat ctcaacgtcg gaactaacta ttactatgaa tcataaagac tgcgatcccg    24420
tcttcttaat aaggtagcga cttcaggttt ctttacagga gaaagtgtg cactctgaat    24480 ttcgagatta aatgcaataa caaagattct tcctccaaac agttaacgaa agcaaagaat    24540
gatactatca tgccgcattc ggagacagta actctagcgt cgacatctat atactatata    24600
gtaataccaa tactcaagac tacgaaactg atacaatctc ttatcatgtg ggtaatgtag    24660
ccatatgccc ggtagttgcg atatacataa actgatcact aattccaaac ccacccgctt    24720
tttatagtaa gttttttcacc cataaataca ataattaatt tctcgtaaaa gtagaaaata    24780
tattctaatt tattgcacgg taaggaagta gaatcataaa gaacagtact caatcaatag    24840
caatcatgaa acaatatatc gtactggcat gcatgtgcct gccagtcttc agcaatcatc    24900
ctcatcgtgt acgaagaag aaaacaaaca tcatatggga atcgatgtta ttatcaaagt    24960
cacaaagcaa gaccaaacac cgaccgatga taagatttgc caatccgtaa cggaaattac    25020
agagtccgag tcagatccag atcccgaggt ggaatcagtc gaggatgtag atcctcctac    25080
cacttattac tccatcatcg gtggaggtct gagaatgaac tttggattca ccaaatgtcc    25140
tcagattaaa tccatctcag aatccgctga tggaaagact gtgaggtgtc tatcgacatc    25200
agatgtagcg aagaagagaa agacagcgac atcaagaccc atccagtact cgggtctaac    25260
atctctcata agaaagtgag ttacgaagat atcatcggtt caacgatcgt cgatacaaaa    25320
tgtgtcaaga atctagagtt tagcgttcgt atcggagaca tgtgcaagga atcatctgaa    25380
```

```
cttgaggtca agtatgtcga cggatcggca tctgaaggtg caaccgatga tacttcactc    25440
atcgattcaa caaaactcaa agcgtgtgtc tgaatcgata actctattca tctgaaattg    25500
gatgagtagg gttaatcgaa cgattcaggc acaccacgaa ttaaaaaagt gtaccggaca    25560
ctatattccg gtttgcaaaa caaaaagtta cctctcgcga cttcttcttt ttctgtctca    25620
atagtgtgat acgattatga cactattcct atttcctttc agggtatcac aaaaatatta    25680
aacctctttc tgatggtctc atacaaaaat attttattc tctttctctc tttgatggtc     25740
tcataaaaaa tattttatt ctctttctct ctttgatggt ctcataaaat attttattc      25800 tctttctctc tttgatggtc tcataaaaaa tattttatt ctctttctct ctttgatggt     25860
ctcataaaat attttattc tctttctctc tttgatggtc tcataaaaaa tattttatt      25920 ctctttctct cttgatggt ctcataaaaa atattaaacc tctttctgat ggtgtcacta     25980 aaatatttt attctctttc tctcttcaat ggagtcataa atattttta ttctctttct      26040 ctcttcgatg gtctcacaaa aatattaaac ctctttctga tggtgtcact aaaatatttt    26100
tattctcttt ctctcttcaa tggagtcata aaatatttt attctctttc tctctttgat     26160
ggtctcacaa aaatattttt attctctttc tctctttgat ggtctcacaa aaatatttt     26220 attctctttc tctctttgat ggtctcacaa aaatattttt attctctttc tctctttgat    26280
ggtctcataa aaaagttttt acaaaaatat tttattctc tttctctctt tgatggtctc     26340
ataaaaaaag ttttacaaaa atatttttat tctctttctc tctttgatgg tctcataaaa    26400
aaagttttac aaaaatattt ttattctctt tctctctttg atggtctcat aaaaaatatt    26460
aaacctcttt ctgatggtgt cactaaaata tttttattct cattctctct tcaatggagt    26520
cataaaatat ttttattctc tttctctctt cgatggtctc acaaaaatat taaacctctt    26580
tctgatggtg tcactaaaat atttttattc tcattctctc ttcaatggag tcataaaata    26640
tttttattct ctttctctct tcgatggtct cacaaaaata ttaaacctct ttctgatggt    26700
gtcactaaaa tatttttatt ctcattctct cttcaatgga gtcataaaat atttttattc    26760
tctttctctc tttgatggtc tcataaaaaa agttttacaa aaatatttt attctctttc     26820 tctctttgat ggtctcataa aaatattaa acctcttct gatggtgtca ctaaaatatt      26880
tttattctct ttctctcttc aatggagtca taaaatattt ttattctctt tctctcttcg    26940
atggtctcac aaaaatatta aacctctttc tgatggtgtc actaaaatat tttattctc     27000 attctctctt caatggagtc ataaaatatt tttattctct ttctctcttt gatggtctca    27060
taaaaaaagt tttacaaaaa tatttttatt ctctttctct ctttgatggt ctcataaaaa    27120
aagttttaca aaatatttt tattctcttt ctctctttga tggtctcata aaaaagttt      27180 tacaaaaata tttttattct ctttctctct tgatggtct cataaaaaaa gttttacaaa     27240
aatattttta ttctctttct ctctttgatg gtctcataaa aatattaaa cctctttctg     27300 atggtgtcac taaatatttt ttattctcat tctctcttca atggagtcat aaatatttt     27360 tattctcttt ctctcttcga tggtctcaca aaaatattaa acctctttct gatggtgtca    27420
ctaaaatatt tttattctca ttctctcttc aatggagtca taaaatattt ttattctctt    27480
tctctctttg atggtctcat aaaaaagtt ttacaaaaat atttttattc tctttctctc     27540
tttgatggtc tcataaaaaa agttttacaa aaatattttt attctctttc tctctttgat    27600
ggtctcataa aaaagttttt acaaaaatat tttattctc tttctctctt tgatggtctc     27660
ataaaaaaag ttttacaaaa atatttttat tctctttctc tctttgatgg tctcacaaaa    27720
```

```
atattaaacc tctttctgat ggagtcgtaa aaaagttttta tctctttctc cttcgatggt   27780
ctcacaaaaa tattaaacct ctttctgatg gagtcgtaaa aaagttttat ctctttctct   27840
cttcgatggt ctcacaaaaa tattaaacct ctttctgatg gagtcgtaaa aaagttttat   27900
ctctttctct cttcgatggt ctcactaaaa tatttttat tctctttctg atgcatcaac    27960
tatttcttaa acaataacgt ccaacaacat atactcgtcg agcttatcaa catccctat    28020 gcccatctag gttaccagac aattgtatat cataaaataa tgtttataat ttttacaaaa   28080 atattttat tctctttctc tctttgatgg tctcataaaa aaagttttac aaaaatattt    28140
ttattctctt tctctctttg atggtctcat aaaaaatatt aaacctcttt ctgatggtgt   28200
cactaaaata ttttattct cattctctct tcaatggagt cataaaatat ttttattctc    28260
tttctctctt cgatggtctc acaaaaatat taaacctctt tctgatggtg tcactaaaat   28320 attttattc tcattctctc ttcaatggag tcataaaata ttttattct ctttctctct     28380 ttgatggtct cataaaaaaa gttttacaaa aatatttta ttctctttct ctctttgatg    28440
gtctcataaa aaagtttta caaaaatatt tttattctct ttctctcttt gatggtctca    28500 taaaaaagt tttacaaaaa tatttttatt ctctttctct ctttgatggt ctcataaaaa    28560
aagttttaca aaaatatttt tattctcttt ctctctttga tggtctcata aaaaagttt    28620 tacaaaaata ttttattct ctttctctct tgatggtct cataaaaaaa gttttacaaa    28680
aatattttta ttctctttct ctctttgatg gtctcataaa aaagttttta caaaaatatt   28740
tttattctct ttctctcttt gatggtctca taaaaaatat taaacctctt tctgatggtg   28800
tcactaaaat attttattc tctttctctc ttcaatggag tcataaaata ttttattct    28860 ctttctctct tcgatggtct cacaaaaata ttaaacctct ttctgatggt gtcactaaaa   28920
tatttttatt ctcattctct cttcaatgga gtcataaaat attttattc tctttctctc    28980 tttgatggtc tcataaaaaa agttttacaa aaatatttt attctctttc tctctttgat    29040
ggtctcataa aaaagttttt acaaaatat ttttattctc tttctctctt tgatggtctc    29100
ataaaaaaag ttttacaaaa atattttat tctctttctc tctttgatgg tctcataaaa    29160
aaagttttac aaaaatattt ttattctctt tctctctttg atggtctcat aaaaaaagtt   29220
ttacaaaaat attttattc tctttctctc tttgatggtc tcataaaaaa tattaaacct    29280
ctttctgatg gtgtcactaa aatattttta ttctctttct ctcttcaatg gagtcataaa   29340 atattttat tctctttctc tcttcgatgg tctcacaaaa atattaaacc tctttctgat    29400
ggtgtcacta aaatattttt attctctttc tctcttcaat ggagtcataa aatattttta   29460
ttctctttct ctctttgatg gtctcataaa aaagttttta caaaaatatt tttattctct   29520
ttctctcttt gatggtctca taaaaaagt tttacaaaaa tatttttatt ctctttctct    29580
ctttgatggt ctcataaaaa aagttttaca aaaatatttt tattctcttt ctctctttga   29640
tggtctcata aaaaagttt tacaaaaata ttttattct ctttctctct tgatggtct     29700 cataaaaaaa gttttacaaa aatattttta ttctctttct ctctttgatg gtctcataaa   29760
aaagttttta caaaaatatt tttattctct ttctctcttt gatggtctca taaaaaagt    29820 tttacaaaaa tatttttatt ctctttctct ctttgatggt ctcataaaaa aatattaaacc   29880 tctttctgat ggtgtcacta aaatattttt attctcattt tctctttctc tcttcaatgg   29940
agtcataaaa tatttttatt ctctttctct ctttgatggt ctcataaaaa aatattaaacc   30000 tctttctgat ggtgtcacta aaatattttt attctcattc tctcttcaat ggagtcataa   30060
aaagttttta tctctttctc tcttcgatgg tctcacaaaa atattaaacc tctttctgat   30120
```

```
ggagtcgtaa aaaagttttta tctctttctc tcttcgatgg tctcacaaaa atattaaacc    30180
tctttctgat gcatcaacta tttcttaaac aataacgtcc aacaacatat actcatcccc    30240
tatgcccatc taggttacca gacaattgta tatcataaaa taatgtttat aatttacacg    30300
ttaaaatcat ataataaaac gtagatcgta taatattttt tggtatataa atgatctagt    30360
aaaatccatg taggggatac tgctcacatt ttttctttgg tacaaaattt cacacaagtt    30420
tttatacaga caaattcttg tccatatatt ttaaaacatt gacttttgta ctaagaaaaa    30480
tatctagact aactatctct ttctctttct ctcttcgatg gtctttctga tggagtcgta    30540
aaaaagtttt atctctttct ctcttcgatg gtctcacaaa atattaaaac ctctttctga    30600
tggagtcgta aaaagttttt atctctttct ctcttcgatg gtctcacaaa atattaaac     30660 ctctttctga tggagtcgta aaaagttttt atctctttct ccttcgatgg tctcacaaaa    30720
atattaaacc tctttctgat ggagtcgtaa aaaagtttta tctctttctc tcttcgatgg    30780
tctcacaaaa atattaaacc tctttctgat ggtgtcacta aaatattttt attctctttc    30840
tctcttcgat ggtctcacaa aaatattaaa cctctttctg atggagtcgt aaaaaagttt    30900
tatctctttc tccttcgatg gtctcacaaa aatattaaac ctctttctga tggagtcgta    30960
aaaagttttt atctctttct ctcttcgatg gtctcacaaa aatattaaac ctctttctga    31020
tggagtcgta aaaagttttt atctctttct ccttcgatgg tctcacaaaa atattaaacc    31080
tctttctgat ggagtcgtaa aaaagtttta tctctttctc cttcgatggt ctcacaaaaa    31140
tattaaacct ctttctgatg gagtcgtaaa aagttttat ctctttctcc ttcgatggtc     31200
tcacaaaaat attaaacctc tttctgatgg agtcgtaaaa aagttttatc tctttctctc    31260
ttcgatggtc tcacaaaaat attaaacctc tttctgatgg agtcgtaaaa aagttttatc    31320
tctttctctc ttcgatggtc tcacaaaaat attaaacctc tttctgatgg agtcgtaaaa    31380
aagttttatc tctttctcct tcgatggtct cacaaaaata ttaaacctct ttctgatggt    31440
ctctataaag cgattgattt ttcttaccct ctagagtttc ctacggtcgt tggtcacaca    31500 ttttttttcta gacactaaat aaatatttaa aatataatat taatatacta aaatttatgt    31560
attattaatt tataatatta atatactaaa atttatgtat tattaattta tctaactaaa    31620
gttagtaaat catatacata atttataat taatatatta tacataattt tataattaat    31680
ttaatcttac                                                           31690
```

<210> SEQ ID NO 71
<211> LENGTH: 3948
<212> TYPE: DNA
<213> ORGANISM: Artificial Sequence
<220> FEATURE:
<223> OTHER INFORMATION: vaccine construct

<400> SEQUENCE: 71

```
atggatgcta tgaagagggg cctgctgctg gtgctgctgc tgtgtggcgc cgtgtttgtg     60
tcccccagcc aggaaatcca cgcccggttc agaagaggca gcaagctggc tgctcagctg    120
gccgacagcg acagcaatgc ctgcgccttc ctgaagctga gatacctgca cagccggatc    180
cacgtgctgc agtttctgaa cccccttcacc ctgcacgagt acatgctgga cctgcagccc    240
gagacaaccg acctgtactg ctacgagcag gacgaggatg aggacgaggt ggaccatctg    300
caggaacagc cccagcaggc cagaagggat gagcagcacc cctgctacct gatcgagaca    360
cagtgctgca gatgcgagag cctggtggcc cagctggctg acgtgaactc taacgccgca    420
```

```
gcctttctga agaacagcat cgactgcaac gacagcatgt gcagcacctt cgacgacaac    480
gtgtccgcca ccgagctcgt gaagagaatc cctgcccctt gccctgggc ccctgaggaa    540
aatgacgaga tcgacggcgt gaaccaccag catctgcccg ctagaagggc cgagcctcag    600
agacacacca tgctgtgcat gtgctgcaag tgcgaggccc ggatctgctt cctgctgtgc    660
ttttgtgtgc tgctgtgcgt gtgcctgctg atcagacccc tgctgctgag tgtgtccacc    720
tactgccagc ggccgctgtg tcctcaggaa aagaaacggc acgtggacct gaacaagcgg    780
ttccacatct acatctgcga ggacgcccag tgcaccgtgg tggaaggcca ggtggacagc    840
aaggtgtccg agttccggtg gtacagatac agcgtgtacg gcaccaccct gggccagcgg    900
agaatcaaga ggcccagatc cgaggtgtac tgcaagggac agctgaccga gacagaggtg    960
ctggacttcg ccttcaccga cctgaccatc gtgtaccggg acatccggct ggaatgcgcc   1020
atcatgtaca aggccagaga gatgggcttc cacgaccaca tcgactactg gaagctgatt   1080
agactggaat gtgctatctt ctacaaagcc cggatcctga gtgcctgcg gtacagattc   1140
aagaagcact gcaagctgta cgtggcctgg gactccgtgt actactgcgg cgacgatggc   1200
tggtgcaaga ccagctctac ctggcactgg acatgccacg acggcaagca caagaacgtg   1260
tgccaggaca agatcctgga acactacgag aacgactcca aggacgacga ggacgagaca   1320
gcctacgaca gcggcaccga tctgatcgac ttcatcgacg atagcaactg ccaccccaac   1380
aagctgctgc ggagactgag cagcgaccag gaccagtctc agaggccccc caacatggga   1440
gtgaaggccc acggcaagtg catctgggag aacaaggtgt tcatcgtgcc caccctgtgc   1500
cccgtgcctc tggatccaac ataccccctg ctgaagctgc tgaccccga accacagat   1560
ctgcactgtt atgagcagct gggcgactcc tccgacgaag aggatacagg cggcctggat   1620
ggctacgagg ccgacaagaa cgacctgaac gcccagatcg agcactggaa actgatccgg   1680
atggaatgtg caattttcta taggccaaa gagctgggga tcagcgacga gaatgagaac   1740
gacagcgata ccggcgagga catggtggat ttcatcgaca tgaggccga gaagtacggc   1800
tgcaagggca cctgggaggt gcacttcggc tttaagaagc acggcatcac catcaccgtg   1860
cagtacgaca acgacaaggc caacaccatg gactacacca actggaaaga gatctacccc   1920
cctccccccc cacggccttg ggctcctcca attcctaagc cctctccatg gcccctcag   1980
ttcgacggcg acatctgcaa taccatgcac tataccaatt gggtggtgta cagagacagc   2040
atcccccacg ccgcctgcca aagtgtatc gacttctaca gcagaatcag agagctgcgg   2100
cactacagcg actctgtgta cggcgatacc ctggaaaagc tgaccaacac cggcctgtac   2160
aatctgctga tccggtgcct gaggctcgtg accaagtatc ctctgctgaa actgctgtcc   2220
aactgcatcc tgtacggcgc tgccaatacc ggcaagagcc tgttcggcat gagcctgagc   2280
aaagtgcgga agctgaggta ctacaactgc tccgtgtatg gggccagcct gtgcgtggaa   2340
tgcaagaaaa ccctgcagcg gagcgaagtg tacgacgacg aaaccgacga ggaaagcacc   2400
gagagcgacc tggacggctt catcgataac agcgtgatcg tgtgccccgc ctccatcccc   2460
tccgatgaga tctctaccga ggaagccccc agacccctc actgtccttg ggtgccagtg   2520
ttctgcaaga aggccctgac cgcctctgag gtgtacaatt ttgcctatac cgacctgcgc   2580
gtggtgtata gggacattct ggaacattat gagaatgata gcaaggacct gtgcgatcac   2640
atcaactgcc tcgtgatcta cggccctcct aacaccggca gtcctgctt cgccatgtcc   2700
ctgtggaaca ccgagcccaa gcactgcttc aagaagggcg ccagcacat cgaagtgtgg   2760
ttcgatattg tgtacaggga cggcaaccct tacgccgtgt gcgacaagtg cctgaagttc   2820
```

```
tactccaaga tcagcgagta ccgccactac tgctactccc tgtatggcac aacactggaa    2880
cagcagtaca acaagcccct gtgcgacctg ctgattcgct gcatcaacac caccagatac    2940
cctctgctgt ccctgctgaa cagctacagc accccccctc atcggattcc cgccccatgt    3000
ccatgggctc cacagaggcc tacccagacc accaccccg agaataccte cctggtggaa     3060 ctgagagtga ccaccccaa gagcacagtc gtgatcaggc tgcacctgtg ccctacctg      3120 cactccagac tggtggtgtt caccttcccc aaccccttc accaggtggt gcccgccctg     3180
aatatctgca aggccaaggc ctgcaaagcc atcgagaaga atgggaagt gcacgctggc     3240 ggccaagtga tcctgtgtcc tgagagcctg cggcctctgc tgctgtccat tagcgtgtac    3300
gcccaggtgc tggtgctggt gctgctgctg tgggtgtcca tcggcagcaa ctgtctggtg    3360
ctgtgcggcc ctgccaacac agggaagagt tacttcggca tgtctctgat ctgccatcag    3420
gtggtgcctc cactggccgc ctctaaggct aaagcctgtc aggccatcga actgcagctg    3480
gccctggaag ccctgaatgc cagcccctat gatcacattg attactgaa agccatccgg    3540 caggaaaatg ccatcttctt cgccgccaga tggcattgga cctgtcacga tggaaaacac    3600
aagaatgcca ttgtgaccct gacctacctg ctgcccagcg tgtgtatgtg cgcctacgct    3660
tgggtgctgg tgttcgtgta catcgtcgtg attaccagcc ccgccaccgc cgatgagtgg    3720
acactgcagc agacaagcct ggaaatgtgg ctggccgagc cccagtgtga ccatatcgat    3780
tattggaaac acatccgcct ggaatgtgct attatgtata aggcccggtg gccttacctg    3840
gaaagcagaa ccgtgttcga gttccccaat gccttcgccg ctctggacc tggcgcctct    3900 ggaaaaccca tccccaatcc actgctgggc ctggactcca cccggacc                 3948
```

<210> SEQ ID NO 72
<211> LENGTH: 1316
<212> TYPE: PRT
<213> ORGANISM: Artificial Sequence
<220> FEATURE:
<223> OTHER INFORMATION: vaccine construct

<400> SEQUENCE: 72

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ser Lys Leu Ala Ala Gln Leu Ala Asp Ser Asp Ser Asn Ala Cys
        35                  40                  45

Ala Phe Leu Lys Leu Arg Tyr Leu His Ser Arg Ile His Val Leu Gln
    50                  55                  60

Phe Leu Asn Pro Phe Thr Leu His Glu Tyr Met Leu Asp Leu Gln Pro
65                  70                  75                  80

Glu Thr Thr Asp Leu Tyr Cys Tyr Glu Gln Asp Glu Asp Glu Asp Glu
                85                  90                  95

Val Asp His Leu Gln Glu Gln Pro Gln Gln Ala Arg Arg Asp Glu Gln
            100                 105                 110

His Pro Cys Tyr Leu Ile Glu Thr Gln Cys Cys Arg Cys Glu Ser Leu
        115                 120                 125

Val Ala Gln Leu Ala Asp Val Asn Ser Asn Ala Ala Phe Leu Lys
    130                 135                 140

Asn Ser Ile Asp Cys Asn Asp Ser Met Cys Ser Thr Phe Asp Asp Asn
145                 150                 155                 160
```

```
Val Ser Ala Thr Glu Leu Val Lys Arg Ile Pro Ala Pro Cys Pro Trp
            165                 170                 175
Ala Pro Glu Glu Asn Asp Glu Ile Asp Gly Val Asn His Gln His Leu
        180                 185                 190
Pro Ala Arg Arg Ala Glu Pro Gln Arg His Thr Met Leu Cys Met Cys
    195                 200                 205
Cys Lys Cys Glu Ala Arg Ile Cys Phe Leu Leu Cys Phe Cys Val Leu
210                 215                 220
Leu Cys Val Cys Leu Leu Ile Arg Pro Leu Leu Ser Val Ser Thr
225                 230                 235                 240
Tyr Cys Gln Arg Pro Leu Cys Pro Gln Glu Lys Lys Arg His Val Asp
                245                 250                 255
Leu Asn Lys Arg Phe His Ile Tyr Ile Cys Glu Asp Ala Gln Cys Thr
            260                 265                 270
Val Val Glu Gly Gln Val Asp Ser Lys Val Ser Glu Phe Arg Trp Tyr
        275                 280                 285
Arg Tyr Ser Val Tyr Gly Thr Thr Leu Gly Gln Arg Ile Lys Arg
    290                 295                 300
Pro Arg Ser Glu Val Tyr Cys Lys Gly Gln Leu Thr Glu Thr Glu Val
305                 310                 315                 320
Leu Asp Phe Ala Phe Thr Asp Leu Thr Ile Val Tyr Arg Asp Ile Arg
                325                 330                 335
Leu Glu Cys Ala Ile Met Tyr Lys Ala Arg Glu Met Gly Phe His Asp
            340                 345                 350
His Ile Asp Tyr Trp Lys Leu Ile Arg Leu Glu Cys Ala Ile Phe Tyr
        355                 360                 365
Lys Ala Arg Ile Leu Lys Cys Leu Arg Tyr Arg Phe Lys Lys His Cys
    370                 375                 380
Lys Leu Tyr Val Ala Trp Asp Ser Val Tyr Tyr Cys Gly Asp Asp Gly
385                 390                 395                 400
Trp Cys Lys Thr Ser Ser Thr Trp His Trp Thr Cys His Asp Gly Lys
                405                 410                 415
His Lys Asn Val Cys Gln Asp Lys Ile Leu Glu His Tyr Glu Asn Asp
            420                 425                 430
Ser Lys Asp Asp Glu Asp Glu Thr Ala Tyr Asp Ser Gly Thr Asp Leu
        435                 440                 445
Ile Asp Phe Ile Asp Asp Ser Asn Cys His Pro Asn Lys Leu Leu Arg
    450                 455                 460
Arg Leu Ser Ser Asp Gln Asp Gln Ser Gln Arg Pro Pro Asn Met Gly
465                 470                 475                 480
Val Lys Ala His Gly Lys Cys Ile Trp Glu Asn Lys Val Phe Ile Val
                485                 490                 495
Pro Thr Leu Cys Pro Val Pro Leu Asp Pro Thr Tyr Pro Leu Leu Lys
            500                 505                 510
Leu Leu Thr Pro Glu Thr Thr Asp Leu His Cys Tyr Glu Gln Leu Gly
        515                 520                 525
Asp Ser Ser Asp Glu Glu Asp Thr Gly Gly Leu Asp Gly Tyr Glu Ala
    530                 535                 540
Asp Lys Asn Asp Leu Asn Ala Gln Ile Glu His Trp Lys Leu Ile Arg
545                 550                 555                 560
Met Glu Cys Ala Ile Phe Tyr Lys Ala Lys Glu Leu Gly Ile Ser Asp
                565                 570                 575
Glu Asn Glu Asn Asp Ser Asp Thr Gly Glu Asp Met Val Asp Phe Ile
```

-continued

```
            580                 585                 590
Asp Asn Glu Ala Glu Lys Tyr Gly Cys Lys Gly Thr Trp Glu Val His
            595                 600                 605
Phe Gly Phe Lys Lys His Gly Ile Thr Ile Thr Val Gln Tyr Asp Asn
            610                 615                 620
Asp Lys Ala Asn Thr Met Asp Tyr Thr Asn Trp Lys Glu Ile Tyr Pro
625                 630                 635                 640
Pro Pro Pro Pro Arg Pro Trp Ala Pro Pro Ile Pro Lys Pro Ser Pro
                    645                 650                 655
Trp Ala Pro Gln Phe Asp Gly Asp Ile Cys Asn Thr Met His Tyr Thr
                660                 665                 670
Asn Trp Val Val Tyr Arg Asp Ser Ile Pro His Ala Ala Cys His Lys
            675                 680                 685
Cys Ile Asp Phe Tyr Ser Arg Ile Arg Glu Leu Arg His Tyr Ser Asp
            690                 695                 700
Ser Val Tyr Gly Asp Thr Leu Glu Lys Leu Thr Asn Thr Gly Leu Tyr
705                 710                 715                 720
Asn Leu Leu Ile Arg Cys Leu Arg Leu Val Thr Lys Tyr Pro Leu Leu
                    725                 730                 735
Lys Leu Leu Ser Asn Cys Ile Leu Tyr Gly Ala Ala Asn Thr Gly Lys
                740                 745                 750
Ser Leu Phe Gly Met Ser Leu Ser Lys Val Arg Lys Leu Arg Tyr Tyr
            755                 760                 765
Asn Cys Ser Val Tyr Gly Ala Ser Leu Cys Val Glu Cys Lys Lys Thr
            770                 775                 780
Leu Gln Arg Ser Glu Val Tyr Asp Asp Glu Thr Asp Glu Glu Ser Thr
785                 790                 795                 800
Glu Ser Asp Leu Asp Gly Phe Ile Asp Asn Ser Val Ile Val Cys Pro
                    805                 810                 815
Ala Ser Ile Pro Ser Asp Glu Ile Ser Thr Glu Glu Ala Pro Arg Pro
                820                 825                 830
Pro His Cys Pro Trp Val Pro Val Phe Cys Lys Lys Ala Leu Thr Ala
            835                 840                 845
Ser Glu Val Tyr Asn Phe Ala Tyr Thr Asp Leu Arg Val Val Tyr Arg
850                 855                 860
Asp Ile Leu Glu His Tyr Glu Asn Asp Ser Lys Asp Leu Cys Asp His
865                 870                 875                 880
Ile Asn Cys Leu Val Ile Tyr Gly Pro Pro Asn Thr Gly Lys Ser Cys
                    885                 890                 895
Phe Ala Met Ser Leu Trp Asn Thr Glu Pro Lys His Cys Phe Lys Lys
                900                 905                 910
Gly Gly Gln His Ile Glu Val Trp Phe Asp Ile Val Tyr Arg Asp Gly
            915                 920                 925
Asn Pro Tyr Ala Val Cys Asp Lys Cys Leu Lys Phe Tyr Ser Lys Ile
            930                 935                 940
Ser Glu Tyr Arg His Tyr Cys Tyr Ser Leu Tyr Gly Thr Thr Leu Glu
945                 950                 955                 960
Gln Gln Tyr Asn Lys Pro Leu Cys Asp Leu Leu Ile Arg Cys Ile Asn
                    965                 970                 975
Thr Thr Arg Tyr Pro Leu Leu Ser Leu Leu Asn Ser Tyr Ser Thr Pro
                980                 985                 990
Pro His Arg Ile Pro Ala Pro Cys  Pro Trp Ala Pro Gln  Arg Pro Thr
            995                 1000                1005
```

Gln Thr Thr Thr Pro Glu Asn Thr Ser Leu Val Glu Leu Arg Val
    1010                1015                1020

Thr Thr Pro Lys Ser Thr Val Val Ile Arg Leu His Leu Trp Pro
    1025                1030                1035

Tyr Leu His Ser Arg Leu Val Val Phe Thr Phe Pro Asn Pro Phe
    1040                1045                1050

His Gln Val Val Pro Ala Leu Asn Ile Cys Lys Ala Lys Ala Cys
    1055                1060                1065

Lys Ala Ile Glu Lys Lys Trp Glu Val His Ala Gly Gly Gln Val
    1070                1075                1080

Ile Leu Cys Pro Glu Ser Leu Arg Pro Leu Leu Leu Ser Ile Ser
    1085                1090                1095

Val Tyr Ala Gln Val Leu Val Leu Val Leu Leu Leu Trp Val Ser
    1100                1105                1110

Ile Gly Ser Asn Cys Leu Val Leu Cys Gly Pro Ala Asn Thr Gly
    1115                1120                1125

Lys Ser Tyr Phe Gly Met Ser Leu Ile Cys His Gln Val Val Pro
    1130                1135                1140

Pro Leu Ala Ala Ser Lys Ala Lys Ala Cys Gln Ala Ile Glu Leu
    1145                1150                1155

Gln Leu Ala Leu Glu Ala Leu Asn Ala Ser Pro Tyr Asp His Ile
    1160                1165                1170

Asp Tyr Trp Lys Ala Ile Arg Gln Glu Asn Ala Ile Phe Phe Ala
    1175                1180                1185

Ala Arg Trp His Trp Thr Cys His Asp Gly Lys His Lys Asn Ala
    1190                1195                1200

Ile Val Thr Leu Thr Tyr Leu Leu Pro Ser Val Cys Met Cys Ala
    1205                1210                1215

Tyr Ala Trp Val Leu Val Phe Val Tyr Ile Val Ile Thr Ser
    1220                1225                1230

Pro Ala Thr Ala Asp Glu Trp Thr Leu Gln Gln Thr Ser Leu Glu
    1235                1240                1245

Met Trp Leu Ala Glu Pro Gln Cys Asp His Ile Asp Tyr Trp Lys
    1250                1255                1260

His Ile Arg Leu Glu Cys Ala Ile Met Tyr Lys Ala Arg Trp Pro
    1265                1270                1275

Tyr Leu Glu Ser Arg Thr Val Phe Glu Phe Pro Asn Ala Phe Ala
    1280                1285                1290

Gly Ser Gly Pro Gly Ala Ser Gly Lys Pro Ile Pro Asn Pro Leu
    1295                1300                1305

Leu Gly Leu Asp Ser Thr Arg Thr
    1310                1315

<210> SEQ ID NO 73
<211> LENGTH: 3321
<212> TYPE: DNA
<213> ORGANISM: Artificial Sequence
<220> FEATURE:
<223> OTHER INFORMATION: vaccine construct

<400> SEQUENCE: 73
atggatgcta tgaagcgagg actgtgctgc gtgctgctgc tgtgtggcgc tgtgtttgtg      60 tccccctagcc aagagatcca cgccagattc agacggggca gcaaactggc cgacgaggat    120
gagacagcct acgactctgg caccgacctg atcgacttca tcgacgacag cgacgagaac    180

```
gagaatgaca gcgacaccgg cgaggacatg gtggatttca tcgacaatgc ccagctggcc    240
gactccgact ctaatgcctg tgcctttctg aaggctcagc tggctgacgt gaacagcaat    300
gccgccgctt tcctgaagaa ctgcatcctg ctgtacggcg ctgccaacac aggcaagagc    360
ctgtttggca tgagcctgaa ctgcctggtg ctgtgcggac tgccaatac cggcaaaagc     420
tacttcggca tgtccctgtg gccttacctg cacagcagac tggtggtgtt tacattcccc    480
aatcctttct ggccctacct ggaaagccgg atcaccgtgt tcgagttccc caacgccttc    540
aacgtgtgcc aggacaagat cctggaacac tatgagaacg acagcaagga catccttgag    600
cactacgaaa acgactccaa ggacctgtgc gaccacatct gcgatcacat cgactactgg    660
aagcacatcc ggctggaatg cgccatcatg tacaaggccc ggatcagact ggaatgtgct    720
attatgtata aggctcgcga gatgggcttc accagttcg acggcgacat ctgcaacacc     780
atgcactaca ccaactggat ctatatctgc gaggacgccc agtgcaccgt ggtggaagga    840
caggtggaca agaaatggga agtgcacgct ggcggccaag tgattctgtg tcctgagagc    900
ggccagcgga gaatcaagag gcccagatcc gagaactgtc accccaacaa gctgctgatc    960
ctgaagtgcc tgcggtacag attcaagaag cactgcaagc tgagcagcac ctggcactgg    1020
acatgccacg atggcaagca caagtggcat tggacctgtc acgacgggaa acacaagaac    1080
gccatcgtga ccctgaccta ctacgaggcc gacaagaacg acctgaacgc ccagattgag    1140
cactggaaac tgatccggat ggaatgtgca atcttctata aggccaaaga gctggggatc    1200
agcatctgcc accaggtggt gcctccactg gctgcctcta agccaaagc ctgtcaggcc     1260
atcgaactgc agctggccct ggaagccctg aacgctagcc cttacgatga gtggaccctg    1320
cagcagacca gcctggaaat gtggctggcc gagcctcagt ttaagaagca cggcatcacc    1380
atcaccgtgc agtacgacaa cgacaaggcc aataccatgg attacacgaa ttggaaagaa    1440
atctacgtga tcgtgtgccc cgccagcatt ccctccgatg agatctctac cgaggaagcc    1500
gaccacattg attattggaa ggccatccgg caagagaatg ccatcttctt cgccgccaga    1560
catcaggtgg tcccgctct gaatatctgc aaggccaagg cctgcaaagc catcgagtgg     1620
aacaccgagc ctaagcactg cttcaagaaa ggcggccagc acatcgaagt ttggttcgac    1680
tacgtggcct gggacagcgt gtactactgc ggagatgatg ctggtgcaa gaccgaggcc     1740
gagaagtacg ctgtaaagg cacctgggaa gtccacttcg gcaacagcat cgactgcaac     1800
gatagcatgt gcagcacctt cgacgacaac gtgtccgcca cagagctggt caaggaccat    1860
atagactatt ggaagctgat caggcttgag tgcgccattt tctacaaggc cagacggcgg    1920
ctgtccagcg accaggatca atctcagctc gtgaccaagt atcccctgct gaagctgctg    1980
tctacccaga ccaccacacc tgagaacaca agcctggtgg aactgagagt gaccacacct    2040
aagagcaccg tcgtgattcg gctgcacctg accacaagat accctctgct gagcctgctg    2100
aacagctaca gcacccctcc acacaggatc cccgctccat gtccttgggc tcctcagagg    2160
cctcctattc ctaagccttc tccatgggct cctagaatcc ccgcaccttg tccatgggca    2220
ccaccaagac ctccacattg cccttgggtg ccctgtttcc tgctgtgctt ttgcgtgctc    2280
ctgtgcgtgt gcctgctgat cagacctctg ctgctgagcg tgtccaccta ccttagacca    2340
ctgctcctgt ccatctccgt gtacgcacag gtgctggtgc tggtcctgct tctgtgggtg    2400
tccatcggaa gcctgctgcc tagcgtgtgc atgtgtgcct atgcttgggt gctcgtgttc    2460
gtgtacatcg tggtcatcac aagccccgcc acagccatcg tgtacagaga tggcaatccc    2520
```

-continued

```
tacgccgtgt gcgacaagtg cctgaagttc tacagcaaga tcagcgagta ccggcactac   2580
tgctacagcc tgtacggcac cacactggaa cagcagtaca acaagcccct gtgcgatctg   2640
ctgattcggt gcatcaacgt ggtgtaccgg gacagcattc ctcacgccgc ctgccacaag   2700
tgcatcgact ctactccag aatcagagag ctgcggcact acagcgactc tgtgtacggc   2760
gacaccctgg aaaagctgac caacaccggc ctgtacaacc tgctgattag atgcctgcgg   2820
gtgtactgca agggacagct gacagagaca gaggtgctgg acttcgcctt caccgatctg   2880
acaatcgtgt atcgggatag caaggtgtcc gagttccggt ggtacagata tagcgtgtac   2940
ggaacaaccc tgtgcgtcga gtgcaagaaa accctgcaga gaagcgaggt gtacgactgc   3000
cagaggccac tgtgccctca agagaagaaa cggcacgtgg acctgaacaa gcggtttcac   3060
accctgcacg agtacatgct ggacctgcag cctgagacaa ccgacctgta ctgctacgag   3120
cagcccgaaa ccacagatct gcactgttat gagcagctgg cgacagcag cgacgaagag   3180 gatacaggcg gactggacgg cgaggaaaac gacgaaattg acggcgtgaa ccaccagcat   3240
ctccccgcca gaagggctga acctcagaga cacaccatgc tgtgtatgtg ctgcaagtgc   3300
gaggccagaa tcgcctgatg a                                             3321
```

<210> SEQ ID NO 74
<211> LENGTH: 1105
<212> TYPE: PRT
<213> ORGANISM: Artificial Sequence
<220> FEATURE:
<223> OTHER INFORMATION: vaccine construct

<400> SEQUENCE: 74

```
Met Asp Ala Met Lys Arg Gly Leu Cys Cys Val Leu Leu Cys Gly
1               5                   10                  15

Ala Val Phe Val Ser Pro Ser Gln Glu Ile His Ala Arg Phe Arg Arg
            20                  25                  30

Gly Ser Lys Leu Ala Asp Glu Asp Glu Thr Ala Tyr Asp Ser Gly Thr
        35                  40                  45

Asp Leu Ile Asp Phe Ile Asp Asp Ser Asp Glu Asn Glu Asn Asp Ser
    50                  55                  60

Asp Thr Gly Glu Asp Met Val Asp Phe Ile Asp Asn Ala Gln Leu Ala
65                  70                  75                  80

Asp Ser Asp Ser Asn Ala Cys Ala Phe Leu Lys Ala Gln Leu Ala Asp
                85                  90                  95

Val Asn Ser Asn Ala Ala Ala Phe Leu Lys Asn Cys Ile Leu Leu Tyr
            100                 105                 110

Gly Ala Ala Asn Thr Gly Lys Ser Leu Phe Gly Met Ser Leu Asn Cys
        115                 120                 125

Leu Val Leu Cys Gly Pro Ala Asn Thr Gly Lys Ser Tyr Phe Gly Met
    130                 135                 140

Ser Leu Trp Pro Tyr Leu His Ser Arg Leu Val Val Phe Thr Phe Pro
145                 150                 155                 160

Asn Pro Phe Trp Pro Tyr Leu Glu Ser Arg Ile Thr Val Phe Glu Phe
                165                 170                 175

Pro Asn Ala Phe Asn Val Cys Gln Asp Lys Ile Leu Glu His Tyr Glu
            180                 185                 190

Asn Asp Ser Lys Asp Ile Leu Glu His Tyr Glu Asn Asp Ser Lys Asp
        195                 200                 205

Leu Cys Asp His Ile Cys Asp His Ile Asp Tyr Trp Lys His Ile Arg
    210                 215                 220
```

-continued

```
Leu Glu Cys Ala Ile Met Tyr Lys Ala Arg Ile Arg Leu Glu Cys Ala
225                 230                 235                 240

Ile Met Tyr Lys Ala Arg Glu Met Gly Phe His Gln Phe Asp Gly Asp
                245                 250                 255

Ile Cys Asn Thr Met His Tyr Thr Asn Trp Ile Tyr Ile Cys Glu Asp
            260                 265                 270

Ala Gln Cys Thr Val Val Glu Gly Gln Val Asp Lys Lys Trp Glu Val
        275                 280                 285

His Ala Gly Gly Gln Val Ile Leu Cys Pro Glu Ser Gly Gln Arg Arg
    290                 295                 300

Ile Lys Arg Pro Arg Ser Glu Asn Cys His Pro Asn Lys Leu Leu Ile
305                 310                 315                 320

Leu Lys Cys Leu Arg Tyr Arg Phe Lys Lys His Cys Lys Leu Ser Ser
                325                 330                 335

Thr Trp His Trp Thr Cys His Asp Gly Lys His Lys Trp His Trp Thr
            340                 345                 350

Cys His Asp Gly Lys His Lys Asn Ala Ile Val Thr Leu Thr Tyr Tyr
        355                 360                 365

Glu Ala Asp Lys Asn Asp Leu Asn Ala Gln Ile Glu His Trp Lys Leu
    370                 375                 380

Ile Arg Met Glu Cys Ala Ile Phe Tyr Lys Ala Lys Glu Leu Gly Ile
385                 390                 395                 400

Ser Ile Cys His Gln Val Pro Pro Leu Ala Ala Ser Lys Ala Lys
                405                 410                 415

Ala Cys Gln Ala Ile Glu Leu Gln Leu Ala Leu Glu Ala Leu Asn Ala
            420                 425                 430

Ser Pro Tyr Asp Glu Trp Thr Leu Gln Gln Thr Ser Leu Glu Met Trp
        435                 440                 445

Leu Ala Glu Pro Gln Phe Lys Lys His Gly Ile Thr Ile Thr Val Gln
    450                 455                 460

Tyr Asp Asn Asp Lys Ala Asn Thr Met Asp Tyr Thr Asn Trp Lys Glu
465                 470                 475                 480

Ile Tyr Val Ile Val Cys Pro Ala Ser Ile Pro Ser Asp Glu Ile Ser
                485                 490                 495

Thr Glu Glu Ala Asp His Ile Asp Tyr Trp Lys Ala Ile Arg Gln Glu
            500                 505                 510

Asn Ala Ile Phe Phe Ala Ala Arg His Gln Val Val Pro Ala Leu Asn
        515                 520                 525

Ile Cys Lys Ala Lys Ala Cys Lys Ala Ile Glu Trp Asn Thr Glu Pro
    530                 535                 540

Lys His Cys Phe Lys Lys Gly Gln His Ile Glu Val Trp Phe Asp
545                 550                 555                 560

Tyr Val Ala Trp Asp Ser Val Tyr Tyr Cys Gly Asp Gly Trp Cys
                565                 570                 575

Lys Thr Glu Ala Glu Lys Tyr Gly Cys Lys Gly Thr Trp Glu Val His
            580                 585                 590

Phe Gly Asn Ser Ile Asp Cys Asn Asp Ser Met Cys Ser Thr Phe Asp
        595                 600                 605

Asp Asn Val Ser Ala Thr Glu Leu Val Lys Asp His Ile Asp Tyr Trp
    610                 615                 620

Lys Leu Ile Arg Leu Glu Cys Ala Ile Phe Tyr Lys Ala Arg Arg Arg
625                 630                 635                 640
```

```
Leu Ser Ser Asp Gln Asp Gln Ser Gln Leu Val Thr Lys Tyr Pro Leu
                645                 650                 655
Leu Lys Leu Leu Ser Thr Gln Thr Thr Thr Pro Glu Asn Thr Ser Leu
            660                 665                 670
Val Glu Leu Arg Val Thr Thr Pro Lys Ser Thr Val Val Ile Arg Leu
            675                 680                 685
His Leu Thr Thr Arg Tyr Pro Leu Leu Ser Leu Leu Asn Ser Tyr Ser
690                 695                 700
Thr Pro Pro His Arg Ile Pro Ala Pro Cys Pro Trp Ala Pro Gln Arg
705                 710                 715                 720
Pro Pro Ile Pro Lys Pro Ser Pro Trp Ala Pro Arg Ile Pro Ala Pro
                725                 730                 735
Cys Pro Trp Ala Pro Pro Arg Pro Pro His Cys Pro Trp Val Pro Cys
                740                 745                 750
Phe Leu Leu Cys Phe Cys Val Leu Leu Cys Val Cys Leu Leu Ile Arg
                755                 760                 765
Pro Leu Leu Leu Ser Val Ser Thr Tyr Leu Arg Pro Leu Leu Leu Ser
            770                 775                 780
Ile Ser Val Tyr Ala Gln Val Leu Val Leu Val Leu Leu Leu Trp Val
785                 790                 795                 800
Ser Ile Gly Ser Leu Leu Pro Ser Val Cys Met Cys Ala Tyr Ala Trp
                805                 810                 815
Val Leu Val Phe Val Tyr Ile Val Val Ile Thr Ser Pro Ala Thr Ala
                820                 825                 830
Ile Val Tyr Arg Asp Gly Asn Pro Tyr Ala Val Cys Asp Lys Cys Leu
            835                 840                 845
Lys Phe Tyr Ser Lys Ile Ser Glu Tyr Arg His Tyr Cys Tyr Ser Leu
    850                 855                 860
Tyr Gly Thr Thr Leu Glu Gln Gln Tyr Asn Lys Pro Leu Cys Asp Leu
865                 870                 875                 880
Leu Ile Arg Cys Ile Asn Val Val Tyr Arg Asp Ser Ile Pro His Ala
                885                 890                 895
Ala Cys His Lys Cys Ile Asp Phe Tyr Ser Arg Ile Arg Glu Leu Arg
            900                 905                 910
His Tyr Ser Asp Ser Val Tyr Gly Asp Thr Leu Glu Lys Leu Thr Asn
            915                 920                 925
Thr Gly Leu Tyr Asn Leu Leu Ile Arg Cys Leu Arg Val Tyr Cys Lys
            930                 935                 940
Gly Gln Leu Thr Glu Thr Glu Val Leu Asp Phe Ala Phe Thr Asp Leu
945                 950                 955                 960
Thr Ile Val Tyr Arg Asp Ser Lys Val Ser Glu Phe Arg Trp Tyr Arg
                965                 970                 975
Tyr Ser Val Tyr Gly Thr Thr Leu Cys Val Glu Cys Lys Lys Thr Leu
            980                 985                 990
Gln Arg Ser Glu Val Tyr Asp Cys Gln Arg Pro Leu Cys Pro Gln Glu
            995                 1000                1005
Lys Lys Arg His Val Asp Leu Asn Lys Arg Phe His Thr Leu His
    1010                1015                1020
Glu Tyr Met Leu Asp Leu Gln Pro Glu Thr Thr Asp Leu Tyr Cys
    1025                1030                1035
Tyr Glu Gln Pro Glu Thr Thr Asp Leu His Cys Tyr Glu Gln Leu
    1040                1045                1050
Gly Asp Ser Ser Asp Glu Glu Asp Thr Gly Gly Leu Asp Gly Glu
```

| | | | | | | | | | | | | |
|---|---|---|---|---|---|---|---|---|---|---|---|---|
| | | 1055 | | | 1060 | | | | 1065 | | | |
| Glu | Asn | Asp | Glu | Ile | Asp | Gly | Val | Asn | His | Gln | His | Leu Pro Ala |
| | | 1070 | | | | 1075 | | | | 1080 | | |

| | | | | | | | | | | | | |
|---|---|---|---|---|---|---|---|---|---|---|---|---|
| Arg | Arg | Ala | Glu | Pro | Gln | Arg | His | Thr | Met | Leu | Cys | Met Cys Cys |
| | 1085 | | | | 1090 | | | | 1095 | | | |

| | | | | | | |
|---|---|---|---|---|---|---|
| Lys | Cys | Glu | Ala | Arg | Ile | Ala |
| | 1100 | | | | 1105 | |

<210> SEQ ID NO 75
<211> LENGTH: 4470
<212> TYPE: DNA
<213> ORGANISM: Artificial Sequence
<220> FEATURE:
<223> OTHER INFORMATION: vaccine construct

<400> SEQUENCE: 75

```
atggatgcta tgaagagggg cctgtgctgc gtgctgctgc tgtgtggcgc cgtgtttgtg      60
tcccccagcc aggaaatcca cgcccggttc agaagaggca gcaagctggc cgacgaggac     120
gagacagcct acgacagcgg caccgacctg atcgacttca tcgacgatag cgccgctgcc     180
gacgagaatg agaacgacag cgataccggc gaggacatgg tggatttcat cgacaacgct     240
gccgccgacg aaaccgacga agagagcacc gagagcgacc tggacggctt tatcgacaac     300
agcgcagccg cccagctggc tgacagcgac tctaatgcct cgccttcct gaaggccgct      360
gctcagctgg cagacgtgaa cagcaatgcc gccgcttttc tgaaggctgc cgccaactgc     420
atcctgctgt acggcgctgc caacaccggc aagagcctgt cggcatgtc tctggccgca      480
gccaactgcc tggtgctgtg cggacctgcc aatactggca aaagctactt cggcatgagc     540
ctggcagccg ccaattgtct cgtgatctac ggccctccta ataccggcaa gtcctgcttt     600
gccatgagtc tggccgctgc ctggccctac ctgcactcta ctggtggt gttcaccttc       660
cccaacccct tcgctgccgc ttggccttac ctggaaagcc ggatcaccgt gttcgagttc     720
cccaatgcct tcgccgcagc cctgagatac ctgcacagca gaatccacgt gctgcagttt     780
ctgaacccct tgccgccgc aaacgtgtgt caggacaaga tcctggaaca ctacgagaac     840
gactccaagg atgccgctgc cattctggaa cattatgaga atgatagcaa ggacctgtgc     900
gaccacattg ctgccgcctg cgatcacatc gactactgga agcacatccg gctggaatgc     960
gccatcatgt acaaggccag agccgccgct atcagactgg aatgtgctat tatgtataag    1020
gctcgcgaga tgggcttcca cgctgctgcc cagttcgacg gcgacatctg caacaccatg    1080
cactacacca actgggctgc cgctatctac atctgcgagg acgcccagtg caccgtggtg    1140
gaaggacagg tggacgccgc tgctaagaaa tgggaggtgc acgctggcgg ccaagtgatc    1200
ctgtgtccag agtctgctgc cgcaggccag cggagaatca gaggcctag aagcgaggca    1260
gccgctaact gccacccaa caaactgctg gctgctgcca tcctgaagtg cctgcggtac    1320
agattcaaga gcactgcaa actggctgca gctagcagca cctggcactg acctgtcac     1380
gacggcaagc acaaagccgc cgcatggcat tggacatgcc acgatggaaa acacaagaac    1440
gccatcgtga ccctgaccta tgcagccgcc tacgaggccg acaagaacga cctgaacgcc    1500
cagatcgagc actggaagct gatcaggatg gaatgtgcaa tcttctataa ggccaaagag    1560
ctgggcatca gcgctgccgc aatctgccac caggtggtgc ctccactggc cgcctctaaa    1620
gccaaagcct gccaggccat cgaactgcag ctggccctgg aagccctgaa tgccagccct    1680
tatgccgcag ccgatgagtg gaccctgcag cagaccagcc tggaaatgtg gctggccgaa    1740
```

```
cctcaggccg cagcttttaa gaagcacggc atcaccatca ccgtgcagta cgacaacgac    1800
aaggccaata ccatggatta caccaattgg aaagagatct acgccgcagc tgtgatcgtg    1860
tgccccgcca gcatccctag cgacgagatc agcacagagg aagcagccgc cgaccacatc    1920
gattattgga aagccatcag acaggaaaac gccatcttct cgccgctag agccgctgcc    1980 caccaggtgg tgccagccct gaatatctgc aaggccaagg cctgtaaagc catcgaagcc    2040
gctgcttgga acaccgagcc caagcactgc ttcaagaagg gcggccagca catcgaagtg    2100
tggttcgacg ctgcagccta cgtggcctgg gacagcgtgt actactgtgg cgacgacggc    2160
tggtgcaaga ccgccgctgc agaggccgag aagtatggct gcaagggcac ctgggaagtg    2220
catttcggcg cagctgccaa ctccatcgac tgcaacgaca gcatgtgcag caccttcgac    2280
gacaacgtgt ccgccaccga gctcgtgaaa gctgccgctg accatattga ttactggaaa    2340
ctgattcgcc tggaatgcgc tatttttctac aaagccaggg ccgcagcacg gcggctgtcc    2400
tcagatcagg atcagagcca ggctgctgca ctcgtgacca agtacccct gctgaagctg    2460 ctgagcgccg cagcaagacc ccccaacatg ggagtgaagg cccacggcaa gtgcatctgg    2520
gagaacaagg tgttcatcgt gcccaccctg tgccccgtgc ctctggatcc aacatatcct    2580
ctgctgaaac tgctgaccgc tgccgccacc cagaccacca cacctgagaa tacctccctg    2640
gtggaactga gagtgaccac ccccaagagc acagtcgtga tcaggctgca cctggctgcc    2700
gcaaccacca gataccctct gctgtccctg ctgaacagct acagcacccc ccctcatcgg    2760
atccctgccc cttgtccttg ggctcctcag aggcctgccg ctgcacctat ccctaagcct    2820
tctccatggg cccctgccgc agctagaatc ccagctccat gtccatgggc accagctgct    2880
gctcccagac ctcctcattg cccttgggtg ccagcagccg ctcctccacc tcctcctaga    2940
ccttgggccc cagccgccgc ttgtttcctg ctgtgcttct gtgtgctgct gtgcgtgtgc    3000
ctgctgatca gaccctgct gctgagtgtg tccacctacg cagctgctct gcggccactg    3060
ctgctgtcca tctctgtgta cgcacaggtg ctggtgctgg tgctgctgct gtgggtgtcc    3120
atcggatctg ccgcagcact gctgccctcc gtgtgcatgt gtgcctatgc ctgggtgctg    3180
gtgttcgtgt acatcgtcgt gattaccagc ccgccaccg cagccgcaat cgtgtacagg    3240
gacggcaacc cttacgccgt gtgcgacaag tgcctgaagt tctacagcaa gatcagcgag    3300
taccgccact actgctacag cctgtacggg accacctgg aacagcagta caacaagccc    3360
ctgtgcgatc tgctgatccg gtgcatcaac gcagccgctg tggtgtacag agacagcatc    3420
ccacacgccg cctgccacaa gtgtatcgac ttctactccc ggatcagaga gctgagacac    3480
tactccgact ccgtgtacgg cgatacctg gaaaagctga ccaataccgg cctgtacaac    3540
ctgctgatta gatgcctgcg ggcagccgca gtgttctgca gaaagcccct gaccgccagc    3600
gaggtgtaca cttcgccta caccgatctg cgggtggtgt accgggatgc tgctgcctcc    3660
aaagtgcgga agctgcggta ctacaactgc tctgtgtatg cgcctccct ggcagctgcc    3720 gtgtattgca agggacagct gaccgagaca gaggtgctga tttcgccttt cacagacctg    3780
accatcgtgt atagagatgc agctgctagc aaggtgtccg agttccggtg gtacagatat    3840
agcgtgtacg aacaacact ggcagcagct tgcgtggaat gcaagaaaac actgcagcgg    3900
agcgaagtgt acgatgctgc agcttgccag aggccgctgt gtcctcagga aaagaaaaga    3960
cacgtggacc tgaacaagcg gttccacgca gcagctaccc tgcacgagta catgctggac    4020
ctgcagcccg agacaaccga cctgtactgc tacgagcagg cagctgcacc cgaaaccaca    4080
gatctgcact gttatgagca gctgggagac agctccgatg aagaggacac cggcggactg    4140
```

-continued

```
gatgctgccg ctgggatga ggacgaggat gaggtggacc atctgcagga acagccccag    4200
caggccagaa gggatgagca gcacccctgc tatctgatcg agacacagtg ctgcagatgc    4260
gagagcctgg tggccgctgc tgaggaaaac gacgagatcg acggcgtgaa ccaccagcat    4320
ctgcccgcta aaggccga gcctcagaga cacaccatgc tgtgtatgtg ttgcaagtgc      4380
gaggcccgga tcgccggatc tggacctggc gctagcggaa agcccatccc caatccactg    4440
ctgggcctgg actccacccg gacctgataa                                     4470
```

<210> SEQ ID NO 76
<211> LENGTH: 1488
<212> TYPE: PRT
<213> ORGANISM: Artificial Sequence
<220> FEATURE:
<223> OTHER INFORMATION: vaccine construct

<400> SEQUENCE: 76

```
Met Asp Ala Met Lys Arg Gly Leu Cys Cys Val Leu Leu Cys Gly
1               5                   10                  15

Ala Val Phe Val Ser Pro Ser Gln Glu Ile His Ala Arg Phe Arg Arg
                20                  25                  30

Gly Ser Lys Leu Ala Asp Glu Asp Glu Thr Ala Tyr Asp Ser Gly Thr
            35                  40                  45

Asp Leu Ile Asp Phe Ile Asp Asp Ser Ala Ala Asp Glu Asn Glu
        50                  55                  60

Asn Asp Ser Asp Thr Gly Glu Asp Met Val Asp Phe Ile Asp Asn Ala
65                  70                  75                  80

Ala Ala Asp Glu Thr Asp Glu Glu Ser Thr Glu Ser Asp Leu Asp Gly
                85                  90                  95

Phe Ile Asp Asn Ser Ala Ala Gln Leu Ala Asp Ser Asp Ser Asn
                100                 105                 110

Ala Cys Ala Phe Leu Lys Ala Ala Ala Gln Leu Ala Asp Val Asn Ser
            115                 120                 125

Asn Ala Ala Ala Phe Leu Lys Ala Ala Ala Asn Cys Ile Leu Leu Tyr
        130                 135                 140

Gly Ala Ala Asn Thr Gly Lys Ser Leu Phe Gly Met Ser Leu Ala Ala
145                 150                 155                 160

Ala Asn Cys Leu Val Leu Cys Gly Pro Ala Asn Thr Gly Lys Ser Tyr
                165                 170                 175

Phe Gly Met Ser Leu Ala Ala Ala Asn Cys Leu Val Ile Tyr Gly Pro
            180                 185                 190

Pro Asn Thr Gly Lys Ser Cys Phe Ala Met Ser Leu Ala Ala Ala Trp
        195                 200                 205

Pro Tyr Leu His Ser Arg Leu Val Val Phe Thr Phe Pro Asn Pro Phe
    210                 215                 220

Ala Ala Ala Trp Pro Tyr Leu Glu Ser Arg Ile Thr Val Phe Glu Phe
225                 230                 235                 240

Pro Asn Ala Phe Ala Ala Ala Leu Arg Tyr Leu His Ser Arg Ile His
                245                 250                 255

Val Leu Gln Phe Leu Asn Pro Phe Ala Ala Ala Asn Val Cys Gln Asp
            260                 265                 270

Lys Ile Leu Glu His Tyr Glu Asn Asp Ser Lys Asp Ala Ala Ala Ile
        275                 280                 285

Leu Glu His Tyr Glu Asn Asp Ser Lys Asp Leu Cys Asp His Ile Ala
    290                 295                 300
```

```
Ala Ala Cys Asp His Ile Asp Tyr Trp Lys His Ile Arg Leu Glu Cys
305                 310                 315                 320
Ala Ile Met Tyr Lys Ala Arg Ala Ala Ile Arg Leu Glu Cys Ala
            325                 330                 335
Ile Met Tyr Lys Ala Arg Glu Met Gly Phe His Ala Ala Gln Phe
            340                 345                 350
Asp Gly Asp Ile Cys Asn Thr Met His Tyr Thr Asn Trp Ala Ala Ala
            355                 360                 365
Ile Tyr Ile Cys Glu Asp Ala Gln Cys Thr Val Val Glu Gly Gln Val
            370                 375                 380
Asp Ala Ala Lys Lys Trp Glu Val His Ala Gly Gln Val Ile
385                 390                 395                 400
Leu Cys Pro Glu Ser Ala Ala Ala Gly Gln Arg Arg Ile Lys Arg Pro
                405                 410                 415
Arg Ser Glu Ala Ala Ala Asn Cys His Pro Asn Lys Leu Leu Ala Ala
                420                 425                 430
Ala Ile Leu Lys Cys Leu Arg Tyr Arg Phe Lys Lys His Cys Lys Leu
            435                 440                 445
Ala Ala Ala Ser Ser Thr Trp His Trp Thr Cys His Asp Gly Lys His
            450                 455                 460
Lys Ala Ala Ala Trp His Trp Thr Cys His Asp Gly Lys His Lys Asn
465                 470                 475                 480
Ala Ile Val Thr Leu Thr Tyr Ala Ala Ala Tyr Glu Ala Asp Lys Asn
                485                 490                 495
Asp Leu Asn Ala Gln Ile Glu His Trp Lys Leu Ile Arg Met Glu Cys
                500                 505                 510
Ala Ile Phe Tyr Lys Ala Lys Glu Leu Gly Ile Ser Ala Ala Ala Ile
            515                 520                 525
Cys His Gln Val Val Pro Pro Leu Ala Ser Lys Ala Lys Ala Cys
            530                 535                 540
Gln Ala Ile Glu Leu Gln Leu Ala Leu Glu Ala Leu Asn Ala Ser Pro
545                 550                 555                 560
Tyr Ala Ala Ala Asp Glu Trp Thr Leu Gln Gln Thr Ser Leu Glu Met
                565                 570                 575
Trp Leu Ala Glu Pro Gln Ala Ala Phe Lys Lys His Gly Ile Thr
            580                 585                 590
Ile Thr Val Gln Tyr Asp Asn Asp Lys Ala Asn Thr Met Asp Tyr Thr
            595                 600                 605
Asn Trp Lys Glu Ile Tyr Ala Ala Val Ile Val Cys Pro Ala Ser
            610                 615                 620
Ile Pro Ser Asp Glu Ile Ser Thr Glu Glu Ala Ala Asp His Ile
625                 630                 635                 640
Asp Tyr Trp Lys Ala Ile Arg Gln Glu Asn Ala Ile Phe Phe Ala Ala
                645                 650                 655
Arg Ala Ala Ala His Gln Val Val Pro Ala Leu Asn Ile Cys Lys Ala
                660                 665                 670
Lys Ala Cys Lys Ala Ile Glu Ala Ala Ala Trp Asn Thr Glu Pro Lys
            675                 680                 685
His Cys Phe Lys Lys Gly Gly Gln His Ile Glu Val Trp Phe Asp Ala
            690                 695                 700
Ala Ala Tyr Val Ala Trp Asp Ser Val Tyr Tyr Cys Gly Asp Asp Gly
705                 710                 715                 720
```

```
Trp Cys Lys Thr Ala Ala Ala Glu Ala Glu Lys Tyr Gly Cys Lys Gly
            725                 730                 735

Thr Trp Glu Val His Phe Gly Ala Ala Ala Asn Ser Ile Asp Cys Asn
        740                 745                 750

Asp Ser Met Cys Ser Thr Phe Asp Asp Asn Val Ser Ala Thr Glu Leu
            755                 760                 765

Val Lys Ala Ala Ala Asp His Ile Asp Tyr Trp Lys Leu Ile Arg Leu
    770                 775                 780

Glu Cys Ala Ile Phe Tyr Lys Ala Arg Ala Ala Arg Arg Leu Ser
785                 790                 795                 800

Ser Asp Gln Asp Gln Ser Gln Ala Ala Ala Leu Val Thr Lys Tyr Pro
                805                 810                 815

Leu Leu Lys Leu Leu Ser Ala Ala Ala Arg Pro Pro Asn Met Gly Val
            820                 825                 830

Lys Ala His Gly Lys Cys Ile Trp Glu Asn Lys Val Phe Ile Val Pro
            835                 840                 845

Thr Leu Cys Pro Val Pro Leu Asp Pro Thr Tyr Pro Leu Leu Lys Leu
    850                 855                 860

Leu Thr Ala Ala Ala Thr Gln Thr Thr Thr Pro Glu Asn Thr Ser Leu
865                 870                 875                 880

Val Glu Leu Arg Val Thr Thr Pro Lys Ser Thr Val Val Ile Arg Leu
            885                 890                 895

His Leu Ala Ala Ala Thr Thr Arg Tyr Pro Leu Leu Ser Leu Leu Asn
                900                 905                 910

Ser Tyr Ser Thr Pro Pro His Arg Ile Pro Ala Pro Cys Pro Trp Ala
            915                 920                 925

Pro Gln Arg Pro Ala Ala Pro Ile Pro Lys Pro Ser Pro Trp Ala
    930                 935                 940

Pro Ala Ala Ala Arg Ile Pro Ala Pro Cys Pro Trp Ala Pro Ala Ala
945                 950                 955                 960

Ala Pro Arg Pro Pro His Cys Pro Trp Val Pro Ala Ala Ala Pro Pro
            965                 970                 975

Pro Pro Pro Arg Pro Trp Ala Pro Ala Ala Ala Cys Phe Leu Leu Cys
        980                 985                 990

Phe Cys Val Leu Leu Cys Val Cys Leu Leu Ile Arg Pro Leu Leu Leu
        995                 1000                1005

Ser Val Ser Thr Tyr Ala Ala Ala Leu Arg Pro Leu Leu Leu Ser
    1010                1015                1020

Ile Ser Val Tyr Ala Gln Val Leu Val Leu Val Leu Leu Leu Trp
    1025                1030                1035

Val Ser Ile Gly Ser Ala Ala Ala Leu Leu Pro Ser Val Cys Met
    1040                1045                1050

Cys Ala Tyr Ala Trp Val Leu Val Phe Val Tyr Ile Val Val Ile
    1055                1060                1065

Thr Ser Pro Ala Thr Ala Ala Ala Ile Val Tyr Arg Asp Gly Asn
    1070                1075                1080

Pro Tyr Ala Val Cys Asp Lys Cys Leu Lys Phe Tyr Ser Lys Ile
    1085                1090                1095

Ser Glu Tyr Arg His Tyr Cys Tyr Ser Leu Tyr Gly Thr Thr Leu
    1100                1105                1110

Glu Gln Gln Tyr Asn Lys Pro Leu Cys Asp Leu Leu Ile Arg Cys
    1115                1120                1125

Ile Asn Ala Ala Ala Val Val Tyr Arg Asp Ser Ile Pro His Ala
```

```
                1130                1135                1140

Ala Cys His Lys Cys Ile Asp Phe Tyr Ser Arg Ile Arg Glu Leu
    1145                1150                1155

Arg His Tyr Ser Asp Ser Val Tyr Gly Asp Thr Leu Glu Lys Leu
    1160                1165                1170

Thr Asn Thr Gly Leu Tyr Asn Leu Leu Ile Arg Cys Leu Arg Ala
    1175                1180                1185

Ala Ala Val Phe Cys Lys Lys Ala Leu Thr Ala Ser Glu Val Tyr
    1190                1195                1200

Asn Phe Ala Tyr Thr Asp Leu Arg Val Val Tyr Arg Asp Ala Ala
    1205                1210                1215

Ala Ser Lys Val Arg Lys Leu Arg Tyr Tyr Asn Cys Ser Val Tyr
    1220                1225                1230

Gly Ala Ser Leu Ala Ala Ala Val Tyr Cys Lys Gly Gln Leu Thr
    1235                1240                1245

Glu Thr Glu Val Leu Asp Phe Ala Phe Thr Asp Leu Thr Ile Val
    1250                1255                1260

Tyr Arg Asp Ala Ala Ala Ser Lys Val Ser Glu Phe Arg Trp Tyr
    1265                1270                1275

Arg Tyr Ser Val Tyr Gly Thr Thr Leu Ala Ala Ala Cys Val Glu
    1280                1285                1290

Cys Lys Lys Thr Leu Gln Arg Ser Glu Val Tyr Asp Ala Ala Ala
    1295                1300                1305

Cys Gln Arg Pro Leu Cys Pro Gln Glu Lys Lys Arg His Val Asp
    1310                1315                1320

Leu Asn Lys Arg Phe His Ala Ala Ala Thr Leu His Glu Tyr Met
    1325                1330                1335

Leu Asp Leu Gln Pro Glu Thr Thr Asp Leu Tyr Cys Tyr Glu Gln
    1340                1345                1350

Ala Ala Ala Pro Glu Thr Thr Asp Leu His Cys Tyr Glu Gln Leu
    1355                1360                1365

Gly Asp Ser Ser Asp Glu Glu Asp Thr Gly Gly Leu Asp Ala Ala
    1370                1375                1380

Ala Gly Asp Glu Asp Glu Glu Val Asp His Leu Gln Glu Gln
    1385                1390                1395

Pro Gln Gln Ala Arg Arg Asp Glu Gln His Pro Cys Tyr Leu Ile
    1400                1405                1410

Glu Thr Gln Cys Cys Arg Cys Glu Ser Leu Val Ala Ala Ala Glu
    1415                1420                1425

Glu Asn Asp Glu Ile Asp Gly Val Asn His Gln His Leu Pro Ala
    1430                1435                1440

Arg Arg Ala Glu Pro Gln Arg His Thr Met Leu Cys Met Cys Cys
    1445                1450                1455

Lys Cys Glu Ala Arg Ile Ala Gly Ser Gly Pro Ala Ser Gly
    1460                1465                1470

Lys Pro Ile Pro Asn Pro Leu Leu Gly Leu Asp Ser Thr Arg Thr
    1475                1480                1485

<210> SEQ ID NO 77
<211> LENGTH: 20
<212> TYPE: PRT
<213> ORGANISM: Artificial Sequence
<220> FEATURE:
<223> OTHER INFORMATION: consensus sequence
<220> FEATURE:
```

```
<221> NAME/KEY: misc_feature
<222> LOCATION: (11)..(11)
<223> OTHER INFORMATION: Xaa can be any naturally occurring amino acid

<400> SEQUENCE: 77

Asp Glu Asp Glu Asn Ala Ser Asp Thr Gly Xaa Asp Leu Val Asp Phe
1               5                   10                  15

Ile Asp Asn Ser
            20

<210> SEQ ID NO 78
<211> LENGTH: 19
<212> TYPE: PRT
<213> ORGANISM: Human papillomavirus type 16

<400> SEQUENCE: 78

Asp Glu Asn Glu Asn Asp Ser Thr Gly Glu Asp Leu Val Asp Phe Ile
1               5                   10                  15

Val Asn Asp

<210> SEQ ID NO 79
<211> LENGTH: 20
<212> TYPE: PRT
<213> ORGANISM: Human papillomavirus type 18

<400> SEQUENCE: 79

Asp Glu Asp Glu Asn Ala Thr Asp Thr Gly Ser Asp Met Val Asp Phe
1               5                   10                  15

Ile Asp Thr Gln
            20

<210> SEQ ID NO 80
<211> LENGTH: 20
<212> TYPE: PRT
<213> ORGANISM: Human papillomavirus type 31

<400> SEQUENCE: 80

Asp Glu Asn Glu Asp Ser Ser Asp Thr Gly Glu Asp Met Val Asp Phe
1               5                   10                  15

Ile Asp Asn Cys
            20

<210> SEQ ID NO 81
<211> LENGTH: 20
<212> TYPE: PRT
<213> ORGANISM: Human papillomavirus type 52

<400> SEQUENCE: 81

Asp Glu Asp Glu Asn Ala Tyr Asp Ser Gly Thr Asp Leu Ile Asp Phe
1               5                   10                  15

Ile Asp Asp Ser
            20

<210> SEQ ID NO 82
<211> LENGTH: 19
<212> TYPE: PRT
<213> ORGANISM: Human papillomavirus type 53

<400> SEQUENCE: 82

Asp Glu Thr Asp Glu Glu Ser Thr Glu Ser Asp Leu Asp Gly Phe Ile
1               5                   10                  15

Asp Asn Ser
```

<210> SEQ ID NO 83
<211> LENGTH: 20
<212> TYPE: PRT
<213> ORGANISM: Human papillomavirus type 58

<400> SEQUENCE: 83

Asp Glu Asp Glu Thr Ala Asp Asp Ser Gly Thr Asp Leu Ile Glu Phe
1               5                   10                  15

Ile Asp Asp Ser
            20

<210> SEQ ID NO 84
<211> LENGTH: 15
<212> TYPE: PRT
<213> ORGANISM: Artificial Sequence
<220> FEATURE:
<223> OTHER INFORMATION: concensus sequence

<400> SEQUENCE: 84

Ala Gln Leu Ala Asp Val Asn Ser Asn Ala Ala Ala Phe Leu Lys
1               5                   10                  15

<210> SEQ ID NO 85
<211> LENGTH: 15
<212> TYPE: PRT
<213> ORGANISM: Human papillomavirus type 16

<400> SEQUENCE: 85

Ala Gln Leu Ala Asp Thr Asn Ser Asn Ala Ser Ala Phe Leu Lys
1               5                   10                  15

<210> SEQ ID NO 86
<211> LENGTH: 15
<212> TYPE: PRT
<213> ORGANISM: Human papillomavirus type 18

<400> SEQUENCE: 86

Ala Leu Leu Ala Asp Ser Asn Ser Asn Ala Ala Ala Phe Leu Lys
1               5                   10                  15

<210> SEQ ID NO 87
<211> LENGTH: 15
<212> TYPE: PRT
<213> ORGANISM: Human papillomavirus type 31

<400> SEQUENCE: 87

Ala Gln Leu Ala Asp Ser Asp Ser Asn Ala Cys Ala Phe Leu Lys
1               5                   10                  15

<210> SEQ ID NO 88
<211> LENGTH: 15
<212> TYPE: PRT
<213> ORGANISM: Human papillomavirus type 52

<400> SEQUENCE: 88

Ala Gln Leu Ala Asp Val Asn Ser Asn Ala Ala Ala Phe Leu Lys
1               5                   10                  15

<210> SEQ ID NO 89
<211> LENGTH: 15
<212> TYPE: PRT
<213> ORGANISM: Human papillomavirus type 53

<400> SEQUENCE: 89

```
Ala Gln Leu Ala Asp Val Asp Ser Asn Ala Gln Ala Phe Leu Lys
1               5                   10                  15

<210> SEQ ID NO 90
<211> LENGTH: 15
<212> TYPE: PRT
<213> ORGANISM: Human papillomavirus type 58

<400> SEQUENCE: 90

Ala Gln Leu Ala Asp Val Asn Ser Asn Ala Ala Ala Phe Leu Arg
1               5                   10                  15

<210> SEQ ID NO 91
<211> LENGTH: 20
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 91

Asn Cys Leu Xaa Leu Tyr Gly Pro Ala Asn Thr Gly Lys Ser Tyr Phe
1               5                   10                  15

Gly Met Ser Leu
            20

<210> SEQ ID NO 92
<211> LENGTH: 20
<212> TYPE: PRT
<213> ORGANISM: Human papillomavirus type 16

<400> SEQUENCE: 92

Asn Cys Ile Leu Leu Tyr Gly Ala Ala Asn Thr Gly Lys Ser Leu Phe
1               5                   10                  15

Gly Met Ser Leu
            20

<210> SEQ ID NO 93
<211> LENGTH: 20
<212> TYPE: PRT
<213> ORGANISM: Human papillomavirus type 18

<400> SEQUENCE: 93

Asn Cys Leu Val Phe Cys Gly Pro Ala Asn Thr Gly Lys Ser Tyr Phe
1               5                   10                  15

Gly Met Ser Phe
            20

<210> SEQ ID NO 94
<211> LENGTH: 20
<212> TYPE: PRT
<213> ORGANISM: Human papillomavirus type 31

<400> SEQUENCE: 94

Asn Cys Ile Leu Ile His Gly Ala Pro Asn Thr Gly Lys Ser Tyr Phe
1               5                   10                  15

Gly Met Ser Leu
            20

<210> SEQ ID NO 95
```

```
<211> LENGTH: 20
<212> TYPE: PRT
<213> ORGANISM: Human papillomavirus type 52

<400> SEQUENCE: 95

Asn Cys Leu Val Leu Tyr Gly Pro Ala Asn Thr Gly Lys Ser Tyr Phe
1               5                   10                  15

Gly Met Ser Leu
            20

<210> SEQ ID NO 96
<211> LENGTH: 20
<212> TYPE: PRT
<213> ORGANISM: Human papillomavirus type 53

<400> SEQUENCE: 96

Asn Cys Leu Val Ile Tyr Gly Pro Pro Asn Thr Gly Lys Ser Cys Gly
1               5                   10                  15

Ala Met Ser Leu
            20

<210> SEQ ID NO 97
<211> LENGTH: 20
<212> TYPE: PRT
<213> ORGANISM: Human papillomavirus type 58

<400> SEQUENCE: 97

Ser Cys Met Leu Leu Cys Gly Pro Ala Asn Thr Gly Lys Ser Tyr Phe
1               5                   10                  15

Gly Met Ser Leu
            20

<210> SEQ ID NO 98
<211> LENGTH: 20
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (11)..(11)
<223> OTHER INFORMATION: Xaa can be any naturally occurring amino acid

<400> SEQUENCE: 98

Asp Glu Asp Glu Asn Ala Ser Asp Thr Gly Xaa Asp Leu Val Asp Phe
1               5                   10                  15

Ile Asp Asn Ser
            20

<210> SEQ ID NO 99
<211> LENGTH: 20
<212> TYPE: PRT
<213> ORGANISM: Human papillomavirus type 16

<400> SEQUENCE: 99

Asp Glu Asn Glu Asn Asp Ser Asp Thr Gly Glu Asp Leu Val Asp Phe
1               5                   10                  15

Ile Val Asn Asp
            20

<210> SEQ ID NO 100
<211> LENGTH: 20
<212> TYPE: PRT
<213> ORGANISM: Human papillomavirus type 18
```

<400> SEQUENCE: 100

Asp Glu Asp Glu Asn Ala Thr Asp Thr Gly Ser Asp Met Val Asp Phe
1               5                   10                  15

Ile Asp Thr Gln
            20

<210> SEQ ID NO 101
<211> LENGTH: 20
<212> TYPE: PRT
<213> ORGANISM: Human papillomavirus type 31

<400> SEQUENCE: 101

Asp Glu Asn Glu Asp Ser Ser Asp Thr Gly Glu Asp Met Val Asp Phe
1               5                   10                  15

Ile Asp Asn Cys
            20

<210> SEQ ID NO 102
<211> LENGTH: 20
<212> TYPE: PRT
<213> ORGANISM: Human papillomavirus type 52

<400> SEQUENCE: 102

Asp Glu Asp Glu Asn Ala Tyr Asp Ser Gly Thr Asp Leu Ile Asp Phe
1               5                   10                  15

Ile Asp Asp Ser
            20

<210> SEQ ID NO 103
<211> LENGTH: 19
<212> TYPE: PRT
<213> ORGANISM: Human papillomavirus type 53

<400> SEQUENCE: 103

Asp Glu Thr Asp Glu Glu Ser Thr Glu Ser Asp Leu Asp Gly Phe Ile
1               5                   10                  15

Asp Asn Ser

<210> SEQ ID NO 104
<211> LENGTH: 20
<212> TYPE: PRT
<213> ORGANISM: Human papillomavirus type 58

<400> SEQUENCE: 104

Asp Glu Asp Glu Thr Ala Asp Asp Ser Gly Thr Asp Leu Ile Glu Phe
1               5                   10                  15

Ile Asp Asp Ser
            20

<210> SEQ ID NO 105
<211> LENGTH: 20
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

```
<220> FEATURE:
<221> NAME/KEY: misc_feature
<222> LOCATION: (15)..(15)
<223> OTHER INFORMATION: Xaa can be any naturally occurring amino acid

<400> SEQUENCE: 105

Asp Glu Asp Glu Xaa Ala Xaa Asp Ser Gly Thr Asp Leu Ile Xaa Phe
1               5                   10                  15

Ile Asp Asp Ser
            20

<210> SEQ ID NO 106
<211> LENGTH: 20
<212> TYPE: PRT
<213> ORGANISM: Human papillomavirus type 52

<400> SEQUENCE: 106

Asp Glu Asp Glu Asn Ala Tyr Asp Ser Gly Thr Asp Leu Ile Asp Phe
1               5                   10                  15

Ile Asp Asp Ser
            20

<210> SEQ ID NO 107
<211> LENGTH: 20
<212> TYPE: PRT
<213> ORGANISM: Human papillomavirus type 58

<400> SEQUENCE: 107

Asp Glu Asp Glu Thr Ala Asp Asp Ser Gly Thr Asp Leu Ile Glu Phe
1               5                   10                  15

Ile Asp Asp Ser
            20

<210> SEQ ID NO 108
<211> LENGTH: 15
<212> TYPE: PRT
<213> ORGANISM: Artificial Sequence
<220> FEATURE:
<223> OTHER INFORMATION: consensus sequence

<400> SEQUENCE: 108

Ala Gln Leu Ala Asp Ser Asp Ser Asn Ala Cys Ala Phe Leu Lys
1               5                   10                  15

<210> SEQ ID NO 109
<211> LENGTH: 15
<212> TYPE: PRT
<213> ORGANISM: Human papillomavirus type 31

<400> SEQUENCE: 109

Ala Gln Leu Ala Asp Ser Asp Ser Asn Ala Cys Ala Phe Leu Lys
1               5                   10                  15

<210> SEQ ID NO 110
<211> LENGTH: 15
<212> TYPE: PRT
<213> ORGANISM: Human papillomavirus type 53

<400> SEQUENCE: 110

Ala Gln Leu Ala Asp Val Asp Ser Asn Ala Gln Ala Phe Leu Lys
1               5                   10                  15

<210> SEQ ID NO 111
<211> LENGTH: 20
```

```
<212> TYPE: PRT
<213> ORGANISM: Artificial Sequence
<220> FEATURE:
<223> OTHER INFORMATION: consensus sequence

<400> SEQUENCE: 111

Asn Cys Ile Leu Leu Tyr Gly Ala Ala Asn Thr Gly Lys Ser Leu Phe
1               5                   10                  15

Gly Met Ser Leu
            20

<210> SEQ ID NO 112
<211> LENGTH: 20
<212> TYPE: PRT
<213> ORGANISM: Human papillomavirus type 16

<400> SEQUENCE: 112

Asn Cys Ile Leu Leu Tyr Gly Ala Ala Asn Thr Gly Lys Ser Leu Phe
1               5                   10                  15

Gly Met Ser Leu
            20

<210> SEQ ID NO 113
<211> LENGTH: 20
<212> TYPE: PRT
<213> ORGANISM: Human papillomavirus type 31

<400> SEQUENCE: 113

Asn Cys Ile Leu Ile His Gly Ala Pro Asn Thr Gly Lys Ser Tyr Phe
1               5                   10                  15

Gly Met Ser Leu
            20

<210> SEQ ID NO 114
<211> LENGTH: 17
<212> TYPE: PRT
<213> ORGANISM: Artificial Sequence
<220> FEATURE:
<223> OTHER INFORMATION: consensus sequence

<400> SEQUENCE: 114

Trp Pro Tyr Leu His Ser Arg Leu Val Val Phe Thr Phe Pro Asn Pro
1               5                   10                  15

Phe

<210> SEQ ID NO 115
<211> LENGTH: 17
<212> TYPE: PRT
<213> ORGANISM: Human papillomavirus type 16

<400> SEQUENCE: 115

Trp Pro Tyr Leu His Asn Arg Leu Val Val Phe Thr Phe Pro Asn Glu
1               5                   10                  15

Phe

<210> SEQ ID NO 116
<211> LENGTH: 17
<212> TYPE: PRT
<213> ORGANISM: Human papillomavirus type 31

<400> SEQUENCE: 116

Trp Pro Tyr Leu His Ser Arg Leu Val Val Phe Thr Phe Pro Asn Pro
1               5                   10                  15
```

Phe

```
<210> SEQ ID NO 117
<211> LENGTH: 17
<212> TYPE: PRT
<213> ORGANISM: Human papillomavirus type 52

<400> SEQUENCE: 117
```

Trp Pro Tyr Leu His Ser Arg Leu Val Val Phe His Phe Lys Asn Pro
1               5                   10                  15

Phe

```
<210> SEQ ID NO 118
<211> LENGTH: 19
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (6)..(6)
<223> OTHER INFORMATION: Xaa can be any naturally occurring amino acid

<400> SEQUENCE: 118
```

Asp Glu Asn Glu Asn Xaa Ser Asp Thr Gly Glu Asp Met Val Asp Phe
1               5                   10                  15

Ile Asp Asn

```
<210> SEQ ID NO 119
<211> LENGTH: 19
<212> TYPE: PRT
<213> ORGANISM: Human papillomavirus type 31

<400> SEQUENCE: 119
```

Asp Glu Asn Glu Asp Ser Ser Asp Thr Gly Glu Asp Met Val Asp Phe
1               5                   10                  15

Ile Asp Asn

```
<210> SEQ ID NO 120
<211> LENGTH: 19
<212> TYPE: PRT
<213> ORGANISM: Human papillomavirus type 16

<400> SEQUENCE: 120
```

Asp Glu Asn Glu Asn Asp Ser Asp Thr Gly Glu Asp Leu Val Asp Phe
1               5                   10                  15

Ile Val Asn

```
<210> SEQ ID NO 121
<211> LENGTH: 19
<212> TYPE: PRT
<213> ORGANISM: Human papillomavirus type 18

<400> SEQUENCE: 121
```

Asp Glu Asp Glu Asn Ala Thr Asp Thr Gly Ser Asp Met Val Asp Phe
1               5                   10                  15

Ile Asp Thr

```
<210> SEQ ID NO 122
<211> LENGTH: 19
<212> TYPE: PRT
<213> ORGANISM: Human papillomavirus type 53
```

<400> SEQUENCE: 122

Asp Glu Thr Asp Glu Glu Ser Thr Glu Ser Asp Leu Asp Gly Phe Ile
1               5                   10                  15

Asp Asn Ser

<210> SEQ ID NO 123
<211> LENGTH: 15
<212> TYPE: PRT
<213> ORGANISM: Artificial Sequence
<220> FEATURE:
<223> OTHER INFORMATION: consensus sequence

<400> SEQUENCE: 123

Ala Gln Leu Ala Asp Val Asn Ser Asn Ala Ala Ala Phe Leu Lys
1               5                   10                  15

<210> SEQ ID NO 124
<211> LENGTH: 15
<212> TYPE: PRT
<213> ORGANISM: Human papillomavirus type 52

<400> SEQUENCE: 124

Ala Gln Leu Ala Asp Val Asn Ser Asn Ala Ala Ala Phe Leu Lys
1               5                   10                  15

<210> SEQ ID NO 125
<211> LENGTH: 15
<212> TYPE: PRT
<213> ORGANISM: Human papillomavirus type 58

<400> SEQUENCE: 125

Ala Gln Leu Ala Asp Val Asn Ser Asn Ala Ala Ala Phe Leu Arg
1               5                   10                  15

<210> SEQ ID NO 126
<211> LENGTH: 15
<212> TYPE: PRT
<213> ORGANISM: Human papillomavirus type 18

<400> SEQUENCE: 126

Ala Leu Leu Ala Asp Ser Asn Ser Asn Ala Ala Ala Phe Leu Lys
1               5                   10                  15

<210> SEQ ID NO 127
<211> LENGTH: 15
<212> TYPE: PRT
<213> ORGANISM: Human papillomavirus type 16

<400> SEQUENCE: 127

Ala Gln Leu Ala Asp Thr Asn Ser Asn Ala Ser Ala Phe Leu Lys
1               5                   10                  15

<210> SEQ ID NO 128
<211> LENGTH: 20
<212> TYPE: PRT
<213> ORGANISM: Artificial Sequence
<220> FEATURE:
<223> OTHER INFORMATION: consensus sequence

<400> SEQUENCE: 128

Asn Cys Leu Val Leu Cys Gly Pro Ala Asn Thr Gly Lys Ser Tyr Phe
1               5                   10                  15

Gly Met Ser Leu

<210> SEQ ID NO 129
<211> LENGTH: 20
<212> TYPE: PRT
<213> ORGANISM: Human papillomavirus type 18

<400> SEQUENCE: 129

Asn Cys Leu Val Phe Cys Gly Pro Ala Asn Thr Gly Lys Ser Tyr Phe
1               5                   10                  15

Gly Met Ser Phe
            20

<210> SEQ ID NO 130
<211> LENGTH: 20
<212> TYPE: PRT
<213> ORGANISM: Human papillomavirus type 52

<400> SEQUENCE: 130

Asn Cys Leu Val Leu Tyr Gly Pro Ala Asn Thr Gly Lys Ser Tyr Phe
1               5                   10                  15

Gly Met Ser Leu
            20

<210> SEQ ID NO 131
<211> LENGTH: 20
<212> TYPE: PRT
<213> ORGANISM: Human papillomavirus type 58

<400> SEQUENCE: 131

Ser Cys Met Leu Leu Cys Gly Pro Ala Asn Thr Gly Lys Ser Tyr Phe
1               5                   10                  15

Gly Met Ser Leu
            20

<210> SEQ ID NO 132
<211> LENGTH: 20
<212> TYPE: PRT
<213> ORGANISM: Human papillomavirus type 53

<400> SEQUENCE: 132

Asn Cys Leu Val Ile Tyr Gly Pro Pro Asn Thr Gly Lys Ser Cys Phe
1               5                   10                  15

Ala Met Ser Leu
            20

<210> SEQ ID NO 133
<211> LENGTH: 16
<212> TYPE: PRT
<213> ORGANISM: Artificial Sequence
<220> FEATURE:
<223> OTHER INFORMATION: consensus sequence

<400> SEQUENCE: 133

Trp Pro Tyr Leu Glu Ser Arg Thr Val Phe Glu Phe Pro Asn Ala Phe
1               5                   10                  15

<210> SEQ ID NO 134
<211> LENGTH: 17
<212> TYPE: PRT
<213> ORGANISM: Human papillomavirus type 18

<400> SEQUENCE: 134

```
Trp Pro Tyr Leu Glu Ser Arg Ile Thr Val Phe Glu Phe Pro Asn Ala
1               5                   10                  15

Phe

<210> SEQ ID NO 135
<211> LENGTH: 17
<212> TYPE: PRT
<213> ORGANISM: Human papillomavirus type 58

<400> SEQUENCE: 135

Trp Pro Tyr Leu His Ser Arg Leu Thr Val Phe Glu Phe Asn Asn Pro
1               5                   10                  15

Phe

<210> SEQ ID NO 136
<211> LENGTH: 17
<212> TYPE: PRT
<213> ORGANISM: Human papillomavirus type 53

<400> SEQUENCE: 136

Leu Arg Tyr Leu His Ser Arg Ile His Val Leu Gln Phe Leu Asn Pro
1               5                   10                  15

Phe

<210> SEQ ID NO 137
<211> LENGTH: 20
<212> TYPE: PRT
<213> ORGANISM: Artificial Sequence
<220> FEATURE:
<223> OTHER INFORMATION: consensus sequence

<400> SEQUENCE: 137

Asp His Ile Asp Tyr Trp Lys His Met Arg Leu Glu Cys Ala Ile Tyr
1               5                   10                  15

Tyr Lys Ala Arg
            20

<210> SEQ ID NO 138
<211> LENGTH: 20
<212> TYPE: PRT
<213> ORGANISM: Human papillomavirus type 16

<400> SEQUENCE: 138

Asp His Ile Asp Tyr Trp Lys His Met Arg Leu Glu Cys Ala Ile Tyr
1               5                   10                  15

Tyr Lys Ala Arg
            20

<210> SEQ ID NO 139
<211> LENGTH: 20
<212> TYPE: PRT
<213> ORGANISM: Human papillomavirus type 18

<400> SEQUENCE: 139

Ser Gln Ile Gln Tyr Trp Gln Leu Ile Arg Trp Glu Asn Ala Ile Phe
1               5                   10                  15

Phe Ala Ala Arg
            20

<210> SEQ ID NO 140
<211> LENGTH: 20
<212> TYPE: PRT
```

<213> ORGANISM: Human papillomavirus type 31

<400> SEQUENCE: 140

Asp His Ile Asp Tyr Trp Lys His Ile Arg Leu Glu Cys Val Leu Met
1               5                   10                  15

Tyr Lys Ala Arg
            20

<210> SEQ ID NO 141
<211> LENGTH: 20
<212> TYPE: PRT
<213> ORGANISM: Human papillomavirus type 52

<400> SEQUENCE: 141

Ala Gln Ile Glu His Trp Lys Leu Thr Arg Met Glu Cys Val Leu Phe
1               5                   10                  15

Tyr Lys Ala Lys
            20

<210> SEQ ID NO 142
<211> LENGTH: 20
<212> TYPE: PRT
<213> ORGANISM: Human papillomavirus type 53

<400> SEQUENCE: 142

Asp His Ile Asp Tyr Trp Lys Ala Val Arg Gln Glu Asn Val Ile Tyr
1               5                   10                  15

Tyr Lys Ala Arg
            20

<210> SEQ ID NO 143
<211> LENGTH: 20
<212> TYPE: PRT
<213> ORGANISM: Human papillomavirus type 58

<400> SEQUENCE: 143

Ser Gln Ile Glu His Trp Lys Leu Ile Arg Met Glu Cys Ala Ile Met
1               5                   10                  15

Tyr Thr Ala Arg
            20

<210> SEQ ID NO 144
<211> LENGTH: 20
<212> TYPE: PRT
<213> ORGANISM: Artificial Sequence
<220> FEATURE:
<223> OTHER INFORMATION: consensus sequence

<400> SEQUENCE: 144

Asp His Ile Asp Tyr Trp Lys Leu Ile Arg Leu Glu Cys Ala Ile Phe
1               5                   10                  15

Tyr Lys Ala Arg
            20

<210> SEQ ID NO 145
<211> LENGTH: 15
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (1)..(3)
<223> OTHER INFORMATION: Xaa can be any naturally occurring amino acid

```
<400> SEQUENCE: 145

Xaa Xaa Xaa Pro Ile Pro Pro Pro Cys Pro Trp Ala Pro Lys Lys
1               5                   10                  15

<210> SEQ ID NO 146
<211> LENGTH: 16
<212> TYPE: PRT
<213> ORGANISM: Human papillomavirus type 16

<400> SEQUENCE: 146

Thr Pro Pro Arg Pro Ile Pro Lys Pro Ser Pro Trp Ala Pro Lys Lys
1               5                   10                  15

<210> SEQ ID NO 147
<211> LENGTH: 16
<212> TYPE: PRT
<213> ORGANISM: Human papillomavirus type 18

<400> SEQUENCE: 147

Thr Pro Pro His Arg Ile Pro Ala Pro Cys Pro Trp Ala Pro Gln Arg
1               5                   10                  15

<210> SEQ ID NO 148
<211> LENGTH: 16
<212> TYPE: PRT
<213> ORGANISM: Human papillomavirus type 31

<400> SEQUENCE: 148

Thr Pro Pro His Arg Ile Pro Lys Pro Ala Pro Trp Ala Pro Val Lys
1               5                   10                  15

<210> SEQ ID NO 149
<211> LENGTH: 12
<212> TYPE: PRT
<213> ORGANISM: Human papillomavirus type 52

<400> SEQUENCE: 149

Pro Arg Pro Pro His Cys Pro Trp Val Pro Lys Thr
1               5                   10

<210> SEQ ID NO 150
<211> LENGTH: 12
<212> TYPE: PRT
<213> ORGANISM: Human papillomavirus type 53

<400> SEQUENCE: 150

Pro Pro Pro Pro Pro Arg Pro Trp Ala Pro Thr Lys
1               5                   10

<210> SEQ ID NO 151
<211> LENGTH: 5
<212> TYPE: PRT
<213> ORGANISM: Human papillomavirus type 58

<400> SEQUENCE: 151

Pro Pro Thr Thr Lys
1               5

<210> SEQ ID NO 152
<211> LENGTH: 10
<212> TYPE: PRT
<213> ORGANISM: Artificial Sequence
<220> FEATURE:
<223> OTHER INFORMATION: consensus sequence
```

<400> SEQUENCE: 152

Pro Ile Pro Lys Pro Ser Pro Trp Ala Pro
1               5                   10

<210> SEQ ID NO 153
<211> LENGTH: 10
<212> TYPE: PRT
<213> ORGANISM: Human papillomavirus type 16

<400> SEQUENCE: 153

Pro Ile Pro Lys Pro Ser Pro Trp Ala Pro
1               5                   10

<210> SEQ ID NO 154
<211> LENGTH: 10
<212> TYPE: PRT
<213> ORGANISM: Human papillomavirus type 31

<400> SEQUENCE: 154

Arg Ile Pro Lys Pro Ala Pro Trp Ala Pro
1               5                   10

<210> SEQ ID NO 155
<211> LENGTH: 10
<212> TYPE: PRT
<213> ORGANISM: Human papillomavirus type 18

<400> SEQUENCE: 155

Arg Ile Pro Ala Pro Cys Pro Trp Ala Pro
1               5                   10

<210> SEQ ID NO 156
<211> LENGTH: 10
<212> TYPE: PRT
<213> ORGANISM: Human papillomavirus type 52

<400> SEQUENCE: 156

Pro Arg Pro Pro His Cys Pro Trp Val Pro
1               5                   10

<210> SEQ ID NO 157
<211> LENGTH: 10
<212> TYPE: PRT
<213> ORGANISM: Human papillomavirus type 53

<400> SEQUENCE: 157

Pro Pro Pro Pro Pro Arg Pro Trp Ala Pro
1               5                   10

<210> SEQ ID NO 158
<211> LENGTH: 9713
<212> TYPE: DNA
<213> ORGANISM: Artificial Sequence
<220> FEATURE:
<223> OTHER INFORMATION: Plasmid construct

<400> SEQUENCE: 158
agcgcccaat acgcaaaccg cctctccccg cgcgttggcc gattcattaa tgcagctggc    60
acgacaggtt tcccgactgg aaagcgggca gtgagcgcaa cgcaattaat gtgagttagc   120
tcactcatta ggcaccccag gctttacact ttatgcttcc ggctcgtatg ttgtgtggaa   180
ttgtgagcgg ataacaattt cacacaggaa acagctatga ccatgattac gccaagcttg   240

-continued

| | | | |
|---|---|---|---|
| catgcatctg gaaacgggca tctccattta agactagatg ccacggggtt taaaatacta | 300 | | |
| atcatgacat tttgtagagc gtaattactt agtaaatccg ccgtactagg ttcatttcct | 360 | | |
| cctcgtttgg atctcacatc agaaattaaa ataatcttag aaggatgcag ttgttttttg | 420 | | |
| atggatcgta gatattcctc atcaacgaac cgagtcacta gagtcacatc acgcaatcca | 480 | | |
| tttaaaatag gatcatgatg gcggccgtca attagcatcc atttgatgat cactcctaaa | 540 | | |
| ttatagaaat gatctctcaa ataacgtata tgtgtaccgg gagcagatcc tatatacact | 600 | | |
| acggtggcac catctaatat accgtgtcgc tgtaacttac taagaaaaaa taattctcct | 660 | | |
| agtaatagtt ttaactgtcc ttgataccgt agtttttttg cgacctcatt tgcactttct | 720 | | |
| ggttcgtaat ctaactcatt atcaatttcc tcaaaataca taaacggttt atctaacgac | 780 | | |
| acaacatcca tttttaagta ttatattaaa atttaatcaa tgtttatttt tagtttttta | 840 | | |
| gataaaaaat ataatattat gagtcgatgt aacactttct acacaccgat tgatacatat | 900 | | |
| cattacctcc tattatctct atctcggttt cctcacccaa tcgtttagaa aaggaagcct | 960 | | |
| ccttaaagca tttcatacac acagcagtta gttttaccac catttcagat aatggaataa | 1020 | | |
| gattcaaaat attattaaac ggtttacgtt gaaatgtccc atcgagtgcg gctactataa | 1080 | | |
| ctattttttcc ttcgtttgcc atacagatcc tacgtactcg agcggccgct tatcaggtcc | 1140 | | |
| gggtggagtc caggcccagc agtggattgg ggataggctt gccagaggcg ccaggtccag | 1200 | | |
| agccggcgat tctggcctcg cacttgcagc acatacacag catggtgtgt ctctgaggct | 1260 | | |
| cggcccttct agcgggcaga tgctggtggt tcacgccgtc gatctcgtcg ttctcttcca | 1320 | | |
| ccagagattc gcatctgcag cactgtgtct cgatcagata gcaagggtgc tgttcgtccc | 1380 | | |
| gtctagcctg ctggggctgt tcctgcagat ggtccacttc gtcctcatcc tcgtcccat | 1440 | | |
| ccaggccgcc agtgtcctct tcatcggagc tgtctcccag ctgctcataa cagtgcagat | 1500 | | |
| cagtggtttc aggctgctcg tagcagtaca ggtcggttgt ctcgggctgc agatccagca | 1560 | | |
| tgtactcgtg cagggtgtgg aaccgcttgt tcaggtccac gtgtcttttc ttttcctgcg | 1620 | | |
| gacacagtgg ccgctggcag tcgtacacct cagatctctg cagggttttc ttgcattcca | 1680 | | |
| cgcacagtgt ggtgccatac acggaatatc tgtaccaccg gaactcggac accttggagt | 1740 | | |
| cgcgatacac gattgtcagg tctgtgaagg cgaaatccag cacctctgtc tcggtcagct | 1800 | | |
| gtcccttgca ataccaggg ctggcgccat acacagagca gttgtagtac ctcagcttcc | 1860 | | |
| gcactttgct gtcccgatac accacccgca gatcggtgta ggcgaagttg tacacctcgc | 1920 | | |
| tggctgtcag ggccttcttg cagaacaccc gcaggcatct aatcagcagg ttgtacaggc | 1980 | | |
| cagtgttggt cagcttttcc agggtatcgc cgtacacgga gtcgctgtag tgccgcagct | 2040 | | |
| ctctgattct ggagtagaag tcgatacact tgtggcaggc ggcgtggggg atggagtctc | 2100 | | |
| tgtacaccac gttgatgcac cgaatcagca gatcgcacag gggcttgttg tactgctgtt | 2160 | | |
| ccagggtggt gccgtacagg ctgtagcagt agtgccggta ctcgctgatc ttgctgtaga | 2220 | | |
| acttcaggca cttgtcgcac acggcgtaag gattgccatc ccggtacacg atggcggtgg | 2280 | | |
| cggggctggt aatcacgacg atgtacacga acaccagcac ccaggcatag gcacacatgc | 2340 | | |
| acacgctggg cagcaggctt ccgatggaca cccacagcag cagcaccagc accagcacct | 2400 | | |
| gagcgtacac gctgatagac agcagcagag gcctcaggta ggtggacaca ctcagcagca | 2460 | | |
| ggggtctgat cagcaggcac acgcacagca gcacacaaaa gcacagcagg aagcaagggg | 2520 | | |
| cccaaggtct tggaggaggt ggaggggca cccatggaca gtgtggaggt ctaggaggtg | 2580 | | |
| cccaggggca aggggcaggg attctagggg cccatggaga aggcttaggg atgggggcc | 2640 | | |

-continued

```
tctgaggagc ccaaggacat ggagcaggga tccggtgagg gggggtgctg tagctgttca      2700
gcagtgacag cagtgggtat ctggtggtca ggtgcagcct gatcacgact gtgctcttgg      2760
gggtggtcac tctcagttcc accagggagg tattctcggg ggtggtggtc tgggtggtca      2820
gcagtttcag cagaggatat gttggatcca gaggcacggg cacagggtg  ggcacgatga      2880 acaccttgtt ctcccagatg cacttgccgt gggccttcac gcccatgttg ggggtctgg       2940 acagcagctt cagcagggg  tacttggtca cgagctgaga ctgatcctgg tcgctggaca      3000
gccgccgtct ggccttgtaa aaaatggcac attccaggcg aatcagcttc caatagtcga      3060
tatggtcctt cacgagctcg gtggcggaca cgttgtcgtc gaaggtgctg cacatggagt      3120
cgttgcagtc gatgctgttg ccgaaatgca cttcccaggt gcccttgcag ccgtacttct      3180
cggcctcggt cttgcaccag ccatcgtcgc cgcagtagta cacgctgtcc caggccacgt      3240
agtcgaacca cacttcgatg tgctggccgc ccttcttgaa gcagtgcttg ggctcggtgt      3300
tccactcgat ggctttacag gccttggcct tgcagatatt cagggcgggc accacctggt      3360
gtctggcggc gaagaagatg gcgttttcct gcctgatggc tttccaataa tcaatgtggt      3420
cggcttcctc ggtgctgatc tcatcggagg ggatgctggc ggggcacacg atcacgtaga      3480
tttctttcca atttgtgtaa tccatggtat tggccttgtc attgtcgtac tgcacggtga      3540
tggtgatgcc gtgcttctta aactggggct cggccagcca catttccagg ctggtctgct      3600
gcagggtcca ctcatcgtag gggctggcat tcagggcttc cagggccagc tgcagttcga      3660
tggcctggca ggctttggct ttagaggcgg ccagtggagg caccacctgg tggcagatgc      3720
tgatgcccag ctctttggcc ttatagaaga ttgcacattc catccggatc agtttccagt      3780
gctcgatctg ggcgttcagg tcgttcttgt cggcctcgta gtaggtcagg gtcacaatgg      3840
cgttcttgtg tttcccatcg tgacatgtcc aatgccactt gtgcttgccg tcgtggcagg      3900
tccagtgcca ggtgctgctc agcttgcagt gcttcttgaa tctgtaccgc aggcacttca      3960
ggatcagcag cttgttgggg tggcagttct cgcttctggg cctcttgatc cgccgctggc      4020
cgctctcagg acacaggatc acttggccgc cagcgtgcac ctcccatttc ttgtccacct      4080
ggccttccac cacggtgcac tgggcgtcct cgcagatata gatccagttg gtgtagtgca      4140
tggtgttgca gatgtcgccg tcgaactggt ggaagcccat ctcgcgagcc ttatacataa      4200
tagcacattc cagtctgatc cgggccttgt acatgatggc gcattccagc cggatgtgct      4260
tccagtagtc gatgtgatcg cagatgtggt cgcacaggtc cttggaatca ttctcataat      4320
gttccagaat gtccttgctg tcgttctcgt agtgttccag gatcttgtcc tggcacacgt      4380 tgaagggggtt cagaaactgc agcacgtgga tccgggagtg caggtatctc agaaaggcat      4440
tggggaactc gaacacggtg atccggcttt ccaggtaagg ccagaagggg ttggggaagg      4500
taaacaccac cagtctgctg tgcaggtagg gccacagaga catggcaaag caggacttgc      4560
ctgtgttagg tgggccgtag atcacgagac aattcaggga catgccgaag taggactttc      4620
cggtattggc tgggccgcac agcaccaggc agttcaggct catgccgaac aggctcttgc      4680
cggtgttggc agcgccgtac agcaggatgc agttcttcag aaaagcagcg gcgttgctgt      4740
tcacgtctgc cagctgagcc ttcaggaagg cgcaggcatt gctgtcgctg tcagccagct      4800
gggcggagtt gtcgataaag ccgtccaggt cgctctcggt gctctcttcg tcggtttcgt      4860
cgttgtcgat gaaatccacc atgtcctcgc cggtgtcgga gtcgttctca ttctcgtcgc      4920
tgtcgtcgat gaagtcgatc aggtcggtgc cgctgtcgta ggctgtctcg tcctcgtcgg      4980
```

```
ccagcttgct gcctcttctg aaccgggcgt ggatttcctg gctgggggac acaaacacgg    5040
cgccacacag cagcagcacg cagcacaggc ccctcttcat agcatccatg gtggcggcgc    5100
ggctagcggt accggatcta gatggggatc cgtcactgtt ctttatgatt ctacttcctt    5160
accgtgcaat aaattagaat atattttcta cttttacgag aaattaatta ttgtatttat    5220
tatttatggg tgaaaaactt actataaaaa gcgggtgggt ttggaattag tgatcagttt    5280
atgtatatcg caactaccgg gcatatggct atcgacatcg agaacattac ccacatgata    5340
agagattgta tcagtttcgt agtcttgagt attggtatta ctatatagta tatagatgtc    5400
gacctgcagg tcgacgaagt tcctatactt tctagagaat aggaacttcg cagccaagct    5460
ggaattcatc cactttggat aagaaatctg catgataaat atattgatat cctaccacct    5520
attaaagtac cattatctaa tagcaataag atagataaac aaatgttttt tgatgaagtt    5580
attacgtgga taaatatata tcttcaggaa aagggtatta tgttaccaga tgatataaga    5640
gaactcagag atgctattat tccttaacta gttacgtctc tttaggtact tattttgata    5700
cgttacaagt aaaaaactat caaatataaa tggaatctga ttctaatata gcgattgaag    5760
aggatccacc ggtcgccacc atggtgagca agggcgagga gctgttcacc ggggtggtgc    5820
ccatcctggt cgagctggac ggcgacgtaa acggccacaa gttcagcgtg tccggcgagg    5880
gcgagggcga tgccacctac ggcaagctga ccctgaagtt catctgcacc accggcaagc    5940
tgcccgtgcc ctggcccacc ctcgtgacca ccctgaccta cggcgtgcag tgcttcagcc    6000
gctaccccga ccacatgaag cagcacgact tcttcaagtc cgccatgccc gaaggctacg    6060
tccaggagcg caccatcttc ttcaaggacg acggcaacta caagacccgc gccgaggtga    6120
agttcgaggg cgacaccctg gtgaaccgca tcgagctgaa gggcatcgac ttcaaggagg    6180
acggcaacat cctggggcac aagctggagt acaactacaa cagccacaac gtctatatca    6240
tggccgacaa gcagaagaac ggcatcaagg tgaacttcaa gatccgccac aacatcgagg    6300
acggcagcgt gcagctcgcc gaccactacc agcagaacac ccccatcggc gacggccccg    6360
tgctgctgcc cgacaaccac tacctgagca cccagtccgc cctgagcaaa gaccccaacg    6420
agaagcgcga tcacatggtc ctgctggagt tcgtgaccgc cgccgggatc actctcggca    6480
tggacgagct gtacaagtaa agcggccgcg aagttcctat actttctaga aataggaac    6540 ttcaacaatg tctggaaaga actgtccttc atcgatacct atcacggaga aatctgtaat    6600
tgattccaag acatcacata gtttagttgc ttccaatgct tcaaaattat tcttatcatg    6660
cgtccatagt cccgttccgt atctattatc gttagaatat tttatagtca cgcatttata    6720
ttgagctatt tgataacgtc taactcgtct aattaattct gtactttac ctgaaaacat    6780 ggggccgatt atcaactgaa tatgtccgcc gttcatgatg acaataaaga attaattatt    6840 gttcactttta ttcgactta atatatccat cacgttagaa aatgcgatat cgcgacgagg    6900
atctatgtat ctaacaggat ctattgcggt ggtagctaga gctgattctt tttttgaatcg    6960 catcaaacta atcacaaagt cgaacaaata tcctttatta agtttgaccc ttccatctgt    7020
aacaataggg accttgttaa acagtttttt aaaatcttga gagtctgtga attttgtcaa    7080
ttgtctgtat tcctctgaaa gagattcata acaatgaccc acggcttcta atttattttt    7140
tgattggatc aataataata acagaaagtc tagatattga gtgatttgca atatatcaga    7200
taatgaagat tcatcatctt gactagccaa atacttaaaa aatgaatcat catctgcgaa    7260
gaacatcgtt aagagatact ggttgtgatc catttatgag ctcgcgaaag cttggcactg    7320
gccgtcgttt tacaacgtcg tgactgggaa aaccctggcg ttacccaact taatcgcctt    7380
```

```
gcagcacatc cccctttcgc cagctggcgt aatagcgaag aggcccgcac cgatcgccct   7440
tcccaacagt tgcgcagcct gaatggcgaa tggcgcctga tgcggtattt tctccttacg   7500
catctgtgcg gtatttcaca ccgcatatgg tgcactctca gtacaatctg ctctgatgcc   7560
gcatagttaa gccagccccg acacccgcca cacccgctg acgcgccctg acgggcttgt    7620
ctgctcccgg catccgctta cagacaagct gtgaccgtct ccgggagctg catgtgtcag   7680
aggttttcac cgtcatcacc gaaacgcgcg agacgaaagg gcctcgtgat acgcctattt   7740
ttataggtta atgtcatgat aataatggtt tcttagacgt caggtggcac ttttcgggga   7800
aatgtgcgcg gaacccctat ttgtttattt ttctaaatac attcaaatat gtatccgctc   7860
atgagacaat aaccctgata aatgcttcaa taatattgaa aaaggaagag tatgagtatt   7920
caacatttcc gtgtcgccct tattccctt tttgcggcat tttgccttcc tgttttgct     7980
cacccagaaa cgctggtgaa agtaaaagat gctgaagatc agttgggtgc acgagtgggt   8040
tacatcgaac tggatctcaa cagcggtaag atccttgaga gttttcgccc cgaagaacgt   8100
tttccaatga tgagcacttt taaagttctg ctatgtggcg cggtattatc ccgtattgac   8160
gccgggcaag agcaactcgg tcgccgcata cactattctc agaatgactt ggttgagtac   8220
tcaccagtca cagaaaagca tcttacggat ggcatgacag taagagaatt atgcagtgct   8280
gccataacca tgagtgataa cactgcggcc aacttacttc tgacaacgat cggaggaccg   8340
aaggagctaa ccgcttttt gcacaacatg ggggatcatg taactcgcct tgatcgttgg    8400
gaaccggagc tgaatgaagc cataccaaac gacgagcgtg acaccacgat gcctgtagca   8460
atggcaacaa cgttgcgcaa actattaact ggcgaactac ttactctagc ttcccggcaa   8520
caattaatag actggatgga ggcggataaa gttgcaggac cacttctgcg ctcggccctt   8580
ccggctggct ggtttattgc tgataaatct ggagccggtg agcgtgggtc tcgcggtatc   8640
attgcagcac tggggccaga tggtaagccc tcccgtatcg tagttatcta cacgacgggg   8700
agtcaggcaa ctatggatga acgaaataga cagatcgctg agataggtgc ctcactgatt   8760
aagcattggt aactgtcaga ccaagtttac tcatatatac tttagattga tttaaaactt   8820
catttttaat ttaaaaggat ctaggtgaag atcctttttg ataatctcat gaccaaaatc   8880
ccttaacgtg agttttcgtt ccactgagcg tcagaccccg tagaaaagat caaaggatct   8940
tcttgagatc ctttttttct gcgcgtaatc tgctgcttgc aaacaaaaaa accaccgcta   9000
ccagcggtgg tttgtttgcc ggatcaagag ctaccaactc ttttccgaa ggtaactggc     9060
ttcagcagag cgcagatacc aaatactgtt cttctagtgt agccgtagtt aggccaccac   9120
ttcaagaact ctgtagcacc gcctacatac ctcgctctgc taatcctgtt accagtggct   9180
gctgccagtg gcgataagtc gtgtcttacc gggttggact caagacgata gttaccggat   9240
aaggcgcagc ggtcgggctg aacggggggt tcgtgcacac agcccagctt ggagcgaacg   9300
acctacaccg aactgagata cctacagcgt gagctatgag aaagcgccac gcttcccgaa   9360
gggagaaagg cggacaggta tccggtaagc ggcagggtcg aacaggaga gcgcacgagg    9420
gagcttccag ggggaaacgc ctggtatctt tatagtcctg tcgggtttcg ccacctctga   9480
cttgagcgtc gatttttgtg atgctcgtca gggggggcgga gcctatggaa aaacgccagc   9540
aacgcggcct ttttacggtt cctggccttt tgctggcctt tgctcacat gttctttcct     9600
gcgttatccc ctgattctgt ggataaccgt attaccgcct ttgagtgagc tgataccgct   9660
cgccgcagcc gaacgaccga gcgcagcgag tcagtgagcg aggaagcgga aga           9713
```

<210> SEQ ID NO 159
<211> LENGTH: 10405
<212> TYPE: DNA
<213> ORGANISM: Artificial Sequence
<220> FEATURE:
<223> OTHER INFORMATION: Plasmid construct

<400> SEQUENCE: 159

```
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagctat     240
ttaggtgaca ctatagaata ctcaagctat gcatcaagct tggtaccgag ctcggatcca     300
ctagtaacgg ccgccagtgt gctggaattc gcccttgtaa tctattcgat ataccgttgc     360
taacagtata ctggcccaat aactgtggat ggaaaatcta ataatacatt aatatcat     420
ccgatggtgc tagggttatt tggatggatg cgtataaatt ttcttgcggt ttatctttac     480
aagactattg ttatcattgg ggtagcaaac cagagagccg accattcgat ttaataaaaa     540
aatcagatgc taaacgcaat tctaaatcgt tggtcaaaga atctatggca tccttgaaat     600
ccttgtacga ggcattcgag acacaatcag gagcgttaga agttttaatg agtccatgta     660
ggatgttttc gttttctaga atagaagaca tgttcttaac tagtgtcatt aatagagtat     720
ccgagaatac tggaatgggg atgtattatc ctaccaacga tatccttct ctatttatcg     780
aatcatctat ctgtctagat tatattatag taaataatca ggaatccaac aaatatcgta     840
tcaaatctgt tctcgatatc atttcttcaa acaatacccc tgcaggacgt cccaactacg     900
ttaaaaatgg tacaaaagga aagttatata tcgcgttgtg taaagttacc gtacctacta     960
acgaccatat tccagtagtt tatcacgatg atgacaatac taccacctt attacagtat    1020
tgacgtccgt cgatattgaa actgctatca gagcaggata ttcgatagtc gaattagggg    1080
ctttacaatg gataataat attccagaac ttaaaaacgg tttactggat agtatcaaga    1140
tgatttatga cttgaacgca gttacaacaa ataatttatt ggaacagctc atagaaaata    1200
ttaactttaa caactctagt ataatttcgt tgttttatac atttgccatt agttattgcc    1260
gagcattcat ttactcaatt atggaaacca tagatccggt gtatatatct cagttcagtt    1320
ataaagaatt atacgttagt agctcttata aagatattaa tgaatccatg agtcagatgg    1380
taaaattata aaaagtgaaa aacaatatta ttttttatcgt tggttgttac actatggatg    1440
ctatgaagag gggcctgtgc tgcgtgctgc tgctgtgtgg cgccgtgttt gtgtccccca    1500
gccaggaaat ccacgcccgg ttcagaagag gcagcaagct ggccgacgag gacgagacag    1560
cctacgacag cggcaccgac ctgatcgact tcatcgacga cagcgacgag aatgagaacg    1620
actccgacac cggcgaggac atggtggatt tcatcgacaa cgacgaaacc gacgaagaga    1680
gcaccgagag cgacctggac ggctttatcg acaactccgc ccagctggct gacagcgaca    1740
gcaatgcctg cgccttcctg aaggctcagc tggcagacgt gaacagcaac gccgctgctt    1800
ttctgaagaa ctgcatcctg ctgtacgcg ctgccaacac cggcaagagc ctgttcggca    1860
tgagcctgaa ctgcctggtg ctgtgcggcc cagccaatac cggaaagtcc tacttcggca    1920
tgtccctgaa ttgtctcgtg atctacggcc cacctaacac aggcaagtcc tgctttgcca    1980
tgtctctgtg gcccctacctg cacagcagac tggtggtgtt taccttcccc aacccccttct    2040
ggccttacct ggaaagccgg atcaccgtgt tcgagttccc caatgccttt ctgagatacc    2100
```

```
tgcactcccg gatccacgtg ctgcagtttc tgaaccccttt caacgtgtgc caggacaaga    2160
tcctggaaca ctacgagaac gacagcaagg acattctgga acattatgag aatgattcca    2220
aggacctgtg cgaccacatc tgcgatcaca tcgactactg aagcacatc cggctggaat     2280 gcgccatcat gtacaaggcc cggatcagac tggaatgtgc tattatgtat aaggctcgcg    2340
agatgggctt ccaccagttc gacggcgaca tctgcaacac catgcactac accaactgga    2400
tctatatctg cgaggacgcc cagtgcaccg tggtggaagg ccaggtggac aagaaatggg    2460
aggtgcacgc tggcggccaa gtgatcctgt gtcctgagag cggccagcgg cggatcaaga    2520
ggcccagaag cgagaactgc caccccaaca agctgctgat cctgaagtgc ctgcggtaca    2580
gattcaagaa gcactgcaag ctgagcagca cctggcactg gacctgccac gacggcaagc    2640
acaagtggca ttggacatgt cacgatggga acacaagaa cgccattgtg accctgacct     2700
actacgaggc cgacaagaac gacctgaacg cccagatcga gcactggaaa ctgatccgga    2760
tggaatgtgc aatcttctat aaggccaaag agctgggcat cagcatcgc caccaggtgg     2820 tgcctccact ggccgcctct aaagccaaag cctgccaggc catcgaactg cagctggccc    2880
tggaagccct gaatgccagc ccctacgatg agtggaccct gcagcagacc agcctggaaa    2940
tgtggctggc cgagccccag tttaagaagc acggcatcac catcaccgtg cagtacgaca    3000
atgacaaggc caataccatg gattacacaa attggaaaga atctacgtg atcgtgtgcc      3060 ccgccagcat ccctccgat gagatcagca ccgaggaagc cgaccacatt gattattgga       3120
aagccatcag gcaggaaaac gccatcttct tcgccgccag acaccaggtg gtgcccgccc    3180
tgaatatctg caaggccaag gcctgtaaag ccatcgagtg gaacaccgag cccaagcact    3240
gcttcaagaa gggcggccag cacatcgaag tgtggttcga ctacgtggcc tgggacagcg    3300
tgtactactg cggcgacgat ggctggtgca agaccgaggc cgagaagtac ggctgcaagg    3360
gcacctggga agtgcatttc ggcaacagca tcgactgcaa cgactccatg tgcagcacct    3420
tcgacgacaa cgtgtccgcc accgagctcg tgaaggacca tatcgactat ggaagctga    3480 ttcgcctgga atgtgccatt ttttacaagg ccagacggcg ctgtccagc gaccaggatc      3540 agtctcagct cgtgaccaag tacccctgc tgaagctgct gtccagaccc ccaacatgg      3600 gcgtgaaggc ccacggcaag tgcatctggg agaacaaggt gttcatcgtg cccaccctgt    3660
gccccgtgcc tctggatcca acatatcctc tgctgaaact gctgaccacc agaccacca    3720 ccccgagaa tacctccctg gtggaactga gagtgaccac cccaagagc acagtcgtga     3780 tcaggctgca cctgaccacc agatacccac tgctgtcact gctgaacagc tacagcaccc    3840
cccctcaccg gatccctgct ccatgtcctt gggctcctca gaggccccc atccctaagc      3900 cttctccatg ggcccctaga atccctgccc cttgcccctg gcacctcct agacctccac       3960 actgtccatg ggtgccccct ccacctcctc caagaccttg ggccccttgc ttcctgctgt    4020
gcttttgtgt gctgctgtgc gtgtgcctgc tgatcagacc cctgctgctg agtgtgtcca    4080
cctacctgag gcctctgctg ctgtctatca gcgtgtacgc tcaggtgctg gtgctggtgc    4140
tgctgctgtg ggtgtccatc ggaagcctgc tgcccagcgt gtgcatgtgt gcctatgcct    4200
gggtgctggt gttcgtgtac atcgtcgtga ttaccagccc cgccaccgcc atcgtgtacc    4260
gggatggcaa tccttacgcc gtgtgcgaca gtgcctgaa gttctacagc aagatcagcg      4320
agtaccggca ctactgctac agcctgtacg gcaccacct ggaacagcag tacaacaagc      4380
ccctgtgcga tctgctgatt cggtgcatca acgtggtgta cagagactcc atccccacg      4440
```

```
ccgcctgcca caagtgtatc gacttctact ccagaatcag agagctgcgg cactacagcg    4500
actccgtgta cggcgatacc ctggaaaagc tgaccaacac tggcctgtac aacctgctga    4560
ttagatgcct gcgggtgttc tgcaagaagg ccctgacagc cagcgaggtg tacaacttcg    4620
cctacaccga tctgcgggtg gtgtatcggg acagcaaagt gcggaagctg aggtactaca    4680
actgctctgt gtatggcgcc agcctggtgt attgcaaggg acagctgacc gagacagagg    4740
tgctggattt cgccttcaca gacctgacaa tcgtgtatcg cgactccaag gtgtccgagt    4800
tccggtggta cagatattcc gtgtatggca ccacactgtg cgtggaatgc aagaaaaccc    4860
tgcagagatc tgaggtgtac gactgccagc ggccactgtg tccgcaggaa aagaaaagac    4920
acgtggacct gaacaagcgg ttccacaccc tgcacgagta catgctggat ctgcagcccg    4980
agacaaccga cctgtactgc tacgagcagc tgaaaccac tgatctgcac tgttatgagc    5040
agctgggaga cagctccgat gaagaggaca ctggcggcct ggatggggac gaggatgagg    5100
acgaagtgga ccatctgcag gaacagcccc agcaggctag acgggacgaa cagcacccctt    5160
gctatctgat cgagacacag tgctgcagat gcgaatctct ggtggaagag aacgacgaga    5220
tcgacggcgt gaaccaccag catctgcccg ctagaagggc cgagcctcag agacacacca    5280
tgctgtgtat gtgctgcaag tgcgaggcca gaatcgccgg ctaattttta taaccgagtt    5340
tctgcattat tgtaattcgt atgctggcac catcaaagaa tcacttctaa agatatcaa    5400
tatcacacat acaaatatta ctaccctatt gaatgagaca gccaaggtta tcaagttagt    5460
aaaatctctg gtagataaag aagatactga tattgtgaat aatttcatta ccaaagaaat    5520
taaaaacaga gacaaaatag ttaatagttt gtctctatca aacctggact ttcgtttgta    5580
aattggggct ttttgtacaa taaatgggtg ttgccaatga ttcatcccct gaatatcaat    5640
ggatgtctcc ccatagatta tcagatactg ttatattagg agactgtttg tattttaaca    5700
atataatgtc ccaattagat ttacaccaaa attgggctcc atcagttaga ttgttaaatt    5760
attttaagaa ttttaataag gaaacactac taaagataga agagaatgat tacattaatt    5820
catccttttt ccaacaaaag gataaacgat tttatcctat aaacgacgat ttttatcaca    5880
tatctacagg aggatatggt atagtctttta agatagataa ctatgtagta aaatttgtat    5940
tcgaggccac aaaattatat agtcccatgg aaactacggc ggagttcaca gtacccaaat    6000
ttctatacaa caatcaaag ggagatgaaa aaaaattaat cgtgtgtgcg tgggccatgg    6060
gattaaacta taaattaaca ttttttacata ctctgtataa acgtgttctt catatgttgc    6120
tattattgat acaaactatg gatggtcagg aactatcatt gagatattct tctaaagttt    6180
ttttaaaggc gtttaacgag agaaaggaca gtatcaaatt cgtgaaatta ctatcccact    6240
tttatccggc agttattaac agtaatatta atgttataaa ctattttaac cgcatgtttc    6300
acttttttcga acatgaaaag agaactaact acgaatacga aagaggaaat attataattt    6360
ttcccctagc actgtattcg gcagataaag tagataccga gctagctatc aaattaggat    6420
ttaaatcttt ggtacaatac ataaagtta tctttttaca gatggctctg ttatacatta    6480
aaatttacga actaccatgc tgcgacaact ttttacacgc agatcttaaa cccgataata    6540
tcttactttt tgattccaat gaaccaataa taattcatct aaaggataaa agtttgttt    6600
ttaatgaacg tattaaatcg gcattaaacg actttgactt ttcccaagaa gggcgaattc    6660
tgcagatatc catcacactg gcggccgctt acttgtacag ctcgtccatg ccgagagtga    6720
tcccggcggc ggtcacgaac tccagcagga ccatgtgatc gcgcttctcg ttgggtctt    6780
tgctcagggc ggactgggtg ctcaggtagt ggttgtcggg cagcagcacg ggccgtcgc    6840
```

```
cgatggggt gttctgctgg tagtggtcgg cgagctgcac gctgccgtcc tcgatgttgt   6900
ggcggatctt gaagttcacc ttgatgccgt tcttctgctt gtcggccatg atatagacgt   6960
tgtggctgtt gtagttgtac tccagcttgt gccccaggat gttgccgtcc tccttgaagt   7020
cgatgcccctt cagctcgatg cggttcacca gggtatcgcc ctcgaacttc acctcggcgc   7080
gggtcttgta gttgccgtcg tccttgaaga agatggtgcg ctcctggacg tagccttcgg   7140
gcatggcgga cttgaagaag tcgtgctgct tcatgtggtc ggggtagcgg ctgaagcact   7200
gcacgccgta ggtcagggtg gtcacgaggg tcggccaggg cacgggcagc ttgccggtgg   7260
tgcagatgaa cttcagggtc agcttgccgt aggtggcatc gccctcgccc tcgccggaca   7320
cgctgaactt gtggccgttt acgtcgccgt ccagctcgac caggatgggc accaccccgg   7380
taaacagctc ctcgcccttg ctcaccatgt ttaaacttta tattccaaaa aaaaaaaata   7440
aaatttcaat ttttgtttaa acgttgtacg gcagtttaag gtttacacct ataaagaga   7500
gagccgttat cgtctgtttg tggatgtaca gagtgatatt attgcacgc cggggcgacg    7560
gatggtgatc ccctggcca gtgcacgtct gctgtcagat aaagtctccc gtgaacttta    7620
cccggtggtg catatcgggg atgaaagctg gcgcatgatg accaccgata tggccagtgt   7680
gccggtctcc gttatcgggg aagaagtggc tgatctcagc caccgcgaaa atgacatcaa   7740
aaacgccatt aacctgatgt tctggggaat ataaatgtca ggcatgagat tatcaaaaag   7800
gatcttcacc tagatccttt tcacgtagaa agccagtccg cagaaacggt gctgaccccg   7860
gatgaatgtc agctactggg ctatctggac aagggaaaac gcaagcgcaa agagaaagca   7920
ggtagcttgc agtgggctta catggcgata gctagactgg gcggttttat ggacagcaag   7980
cgaaccggaa ttgccagctg gggcgccctc tggtaaggtt gggaagccct gcaaagtaaa   8040
ctggatggct ttctcgccgc caaggatctg atggcgcagg ggatcaagct ctgatcaaga   8100
gacaggatga ggatcgtttc gcatgattga acaagatgga ttgcacgcag gttctccggc   8160
cgcttgggtg gagaggctat tcggctatga ctgggcacaa cagacaatcg gctgctctga   8220
tgccgccgtg ttccggctgt cagcgcaggg gcgcccggtt ctttttgtca agaccgacct   8280
gtccggtgcc ctgaatgaac tgcaagacga ggcagcgcgg ctatcgtggc tggccacgac   8340
gggcgttcct tgcgcagctg tgctcgacgt tgtcactgaa gcgggaaggg actggctgct   8400
attgggcgaa gtgccggggc aggatctcct gtcatctcac cttgctcctg ccgagaaagt   8460
atccatcatg gctgatgcaa tgcggcggct gcatacgctt gatccggcta cctgcccatt   8520
cgaccaccaa gcgaaacatc gcatcgagcg agcacgtact cggatggaag ccggtcttgt   8580
cgatcaggat gatctggacg aagagcatca ggggctcgcg ccagccgaac tgttcgccag   8640
gctcaaggcg agcatgcccg acggcgagga tctcgtcgtg acccatggcg atgcctgctt   8700
gccgaatatc atggtggaaa atggccgctt ttctggattc atcgactgtg gccggctggg   8760
tgtggcggac cgctatcagg acatagcgtt ggctacccgt gatattgctg aagagcttgg   8820
cggcgaatgg gctgaccgct tcctcgtgct ttacggtatc gccgctcccg attcgcagcg   8880
catcgccttc tatcgccttc ttgacgagtt cttctgaatt attaacgctt acaatttcct   8940
gatgcggtat tttctcctta cgcatctgtg cggtatttca caccgcatac aggtggcact   9000
tttcggggaa atgtgcgcgg aacccctatt tgtttatttt tctaaataca ttcaaatatg   9060
tatccgctca tgagacaata accctgataa atgcttcaat aatagcacgt gaggagggcc   9120
accatggcca agttgaccag tgccgttccg gtgctcaccg cgcgcgacgt cgccggagcg   9180
```

```
gtcgagttct ggaccgaccg gctcgggttc tcccgggact tcgtggagga cgacttcgcc    9240
ggtgtggtcc gggacgacgt gaccctgttc atcagcgcgg tccaggacca ggtggtgccg    9300
gacaacaccc tggcctgggt gtgggtgcgc ggcctggacg agctgtacgc cgagtggtcg    9360
gaggtcgtgt ccacgaactt ccgggacgcc tccgggccgg ccatgaccga gatcggcgag    9420
cagccgtggg ggcgggagtt cgccctgcgc gaccggccg gcaactgcgt gcacttcgtg    9480
gccgaggagc aggactgaca cgtgctaaaa cttcattttt aatttaaaag gatctaggtg    9540
aagatccttt ttgataatct catgaccaaa atcccttaac gtgagttttc gttccactga    9600
gcgtcagacc ccgtagaaaa gatcaaagga tcttcttgag atcctttttt tctgcgcgta    9660
atctgctgct tgcaaacaaa aaaaccaccg ctaccagcgg tggtttgttt gccggatcaa    9720
gagctaccaa ctctttttcc gaaggtaact ggcttcagca gagcgcagat accaaatact    9780
gtccttctag tgtagccgta gttaggccac cacttcaaga actctgtagc accgcctaca    9840
tacctcgctc tgctaatcct gttaccagtg gctgctgcca gtggcgataa gtcgtgtctt    9900
accgggttgg actcaagacg atagttaccg gataaggcgc agcggtcggg ctgaacgggg    9960
ggttcgtgca cacagcccag cttggagcga acgacctaca ccgaactgag atacctacag   10020
cgtgagctat gagaaagcgc cacgcttccc gaagggagaa aggcggacag gtatccggta   10080
agcggcaggg tcggaacagg agagcgcacg agggagcttc caggggggaaa cgcctggtat   10140 ctttatagtc ctgtcgggtt tcgccacctc tgacttgagc gtcgatttt gtgatgctcg   10200 tcagggggc ggagcctatg gaaaaacgcc agcaacgcgg cctttttacg gttcctgggc   10260
ttttgctggc cttttgctca catgttcttt cctgcgttat cccctgattc tgtggataac   10320
cgtattaccg cctttgagtg agctgatacc gctcgccgca gccgaacgac cgagcgcagc   10380
gagtcagtga gcgaggaagc ggaag                                         10405
```

HPV VACCINE

CROSS-REFERENCE TO RELATED APPLICATIONS

This application is the National Stage of International Application No. PCT/GB2018/052335, filed Aug. 16, 2018, which claims priority to GB 1713163.2, filed Aug. 16, 2017, which are entirely incorporated herein by reference.

SEQUENCE LISTING

This application contains a sequence listing filed in electronic form as an 15 ASCII.txt file entitled "820926_1180 Sequence Listing_ST25.txt", created on Feb. 22, 2021 and having a size of 489 kb. The content of the sequence listing is incorporated herein in its entirety.

This invention relates to viral-vectored vaccines for use in a vaccination against HPV infection.

Human papillomavirus infection is an infection by human papillomavirus (HPV). Most HPV infections cause no symptoms and resolve spontaneously. However, in some cases they persist and this can result in the development of warts or precancerous lesions. The precancerous lesions increase the risk of cancer of the cervix, vulva, vagina, penis, anus, mouth, or throat.

There are approximately 0.5 million cases of HPV-attributable cervical cancer that occur annually worldwide, and over half of these are fatal. About 85% of cases occur in low/middle income countries where there is limited or no treatment available. Women who have not received a prophylactic vaccine require 3-yearly screening to identify and treat cervical intra-epithelial neoplasia (CIN). Screening costs the UK National Health Service approximately £175 million annually.

Current therapy for CIN is ablation of abnormal cervical tissue by electrocautery or surgery. There is no current therapy available that eliminates HPV viral infection. Women require multiple follow-up visits after treatment to ensure that there is no recurrence. Therapy is also associated with increased risk of pre-term birth.

HPV vaccines that have been developed for therapy of existing HPV infection include Inovio—VGX-3100 (DNA encoding E6, E7) similarly Genexine (GX-188E); Janssen—Ad26/Ad35+/−MVA encoding E2, E6, E7 fusion protein; Synthetic long peptides (E6, E7) and similar eg. PepCan, GTL001; Advaxis—ADXS-HPV; and *L. Monocytogenes* encoding E7. However, such developed vaccines have been targeted to HPV16 and 18 only, have safety concerns, and/or are low efficiency. For example, the net efficacy of VGX-3100 was 18% in a phase IIb randomised controlled trial (48% in vaccine arm vs. 30% in placebo arm).

What is needed is a vaccine that is safe, easy to deliver and to have greater efficacy than the therapeutic vaccine candidates tested to date. Therefore, an aim of the present invention is to provide an improved vaccine for HPV infection.

According to a first aspect of the invention, there is provided a nucleic acid encoding a polypeptide comprising a plurality of conserved peptide sequences, or variants thereof,
wherein the conserved sequences are conserved across one or more HPV genotypes 16, 18, 31, 52, 53, and 58; and
wherein the polypeptide comprises a conserved peptide sequence of each of the HPV proteins E1, E2, E4, E5, E6, and E7.

The invention advantageously provides a novel alternative and safer approach to vaccination whereby T cells can be induced to the relatively conserved antigens of the virion. The use of specially designed conserved viral segments from the non-structural proteins can provide protection against multiple important genotypes.

In one embodiment, the polypeptide is a fusion polypeptide. The polypeptide may not be a wild-type polypeptide. The polypeptide may be synthetic/artificial, for example, the polypeptide may not exist in nature. In one embodiment, the polypeptide may not comprise a complete gene sequence. The polypeptide may consist essentially of conserved peptide sequences. In another embodiment, the polypeptide may consist essentially of conserved peptide sequences and a peptide adjuvant sequence. In another embodiment, the polypeptide may consist essentially of conserved peptide sequences and one or more linkers therebetween. In another embodiment, the polypeptide may consist essentially of conserved peptide sequences, a peptide adjuvant sequence and one or more linkers therebetween. In one embodiment, the polypeptide is a recombinant polypeptide, such as a recombinant fusion polypeptide.

The term "fusion polypeptide" used herein is understood to mean a polypeptide comprising a combination of sequences derived from different gene products (for example different HPV proteins) or combinations of sequences from the same gene product (for example a single HPV protein), wherein the sequences are from distinct/separate regions of the wild-type gene product. For example the fusion polypeptide may comprise combinations of sequences which are normally separated by other sequence segments in wild-type, and the separating sequence(s) have been removed.

The term "conserved peptide sequence" or "conserved segment" used herein is defined as a sequence that is conserved in one or more genotypes, as defined below. Prior to assessment of conservation all available full-length sequences for HPV proteins E1, E2, E4, E5, E6 and E7 from genotypes 16, 18, 31, 52, 53 and 58 were collected from the NCBI Protein database (accessed 2014) and used as input for the approach of the invention. All available sequences were used to ensure the selected conserved peptide sequences would equally represent the whole environmental population (See Table 1). Conserved peptide sequences were identified using the 'variant' approach (FIG. 1A); all genotypes were aligned and sequences within each genotype weighted prior to conservation assessment to ensure equal representation of genotype diversity and thus ensure the vaccine candidates were representative of the whole environmental population. Conservation within genotypes (intra-genotype conservation) was then assessed using a 15 amino acid sliding window, whereby for each window a conservation value was determined based on combining the amino acid prevalence within the window and weighting value of each sequence to identify fragments conserved within each genotype, and a normalised intra-genotype consensus created for each window. 'Normalised consensus' meaning an amino acid sequence that represented the weighted set of genotype sequence, not the most common amino acid at each position. To be classed as conserved the window must have a conservation value within the first quartile of all window conservation values for the protein. Subsequently, conserved intra-genotype windows at the same position across all genotypes were identified independent of the percentage identity of shared intra-genotype normalised consensus between genotypes (inter-genotype conservation). A phylogeny was then created of the resultant regions and tree ingroup sequences combined to create an inter-genotype consensus with a high level of shared consensus identity. In this case 'inter-genotype consensus' refers to a consensus created using the normalised consensus created from each genotype. In some scenarios, a 'modified variant' was created where conserved intra-genotype windows at the same position across all proteins were identified which shared greater than 60% shared intra-genotype normalised consensus percentage identity between genotypes.

If the identified inter-serotype fragments from tree ingroups had a percentage identity less than 60%, the sequences were classed as "highly divergent", in contrast to "less divergent" sequences used in the variant approach. For proteins highly divergent between genotypes a 'chimeric' approach was used to identify conserved peptide sequences (FIG. 1B); a phylogeny was created and only genotype ingroups were aligned together and intra-genotype conserved assessed. Therefore, inter-genotype conservation was only assessed between ingroups and intra-serotype conserved windows with greater than 60% shared consensus identity across genotypes selected. In some cases genotypes were run as 'chimerics' but inter-genotype conservation was not assessed ('chimeric-variants').

The plurality of conserved peptide sequences may comprise 10 or more conserved peptide sequences. In another embodiment, the plurality of conserved peptide sequences may comprise 15 or more conserved peptide sequences. In another embodiment, the plurality of conserved peptide sequences may comprise 20 or more conserved peptide sequences. In another embodiment, the plurality of conserved peptide sequences may comprise 25 or more conserved peptide sequences. In another embodiment, the plurality of conserved peptide sequences may comprise 30 or more conserved peptide sequences. The plurality of conserved sequences may comprise 35 or more conserved peptide sequences. In another embodiment, the plurality of conserved peptide sequences may comprise 40 or more conserved peptide sequences. The plurality of conserved peptide sequences may comprise 45 or more conserved peptide sequences. In another embodiment, the plurality of conserved peptide sequences may comprise 50 or more conserved peptide sequences. In another embodiment, the plurality of conserved peptide sequences may comprise 55 or more conserved peptide sequences. In one embodiment, the plurality of conserved peptide sequences consists of about 56 or more conserved peptide sequences. In one embodiment, the plurality of conserved peptide sequences consists of about 57 or more conserved peptide sequences. In one embodiment, the plurality of conserved peptide sequences consists of about 58 or more conserved peptide sequences. In one embodiment, the plurality of conserved peptide sequences consists of about 59 or more conserved peptide sequences. In one embodiment, the plurality of conserved peptide sequences consists of about 59 conserved peptide sequences.

The encoded polypeptide may comprise at least 3 different conserved peptide sequences of each of the HPV proteins E1, E2, E4, E5, E6, and E7. The encoded polypeptide may comprise at least 3 different conserved peptide sequences of HPV protein E1. The encoded polypeptide may comprise at least 3 different conserved peptide sequences of HPV protein E2. The encoded polypeptide may comprise at least 3 different conserved peptide sequences of HPV protein E4. The encoded polypeptide may comprise at least 3 different conserved peptide sequences of HPV protein E5. The encoded polypeptide may comprise at least 3 different conserved peptide sequences of HPV protein E6. The encoded polypeptide may comprise at least 3 different conserved peptide sequences of HPV protein E7.

The encoded polypeptide may comprise at least 4 different conserved peptide sequences of HPV protein E1. The encoded polypeptide may comprise at least 4 different conserved peptide sequences of HPV protein E2. The encoded polypeptide may comprise at least 4 different conserved peptide sequences of HPV protein E4. The encoded polypeptide may comprise at least 4 different conserved peptide sequences of HPV protein E6. The encoded polypeptide may comprise at least 4 different conserved peptide sequences of HPV protein E7.

The encoded polypeptide may comprise at least 5 different conserved peptide sequences of HPV protein E1. The encoded polypeptide may comprise at least 5 different conserved peptide sequences of HPV protein E2. The encoded polypeptide may comprise at least 5 different conserved peptide sequences of HPV protein E4. The encoded polypeptide may comprise at least 5 different conserved peptide sequences of HPV protein E6.

The encoded polypeptide may comprise at least 6 different conserved peptide sequences of HPV protein E1. The encoded polypeptide may comprise at least 6 different conserved peptide sequences of HPV protein E2. The encoded polypeptide may comprise at least 6 different conserved peptide sequences of HPV protein E4. The encoded polypeptide may comprise at least 6 different conserved peptide sequences of HPV protein E6.

The encoded polypeptide may comprise at least 7 different conserved peptide sequences of HPV protein E1. The encoded polypeptide may comprise at least 7 different conserved peptide sequences of HPV protein E2. The encoded polypeptide may comprise at least 7 different conserved peptide sequences of HPV protein E4. The encoded polypeptide may comprise at least 7 different conserved peptide sequences of HPV protein E6.

The encoded polypeptide may comprise at least 8 different conserved peptide sequences of HPV protein E1. The encoded polypeptide may comprise at least 8 different conserved peptide sequences of HPV protein E2. The encoded polypeptide may comprise at least 8 different conserved peptide sequences of HPV protein E4. The encoded polypeptide may comprise at least 8 different conserved peptide sequences of HPV protein E6.

The encoded polypeptide may comprise at least 9 different conserved peptide sequences of HPV protein E1. The encoded polypeptide may comprise at least 9 different conserved peptide sequences of HPV protein E2. The encoded polypeptide may comprise at least 9 different conserved peptide sequences of HPV protein E4.

The encoded polypeptide may comprise at least 10 different conserved peptide sequences of HPV protein E1. The encoded polypeptide may comprise at least 10 different conserved peptide sequences of HPV protein E2.

The encoded polypeptide may comprise at least 11 different conserved peptide sequences of HPV protein E1. The encoded polypeptide may comprise at least 11 different conserved peptide sequences of HPV protein E2.

The encoded polypeptide may comprise at least 12, 13, 14, 15, 16, 17, 18, 19, 20, 21, 22, 23, or 24 different conserved peptide sequences of HPV protein E2.

The encoded polypeptide may comprise or consist of 11 or more different conserved peptide sequences of HPV protein E1, 24 or more different conserved peptide sequences of HPV protein E2, 9 or more different conserved peptide sequences of HPV protein E4, 3 or more different conserved peptide sequences of HPV protein E5, 8 or more different conserved peptide sequences of HPV protein E6, and 4 or more different conserved peptide sequences of HPV protein E7.

The plurality of conserved peptide sequences may be derived from distinct regions of sequence relative to each other (i.e. not-naturally concurrent). For example, reference to "different conserved peptide sequences" may comprise sequences that are derived from distinct regions of wild-type sequence relative to each other (i.e. not-naturally concurrent). For example, in the wild-type genotype the conserved sequences may be separated in the wild-type genotypes by variable/non-conserved sequences. The plurality of conserved peptide sequences may not, or may not significantly, overlap with each other. Two or more, or all, of the plurality of conserved peptide sequences may be directly joined together in the polypeptide, for example not comprising any non-conserved/variable residues therebetween. The polypeptide sequence may not be found in nature. The polypeptide may not comprise non-conserved sequences or residues. The conserved peptide sequences may not be distanced apart by more than 1, 2, 3, 4, or 5 residues in the polypeptide sequence, for example in embodiments where there are linker/junction residues between the conserved peptide sequences. Alternatively, the conserved peptide sequences may not be distanced apart by more than 6, 7, 8, 9, or 10 residues in the polypeptide sequence, for example in embodiments where there are linker/junction residues between the conserved peptide sequences. The polypeptide may not comprise non-conserved sequences longer than 2, 3, 4, 5, 6, 7, 8, 9, or 10 amino acids.

In one embodiment, linker residues may be provided between one or more, or all, conserved peptide sequences (e.g. providing junctions between the conserved peptide sequences in the polypeptide). The linker residues may comprise random amino acid sequences, or amino acids that have been selected to be non-immunogenic based on epitope prediction computer programs or experiments in animal models. For example, a linker may not be considered if it is predicted or known to be an epitope (i.e. in order to avoid an immune response to epitopes, e.g. artificial epitopes, not found in HPV. The linker may be flexible. The linker may comprise or consist of K, G, P, A or S amino acid residues, or combinations thereof. In one embodiment, the linker may comprise or consist of G and/or P amino acid residues. In one embodiment, the linker may comprise or consist of one or more alanine (A) amino acid residues. The linker residues may be between 1 and 10 amino acids in length. In another embodiment, the linker residues may be between 2 and 8 residues in length. In another embodiment, the linker residues may be between 1 and 6 residues in length. The conserved peptide sequences may be distanced apart by between 1 and 10 residues in the polypeptide sequence, for example in embodiments where there are linker/junction residues between the conserved peptide sequences.

In one embodiment, the polypeptide may consist essentially of conserved peptide sequences and one or more linkers, optionally wherein the one or more linkers are disposed between adjacent conserved peptide sequence.

The conserved peptide sequences may be selected from any of the group comprising SEQ ID NOs: 1 to 59; variants thereof or combinations thereof. In another embodiment, the conserved peptide sequences may be selected from any of the group comprising SEQ ID NOs: 1 to 59; variants thereof or combinations thereof, in any order. In one embodiment, the conserved peptide sequences may consist of the group comprising SEQ ID NOs: 1 to 59.

The polypeptide may comprise one or more conserved E1 sequence(s) selected from any one of SEQ ID NOs: 1-11; one or more conserved E2 sequence(s) selected from any one of SEQ ID NOs: 12-35; one or more conserved E4 sequence(s) selected from any one of SEQ ID NOs: 36-44; one or more conserved E5 sequence(s) selected from any one of SEQ ID NOs: 45-47; one or more conserved E6 sequence(s) selected from any one of SEQ ID NOs: 48-55; and one or more conserved E7 sequence(s) selected from any one of SEQ ID NOs: 56-59.

The polypeptide may comprise two or more conserved E1 sequence(s) selected from any of SEQ ID NOs: 1-11; two or more conserved E2 sequence(s) selected from any of SEQ ID NOs: 12-35; two or more conserved E4 sequence(s) selected from any of SEQ ID NOs: 36-44; two or more conserved E5 sequence(s) selected from any of SEQ ID NOs: 45-47; two or more conserved E6 sequence(s) selected from any of SEQ ID NOs: 48-55; and two or more conserved E7 sequence(s) selected from any of SEQ ID NOs: 56-59.

The polypeptide may comprise three or more conserved E1 sequence(s) selected from any of SEQ ID NOs: 1-11; three or more conserved E2 sequence(s) selected from any of SEQ ID NOs: 12-35; three or more conserved E4 sequence(s) selected from any of SEQ ID NOs: 36-44; three or more conserved E5 sequence(s) selected from any of SEQ ID NOs: 45-47; three or more conserved E6 sequence(s) selected from any of SEQ ID NOs: 48-55; and three or more conserved E7 sequence(s) selected from any of SEQ ID NOs: 56-59.

The conserved sequences are conserved across one or more of HPV genotypes 16, 18, 31, 52, and 58. The conserved sequences are conserved across all of HPV genotypes 16, 18, 31, 52, and 58.

The polypeptide may comprise:
one or more conserved E1 sequence(s) selected from any one of SEQ ID NOs: 1-11, wherein each of the genotypes 16, 18, 31, 52, 53, and 58 are represented by at least one conserved E1 sequence;
one or more conserved E2 sequence(s) selected from any one of SEQ ID NOs: 12-35, wherein each of the genotypes 16, 18, 31, 52, 53, and 58 are represented by at least one conserved E2 sequence;
one or more conserved E4 sequence(s) selected from any one of SEQ ID NOs: 36-44, wherein each of the genotypes 16, 18, 31, 52, 53, and 58 are represented by at least one conserved E4 sequence;
one or more conserved E5 sequence(s) selected from any one of SEQ ID NOs: 45-47, wherein each of the genotypes 16, 18, 31, 52, 53, and 58 are represented by at least one conserved E5 sequence;
one or more conserved E6 sequence(s) selected from any one of SEQ ID NOs: 48-55, wherein each of the genotypes 16, 18, 31, 52, 53, and 58 are represented by at least one conserved E6 sequence; and
one or more conserved E7 sequence(s) selected from any one of SEQ ID NOs: 56-59, wherein each of the genotypes 16, 18, 31, 52, 53, and 58 are represented by at least one conserved E7 sequence.

The polypeptide may comprise:
one or more conserved E1 sequence(s) selected from any one of SEQ ID NOs: 1-11, wherein each of the genotypes 16, 18, 31, 52, and 58 are represented by at least one conserved E1 sequence;
one or more conserved E2 sequence(s) selected from any one of SEQ ID NOs: 12-35, wherein each of the genotypes 16, 18, 31, 52, and 58 are represented by at least one conserved E2 sequence;

one or more conserved E4 sequence(s) selected from any one of SEQ ID NOs: 36-44, wherein each of the genotypes 16, 18, 31, 52, and 58 are represented by at least one conserved E4 sequence;

one or more conserved E5 sequence(s) selected from any one of SEQ ID NOs: 45-47, wherein each of the genotypes 16, 18, 31, 52, and 58 are represented by at least one conserved E5 sequence;

one or more conserved E6 sequence(s) selected from any one of SEQ ID NOs: 48-55, wherein each of the genotypes 16, 18, 31, 52, and 58 are represented by at least one conserved E6 sequence; and one or more conserved E7 sequence(s) selected from any one of SEQ ID NOs: 56-59, wherein each of the genotypes 16, 18, 31, 52, and 58 are represented by at least one conserved E7 sequence.

The polypeptide may comprise:

two or more conserved E1 sequence(s) selected from any of SEQ ID NOs: 1-11, wherein each of the genotypes 16, 18, 31, 52, 53, and 58 are represented in the group of conserved E1 sequences;

two or more conserved E2 sequence(s) selected from any of SEQ ID NOs: 12-35, wherein each of the genotypes 16, 18, 31, 52, 53, and 58 are represented in the group of conserved E2 sequences;

two or more conserved E4 sequence(s) selected from any of SEQ ID NOs: 36-44, wherein each of the genotypes 16, 18, 31, 52, 53, and 58 are represented in the group of conserved E4 sequences;

two or more conserved E5 sequence(s) selected from any of SEQ ID NOs: 45-47, wherein each of the genotypes 16, 18, 31, 52, 53, and 58 are represented in the group of conserved E5 sequences;

two or more conserved E6 sequence(s) selected from any of SEQ ID NOs: 48-55, wherein each of the genotypes 16, 18, 31, 52, 53, and 58 are represented in the group of conserved E6 sequences; and two or more conserved E7 sequence(s) selected from any of SEQ ID NOs: 56-59, wherein each of the genotypes 16, 18, 31, 52, 53, and 58 are represented in the group of conserved E7 sequences.

The polypeptide may comprise:

two or more conserved E1 sequence(s) selected from any of SEQ ID NOs: 1-11, wherein each of the genotypes 16, 18, 31, 52, and 58 are represented in the group of conserved E1 sequences;

two or more conserved E2 sequence(s) selected from any of SEQ ID NOs: 12-35, wherein each of the genotypes 16, 18, 31, 52, and 58 are represented in the group of conserved E2 sequences;

two or more conserved E4 sequence(s) selected from any of SEQ ID NOs: 36-44, wherein each of the genotypes 16, 18, 31, 52, and 58 are represented in the group of conserved E4 sequences;

two or more conserved E5 sequence(s) selected from any of SEQ ID NOs: 45-47, wherein each of the genotypes 16, 18, 31, 52, and 58 are represented in the group of conserved E5 sequences;

two or more conserved E6 sequence(s) selected from any of SEQ ID NOs: 48-55, wherein each of the genotypes 16, 18, 31, 52, and 58 are represented in the group of conserved E6 sequences; and two or more conserved E7 sequence(s) selected from any of SEQ ID NOs: 56-59, wherein each of the genotypes 16, 18, 31, 52, and 58 are represented in the group of conserved E7 sequences.

The polypeptide may comprise:

three or more conserved E1 sequence(s) selected from any of SEQ ID NOs: 1-11, wherein each of the genotypes 16, 18, 31, 52, 53, and 58 are represented in the group of conserved E1 sequences;

three or more conserved E2 sequence(s) selected from any of SEQ ID NOs: 12-35, wherein each of the genotypes 16, 18, 31, 52, 53, and 58 are represented in the group of conserved E2 sequences;

three or more conserved E4 sequence(s) selected from any of SEQ ID NOs: 36-44, wherein each of the genotypes 16, 18, 31, 52, 53, and 58 are represented in the group of conserved E4 sequences;

three conserved E5 sequence(s) selected from SEQ ID NOs: 45-47, wherein each of the genotypes 16, 18, 31, 52, 53, and 58 are represented in the group of conserved E5 sequences;

three or more conserved E6 sequence(s) selected from any of SEQ ID NOs: 48-55, wherein each of the genotypes 16, 18, 31, 52, 53, and 58 are represented in the group of conserved E6 sequences; and three or more conserved E7 sequence(s) selected from any of SEQ ID NOs: 56-59, wherein each of the genotypes 16, 18, 31, 52, 53, and 58 are represented in the group of conserved E7 sequences.

The polypeptide may comprise:

three or more conserved E1 sequence(s) selected from any of SEQ ID NOs: 1-11, wherein each of the genotypes 16, 18, 31, 52, and 58 are represented in the group of conserved E1 sequences;

three or more conserved E2 sequence(s) selected from any of SEQ ID NOs: 12-35, wherein each of the genotypes 16, 18, 31, 52, and 58 are represented in the group of conserved E2 sequences;

three or more conserved E4 sequence(s) selected from any of SEQ ID NOs: 36-44, wherein each of the genotypes 16, 18, 31, 52, and 58 are represented in the group of conserved E4 sequences;

three conserved E5 sequence(s) selected from SEQ ID NOs: 45-47, wherein each of the genotypes 16, 18, 31, 52, and 58 are represented in the group of conserved E5 sequences;

three or more conserved E6 sequence(s) selected from any of SEQ ID NOs: 48-55, wherein each of the genotypes 16, 18, 31, 52, and 58 are represented in the group of conserved E6 sequences; and three or more conserved E7 sequence(s) selected from any of SEQ ID NOs: 56-59, wherein each of the genotypes 16, 18, 31, 52, and 58 are represented in the group of conserved E7 sequences.

Reference to "each of the genotypes 16, 18, 31, 52, 53, and 58 are represented" or "each of the genotypes 16, 18, 31, 52, and 58 are represented" is intended to mean that each of the identified genotypes has been used to define at least one consensus sequence of a conserved peptide sequence. Therefore, a given group may comprise a conserved peptide from each genotype, or a conserved peptide may be derived from a consensus of two or more genotypes. If sequence identities are sufficiently similar, all the genotypes 16, 18, 31, 52, 53, and 58 or 16, 18, 31, 52, and 58 could be represented by a single conserved peptide sequence, which may be a consensus of all the genotypes 16, 18, 31, 52, 53, and 58 or 16, 18, 31, 52, and 58 respectively. However, due to differences in sequence identities, a single conserved peptide may not be able to represent a consensus sequence from all genotypes 16, 18, 31, 52, 53, and 58 or 16, 18, 31, 52, and 58 and instead two or more conserved peptide sequences are required to cover/represent all the genotypes 16, 18, 31, 52, 53, and 58 or 16, 18, 31, 52, and 58. For example (for illustrative purposes only), one conserved E6 peptide sequence may represent E6 genotypes 16 and 18, another may represent E6 genotype 52, and a third may represent E6 genotypes 53 and 58, such that all three conserved E6 peptide sequences in a group represent all E6 genotypes 16, 18, 31, 52, 53, and 58 or 16, 18, 31, 52, and 58.

The nucleic acid may comprise or consist of the sequence of SEQ ID NO: 60, or variants thereof. In another embodiment, the nucleic acid may comprise or consist of the sequence of SEQ ID NO: 60, or variants thereof, and without encoding the TPA lead sequence. In another embodiment, the nucleic acid may comprise or consist of the sequence of SEQ ID NO: 60, or variants thereof, with a different/alternative peptide adjuvant encoded than the TPA lead sequence. In another embodiment, the nucleic acid may comprise or consist of the sequence of SEQ ID NO: 65, or variants thereof.

Variants of the nucleic acid may comprise or consist of a sequence having at least 80% identity with SEQ ID NO: 60 or 65. Alternatively, variants of the nucleic acid may comprise or consist of a sequence having at least 85% identity with SEQ ID NO: 60 or 65. Variants of the nucleic acid may comprise or consist of a sequence having at least 90% identity with SEQ ID NO: 60 or 65. Variants of the nucleic acid may comprise or consist of a sequence having at least 95% identity with SEQ ID NO: 60 or 65. Variants of the nucleic acid may comprise or consist of a sequence having at least 98% identity with SEQ ID NO: 60 or 65. Variants of the nucleic acid may comprise or consist of a sequence having at least 99% identity with SEQ ID NO: 60 or 65. The skilled person will understand that a variant of the nucleic acid may include redundant codon variants that encode the same peptide as SEQ ID NO: 60 or 65.

The nucleic acid may comprise or consist of the sequence of SEQ ID NO: 62, or variants thereof. In another embodiment, the nucleic acid may comprise or consist of the sequence of SEQ ID NO: 62, or variants thereof, and without encoding the TPA lead sequence. In another embodiment, the nucleic acid may comprise or consist of the sequence of SEQ ID NO: 62, or variants thereof, with a different/alternative peptide adjuvant encoded than the TPA lead sequence.

Variants of the nucleic acid may comprise or consist of a sequence having at least 80% identity with SEQ ID NO: 62. Alternatively, variants of the nucleic acid may comprise or consist of a sequence having at least 85% identity with SEQ ID NO: 62. Variants of the nucleic acid may comprise or consist of a sequence having at least 90% identity with SEQ ID NO: 62. Variants of the nucleic acid may comprise or consist of a sequence having at least 95% identity with SEQ ID NO: 62. Variants of the nucleic acid may comprise or consist of a sequence having at least 98% identity with SEQ ID NO: 62. Variants of the nucleic acid may comprise or consist of a sequence having at least 99% identity with SEQ ID NO: 62. Variants of the nucleic acid may comprise or consist of a sequence having at least 99.5% identity with SEQ ID NO: 62. Variants of the nucleic acid may comprise or consist of a sequence having at least 99.9% identity with SEQ ID NO: 62. The skilled person will understand that a variant of the nucleic acid may include redundant codon variants that encode the same viral vector and/or peptide as SEQ ID NO: 62.

The nucleic acid may comprise or consist of the sequence of SEQ ID NO: 71, 73 or 75, or variants thereof. In another embodiment, the nucleic acid may comprise or consist of the sequence of SEQ ID NO: 71, 73 or 75, or variants thereof, and without encoding the TPA lead sequence. In another embodiment, the nucleic acid may comprise or consist of the sequence of SEQ ID NO: 71, 73 or 75, or variants thereof, with a different/alternative peptide adjuvant encoded than the TPA lead sequence.

Variants of the nucleic acid may comprise or consist of a sequence having at least 80% identity with SEQ ID NO: 71, 73 or 75. Alternatively, variants of the nucleic acid may comprise or consist of a sequence having at least 85% identity with SEQ ID NO: 71, 73 or 75. Variants of the nucleic acid may comprise or consist of a sequence having at least 90% identity with SEQ ID NO: 71, 73 or 75. Variants of the nucleic acid may comprise or consist of a sequence having at least 95% identity with SEQ ID NO: 71, 73 or 75. Variants of the nucleic acid may comprise or consist of a sequence having at least 98% identity with SEQ ID NO: 71, 73 or 75. Variants of the nucleic acid may comprise or consist of a sequence having at least 99% identity with SEQ ID NO: 71, 73 or 75. Variants of the nucleic acid may comprise or consist of a sequence having at least 99.5% identity with SEQ ID NO: 71, 73 or 75. Variants of the nucleic acid may comprise or consist of a sequence having at least 99.9% identity with SEQ ID NO: 71, 73 or 75. The skilled person will understand that a variant of the nucleic acid may include redundant codon variants that encode the same viral vector and/or peptide as SEQ ID NO: 71, 73 or 75.

The polypeptide may comprise or consist of the sequence of SEQ ID NO: 61, or variants thereof. In another embodiment, the polypeptide may comprise or consist of the sequence of SEQ ID NO: 61, or variants thereof, and without the TPA lead sequence. In another embodiment, the polypeptide may comprise or consist of the sequence of SEQ ID NO: 61, or variants thereof, with a different/alternative peptide adjuvant than the TPA lead sequence. In another embodiment, the polypeptide may comprise or consist of the sequence of SEQ ID NO: 66, or variants thereof.

The polypeptide may comprise or consist of the sequence of SEQ ID NO: 72, 74 or 76, or variants thereof. In another embodiment, the polypeptide may comprise or consist of the sequence of SEQ ID NO: 72, 74 or 76, or variants thereof, and without the TPA lead sequence. In another embodiment, the polypeptide may comprise or consist of the sequence of SEQ ID NO: 72, 74 or 76, or variants thereof, with a different/alternative peptide adjuvant than the TPA lead sequence. In another embodiment, the polypeptide may comprise or consist of the sequence of SEQ ID NO: 72, 74 or 76, or variants thereof.

In one embodiment, the polypeptide may consist essentially of conserved peptide sequences and a peptide adjuvant. In one embodiment, the polypeptide may consist essentially of conserved peptide sequences, one or more linkers, and a peptide adjuvant. The one or more linkers may be disposed between adjacent conserved peptide sequence. The peptide adjuvant may be N-terminal.

Variants of the polypeptide may comprise or consist of a sequence having at least 80% identity with SEQ ID NO: 61, 66, 72, 74 or 76. Alternatively, variants of the polypeptide may comprise or consist of a sequence having at least 85% identity with SEQ ID NO: 61, 66, 72, 74 or 76. Variants of the polypeptide may comprise or consist of a sequence having at least 90% identity with SEQ ID NO: 61, 66, 72, 74 or 76. Variants of the polypeptide may comprise or consist of a sequence having at least 95% identity with SEQ ID NO: 61, 66, 72, 74 or 76. Variants of the polypeptide may comprise or consist of a sequence having at least 98% identity with SEQ ID NO: 61, 66, 72, 74 or 76. Variants of the polypeptide may comprise or consist of a sequence having at least 99% identity with SEQ ID NO: 61, 66, 72, 74 or 76.

Variants of conserved peptide sequences may comprise or consist of a truncated sequence of the conserved peptide sequences. For example, any one or more of the sequences of SEQ ID NOs: 1 to 59, herein may be truncated and still provide immunogenicity in the polypeptide. The truncated sequence may comprise a sufficient number of amino acids to form a recognisable epitope (e.g. at least the minimum number of residues for specific T cell recognition) from a sequence within any one of the sequences of SEQ ID NOs: 1 to 59. The truncated sequence may comprise at least 7 amino acids of the sequences of SEQ ID NOs: 1 to 59. Alternatively, the truncated sequence may comprise at least 8 amino acids of the sequences of SEQ ID NOs: 1 to 59. Alternatively, the truncated sequence may comprise at least 9, 10, 11 or 12 amino acids of the sequences of SEQ ID NOs: 1 to 59. Multiple truncated sequences may be provided within one of the conserved peptide sequences of SEQ ID NOs: 1 to 59.

In one embodiment, any one of the conserved peptide sequences of SEQ ID NOs: 1 to 59 may be varied, for example by residue substitution, addition or deletion. In another embodiment, some or all of the conserved peptide sequences of SEQ ID NOs: 1 to 59 may be varied, for example by residue substitution, addition or deletion. The variant conserved peptide sequences may still function to provide recognisable HPV epitopes. The skilled person will understand that natural variation exists in any given population and that these variants may have some sequence variation with the consensus sequence, or example patient sequences provided in SEQ ID NOs: 1 to 59. Therefore, a variant conserved peptide sequence may have at least 70% sequence identity with any one of SEQ ID NOs: 1 to 59. In another embodiment, a variant conserved peptide sequence may have at least 74% sequence identity with any one of SEQ ID NOs: 1 to 59. In another embodiment, a variant conserved peptide sequence may have at least 75% sequence identity with any one of SEQ ID NOs: 1 to 59. In another embodiment, a variant conserved peptide sequence may have at least 79% sequence identity with any one of SEQ ID NOs: 1 to 59. In another embodiment, a variant conserved peptide sequence may have at least 80% sequence identity with any one of SEQ ID NOs: 1 to 59. In another embodiment, a variant conserved peptide sequence may have at least 82% sequence identity with any one of SEQ ID NO s: 1 to 59. In another embodiment, a variant conserved peptide sequence may have at least 83% sequence identity with any one of SEQ ID NOs: 1 to 59. In another embodiment, a variant conserved peptide sequence may have at least 85% sequence identity with any one of SEQ ID NOs: 1 to 59. In another embodiment, a variant conserved peptide sequence may have at least 88% sequence identity with any one of SEQ ID NOs: 1 to 59. In another embodiment, a variant conserved peptide sequence may have at least 90% sequence identity with any one of SEQ ID NOs: 1 to 59. In another embodiment, a variant conserved peptide sequence may have at least 92% sequence identity with any one of SEQ ID NOs: 1 to 59. In another embodiment, a variant conserved peptide sequence may have at least 95% sequence identity with any one of SEQ ID NOs: 1 to 59. In another embodiment, a variant conserved peptide sequence may have at least 98% sequence identity with any one of SEQ ID NOs: 1 to 59. In another embodiment, a variant conserved peptide sequence may have at least 99% sequence identity with any one of SEQ ID NOs: 1 to 59. In another embodiment, a variant conserved peptide sequence may have at least 99.5% sequence identity with any one of SEQ ID NOs: 1 to 59.

Reference to sequence "identity" used herein may refer to the percentage identity between two aligned sequences using standard NCBI BLASTp parameters (http://blast.ncbi.nlm.nih.gov).

The conserved peptide sequences may vary in length, with the minimum length being defined as the minimum number of residues required to form a recognisable epitope. Therefore, the conserved peptide sequence may be from about 7 to 250 amino acids in length, or more. For example, at least one conserved peptide sequence may be at least about 7 amino acids in length. In another embodiment, at least one conserved peptide sequence may be at least about 8 amino acids in length. In another embodiment, at least one conserved peptide sequence may be at least about 10 amino acids in length.

In another embodiment, at least one conserved peptide sequence may be at least about 15 amino acids in length. In another embodiment, at least one conserved peptide sequence may be at least about 20 amino acids in length. In another embodiment, at least one conserved peptide sequence may be at least about 30 amino acids in length. In one embodiment, at least one conserved peptide sequence may be between about 20 and about 220 amino acids in length. In one embodiment, at least one conserved peptide sequence may be no more than about 300 amino acids in length. In another embodiment, at least one conserved peptide sequence may be no more than about 250 amino acids in length. In another embodiment, at least one conserved peptide sequence may be no more than about 200 amino acids in length. In another embodiment, at least one conserved peptide sequence may be no more than about 150 amino acids in length. In another embodiment, at least one conserved peptide sequence may be no more than about 100 amino acids in length. In another embodiment, at least one conserved peptide sequence may be no more than about 55 amino acids in length. In another embodiment, at least one conserved peptide sequence may be no more than about 54 amino acids in length.

The conserved peptide sequences may be an average length of between about 15 and about 50 amino acids in a population of conserved peptide sequences.

In some embodiments of the invention, the polypeptide may further comprise a peptide adjuvant, such as a TPA (tissue plasminogen activator) sequence, or functional variants thereof. The TPA may comprise or consist of the sequence: MDAMKRGLCCVLLLCGAVFVSPSQEIHARFRR (SEQ ID NO: 63), or a functional variant thereof. In one embodiment, the peptide adjuvant may comprise a Shark invariant chain, for example of the sequence SLLWGGVTVLAAMLIAGQVASSVVFLV (SEQ ID NO: 64), or a functional variant thereof. The peptide adjuvant may be N-terminal on the polypeptide of the invention. A functional variant of a peptide adjuvant may be a truncated or mutated peptide variant, which can still function as an adjuvant, for example a truncated or mutated variant of the TPA or shark invariant chain, which still function as an adjuvant. The skilled person will appreciate that 1, 2, 3, 4, 5 or more amino acid residues may be substituted, added or removed without affecting function. For example, conservative substitutions may be considered. In embodiments, where a peptide adjuvant is provided (or encoded as appropriate), there may additionally be provided a linker sequence provided (or encoded) between the peptide adjuvant and the first conserved peptide sequence. In embodiments without the peptide adjuvant, the first linker sequence may not be provided.

Combinations of nucleic acids may encode different polypeptides according to the invention may be provided as a vaccine. For example, a prime and/or boost vaccine formulation may comprise nucleic acid or viral vector encoding two or more polypeptides of the invention, which may be different relative to each other.

The nucleic acid may be used in a vaccine in combination with another therapeutically or prophylactically active ingredient. The nucleic acid may be used in a vaccine in combination with an adjuvant.

According to another aspect of the invention there is provided a composition comprising a plurality of different nucleic acids according to the invention, optionally wherein the composition is a pharmaceutically acceptable composition.

According to another aspect of the invention there is provided a polypeptide encoded by the nucleic acid according to the invention herein.

In one embodiment the polypeptide is an isolated polypeptide. The polypeptide, nucleic acid encoding the polypeptide, or associated viral particle may be provided in a pharmaceutically acceptable carrier.

The nucleic acid may be a plasmid vector for vaccination. The nucleic acid may comprise viral vector sequences.

According to another aspect of the invention there is provided a viral vector comprising the nucleic acid according to the invention herein.

The viral vector may comprise a virus. The viral vector may comprise an adenovirus, such as a human or simian adenovirus. The viral vector may comprise an adenovirus when used in a prime vaccine of a prime boost regime. The viral vector may comprise ChAdOx1 (a group E simian adenovirus, like the AdCh63 vector used safely in malaria trials) or ChAdOx2 (as described in Morris et al 2016. Future Virol 11(9), pp. 649-659). The ChAdOx2 sequence may comprise or consist of the sequence described herein (e.g. SEQ ID NOs: 67+68). The viral vector may comprise AdCh63. The viral vector may comprise AdC3 or AdH6. The viral vector may be a human serotype. The viral vector may comprise Modified Vaccinia Ankara (MVA). The viral vector may comprise F11 MVA (e.g. MVA with the nucleic acid construct insert at the F11 locus). The nucleic acid of the invention (the HPV vaccine construct insert) may be inserted at the TK locus of parental MVA virus under the control of the p7.5 promoter, for example through recombination with the p7.5 MVA shuttle plasmid (SEQ ID NO: 158). The nucleic acid may comprise the sequence of SEQ ID NO: 158 with the nucleic acid vaccine construct insert as provided in SEQ ID NO: 158 (underlined), or with an alternative nucleic acid vaccine construct in accordance with the invention herein. In another embodiment, the nucleic acid of the invention (the HPV vaccine construct insert) may be inserted at the F11 locus of parental MVA virus under the control of the F11 promoter, for example through recombination with the F11 shuttle plasmid (SEQ ID NO: 159). The nucleic acid may comprise the sequence of SEQ ID NO: 159 with the nucleic acid vaccine construct insert as provided in SEQ ID NO: 159 (underlined), or with an alternative nucleic acid vaccine construct in accordance with the invention herein. The MVA sequence may comprise or consist of the sequence described herein (e.g. SEQ ID NOs: 69+70). The viral vector may comprise MVA when used as a vaccine boost in a prime boost regime. The viral vector may comprise Adeno-associated virus (AAV) or lentivirus. The viral vector may be an attenuated viral vector. The polypeptide sequence of the invention may be cloned into any suitable viral vector that is known to elicit good immune response. Suitable viral vectors have been described in Dicks et al (Vaccine. 2015 Feb. 25; 33(9):1121-8. doi: 10.1016/j.vaccine.2015.01.042. Epub 2015 Jan. 25), Antrobus et al (Mol Ther. 2014 March; 22(3):668-74. doi: 10.1038/mt.2013.284. Epub 2013 Dec. 30), and (Warimwe et al. (Virol J. 2013 Dec. 5; 10:349. doi: 10.1186/1743-422X-10-349), which are incorporated herein by reference.

According to another aspect of the invention there is provided a composition comprising one or more of:
the polypeptide according to the invention;
the nucleic acid according to the invention; and
the viral vector according to the invention.

The composition may be immunogenic, for example in a mammal, such as a human. The composition may comprise a pharmaceutically acceptable carrier. The composition may be a pharmaceutical composition comprising a pharmaceutically acceptable carrier. The composition may be for use in the prophylaxis or treatment of HPV infection.

According to another aspect of the invention there is provided a method of treatment or prophylaxis of HPV infection comprising the administration of:
the polypeptide according to the invention;
the nucleic acid according to the invention;
the composition according to the invention or
the viral vector according to the invention.

The method of treatment or prophylaxis of HPV infection may be a method of vaccination.

According to another aspect of the invention there is provided an agent for use in the prophylaxis or treatment of HPV infection, the agent comprising or consisting of:
the polypeptide according to the invention;
the composition according to the invention;
the nucleic acid according to the invention; or
the viral vector according to the invention.

In one embodiment, the treatment or prophylaxis of HPV infection comprises the treatment or prophylaxis of an anogenital HPV-driven lesion, such as anal, vulval, vaginal, or penile intraepithelial neoplasia. Additionally or alternatively, the treatment or prophylaxis of HPV infection comprises the treatment or prophylaxis of an oropharyngeal lesion that is caused by HPV.

According to another aspect of the invention there is provided the polypeptide according to the invention; the composition according to the invention; the nucleic acid according to the invention; or the viral vector according to the invention; for use in, or as, a vaccine.

According to another aspect of the invention there is provided a vaccine comprising the nucleic acid of the invention; the polypeptide according to the invention; the composition according to the invention; or the viral vector according to the invention.

The vaccine may be a prime vaccine. The vaccine may be a boost vaccine. Where a boost vaccine is provided following a prime vaccine, the polypeptide may be different. For example, the polypeptide may comprise a re-ordered sequence of conserved peptide sequences. The conserved peptide sequences may be identical, but the order in which they are provided in the polypeptide may be changed. Therefore, the invention herein provides any of the sequences/embodiments of the invention wherein the order in which conserved peptide sequences are provided may be changed. Such embodiments may also include re-ordered or differed linker/junction sequences.

Advantageously, the re-ordering of the conserved peptide sequences of the polypeptide between prime and boost vaccines can avoid the provision of "false" epitopes formed across junctions of one conserved peptide sequence with another conserved peptide sequence. i.e. the same junction may not occur in the re-ordered polypeptide.

According to another aspect of the invention, there is provided a nucleic acid or polypeptide according to the invention for use in, or as, a vaccine.

According to another aspect of the invention, there is provided a prime boost vaccination kit comprising
a prime vaccination according to the invention;
a boost vaccination according to the invention.

The prime and boost vaccinations may be different. The prime and boost vaccination may differ in the polypeptide sequence. The prime and boost vaccination may comprise different viral vectors (i.e. from different virus families such as MVA vs adenovirus).

According to another aspect of the invention, there is provided a composition comprising a nucleic acid according to the invention herein, and a pharmaceutically acceptable carrier.

The composition may not comprise wild-type HPV. The composition may not comprise full length HPV protein sequence. The viral vector or nucleic acid may not encode non-conserved protein/peptide sequence of HPV.

The use may be with a pharmaceutically acceptable carrier. Additionally or alternatively, the use may be with an adjuvant.

The term "immunogenic", when applied to the nucleic acid, polypeptide or composition of the present invention means capable of eliciting an immune response in a human or animal body. The immune response may be protective.

The term "protective" means prevention of a disease, a reduced risk of disease infection, transmission and/or progression, reduced severity of disease, a cure of a condition or disease, an alleviation of symptoms, or a reduction in severity of a disease or disease symptoms.

The term "prophylaxis" means prevention of or protective treatment for a disease. The prophylaxis may include a reduced risk of disease infection, transmission and/or progression, or reduced severity of disease.

The term "treatment", means a cure of a condition or disease, an alleviation of symptoms, or a reduction in severity of a disease or disease symptoms.

The skilled person will understand that optional features of one embodiment or aspect of the invention may be applicable, where appropriate, to other embodiments or aspects of the invention.

Embodiments of the invention will now be described in more detail, by way of example only, with reference to the accompanying drawings.

FIG. 1—Chimeric and Variant methods used to create HPV candidates.

FIG. 2—Conserved regions with resultant variants below. See Table 9 for sequences and associated SEQ ID NO identifiers.

FIG. 3—A) Regions identified as conserved in the two genotypes used to form chimerics. B) Conservation plot of Modified variant. See Table 9 for sequences and associated SEQ ID NO identifiers.

FIG. 4—A) Regions identified as conserved in the two genotypes used to form chimerics. B) Conservation plot of variants, See Table 9 for sequences and associated SEQ ID NO identifiers.

FIG. 5—Regions identified as conserved in the two genotypes used to form chimerics FIG. 6—Regions identified as conserved in the two genotypes used to form chimeric-variants FIG. 7—Regions identified as conserved in the two genotypes used to form chimeric FIG. 8—High frequencies of vaccine-specific T cells are induced following prime boost vaccination. IFNγ Elispot performed on PBMCs from C57BL/6 mice (six/group) primed intramuscularly with DNA-HPV, MVA-HPV or ChAdOx1-5GHPV3 and then boosted intramuscularly with a heterologous or homologous vaccine two weeks later. PBMCs were collected by tail vein bleed two weeks post prime and one and two weeks post boost.

FIG. 9—Prime boost vaccination is capable of inducing responses to all antigens encoded in the immunogen. PBMCs were collected at two weeks boost and used in an IFNγ Elispot with peptides spanning the entire immunogen sequence, pooled according to protein source. Peptides spanning the E2 region of the immunogen were split into two pools because of the large number of peptides and peptides for regions spanning E4 and E5 were combined into one pool.

FIG. 10—Vaccine-specific CD8+ T cells can be detected at high frequencies six weeks after ChAdOx1-5GHPV3 prime MVA-5GHPV3 boost. 10a IFNγ Elispot using PBMCs collected by tail vein bleed two, three, four and six weeks post boost (DM; DNA-5GHPV3 prime MVA-5GHPV3 boost, CM; ChAdOx1-5GHPV3 prime MVA-5GHPV3 boost). 10b ICS performed on PBMCs obtained one week and six weeks post ChAdOx1-5GHPV3 prime, MVA-5GHPV3 boost. PBMCs stimulated with E6 and E7 peptide pools. Measured IFN-γ, CD107, TNF-α and IL2.

FIG. 11—HPV E6- and E7-specific CD8+ T cell responses are polyfunctional and have cytotoxic potential. PBMCs from a tail vein bleed collected one week post ChAdOx1-5GHPV3 prime MVA-5GHPV3 boost were stimulated with immunodominant peptide pools E6 and E7 and sub pool 22 which is the dominant sub pool within E6. Responding CD8+ T cells predominantly express three functions (CD107, IFNγ and TNFα).

FIG. 12—ChAdOx1-5GHPV3 prime MVA-5GHPV3 boost also primes HPV E6- and E7-specific CD4+ T cell responses that are still detectable six weeks post boost. ICS performed on PBMCs obtained one week and six weeks post ChAdOx1-5GHPV3 prime, MVA-5GHPV3 boost. PBMCs stimulated with E6 and E7 peptide pools. Measured IFN-γ, CD107, TNF-α and IL2.

FIG. 13—Most E6 and E7-specific CD4+ T cells express two functions. PBMCs from a tail vein bleed collected one week post ChAdOx1-5GHPV3 prime MVA-5GHPV3 boost were stimulated with immunodominant peptide pools E6 and E7 and sub pool 22 which is the dominant sub pool within E6. Responding CD4+ T cells predominantly express two functions (Discounting CD107+ monofunctional cells).

FIG. 14—HPV E6- and E7-specific CD8+ T cells can be detected in the cervix. ICS was performed on cervicovaginal lymphocytes isolated from mice two weeks post ChAdOx1-5GHPV3 prime MVA-5GHPV3 boost and stimulated with immunodominant peptide pools E6 and E7 and sub pool 22. Measured IFN-γ, CD107, TNF-α and IL2.

Figure 15:
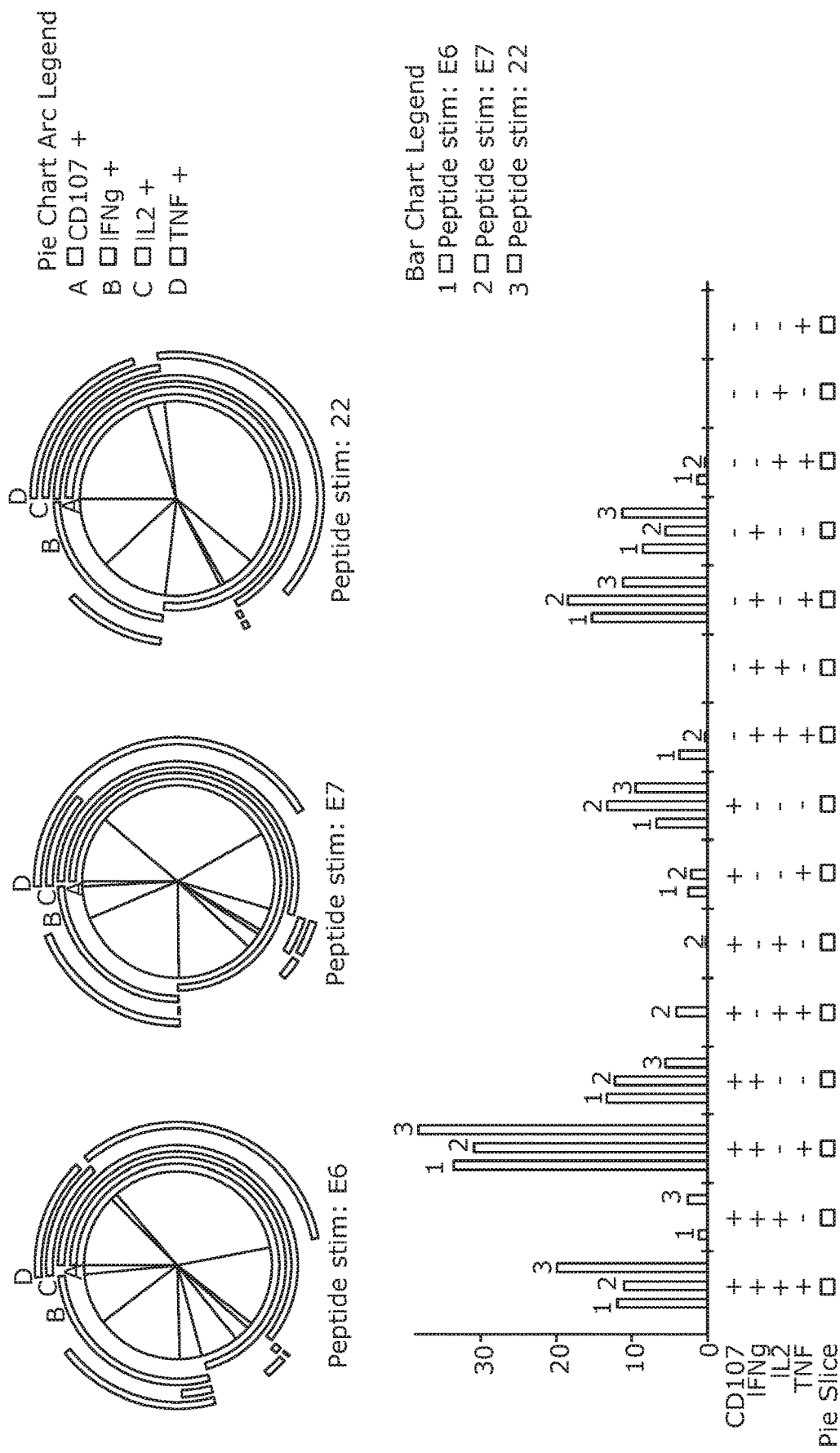

FIG. 15—Cervicovaginal HPV E6- and E7-specific CD8+ T cell responses are polyfunctional. Cervicovaginal lymphocytes collected one week post ChAdOx1-5GHPV3 prime MVA-5GHPV3 boost were stimulated with immunodominant peptide pools E6 and E7 and sub pool 22 which is the dominant sub pool within E6. Responding CD8+ T cells predominantly express three functions (CD107, IFNγ and TNFα).

Figure 16:
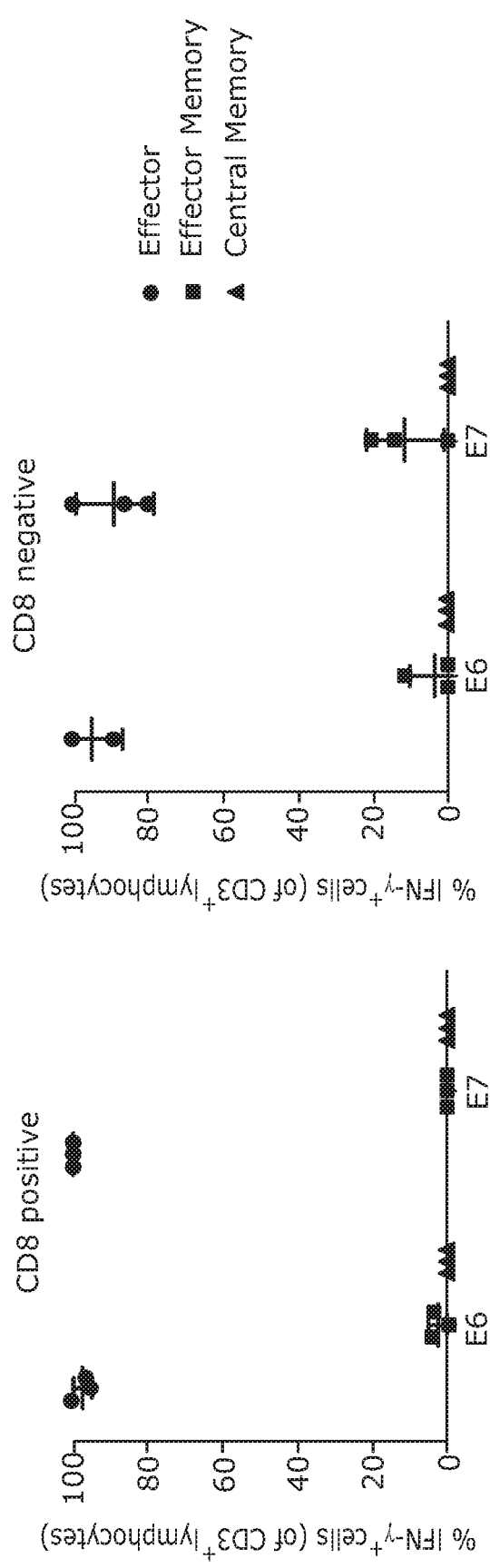
Figure 17:
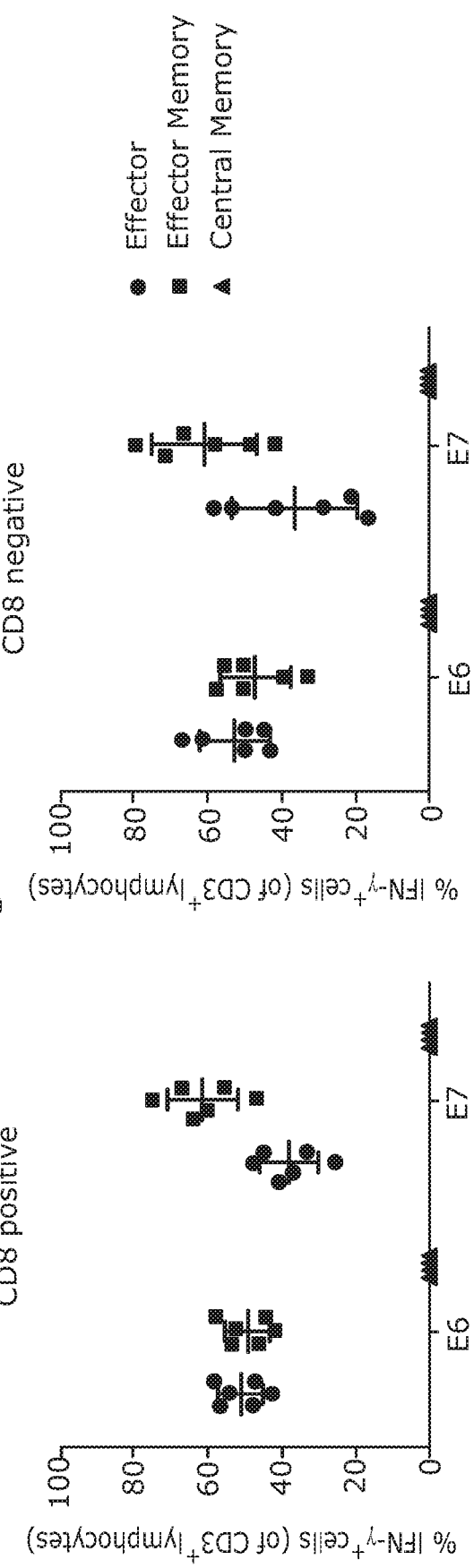

FIG. 16—Vaccine-induced E6 and E7-specific CD8+ and CD4+ T cells in the cervix are almost exclusively of effector phenotype. Naïve: CD44-CD62L+. Antigen-experienced: Central memory—CD62L+, CD127+; Effector memory—CD62L-, CD127+; Effector—CD62L-, CD127-. Cervical lymphocytes from six mice pooled into three pairs, due to low lymphocyte numbers FIG. 17—In contrast to cervix, vaccine-induced E6 and E7-specific CD8+ and CD4+ T cells in the spleen comprise effector and effector memory populations.

Figure 18:
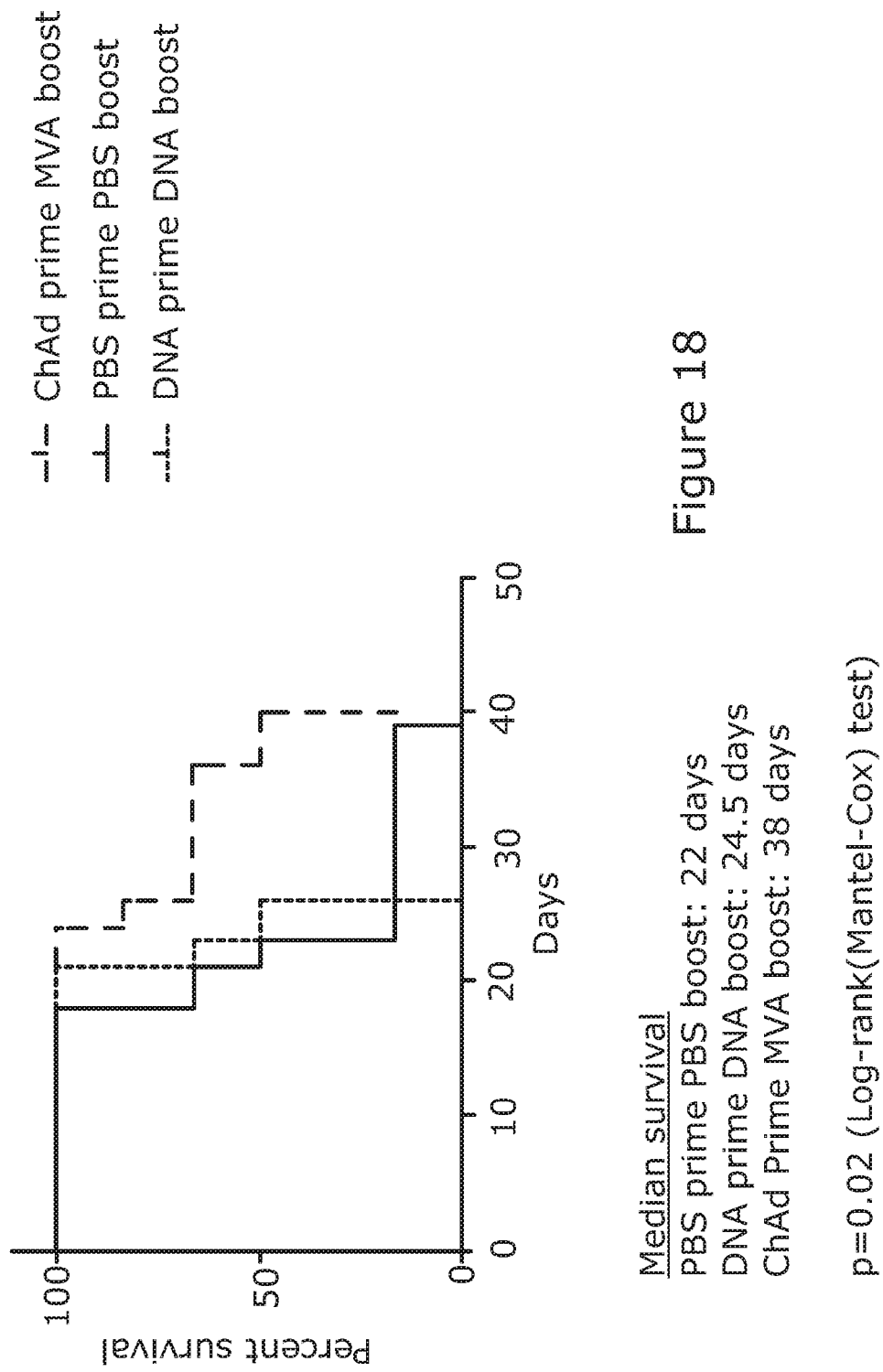

FIG. 18—Mice vaccinated with ChAdOx1-5GHPV3 prime, MVA-5GHPV3 boost show increased survival over control mice. Mice were inoculated with $5\times10^4$ TC-1 cells on day 0 and then primed on day 3 and boosted on day 17. Tumours were measured with digital callipers every two days and mice culled when tumours reached 10 mm in any one direction.

Figure 19:
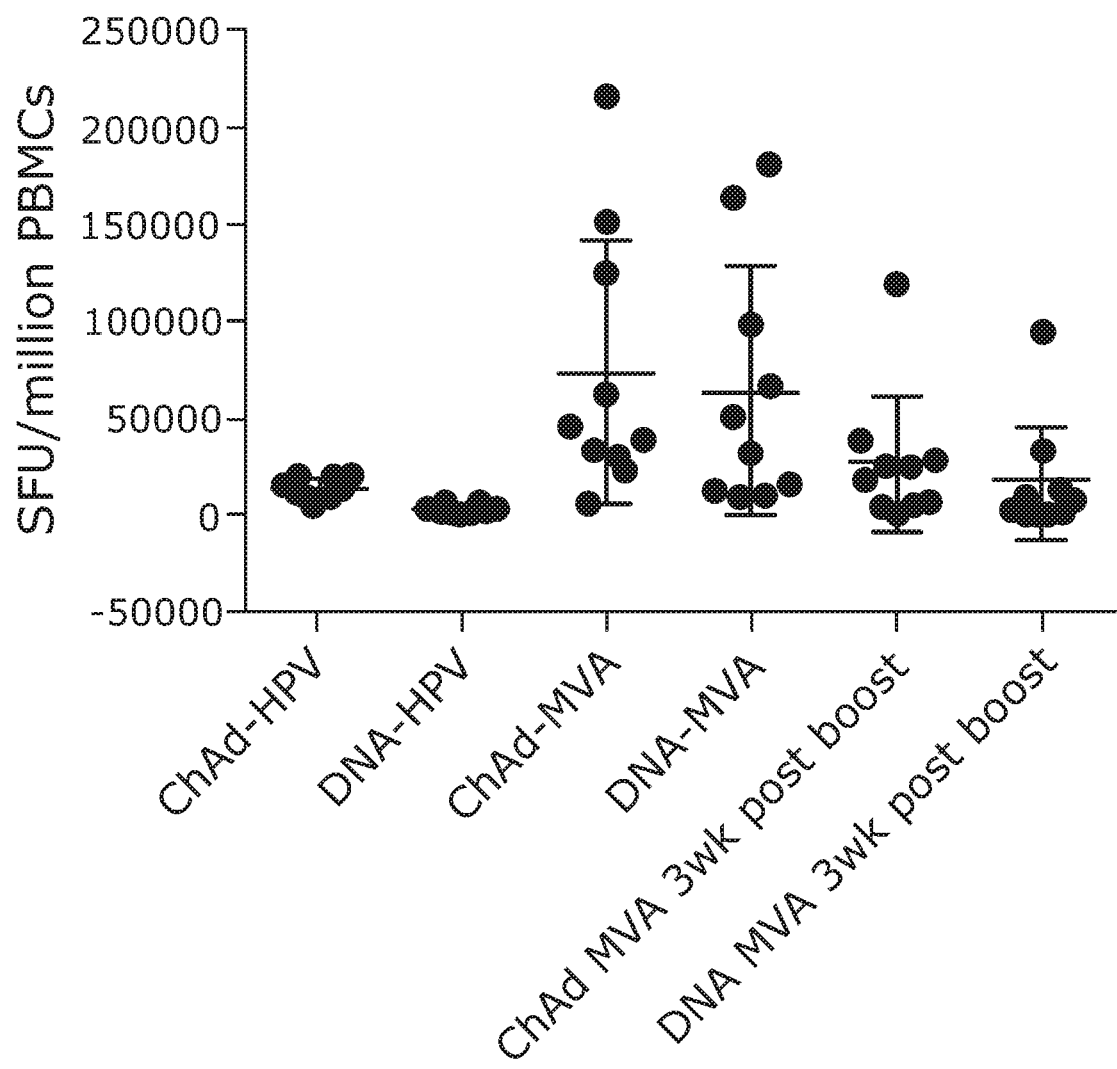

FIG. 19—Vaccination of outbred CD1 mice induces high frequency T cell responses. IFNγ Elispot performed on PBMCs from CD1 mice (ten/group) primed intramuscularly with DNA-5GHPV3, MVA-5GHPV3 or ChAdOx1-5GHPV3 and then boosted intramuscularly with a heterologous or homologous vaccine two weeks later. PBMCs were collected by tail vein bleed two weeks post prime and two and three weeks post boost.

Figure 20:
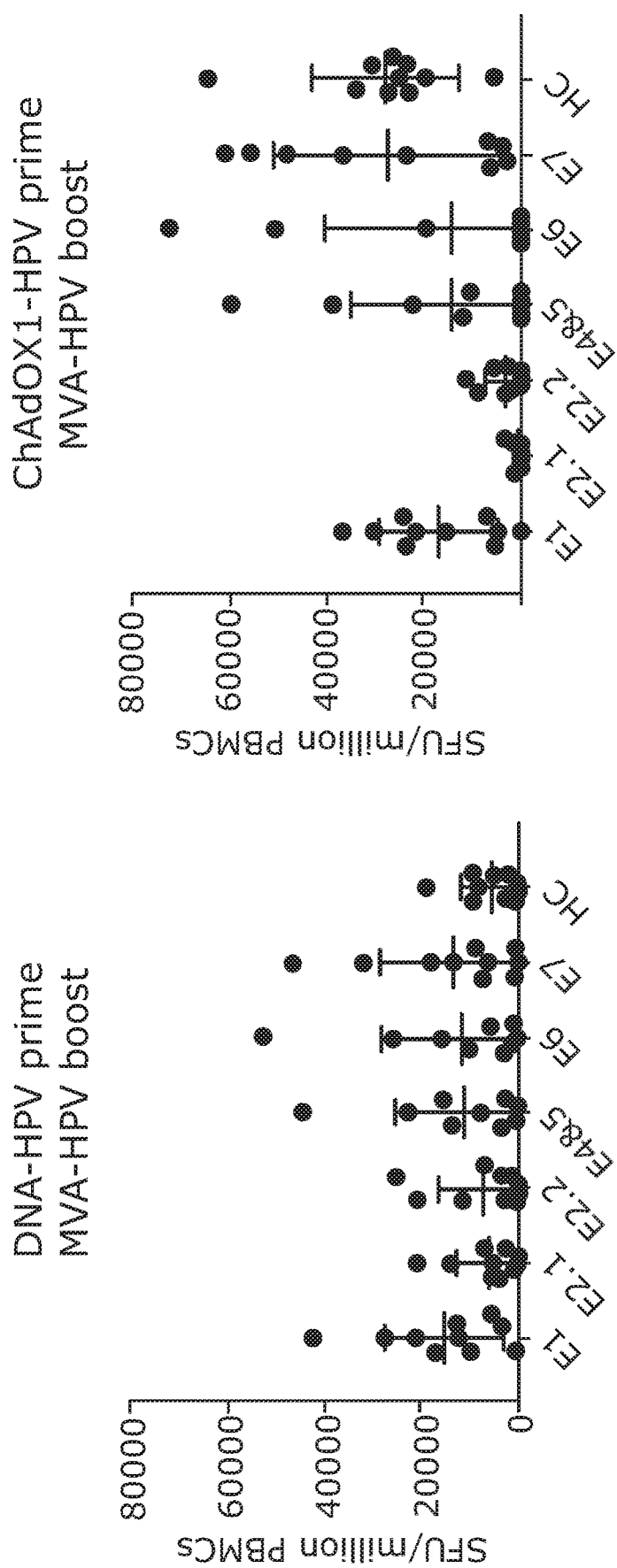

FIG. 20—T cell responses in vaccinated CD1 mice are directed across the entire immunogen. PBMCs were collected at two weeks boost and used in an IFNγ Elispot with peptides spanning the entire immunogen sequence, pooled according to protein source. Peptides spanning the E2 region of the immunogen were split into two pools because of the large number of peptides and peptides for regions spanning E4 and E5 were combined into one pool.

Figure 21:
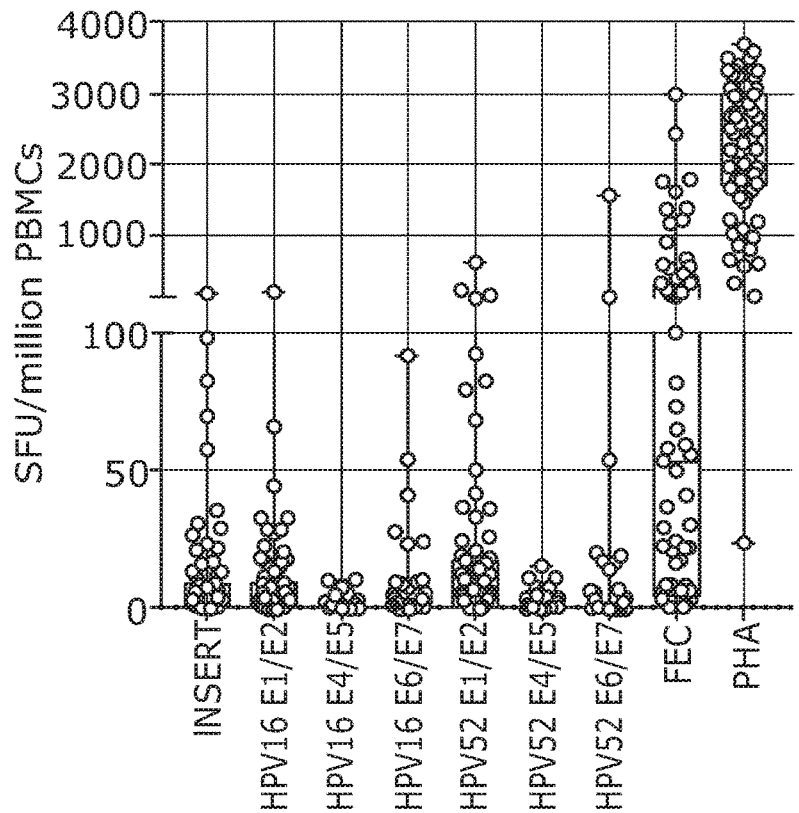
Figure 21:
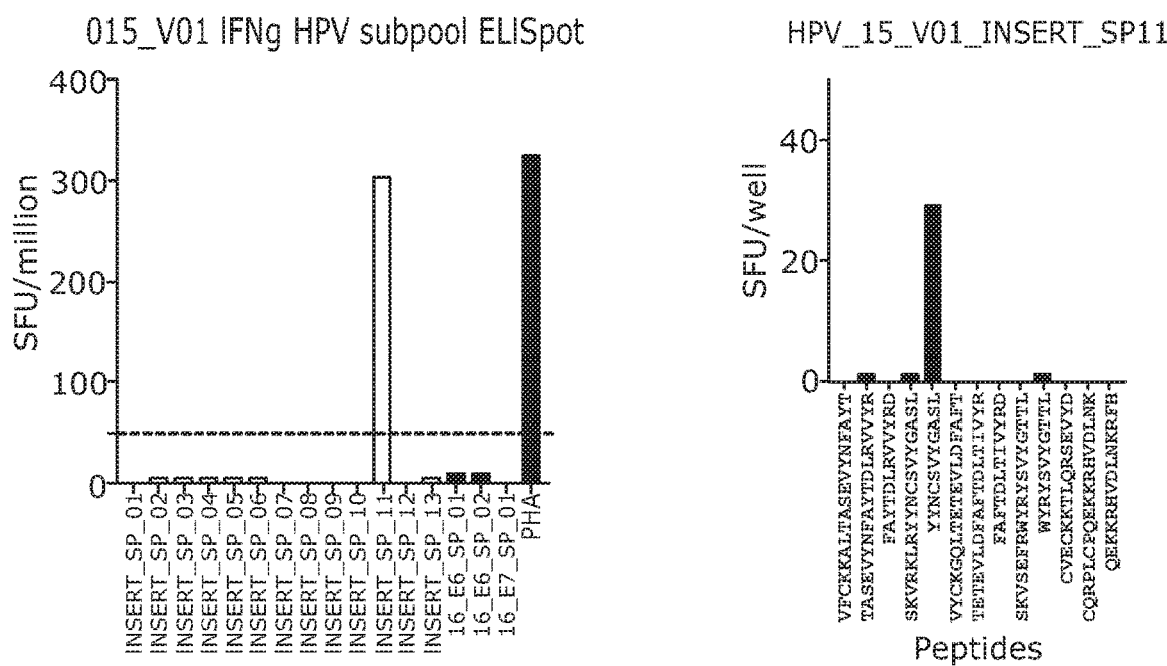

FIG. 21—Top panel: Peripheral blood mononuclear cells (PBMC) from 76 women aged 16-24 years were tested for recognition of peptides based on early proteins from high risk HPV (hrHPV) in ex vivo IFN-γ Elispot assays. 'Insert' is a pool of 15-mer peptides overlapping by 11 amino acid spanning the hrHPV transgene. 'Reference' peptides were pools of peptides based on early proteins from HPV16 and HPV52, which were combined as follows: E1/E2, E4/E5 and E6/E7. TEC' (flu, EBV and CMV) peptides and PHA (phytohaemaglutinnin) were used as positive controls. The data shown are the spot-forming units (SFU) obtained from peptide-stimulated wells after subtraction of negative control values (mock-stimulated cells). The cut-off for a positive response was set at 25 SFU/million PBMC (derived from the mean of mock-stimulated values from all donors+2 standard deviations). Women were tested concurrently for hrHPV DNA on vaginal sampling: 26% tested positive. The data show that 9/76 women with current hrHPV infection or prior exposure recognised HPV sequences encoded in the transgene. Bottom panel: Responses to the insert pool were interrogated further in one responding donor by testing PBMC with subpools of the insert pool (left, SFU per million PBMC), followed by individual peptides within the pools (right, SFU per well), thus confirming the presence of a true HPV-specific response. SFU—spot-forming units reported as either per well, which contains 200,000 PBMC or per million PBMC).

Figure 22:
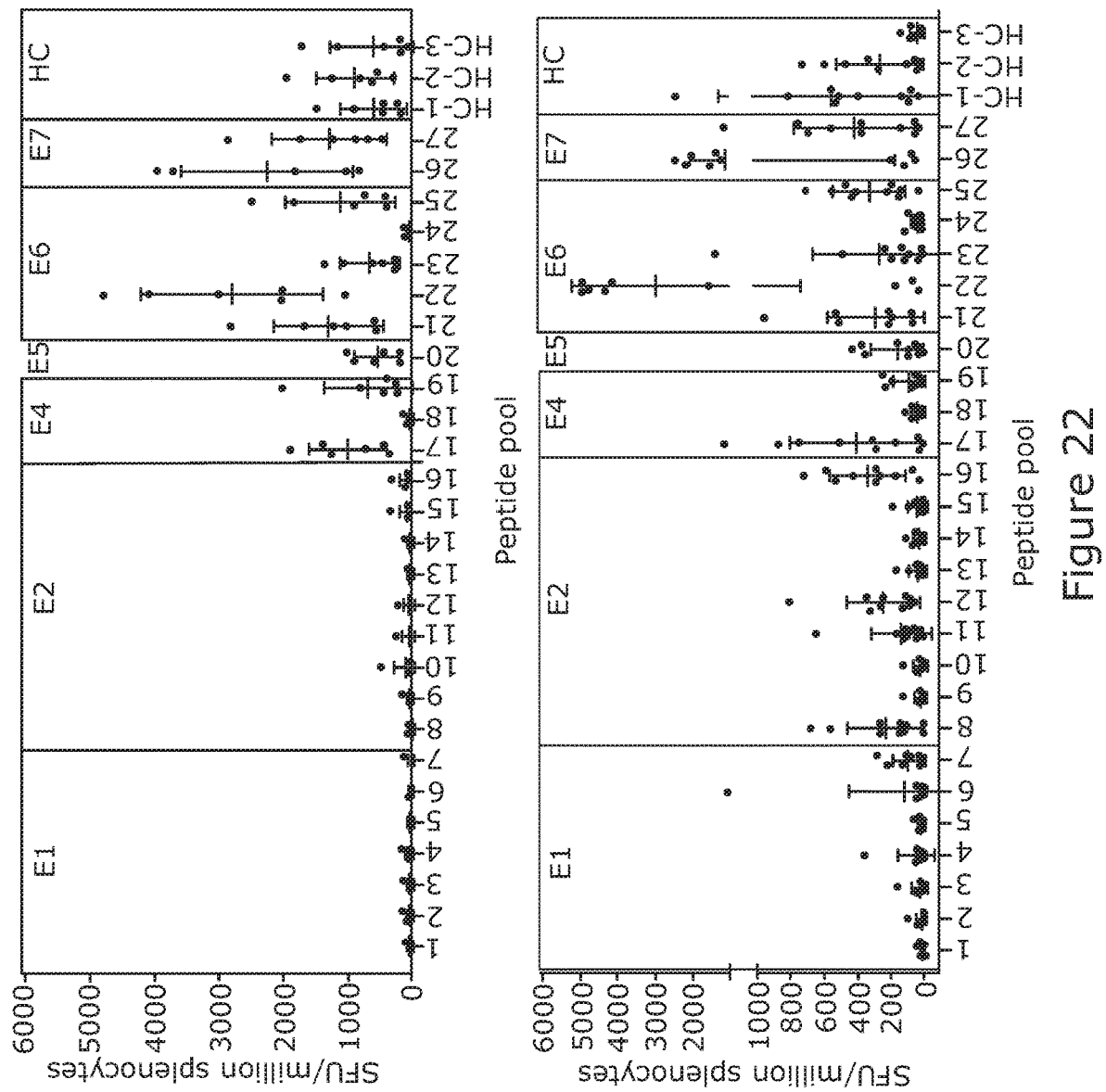

FIG. 22—Subpool mapping in C57BL/6 mice (top panel) and CD1 mice (bottom panel) following ChAdOX1-5G-HPV3 prime MVA-5GHPV3 boost. Mice were culled two weeks post boost and splenocytes isolated. Splenocytes used in an IFNγ Elispot assay using subpools that cover the immunogen sequence. Subpools 21, 25 and 26 (for example) contain no HPV53 sequences and still get high magnitude responses, thus providing evidence that a sequence without the HPV53 segments would still be immunogenic.

HPV Immunogen Design

The HPV immunogen is composed of amino acid fragments conserved and geographically representative of the global HPV population at a protein level. Each fragment is created using a conservation algorithm which has been utilised to create either Chimeric or Variant based fragments. The choice being dependent on characteristics of each HPV protein used.

The core conservation algorithm uses a sliding window approach in combination with a normalisation method that accounts for collection bias to identify windows which are conserved both within (intra-genotype) and between (inter-genotype) genotypes. Intra-genotype conserved windows are classed as windows with a conservation value less than one quartile of the sum of all window conservation values for the whole sequence. A normalised representative consensus sequence is created for each genotype during this process. Subsequently inter-genotype windows are identified as windows at the same position in each genotype which are conserved and have a shared consensus identity of >60%.

A key challenge in creating sequences which represent all the selected genotypes for a region of each protein was that many genotypes showed unique phylogenetic clustering. There is a critical balance between the identification of regions conserved across genotypes and the level of shared % consensus identity between these regions. In many cases the inter-genotype diversity was so extreme that you sacrifice shared % consensus identity. Meaning some genotypes were so distinct from one another it was impossible to create a representative sequence. To solve this, raw sequences were inputted into the core algorithm in one of two ways (FIG. 1). (i) Variants; Sequences for all genotypes are input into the algorithm and regions of inter-genotype conservation are identified independent of shared % consensus identity. A phylogeny was created from the resultant regions and ingroup sequences combined to create a consensus with a high level of shared consensus identity (FIG. 1*b*). (ii) Chimerics; in some instances the distance between genotypes is so significant that genotypes do not align suitably. Therefore, only genotype ingroups are inputted together into the algorithm, and regions conserved between ingroups with >60% shared consensus identity are identified (FIG. 1*a*).

HPV Candidates

Candidate sequences were created for six HPV proteins (E1-2, E4-7) using input sequences collected from the NCBI protein database, aligned and manually audited to remove incomplete and poor quality sequences (Table 1).

TABLE 1

Number of sequences used as input post audit.

| Protein | Genotype 16 | 18 | 31 | 52 | 53 | 58 |
|---|---|---|---|---|---|---|
| E1 | 126 | 49 | 24 | 27 | 15 | 53 |
| E2 | 195 | 56 | 26 | 32 | 18 | 54 |
| E4 | 161 | 48 | 24 | 24 | 14 | 52 |
| E5 | 197 | 48 | 24 | 24 | — | 60 |
| E6 | 1205 | 78 | 90 | 218 | 131 | 185 |
| E7 | 566 | 70 | 85 | 193 | 114 | 199 |

| Approach: | | Variants |
|---|---|---|
| Fragments: | 1 | E1_V1_52 + 58: DEDETAYDSGTDLIDFIDDS (SEQ ID NO: 1)<br>E1_V1_31 + 16 + 18: DENENDSDTGEDMVDFIDN (SEQ ID NO: 2)<br>E1_V1_53: DETDEESTESDLDGFIDNS (SEQ ID NO: 3) |
| | 2 | Excluded |
| | 3 | E1_V3_31 + 53: AQLADSDSNACAFLK (SEQ ID NO: 4)<br>E1_V3_52 + 58 + 18 + 3016: AQLADVNSNAAAFLK (SEQ ID NO: 5) |
| | 4 | E1_V4_16 + 31: NCILLYGAANTGKSLFGMSL (SEQ ID NO: 6)<br>E1_V4_18 + 52 + 58: NCLVLCGPANTGKSYFGMSL (SEQ ID NO: 7)<br>E1_V4_53: NCLVIYGPPNTGKSCFAMSL (SEQ ID NO: 8) |
| | 5 | E1_V5_16 + 31 + 52: WPYLHSRLVVFTFPNPF (SEQ ID NO: 9)<br>E1_V5_18 + 58: WPYLESRITVFEFPNAF (SEQ ID NO: 10)<br>E1_V5_53: LRYLHSRIHVLQFLNPF (SEQ ID NO: 11) |

Figure 2:
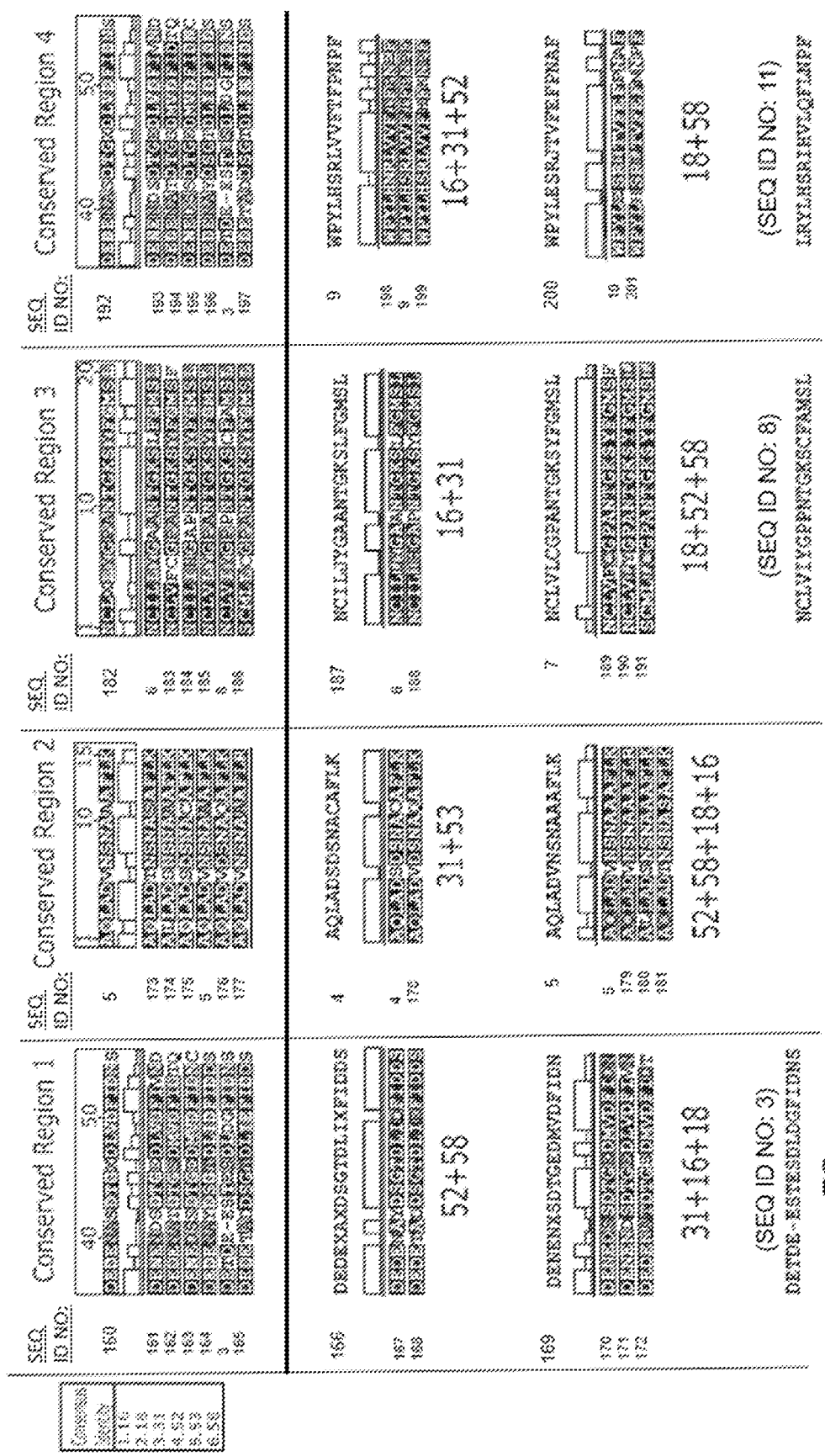

Identified 5 fragments within the E1 protein with windows conserved at the same position within their respective genotypes. Cladistics identified the most suitable genotype combinations providing high level shared consensus identity (FIG. 2).

| Approach: | | Chimerics |
|---|---|---|
| Fragments: | 1<br>(16 + 31) | E2_C1-1_16 + 31 NVCQDKILEHYENDSKD (SEQ ID NO: 12)<br>E2_C1-2_16 + 31 ILEHYENDSKDLCDHI (SEQ ID NO: 13)<br>E2_C1-3_16 + 31 CDHIDYWKHIRLECAIMYKAR (SEQ ID NO: 14)<br>E2_C1-4_16 + 31 IRLECAIMYKAREMGFH (SEQ ID NO: 15)<br>E2_C1-5_16 + 31 QFDGDICNTMHYTNW (SEQ ID NO: 16)<br>E2_C1-6_16 + 31 IYICEDAQCTVVEGQVD (SEQ ID NO: 17)<br>E2_C1-7_16 + 31 KKWEVHAGGQVILCPES (SEQ ID NO: 18)<br>E2_C1-8_16 + 31 GQRRIKRPRSE (SEQ ID NO: 19)<br>E2_C1-9_16 + 31 NCHPNKLL (SEQ ID NO: 20)<br>E2_C1-10_16 + 31 ILKCLRYRFKKHCKL (SEQ ID NO: 21)<br>E2_C1-11_16 + 31 SSTWHWTCHDGKHK (SEQ ID NO: 22)<br>E2_C1-12_16 + 31 WHWTCHDGKHKNAIVTLTY (SEQ ID NO: 23) |
| | 2<br>(52 + 58) | E2_C1-1_52 + 58 YEADKNDLNAQIEHWKLIRMECAIFYKAKELGIS (SEQ ID NO: 24)<br>E2_C1-2_52 + 58 ICHQVVPPLAASKAKACQAIELQLALEALNASPY (SEQ ID NO: 25)<br>E2_C1-3_52 + 58 DEWTLQQTSLEMWLAEPQ (SEQ ID NO: 26)<br>E2_C1-4_52 + 58 FKKHGITITVQYDNDKANTMDYTNWKEIY (SEQ ID NO: 27)<br>E2_C1-5_52 + 58 VIVCPASIPSDEISTEEA (SEQ ID NO: 28) |
| | 3<br>(53 + 18) | E2_C1-1_53 + 18 DHIDYWKAIRQENAIFFAAR (SEQ ID NO: 29)<br>E2_C1-2_53 + 18 HQVVPALNICKAKACKAIE (SEQ ID NO: 30)<br>E2_C1-3_53 + 18 WNTEPKHCFKKGGQHIEVWFD (SEQ ID NO: 31)<br>E2_C1-4_53 + 18 YVAWDSVYYCGDDGWCKT (SEQ ID NO: 32) |

-continued

| | | |
|---|---|---|
| | E2_C1-5_53 + 18 | EAEKYGCKGTWEVHFG (SEQ ID NO: 33) |
| | E2_C1-6_53 + 18 | NSIDCNDSMCSTFDDNVSATELVK (SEQ ID NO: 34) |
| Approach: | | Modified Variant |
| Fragments: 1 | E2_FC1_All | DHIDYWKLIRLECAIFYKAR (SEQ ID NO: 35) |

Due to alignment inconsistencies three chimerics were created based on phylogeny (16 & 31, 52 & 58, 53 & 18) (FIG. 3a). Additionally all genotypes were inputted into the algorithm in a similar fashion to creation of variants but the programs filter for only selecting conserved windows from each genotype with a shared % consensus identity of greater than 60% was not disabled. This identified one fragment, referred to as 'modified variant' (FIG. 3*b*).

| Approach: | | Chimerics |
|---|---|---|
| Fragments: | 1 (16 + 31) | E4_C1-1_16 + 31 RRLSSDQDQSQ (SEQ ID NO: 36) |
| | 2 (52 + 58) | E4_C1-1_52 + 58 LVTKYPLLKLLS (SEQ ID NO: 37) |
| | 3 (53) | E4_C1-1_53 RPPNMGVKAHGKCIWENKVFIVPTLCPVPLDPTYP LLKLLT (SEQ ID NO: 38)<br>E4_C1-2_53 TQTTTPENTSLVELRVTTPKSTVVIRLHL (SEQ ID NO: 39) |
| | 4 (18) | E4_C1-1_18 TTRYPLLSLLNSYSTPPHRIPAPCPWAPQRP (SEQ ID NO: 40) |
| Approach: | | Variants |
| Fragments: | 1 | E4_V1_16 + 31 PIPKPSPWAP (SEQ ID NO: 41)<br>E4_V1_18 RIPAPCPWAP (SEQ ID NO: 42)<br>E4_V1_52 PRPPHCPWVP (SEQ ID NO: 43)<br>E4_V1_53 PPPPPRPWAP (SEQ ID NO: 44)<br>E4_V1_58 Excluded |

Four chimerics were created, two of the fragments are genotype specific (FIG. 4*a*). Additionally, variant analysis identified one region (FIG. 4*b*).

| Approach: | | Chimerics |
|---|---|---|
| Fragments: | 1 (16 + 31) | E5_C1_16_31 CFLLCFCVLLCVCLLIRPLLLSVSTY (SEQ ID NO: 45) |
| | 2 (52 + 58) | E5_C1_52 + 58 LRPLLLSISVYAQVLVLVLLLWVSIGS (SEQ ID NO: 46) |
| | 3 (18) | E5_C1_18 LLPSVCMCAYAWVLVFVYIVVITSPATA (SEQ ID NO: 47) |

Three chimerics were created (FIG. 5).

| Approach: | | Chimeric-Variants |
|---|---|---|
| Fragments: | 1 (16 + 18) | E6_CV1_16 IVYRDGNPYAVCDKCLKFYSKISEYRHYCYSLYGTTLEQQY NKPLCDLLIRCIN (SEQ ID NO: 48)<br>E6_CV1_18 VVYRDSIPHAACHKCIDFYSRIRELRHYSDSVYGDTLEKLTN TGLYNLLIRCLR (SEQ ID NO: 49) |
| | 2 (53 + 31) | E6_CV2-1_53 VFCKKALTASEVYNFAYTDLRVVYRD (SEQ ID NO: 50)<br>E6_CV2-2_53 SKVRKLRYYNCSVYGASL (SEQ ID NO: 51)<br>E6_CV2-1_31 VYCKGQLTETEVLDFAFTDLTIVYRD (SEQ ID NO: 52)<br>E6_CV2-2_31 SKVSEFRWYRYSVYGTTL (SEQ ID NO: 53) |

-continued

| Approach: | Chimeric-Variants |
| --- | --- |
| 3 (5258) | E6_CV3-1_52 + 58 CVECKKTLQRSEVYD (SEQ ID NO: 54)<br>E6_CV3-2_52 + 58 CQRPLCPQEKKRHVDLNKRFH (SEQ ID NO: 55) |

Figure 6:
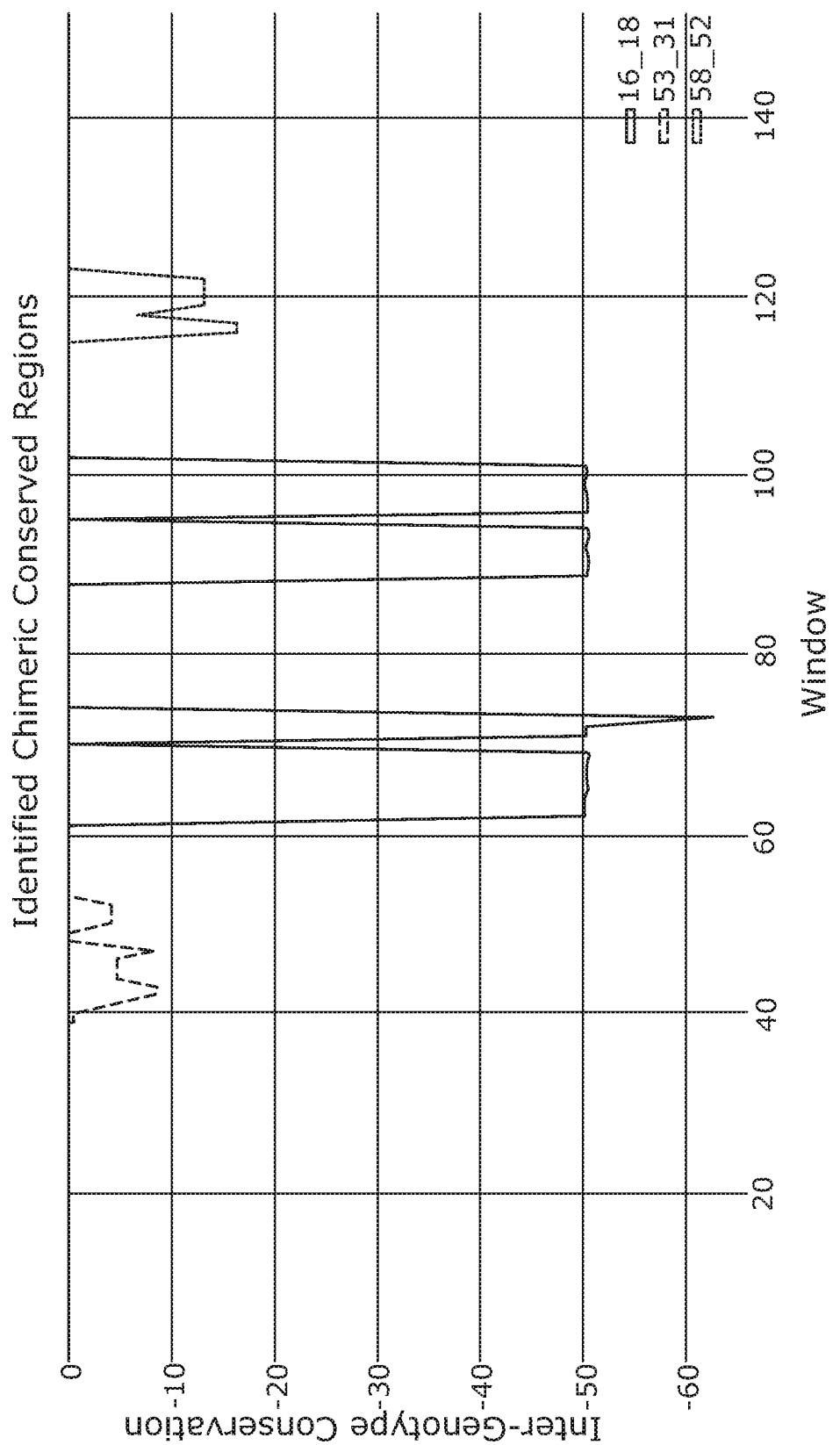

The E6 protein showed very limited conservation across genotypes. Instead ingroups were processed to produce chimerics without the shared % consensus identity filter, but the conserved windows were not combined to produce a consensus, except for genotypes 52 and 58. (FIG. 6)

| Approach: | | Chimerics |
| --- | --- | --- |
| Fragments: | 1 (16 + 31) | E7_C1_16 + 31 TLHEYMLDLQPETTDLYCYEQ (SEQ ID NO: 56) |
| | 2 (52 + 58) | E7_58_52 PETTDLHCYEQLGDSSDEEDTGGLDG (SEQ ID NO: 57) |
| | 3 (53 + 18) | Excluded |

| Approach: | | Chimeric-Variants |
| --- | --- | --- |
| Fragments: | 1 | E7_V1_53 DEDEDEVDHLQEQPQQARRDEQHPCYLIETQCCR CESLV (SEQ ID NO: 58)<br>E7_V1_18 EENDEIDGVNHQHLPARRAEPQRHTMLCMCCKCE ARI (SEQ ID NO: 59) |

Figure 7:
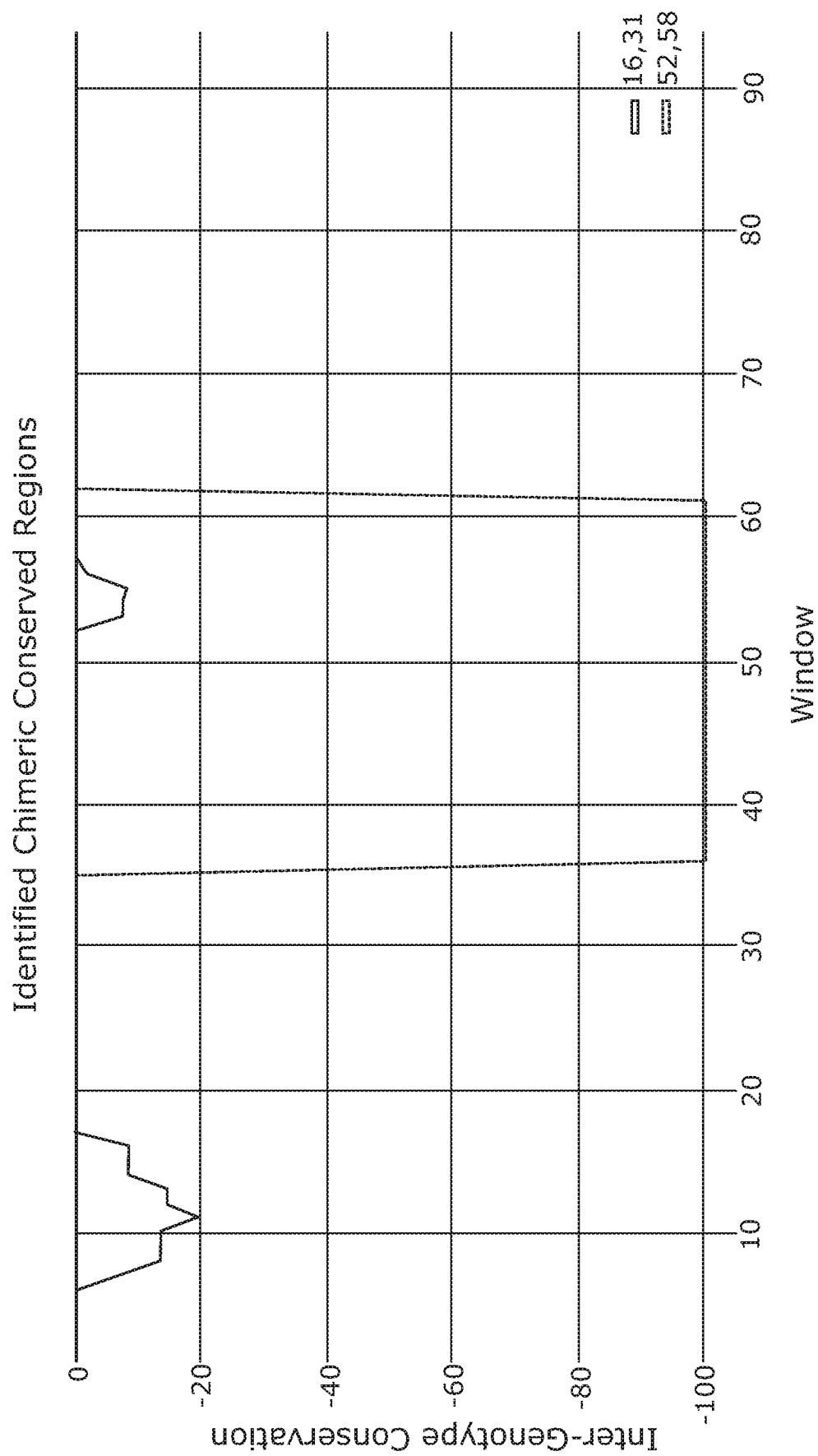
Figure 8:
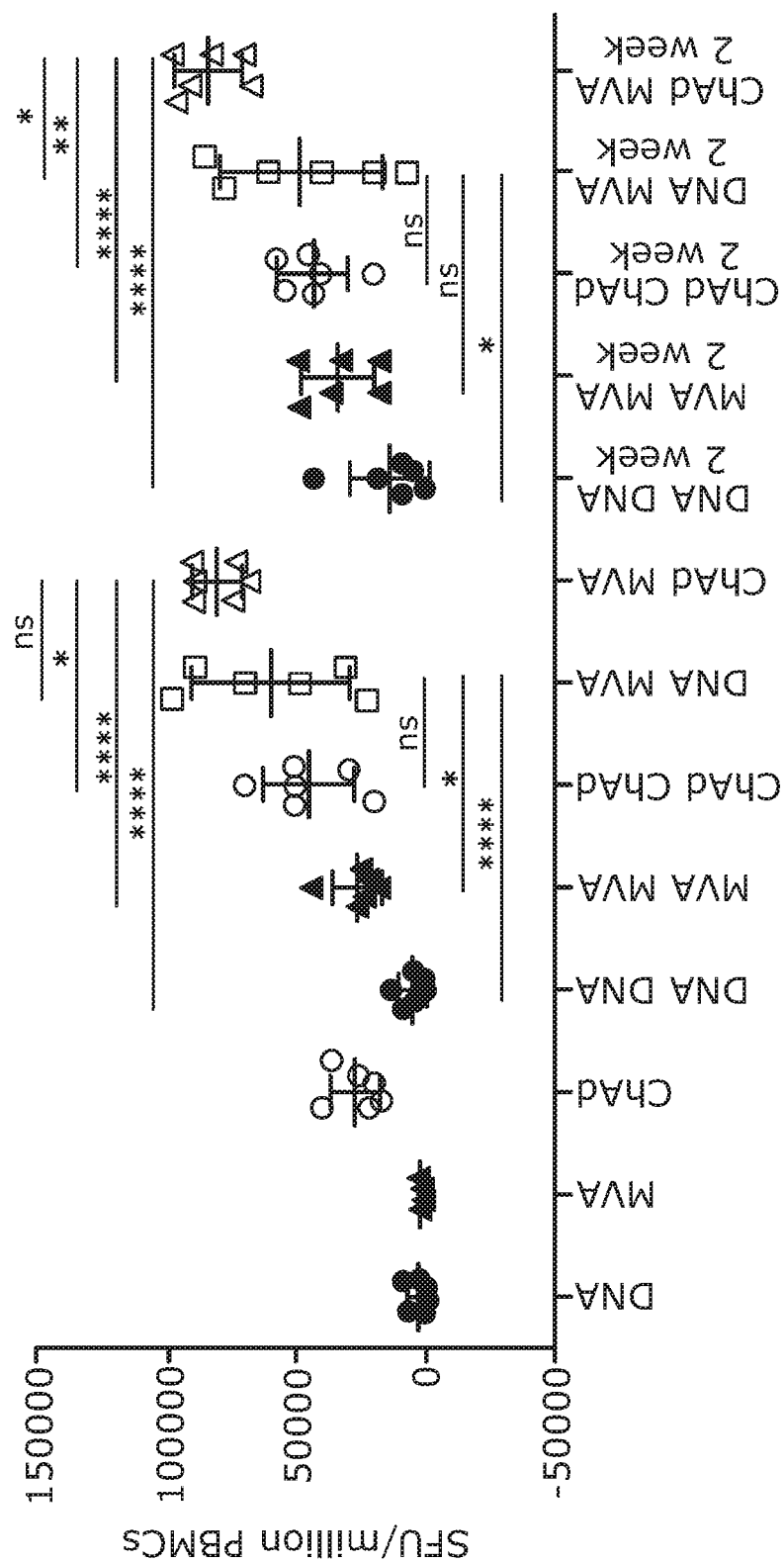
Figure 9:
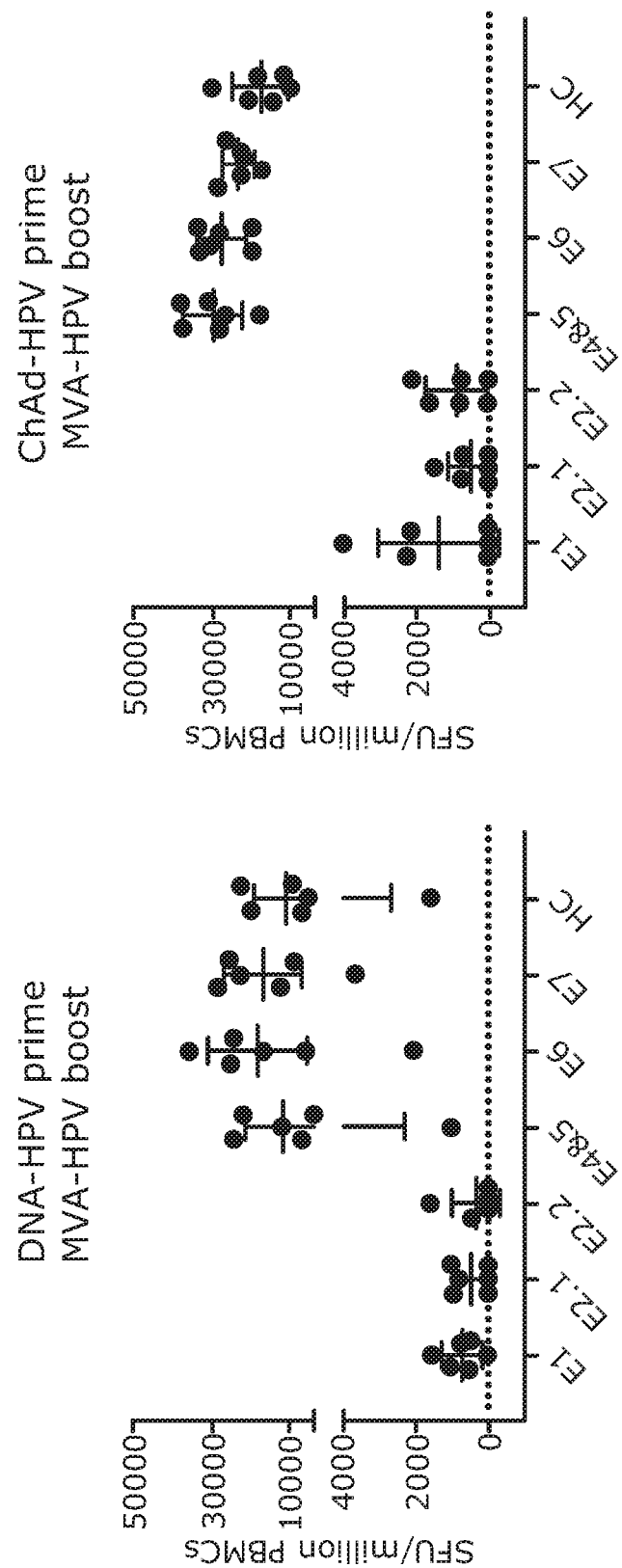
Figure 10A:
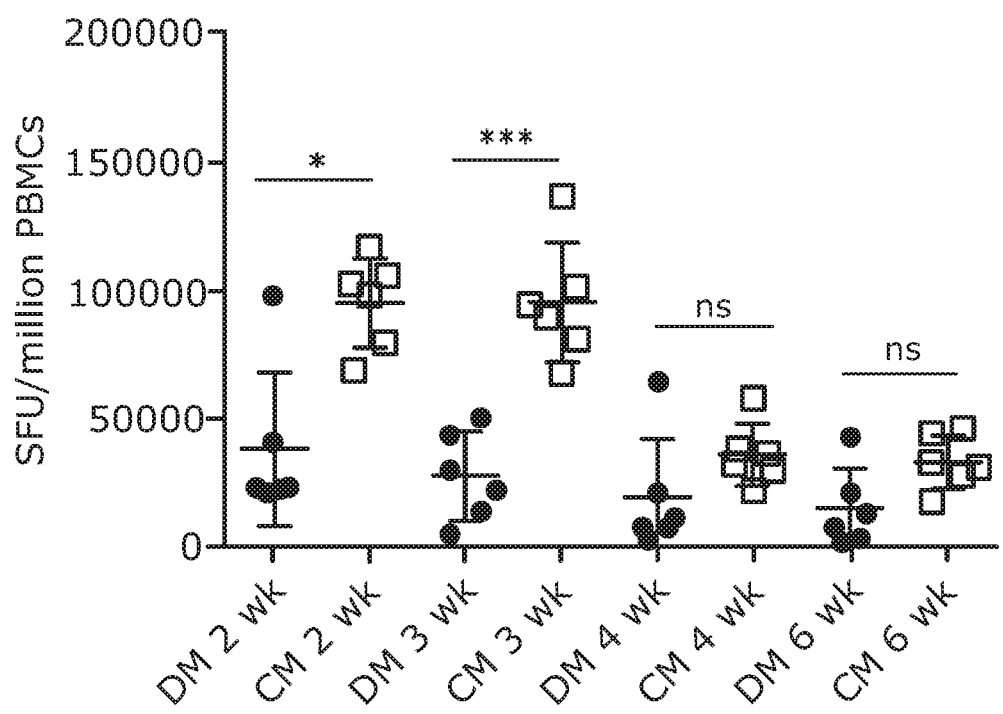
Figure 10B:
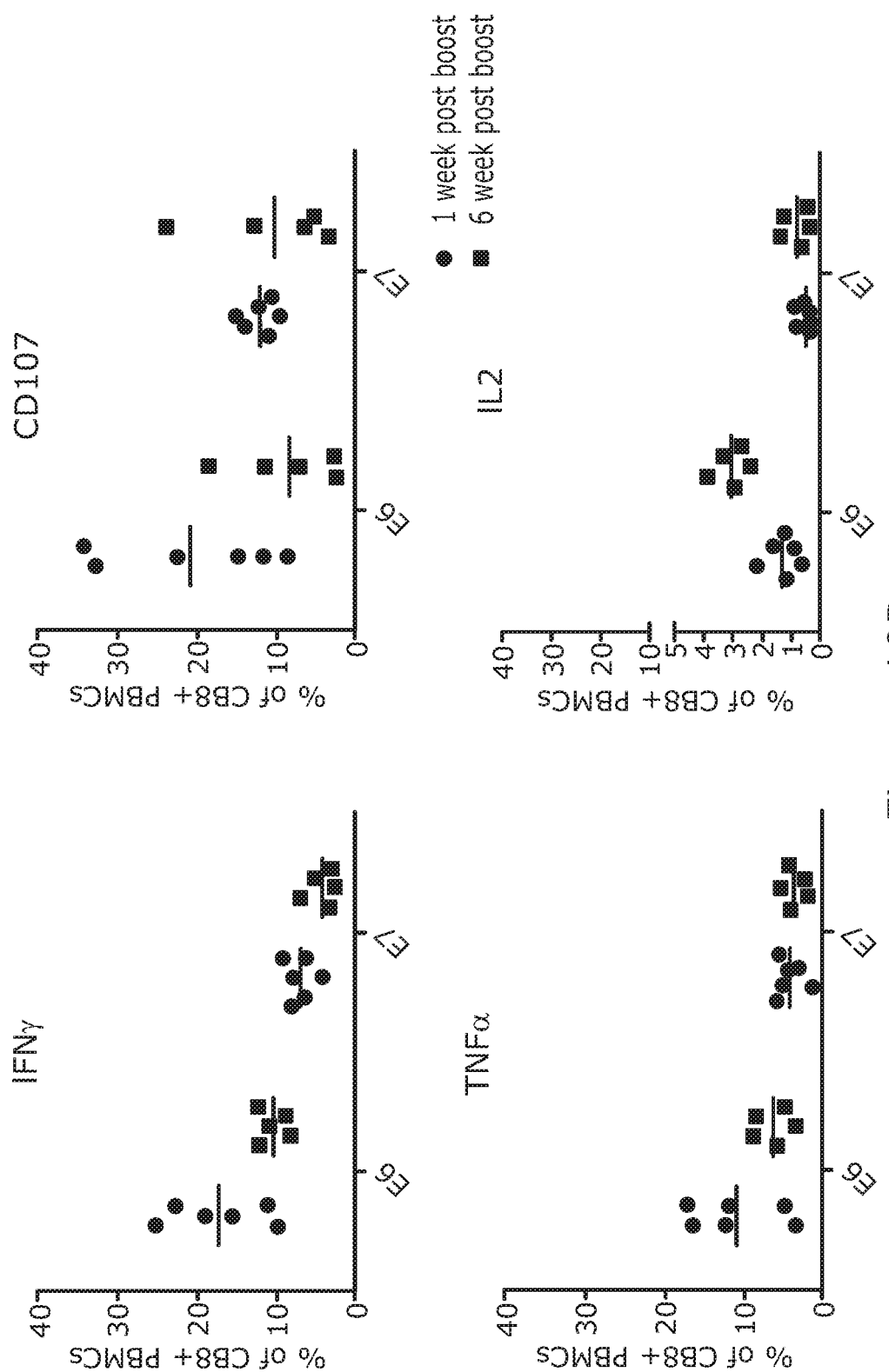
Figure 11:
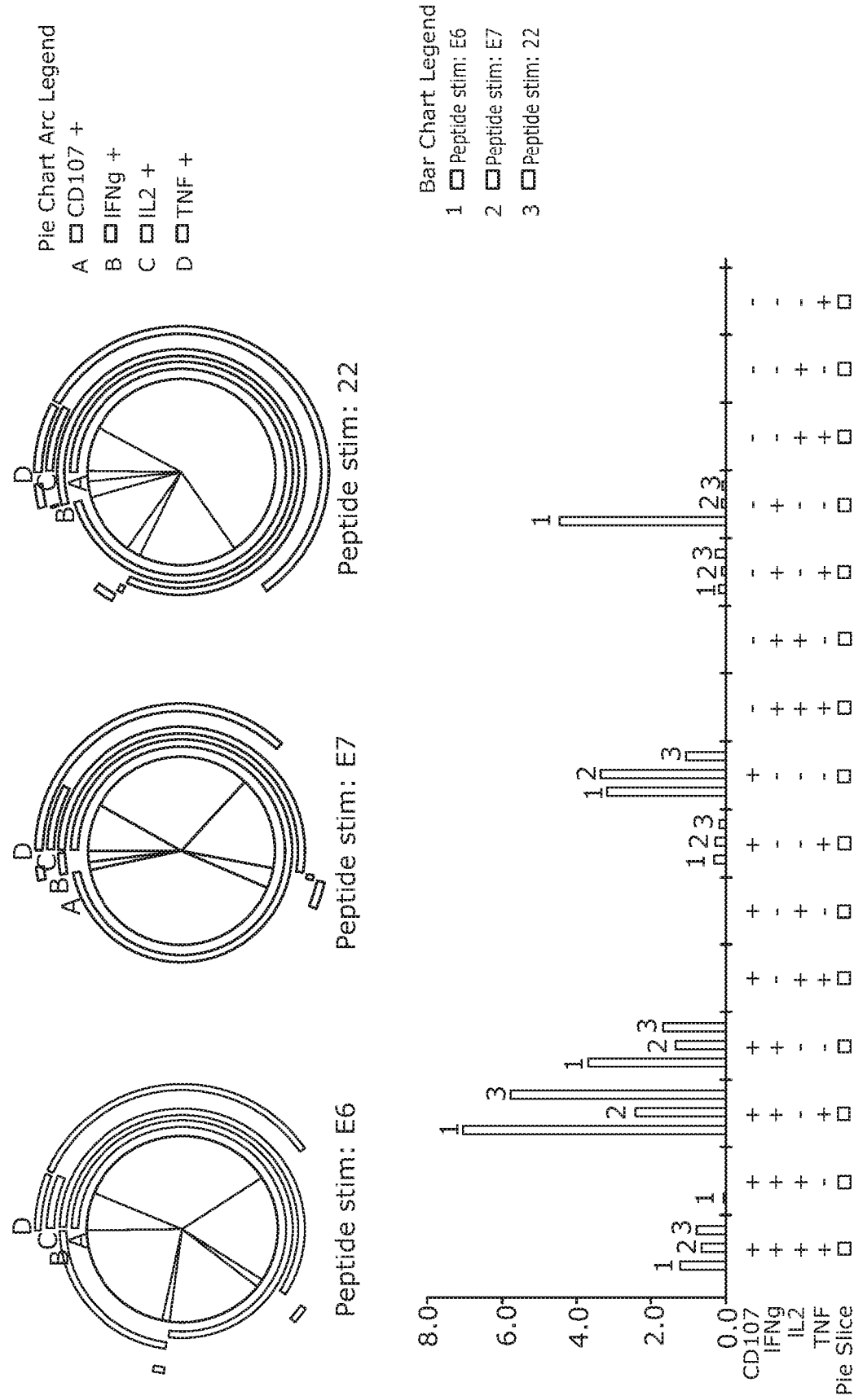
Figure 12:
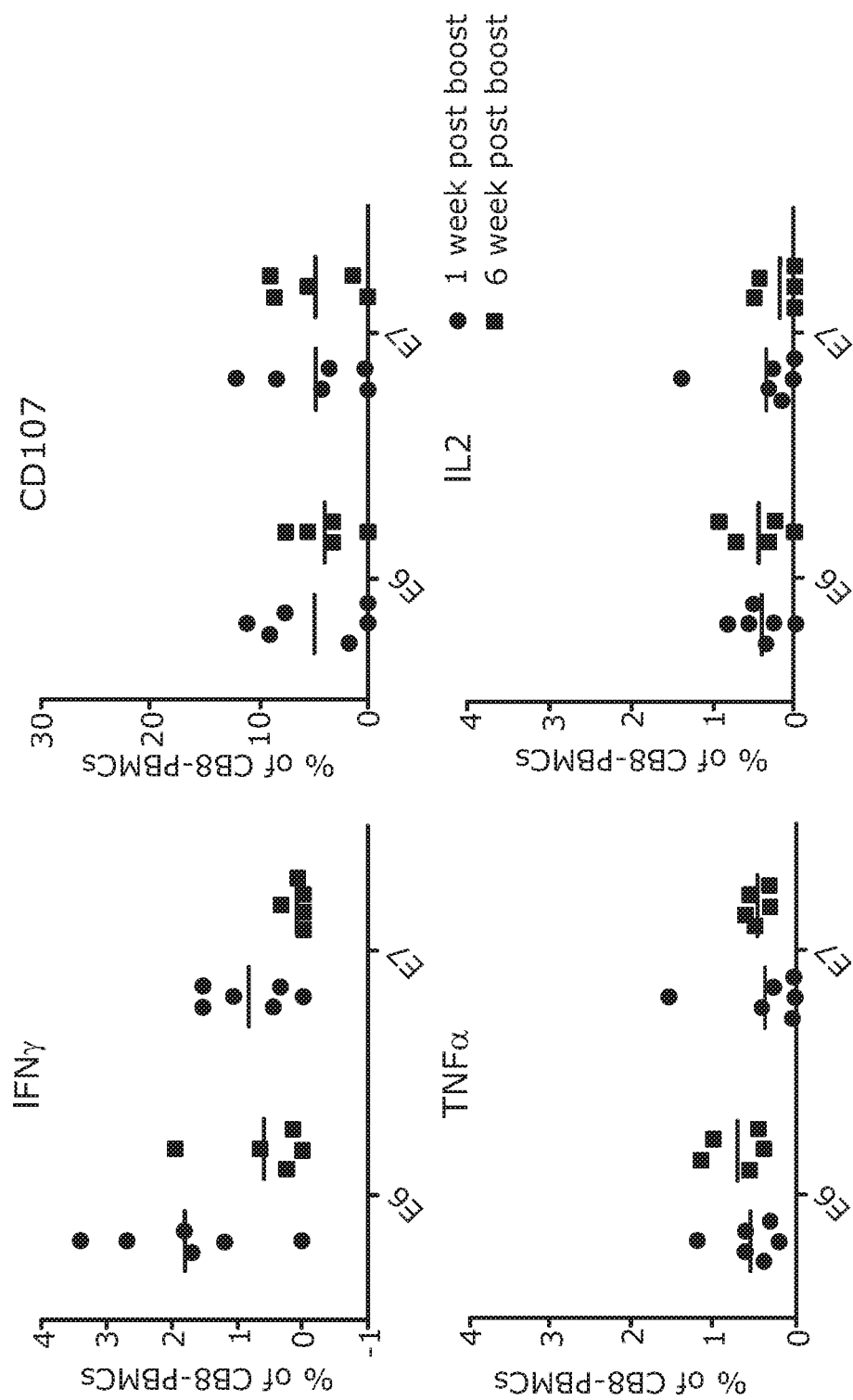
Figure 13:
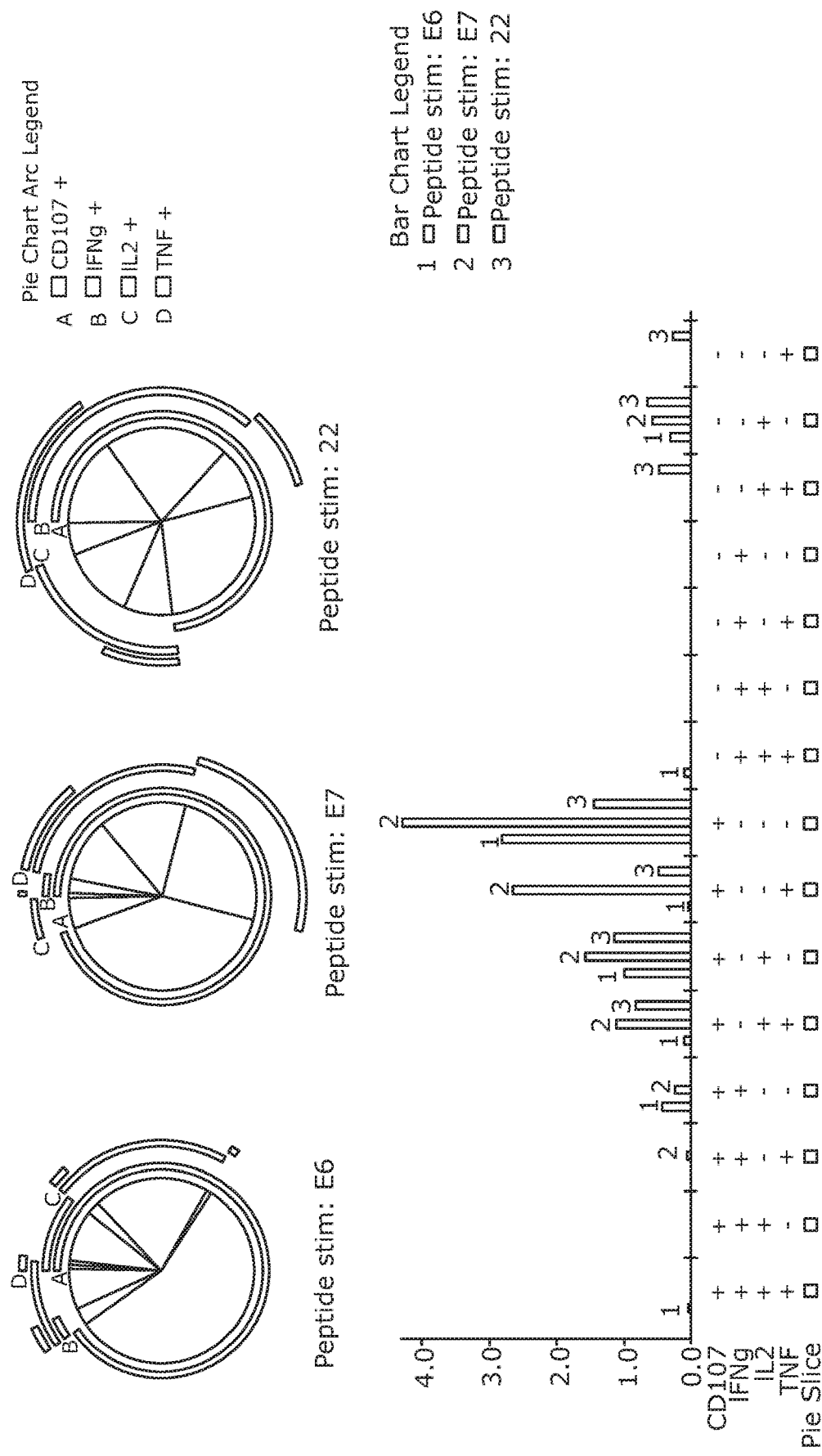
Figure 14:
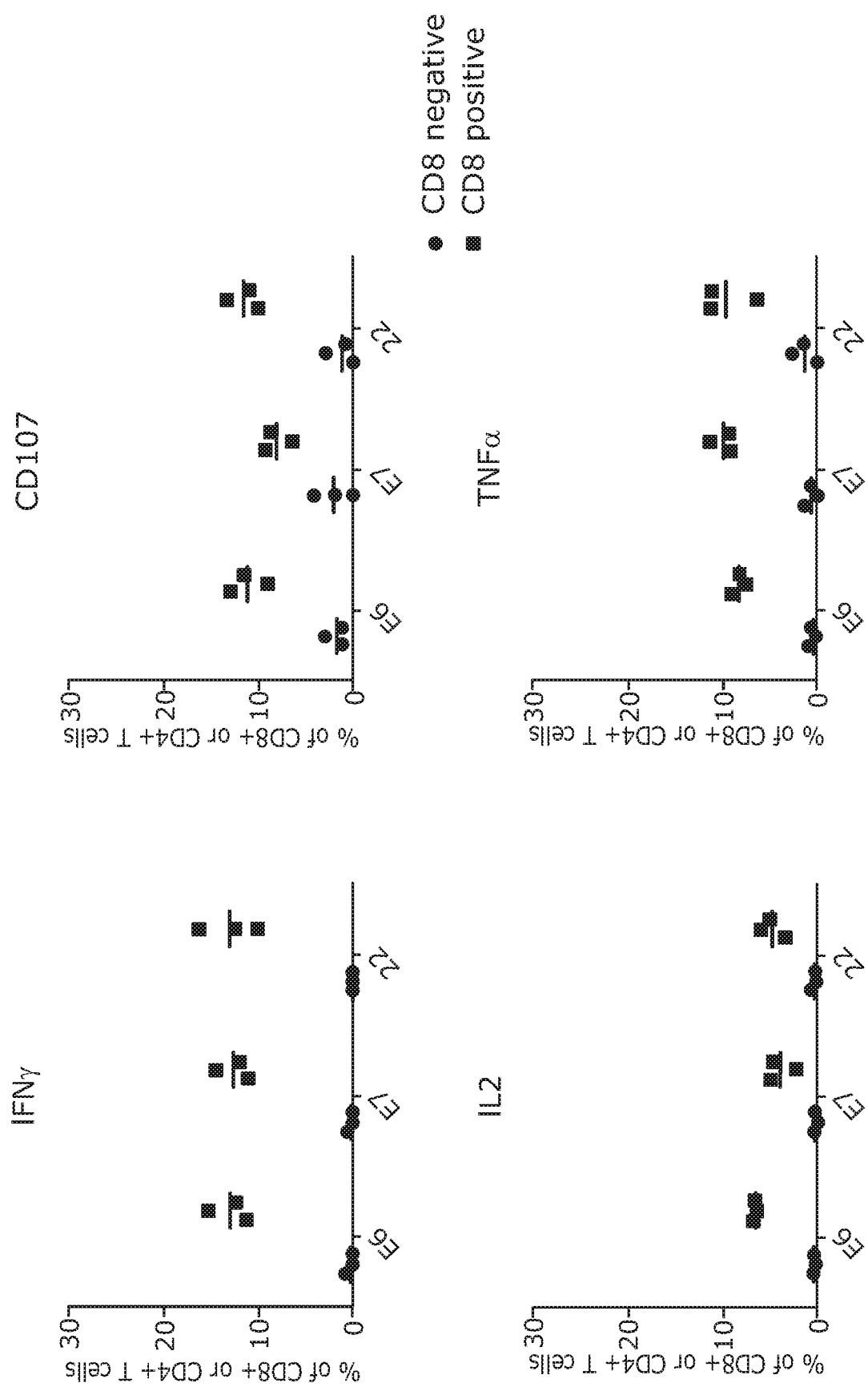

Chimerics were created for Genotypes 16 & 31 and 52 & 58 (FIG. 7). Genotypes 53 and 18 are chimeric variants.

| SEQ ID NO: | Protein | Fragment |
| --- | --- | --- |
| 1 | E1_V1_52 + 58 | DEDETAYDSGTDLIDFIDDS |
| 2 | E1_V1_31 + 16 + 18 | DENENDSDTGEDMVDFIDN |
| 3 | E1_V1_53 | DETDEESTESDLDGFIDNS |
| 4 | E1_V3_31 + 53 | AQLADSDSNACAFLK |
| 5 | E1_V3_52 + 58 + 18 + 16 | AQLADVNSNAAAFLK |
| 6 | E1_V4_16 + 31 | NCILLYGAANTGKSLFGMSL |
| 7 | E1_V4_18 + 52 + 58 | NCLVLCGPANTGKSYFGMSL |
| 8 | E1_V4_53 | NCLVIYGPPNTGKSCFAMSL |
| 9 | E1_V5_16 + 31 + 52 | WPYLHSRLVVFTFPNPF |
| 10 | E1_V5_18 + 58 | WPYLESRITVFEFPNAF |
| 11 | E1_V5_53 | LRYLHSRIHVLQFLNPF |
| 12 | E2_C1-1_16 + 31 | NVCQDKILEHYENDSKD |
| 13 | E2_C1-2_16 + 31 | ILEHYENDSKDLCDHI |
| 14 | E2_C1-3_16 + 31 | CDHIDYWKHIRLECAIMYKAR |
| 15 | E2_C1-4_16 + 31 | IRLECAIMYKAREMGFH |
| 16 | E2_C1-5_16 + 31 | QFDGDICNTMHYTNW |
| 17 | E2_C1-6_16 + 31 | IYICEDAQCTVVEGQVD |

-continued

| SEQ ID NO: | Protein | Fragment |
|---|---|---|
| 18 | E2_C1-7_16 + 31 | KKWEVHAGGQVILCPES |
| 19 | E2_C1-8_16 + 31 | GQRRIKRPRSE |
| 20 | E2_C1-9_16 + 31 | NCHPNKLL |
| 21 | E2_C1-10_16 + 31 | ILKCLRYRFKKHCKL |
| 22 | E2_C1-11_16 + 31 | SSTWHWTCHDGKHK |
| 23 | E2_C1-12_16 + 31 | WHWTCHDGKHKNAIVTLTY |
| 24 | E2_C1-1_52 + 58 | YEADKNDLNAQIEHWKLIRMECAIFYKAKELGIS |
| 25 | E2_C1-2_52 + 58 | ICHQVVPPLAASKAKACQAIELQLALEALNASPY |
| 26 | E2_C1-3_52 + 58 | DEWTLQQTSLEMWLAEPQ |
| 27 | E2_C1-4_52 + 58 | FKKHGITITVQYDNDKANTMDYTNWKEIY |
| 28 | E2_C1-5_52 + 58 | VIVCPASIPSDEISTEEA |
| 29 | E2_C1-1_53 + 18 | DHIDYWKAIRQENAIFFAAR |
| 30 | E2_C1-2_53 + 18 | HQVVPALNICKAKACKAIE |
| 31 | E2_C1-3_53 + 18 | WNTEPKHCFKKGGQHIEVWFD |
| 32 | E2_C1-4_53 + 18 | YVAWDSVYYCGDDGWCKT |
| 33 | E2_C1-5_53 + 18 | EAEKYGCKGTWEVHFG |
| 34 | E2_C1-6_53 + 18 | NSIDCNDSMCSTFDDNVSATELVK |
| 35 | E2_FC1_All | DHIDYWKLIRLECAIFYKAR |
| 36 | E4_C1-1_16 + 31 | RRLSSDQDQSQ |
| 37 | E4_C1-1_52 + 58 | LVTKYPLLKLLS |
| 38 | E4_C1-1_53 | RPPNMGVKAHGKCIWENKVFIVPTLCPVPLDPTYPLLKLLT |
| 39 | E4_C1-2_53 | TQTTTPENTSLVELRVTTPKSTVVIRLHL |
| 40 | E4_C1-1_18 | TTRYPLLSLLNSYSTPPHRIPAPCPWAPQRP |
| 41 | E4_V1_16 + 31 | PIPKPSPWAP |
| 42 | E4_V1_18 | RIPAPCPWAP |
| 43 | E4_V1_52 | PRPPHCPWVP |
| 44 | E4_V1_53 | PPPPPRPWAP |
| 45 | E5_C1_16_31 | CFLLCFCVLLCVCLLIRPLLLSVSTY |
| 46 | E5_C1_52 + 58 | LRPLLLSISVYAQVLVLVLLLWVSIGS |
| 47 | E5_C1_18 | LLPSVCMCAYAWVLVFVYIVVITSPATA |
| 48 | E6_CV1_16 | IVYRDGNPYAVCDKCLKFYSKISEYRHYCYSLYGTTLEQQYNKPLCDLLIRCIN |
| 49 | E6_CV1_18 | VVYRDSIPHAACHKCIDFYSRIRELRHYSDSVYGDTLEKLTNTGLYNLLIRCLR |
| 50 | E6_CV2-1_53 | VFCKKALTASEVYNFAYTDLRVVYRD |
| 51 | E6_CV2-2_53 | SKVRKLRYYNCSVYGASL |
| 52 | E6_CV2-1_31 | VYCKGQLTETEVLDFAFTDLTIVYRD |
| 53 | E6_CV2-2_31 | SKVSEFRWYRYSVYGTTL |
| 54 | E6_CV3-1_52 + 58 | CVECKKTLQRSEVYD |

| SEQ ID NO: | Protein | Fragment |
|---|---|---|
| 55 | E6_CV3-2_52 + 58 | CQRPLCPQEKKRHVDLNKRFH |
| 56 | E7_C1_16 + 31 | TLHEYMLDLQPETTDLYCYEQ |
| 57 | E7_C1_58_52 | PETTDLHCYEQLGDSSDEEDTGGLDG |
| 58 | E7_V1_53 | DEDEDEVDHLQEQPQQARRDEQHPCYLIETQCCRCESLV |
| 59 | E7_V1_18 | EENDEIDGVNHQHLPARRAEPQRHTMLCMCCKCEARI |

HPV3 Nucleotide Sequence (SEQ ID NO: 60)

From Start codon, starting with the TPA leading sequence encoded with an additional linker (TPA and linker are bold and underlined).

ATGGATGCTATGAAGAGGGGCCTGTGCTGCGTGCTGCTGCTGTGTGGCGC
CGTGTTTGTGTCCCCCAGCCAGGAAATCCACGCCCGGTTCAGAAGAGGCA
GCAAGCTGGCCGACGAGGACGAGACAGCCTACGACAGCGGCACCGACCTG
ATCGACTTCATCGACGACAGCGACGAGAATGAGAACGACTCCGACACCGG
CGAGGACATGGTGGATTTCATCGACAACGACGAAACCGACGAAGAGAGCA
CCGAGAGCGACCTGGACGGCTTTATCGACAACTCCGCCCAGCTGGCTGAC
AGCGACAGCAATGCCTGCGCCTTCCTGAAGGCTCAGCTGGCAGACGTGAA
CAGCAACGCCGCTGCTTTTCTGAAGAACTGCATCCTGCTGTACGGCGCTG
CCAACACCGGCAAGAGCCTGTTCGGCATGAGCCTGAACTGCCTGGTGCTG
TGCGGCCCAGCCAATACCGGAAAGTCCTACTTCGGCATGTCCCTGAATTG
TCTCGTGATCTACGGCCCACCTAACACAGGCAAGTCCTGCTTTGCCATGT
CTCTGTGGCCCTACCTGCACAGCAGACTGGTGGTGTTTACCTTCCCCAAC
CCCTTCTGGCCTTACCTGGAAAGCCGGATCACCGTGTTCGAGTTCCCCAA
TGCCTTTCTGAGATACCTGCACTCCCGGATCCACGTGCTGCAGTTTCTGA
ACCCCTTCAACGTGTGCCAGGACAAGATCCTGGAACACTACGAGAACGAC
AGCAAGGACATTCTGGAACATTATGAGAATGATTCCAAGGACCTGTGCGA
CCACATCTGCGATCACATCGACTACTGGAAGCACATCCGGCTGGAATGCG
CCATCATGTACAAGGCCCGGATCAGACTGGAATGTGCTATTATGTATAAG
GCTCGCGAGATGGGCTTCCACCAGTTCGACGGCGACATCTGCAACACCAT
GCACTACACCAACTGGATCTATATCTGCGAGGACGCCCAGTGCACCGTGG
TGGAAGGCCAGGTGGACAAGAAATGGAGGTGCACGCTGGCGGCCAAGTG
ATCCTGTGTCCTGAGAGCGGCCAGCGGCGGATCAAGAGGCCCAGAAGCGA
GAACTGCCACCCCAACAAGCTGCTGATCCTGAAGTGCCTGCGGTACAGAT
TCAAGAAGCACTGCAAGCTGAGCAGCACCTGGCACTGGACCTGCCACGAC
GGCAAGCACAAGTGGCATTGGACATGTCACGATGGGAAACACAAGAACGC
CATTGTGACCCTGACCTACTACGAGGCCGACAAGAACGACCTGAACGCCC
AGATCGAGCACTGGAAACTGATCCGGATGGAATGTGCAATCTTCTATAAG
GCCAAAGAGCTGGGCATCAGCATCTGCCACCAGGTGGTGCCTCCACTGGC
CGCCTCTAAAGCCAAAGCCTGCCAGGCCATCGAACTGCAGCTGGCCCTGG
AAGCCCTGAATGCCAGCCCCTACGATGAGTGGACCCTGCAGCAGACCAGC
CTGGAAATGTGGCTGGCCGAGCCCAGTTTAAGAAGCACGGCATCACCAT
CACCGTGCAGTACGACAATGACAAGGCCAATACCATGGATTACACAAATT
GGAAAGAAATCTACGTGATCGTGTGCCCCGCCAGCATCCCCTCCGATGAG
ATCAGCACCGAGGAAGCCGACCACATTGATTATTGGAAAGCCATCAGGCA
GGAAAACGCCATCTTCTTCGCCGCCAGACACCAGGTGGTGCCCGCCCTGA
ATATCTGCAAGGCCAAGGCCTGTAAAGCCATCGAGTGGAACACCGAGCCC
AAGCACTGCTTCAAGAAGGGCGGCCAGCACATCGAAGTGTGGTTCGACTA
CGTGGCCTGGGACAGCGTGTACTACTGCGGCGACGATGGCTGGTGCAAGA
CCGAGGCCGAGAAGTACGCTGCAAGGGCACCTGGGAAGTGCATTTCGGC
AACAGCATCGACTGCAACGACTCCATGTGCAGCACCTTCGACGACAACGT
GTCCGCCACCGAGCTCGTGAAGGACCATATCGACTATTGGAAGCTGATTC
GCCTGGAATGTGCCATTTTTTACAAGGCCAGACGGCGGCTGTCCAGCGAC
CAGGATCAGTCTCAGCTCGTGACCAAGTACCCCCTGCTGAAGCTGCTGTC
CAGACCCCCCAACATGGGCGTGAAGGCCCACGGCAAGTGCATCTGGGAGA
ACAAGGTGTTCATCGTGCCCACCCTGTGCCCCGTGCCTCTGGATCAACA
TATCCTCTGCTGAAACTGCTGACCACCCAGACCACCACCCCCGAGAATAC
CTCCCTGGTGGAACTGAGAGTGACCACCCCCAAGAGCACAGTCGTGATCA
GGCTGCACCTGACCACCAGATACCCACTGCTGTCACTGCTGAACAGCTAC
AGCACCCCCCCTCACCGGATCCCTGCTCCATGTCCTTGGGCTCCTCAGAG
GCCCCCCATCCCTAAGCTTCTCCATGGGCCCCTAGAATCCCTGCCCCCTT
GCCCCTGGGCACCTCCTAGACCTCCACACTGTCCATGGGTGCCCCCTCCA
CCTCCTCCAAGACCTTGGGCCCCTTGCTTCCTGCTGTGCTTTTGTGTGCT
GCTGTGCGTGTGCCTGCTGATCAGACCCCTGCTGCTGAGTGTGTCCACCT
ACCTGAGGCCTCTGCTGCTGTCTATCAGCGTGTACGCTCAGGTGCTGGTG
CTGGTGCTGCTGCTGTGGGTGTCCATCGGAAGCTGCTGCCCAGCGTGTG
CATGTGTGCCTATGCCTGGGTGCTGGTGTTCGTGTACATCGTCGTGATTA
CCAGCCCCGCCACCGCCATCGTGTACCGGGATGGCAATCCTTACGCCGTG
TGCGACAAGTGCCTGAAGTTCTACAGCAAGATCAGCGAGTACCGGCACTA
CTGCTACAGCCTGTACGGCACCACCCTGGAACAGCAGTACAACAAGCCCC

```
TGTGCGATCTGCTGATTCGGTGCATCAACGTGGTGTACAGAGACTCCATC
CCCCACGCCGCCTGCCACAAGTGTATCGACTTCTACTCCAGAATCAGAGA
GCTGCGGCACTACAGCGACTCCGTGTACGGCGATACCCTGGAAAAGCTGA
CCAACACTGGCCTGTACAACCTGCTGATTAGATGCCTGCGGGTGTTCTGC
AAGAAGGCCCTGACAGCCAGCGAGGTGTACAACTTCGCCTACACCGATCT
GCGGGTGGTGTATCGGGACAGCAAAGTGCGGAAGCTGAGGTACTACAACT
GCTCTGTGTATGGCGCCAGCCTGGTGTATTGCAAGGGACAGCTGACCGAG
ACAGAGGTGCTGGATTTCGCCTTCACAGACCTGACAATCGTGTATCGCGA
CTCCAAGGTGTCCGAGTTCCGGTGGTACAGATATTCCGTGTATGGCACCA
CACTGTGCGTGAATGCAAGAAAACCCTGCAGAGATCTGAGGTGTACGAC
TGCCAGCGGCCACTGTGTCCGCAGGAAAAGAAAAGACACGTGGACCTGAA
CAAGCGGTTCCACACCCTGCACGAGTACATGCTGGATCTGCAGCCCGAGA
CAACCGACCTGTACTGCTACGAGCAGCCTGAAACCACTGATCTGCACTGT
TATGAGCAGCTGGGAGACAGCTCCGATGAAGAGGACACTGGCGGCCTGGA
TGGGGACGAGGATGAGGACGAAGTGGACCATCTGCAGGAACAGCCCCAGC
AGGCTAGACGGGACGAACAGCACCCTTGCTATCTGATCGAGACACAGTGC
TGCAGATGCGAATCTCTGGTGAAGAGAACGACGAGATCGACGGCGTGAA
CCACCAGCATCTGCCCGCTAGAAGGGCCGAGCCTCAGAGACACACCATGC
TGTGTATGTGCTGCAAGTGCGAGGCCAGAATCGCCGGCTCTGGACCTGGC
GCCTCTGGCAAGCCTATCCCCAATCCACTGCTGGGCCTGGACTCCACCCG
GACCTGATAA
```

HPV3 Nucleotide Sequence without Encoding a Peptide Adjuvant/TPA (SEQ ID NO: 65)

```
GACGAGGACGAGACAGCCTACGACAGCGGCACCGACCTG
ATCGACTTCATCGACGACAGCGACGAGAATGAGAACGACTCCGACACCGG
CGAGGACATGGTGGATTTCATCGACAACGACGAAACCGACGAAGAGAGCA
CCGAGAGCGACCTGGACGGCTTTATCGACAACTCCGCCCAGCTGGCTGAC
AGCGACAGCAATGCCTGCGCCTTCCTGAAGGCTCAGCTGGCAGACGTGAA
CAGCAACGCCGCTGCTTTTCTGAAGAACTGCATCCTGCTGTACGGCGCTG
CCAACACCGGCAAGAGCCTGTTCGGCATGAGCCTGAACTGCCTGGTGCTG
TGCGGCCCAGCCAATACCGGAAAGTCCTACTTCGGCATGTCCCTGAATTG
TCTCGTGATCTACGGCCCACCTAACACAGGCAAGTCCTGCTTTGCCATGT
CTCTGTGGCCCTACCTGCACAGCAGACTGGTGGTGTTTACCTTCCCCAAC
CCCTTCTGGCCTTACCTGGAAAGCCGGATCACCGTGTTCGAGTTCCCCAA
TGCCTTTCTGAGATACCTGCACTCCCGGATCCACGTGCTGCAGTTTCTGA
ACCCCTTCAACGTGTGCCAGGACAAGATCCTGGAACACTACGAGAACGAC
AGCAAGGACATTCTGGAACATTATGAGAATGATTCCAAGGACCTGTGCGA
CCACATCTGCGATCACATCGACTACTGGAAGCACATCCGGCTGGAATGCG
CCATCATGTACAAGGCCCGGATCAGACTGGAATGTGCTATTATGTATAAG
GCTCGCGAGATGGGCTTCCACCAGTTCGACGGCGACATCTGCAACACCAT
GCACTACACCAACTGGATCTATATCTGCGAGGACGCCCAGTGCACCGTGG
TGGAAGGCCAGGTGGACAAGAAATGGGAGGTGCACGCTGGCGGCCAAGTG
ATCCTGTGTCCTGAGAGCGGCCAGCGGCGGATCAAGAGGCCCAGAAGCGA
GAACTGCCACCCCAACAAGCTGCTGATCCTGAAGTGCCTGCGGTACAGAT
TCAAGAAGCACTGCAAGCTGAGCAGCACCTGGCACTGGACCTGCCACGAC
GGCAAGCACAAGTGGCATTGGACATGTCACGATGGGAAACACAAGAACGC
CATTGTGACCCTGACCTACTACGAGGCCGACAAGAACGACCTGAACGCCC
AGATCGAGCACTGGAAACTGATCCGGATGGAATGTGCAATCTTCTATAAG
GCCAAAGAGCTGGGCATCAGCATCTGCCACCAGGTGGTGCCTCCACTGGC
CGCCTCTAAAGCCAAAGCCTGCCAGGCCATCGAACTGCAGCTGGCCCTGG
AAGCCCTGAATGCCAGCCCCTACGATGAGTGGACCCTGCAGCAGACCAGC
CTGGAAATGTGGCTGGCCGAGCCCCAGTTTAAGAAGCACGGCATCACCAT
CACCGTGCAGTACGACAATGACAAGGCCAATACCATGGATTACACAAATT
GGAAAGAAATCTACGTGATCGTGTGCCCCGCCAGCATCCCCTCCGATGAG
ATCAGCACCGAGGAAGCCGACCACATTGATTATTGGAAAGCCATCAGGCA
GGAAAACGCCATCTTCTTCGCCGCCAGACACCAGGTGGTGCCCGCCCTGA
ATATCTGCAAGGCCAAGGCCTGTAAAGCCATCGAGTGGAACACCGAGCCC
AAGCACTGCTTCAAGAAGGGCGGCCAGCACATCGAAGTGTGGTTCGACTA
CGTGGCCTGGGACAGCGTGTACTACTGCGGCGACGATGGCTGGTGCAAGA
CCGAGGCCGAGAAGTACGGCTGCAAGGGCACCTGGGAAGTGCATTTCGGC
AACAGCATCGACTGCAACGACTCCATGTGCAGCACCTTCGACGACAACGT
GTCCGCCACCGAGCTCGTGAAGGACCATATCGACTATTGGAAGCTGATTC
GCCTGGAATGTGCCATTTTTTACAAGGCCAGACGGCGGCTGTCCAGCGAC
CAGGATCAGTCTCAGCTCGTGACCAAGTACCCCCTGCTGAAGCTGCTGTC
CAGACCCCCCAACATGGGCGTGAAGGCCCACGGCAAGTGCATCTGGGAGA
ACAAGGTGTTCATCGTGCCCACCCTGTGCCCCGTGCCTCTGGATCCAACA
TATCCTCTGCTGAAACTGCTGACCACCCAGACCACCACCCCCGAGAATAC
CTCCCTGGTGGAACTGAGAGTGACCACCCCCAAGAGCACAGTCGTGATCA
GGCTGCACCTGACCACCAGATACCCACTGCTGTCACTGCTGAACAGCTAC
AGCACCCCCCCTCACCGGATCCCTGCTCCATGTCCTTGGGCTCCTCAGAG
GCCCCCATCCCTAAGCCTTCTCCATGGGCCCCTAGAATCCCTGCCCCTT
GCCCCTGGGCACCTCCTAGACCTCCACACTGTCCATGGGTGCCCCCTCCA
CCTCCTCCAAGACCTTGGGCCCCTTGCTTCCTGCTGTGCTTTTGTGTGCT
GCTGTGCGTGTGCCTGCTGATCAGACCCCTGCTGCTGAGTGTGTCCACCT
ACCTGAGGCCTCTGCTGCTGTCTATCAGCGTGTACGCTCAGGTGCTGGTG
CTGGTGCTGCTGCTGTGGGTGTCCATCGGAAGCCTGCTGCCCAGCGTGTG
CATGTGTGCCTATGCCTGGGTGCTGGTGTTCGTGTACATCGTCGTGATTA
CCAGCCCCGCCACCGCCATCGTGTACCGGGATGGCAATCCTTACGCCGTG
TGCGACAAGTGCCTGAAGTTCTACAGCAAGATCAGCGAGTACCGGCACTA
CTGCTACAGCCTGTACGGCACCACCCTGGAACAGCAGTACAACAAGCCCC
TGTGCGATCTGCTGATTCGGTGCATCAACGTGGTGTACAGAGACTCCATC
```

```
CCCCACGCCGCCTGCCACAAGTGTATCGACTTCTACTCCAGAATCAGAGA

GCTGCGGCACTACAGCGACTCCGTGTACGGCGATACCCTGGAAAAGCTGA

CCAACACTGGCCTGTACAACCTGCTGATTAGATGCCTGCGGGTGTTCTGC

AAGAAGGCCCTGACAGCCAGCGAGGTGTACAACTTCGCCTACACCGATCT

GCGGGTGGTGTATCGGGACAGCAAAGTGCGGAAGCTGAGGTACTACAACT

GCTCTGTGTATGGCGCCAGCCTGGTGTATTGCAAGGGACAGCTGACCGAG

ACAGAGGTGCTGGATTTCGCCTTCACAGACCTGACAATCGTGTATCGCGA

CTCCAAGGTGTCCGAGTTCCGGTGGTACAGATATTCCGTGTATGGCACCA

CACTGTGCGTGGAATGCAAGAAAACCCTGCAGAGATCTGAGGTGTACGAC

TGCCAGCGGCCACTGTGTCCGCAGGAAAAGAAAAGACACGTGGACCTGAA

CAAGCGGTTCCACACCCTGCACGAGTACATGCTGGATCTGCAGCCCGAGA

CAACCGACCTGTACTGCTACGAGCAGCCTGAAACCACTGATCTGCACTGT

TATGAGCAGCTGGGAGACAGCTCCGATGAAGAGGACACTGGCGGCCTGGA

TGGGGACGAGGATGAGGACGAAGTGGACCATCTGCAGGAACAGCCCCAGC

AGGCTAGACGGGACGAACAGCACCCTTGCTATCTGATCGAGACACAGTGC

TGCAGATGCGAATCTCTGGTGGAAGAGAACGACGAGATCGACGGCGTGAA

CCACCAGCATCTGCCCGCTAGAAGGGCCGAGCCTCAGAGACACACCATGC

TGTGTATGTGCTGCAAGTGCGAGGCCAGAATCGCCGGCTCTGGACCTGGC

GCCTCTGGCAAGCCTATCCCCAATCCACTGCTGGGCCTGGACTCCACCCG

GACCTGATAA
```

HPV3 Polypeptide Sequence (SEQ ID NO: 61)
From Start codon, starting with the TPA leading sequence.

MDAMKRGLCCVLLLCGAVEVSPSQEIHARFRRGSKLADEDETAYDSGTDL
IDFIDDSDENENDSDTGEDMVDFIDNDETDEESTESDLDGFIDNSAQLAD
SDSNACAFLKAQLADVNSNAAAFLKNCILLYGAANTGKSLFGMSLNCLVL
CGPANTGKSYEGMSLNCLVIYGPPNTGKSCFAMSLWPYLHSRLVVETFPN
PFWPYLESRITVFEFPNAFLRYLHSRIHVLQFLNPFNVCQDKILEHYEND
SKDILEHYENDSKDLCDHICDHIDYWKHIRLECAIMYKARIRLECAIMYK
AREMGFHQFDGDICNTMHYTNWIYICEDAQCTVVEGQVDKKWEVHAGGQV
ILCPESGQRRIKRPRSENCHPNKLLILKCLRYRFKKHCKLSSTWHWTCHD
GKHKWHWTCHDGKHKNAIVTLTYYEADKNDLNAQIEHWKLIRMECAIFYK
AKELGISICHQVVPPLAASKAKACQAIELQLALEALNASPYDEWTLQQTS
LEMWLAEPQFKKHGITITVQYDNDKANTMDYTNWKEIYVIVCPASIPSDE
ISTEEADHIDYWKAIRQENAIFFAARHQVVPALNICKAKACKAIEWNTEP
KHCFKKGGQHIEVWFDYVAWDSVYYCGDDGWCKTEAEKYGCKGTWEVHFG
NSIDCNDSMCSTFDDNVSATELVKDHIDYWKLIRLECAIFYKARRRLSSD
QDQSQLVTKYPLLKLLSRPPNMGVKAHGKCIWENKVFIVPTLCPVPLDPT
YPLLKLLTTQTTTPENTSLVELRVTTPKSTVVIRLHLTTRYPLLSLLNSY
STPPHRIPAPCPWAPQRPPIPKPSPWAPRIPAPCPWAPPRPPHCPWVPPP
PPPRPWAPCFLLCFCVLLCVCLLIRPLLLSVSTYLRPLLLSISVYAQVLV
LVLLLWVSIGSLLPSVCMCAYAWVLVFVYIVVITSPATAIVYRDGNPYAV
CDKCLKFYSKISEYRHYCYSLYGTTLEQQYNKPLCDLLIRCINVVYRDSI
PHAACHKCIDFYSRIRELRHYSDSVYGDTLEKLTNTGLYNLLIRCLRVFC
KKALTASEVYNFAYTDLRVVYRDSKVRKLRYYNCSVYGASLVYCKGQLTE
TEVLDFAFTDLTIVYRDSKVSEFRWYRYSVYGTTLCVECKKTLQRSEVYD
CQRPLCPQEKKRHVDLNKRFHTLHEYMLDLQPETTDLYCYEQPETTDLHC
YEQLGDSSDEEDTGGLDGDEDEDEVDHLQEQPQQARRDEQHPCYLIETQC
CRCESLVEENDEIDGVNHQHLPARRAEPQRHTMLCMCCKCEARIAGSGPG
ASGKPIPNPLLGLDSTRT**

HPV3 Polypeptide Sequence without the TPA/Peptide Adjuvant Sequence (SEQ ID NO: 66)

DEDETAYDSGTDL
IDFIDDSDENENDSDTGEDMVDFIDNDETDEESTESDLDGFIDNSAQLAD
SDSNACAFLKAQLADVNSNAAAFLKNCILLYGAANTGKSLFGMSLNCLVL
CGPANTGKSYFGMSLNCLVIYGPPNIGKSCFAMSLWPYLHSRLVVETFPN
PFWPYLESRITVFEFPNAFLRYLHSRIHVLQFLNPFNVCQDKILEHYEND
SKDILEHYENDSKDLCDHICDHIDYWKHIRLECAIMYKARIRLECAIMYK
AREMGFHQFDGDICNTMHYTNWIYICEDAQCTVVEGQVDKKWEVHAGGQV
ILCPESGQRRIKRPRSENCHPNKLLILKCLRYRFKKHCKLSSTWHWTCHD
GKHKWHWTCHDGKHKNAIVTLTYYEADKNDLNAQIEHWKLIRMECAIFYK
AKELGISICHQVVPPLAASKAKACQAIELQLALEALNASPYDEWTLQQTS
LEMWLAEPQFKKHGITITVQYDNDKANTMDYTNWKEIYVIVCPASIPSDE
ISTEEADHIDYWKAIRQENAIFFAARHQVVPALNICKAKACKAIEWNTEP
KHCFKKGGQHIEVWFDYVAWDSVYYCGDDGWCKTEAEKYGCKGTWEVHFG
NSIDCNDSMCSTFDDNVSATELVKDHIDYWKLIRLECAIFYKARRRLSSD
QDQSQLVTKYPLLKLLSRPPNMGVKAHGKCIWENKVFIVPTLCPVPLDPT
YPLLKLLTTQTTTPENTSLVELRVTTPKSTVVIRLHLTTRYPLLSLLNSY
STPPHRIPAPCPWAPQRPPIPKPSPWAPRIPAPCPWAPPRPPHCPWVPPP
PPPRPWAPCFLLCFCVLLCVCLLIRPLLLSVSTYLRPLLLSISVYAQVLV
LVLLLWVSIGSLLPSVCMCAYAWVLVFVYIVVITSPATAIVYRDGNPYAV
CDKCLKFYSKISEYRHYCYSLYGTTLEQQYNKPLCDLLIRCINVVYRDSI
PHAACHKCIDEYSRIRELRHYSDSVYGDTLEKLTNTGLYNLLIRCLRVFC
KKALTASEVYNFAYTDLRVVYRDSKVRKLRYYNCSVYGASLVYCKGQLTE
TEVLDFAFTDLTIVYRDSKVSEFRWYRYSVYGTTLCVECKKTLQRSEVYD
CQRPLCPQEKKRHVDLNKRFHTLHEYMLDLQPETTDLYCYEQPETTDLHC
YEQLGDSSDEEDTGGLDGDEDEDEVDHLQEQPQQARRDEQHPCYLIETQC
CRCESLVEENDEIDGVNHQHLPARRAEPQRHTMLCMCCKCEARIAGSGPG
ASGKPIPNPLLGLDSTRT**

Viral Vector Sequence ChAdOx1 with Immunogen Coding Sequence Insert.
Start and end codons of the immunogen coding sequence insert are underlined. Lead TPA sequence and linker is in bold.

(SEQ ID NO: 62)
GTTTAAACGCGGCCGCCAGGCCTACCCACTAGTCAATTCGGGAGGATCGAAACGGCAGATCGCAA

AAAACAGTACATACAGAAGGAGACATGAACATGAACATCAAAAAAATTGTAAAACAAGCCACAGT

TCTGACTTTTACGACTGCACTTCTGGCAGGAGGAGCGACTCAAGCCTTCGCGAAAGAAAATAACC

AAAAAGCATACAAAGAAACGTACGGCGTCTCTCATATTACACGCCATGATATGCTGCAGATCCCT

AAACAGCAGCAAAACGaAAAATACCAAGTGCCTCAATTCGATCAATCAACGATTAAAAATATTGA

GTCTGCAAAAGGACTTGATGTGTGGGACAGCTGGCCGCTGCAAAACGCTGACGGAACAGTAGCTG

AATACAACGGCTATCACGTTGTGTTTGCTCTTGCGGGAAGCCCGAAAGACGCTGATGACACATCA

ATCTACATGTTTTATCAAAAGGTCGGCGACAACTCAATCGACAGCTGGAAAAACGCGGGCCGTGT

CTTTAAAGACAGCGATAAGTTCGACGCCAACGATCCGATCCTGAAAGATCAGACGCAAGAATGGT

CCGGTTCTGCAACCTTTACATCTGACGGAAAAATCCGTTTATTCTACACTGACTATTCCGGTAAA

CATTACGGCAAACAAAGCCTGACAACAGCGCAGGTAAATGTGTCAAAATCTGATGACACACTCAA

AATCAACGGAGTGGAAGATCACAAAACGATTTTTGACGGAGACGGAAAAACATATCAGAACGTTC

AGCAGTTTATCGATGAAGGCAATTATACATCCGGCGACAACCATACGCTGAGAGACCCTCACTAC

GTTGAAGACAAAGGCCATAAATACCTTGTATTCGAAGCCAACACGGGAACAGAAAACGGATACCA

AGGCGAAGAATCTTTATTTAACAAAGCGTACTACGGCGGCGGCACGAACTTCTTCCGTAAAGAAA

GCCAGAAGCTTCAGCAGAGCGCTAAAAAACGCGATGCTGAGTTAGCGAACGGCGCCCTCGGTATC

ATAGAGTTAAATAATGATTACACATTGAAAAAAGTAATGAAGCCGCTGATCACTTCAAACACGGT

AACTGATGAAATCGAGCGCGCGAATGTTTTCAAAATGAACGGCAAATGGTACTTGTTCACTGATT

CACGCGGTTCAAAAATGACGATCGATGGTATTAACTCAAACGATATTTACATGCTTGGTTATGTA

TCAAACTCTTTAACCGGCCCTTACAAGCCGCTGAACAAAACAGGGCTTGTGCTGCAAATGGGTCT

TGATCCAAACGATGTGACATTCACTTACTCTCACTTCGCAGTGCCGCAAGCCAAAGGCAACAATG

TGGTTATCACAAGCTACATGACAAACAGAGGCTTCTTCGAGGATAAAAAGGCAACATTTGCGCCA

AGCTTCTTAATGAACATCAAAGGCAATAAAACATCCGTTGTCAAAAACAGCATCCTGGAGCAAGG

ACAGCTGACAGTCAACTAATAACAGCAAAAAGaAAATGCCGATACTTCATTGGCATTTTCTTtTA

TTTCTCAACAAGATGGTGAATTGACTAGTGGGTAGATCCACAGGACGGGTGTGGTCGCCATGATC

GCGTAGTCGATAGTGGCTCCAAGTAGCGAAGCGAGCAGGACTGGGCGGCGGCCAAAGCGGTCGGA

CAGTGCTCCGAGAACGGGTGCGCATAGAAATTGCATCAACGCATATAGCGCTAGCAGCACGCCAT

AGTGACTGGCGATGCTGTCGGAATGGACGATATCCCGCAAGAGGCCCGGCAGTACCGGCATAACC

AAGCCTATGCCTACAGCATCCAGGGTGACGGTGCCGAGGATGACGATGAGCGCATTGTTAGATTT

CATACACGGTGCCTGACTGCGTTAGCAATTTAACTGTGATAAACTACCGCATTAAAGCTTATCGA

TGATAAGCTGTCAAACATGAGAATTGATCCGGAACCCTTAATATAACTTCGTATAATGTATGCTA

TACGAAGTTATTAGGTCCCTCGACTATAGGGTCACCGTCGACAGCGACACACTTGCATCGGATGC

AGCCCGGTTAACGTGCCGGCACGGCCTGGGTAACCAGGTATTTTGTCCACATAACCGTGCGCAAA

ATGTTGTGGATAAGCAGGACACAGCAGCAATCCACAGCAGGCATACAACCGCACACCGAGGTTAC

TCCGTTCTACAGGTTACGACGACATGTCAATACTTGCCCTTGACAGGCATTGATGGAATCGTAGT

CTCACGCTGATAGTCTGATCGACAATACAAGTGGGACCGTGGTCCCAGACCGATAATCAGACCGA

CRAYACGAGTGGGAYCGTGGTCCCAGACTAATAATCAGACCGACGATACGAGTGGGACCGTGGTC

CCAGACTAATAATCAGACCGACGATACGAGTGGGACCGTGGTYCCAGWCTRATWATCAGACCGAC

GATACRAGTGGRACMGTGGKCCCAGASAKAATAWTCAGRCCgAGWTAYGcWKTCKGGCCTGTAAC

AAAGGACATTAAGTAAAGACAGATAMRMGTgRGACtaaaaCGTGGTCCCAGTCTGATTATCAGAC

-continued

```
CGACGATACGAGTGGGACCGTGGTCCCAGACTAATAATCAGACCGACGATACGAGTGGGACCGTG

GTCCCAGACTAATAATCAGACCGACGATACGAGTGGGACCGTGGTCCCAGTCTGATTATCAGACC

GACGATACAAGTGGAACAGTGGGCCCAGAGAGAATATTCAGGCCAGTTATGCTTTCTGGCCTGTA

ACAAAGGACATTAAGTAAAGACAGATAAACGTAGACTAAAACGTGGTCGCATCAGGGTGCTGGCT

TTTCAAGTTCCTTAAGAATGGCCTCAATTTTCTCTATACACTCAGTTGGAACACGAGACCTGTCC

AGGTTAAGCACCATTTTATCGCCCTTATACAATACTGTCGCTCCAGGAGCAAACTGATGTCGTGA

GCTTAAACTAGTTCTTGATGCAGATGACGTTTTAAGCACAGAAGTTAAAAGAGTGATAACTTCTT

CAGCTTCAAATATCACCCCAGCTTTTTTCTGCTCATGAAGGTTAGATGCCTGCTGCTTAAGTAAT

TCCTCTTTATCTGTAAAGGCTTTTTGAAGTGCATCACCTGACCGGGCAGATAGTTCACCGGGGTG

AGAAAAAGAGCAACAACTGATTTAGGCAATTTGGCGGTGTTGATACAGCGGGTAATAATCTTAC

GTGAAATATTTTCCGCATCAGCCAGCGCAGAAATATTTCCAGCAAATTCATTCTGCAATCGGCTT

GCATAACGCTGACCACGTTCATAAGCACTTGTTGGGCGATAATCGTTACCCAATCTGGATAATGC

AGCCATCTGCTCATCATCCAGCTCGCCAACCAGAACACGATAATCACTTTCGGTAAGTGCAGCAG

CTTTACGACGGCGACTCCCATCGGCAATTTCTATGACACCAGATACTCTTCGACCGAACGCCGGT

GTCTGTTGACCAGTCAGTAGAAAAGAAGGGATGAGATCATCCAGTGCGTCCTCAGTAAGCAGCTC

CTGGTCACGTTCATTACCTGACCATACCCGAGAGGTCTTCTCAACACTATCACCCCGGAGCACTT

CAAGAGTAAACTTCACATCCCGACCACATACAGGCAAAGTAATGGCATTACCGCGAGCCATTACT

CCTACGCGCGCAATTAACGAATCCACCATCGGGGCAGCTGGTGTCGATAACGAAGTATCTTCAAC

CGGTTGAGTATTGAGCGTATGTTTTGGAATAACAGGCGCACGCTTCATTATCTAATCTCCCAGCG

TGGTTTAATCAGACGATCGAAAATTTCATTGCAGACAGGTTCCCAAATAGAAAGAGCATTTCTCC

AGGCACCAGTTGAAGAGCGTTGATCAATGGCCTGTTCAAAAACAGTTCTCATCCGGATCTGACCT

TTACCAACTTCATCCGTTTCACGTACAACATTTTTTAGAACCATGCTTCCCCAGGCATCCCGAAT

TTGCTCCTCCATCCACGGGGACTGAGAGCCATTACTATTGCTGTATTTGGTAAGCAAAATACGTA

CATCAGGCTCGAACCCTTTAAGATCAACGTTCTTGAGCAGATCACGAAGCATATCGAAAAACTGC

AGTGCGGAGGTGTAGTCAAACAACTCAGCAGGCGTGGGAACAATCAGCACATCAGCAGCACATAC

GACATTAATCGTGCCGATACCCAGGTTAGGCGCGCTGTCAATAACTATGACATCATAGTCATGAG

CAACAGTTTCAATGGCCAGTCGGAGCATCAGGTGTGGATCGGTGGGCAGTTTACCTTCATCAAAT

TTGCCCATTAACTCAGTTTCAATACGGTGCAGAGCCAGACAGGAAGGAATAATGTCAAGCCCCGG

CCAGCAAGTGGGCTTTATTGCATAAGTGACATCGTCCTTTTCCCCAAGATAGAAAGGCAGGAGAG

TGTCTTCTGCATGAATATGAAGATCTGGTACCCATCCGTGATACATTGAGGCTGTTCCCTGGGGG

TCGTTACCTTCCACGAGCAAAACACGTAGCCCCTTCAGAGCCAGATCCTGAGCAAGATGAACAGA

AACTGAGGTTTTGTAAACGCCACCTTTATGGGCAGCAACCCCGATCACCGGTGGAAATACGTCTT

CAGCACGTCGCAATCGCGTACCAAACACATCACGCATATGATTAATTTGTTCAATTGTATAACCA

ACACGTTGCTCAACCCGTCCTCGAATTTCCATATCCGGGTGCGGTAGTCGCCCTGCTTTCTCGGC

ATCTCTGATAGCCTGAGAAGAAACCCCAACTAAATCCGCTGCTTCACCTATTCTCCAGCGCCGGG

TTATTTTCCTCGCTTCCGGGCTGTCATCATTAAACTGTGCAATGGCGATAGCCTTCGTCATTTCA

TGACCAGCGTTTATGCACTGGTTAAGTGTTTCCATGAGTTTCATTCTGAACATCCTTTAATCATT

GCTTTGCGTTTTTTATTAAATCTTGCAATTTACTGCAAAGCAACAACAAAATCGCAAAGTCATC

AAAAAACCGCAAAGTTGTTTAAAATAAGAGCAACACTACAAAAGGAGATAAGAAGAGCACATACC

TCAGTCACTTATTATCACTAGCGCTCGCCGCAGCCGTGTAACCGAGCATAGCGAGCGAACTGGCG

AGGAAGCAAAGAAGAACTGTTCTGTCAGATAGCTCTTACGCTCAGCGCAAGAAGAAATATCCACC
```

-continued

```
GTGGGAAAAACTCCAGGTAGAGGTACACACGCGGATAGCCAATTCAGAGTAATAAACTGTGATAA

TCAACCCTCATCAATGATGACGAACTAACCCCCGATATCAGGTCACATGACGAAGGGAAAGAGAA

GGAAATCAACTGTGACAAACTGCCCTCAAATTTGGCTTCCTTAAAAATTACAGTTCAAAAAGTAT

GAGAAAATCCATGCAGGCTGAAGGAAACAGCAAAACTGTGACAAATTACCCTCAGTAGGTCAGAA

CAAATGTGACGAACCACCCTCAAATCTGTGACAGATAACCCTCAGACTATCCTGTCGTCATGGAA

GTGATATCGCGGAAGGAAAATACGATATGAGTCGTCTGGCGGCCTTTCTTTTTCTCAATGTATGA

GAGGCGCATTGGAGTTCTGCTGTTGATCTCATTAACACAGACCTGCAGGAAGCGGCGGCGGAAGT

CAGGCATACGCTGGTAACTTTGAGGCAGCTGGTAACGCTCTATGATCCAGTCGATTTTCAGAGAG

ACGATGCCTGAGCCATCCGGCTTACGATACTGACACAGGGATTCGTATAAACGCATGGCATACGG

ATTGGTGATTTCTTTTGTTTCACTAAGCCGAAACTGCGTAAACCGGTTCTGTAACCCGATAAAGA

AGGGAATGAGATATGGGTTGATATGTACACTGTAAAGCCCTCTGGATGGACTGTGCGCACGTTTG

ATAAACCAAGGAAAAGATTCATAGCCTTTTTCATCGCCGGCATCCTCTTCAGGGCGATaAAAAAC

CACTTCCTTCCCCGCGAAACTCTTCAATGCCTGCCGTATATCCTTACTGGCTTCCGCAGAGGTCA

ATCCGAATATTTCAGCATATTTAGCAACATGGATCTCGCAGATACCGTCATGTTCCTGTAGGGTG

CCATCAGATTTTCTGATCTGGTCAACGAACAGATACAGCATACGTTTTTGATCCCGGGAGAGACT

ATATGCCGCCTCAGTGAGGTCGTTTGACTGGACGATTCGCGGGCTATTTTTACGTTTCTTGTGAT

TGATAACCGCTGTTTCCGCCATGACAGATCCATGTGAAGTGTGACAAGTTTTTAGATTGTCACAC

TAAATAAAAAAGAGTCAATAAGCAGGGATAACTTTGTGAAAAAACAGCTTCTTCTGAGGGCAATT

TGTCACAGGGTTAAGGGCAATTTGTCACAGACAGGACTGTCATTTGAGGGTGATTTGTCACACTG

AAAGGGCAATTTGTCACAACACCTTCTCTAGAACCAGCATGGATAAAGGCCTACAAGGCGCTCTA

AAAAAGAAGATCTAAAAACTATaAAAAAAATAATTATAAAAATATCCCCGTGGATAAGTGGATAA

CCCCAAGGGAAGTTTTTtCAGGCATCGTGTGTAAGCAGAATATATAAGTGCTGTTCCCTGGTGCT

TCCTCGCTCACTCGAGGGCTTCGCCCTGTCGCTCAACTGCGGCGAGCACTACTGGCTGTAAAAGG

ACAGACCACATCATGGTTCTGTGTTCATTAGGTTGTTCTGTCCATTGCTGACATAATCCGCTCCA

CTTCAACGTAACACCGCACGAAGATTTCTATTGTTCCTGAAGGCATATTCAAATCGTTTTCGTTA

CCGCTTGCAGGCATCATGACAGAACACTACTTCCTATAAACGCTACACAGGCTCCTGAGATTAAT

AATGCGGATCTCTACGATAATGGGAGATTTTCCCGACTGTTTCGTTCGCTTCTCAGTGGATAACA

GCCAGCTTCTCTGTTTAACAGACAAAAACAGCATATCCACTCAGTTCCACATTTCCATATAAGG

CCAAGGCATTTATTCTCAGGATAATTGTTTCAGCATCGCAACCGCATCGACTCCGGCATCGCAA

ACTGCACCCGGTGCCGGGCAGCCACATCCAGCGCAAAAACCTTCGTGTAGACTTCCGTTGAACTG

ATGGACTTATGTCCCATCAGGCTTTGCAGAACTTTCAGCGGTATACCGGCATACAGCATGTGCAT

CGCATAGGAATGGCGGAACGTATGTGGTGTGACCGGAACAGAGAACGTCACACCGTCAGCAGCAG

CGGCGGCAACCGCCTCCCCAATCCAGGTCCTGACCGTTCTGTCCGTCACTTCCCAGATCCGCGCT

TTCTCTGTCCTTCCTGTGCGACGGTTACGCCGCTCCATGAGCTTATCGCGAATAAATACCTGTGA

CGGAAGATCACTTCGCAGAATAAATAAATCCTGGTGTCCCTGTTGATACCGGGAAGCCCTGGGCC

AACTTTTGGCGAAAATGAGACGTTGATCGGCACGTAAGAGGTTCCAACTTTCACCATAATGAAAT

AAGATCACTACCGGGCGTATTTTTTGAGTTATCGAGATTTTCAGGAGCTAAGGAAGCTAAAATGG

AGAAAAAAATCACTGGATATACCACCGTTGATATATCCCAATGGCATCGTAAAGAACATTTTGAG

GCATTTCAGTCAGTTGCTCAATGTACCTATAACCAGACCGTTCAGCTGGATATTACGGCCTTTTT

AAAGACCGTAAAGAAAAATAAGCACAAGTTTTATCCGGCCTTTATTCACATTCTTGCCCGCCTGA

TGAATGCTCATCCGGAGTTCCGTATGGCAATGAAAGACGGTGAGCTGGTGATATGGGATAGTGTT
```

-continued

```
CACCCTTGTTACACCGTTTTCCATGAGCAAACTGAAACGTTTTCATCGCTCTGGAGTGAATACCA
CGACGATTTCCGGCAGTTTCTACACATATATTCGCAAGATGTGGCGTGTTACGGTGAAAACCTGG
CCTATTTCCCTAAAGGGTTTATTGAGAATATGTTTTTCGTCTCAGCCAATCCCTGGGTGAGTTTC
ACCAGTTTTGATTTAAACGTGGCCAATATGGACAACTTCTTCGCCCCCGTTTTCACCATGGGCAA
ATATTATACGCAAGGCGACAAGGTGCTGATGCCGCTGGCGATTCAGGTTCATCATGCCGTTTGTG
ATGGCTTCCATGTCGGCAGAATGCTTAATGAATTACAACAGTACTGCGATGAGTGGCAGGGCGGG
GCGTAAtTTTTTTAAGGCAGTTATTGGTGCCCTTAAACGCCTGGTTGCTACGCCTGAATAAGTGA
TAATAAGCGGATGAATGGCAGAAATTCGATGATAAGCTGTCAAACATGAGAATTGGTCGACGGCG
CGCCAAAGCTTGCATGCCTGCAGCCGCGTAACCTGGCAAAATCGGTTACGGTTGAGTAATAAATG
GATGCCCTGCGTAAGCGGGGCACATTTCATTACCTCTTTCTCCGCACCCGACATAGATAATAACT
TCGTATAGTATACATTATACGAAGTTATCTAGTAGACTTAATCGCGTTTAAACCCATCATCAATA
ATATACCTCAAACTTTTTGTGCGCGTTAATATGCAAATGAGGCGTTTGAATTTGGGAAGGGAGGA
AGGTGATTGGCCGAGAGAAGGGCGACCGTTAGGGGCGGGGCGAGTGACGTTTTGATGACGTGACC
GCGAGGAGGAGCCAGTTTGCAAGTTCTCGTGGGAAAAGTGACGTCAAACGAGGTGTGGTTTGAAC
ACGGAAATACTCAATTTTCCCGCGCTCTCTGACAGGAAATGAGGTGTTTCTAGGCGGATGCAAGT
GAAAACGGGCCATTTTCGCGCGAAAACTGAATGAGGAAGTGAAAATCTGAGTAATTTCGCGTTTA
TGACAGGGAGGAGTATTTGCCGAGGGCCGAGTAGACTTTGACCGATTACGTGGGGGTTTCGATTA
CCGTGTTTTTCACCTAAATTTCCGCGTACGGTGTCAAAGTCCGGTGTTTTTACGTAGGTGTCAGC
TGATCGCCAGGGTATTTAAACCTGCGCTCTCCAGTCAAGAGGCCACTCTTGAGTGCCAGCGAGAA
GAGTTTTCTCCTCCGCGCGCGAGTCAGATCTACACTTTGAAAGGCGATCGCTAGCGACATCGATC
ACAAGTTTGTACAAAAAAGCAGGCTCCACCATGGGAACCAATTCAgTCGAGCCTTTCACTCATTA
GATGCATGTCGTTACATAACTTACGGTAAATGGCCCGCCTGGCTGACCGCCCAACGACCCCCGCC
CATTGACGTCAATAATGACGTATGTTCCCATAGTAACGCCAATAGGGACTTTCCATTGACGTCAA
TGGGTGGAGTATTTACGGTAAACTGCCCACTTGGCAGTACATCAAGTGTATCATATGCCAAGTAC
GCCCCCTATTGACGTCAATGACGGTAAATGGCCCGCCTGGCATTATGCCCAGTACATGACCTTAT
GGGACTTTCCTACTTGGCAGTACATCTACGTATTAGTCATCGCTATTACCATGGTGATGCGGTTT
TGGCAGTACATCAATGGGCGTGGATAGCGGTTTGACTCACGGGGATTTCCAAGTCTCCACCCCAT
TGACGTCAATGGGAGTTTGTTTTGGCACCAAAATCAACGGGACTTTCCAAAATGTCGTAACAACT
CCGCCCCATTGACGCAAATGGGCGGTAGGCGTGTACGGTGGGAGGTCTATATAAGCAGAGCTCTC
CCTATCAGTGATAGAGATCTCCCTATCAGTGATAGAGATCGTCGACGAGCTCGTTTAGTGAACCG
TCAGATCGCCTGGAGACGCCATCCACGCTGTTTTGACCTCCATAGAAGACACCGGGACCGATCCA
GCCTCCGGTTAAGCTcGgtacCGCTAGCCGCGCCGCCACCATGGATGCTATGAAGAGGGGCCTGT
GCTGCGTGCTGCTGCTGTGTGGCGCCGTGTTTGTGTCCCCCAGCCAGGAAATCCACGCCCGGTTC
AGAAGAGGCAGCAAGCTGGCCGACGAGGACGAGACAGCCTACGACAGCGGCACCGACCTGATCGA
CTTCATCGACGACAGCGACGAGAATGAGAACGACTCCGACACCGGCGAGGACATGGTGGATTTCA
TCGACAACGACGAAACCGACGAAGAGAGCACCGAGAGCGACCTGGACGGCTTTATCGACAACTCC
GCCCAGCTGGCTGACAGCGACAGCAATGCCTGCGCCTTCCTGAAGGCTCAGCTGGCAGACGTGAA
CAGCAACGCCGCTGCTTTTCTGAAGAACTGCATCCTGCTGTACGGCGCTGCCAACACCGGCAAGA
GCCTGTTCGGCATGAGCCTGAACTGCCTGGTGCTGTGCGGCCCAGCCAATACCGGAAAGTCCTAC
TTCGGCATGTCCCTGAATTGTCTCGTGATCTACGGCCCACCTAACACAGGCAAGTCCTGCTTTGC
CATGTCTCTGTGGCCCTACCTGCACAGCAGACTGGTGGTGTTTACCTTCCCCAACCCCTTCTGGC
```

-continued

```
CTTACCTGGAAAGCCGGATCACCGTGTTCGAGTTCCCCAATGCCTTTCTGAGATACCTGCACTCC

CGGATCCACGTGCTGCAGTTTCTGAACCCCTTCAACGTGTGCCAGGACAAGATCCTGGAACACTA

CGAGAACGACAGCAAGGACATTCTGGAACATTATGAGAATGATTCCAAGGACCTGTGCGACCACA

TCTGCGATCACATCGACTACTGGAAGCACATCCGGCTGGAATGCGCCATCATGTACAAGGCCCGG

ATCAGACTGGAATGTGCTATTATGTATAAGGCTCGCGAGATGGGCTTCCACCAGTTCGACGGCGA

CATCTGCAACACCATGCACTACACCAACTGGATCTATATCTGCGAGGACGCCCAGTGCACCGTGG

TGGAAGGCCAGGTGGACAAGAAATGGGAGGTGCACGCTGGCGGCCAAGTGATCCTGTGTCCTGAG

AGCGGCCAGCGGCGGATCAAGAGGCCCAGAAGCGAGAACTGCCACCCCAACAAGCTGCTGATCCT

GAAGTGCCTGCGGTACAGATTCAAGAAGCACTGCAAGCTGAGCAGCACCTGGCACTGGACCTGCC

ACGACGGCAAGCACAAGTGGCATTGGACATGTCACGATGGGAAACACAAGAACGCCATTGTGACC

CTGACCTACTACGAGGCCGACAAGAACGACCTGAACGCCCAGATCGAGCACTGGAAACTGATCCG

GATGGAATGTGCAATCTTCTATAAGGCCAAAGAGCTGGGCATCAGCATCTGCCACCAGGTGGTGC

CTCCACTGGCCGCCTCTAAAGCCAAAGCCTGCCAGGCCATCGAACTGCAGCTGGCCCTGGAAGCC

CTGAATGCCAGCCCCTACGATGAGTGGACCCTGCAGCAGACCAGCCTGGAAATGTGGCTGGCCGA

GCCCCAGTTTAAGAAGCACGGCATCACCATCACCGTGCAGTACGACAATGACAAGGCCAATACCA

TGGATTACACAAATTGGAAAGAAATCTACGTGATCGTGTGCCCCGCCAGCATCCCCTCCGATGAG

ATCAGCACCGAGGAAGCCGACCACATTGATTATTGGAAAGCCATCAGGCAGGAAAACGCCATCTT

CTTCGCCGCCAGACACCAGGTGGTGCCCGCCCTGAATATCTGCAAGGCCAAGGCCTGTAAAGCCA

TCGAGTGGAACACCGAGCCCAAGCACTGCTTCAAGAAGGGCGGCCAGCACATCGAAGTGTGGTTC

GACTACGTGGCCTGGGACAGCGTGTACTACTGCGGCGACGATGGCTGGTGCAAGACCGAGGCCGA

GAAGTACGGCTGCAAGGGCACCTGGGAAGTGCATTTCGGCAACAGCATCGACTGCAACGACTCCA

TGTGCAGCACCTTCGACGACAACGTGTCCGCCACCGAGCTCGTGAAGGACCATATCGACTATTGG

AAGCTGATTCGCCTGGAATGTGCCATTTTTTACAAGGCCAGACGGCGGCTGTCCAGCGACCAGGA

TCAGTCTCAGCTCGTGACCAAGTACCCCCTGCTGAAGCTGCTGTCCAGACCCCCCAACATGGGCG

TGAAGGCCCACGGCAAGTGCATCTGGGAGAACAAGGTGTTCATCGTGCCCACCCTGTGCCCCGTG

CCTCTGGATCCAACATATCCTCTGCTGAAACTGCTGACCACCCAGACCACCACCCCCGAGAATAC

CTCCCTGGTGGAACTGAGAGTGACCACCCCCAAGAGCACAGTCGTGATCAGGCTGCACCTGACCA

CCAGATACCCACTGCTGTCACTGCTGAACAGCTACAGCACCCCCCCTCACCGGATCCCTGCTCCA

TGTCCTTGGGCTCCTCAGAGGCCCCCCATCCCTAAGCCTTCTCCATGGGCCCCTAGAATCCCTGC

CCCTTGCCCCTGGGCACCTCCTAGACCTCCACACTGTCCATGGGTGCCCCCTCCACCTCCTCCAA

GACCTTGGGCCCCTTGCTTCCTGCTGTGCTTTTGTGTGCTGCTGTGCGTGTGCCTGCTGATCAGA

CCCCTGCTGCTGAGTGTGTCCACCTACCTGAGGCCTCTGCTGCTGTCTATCAGCGTGTACGCTCA

GGTGCTGGTGCTGGTGCTGCTGTGGGTGTCCATCGGAAGCCTGCTGCCCAGCGTGTGCATGT

GTGCCTATGCCTGGGTGCTGGTGTTCGTGTACATCGTCGTGATTACCAGCCCCGCCACCGCCATC

GTGTACCGGGATGGCAATCCTTACGCCGTGTGCGACAAGTGCCTGAAGTTCTACAGCAAGATCAG

CGAGTACCGGCACTACTGCTACAGCCTGTACGGCACCACCCTGGAACAGCAGTACAACAAGCCCC

TGTGCGATCTGCTGATTCGGTGCATCAACGTGGTGTACAGAGACTCCATCCCCCACGCCGCCTGC

CACAAGTGTATCGACTTCTACTCCAGAATCAGAGAGCTGCGGCACTACAGCGACTCCGTGTACGG

CGATACCCTGGAAAAGCTGACCAACACTGGCCTGTACAACCTGCTGATTAGATGCCTGCGGGTGT

TCTGCAAGAAGGCCCTGACAGCCAGCGAGGTGTACAACTTCGCCTACACCGATCTGCGGGTGGTG

TATCGGGACAGCAAAGTGCGGAAGCTGAGGTACTACAACTGCTCTGTGTATGGCGCCAGCCTGGT
```

```
GTATTGCAAGGGACAGCTGACCGAGACAGAGGTGCTGGATTTCGCCTTCACAGACCTGACAATCG

TGTATCGCGACTCCAAGGTGTCCGAGTTCCGGTGGTACAGATATTCCGTGTATGGCACCACACTG

TGCGTGGAATGCAAGAAAACCCTGCAGAGATCTGAGGTGTACGACTGCCAGCGGCCACTGTGTCC

GCAGGAAAAGAAAAGACACGTGGACCTGAACAAGCGGTTCCACACCCTGCACGAGTACATGCTGG

ATCTGCAGCCCGAGACAACCGACCTGTACTGCTACGAGCAGCCTGAAACCACTGATCTGCACTGT

TATGAGCAGCTGGGAGACAGCTCCGATGAAGAGGACACTGGCGGCCTGGATGGGGACGAGGATGA

GGACGAAGTGGACCATCTGCAGGAACAGCCCCAGCAGGCTAGACGGGACGAACAGCACCCTTGCT

ATCTGATCGAGACACAGTGCTGCAGATGCGAATCTCTGGTGGAAGAGAACGACGAGATCGACGGC

GTGAACCACCAGCATCTGCCCGCTAGAAGGGCCGAGCCTCAGAGACACACCATGCTGTGTATGTG

CTGCAAGTGCGAGGCCAGAATCGCCGGCTCTGGACCTGGCGCCTCTGGCAAGCCTATCCCCAATC

CACTGCTGGGCCTGGACTCCACCCGGACCTGATAAGCggccgctcgagcatgcatctagagggcc ctattctatagtgtcacctaaatgctagagctcgctgatcagcctcgactgtgccttctagttgc cagccatctgttgtttgcccctcccccgtgccttccttgaccctggaaggtgccactcccactgt cctttcctaataaaatgaggaaattgcatcgcattgtctgagtaggtgtcattctattctggggg gtggggtggggcaggacagcaaggggggaggattgggaagacaatagcaggcatgctggggatgcg gtgggctctatggcttctgaggcggaaagaaccagctggggctcgaggggggatcgatcccgtcG

AGATATCTAGACCCAGCTTTCTTGTACAAAGTGGTGATCGATTCGACAGATCGCGATCGCAGTGA

GTAGTGTTCTGGGGCGGGGGAGGACCTGCATGAGGGCCAGAATGACTGAAATCTGTGCTTTTCTG

TGTGTTGCAGCATCATGAGCGGAAGCGGCTCCTTTGAGGGAGGGGTATTCAGCCCTTATCTGACG

GGGCGTCTCCCCTCCTGGGCGGGAGTGCGTCAGAATGTGATGGGATCCACGGTGGACGGCCGGCC

CGTGCAGCCCGCGAACTCTTCAACCCTGACCTATGCAACCCTGAGCTCTTCGTCGGTGGACGCAG

CTGCCGCCGCAGCTGCTGCATCCGCCGCCAGCGCCGTGCGCGGAATGGCCATGGGCGCCGGCTAC

TACGGCACTCTGGTGGCCAACTCGAGTTCCACCAATAATCCCGCCAGCCTGAACGAGGAGAAGCT

GCTGCTGCTGATGGCCCAGCTTGAGGCCTTGACCCAGCGCCTGGGCGAGCTGACCCAGCAGGTGG

CTCAGCTGCAGGAGCAGACGCGGGCCGCGGTTGCCACGGTGAAATCCAAATAAAAAATGAATCAA

TAAATAAACGGAGACGGTTGTTGATTTTAACACAGAGTCTGAATCTTTATTTGATTTTTCGCGCG

CGGTAGGCCCTGGACCACCGGTCTCGATCATTGAGCACCCGGTGGATCTTTTCCAGGACCCGGTA

GAGGTGGGCTTGGATGTTGAGGTACATGGGCATGAGCCCGTCCCGGGGGTGGAGGTAGCTCCATT

GCAGGGCCTCGTGCTCGGGGGTGGTGTTGTAAATCACCCAGTCATAGCAGGGGCGCAGGGCGTGG

TGTTGCACAATATCTTTGAGGAGGAGACTGATGGCCACGGGCAGCCCTTTGGTGTAGGTGTTTAC

AAATCTGTTGAGCTGGGAGGGATGCATGCGGGGGAGATGAGGTGCATCTTGGCCTGGATCTTGA

GATTGGCGATGTTACCGCCCAGATCCCGCCTGGGGTTCATGTTGTGCAGGACCACCAGCACGGTG

TATCCGGTGCACTTGGGGAATTTATCATGCAACTTGGAAGGGAAGGCGTGAAAGAATTTGGCGAC

GCCCTTGTGTCCGCCCAGGTTTTCCATGCACTCATCCATGATGATGGCAATGGGCCCGTGGGCGG

CGGCCTGGGCAAAGACGTTTCGGGGGTCGGACACATCATAGTTGTGGTCCTGGGTGAGGTCATCA

TAGGCCATTTTAATGAATTTGGGGCGGAGGGTGCCGGACTGGGGGACAAAGGTACCCTCGATCCC

GGGGGCGTAGTTCCCCTCACAGATCTGCATCTCCCAGGCTTTGAGCTCAGAGGGGGGATCATGT

CCACCTGCGGGGCGATAAAGAACACGGTTTCCGGGGCGGGGAGATGAGCTGGGCCGAAAGCAAG

TTCCGGAGCAGCTGGGACTTGCCGCAGCCGGTGGGGCCGTAAATGACCCCGATGACCGGCTGCAG

GTGGTAGTTGAGGGAGAGACAGCTGCCGTCCTCCCGGAGGAGGGGGGCCACCTCGTTCATCATCT

CGCGCACGTGCATGTTCTCGCGCACCAGTTCCGCCAGGAGGCGCTCTCCCCCCAGAGATAGGAGC
```

-continued
```
TCCTGGAGCGAGGCGAAGTTTTTCAGCGGCTTGAGTCCGTCGGCCATGGGCATTTTGGAGAGGGT
CTGTTGCAAGAGTTCCAAGCGGTCCCAGAGCTCGGTGATGTGCTCTACGGCATCTCGATCCAGCA
GACCTCCTCGTTTCGCGGGTTGGGACGACTGCGGGAGTAGGGCACCAGACGATGGGCGTCCAGCG
CAGCCAGGGTCCGGTCCTTCCAGGGCCGCAGCGTCCGCGTCAGGGTGGTCTCCGTCACGGTGAAG
GGGTGCGCGCCGGGCTGGGCGCTTGCGAGGGTGCGCTTCAGGCTCATCCGGCTGGTCGAAAACCG
CTCCCGATCGGCGCCCTGCGCGTCGGCCAGGTAGCAATTGACCATGAGTTCGTAGTTGAGCGCCT
CGGCCGCGTGGCCTTTGGCGCGGAGCTTACCTTTGGAAGTCTGCCCGCAGGCGGGACAGAGGAGG
GACTTGAGGGCGTAGAGCTTGGGGGCGAGGAAGACGGAATCGGGGGCGTAGGCGTCCGCGCCGCA
GTGGGCGCAGACGGTCTCGCACTCCACGAGCCAGGTGAGGTCGGGCTGGTCGGGGTCAAAAACCA
GTTTCCCGCCGTTCTTTTTGATGCGTTTCTTACCTTTGGTCTCCATGAGCTCGTGTCCCCGCTGG
GTGACAAAGAGGCTGTCCGTGTCCCCGTAGACCGACTTTATGGGCCGGTCCTCGAGCGGTGTGCC
GCGGTCCTCCTCGTAGAGGAACCCCGCCCACTCCGAGACGAAAGCCCGGGTCCAGGCCAGCACGA
AGGAGGCCACGTGGGACGGGTAGCGGTCGTTGTCCACCAGCGGGTCCACTTTTTCCAGGGTATGC
AAACACATGTCCCCCTCGTCCACATCCAGGAAGGTGATTGGCTTGTAAGTGTAGGCCACGTGACC
GGGGGTCCCGGCCGGGGGGTATAAAAGGGGGCGGGCCCCTGCTCGTCCTCACTGTCTTCCGGAT
CGCTGTCCAGGAGCGCCAGCTGTTGGGGTAGGTATTCCCTCTCGAAGGCGGGCATGACCTCGGCA
CTCAGGTTGTCAGTTTCTAGAAACGAGGAGGATTTGATATTGACGGTGCCAGCGGAGATGCCTTT
CAAGAGCCCCTCGTCCATCTGGTCAGAAAAGACGAtTTTTTTGTTGTCGAGCTTGGTGGCGAAGG
AGCCGTAGAGGGCGTTGGAAAGGAGCTTGGCGATGGAGCGCATGGTCTGGTTTTTTtCCTtGTCG
GCGCGCTCCTTGGCCGCGATGTTGAGCTGCACGTACTCGCGCGCCACGCACTTCCATTCGGGGAA
GACGGTGGTCATCTCGTCGGGCACGATTCTGACCTGCCAACCTCGATTATGCAGGGTGATGAGGT
CCACACTGGTGGCCACCTCGCCGCGCAGGGGCTCGTTGGTCCAGCAGAGGCGGCCGCCCTTGCGC
GAGCAGAAGGGGGGCAGAGGGTCCAGCATGACCTCGTCGGGGGGTCGGCATCGATGGTGAAGAT
GCCGGGCAGGAGATCGGGGTCGAAGTAGCTGATGGAAGTGGCCAGATCGTCCAGGGAAGCTTGCC
ATTCGCGCACGGCCAGCGCGCGCTCGTAGGGACTGAGGGGCGTGCCCCAGGGCATGGGGTGGGTG
AGCGCGGAGGCGTACATGCCGCAGATGTCGTAGACGTAGAGGGGCTCCTCGAGGATGCCGATGTA
GGTGGGGTAGCAGCGCCCCCCGCGGATGCTGGCGCGCACGTAGTCATACAGCTCGTGCGAGGGCG
CGAGGAGCCCCGGGCCCAGGTTGGTGCGACTGGGCTTTTCGGCGCGGTAGACGATCTGGCGAAAG
ATGGCATGCGAGTTGGAGGAGATGGTGGGCCTTTGGAAGATGTTGAAGTGGGCGTGGGGGAGGCC
GACCGAGTCGCGGATGAAGTGGGCGTAGGAGTCTTGCAGTTTGGCGACGAGCTCGGCGGTGACGA
GGACGTCCAGAGCGCAGTAGTCGAGGGTCTCCTGGATGATGTCATACTTGAGCTGGCCCTTTTGT
TTCCACAGCTCGCGGTTGAGAAGGAACTCTTCGCGGTCCTTCCAGTACTCTTCGAGGGGGAACCC
GTCCTGATCTGCACGGTAAGAGCCTAGCATGTAGAACTGGTTGACGGCCTTGTAGGCGCAGCAGC
CCTTCTCCACGGGGAGGGCGTAGGCCTGGGCGGCCTTGCGCAGGGAGGTGTGCGTGAGGGCGAAG
GTGTCCCTGACCATGACCTTGAGGAACTGGTGCTTGAAATCGATATCGTCGCAGcCCCCCTGCTC
CCAGAGCTGGAAGTCCGTGCGCTTCTTGTAGGCGGGGTTGGGCAAAGCGAAAGTAACATCGTTGA
AAAGGATCTTGCCCGCGCGGGGCATAAAGTTGCGAGTGATGCGGAAAGGCTGGGGCACCTCGGCC
CGGTTGTTGATGACCTGGGCGGCGAGCACGATCTCGTCGAAACCGTTGATGTTGTGGCCCACGAT
GTAGAGTTCCACGAATCGCGGGCGGCCCTTGACGTGGGGCAGCTTCTTGAGCTCCTCGTAGGTGA
GCTCGTCGGGGTCGCTGAGACCGTGCTGCTCGAGCGCCCAGTCGGCGAGATGGGGGTTGGCGCGG
AGGAAGGAAGTCCAGAGATCCACGGCCAGGGCGGTTTGCAGACGGTCCCGGTACTGACGGAACTG
```

-continued

```
CTGCCCGACGGCCATTTTTTCGGGGGTGACGCAGTAGAAGGTGCGGGGGTCCCCGTGCCAGCGGT

CCCATTTGAGCTGGAGGGCGAGATCGAGGGCGAGCTCGACGAGGCGGTCGTCCCCTGAGAGTTTC

ATGACCAGCATGAAGGGGACGAGCTGCTTGCCGAAGGACCCCATCCAGGTGTAGGTTTCCACATC

GTAGGTGAGGAAGAGCCTTTCGGTGCGAGGATGCGAGCCGATGGGGAAGAACTGGATCTCCTGCC

ACCAATTGGAGGAATGGCTGTTGATGTGATGGAAGTAGAAATGCCGACGGCGCGCCGAACACTCG

TGCTTGTGTTTATACAAGCGGCCACAGTGCTCGCAACGCTGCACGGGATGCACGTGCTGCACGAG

CTGTACCTGAGTTCCTTTGACGAGGAATTTCAGTGGGAAGTGGAGTCGTGGCGCCTGCATCTCGT

GCTGTACTACGTCGTGGTGGTCGGCCTGGCCCTCTTCTGCCTCGATGGTGGTCATGCTGACGAGC

CCGCGCGGGAGGCAGGTCCAGACCTCGGCGCGAGCGGGTCGGAGAGCGAGGACGAGGGCGCGCAG

GCCGGAGCTGTCCAGGGTCCTGAGACGCTGCGGAGTCAGGTCAGTGGGCAGCGGCGGCGCGCGGT

TGACTTGCAGGAGTTTTTCCAGGGCGCGCGGGAGGTCCAGATGGTACTTGATCTCCACCGCGCCG

TTGGTGGCGACGTCGATGGCTTGCAGGGTCCCGTGCCCCTGGGGTGTGACCACCGTCCCCCGTTT

CTTCTTGGGCGGCTGGGGCGACGGGGCGGTGCCTCTTCCATGGTTAGAAGCGGCGGCGAGGACG

CGCGCCGGGCGGCAGAGGCGGCTCGGGGCCCGGAGGCAGGGGCGGCAGGGGCACGTCGGCGCCGC

GCGCGGGTAGGTTCTGGTACTGCGCCCGGAGAAGACTGGCGTGAGCGACGACGCGACGGTTGACG

TCCTGGATCTGACGCCTCTGGGTGAAGGCCACGGGACCCGTGAGTTTGAACCTGAAAGAGAGTTC

GACAGAATCAATCTCGGTATCGTTGACGGCGGCCTGCCGCAGGATCTCTTGCACGTCGCCCGAGT

TGTCCTGGTAGGCGATCTCGGTCATGAACTGCTCGATCTCCTCCTCCTGAAGGTCTCCGCGACCG

GCGCGCTCCACGGTGGCCGCGAGGTCGTTGGAGATGCGGCCCATGAGCTGCGAGAAGGCGTTCAT

GCCCGCCTCGTTCCAGACGCGGCTGTAGACCACGACGCCCTCGGGATCGCGGGCGCGCATGACCA

CCTGGGCGAGGTTGAGCTCCACGTGGCGCGTGAAGACCGCGTAGTTGCAGAGGCGCTGGTAGAGG

TAGTTGAGCGTGGTGGCGATGTGCTCGGTGACGAAGAAATACATGATCCAGCGGCGGAGCGGCAT

CTCGCTGACGTCGCCCAGCGCCTCCAAGCGTTCCATGGCCTCGTAAAAGTCCACGGCGAAGTTGA

AAAACTGGGAGTTGCGCGCCGAGACGGTCAACTCCTCCTCCAGAAGACGGATGAGCTCGGCGATG

GTGGCGCGCACCTCGCGCTCGAAGGCCCCCGGGAGTTCCTCCACTTCCTCCTCTTCTTCCTCCTC

CACTAACATCTCTTCTACTTCCTCCTCAGGCGGTGGTGGTGGCGGGGAGGGGCCTGCGTCGCC

GGCGGCGCACGGGCAGACGGTCGATGAAGCGCTCGATGGTCTCGCCGCGCCGGCGTCGCATGGTC

TCGGTGACGGCGCGCCCGTCCTCGCGGGGCCGCAGCGTGAAGACGCCGCCGCGCATCTCCAGGTG

GCCGGGGGGTCCCCGTTGGGCAGGGAGAGGGCGCTGACGATGCATCTTATCAATTGCCCCGTAG

GGACTCCGCGCAAGGACCTGAGCGTCTCGAGATCCACGGGATCTGAAAACCGTTGAACGAAGGCT

TCGAGCCAGTCGCAGTCGCAAGGTAGGCTGAGCACGGTTTCTTCTGCCGGGTCATGTTGGGGAGC

GGGGCGGGCGATGCTGCTGGTGATGAAGTTGAAATAGGCGGTTCTGAGACGGCGGATGGTGGCGA

GGAGCACCAGGTCTTTGGGCCCGGCTTGCTGGATGCGCAGACGGTCGGCCATGCCCCAGGCGTGG

TCCTGACACCTGGCCAGGTCCTTGTAGTAGTCCTGCATGAGCCGCTCCACGGGCACCTCCTCCTC

GCCCGCGCGGCCGTGCATGCGCGTGAGCCCGAAGCCGCGCTGGGGCTGGACGAGCGCCAGGTCGG

CGACGACGCGCTCGGCGAGGATGGCCTGCTGGATCTGGGTGAGGGTGGTCTGGAAGTCGTCAAAG

TCGACGAAGCGGTGGTAGGCTCCGGTGTTGATGGTGTAGGAGCAGTTGGCCATGACGGACCAGTT

GACGGTCTGGTGGCCCGGACGCACGAGCTCGTGGTACTTGAGGCGCGAGTAGGCGCGCGTGTCGA

AGATGTAGTCGTTGCAGGTGCGCACCAGGTACTGGTAGCCGATGAGGAAGTGCGGCGGCGGCTGG

CGGTAGAGCGGCCATCGCTCGGTGGCGGGGGCGCCGGGCGCGAGGTCCTCGAGCATGGTGCGGTG

GTAGCCGTAGATGTACCTGGACATCCAGGTGATGCCGGCGGCGGTGGTGGAGGCGCGCGGGAACT
```

-continued
CGCGGACGCGGTTCCAGATGTTGCGCAGCGGCAGGAAGTAGTTCATGGTGGGCACGGTCTGGCCC
GTGAGGCGCGCGCAGTCGTGGATGCTCTATACGGGCAAAAACGAAAGCGGTCAGCGGCTCGACTC
CGTGGCCTGGAGGCTAAGCGAACGGGTTGGGCTGCGCGTGTACCCCGGTTCGAATCTCGAATCAG
GCTGGAGCCGCAGCTAACGTGGTACTGGCACTCCCGTCTCGACCCAAGCCTGCACCAACCCTCCA
GGATACGGAGGCGGGTCGTTTTGCAACTTTTTTtGGAGGCCGGAAATGAAACTAGTAAGCGCGGA
AAGCGGCCGACCGCGATGGCTCGCTGCCGTAGTCTGGAGAAGAATCGCCAGGGTTGCGTTGCGGT
GTGCCCCGGTTCGAGGCCGGCCGGATTCCGCGGCTAACGAGGGCGTGGCTGCCCCGTCGTTTCCA
AGACCCCATAGCCAGCCGACTTCTCCAGTTACGGAGCGAGCCCCTCTTTTGTTTTGTTTGTTTTT
GCCAGATGCATCCCGTACTGCGGCAGATGCGCCCCCACCACCCTCCACCGCAACAACAGCCCCCT
CCTCCACAGCCGGCGCTTCTGCCCCCGCCCCAGCAGCAGCAGCAACTTCCAGCCACGACCGCCGC
GGCCGCCGTGAGCGGGGCTGGACAGACTTCTCAGTATGATCACCTGGCCTTGGAAGAGGGCGAGG
GGCTGGCGCGCCTGGGGCGTCGTCGCCGGAGCGGCACCCGCGCGTGCAGATGAAAAGGGACGCT
CGCGAGGCCTACGTGCCCAAGCAGAACCTGTTCAGAGACAGGAGCGGCGAGGAGCCCGAGGAGAT
GCGCGCGGCCCGGTTCCACGCGGGGCGGGAGCTGCGGCGCGGCCTGGACCGAAAGAGGGTGCTGA
GGGACGAGGATTTCGAGGCGGACGAGCTGACGGGGATCAGCCCCGCGCGCGCACGTGGCCGCG
GCCAACCTGGTCACGGCGTACGAGCAGACCGTGAAGGAGGAGAGCAACTTCCAAAAATCCTTCAA
CAACCACGTGCGCACCCTGATCGCGCGCGAGGAGGTGACCCTGGGCCTGATGCACCTGTGGGACC
TGCTGGAGGCCATCGTGCAGAACCCCACCAGCAAGCCGCTGACGGCGCAGCTGTTCCTGGTGGTG
CAGCATAGTCGGGACAACGAGGCGTTCAGGGAGGCGCTGCTGAATATCACCGAGCCCGAGGGCCG
CTGGCTCCTGGACCTGGTGAACATTCTGCAGAGCATCGTGGTGCAGGAGCGCGGGCTGCCGCTGT
CCGAGAAGCTGGCGGCCATCAACTTCTCGGTGCTGAGTCTGGGCAAGTACTACGCTAGGAAGATC
TACAAGACCCCGTACGTGCCCATAGACAAGGAGGTGAAGATCGACGGGTTTTACATGCGCATGAC
CCTGAAAGTGCTGACCCTGAGCGACGATCTGGGGGTGTACCGCAACGACAGGATGCACCGCGCGG
TGAGCGCCAGCAGGCGGCGCGAGCTGAGCGACCAGGAGCTGATGCACAGCCTGCAGCGGGCCCTG
ACCGGGGCCGGGACCGAGGGGGAGAGCTACTTTGACATGGGCGCGGACCTGCACTGGCAGCCCAG
CCGCCGGGCCTTGGAGGCGGCAGGCGGTCCCCCCTACATAGAAGAGGTGGACGATGAGGTGGACG
AGGAGGGCGAGTACCTGGAAGACTGATGGCGCGACCGTATTTTTGCTAGATGCAACAACAGCCAC
CTCCTGATCCCGCGATGCGGGCGGCGCTGCAGAGCCAGCCGTCCGGCATTAACTCCTCGGACGAT
TGGACCCAGGCCATGCAACGCATCATGGCGCTGACGACCCGCAACCCCGAAGCCTTTAGACAGCA
GCCCCAGGCCAACCGGCTCTCGGCCATCCTGGAGGCCGTGGTGCCCTCGCGCTCCAACCCCACGC
ACGAGAAGGTCCTGGCCATCGTGAACGCGCTGGTGGAGAACAAGGCCATCCGCGGCGACGAGGCC
GGCCTGGTGTACAACGCGCTGCTGGAGCGCGTGGCCCGCTACAACAGCACCAACGTGCAGACCAA
CCTGGACCGCATGGTGACCGACGTGCGCGAGGCCGTGGCCCAGCGCGAGCGGTTCCACCGCGAGT
CCAACCTGGGATCCATGGTGGCGCTGAACGCCTTCCTCAGCACCCAGCCCGCCAACGTGCCCCGG
GGCCAGGAGGACTACACCAACTTCATCAGCGCCCTGCGCCTGATGGTGACCGAGGTGCCCCAGAG
CGAGGTGTACCAGTCCGGGCCGGACTACTTCTTCCAGACCAGTCGCCAGGGCTTGCAGACCGTGA
ACCTGAGCCAGGCGTTCAAGAACTTGCAGGGCCTGTGGGGCGTGCAGGCCCCGGTCGGGGACCGC
GCGACGGTGTCGAGCCTGCTGACGCCGAACTCGCGCCTGCTGCTGCTGCTGGTGGCCCCCTTCAC
GGACAGCGGCAGCATCAACCGCAACTCGTACCTGGGCTACCTGATTAACCTGTACCGCGAGGCCA
TCGGCCAGGCGCACGTGGACGAGCAGACCTACCAGGAGATCACCCACGTGAGCCGCGCCCTGGGC
CAGGACGACCCGGGCAATCTGGAAGCCACCCTGAACTTTTTGCTGACCAACCGGTCGCAGAAGAT -continued

```
CCCGCCCCAGTACACGCTCAGCGCCGAGGAGGAGCGCATCCTGCGATACGTGCAGCAGAGCGTGG
GCCTGTTCCTGATGCAGGAGGGGGCCACCCCCAGCGCCGCGCTCGACATGACCGCGCGCAACATG
GAGCCCAGCATGTACGCCAGCAACCGCCCGTTCATCAATAAACTGATGGACTACTTGCATCGGGC
GGCCGCCATGAACTCTGACTATTTCACCAACGCCATCCTGAATCCCCACTGGCTCCCGCCGCCGG
GGTTCTACACGGGCGAGTACGACATGCCCGACCCCAATGACGGGTTCCTGTGGGACGATGTGGAC
AGCAGCGTGTTCTCCCCCCGACCGGGTGCTAACGAGCGCCCCTTGTGGAAGAAGGAAGGCAGCGA
CCGACGCCCGTCCTCGGCGCTGTCCGGCCGCGAGGGTGCTGCCGCGGCGGTGCCCGAGGCCGCCA
GTCCTTTCCCGAGCTTGCCCTTCTCGCTGAACAGTATTCGCAGCAGCGAGCTGGGCAGGATCACG
CGCCCGCGCTTGCTGGGCGAGGAGGAGTACTTGAATGACTCGCTGTTGAGACCCGAGCGGGAGAA
GAACTTCCCCAATAACGGGATAGAGAGCCTGGTGGACAAGATGAGCCGCTGGAAGACGTATGCGC
AGGAGCACAGGGACGATCCGTCGCAGGGGCCACGAGCCGGGCAGCGCCGCCCGTAAACGCCGG
TGGCACGACAGGCAGCGGGACTGATGTGGGACGATGAGGATTCCGCCGACGACAGCAGCGTGTT
GGACTTGGGTGGGAGTGGTAACCCGTTCGCTCACCTGCGCCCCCGCATCGGGCGCATGATGTAAG
AGAAACCGAAAATAAATGATACTCACCAAGGCCATGGCGACCAGCGTGCGTTCGTTTCTTCTCTG
TTGTTGTATCTAGTATGATGAGGCGTGCGTACCCGGAGGGTCCTCCTCCCTCGTACGAGAGCGTG
ATGCAGCAGGCGATGGCGGCGGCGGCGATGCAGCCCCGCTGGAGGCTCCTTACGTGCCCCC
GCGGTACCTGGCGCCTACGGAGGGGCGGAACAGCATTCGTTACTCGGAGCTGGCACCCTTGTACG
ATACCACCCGGTTGTACCTGGTGGACAACAAGTCGGCGGACATCGCCTCGCTGAACTACCAGAAC
GACCACAGCAACTTCCTGACCACCGTGGTGCAGAACAATGACTTCACCCCCACGGAGGCCAGCAC
CCAGACCATCAACTTTGACGAGCGCTCGCGGTGGGCGGTCAGCTGAAAACCATCATGCACACCA
ACATGCCCAACGTGAACGAGTTCATGTACAGCAACAAGTTCAAGGCGCGGGTGATGGTCTCCCGC
AAGACCCCCAACGGGGTGACAGTGACAGATGGTAGTCAGGATATCTTGGAGTATGAATGGGTGGA
GTTTGAGCTGCCCGAAGGCAACTTCTCGGTGACCATGACCATCGACCTGATGAACAACGCCATCA
TCGACAATTACTTGGCGGTGGGGCGGCAGAACGGGGTCCTGGAGAGCGATATCGGCGTGAAGTTC
GACACTAGGAACTTCAGGCTGGGCTGGGACCCCGTGACCGAGCTGGTCATGCCCGGGGTGTACAC
CAACGAGGCCTTCCACCCCGATATTGTCTTGCTGCCCGGCTGCGGGGTGGACTTCACCGAGAGCC
GCCTCAGCAACCTGCTGGGCATTCGCAAGAGGCAGCCCTTCCAGGAGGGCTTCCAGATCATGTAC
GAGGATCTGGAGGGGGGCAACATCCCCGCGCTCCTGGATGTCGACGCCTATGAGAAAAGCAAGGA
GGAGAGCGCCGCCGCGCGACTGCAGCTGTAGCCACCGCCTCTACCGAGGTCAGGGGCGATAATT
TTGCCAGCCCTGCAGCAGTGGCAGCGGCCGAGGCGGCTGAAACCGAAAGTAAGATAGTCATTCAG
CCGGTGGAGAAGGATAGCAAGGACAGGAGCTACAACGTGCTGCCGGACAAGATAAACACCGCCTA
CCGCAGCTGGTACCTGGCCTACAACTATGGCGACCCCGAGAAGGGCGTGCGCTCCTGGACGCTGC
TCACCACCTCGGACGTCACCTGCGGCGTGGAGCAAGTCTACTGGTCGCTGCCCGACATGATGCAA
GACCCGGTCACCTTCCGCTCCACGCGTCAAGTTAGCAACTACCCGGTGGTGGGCGCCGAGCTCCT
GCCCGTCTACTCCAAGAGCTTCTTCAACGAGCAGGCCGTCTACTCGCAGCAGCTGCGCGCCTTCA
CCTCGCTCACGCACGTCTTCAACCGCTTCCCCGAGAACCAGATCCTCGTCCGCCCGCCCGCGCCC
ACCATTACCACCGTCAGTGAAAACGTTCCTGCTCTCACAGATCACGGGACCCTGCCGCTGCGCAG
CAGTATCCGGGGAGTCCAGCGCGTGACCGTTACTGACGCCAGACGCCGCACCTGCCCCTACGTCT
ACAAGGCCCTGGGCATAGTCGCGCCGCGCGTCCTCTCGAGCCGCACCTTCTAAAAAATGTCCATT
CTCATCTCGCCCAGTAATAACACCGGTTGGGGCCTGCGCGCGCCCAGCAAGATGTACGGAGGCGC
TCGCCAACGCTCCACGCAACACCCCGTGCGCGTGCGCGGGCACTTCCGCGCTCCCTGGGCGCCC
```

```
TCAAGGGCCGCGTGCGGTCGCGCACCACCGTCGACGACGTGATCGACCAGGTGGTGGCCGACGCG

CGCAACTACACCCCCGCCGCCGCGCCCGTCTCCACCGTGGACGCCGTCATCGACAGCGTGGTGGC

CGACGCGCGCCGGTACGCCCGCGCCAAGAGCCGGCGGCGGCGCATCGCCCGGCGGCACCGGAGCA

CCCCCGCCATGCGCGCGGCGCGAGCCTTGCTGCGCAGGGCCAGGCGCACGGGACGCAGGGCCATG

CTCAGGGCGGCCAGACGCGCGGCTTCAGGCGCCAGCGCCGGCAGGACCCGGAGACGCGCGGCCAC

GGCGGCGGCAGCGGCCATCGCCAGCATGTCCCGCCCGCGGCGAGGGAACGTGTACTGGGTGCGCG

ACGCCGCCACCGGTGTGCGCGTGCCCGTGCGCACCCGcCCCCCTCGCACTTGAAGATGTTCACTT

CGCGATGTTGATGTGTCCCAGCGGCGAGGAGGATGTCCAAGCGCAAATTCAAGGAAGAGATGCTC

CAGGTCATCGCGCCTGAGATCTACGGCCCCGCGGTGGTGAAGGAGGAAAGAAAGCCCCGCAAAAT

CAAGCGGGTCAAAAAGGACAAAAAGGAAGAAGATGACGATCTGGTGGAGTTTGTGCGCGAGTTCG

CCCCCcGGCGGCGCGTGCAGTGGCGCGGGCGGAAAGTGCACCCGGTGCTGAGACCCGGCACCACC

GTGGTCTTCACGCCCGGCGAGCGCTCCGGCAGCGCTTCCAAGCGCTCCTACGACGAGGTGTACGG

GGACGAGGACATCCTCGAGCAGGCGGCCGAGCGCCTGGGCGAGTTTGCTTACGGCAAGCGCAGCC

GCCCCGCCCTGAAGGAAGAGGCGGTGTCCATCCCGCTGGACCACGGCAACCCCACGCCGAGCCTC

AAGCCCGTGACCCTGCAGCAGGTGCTGCCGAGCGCAGCGCCGCGCCGGGGGTTCAAGCGCGAGGG

CGAGGATCTGTACCCCACCATGCAGCTGATGGTGCCCAAGCGCCAGAAGCTGGAAGACGTGCTGG

AGACCATGAAGGTGGACCCGGACGTGCAGCCCGAGGTCAAGGTGCGGCCCATCAAGCAGGTGGCC

CCGGGCCTGGGCGTGCAGACCGTGGACATCAAGATCCCCACGGAGCCCATGGAAACGCAGACCGA

GCCCATGATCAAGCCCAGCACCAGCACCATGGAGGTGCAGACGGATCCCTGGATGCCATCGGCTC

CTAGCCGAAGACCCCGGCGCAAGTACGGCGCGGCCAGCCTGCTGATGCCCAACTACGCGCTGCAT

CCTTCCATCATCCCCACGCCGGGCTACCGCGGCACGCGCTTCTACCGCGGTCATACAACCAGCCG

CCGCCGCAAGACCACCACCCGCCGCCGCCGTCGCCGCACAGCCGCTGCATCTACCCCTGCCGCCC

TGGTGCGGAGAGTGTACCGCCGCGGCCGCGCGCCTCTGACCCTACCGCGCGCGCGCTACCACCCG

AGCATCGCCATTTAAACTTTCGCCTGCTTTGCAGATGGCCCTCACATGCCGCCTCCGCGTTCCCA

TTACGGGCTACCGAGGAAGAAAACCGCGCCGTAGAAGGCTGGCGGGGAACGGGATGCGTCGCCAC

CACCATCGGCGGCGGCGCGCCATCAGCAAGCGGTTGGGGGgAGGCTTCCTGCCCGCGCTGATCCC

CATCATCGCCGCGGCGATCGGGGCGATCCCCGGCATTGCTTCCGTGGCGGTGCAGGCCTCTCAGC

GCCACTGAGACACTTGGAAAACATCTTGTAATAAACCAATGGACTCTGACGCTCCTGGTCCTGTG

ATGTGTTTTCGTAGACAGATGGAAGACATCAATTTTTCGTCCCTGGCTCCGCGACACGGCACGCG

GCCGTTCATGGGCACCTGGAGCGACATCGGCACCAGCCAACTGAACGGGGGCGCCTTCAATTGGA

GCAGTCTCTGGAGCGGGCTTAAGAATTTCGGGTCCACGCTTAAAACCTATGGCAGCAAGGCGTGG

AACAGCACCACAGGGCAGGCGCTGAGGGATAAGCTGAAAGAGCAGAACTTCCAGCAGAAGGTGGT

CGATGGGCTCGCCTCGGGCATCAACGGGGTGGTGGACCTGGCCAACCAGGCCGTGCAGCGGCAGA

TCAACAGCCGCCTGGACCCGGTGCCGCCCGCCGGCTCCGTGGAGATGCCGCAGGTGGAGGAGGAG

CTGCCTCCCCTGGACAAGCGGGGCGAGAAGCGACCCCGCCCCGACGCGGAGGAGACGCTGCTGAC

GCACACGGACGAGCCGCCCCCGTACGAGGAGGCGGTGAAACTGGGTCTGCCCACCACGCGGCCCA

TCGCGCCCCTGGCCACCGGGGTGCTGAAACCCGAAAGTAATAAGCCCGCGACCCTGGACTTGCCT

CCTCCCGCTTCCCGCCCCTCTACAGTGGCTAAGCCCCTGCCGCCGGTGGCCGTGGCCCGCGCGCG

ACCCGGGGGCTCCGCCCGCCCTCATGCGAACTGGCAGAGCACTCTGAACAGCATCGTGGGTCTGG

GAGTGCAGAGTGTGAAGCGCCGCCGCTGCTATTAAACCTACCGTAGCGCTTAACTTGCTTGTCTG

TGTGTGTATGTATTATGTCGCCGCTGTCCGCCAGAAGGAGGAGTGAAGAGGCGCGTCGCCGAGTT
```

-continued

```
GCAAGATGGCCACCCCATCGATGCTGCCCCAGTGGGCGTACATGCACATCGCCGGACAGGACGCT
TCGGAGTACCTGAGTCCGGGTCTGGTGCAGTTCGCCCGCGCCACAGACACCTACTTCAGTCTGGG
GAACAAGTTTAGGAACCCCACGGTGGCGCCCACGCACGATGTGACCACCGACCGCAGCCAGCGGC
TGACGCTGCGCTTCGTGCCCGTGGACCGCGAGGACAACACCTACTCGTACAAAGTGCGCTACACG
CTGGCCGTGGGCGACAACCGCGTGCTGGACATGGCCAGCACCTACTTTGACATCCGCGGCGTGCT
GGATCGGGGCCCTAGCTTCAAACCCTACTCCGGCACCGCCTACAACAGCCTGGCTCCCAAGGGAG
CGCCCAATTCCAGCCAGTGGGAGCaAAAAAAGGCAGGCAATGGTGACACTATGGAAACACACACA
TTTGGTGTGGCCCCAATGGGCGGTGAGAATATTACAATCGACGGATTACAAATTGGAACTGACGC
TACAGCTGATCAGGATAAACCAATTTATGCTGACAAAACATTCCAGCCTGAACCTCAAGTAGGAG
AAGAAAATTGGCAAGAAACTGAAAGCTTTTATGGCGGTAGGGCTCTTAAAAAAGACACAAGCATG
AAACCTTGCTATGGCTCCTATGCTAGACCCACCAATGTAAAGGGAGGTCAAGCTAAACTTAAAGT
TGGAGCTGATGGAGTTCCTACCAAAGAATTTGACATAGACCTGGCTTTCTTTGATACTCCCGGTG
GCACAGTGAATGGACAAGATGAGTATAAAGCAGACATTGTCATGTATACCGAAAACACGTATCTG
GAAACTCCAGACACGCATGTGGTATACAAACCAGGCAAGGATGATGCAAGTTCTGAAATTAACCT
GGTTCAGCAGTCCATGCCCAATAGACCCAACTATATTGGGTTCAGAGACAACTTTATTGGGCTCA
TGTATTACAACAGTACTGGCAATATGGGGGTGCTGGCTGGTCAGGCCTCACAGCTGAATGCTGTG
GTCGACTTGCAAGACAGAAACACCGAGCTGTCATACCAGCTCTTGCTTGACTCTTTGGGTGACAG
AACCCGGTATTTCAGTATGTGGAATCAGGCGGTGGACAGTTATGATCCTGATGTGCGCATTATTG
AAAACCATGGTGTGGAAGACGAACTTCCCAACTATTGCTTCCCCCTGGATGGGTCTGGCACTAAT
GCCGCTTACCAAGGTGTGAAAGTAAAAAATGGTAACGATGGTGATGTTGAGAGCGAATGGGAAAA
TGATGATACTGTCGCAGCTCGAAATCAATTATGCAAGGGCAACATTTTTGCCATGGAAATTAACC
TCCAAGCCAACCTGTGGAGAAGTTTCCTCTACTCGAACGTGGCCCTGTACCTGCCCGACTCTTAC
AAGTACACGCCAGCCAACATCACCCTGCCCACCAACACCAACACTTATGATTACATGAACGGGAG
AGTGGTGCCTCCCTCGCTGGTGGACGCCTACATCAACATCGGGGCGCGCTGGTCGCTGGACCCCA
TGGACAACGTCAATCCCTTCAACCACCACCGCAACGCGGGCCTGCGCTACCGCTCCATGCTCCTG
GGCAACGGGCGCTACGTGCCCTTCCACATCCAGGTGCCCCAGAAATTTTTCGCCATCAAGAGCCT
CCTGCTCCTGCCCGGGTCCTACACCTACGAGTGGAACTTCCGCAAGGACGTCAACATGATCCTGC
AGAGCTCCCTCGGCAACGACCTGCGCACGGACGGGGCCTCCATCTCCTTCACCAGCATCAACCTC
TACGCCACCTTCTTCCCCATGGCGCACAACACGGCCTCCACGCTCGAGGCCATGCTGCGCAACGA
CACCAACGACCAGTCCTTCAACGACTACCTCTCGGCGGCCAACATGCTCTACCCCATCCCGGCCA
ACGCCACCAACGTGCCCATCTCCATCCCCTCGCGCAACTGGGCCGCCTTCCGCGGCTGGTCCTTC
ACGCGCCTCAAGACCAAGGAGACGCCCTCGCTGGGCTCCGGGTTCGACCCCTACTTCGTCTACTC
GGGCTCCATCCCCTACCTCGACGGCACCTTCTACCTCAACCACACCTTCAAGAAGGTCTCCATCA
CCTTCGACTCCTCCGTCAGCTGGCCCGGCAACGACCGGCTCCTGACGCCCAACGAGTTCGAAATC
AAGCGCACCGTCGACGGCGAGGGATACAACGTGGCCCAGTGCAACATGACCAAGGACTGGTTCCT
GGTCCAGATGCTGGCCCACTACAACATCGGCTACCAGGGCTTCTACGTGCCCGAGGGCTACAAGG
ACCGCATGTACTCCTTCTTCCGCAACTTCCAGCCCATGAGCCGCCAGGTGGTGGACGAGGTCAAC
TACAAGGACTACCAGGCCGTCACCCTGGCCTACCAGCACAACAACTCGGGCTTCGTCGGCTACCT
CGCGCCCACCATGCGCCAGGGCCAGCCCTACCCCGCCAACTACCCGTACCCGCTCATCGGCAAGA
GCGCCGTCACCAGCGTCACCCAGAAAAAGTTCCTCTGCGACAGGGTCATGTGGCGCATCCCCTTC
TCCAGCAACTTCATGTCCATGGGCGCGCTCACCGACCTCGGCCAGAACATGCTCTATGCCAACTC
```

-continued

```
CGCCCACGCGCTAGACATGAATTTCGAAGTCGACCCCATGGATGAGTCCACCCTTCTCTATGTTG
TCTTCGAAGTCTTCGACGTCGTCCGAGTGCACCAGCCCCACCGCGGCGTCATCGAGGCCGTCTAC
CTGCGCACCCCCTTCTCGGCCGGTAACGCCACCACCTAAATTGCTACTTGCATGATGGCTGAGCC
CACAGGCTCCGGCGAGCAGGAGCTCAGGGCCATCATCCGCGACCTGGGCTGCGGGCCCTACTTCC
TGGGCACCTTCGATAAGCGCTTCCCGGGATTCATGGCCCCGCACAAGCTGGCCTGCGCCATCGTC
AACACGGCCGGCCGCGAGACCGGGGGCGAGCACTGGCTGGCCTTCGCCTGGAACCCGCGCTCGAA
CACCTGCTACCTCTTCGACCCCTTCGGGTTCTCGGACGAGCGCCTCAAGCAGATCTACCAGTTCG
AGTACGAGGGCCTGCTGCGCCGTAGCGCCCTGGCCACCGAGGACCGCTGCGTCACCCTGGAAAAG
TCCACCCAGACCGTGCAGGGTCCGCGCTCGGCCGCCTGCGGGCTCTTCTGCTGCATGTTCCTGCA
CGCCTTCGTGCACTGGCCCGACCGCCCCATGGACAAGAACCCCACCATGAACTTGCTGACGGGGG
TGCCCAACGGCATGCTCCAGTCGCCCCAGGTGGAACCCACCCTGCGCCGCAACCAGGAGGCGCTC
TACCGCTTCCTCAACTCCCACTCCGCCTACTTTCGCTCCCACCGCGCGCGCATCGAGAAGGCCAC
CGCCTTCGACCGCATGAACAATCAAGACATGTAAACCGTGTGTGTATGTTTAAAATATCTTTTAA
TAAACAGCACTTTAATGTTACACATGCATCTGAGATGATTTTATTTTAGAAATCGAAAGGGTTCT
GCCGGGTCTCGGCATGGCCCGCGGGCAGGGACACGTTGCGGAACTGGTACTTGGCCAGCCACTTG
AACTCGGGGATCAGCAGTTTGGGCAGCGGGGTGTCGGGGAAGGAGTCGGTCCACAGCTTCCGCGT
CAGCTGCAGGGCGCCCAGCAGGTCGGGCGCGGAGATCTTGAAATCGCAGTTGGGACCCGCGTTCT
GCGCGCGAGAGTTGCGGTACACGGGGTTGCAGCACTGGAACACCATCAGGGCCGGGTGCTTCACG
CTCGCCAGCACCGCCGCGTCGGTGATGCTCTCCACGTCGAGGTCCTCGGCGTTGGCCATCCCGAA
GGGGGTCATCTTGCAGGTCTGCCTTCCCATGGTGGGCACGCACCCGGGCTTGTGGTTGCAATCGC
AGTGCAGGGGGATCAGCATCATCTGGGCCTGGTCGGCGTTCATCCCCGGGTACATGGCCTTCATG
AAAGCCTCCAATTGCCTGAACGCCTGCTGGGCCTTGGCTCCCTCGGTGAAGAAGACCCCGCAGGA
CTTGCTAGAGAACTGGTTGGTGGCACAGCCGGCATCGTGCACGCAGCAGCGCGCGTCGTTGTTGG
CCAGCTGCACCACGCTGCGCCCCCAGCGGTTCTGGGTGATCTTGGCCCGGTCGGGGTTCTCCTTC
AGCGCGCGCTGCCCGTTCTCGCTCGCCACATCCATCTCGATCATGTGCTCCTTCTGGATCATGGT
GGTCCCGTGCAGGCACCGCAGTTTGCCCTCGGCCTCGGTGCACCCGTGCAGCCACAGCGCGCACC
CGGTGCACTCCCAGTTCTTGTGGGCGATCTGGGAATGCGCGTGCACGAACCCTTGCAGGAAGCGG
CCCATCATGGTCGTCAGGGTCTTGTTGCTAGTGAAGGTCAACGGGATGCCGCGGTGCTCCTCGTT
GATGTACAGGTGGCAGATGCGGCGGTACACCTCGCCCTGCTCGGGCATCAGTTGGAAGTTGGCTT
TCAGGTCGGTCTCCACGCGGTAGCGGTCCATCAGCATAGTCATGATTTCCATGCCCTTCTCCCAG
GCCGAGACGATGGGCAGGCTCATAGGGTTCTTCACCATCATCTTAGCACTAGCAGCCGCGGCCAG
GGGGTCGCTCTCATCCAGGGTCTCAAAGCTCCGCTTGCCGTCCTTCTCGGTGATCCGCACCGGGG
GGTAGCTGAAGCCCACGGCCGCCAGCTCCTCCTCGGCCTGTCTTTCGTCCTCGCTGTCCTGGCTG
ACGTCCTGCATGACCACATGCTTGGTCTTGCGGGGTTTCTTCTTGGGCGGCAGTGGCGGCGGAGA
TGCTTGTGGCGAGGGGGAGCGCGAGTTCTCGCTCACCACTACTATCTCTTCCTCTTCTTGGTCCG
AGGCCACGCGGCGGTAGGTATGTCTCTTCGGGGGCAGAGGCGGAGGCGACGGGCTCTCGCCGCCG
CGACTTGGCGGATGGCTGGCAGAGCCCCTTCCGCGTTCGGGGGTGCGCTCCCGGCGGCGCTCTGA
CTGACTTCCTCCGCGGCCGGCCATTGTGTTCTCCTAGGGAGGAACAACAAGCATGGAGACTCAGC
CATCGCCAACCTCGCCATCTGCCCCCACCGCCGGCGACGAGAAGCAGCAGCAGCAGAATGAAAGC
TTAACCGCCCCGCCGCCCAGCCCCGCCTCCGACGCAGCCGCGGTCCCAGACATGCAAGAGATGGA
GGAATCCATCGAGATTGACCTGGGCTATGTGACGCCCGCGGAGCATGAGGAGGAGCTGGCAGTGC
```

-continued

```
GCTTTCAATCGTCAAGCCAGGAAGATAAAGAACAGCCAGAGCAGGAAGCAGAGAACGAGCAGAGT
CAGGCTGGGCTCGAGCATGGCGACTACCTCCACCTGAGCGGGGAGGAGGACGCGCTCATCAAGCA
TCTGGCCCGGCAGGCCACCATCGTCAAGGACGCGCTGCTCGACCGCACCGAGGTGCCCCTCAGCG
TGGAGGAGCTCAGCCGCGCCTACGAGCTCAACCTCTTCTCGCCGCGCGTGcCCCCCAAGCGCCAG
CCCAACGGCACCTGCGAGCCCAACCCCCGCCTCAACTTCTACCCGGTCTTCGCGGTGCCCGAGGC
CCTGGCCACCTACCACATCTTTTtCAAGAACCAAAAGATCCCCGTCTCCTGCCGCGCCAACCGCA
CCCGCGCCGACGCCCTCTTCAACCTGGGTCCCGGCGCCCGCCTACCTGATATCGCCTCCTTGGAA
GAGGTTCCCAAGATCTTCGAGGGTCTGGGCAGCGACGAGACTCGGGCCGCGAACGCTCTGCAAGG
AGAAGGAGGAGGAGAGCATGAGCACCACAGCGCCCTGGTCGAGTTGGAAGGCGACAACGCGCGGC
TGGCGGTGCTCAAACGCACGGTCGAGCTGACCCATTTCGCCTACCCGGCTCTGAACCTGcCCCCG
AAAGTCATGAGCGCGGTCATGGACCAGGTGCTCATCAAGCGCGCGTCGCCCATCTCCGAGGACGA
GGGCATGCAAGACTCCGAGGAGGGCAAGCCCGTGGTCAGCGACGAGCAGCTGGCCCGGTGGCTGG
GTCCTAATGCTACCCCTCAAAGTTTGGAAGAGCGGCGCAAGCTCATGATGGCCGTGGTCCTGGTG
ACCGTGGAGCTGGAGTGCCTGCGCCGCTTCTTCGCCGACGCGGAGACCCTGCGCAAGGTCGAGGA
GAACCTGCACTACCTCTTCAGGCACGGGTTCGTGCGCCAGGCCTGCAAGATCTCCAACGTGGAGC
TGACCAACCTGGTCTCCTACATGGGCATCTTGCACGAGAACCGCCTGGGGCAGAACGTGCTGCAC
ACCACCCTGCGCGGGGAGGCCCGCCGCGACTACATCCGCGACTGCGTCTACCTCTACCTCTGCCA
CACCTGGCAGACGGGCATGGGCGTGTGGCAGCAGTGTCTGGAGGAGCAGAACCTGAAAGAGCTCT
GCAAGCTCCTGCAAAAGAACCTCAAGGGTCTGTGGACCGGGTTCGACGAGCGGACCACCGCCTCG
GACCTGGCCGACCTCATCTTCCCCGAGCGCCTCAGGCTGACGCTGCGCAACGGCCTGCCCGACTT
TATGAGCCAAAGCATGTTGCAAAACTTTCGCTCTTTCATCCTCGAACGCTCCGGAATCCTGCCCG
CCACCTGCTCCGCGCTGCCCTCGGACTTCGTGCCGCTGACCTTCCGCGAGTGCCCCCCGCCGCTG
TGGAGCCACTGCTACCTGCTGCGCCTGGCCAACTACCTGGCCTACCACTCGGACGTGATCGAGGA
CGTCAGCGGCGAGGGCCTGCTCGAGTGCCACTGCCGCTGCAACCTCTGCACGCCGCACCGCTCCC
TGGCCTGCAACCCCCAGCTGCTGAGCGAGACCCAGATCATCGGCACCTTCGAGTTGCAAGGGCCC
AGCGAGGGCGAGGGAGCCAAGGGGGGTCTGAAACTCACCCCGGGGCTGTGGACCTCGGCCTACTT
GCGCAAGTTCGTGCCCGAGGATTACCATCCCTTCGAGATCAGGTTCTACGAGGACCAATCCCAGC
CGCCCAAGGCCGAGCTGTCGGCCTGCGTCATCACCCAGGGGGCGATCCTGGCCCAATTGCAAGCC
ATCCAGAAATCCCGCCAAGAATTCTTGCTGAAAAAGGGCCGCGGGGTCTACCTCGACCCCCAGAC
CGGTGAGGAGCTCAACCCCGGCTTCCCCCAGGATGCCCCGAGGAAACAAGAAGCTGAAAGTGGAG
CTGCCGCCCGTGGAGGATTTGGAGGAAGACTGGGAGAACAGCAGTCAGGCAGAGGAGATGGAGGA
AGACTGGGACAGCACTCAGGCAGAGGAGGACAGCCTGCAAGACAGTCTGGAGGAAGACGAGGAGG
AGGCAGAGGAGGAGGTGGAAGAAGCAGCCGCCGCCAGACCGTCGTCCTCGGCGGGGAGAAAGCA
AGCAGCACGGATACCATCTCCGCTCCGGGTCGGGGTCCCGCTCGGCCCCACAGTAGATGGGACGA
GACCGGGCGATTCCCGAACCCCACCACCCAGACCGGTAAGAAGGAGCGGCAGGGATACAAGTCCT
GGCGGGGGCACAAAAACGCCATCGTCTCCTGCTTGCAGGCCTGCGGGGGCAACATCTCCTTCACC
CGGCGCTACCTGCTCTTCCACCGCGGGGTGAACTTCCCCCGCAACATCTTGCATTACTACCGTCA
CCTCCACAGCCCCTACTACTTCCAAGAAGAGGCAGCAGCAGCAGaAAAAGACCAGAAAACCAGCT
AGAAAATCCACAGCGGCGGCAGCGGCAGGTGGACTGAGGATCGCGGCGAACGAGCCGGCGCAGAC
CCGGGAGCTGAGGAACCGGATCTTTCCCACCCTCTATGCCATCTTCCAGCAGAGTCGGGGGCAGG
AGCAGGAACTGAAAGTCAAGAACCGTTCTCTGCGCTCGCTCACCCGCAGTTGTCTGTATCACAAG
```

-continued

AGCGAAGACCAACTTCAGCGCACTCTCGAGGACGCCGAGGCTCTCTTCAACAAGTACTGCGCGCT

CACTCTTAAAGAGTAGCCCGCGCCCGCCCAGTCGCAGAAAAAGGCGGGAATTACGTCACCTGTGC

CCTTCGCCCTAGCCGCCTCCACCCAGCACCGCCATGAGCAAAGAGATTCCCACGCCTTACATGTG

GAGCTACCAGCCCCAGATGGGCCTGGCCGCCGGCGCCGCCCAGGACTACTCCACCCGCATGAATT

GGCTCAGCGCCGGGCCCGCGATGATCTCACGGGTGAATGACATCCGCGCCCACCGAAACCAGATA

CTCCTAGAACAGTCAGCGCTCACCGCCACGCCCCGCAATCACCTCAATCCGCGTAATTGGCCCGC

CGCCCTGGTGTACCAGGAAATTCCCCAGCCCACGACCGTACTACTTCCGCGAGACGCCCAGGCCG

AAGTCCAGCTGACTAACTCAGGTGTCCAGCTGGCGGGCGGCGCCACCCTGTGTCGTCACCGCCCC

GCTCAGGGTATAAAGCGGCTGGTGATCCGGGGCAGAGGCACACAGCTCAACGACGAGGTGGTGAG

CTCTTCGCTGGGTCTGCGACCTGACGGAGTCTTCCAACTCGCCGGATCGGGGAGATCTTCCTTCA

CGCCTCGTCAGGCGGTCCTGACTTTGGAGAGTTCGTCCTCGCAGCCCCGCTCGGGCGGCATCGGC

ACTCTCCAGTTCGTGGAGGAGTTCACTCCCTCGGTCTACTTCAACCCCTTCTCCGGCTCCCCCGG

CCACTACCCGGACGAGTTCATCCCGAACTTTGACGCCATCAGCGAGTCGGTGGACGGCTACGATT

GATTAATTAATCAACTAACCCCTTACCCCTTTACCCTCCAGTAAAAATAAAGATTAAAAATGATT

GAATTGATCAATAAAGAATCACTTACTTGAAATCTGAAACCAGGTCTCTGTCCATGTTTTCTGTC

AGCAGCACTTCACTCCCTCTTCCCAACTCTGGTACTGCAGGCCCCGGCGGGCTGCAAACTTCCT

CCACACTCTGAAGGGGATGTCAAATTCCTCCTGTCCCTCAATCTTCATTTTTATCTTCTATCAGA

TGTCCAAAAAGCGCGCGGGTGGATGATGGCTTCGACCCCGTGTACCCCTACGATGCAGACAAC

GCACCGACTGTGCCCTTCATCAACCCTCCCTTCGTCTCTTCAGATGGATTCCAAGAAAAGCCCCT

GGGGGTGTTGTCCCTGCGACTGGCCGACCCCGTCACCACCAAGAATGGGGCTGTCACCCTCAAGC

TGGGGGAGGGGGTGGACCTCGACGACTCGGGAAAACTCATCTCCAAAAATGCCACCAAGGCCACT

GCCCCTCTCAGTATTTCCAACGGCACCATTTCCCTTAACATGGCTGCCCCTTTTTACAACAACAA

TGGAACGTTAAGTCTCAATGTTTCTACACCATTAGCAGTATTTCCCACTTTTAACACTTTAGGTA

TCAGTCTTGGAAACGGTCTTCAAACTTCTAATAAGTTGCTGACTGTACAGTTAACTCATCCTCTT

ACATTCAGCTCAAATAGCATCACAGTAAAAACAGACAAAGGACTCTATATTAATTCTAGTGGAAA

CAGAGGGCTTGAGGCTAACATAAGCCTAAAAAGAGGACTGATTTTTGATGGTAATGCTATTGCAA

CATACCTTGGAAGTGGTTTAGACTATGGATCCTATGATAGCGATGGGAAAACAAGACCCATCATC

ACCAAAATTGGAGCAGGTTTGAATTTTGATGCTAATAATGCCATGGCTGTGAAGCTAGGCACAGG

TTTAAGTTTTGACTCTGCCGGTGCCTTAACAGCTGGAAACAAAGAGGATGACAAGCTAACACTTT

GGACTACACCTGACCCAAGCCCTAATTGTCAATTACTTTCAGACAGAGATGCCAAATTTACCCTA

TGTCTTACAAAATGCGGTAGTCAAATACTAGGCACTGTTGCAGTAGCTGCTGTTACTGTAGGTTC

AGCACTAAATCCAATTAATGACACAGTAAAAAGCGCCATAGTATTCCTTAGATTTGACTCTGACG

GTGTGCTCATGTCAAACTCATCAATGGTAGGTGATTACTGGAACTTTAGGGAAGGACAGACCACC

CAAAGTGTGGCCTATACAAATGCTGTGGGATTCATGCCCAATCTAGGTGCATATCCTAAAACCCA

AAGCAAAACACCAAAAAATAGTATAGTAAGTCAGGTATATTTAAATGGAGAAACTACTATGCCAA

TGACACTGACAATAACTTTCAATGGCACTGATGAAAAAGACACAACACCTGTGAGCACTTACTCC

ATGACTTTTACATGGCAGTGGACTGGAGACTATAAGGACAAGAATATTACCTTTGCTACCAACTC

CTTTACTTTCTCCTACATGGCCCAAGAATAAACCCTGCATGCCAACCCCATTGTTCCCACCACTA

TGGAAAACTCTGAAGCAGaAAAAAAATAAAGTTCAAGTGTTTTATTGATTCAACAGTTTTCtcaca gaacccctagtattcaacctgccacctccctcccaacacacagagtacacagtcctttctccccgg ctggccttaaaaagcatcatatcatgggtaacagacatattcttaggtgttatattccacacggt -continued

```
ttcctgtcgagccaaacgctcatcagtgatattaataaactccccgggcagctcacttaagttca tgtcgctgtccagctgctgagccacaggctgctgtccaacttgcggttgcttaacgggcggcgaa ggagaagtccacgcctacatgggggtagagtcataatcgtgcatcaggatagggcggtggtgctg cagcagcgcgcgaataaactgctgccgccgccgctccgtcctgcaggaatacaacatggcagtgg tctcctcagcgatgattcgcaccgcccgcagcataaggcgccttgtcctccgggcacagcagcgc accctgatctcacttaaatcagcacagtaactgcagcacagcaccacaatattgttcaaaatccc acagtgcaaggcgctgtatccaaagctcatggcggggaccacagaacccacgtggccatcatacc acaagcgcaggtagattaagtggcgaccccctcataaacacgctggacataaacattacctctttt ggcatgttgtaattcaccacctcccggtaccatataaacctctgattaaacatggcgccatccac caccatcctaaaccagctggccaaaacctgcccgccggctatacactgcagggaaccgggactgg aacaatgacagtggagagcccaggactcgtaaccatggatcatcatgctcgtcatgatatcaatg ttggcacaacacaggcacacgtgcatacacttcctcaggattacaagctcctcccgcgttagaac catatcccagggaacaacccattcctgaatcagcgtaaatcccacactgcagggaagacctcgca cgtaactcacgttgtgcattgtcaaagtgttacattcgggcagcagcggatgatcctccagtatg gtagcgcgggtttctgtctcaaaaggaggtagacgatccctactgtacggagtgcgccgagacaa ccgagatcgtgttggtcgtagtgtcatgccaaatggaacgccggacgtagtcatatttcctgaag caaaaccaggtgcgggcgtgacaaacagatctgcgtctccggtctcgccgcttagatcgctctgt gtagtagttgtagtatatccactctctcaaagcatccaggcgcccctggcttcgggttctatgt aaactccttcatgcgccgctgccctgataacatccaccaccgcagaataagccacacccagccaa cctacacattcgttctgcgagtcacacacgggaggagcgggaagagctggaagaaccatGATTAA

CTTTATTCCAAACGGTCTCGGAGCACTTCAAAATGCAGGTCCCGGAGGTGGCACCTCTCGCCCCC

ACTGTGTTGGTGGAAAATAACAGCCAGGTCAAAGGTGACACGGTTCTCGAGATGTTCCACGGTGG

CTTCCAGCAAAGCCTCCACGCGCACATCCAGAAACAAGAGGACAGCGAAAGCGGGAGCGTTTTCT

AATTCCTCAATCATCATATTACACTCCTGCACCATCCCCAGATAATTTTCATTTTTCCAGCCTTG

AATGATTCGTATTAGTTCCTGAGGTAAATCCAAGCCAGCCATGATAAAAAGCTCGCGCAGAGCGC

CCTCCACCGGCATTCTTAAGCACACCCTCATAATTCCAAGAGATTCTGCTCCTGGTTCACCTGCA

GCAGATTAACAATGGGAATATCAAAATCTCTGCCGCGATCCCTAAGCTCCTCCCTCAACAATAAC

TGTATGTAATCTTTCATATCATCTCCGAAATTTTTAGCCATAGGGCCGCCAGGAATAAGAGCAGG

GCAAGCCACATTACAGATAAAGCGAAGTCCTCCCCAGTGWGCATTGCCAAATGTAAGATTGAAAT

AAGCATGCTGGCTAGACCCTGTGATATCTTCCAGATAACTGGACAGAAAATCAGGCAAGCAATTT

TTAAGAAAATCAACAAAAGAAAAGTCGTCCAGGTGCAGGTTTAGAGCCTCAGGAACAACGATGGA

ATAAGTGCAAGGAGTGCGTTCCAGCATGGTTAGTGtTTTTTTGGTGATCTGTAGAACAAAAAATA

AACATGCAATATTAAACCATGCTAGCCTGGCGAACAGGTGGGTAAATCACTCTTTCCAGCACCAG

GCAGGCTACGGGGTCTCCGGCGCGACCCTCGTAGAAGCTGTCGCCATGATTGAAAAGCATCACCG

AGAGACCTTCCCGGTGGCCGGCATGGATGATTCGAGAAGAAGCATACACTCCGGGAACATTGGCA

TCCGTGAGTGAAAAAAaGCGACCTATAAAGCCTCGGGCACTACAATGCTCAATCTCAATTCCAG

CAAAGCCACCCCATGCGGATGGAGCACAAAATTGGCAGGTGCGTAAAAAATGTAATTACTCCCCT

CCTGCACAGGCAGCAAAGCCCCCGCTCCCTCCAGAAACACATACAAAGCCTCAGCGTCCATAGCT

TACCGAGCACGGCAGGCGCAAGAGTCAGAGAAAAGGCTGAGCTCTAACCTGACTGCCCGCTCCTG

TGCTCAATATATAGCCCTAACCTACACTGACGTAAAGGCCAAAGTCTAAAAATACCCGCCAAAAT

GACACACACGCCCAGCACACGCCCAGAAACCGGTGACACACTCAAAAAAATACGTGCGCTTCCTC
```

```
AAACGCCCAAACCGGCGTCATTTCCGGGTTCCCACGCTACGTCACCGCTCAGCGACTTTCAAATT

CCGTCGACCGTTAAAAACGTCACTCGCCCCGCCCCTAACGGTCGCCCTTCTCTCGGCCAATCACC

TTCCTCCCTTCCCAAATTCAAACGCCTCATTTGCATATTAACGCGCACAAAAAGTTTGAGGTATA

TATTTGAATGATG
```

ChAdOx2 Sequence (SEQ ID NO: 67+68)

The ChAdOx2 sequence 5' to the immunogen cassette is provided as SEQ ID NO: 67 and the ChAdOx2 sequence 3' to the immunogen cassette is provided as SEQ ID NO: 68.

MVA Sequence (SEQ ID NO: 69+70)

The MVA sequence 5' to the immunogen cassette is provided as SEQ ID NO: 69 and the MVA sequence 3' to the immunogen cassette is provided as SEQ ID NO: 70.

MVA vaccines have been made using two different shuttle plasmids:

1. P7.5 shuttle plasmid. HPV insert with upstream and downstream flanks that are homologous to regions of the TK locus in parental MVA virus. Insert under control of p7.5 promoter.

2. F11 shuttle plasmid. HPV insert with upstream and downstream flanks that are homologous to regions of the F11 locus in parental MVA virus. Insert under control of F11 promoter.

Chicken embryo fibroblast cells are then infected with MVA parental virus and transfected with either p7.5 or F11 MVA shuttle plasmids to allow homologous recombination with the MVA genome. So you get parental MVA with the gene of interest inserted into the MVA genome at either the TK locus (p7.5 shuttle plasmid) or F11 locus (F11 shuttle plasmid). Resulting in two versions of the MVA vaccine.

P7.5 Shuttle Plasmid (SEQ ID NO: 158) (Insert Underlined)

```
agcgcccaatacgcaaaccgcctctcccgcgcgttggccgattcattaatgcagctggcacgacaggtttcccgactggaa agcgggcagtgagcgcaacgcaattaatgtgagttagctcactcattaggcaccccaggctttacactttatgcttccggct cgtatgttgtgtggaattgtgagcggataacaatttcacacaggaaacagctatgaccatgattacgccaagcttgcatgcA TCTGGAAACGGGCATCTCCATTTAAGACTAGAtGCCACGGGGTTTAAAATACTAATCATGACATTTTGTAGAGCGTAATTAC TTAGTAAATCCGCCGTACTAGGTTCATTTCCTCCTCGTTTGGATCTCACATCAGAAATTAAAATAATCTTAGAAGGATGCAG TTGTTTTTTGATGGATCGTAGATATTCCTCATCAACGAACCGAGTCACTAGAGTCACATCACGCAATCCATTTAAAATAGGA TCATGATGGCGGCCGTCAATTAGCATCCATTTGATGATCACTCCTAAATTATAGAAATGATCTCTCAAATAACGTATATGTG TACCGGGAGCAGATCCTATATACACTACGGTGGCACCATCTAATATACCGTGTCGCTGTAACTTACTAAGAAAAAATAATTC TCCTAGTAATAGTTTTAACTGTCCTTGATACGGtAGTTTTTTTGCGACCTCATTTGCACTTTCTGGTTCGTAATCTAACTCA TTATCAATTTCCTCAAAATACATAAACGGTTTATCTAACGACACAACATCCATTTTTAAGTATTATATTAAAATTTAATCAA TGTTTATTTTTAGTTTTTTAGATAAAAAATATAATATTATGAGTCGATGTAACACTTTCTACACACCGATTGATACATATCA TTACCTCCTATTATcTCTATCTCGGTTTCCTCACCCAATCGTTTAGAAAAGGAAGCCTCCTTAAAGCATTTCATACACACAG CAGTTAGTTTTACCACCATTTCAGATAATGGAATAAGATTCAAAATATTATTAAACGGTTTACGTTGAAATGTCCCATCGAG TGCGGCTACTATAACTATTTTTCCTTCGTTTGCCaTACAGATCCTACGTACTCGAGCGGCCGCTTATCAGGTCCGGGTGGAG TCCAGGCCCAGCAGTGGATTGGGGATAGGCTTGCCAGAGGCGCCAGGTCCAGAGCCGGCGATTCTGGCCTCGCACTTGCAGC ACATACACAGCATGGTGTGTCTCTGAGGCTCGGCCCTTCTAGCGGGCAGATGCTGGTGGTTCACGCCGTCGATCTCGTCGTT CTCTTCCACCAGAGATTCGCATCTGCAGCACTGTGTCTCGATCAGATAGCAAGGGTGCTGTTCGTCCCGTCTAGCCTGCTGG GGCTGTTCCTGCAGATGGTCCACTTCGTCCTCATCCTCGTCCCCATCCAGGCCGCCAGTGTCCTCTTCATCGGAGCTGTCTC CCAGCTGCTCATAACAGTGCAGATCAGTGGTTTCAGGCTGCTCGTAGCAGTACAGGTCGGTTGTCTCGGGCTGCAGATCCAG CATGTACTCGTGCAGGGTGTGGAACCGCTTGTTCAGGTCCACGTGTCTTTTCTTTTCCTGCGGACACAGTGGCCGCTGGCAG TCGTACACCTCAGATCTCTGCAGGGTTTTCTTGCATTCCACGCACAGTGTGGTGCCATACACGGAATATCTGTACCACCGGA ACTCGGACACCTTGGAGTCGCGATACACGATTGTCAGGTCTGTGAAGGCGAAATCCAGCACCTCTGTCTCGGTCAGCTGTCC CTTGCAATACACCAGGCTGGCGCCATACACAGAGCAGTTGTAGTACCTCAGCTTCCGCACTTTGCTGTCCCGATACACCACC CGCAGATCGGTGTAGGCGAAGTTGTACACCTCGCTGGCTGTCAGGGCCTTCTTGCAGAACACCCGCAGGCATCTAATCAGCA GGTTGTACAGGCCAGTGTTGGTCAGCTTTTCCAGGGTATCGCCGTACACGGAGTCGCTGTAGTGCCGCAGCTCTCTGATTCT GGAGTAGAAGTCGATACACTTGTGGCAGGCGGCGTGGGGATGGAGTCTCTGTACACCACGTTGATGCACCGAATCAGCAGA
```

-continued

TCGCACAGGGGCTTGTTGTACTGCTGTTCCAGGGTGGTGCCGTACAGGCTGTAGCAGTAGTGCCGGTACTCGCTGATCTTGC

TGTAGAACTTCAGGCACTTGTCGCACACGGCGTAAGGATTGCCATCCCGGTACACGATGGCGGTGGCGGGGCTGGTAATCAC

GACGATGTACACGAACACCAGCACCCAGGCATAGGCACACATGCACACGCTGGGCAGCAGGCTTCCGATGGACACCCACAGC

AGCAGCACCAGCACCAGCACCTGAGCGTACACGCTGATAGACAGCAGCAGAGGCCTCAGGTAGGTGGACACACTCAGCAGCA

GGGGTCTGATCAGCAGGCACACGCACAGCAGCACACAAAAGCACAGCAGGAAGCAAGGGGCCCAAGGTCTTGGAGGAGGTGG

AGGGGGCACCCATGGACAGTGTGGAGGTCTAGGAGGTGCCCAGGGGCAAGGGGCAGGGATTCTAGGGGCCCATGGAGAAGGC

TTAGGGATGGGGGGCCTCTGAGGAGCCCAAGGACATGGAGCAGGGATCCGGTGAGGGGGGTGCTGTAGCTGTTCAGCAGTG

ACAGCAGTGGGTATCTGGTGGTCAGGTGCAGCCTGATCACGACTGTGCTCTTGGGGGTGGTCACTCTCAGTTCCACCAGGGA

GGTATTCTCGGGGGTGGTGGTCTGGGTGGTCAGCAGTTTCAGCAGAGGATATGTTGGATCCAGAGGCACGGGCACAGGGTG

GGCACGATGAACACCTTGTTCTCCCAGATGCACTTGCCGTGGGCCTTCACGCCCATGTTGGGGGGTCTGGACAGCAGCTTCA

GCAGGGGGTACTTGGTCACGAGCTGAGACTGATCCTGGTCGCTGGACAGCCGCCGTCTGGCCTTGTAAAAAATGGCACATTC

CAGGCGAATCAGCTTCCAATAGTCGATATGGTCCTTCACGAGCTCGGTGGCGGACACGTTGTCGTCGAAGGTGCTGCACATG

GAGTCGTTGCAGTCGATGCTGTTGCCGAAATGCACTTCCCAGGTGCCCTTGCAGCCGTACTTCTCGGCCTCGGTCTTGCACC

AGCCATCGTCGCCGCAGTAGTACACGCTGTCCCAGGCCACGTAGTCGAACCACACTTCGATGTGCTGGCCGCCCTTCTTGAA

GCAGTGCTTGGGCTCGGTGTTCCACTCGATGGCTTTACAGGCCTTGGCCTTGCAGATATTCAGGGCGGGCACCACCTGGTGT

CTGGCGGCGAAGAAGATGGCGTTTTCCTGCCTGATGGCTTTCCAATAATCAATGTGGTCGGCTTCCTCGGTGCTGATCTCAT

CGGAGGGGATGCTGGCGGGGCACACGATCACGTAGATTTCTTTCCAATTTGTGTAATCCATGGTATTGGCCTTGTCATTGTC

GTACTGCACGGTGATGGTGATGCCGTGCTTCTTAAACTGGGGCTCGGCCAGCCACATTTCCAGGCTGGTCTGCTGCAGGGTC

CACTCATCGTAGGGGCTGGCATTCAGGGCTTCCAGGGCCAGCTGCAGTTCGATGGCCTGGCAGGCTTTGGCTTTAGAGGCGG

CCAGTGGAGGCACCACCTGGTGGCAGATGCTGATGCCCAGCTCTTTGGCCTTATAGAAGATTGCACATTCCATCCGGATCAG

TTTCCAGTGCTCGATCTGGGCGTTCAGGTCGTTCTTGTCGGCCTCGTAGTAGGTCAGGGTCACAATGGCGTTCTTGTGTTTC

CCATCGTGACATGTCCAATGCCACTTGTGCTTGCCGTCGTGGCAGGTCCAGTGCCAGGTGCTGCTCAGCTTGCAGTGCTTCT

TGAATCTGTACCGCAGGCACTTCAGGATCAGCAGCTTGTTGGGGTGGCAGTTCTCGCTTCTGGGCCTCTTGATCCGCCGCTG

GCCGCTCTCAGGACACAGGATCACTTGGCCGCCAGCGTGCACCTCCCATTTCTTGTCCACCTGGCCTTCCACCACGGTGCAC

TGGGCGTCCTCGCAGATATAGATCCAGTTGGTGTAGTGCATGGTGTTGCAGATGTCGCCGTCGAACTGGTGGAAGCCCATCT

CGCGAGCCTTATACATAATAGCACATTCCAGTCTGATCCGGGCCTTGTACATGATGGCGCATTCCAGCCGGATGTGCTTCCA

GTAGTCGATGTGATCGCAGATGTGGTCGCACAGGTCCTTGGAATCATTCTCATAATGTTCCAGAATGTCCTTGCTGTCGTTC

TCGTAGTGTTCCAGGATCTTGTCCTGGCACACGTTGAAGGGGTTCAGAAACTGCAGCACGTGGATCCGGGAGTGCAGGTATC

TCAGAAAGGCATTGGGGAACTCGAACACGGTGATCCGGCTTTCCAGGTAAGGCCAGAAGGGGTTGGGGAAGGTAAACACCAC

CAGTCTGCTGTGCAGGTAGGGCCACAGAGACATGGCAAAGCAGGACTTGCCTGTGTTAGGTGGGCCGTAGATCACGAGACAA

TTCAGGGACATGCCGAAGTAGGACTTTCCGGTATTGGCTGGGCCGCACAGCACCAGGCAGTTCAGGCTCATGCCGAACAGGC

TCTTGCCGGTGTTGGCAGCGCCGTACAGCAGGATGCAGTTCTTCAGAAAAGCAGCGGCGTTGCTGTTCACGTCTGCCAGCTG

AGCCTTCAGGAAGGCGCAGGCATTGCTGTCGCTGTCAGCCAGCTGGGCGGAGTTGTCGATAAAGCCGTCCAGGTCGCTCTCG

GTGCTCTCTTCGTCGGTTTCGTCGTTGTCGATGAAATCCACCATGTCCTCGCCGGTGTCGGAGTCGTTCTCATTCTCGTCGC

TGTCGTCGATGAAGTCGATCAGGTCGGTGCCGCTGTCGTAGGCTGTCTCGTCCTCGTCGGCCAGCTTGCTGCCTCTTCTGAA

CCGGGCGTGGATTTCCTGGCTGGGGACACAAACACGGCGCCACACAGCAGCAGCACGCAGCACAGGCCCCTCTTCATAGCA

TCCATGGTGGCGGCGCGGCTAGCGGTACCGgatctagatGGGGATCCGTCACtGTTCTTTATGATTCTACTTCCTTACCGTG CAATAAATTAGAATATATTTTCTACTTTTACGAGAAATTAATTATTGTATTTATTATTTATGGGTGAAAAACTTACTATAAA AAGCGGGTGGGTTTGGAATTAGTGATCAGTTTATGTATATCGCAACTACCGGgCATATGGCTATCGACATCGAGAACATTAC CCACATGATAAGAGATTGTATCAGTTTCGTAGTCTTGAGTATTGGTATTACTATATAGTATAtagatGTCGACCTGcaggtc GACGAAGTTCCTATACTTTCTAGAGAATAGGAACTTCGCAGCCAAGCTGGAATTcaTCCACTTTGGATAAGAAATCTGCATG

```
ATAAATATATTGATATCCTACCACCTATTAAAGTACCATTATCTAATAGCAATAAGATAGATAAACAAATGTTTTTTGATGA
AGTTATTACGTGGATAAATATATATCTTCAGGAAAAGGGTATTATGTTACCAGATGATATAAGAGAACTCAGAGATGCTATT
ATTCCTTAACTAGTTACGTCTCTTTAGGTACTTATTTTGATACGTTACAAGTAAAAAACTATCAAATATAAATGGAATCTGA
TTCTAATATAGCGATTGAAGAggaTCCACCGGTCGCCACCATGGTGAGCAAGGGCGAGGAGCTGTTCACCGGGGTGGTGCCC
ATCCTGGTCGAGCTGGACGGCGACGTAAACGGCCACAAGTTCAGCGTGTCCGGCGAGGGCGAGGGCGATGCCACCTACGGCA
AGCTGACCCTGAAGTTCATCTGCACCACCGGCAAGCTGCCCGTGCCCTGGCCCACCCTCGTGACCACCCTGACCTACGGCGT
GCAGTGCTTCAGCCGCTACCCCGACCACATGAAGCAGCACGACTTCTTCAAGTCCGCCATGCCCGAAGGCTACGTCCAGGAG
CGCACCATCTTCTTCAAGGACGACGGCAACTACAAGACCCGCGCCGAGGTGAAGTTCGAGGGCGACACCCTGGTGAACCGCA
TCGAGCTGAAGGGCATCGACTTCAAGGAGGACGGCAACATCCTGGGGCACAAGCTGGAGTACAACTACAACAGCCACAACGT
CTATATCATGGCCGACAAGCAGAAGAACGGCATCAAGGTGAACTTCAAGATCCGCCACAACATCGAGGACGGCAGCGTGCAG
CTCGCCGACCACTACCAGCAGAACACCCCCATCGGCGACGGCCCCGTGCTGCTGCCCGACAACCACTACCTGAGCACCCAGT
CCGCCCTGAGCAAAGACCCCAACGAGAAGCGCGATCACATGGTCCTGCTGGAGTTCGTGACCGCCGCCGGGATCACTCTCGG
CATGGACGAGCTGTACAAGTAAAGCGGccgcgaagttcctatactttctagagaataggaacTTCAACAATGTCTGGAAAGA
ACTGTCCTTCATCGATACCTATCACGGAGAAATCTGTAATTGATTCCAAGAcATCACATAGTTTAGTTGCTTCCAATGCTTC
AAAATTATTCTTATCATGCGTCCATAGTCCCGTTCCGTATCTATTATCGTTAGAATATTTTATAGTCACGCATTTATATTGA
GCTATTTGATAACGTCTAACTCGTCTAATTAATTCTGTACTTTTACCTGAAAACATGGGGCCGATTATCAACTGAATATGTC
CGCCGTTCATGATGACAATAAAGAATTAATTATTGTTCACTTTATTCGACTTTAATATATCCATCACGTTAGAAAATGCGAT
ATcGCGACGAGGATCTATGTATCTAACAGGATCTATTGCGGTGGTAGCTAGAGctGATTCTTTTTTGAATCGCATCAAACTA
ATCACAAAGTCGAACAAATATCCTTTATTAAGTTTGACCCTTCCATCTGTAACAATAGGGACCTTGTTAAACAGTTTTTTAA
AATCTTGAgAGTCTGTGAATTTTGTCAATTGTCTGTATTCCTCTGAAAGAGATTCATAACAATGACCCACGGCTTCTAATTT
ATTTTTTGATTGGATCAATAATAATAACAGAAAGTCTAGATATTGAGTGATTTGCAATATATCAGATAATGAAGATTCATCA
TCTTGACTAGCCAAATACTTAAAAAATGAATCATCATCTGCGAAGAACATCGTTAAGAGATACTGGTTGTGATCCATTTATg
agctcgcgaaagcttggcactggccgtcgttttacaacgtcgtgactgggaaaaccctggcgttacccaacttaatcgcctt
gcagcacatccccctttcgccagctggcgtaatagcgaagaggcccgcaccgatcgcccttcccaacagttgcgcagcctga
atggcgaatggcgcctgatgcggtattttctccttacgcatctgtgcggtatttcacaccgcatatggtgcactctcagtac
aatctgctctgatgccgcatagttaagccagccccgacacccgccaacaccgctgacgcgccctgacgggcttgtctgctc
ccggcatccgcttacagacaagctgtgaccgtctccgggagctgcatgtgtcagaggttttcaccgtcatcaccgaaacgcg
cgagacgaaagggcctcgtgatacgcctattttatagg ttaatgtcatgataataatggtttcttagacgtcaggtggcac
ttttcggggaaatgtgcgcggaacccctatttgtttatttttctaaatacattcaaatatgtatccgctcatgagacaataa
ccctgataaatgcttcaataatattgaaaaaggaagagtatgagtattcaacatttccgtgtcgcccttattccctttttg
cggcattttgccttcctgtttttgctcacccagaaacgctggtgaaagtaaaagatgctgaagatcagttgggtgcacgagt
gggttacatcgaactggatctcaacagcggtaagatccttgagagttttcgccccgaagaacgttttccaatgatgagcact
tttaaagttctgctatgtggcgcggtattatcccgtattgacgccgggcaagagcaactcggtcgccgcatacactattctc
agaatgacttggttgagtactcaccagtcacagaaaagcatcttacggatggcatgacagtaagagaattatgcagtgctgc
cataaccatgagtgataacactgcggccaacttacttctgacaacgatcggaggaccgaaggagctaaccgcttttttgcac
aacatggggatcatgtaactcgccttgatcgttgggaaccggagctgaatgaagccataccaaacgacgagcgtgacacca
cgatgcctgtagcaatggcaacaacgttgcgcaaactattaactggcgaactacttactctagcttcccggcaacaattaat
agactggatggaggcggataaagttgcaggaccacttctgcgctcggcccttccggctggctggtttattgctgataaatct
ggagccggtgagcgtgggtctcgcggtatcattgcagcactggggccagatggtaagccctcccgtatcgtagttatctaca
cgacggggagtcaggcaactatggatgaacgaaatagacagatcgctgagataggtgcctcactgattaagcattggtaact
gtcagaccaagtttactcatatatactttagattgatttaaaacttcatttttaatttaaaaggatctaggtgaagatcctt
```

-continued

```
tttgataatctcatgaccaaaatcccttaacgtgagttttcgttccactgagcgtcagaccccgtagaaaagatcaaaggat
cttcttgagatcctttttttctgcgcgtaatctgctgcttgcaaacaaaaaaaccaccgctaccagcggtggtttgtttgcc
ggatcaagagctaccaactcttttccgaaggtaactggcttcagcagagcgcagataccaaatactgttcttctagtgtag
ccgtagttaggccaccacttcaagaactctgtagcaccgcctacatacctcgctctgctaatcctgttaccagtggctgctg
ccagtggcgataagtcgtgtcttaccgggttggactcaagacgatagttaccggataaggcgcagcggtcgggctgaacggg
gggttcgtgcacacagcccagcttggagcgaacgacctacaccgaactgagatacctacagcgtgagctatgagaaagcgcc
acgcttcccgaagggagaaaggcggacaggtatccggtaagcggcagggtcggaacaggagagcgcacgagggagcttccag
ggggaaacgcctggtatctttatagtcctgtcgggtttcgccacctctgacttgagcgtcgatttttgtgatgctcgtcagg
gggcggagcctatggaaaaacgccagcaacgcggcctttttacggttcctggccttttgctggccttttgctcacatgttc
tttcctgcgttatcccctgattctgtggataaccgtattaccgcctttgagtgagctgataccgctcgccgcagccgaacga
ccgagcgcagcgagtcagtgagcgaggaagcggaaga
```

F11-HPV Shuttle Plasmid (SEQ ID NO: 159) (Vaccine Construct Insert is Underlined)

```
AGCGCCCAATACGCAAACCGCCTCTCCCCGCGCGTTGGCCGATTCATTAATGCAGCTGGCACGAC

AGGTTTCCCGACTGGAAAGCGGGCAGTGAGCGCAACGCAATTAATGTGAGTTAGCTCACTCATTA

GGCACCCCAGGCTTTACACTTTATGCTTCCGGCTCGTATGTTGTGTGGAATTGTGAGCGGATAAC

AATTTCACACAGGAAACAGCTATGACCATGATTACGCCAAGCTATTTAGGTGACACTATAGAATA

CTCAAGCTATGCATCAAGCTTGGTACCGAGCTCGGATCCACTAGTAACGGCCGCCAGTGTGCTGG

AATTCGCCCTTgtaatctattcgatataccgttgctaacagtatactggcccaataactgtggat ggaaaatctataataatacattaatatcatccgatggtgctagggttatttggatggatgcgtat aaatttcttgcggtttatctttacaagactattgttatcattggggtagcaaaccagagagccg accattcgatttaataaaaaaatcagatgctaaacgcaattctaaatcgttggtcaaagaatcta tggcatccttgaaatccttgtacgaggcattcgagacacaatcaggagcgttagaagttttaatg agtccatgtaggatgttttcgttttctagaatagaagacatgttcttaactagtgtcattaatag agtatccgagaatactggaatggggatgtattatcctaccaacgatataccttctctatttatcg aatcatctatctgtctagattatattatagtaaataatcaggaatccaacaaatatcgtatcaaa tctgttctcgatatcatttcttcaaaacaatacctgcaggacgtcccaactacgttaaaaatgg tacaaaaggaaagttatatatcgcgttgtgtaaagttaccgtacctactaacgaccatattccag tagtttatcacgatgatgacaatactaccacctttattacagtattgacgtccgtcgatattgaa actgctatcagagcaggatattcgatagtcgaattaggggctttacaatgggataataatattcc agaacttaaaaacggtttactggatagtatcaagatgatttatgacttgaacgcagttacaacaa ataatttattggaacagctcatagaaaatattaactttaacaactctagtataatttcgttgttt tatacatttgccattagttattgccgagcattcatttactcaattatggaaaccatagatccggt gtatatatctcagttcagttataaagaattatacgttagtagctcttataaagatattaatgaat ccatgagtcagatggtaaaattataaaaagtgaaaaacaatattattttttatcgttggttgttac actATGGATGCTATGAAGAGGGGCCTGTGCTGCGTGCTGCTGCTGTGTGGCGCCGTGTTTGTGTC

CCCCAGCCAGGAAATCCACGCCCGGTTCAGAAGAGGCAGCAAGCTGGCCGACGAGGACGAGACAG

CCTACGACAGCGGCACCGACCTGATCGACTTCATCGACGACAGCGACGAGAATGAGAACGACTCC

GACACCGGCGAGGACATGGTGGATTTCATCGACAACGACGAAACCGACGAAGAGAGCACCGAGAG

CGACCTGGACGGCTTTATCGACAACTCCGCCCAGCTGGCTGACAGCGACAGCAATGCCTGCGCCT
```

-continued

```
TCCTGAAGGCTCAGCTGGCAGACGTGAACAGCAACGCCGCTGCTTTTCTGAAGAACTGCATCCTG

CTGTACGGCGCTGCCAACACCGGCAAGAGCCTGTTCGGCATGAGCCTGAACTGCCTGGTGCTGTG

CGGCCCAGCCAATACCGGAAAGTCCTACTTCGGCATGTCCCTGAATTGTCTCGTGATCTACGGCC

CACCTAACACAGGCAAGTCCTGCTTTGCCATGTCTCTGTGGCCCTACCTGCACAGCAGACTGGTG

GTGTTTACCTTCCCCAACCCCTTCTGGCCTTACCTGGAAAGCCGGATCACCGTGTTCGAGTTCCC

CAATGCCTTTCTGAGATACCTGCACTCCCGGATCCACGTGCTGCAGTTTCTGAACCCCTTCAACG

TGTGCCAGGACAAGATCCTGGAACACTACGAGAACGACAGCAAGGACATTCTGGAACATTATGAG

AATGATTCCAAGGACCTGTGCGACCACATCTGCGATCACATCGACTACTGGAAGCACATCCGGCT

GGAATGCGCCATCATGTACAAGGCCCGGATCAGACTGGAATGTGCTATTATGTATAAGGCTCGCG

AGATGGGCTTCCACCAGTTCGACGGCGACATCTGCAACACCATGCACTACACCAACTGGATCTAT

ATCTGCGAGGACGCCCAGTGCACCGTGGTGGAAGGCCAGGTGGACAAGAAATGGGAGGTGCACGC

TGGCGGCCAAGTGATCCTGTGTCCTGAGAGCGGCCAGCGGCGGATCAAGAGGCCCAGAAGCGAGA

ACTGCCACCCCAACAAGCTGCTGATCCTGAAGTGCCTGCGGTACAGATTCAAGAAGCACTGCAAG

CTGAGCAGCACCTGGCACTGGACCTGCCACGACGGCAAGCACAAGTGGCATTGGACATGTCACGA

TGGGAAACACAAGAACGCCATTGTGACCCTGACCTACTACGAGGCCGACAAGAACGACCTGAACG

CCCAGATCGAGCACTGGAAACTGATCCGGATGGAATGTGCAATCTTCTATAAGGCCAAAGAGCTG

GGCATCAGCATCTGCCACCAGGTGGTGCCTCCACTGGCCGCCTCTAAAGCCAAAGCCTGCCAGGC

CATCGAACTGCAGCTGGCCCTGGAAGCCCTGAATGCCAGCCCCTACGATGAGTGGACCCTGCAGC

AGACCAGCCTGGAAATGTGGCTGGCCGAGCCCCAGTTTAAGAAGCACGGCATCACCATCACCGTG

CAGTACGACAATGACAAGGCCAATACCATGGATTACACAAATTGGAAAGAAATCTACGTGATCGT

GTGCCCCGCCAGCATCCCCTCCGATGAGATCAGCACCGAGGAAGCCGACCACATTGATTATTGGA

AAGCCATCAGGCAGGAAAACGCCATCTTCTTCGCCGCCAGACACCAGGTGGTGCCCGCCCTGAAT

ATCTGCAAGGCCAAGGCCTGTAAAGCCATCGAGTGGAACACCGAGCCCAAGCACTGCTTCAAGAA

GGGCGGCCAGCACATCGAAGTGTGGTTCGACTACGTGGCCTGGGACAGCGTGTACTACTGCGGCG

ACGATGGCTGGTGCAAGACCGAGGCCGAGAAGTACGGCTGCAAGGGCACCTGGGAAGTGCATTTC

GGCAACAGCATCGACTGCAACGACTCCATGTGCAGCACCTTCGACGACAACGTGTCCGCCACCGA

GCTCGTGAAGGACCATATCGACTATTGGAAGCTGATTCGCCTGGAATGTGCCATTTTTTACAAGG

CCAGACGGCGGCTGTCCAGCGACCAGGATCAGTCTCAGCTCGTGACCAAGTACCCCCTGCTGAAG

CTGCTGTCCAGACCCCCCAACATGGGCGTGAAGGCCCACGGCAAGTGCATCTGGGAGAACAAGGT

GTTCATCGTGCCCACCCTGTGCCCCGTGCCTCTGGATCCAACATATCCTCTGCTGAAACTGCTGA

CCACCCAGACCACCACCCCCGAGAATACCTCCCTGGTGGAACTGAGAGTGACCACCCCCAAGAGC

ACAGTCGTGATCAGGCTGCACCTGACCACCAGATACCCACTGCTGTCACTGCTGAACAGCTACAG

CACCCCCCCTCACCGGATCCCTGCTCCATGTCCTTGGGCTCCTCAGAGGCCCCCCATCCCTAAGC

CTTCTCCATGGGCCCCTAGAATCCCTGCCCCTTGCCCCTGGGCACCTCCTAGACCTCCACACTGT

CCATGGGTGCCCCCTCCACCTCCTCCAAGACCTTGGGCCCCTTGCTTCCTGCTGTGCTTTTGTGT

GCTGCTGTGCGTGTGCCTGCTGATCAGACCCCTGCTGCTGAGTGTGTCCACCTACCTGAGGCCTC

TGCTGCTGTCTATCAGCGTGTACGCTCAGGTGCTGGTGCTGGTGCTGCTGCTGTGGGTGTCCATC

GGAAGCCTGCTGCCCAGCGTGTGCATGTGTGCCTATGCCTGGGTGCTGGTGTTCGTGTACATCGT

CGTGATTACCAGCCCCGCCACCGCCATCGTGTACCGGGATGGCAATCCTTACGCCGTGTGCGACA

AGTGCCTGAAGTTCTACAGCAAGATCAGCGAGTACCGGCACTACTGCTACAGCCTGTACGGCACC

ACCCTGGAACAGCAGTACAACAAGCCCCTGTGCGATCTGCTGATTCGGTGCATCAACGTGGTGTA
```

-continued

CAGAGACTCCATCCCCCACGCCGCCTGCCACAAGTGTATCGACTTCTACTCCAGAATCAGAGAGC

TGCGGCACTACAGCGACTCCGTGTACGGCGATACCCTGGAAAAGCTGACCAACACTGGCCTGTAC

AACCTGCTGATTAGATGCCTGCGGGTGTTCTGCAAGAAGGCCCTGACAGCCAGCGAGGTGTACAA

CTTCGCCTACACCGATCTGCGGGTGGTGTATCGGGACAGCAAAGTGCGGAAGCTGAGGTACTACA

ACTGCTCTGTGTATGGCGCCAGCCTGGTGTATTGCAAGGGACAGCTGACCGAGACAGAGGTGCTG

GATTTCGCCTTCACAGACCTGACAATCGTGTATCGCGACTCCAAGGTGTCCGAGTTCCGGTGGTA

CAGATATTCCGTGTATGGCACCACACTGTGCGTGGAATGCAAGAAAACCCTGCAGAGATCTGAGG

TGTACGACTGCCAGCGGCCACTGTGTCCGCAGGAAAAGAAAAGACACGTGGACCTGAACAAGCGG

TTCCACACCCTGCACGAGTACATGCTGGATCTGCAGCCCGAGACAACCGACCTGTACTGCTACGA

GCAGCCTGAAACCACTGATCTGCACTGTTATGAGCAGCTGGGAGACAGCTCCGATGAAGAGGACA

CTGGCGGCCTGGATGGGACGAGGATGAGGACGAAGTGGACCATCTGCAGGAACAGCCCCAGCAG

GCTAGACGGGACGAACAGCACCCTTGCTATCTGATCGAGACACAGTGCTGCAGATGCGAATCTCT

GGTGGAAGAGAACGACGAGATCGACGGCGTGAACCACCAGCATCTGCCCGCTAGAAGGGCCGAGC

CTCAGAGACACACCATGCTGTGTATGTGCTGCAAGTGCGAGGCCAGAATCGCCGGCtaattttta taaccgagtttctgcattattgtaattcgtatgctggcaccatcaaagaatcacttctaaaagat atcaatatcacacatacaaatattactaccctattgaatgagacagccaaggttatcaagttagt aaaatctctggtagataaagaagatactgatattgtgaataatttcattaccaaagaaattaaaa acagagacaaaatagttaatagtttgtctctatcaaacctggactttcgtttgtaaattggggct Ttttgtacaataaatgggtgttgccaatgattcatccctgaatatcaatggatgtctccccata gattatcagatactgttatattaggagactgtttgtattttaacaatataatgtcccaattagat ttacaccaaaattgggctccatcagttagattgttaaattattttaagaattttaataaggaaac actactaaagatagaagagaatgattacattaattcatccttttttccaacaaaaggataaacgat tttatcctataaacgacgattttttatcacatatctacaggaggatatggtatagtctttaagata gataactatgtagtaaaatttgtattcgaggccacaaaattatatagtcccatggaaactacggc ggagttcacagtacccaaatttctatacaacaatctaaagggagatgaaaaaaaattaatcgtgt gtgcgtgggccatgggattaaactataaattaacatttttacatactctgtataaacgtgttctt catatgttgctattattgatacaaactatggatggtcaggaactatcattgagatattcttctaa agttttttttaaaggcgtttaacgagagaaaggacagtatcaaattcgtgaaattactatcccact tttatccggcagttattaacagtaatattaatgttataaactattttaaccgcatgtttcacttt ttcgaacatgaaaagagaactaactacgaatacgaaagaggaaatattataattttttccctagc actgtattcggcagataaagtagataccgagctagctatcaaattaggatttaaatctttggtac aatacataaagtttatcttttttacagatggctctgttatacattaaaatttacgaactaccatgc tgcgacaacttttttacacgcagatcttaaacccgataatatcttactttttgattccaatgaacc aataataattcatctaaaggataaaaagtttgttttaatgaacgtattaaatcggcattaaacg actttgacttttcccaagAAGGGCGAATTCTGCAGATATCCATCACACTGGCggccgcTTACTTG

TACAGCTCGTCCATGCCGAGAGTGATCCCGGCGGCGGTCACGAACTCCAGCAGGACCATGTGATC

GCGCTTCTCGTTGGGGTCTTTGCTCAGGGCGGACTGGGTGCTCAGGTAGTGGTTGTCGGGCAGCA

GCACGGGGCCGTCGCCGATGGGGGTGTTCTGCTGGTAGTGGTCGGCGAGCTGCACGCTGCCGTCC

TCGATGTTGTGGCGGATCTTGAAGTTCACCTTGATGCCGTTCTTCTGCTTGTCGGCCATGATATA

GACGTTGTGGCTGTTGTAGTTGTACTCCAGCTTGTGCCCCAGGATGTTGCCGTCCTCCTTGAAGT

CGATGCCCTTCAGCTCGATGCGGTTCACCAGGGTaTCGCCCTCGAACTTCACCTCGGCGCGGGTC

-continued

```
TTGTAGTTGCCGTCGTCCTTGAAGAAGATGGTGCGCTCCTGGACGTAGCCTTCGGGCATGGCGGA
CTTGAAGAAGTCGTGCTGCTTCATGTGGTCGGGGTAGCGGCTGAAGCACTGCACGCCGTAGGTCA
GGGTGGTCACGAGGGTcGGCCAGGGCACGGGCAGCTTGCCGGTGGTGCAGATGAACTTCAGGGTC
AGCTTGCCGTAGGTGGCATCGCCCTCGCCCTCGCCGGACACGCTGAACTTGTGGCCGTTTACGTC
GCCGTCCAGCTCGACCAGGATGGGCACCACCCCGGTaAACAGCTCCTCGCCCTTGCTCACCATgt
ttaaacTTTATATTCCAAAAAAAAAAAATAAAATTTCAATTTTTgtttaaacgttGTACGGCAGT
TTAAGGTTTACACCTATAAAAGAGAGAGCCGTTATCGTCTGTTTGTGGATGTACAGAGTGATATT
ATTGACACGCCGGGGCGACGGATGGTGATCCCCCTGGCCAGTGCACGTCTGCTGTCAGATAAAGT
CTCCCGTGAACTTTACCCGGTGGTGCATATCGGGGATGAAAGCTGGCGCATGATGACCACCGATA
TGGCCAGTGTGCCGGTCTCCGTTATCGGGGAAGAAGTGGCTGATCTCAGCCACCGCGAAAATGAC
ATCAAAAACGCCATTAACCTGATGTTCTGGGGAATATAAATGTCAGGCATGAGATTATCAAAAAG
GATCTTCACCTAGATCCTTTTCACGTAGAAAGCCAGTCCGCAGAAACGGTGCTGACCCCGGATGA
ATGTCAGCTACTGGGCTATCTGGACAAGGGAAAACGCAAGCGCAAAGAGAAAGCAGGTAGCTTGC
AGTGGGCTTACATGGCGATAGCTAGACTGGGCGGTTTTATGGACAGCAAGCGAACCGGAATTGCC
AGCTGGGGCGCCCTCTGGTAAGGTTGGGAAGCCCTGCAAAGTAAACTGGATGGCTTTCTCGCCGC
CAAGGATCTGATGGCGCAGGGGATCAAGCTCTGATCAAGAGACAGGATGAGGATCGTTTCGCATG
ATTGAACAAGATGGATTGCACGCAGGTTCTCCGGCCGCTTGGGTGGAGAGGCTATTCGGCTATGA
CTGGGCACAACAGACAATCGGCTGCTCTGATGCCGCCGTGTTCCGGCTGTCAGCGCAGGGGCGCC
CGGTTCTTTTTGTCAAGACCGACCTGTCCGGTGCCCTGAATGAACTGCAAGACGAGGCAGCGCGG
CTATCGTGGCTGGCCACGACGGGCGTTCCTTGCGCAGCTGTGCTCGACGTTGTCACTGAAGCGGG
AAGGGACTGGCTGCTATTGGGCGAAGTGCCGGGGCAGGATCTCCTGTCATCTCACCTTGCTCCTG
CCGAGAAAGTATCCATCATGGCTGATGCAATGCGGCGGCTGCATACGCTTGATCCGGCTACCTGC
CCATTCGACCACCAAGCGAAACATCGCATCGAGCGAGCACGTACTCGGATGGAAGCCGGTCTTGT
CGATCAGGATGATCTGGACGAAGAGCATCAGGGGCTCGCGCCAGCCGAACTGTTCGCCAGGCTCA
AGGCGAGCATGCCCGACGGCGAGGATCTCGTCGTGACCCATGGCGATGCCTGCTTGCCGAATATC
ATGGTGGAAAATGGCCGCTTTTCTGGATTCATCGACTGTGGCCGGCTGGGTGTGGCGGACCGCTA
TCAGGACATAGCGTTGGCTACCCGTGATATTGCTGAAGAGCTTGGCGGCGAATGGGCTGACCGCT
TCCTCGTGCTTTACGGTATCGCCGCTCCCGATTCGCAGCGCATCGCCTTCTATCGCCTTCTTGAC
GAGTTCTTCTGAATTATTAACGCTTACAATTTCCTGATGCGGTATTTTCTCCTTACGCATCTGTG
CGGTATTTCACACCGCATACAGGTGGCACTTTTCGGGGAAATGTGCGCGGAACCCCTATTTGTTT
ATTTTTCTAAATACATTCAAATATGTATCCGCTCATGAGACAATAACCCTGATAAATGCTTCAAT
AATAGCACGTGAGGAGGGCCACCATGGCCAAGTTGACCAGTGCCGTTCCGGTGCTCACCGCGCGC
GACGTCGCCGGAGCGGTCGAGTTCTGGACCGACCGGCTCGGGTTCTCCCGGGACTTCGTGGAGGA
CGACTTCGCCGGTGTGGTCCGGGACGACGTGACCCTGTTCATCAGCGCGGTCCAGGACCAGGTGG
TGCCGGACAACACCCTGGCCTGGGTGTGGGTGCGCGCCTGGACGAGCTGTACGCCGAGTGGTCG
GAGGTCGTGTCCACGAACTTCCGGGACGCCTCCGGGCCGGCCATGACCGAGATCGGCGAGCAGCC
GTGGGGGCGGGAGTTCGCCCTGCGCGACCCGGCCGGCAACTGCGTGCACTTCGTGGCCGAGGAGC
AGGACTGACACGTGCTAAAACTTCATTTTTAATTTAAAAGGATCTAGGTGAAGATCCTTTTTGAT
AATCTCATGACCAAAATCCCTTAACGTGAGTTTTCGTTCCACTGAGCGTCAGACCCCGTAGAAAA
GATCAAAGGATCTTCTTGAGATCCTTTTTTTCTGCGCGTAATCTGCTGCTTGCAAACAAAAAAAC
CACCGCTACCAGCGGTGGTTTGTTTGCCGGATCAAGAGCTACCAACTCTTTTTCCGAAGGTAACT
```

-continued

```
GGCTTCAGCAGAGCGCAGATACCAAATACTGTCCTTCTAGTGTAGCCGTAGTTAGGCCACCACTT

CAAGAACTCTGTAGCACCGCCTACATACCTCGCTCTGCTAATCCTGTTACCAGTGGCTGCTGCCA

GTGGCGATAAGTCGTGTCTTACCGGGTTGGACTCAAGACGATAGTTACCGGATAAGGCGCAGCGG

TCGGGCTGAACGGGGGGTTCGTGCACACAGCCCAGCTTGGAGCGAACGACCTACACCGAACTGAG

ATACCTACAGCGTGAGCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGGGGAAACGCCTGGTAT

CTTTATAGTCCTGTCGGGTTTCGCCACCTCTGACTTGAGCGTCGATTTTTGTGATGCTCGTCAGG

GGGGCGGAGCCTATGGAAAAACGCCAGCAACGCGGCCTTTTTACGGTTCCTGGGCTTTTGCTGGC

CTTTTGCTCACATGTTCTTTCCTGCGTTATCCCCTGATTCTGTGGATAACCGTATTACCGCCTTT

GAGTGAGCTGATACCGCTCGCCGCAGCCGAACGACCGAGCGCAGCGAGTCAGTGAGCGAGGAAGC

GGAAG
```

HPV2-Randomised Nucleotide Sequence (Segments are in a Randomisd Order) (Includes tPA Leading Sequence and HindIII Cloning Linker, Underlined) (SEQ ID NO: 71)

```
ATGGATGCTATGAAGAGGGGCCTGTGCTGCGTGCTGCTGCTGTGTGGCGCCGTGTTTGTGTCCCC

CAGCCAGGAAATCCACGCCCGGTTCAGAAGAGGCAGCAAGCTGGCTGCTCAGCTGGCCGACAGCG

ACAGCAATGCCTGCGCCTTCCTGAAGCTGAGATACCTGCACAGCCGGATCCACGTGCTGCAGTTT

CTGAACCCCTTCACCCTGCACGAGTACATGCTGGACCTGCAGCCCGAGACAACCGACCTGTACTG

CTACGAGCAGGACGAGGATGAGGACGAGGTGGACCATCTGCAGGAACAGCCCCAGCAGGCCAGAA

GGGATGAGCAGCACCCCTGCTACCTGATCGAGACACAGTGCTGCAGATGCGAGAGCCTGGTGGCC

CAGCTGGCTGACGTGAACTCTAACGCCGCAGCCTTTCTGAAGAACAGCATCGACTGCAACGACAG

CATGTGCAGCACCTTCGACGACAACGTGTCCGCCACCGAGCTCGTGAAGAGAATCCCTGCCCCTT

GCCCCTGGGCCCCTGAGGAAAATGACGAGATCGACGGCGTGAACCACCAGCATCTGCCCGCTAGA

AGGGCCGAGCCTCAGAGACACACCATGCTGTGCATGTGCTGCAAGTGCGAGGCCCGGATCTGCTT

CCTGCTGTGCTTTTGTGTGCTGCTGTGCGTGTGCCTGCTGATCAGACCCCTGCTGCTGAGTGTGT

CCACCTACTGCCAGCGGCCGCTGTGTCCTCAGGAAAAGAAACGGCACGTGGACCTGAACAAGCGG

TTCCACATCTACATCTGCGAGGACGCCCAGTGCACCGTGGTGGAAGGCCAGGTGGACAGCAAGGT

GTCCGAGTTCCGGTGGTACAGATACAGCGTGTACGGCACCACCCTGGGCCAGCGGAGAATCAAGA

GGCCCAGATCCGAGGTGTACTGCAAGGGACAGCTGACCGAGACAGAGGTGCTGGACTTCGCCTTC

ACCGACCTGACCATCGTGTACCGGGACATCCGGCTGGAATGCGCCATCATGTACAAGGCCAGAGA

GATGGGCTTCCACGACCACATCGACTACTGGAAGCTGATTAGACTGGAATGTGCTATCTTCTACA

AAGCCCGGATCCTGAAGTGCCTGCGGTACAGATTCAAGAAGCACTGCAAGCTGTACGTGGCCTGG

GACTCCGTGTACTACTGCGGCGACGATGGCTGGTGCAAGACCAGCTCTACCTGGCACTGGACATG

CCACGACGGCAAGCACAAGAACGTGTGCCAGGACAAGATCCTGGAACACTACGAGAACGACTCCA

AGGACGACGAGGACGAGACAGCCTACGACAGCGGCACCGATCTGATCGACTTCATCGACGATAGC

AACTGCCACCCCAACAAGCTGCTGCGGAGACTGAGCAGCGACCAGGACCAGTCTCAGAGGCCCCC

CAACATGGGAGTGAAGGCCCACGGCAAGTGCATCTGGGAGAACAAGGTGTTCATCGTGCCCACCC

TGTGCCCCGTGCCTCTGGATCCAACATACCCCCTGCTGAAGCTGCTGACCCCCGAAACCACAGAT

CTGCACTGTTATGAGCAGCTGGGCGACTCCTCCGACGAAGAGGATACAGGCGGCCTGGATGGCTA

CGAGGCCGACAAGAACGACCTGAACGCCCAGATCGAGCACTGGAAACTGATCCGGATGGAATGTG
```

-continued

```
CAATTTTCTATAAGGCCAAAGAGCTGGGGATCAGCGACGAGAATGAGAACGACAGCGATACCGGC
GAGGACATGGTGGATTTCATCGACAATGAGGCCGAGAAGTACGGCTGCAAGGGCACCTGGGAGGT
GCACTTCGGCTTTAAGAAGCACGGCATCACCATCACCGTGCAGTACGACAACGACAAGGCCAACA
CCATGGACTACACCAACTGGAAAGAGATCTACCCCCCTCCCCCCCCACGGCCTTGGGCTCCTCCA
ATTCCTAAGCCCTCTCCATGGGCCCCTCAGTTCGACGGCGACATCTGCAATACCATGCACTATAC
CAATTGGGTGGTGTACAGAGACAGCATCCCCCACGCCGCCTGCCACAAGTGTATCGACTTCTACA
GCAGAATCAGAGAGCTGCGGCACTACAGCGACTCTGTGTACGGCGATACCCTGGAAAAGCTGACC
AACACCGGCCTGTACAATCTGCTGATCCGGTGCCTGAGGCTCGTGACCAAGTATCCTCTGCTGAA
ACTGCTGTCCAACTGCATCCTGTACGGCGCTGCCAATACCGGCAAGAGCCTGTTCGGCATGAGCC
TGAGCAAAGTGCGGAAGCTGAGGTACTACAACTGCTCCGTGTATGGGGCCAGCCTGTGCGTGGAA
TGCAAGAAACCCTGCAGCGGAGCGAAGTGTACGACGACGAAACCGACGAGGAAAGCACCGAGAG
CGACCTGGACGGCTTCATCGATAACAGCGTGATCGTGTGCCCCGCCTCCATCCCCTCCGATGAGA
TCTCTACCGAGGAAGCCCCCAGACCCCCTCACTGTCCTTGGGTGCCAGTGTTCTGCAAGAAGGCC
CTGACCGCCTCTGAGGTGTACAATTTTGCCTATACCGACCTGCGCGTGGTGTATAGGGACATTCT
GGAACATTATGAGAATGATAGCAAGGACCTGTGCGATCACATCAACTGCCTCGTGATCTACGGCC
CTCCTAACACCGGCAAGTCCTGCTTCGCCATGTCCCTGTGGAACACCGAGCCCAAGCACTGCTTC
AAGAAGGGCGGCCAGCACATCGAAGTGTGGTTCGATATTGTGTACAGGGACGGCAACCCTTACGC
CGTGTGCGACAAGTGCCTGAAGTTCTACTCCAAGATCAGCGAGTACCGCCACTACTGCTACTCCC
TGTATGGCACAACACTGGAACAGCAGTACAACAAGCCCCTGTGCGACCTGCTGATTCGCTGCATC
AACACCACCAGATACCCTCTGCTGTCCCTGCTGAACAGCTACAGCACCCCCCCTCATCGGATTCC
CGCCCCATGTCCATGGGCTCCACAGAGGCCTACCCAGACCACCACCCCCGAGAATACCTCCCTGG
TGGAACTGAGAGTGACCACCCCCAAGAGCACAGTCGTGATCAGGCTGCACCTGTGGCCCTACCTG
CACTCCAGACTGGTGGTGTTCACCTTCCCCAACCCCTTTCACCAGGTGGTGCCCGCCCTGAATAT
CTGCAAGGCCAAGGCCTGCAAAGCCATCGAGAAGAAATGGGAAGTGCACGCTGGCGGCCAAGTGA
TCCTGTGTCCTGAGAGCCTGCGGCCTCTGCTGCTGTCCATTAGCGTGTACGCCCAGGTGCTGGTG
CTGGTGCTGCTGCTGTGGGTGTCCATCGGCAGCAACTGTCTGGTGCTGTGCGGCCCTGCCAACAC
AGGGAAGAGTTACTTCGGCATGTCTCTGATCTGCCATCAGGTGGTGCCTCCACTGGCCGCCTCTA
AGGCTAAAGCCTGTCAGGCCATCGAACTGCAGCTGGCCCTGGAAGCCCTGAATGCCAGCCCCTAT
GATCACATTGATTACTGGAAAGCCATCCGGCAGGAAAATGCCATCTTCTTCGCCGCCAGATGGCA
TTGGACCTGTCACGATGGAAAACACAAGAATGCCATTGTGACCCTGACCTACCTGCTGCCCAGCG
TGTGTATGTGCGCCTACGCTTGGGTGCTGGTGTTCGTGTACATCGTCGTGATTACCAGCCCCGCC
ACCGCCGATGAGTGGACACTGCAGCAGACAAGCCTGGAAATGTGGCTGGCCGAGCCCCAGTGTGA
CCATATCGATTATTGGAAACACATCCGCCTGGAATGTGCTATTATGTATAAGGCCCGGTGGCCTT
ACCTGGAAAGCAGAACCGTGTTCGAGTTCCCCAATGCCTTCGCCGGCTCTGGACCTGGCGCCTCT
GGAAAACCCATCCCCAATCCACTGCTGGGCCTGGACTCCACCCGGACC
```

HPV2-Randomised Sequence Polypeptide (Includes tPA Leading Sequence and HindIII Cloning Linker, Underlined) (SEQ ID NO: 72)

<u>MDAMKRGLCCVLLLCGAVFVSPSQEIHARFRRGSKLA</u>AQLADSDSNACAFL
KLRYLHSRIHVLQFLNPFTLHEYMLDLQPETTDLYCYEQDEDEDEVDHLQE
QPQQARRDEQHPCYLIETQCCRCESLVAQLADVNSNAAAFLKNSIDCNDSM
CSTFDDNVSATELVKRIPAPCPWAPEENDEIDGVNHQHLPARRAEPQRHTM
LCMCCKCEARICFLLCFCVLLCVCLLIRPLLLSVSTYCQRPLCPQEKKRHV
DLNKRFHIYICEDAQCTVVEGQVDSKVSEFRWYRYSVYGTTLGQRRIKRPR

SEVYCKGQLTETEVLDFAFTDLTIVYRDIRLECAIMYKAREMGFHDHIDYW
KLIRLECAIFYKARILKCLRYRFKKHCKLYVAWDSVYYCGDDGWCKTSSTW
HWTCHDGKHKNVCQDKILEHYENDSKDDEDETAYDSGTDLIDFIDDSNCHP
NKLLRRLSSDQDQSQRPPNMGVKAHGKCIWENKVFIVPTLCPVPLDPTYPL
LKLLTPETTDLHCYEQLGDSSDEEDTGGLDGYEADKNDLNAQIEHWKLIRM
ECAIFYKAKELGISDENENDSDTGEDMVDFIDNEAEKYGCKGTWEVHFGEK
KHGTTITVQYDNDKANTMDYTNWKEIYPPPPPRPWAPPIPKPSPWAPQFDG
DICNTMHYTNWVVYRDSIPHAACHKCIDFYSRIRELRHYSDSVYGDTLEKL
TNTGLYNLLIRCLRLVTKYPLLKLLSNCILYGAANTGKSLFGMSLSKVRKL
RYYNCSVYGASLCVECKKTLQRSEVYDDETDEESTESDLDGFIDNSVIVCP
ASIPSDEISTEEAPRPPHCPWVPVFCKKALTASEVYNFAYTDLRVVYRDIL
EHYENDSKDLCDHINCLVIYGPPNTGKSCFAMSLWNTEPKHCFKKGGQHIE
VWFDIVYRDGNPYAVCDKCLKEYSKISEYRHYCYSLYGTTLEQQYNKPLCD
LLIRCINTTRYPLLSLLNSYSTPPHRIPAPCPWAPQRPTQTTTPENTSLVE

LRVTTPKSTVVIRLHLWPYLHSRLVVFTFPNPFHQVVPALNICKAKACKAI

EKKWEVHAGGQVILCPESLRPLLLSISVYAQVLVLVLLLWVSIGSNCLVLC

GPANTGKSYFGMSLICHQVVPPLAASKAKACQAIELQLALEALNASPYDHI

DYWKAIRQENAIFFAARWHWTCHDGKHKNAIVTLTYLLPSVCMCAYAWVLV

FVYIVVITSPATADEWTLQQTSLEMWLAEPQCDHIDYWKHIRLECAIMYKA

RWPYLESRTVFEFPNAFAGSGPGASGKPIPNPLLGLDSTRT**

HPV53del Nucleotide Sequence (Segments from HPV53 have been Removed) (Includes tPA Leading Sequence and HindIII Cloning Linker, Underlined) (SEQ ID NO: 73)

ATGGATGCTATGAAGCGAGGACTGTGCTGCGTGCTGCTGCTGTGTGGCGCT

GTGTTTGTGTCCCCTAGCCAAGAGATCCACGCCAGATTCAGACGGGGCAGC

AAACTGGCCGACGAGGATGAGACAGCCTACGACTCTGGCACCGACCTGATC

GACTTCATCGACGACAGCGACGAGAACGAGAATGACAGCGACACCGGCGAG

GACATGGTGGATTTCATCGACAATGCCCAGCTGGCCGACTCCGACTCTAAT

GCCTGTGCCTTTCTGAAGGCTCAGCTGGCTGACGTGAACAGCAATGCCGCC

GCTTTCCTGAAGAACTGCATCCTGCTGTACGGCGCTGCCAACACAGGCAAG

AGCCTGTTTGGCATGAGCCTGAACTGCCTGGTGCTGTGCGGACCTGCCAAT

ACCGGCAAAAGCTACTTCGGCATGTCCCTGTGGCCTTACCTGCACAGCAGA

CTGGTGGTGTTTACATTCCCCAATCCTTTCTGGCCCTACCTGGAAAGCCGG

ATCACCGTGTTCGAGTTCCCCAACGCCTTCAACGTGTGCCAGGACAAGATC

CTGGAACACTATGAGAACGACAGCAAGGACATCCTTGAGCACTACGAAAAC

GACTCCAAGGACCTGTGCGACCACATCTGCGATCACATCGACTACTGGAAG

CACATCCGGCTGGAATGCGCCATCATGTACAAGGCCCGGATCAGACTGGAA

TGTGCTATTATGTATAAGGCTCGCGAGATGGGCTTCCACCAGTTCGACGGC

GACATCTGCAACACCATGCACTACACCAACTGGATCTATATCTGCGAGGAC

GCCCAGTGCACCGTGGTGGAAGGACAGGTGGACAAGAAATGGGAAGTGCAC

GCTGGCGGCCAAGTGATTCTGTGTCCTGAGAGCGGCCAGCGGAGAATCAAG

-continued

AGGCCCAGATCCGAGAACTGTCACCCCAACAAGCTGCTGATCCTGAAGTGC

CTGCGGTACAGATTCAAGAAGCACTGCAAGCTGAGCAGCACCTGGCACTGG

ACATGCCACGATGGCAAGCACAAGTGGCATTGGACCTGTCACGACGGGAAA

CACAAGAACGCCATCGTGACCCTGACCTACTACGAGGCCGACAAGAACGAC

CTGAACGCCCAGATTGAGCACTGGAAACTGATCCGGATGGAATGTGCAATC

TTCTATAAGGCCAAAGAGCTGGGGATCAGCATCTGCCACCAGGTGGTGCCT

CCACTGGCTGCCTCTAAAGCCAAAGCCTGTCAGGCCATCGAACTGCAGCTG

GCCCTGGAAGCCCTGAACGCTAGCCCTTACGATGAGTGGACCCTGCAGCAG

ACCAGCCTGGAAATGTGGCTGGCCGAGCCTCAGTTTAAGAAGCACGGCATC

ACCATCACCGTGCAGTACGACAACGACAAGGCCAATACCATGGATTACACG

AATTGGAAAGAAATCTACGTGATCGTGTGCCCCGCCAGCATTCCCTCCGAT

GAGATCTCTACCGAGGAAGCCGACCACATTGATTATTGGAAGGCCATCCGG

CAAGAGAATGCCATCTTCTTCGCCGCCAGACATCAGGTGGTCCCCGCTCTG

AATATCTGCAAGGCCAAGGCCTGCAAAGCCATCGAGTGGAACACCGAGCCT

AAGCACTGCTTCAAGAAAGGCGGCCAGCACATCGAAGTTTGGTTCGACTAC

GTGGCCTGGGACAGCGTGTACTACTGCGGAGATGATGGCTGGTGCAAGACC

GAGGCCGAGAAGTACGGCTGTAAAGGCACCTGGGAAGTCCACTTCGGCAAC

AGCATCGACTGCAACGATAGCATGTGCAGCACCTTCGACGACAACGTGTCC

GCCACAGAGCTGGTCAAGGACCATATAGACTATTGGAAGCTGATCAGGCTT

GAGTGCGCCATTTTCTACAAGGCCAGACGGCGGCTGTCCAGCGACCAGGAT

CAATCTCAGCTCGTGACCAAGTATCCCCTGCTGAAGCTGCTGTCTACCCAG

ACCACCACACCTGAGAACACAAGCCTGGTGGAACTGAGAGTGACCACACCT

AAGAGCACCGTCGTGATTCGGCTGCACCTGACCACAAGATACCCTCTGCTG

AGCCTGCTGAACAGCTACAGCACCCCTCCACACAGGATCCCCGCTCCATGT

CCTTGGGCTCCTCAGAGGCCTCCTATTCCTAAGCCTTCTCCATGGGCTCCT

AGAATCCCCGCACCTTGTCCATGGGCACCACCAAGACCTCCACATTGCCCT

TGGGTGCCCTGTTTCCTGCTGTGCTTTTGCGTGCTCCTGTGCGTGTGCCTG

CTGATCAGACCTCTGCTGCTGAGCGTGTCCACCTACCTTAGACCACTGCTC

CTGTCCATCTCCGTGTACGCACAGGTGCTGGTGCTGGTCCTGCTTCTGTGG

GTGTCCATCGGAAGCCTGCTGCCTAGCGTGTGCATGTGTGCCTATGCTTGG

GTGCTCGTGTTCGTGTACATCGTGGTCATCACAAGCCCCGCCACAGCCATC

GTGTACAGAGATGGCAATCCCTACGCCGTGTGCGACAAGTGCCTGAAGTTC

TACAGCAAGATCAGCGAGTACCGGCACTACTGCTACAGCCTGTACGGCACC

ACACTGGAACAGCAGTACAACAAGCCCCTGTGCGATCTGCTGATTCGGTGC

ATCAACGTGGTGTACCGGGACAGCATTCCTCACGCCGCCTGCCACAAGTGC

ATCGACTTCTACTCCAGAATCAGAGAGCTGCGGCACTACAGCGACTCTGTG

TACGGCGACACCCTGGAAAAGCTGACCAACACCGGCCTGTACAACCTGCTG

ATTAGATGCCTGCGGGTGTACTGCAAGGGACAGCTGACAGAGACAGAGGTG

CTGGACTTCGCCTTCACCGATCTGACAATCGTGTATCGGGATAGCAAGGTG

TCCGAGTTCCGGTGGTACAGATATAGCGTGTACGGAACAACCCTGTGCGTC

GAGTGCAAGAAAACCCTGCAGAGAAGCGAGGTGTACGACTGCCAGAGGCCA

-continued
CTGTGCCCTCAAGAGAAGAAACGGCACGTGGACCTGAACAAGCGGTTTCAC

ACCCTGCACGAGTACATGCTGGACCTGCAGCCTGAGACAACCGACCTGTAC

TGCTACGAGCAGCCCGAAACCACAGATCTGCACTGTTATGAGCAGCTGGGC

GACAGCAGCGACGAAGAGGATACAGGCGGACTGGACGGCGAGGAAAACGAC

GAAATTGACGGCGTGAACCACCAGCATCTCCCCGCCAGAAGGGCTGAACCT

CAGAGACACACCATGCTGTGTATGTGCTGCAAGTGCGAGGCCAGAATCGCC

TGATGA

HPV53del Polypeptide Sequence (Includes tPA Leading Sequence and HindIII Cloning Linker, Underlined) (SEQ ID NO:74)

<u>MDAMKRGLCCVLLLCGAVFVSPSQEIHARFRRGSKLA</u>DEDETAYDSGTDLI

DFIDDSDENENDSDTGEDMVDFIDNAQLADSDSNACAFLKAQLADVNSNAA

AFLKNCILLYGAANTGKSLFGMSLNCLVLCGPANTGKSYFGMSLWPYLHSR

LVVFTFPNPFWPYLESRITVFEFPNAFNVCQDKILEHYENDSKDILEHYEN

DSKDLCDHICDHIDYWKHIRLECAIMYKARIRLECAIMYKAREMGEHQEDG

DICNTMHYTNWIYICEDAQCTVVEGQVDKKWEVHAGGQVILCPESGQRRIK

RPRSENCHPNKLLILKCLRYRFKKHCKLSSTWHWTCHDGKHKWHWTCHDGK

HKNAIVILTYYEADKNDLNAQIEHWKLIRMECAIFYKAKELGISICHQVVP

PLAASKAKACQAIELQLALEALNASPYDEWTLQQTSLEMWLAEPQFKKHGI

TITVQYDNDKANTMDYTNWKEIYVIVCPASIPSDEISTEEADHIDYWKAIR

QENAIFFAARHQVVPALNICKAKACKAIEWNTEPKHCFKKGGQHIEVWFDY

VAWDSVYYCGDDGWCKTEAEKYGCKGTWEVHFGNSIDCNDSMCSTFDDNVS

ATELVKDHIDYWKLIRLECAIFYKARRRLSSDQDQSQLVTKYPLLKLLSTQ

TTTPENTSLVELRVTTPKSTVVIRLHLTTRYPLLSLLNSYSTPPHRIPAPC

PWAPQRPPIPKPSPWAPRIPAPCPWAPPRPPHCPWVPCFLLCFCVLLCVCL

LIRPLLLSVSTYLRPLLLSISVYAQVLVLVLLLWVSIGSLLPSVCMCAYAW

VLVFVYIVVITSPATAIVYRDGNPYAVCDKCLKFYSKISEYRHYCYSLYGT

TLEQQYNKPLCDLLIRCINVVYRDSIPHAACHKCIDFYSRIRELRHYSDSV

YGDTLEKLTNTGLYNLLIRCLRVYCKGQLTETEVLDFAFTDLTIVYRDSKV

SEFRWYRYSVYGTTLCVECKKTLQRSEVYDCQRPLCPQEKKRHVDLNKRFH

TLHEYMLDLQPETTDLYCYEQPETTDLHCYEQLGDSSDEEDTGGLDGEEND

EIDGVNHQHLPARRAEPQRHTMLCMCCKCEARIA**

HPV3-Linkers Nucleotide Sequence (Includes tPA Leading Sequence and HindIII Cloning Linker, Underlined) (SEQ ID NO: 75)

<u>ATGGATGCTATGAAGAGGGGCCTGTGCTGCGTGCTGCTGCTGTGTGGCGCC</u>

<u>GTGTTTGTGTCCCCAGCCAGGAAATCCACGCCCGGTTCAGAAGAGGCAGC</u>

<u>AAGCTGGCC</u>GACGAGGACGAGACAGCCTACGACAGCGGCACCGACCTGATC

GACTTCATCGACGATAGCGCCGCTGCCGACGAGAATGAGAACGACAGCGAT

ACCGGCGAGGACATGGTGGATTTCATCGACAACGCTGCCGCCGACGAAACC

GACGAAGAGAGCACCGAGAGCGACCTGGACGGCTTTATCGACAACAGCGCA

-continued
GCCGCCCAGCTGGCTGACAGCGACTCTAATGCCTGCGCCTTCCTGAAGGCC

GCTGCTCAGCTGGCAGACGTGAACAGCAATGCCGCCGCTTTTCTGAAGGCT

GCCGCCAACTGCATCCTGCTGTACGGCGCTGCCAACACCGGCAAGAGCCTG

TTCGGCATGTCTCTGGCCGCAGCCAACTGCCTGGTGCTGTGCGGACCTGCC

AATACTGGCAAAAGCTACTTCGGCATGAGCCTGGCAGCCGCCAATTGTCTC

GTGATCTACGGCCCTCCTAATACCGGCAAGTCCTGCTTTGCCATGAGTCTG

GCCGCTGCCTGGCCCTACCTGCACTCTAGACTGGTGGTGTTCACCTTCCCC

AACCCCTTCGCTGCCGCTTGGCCTTACCTGGAAAGCCGGATCACCGTGTTC

GAGTTCCCCAATGCCTTCGCCGCAGCCCTGAGATACCTGCACAGCAGAATC

CACGTGCTGCAGTTTCTGAACCCCTTTGCCGCCGCAAACGTGTGCCAGGAC

AAGATCCTGGAACACTACGAGAACGACTCCAAGGATGCCGCTGCCATTCTG

GAACATTATGAGAATGATAGCAAGGACCTGTGCGACCACATTGCTGCCGCC

TGCGATCACATCGACTACTGGAAGCACATCCGGCTGGAATGCGCCATCATG

TACAAGGCCAGAGCCGCCGCTATCAGACTGGAATGTGCTATTATGTATAAG

GCTCGCGAGATGGGCTTCCACGCTGCTGCCCAGTTCGACGGCGACATCTGC

AACACCATGCACTACACCAACTGGGCTGCCGCTATCTACATCTGCGAGGAC

GCCCAGTGCACCGTGGTGGAAGGACAGGTGGACGCCGCTGCTAAGAAATGG

GAGGTGCACGCTGGCGGCCAAGTGATCCTGTGTCCAGAGTCTGCTGCCGCA

GGCCAGCGGAGAATCAAGAGGCCTAGAAGCGAGGCAGCCGCTAACTGCCAC

CCCAACAAACTGCTGGCTGCTGCCATCCTGAAGTGCCTGCGGTACAGATTC

AAGAAGCACTGCAAACTGGCTGCAGCTAGCAGCACCTGGCACTGGACCTGT

CACGACGGCAAGCACAAAGCCGCCGCATGGCATTGGACATGCCACGATGGA

AAACACAAGAACGCCATCGTGACCCTGACCTATGCAGCCGCCTACGAGGCC

GACAAGAACGACCTGAACGCCCAGATCGAGCACTGGAAGCTGATCAGGATG

GAATGTGCAATCTTCTATAAGGCCAAAGAGCTGGGCATCAGCGCTGCCGCA

ATCTGCCACCAGGTGGTGCCTCCACTGGCCGCCTCTAAAGCCAAAGCCTGC

CAGGCCATCGAACTGCAGCTGGCCCTGGAAGCCCTGAATGCCAGCCCTTAT

GCCGCAGCCGATGAGTGGACCCTGCAGCAGACCAGCCTGGAAATGTGGCTG

GCCGAACCTCAGGCCCAGCTTTTAAGAAGCACGGCATCACCATCACCGTG

CAGTACGACAACGACAAGGCCAATACCATGGATTACACCAATTGGAAAGAG

ATCTACGCCGCAGCTGTGATCGTGTGCCCCGCCAGCATCCCTAGCGACGAG

ATCAGCACAGAGGAAGCAGCCGCCGACCACATCGATTATTGGAAAGCCATC

AGACAGGAAAACGCCATCTTCTTCGCCGCTAGAGCCGCTGCCCACCAGGTG

GTGCCAGCCCTGAATATCTGCAAGGCCAAGGCCTGTAAAGCCATCGAAGCC

GCTGCTTGGAACACCGAGCCCAAGCACTGCTTCAAGAAGGGCGGCCAGCAC

ATCGAAGTGTGGTTCGACTGCTGCAGCCTACGTGGCCTGGGACAGCGTGTAC

TACTGTGGCGACGACGGCTGGTGCAAGACCGCCGCTGCAGAGGCCGAGAAG

TATGGCTGCAAGGGCACCTGGGAAGTGCATTTCGGCGCAGCTGCCAACTCC

ATCGACTGCAACGACAGCATGTGCAGCACCTTCGACGACAACGTGTCCGCC

ACCGAGCTCGTGAAAGCTGCCGCTGACCATATTGATTACTGGAAACTGATT

CGCCTGGAATGCGCTATTTTCTACAAAGCCAGGGCCGCAGCACGGCGGCTG

-continued
```
TCCTCAGATCAGGATCAGAGCCAGGCTGCTGCACTCGTGACCAAGTACCCC
CTGCTGAAGCTGCTGAGCGCCGCAGCAAGACCCCCCAACATGGGAGTGAAG
GCCCACGGCAAGTGCATCTGGGAGAACAAGGTGTTCATCGTGCCCACCCTG
TGCCCCGTGCCTCTGGATCCAACATATCCTCTGCTGAAACTGCTGACCGCT
GCCGCCACCCAGACCACCACACCTGAGAATACCTCCCTGGTGGAACTGAGA
GTGACCACCCCCAAGAGCACAGTCGTGATCAGGCTGCACCTGGCTGCCGCA
ACCACCAGATACCCTCTGCTGTCCCTGCTGAACAGCTACAGCACCCCCCCT
CATCGGATCCCTGCCCCTTGTCCTTGGGCTCCTCAGAGGCCTGCCGCTGCA
CCTATCCCTAAGCCTTCTCCATGGGCCCCTGCCGCAGCTAGAATCCCAGCT
CCATGTCCATGGGCACCAGCTGCTGCTCCCAGACCTCCTCATTGCCCTTGG
GTGCCAGCAGCCGCTCCTCCACCTCCTCCTAGACCTTGGGCCCCAGCCGCC
GCTTGTTTCCTGCTGTGCTTCTGTGTGCTGCTGTGCGTGTGCCTGCTGATC
AGACCCCTGCTGCTGAGTGTGTCCACCTACGCAGCTGCTCTGCGGCCACTG
CTGCTGTCCATCTCTGTGTACGCACAGGTGCTGGTGCTGGTGCTGCTGCTG
TGGGTGTCCATCGGATCTGCCGCAGCACTGCTGCCCTCCGTGTGCATGTGT
GCCTATGCCTGGGTGCTGGTGTTCGTGTACATCGTCGTGATTACCAGCCCC
GCCACCGCAGCCGCAATCGTGTACAGGGACGGCAACCCTTACGCCGTGTGC
GACAAGTGCCTGAAGTTCTACAGCAAGATCAGCGAGTACCGCCACTACTGC
TACAGCCTGTACGGCACCACCCTGGAACAGCAGTACAACAAGCCCCTGTGC
GATCTGCTGATCCGGTGCATCAACGCAGCCGCTGTGGTGTACAGAGACAGC
ATCCCACACGCCGCCTGCCACAAGTGTATCGACTTCTACTCCCGGATCAGA
GAGCTGAGACACTACTCCGACTCCGTGTACGGCGATACCCTGGAAAAGCTG
ACCAATACCGGCCTGTACAACCTGCTGATTAGATGCCTGCGGGCAGCCGCA
GTGTTCTGCAAGAAAGCCCTGACCGCCAGCGAGGTGTACAACTTCGCCTAC
ACCGATCTGCGGGTGGTGTACCGGGATGCTGCTGCCTCCAAAGTGCGGAAG
CTGCGGTACTACAACTGCTCTGTGTATGGCGCCTCCCTGGCAGCTGCCGTG
TATTGCAAGGGACAGCTGACCGAGACAGAGGTGCTGGATTTCGCCTTCACA
GACCTGACCATCGTGTATAGAGATGCAGCTGCTAGCAAGGTGTCCGAGTTC
CGGTGGTACAGATATAGCGTGTACGGAACAACACTGGCAGCAGCTTGCGTG
GAATGCAAGAAAACTGCAGCGGAGCGAAGTGTACGATGCTGCAGCTTGC
CAGAGGCCGCTGTGTCCTCAGGAAAAGAAAAGACACGTGGACCTGAACAAG
CGGTTCCACGCAGCAGCTACCCTGCACGAGTACATGCTGGACCTGCAGCCC
GAGACAACCGACCTGTACTGCTACGAGCAGGCAGCTGCACCCGAAACCACA
GATCTGCACTGTTATGAGCAGCTGGGAGACAGCTCCGATGAAGAGGACACC
GGCGGACTGGATGCTGCCGCTGGGGATGAGGACGAGGATGAGGTGGACCAT
CTGCAGGAACAGCCCCAGCAGGCCAGAAGGGATGAGCAGCACCCCTGCTAT
CTGATCGAGACACAGTGCTGCAGATGCGAGAGCCTGGTGGCCGCTGCTGAG
GAAAACGACGAGATCGACGGCGTGAACCACCAGCATCTGCCCCGCTAGAAGG
GCCGAGCCTCAGAGACACACCATGCTGTGTATGTGTTGCAAGTGCGAGGCC
CGGATCGCCGGATCTGGACCTGGCGCTAGCGGAAAGCCCATCCCCAATCCA
CTGCTGGGCCTGGACTCCACCCGGACCTGATAA
```

HPV3-Linkers Polypeptide Sequence (Includes tPA Leading Sequence and HindIII Cloning Linker, Underlined) (SEQ ID NO: 76)

<u>MDAMKRGLCCVLLLCGAVFVSPSQEIHARFRRGS</u>KLADEDETAYDSGTDLI
DFIDDSAAADENENDSDTGEDMVDFIDNAAADETDEESTESDLDGFIDNSA
AAQLADSDSNACAFLKAAAQLADVNSNAAAFLKAAANCILLYGAANTGKSL
FGMSLAAANCLVLCGPANTGKSYFGMSLAAANCLVIYGPPNTGKSCFAMSL
AAAWPYLHSRLVVFTFPNPFAAAWPYLESRITVFEFPNAFAAALRYLHSRI
HVLQFLNPFAAANVCQDKILEHYENDSKDAAAILEHYENDSKDLCDHIAAA
CDHIDYWKHIRLECAIMYKARAAAIRLECAIMYKAREMGFHAAAQFDGDIC
NTMHYTNWAAAIYICEDAQCTVVEGQVDAAAKKWEVHAGGQVILCPESAAA
GQRRIKRPRSEAAANCHPNKLLAAAILKCLRYRFKKHCKLAAASSTWHWTC
HDGKHKAAAWHWTCHDGKHKNAIVTLTYAAAYEADKNDLNAQIEHWKLIRM
ECAIFYKAKELGISAAAICHQVVPPLAASKAKACQAIELQLALEALNASPY
AAADEWTLQQTSLEMWLAEPQAAAFKKHGITITVQYDNDKANTMDYTNWKE
IYAAAVIVCPASIPSDEISTEEAAADHIDYWKAIRQENAIFFAARAAAHQV
VPALNICKAKACKAIEAAAWNTEPKHCFKKGGQHIEVWFDAAAYVAWDSVY
YCGDDGWCKTAAAEAEKYGCKGTWEVHFGAAANSIDCNDSMCSTFDDNVSA
TELVKAAADHIDYWKLIRLECAIFYKARAAARRLSSDQDQSQAAALVTKYP
LLKLLSAAARPPNMGVKAHGKCIWENKVFIVPTLCPVPLDPTYPLLKLLTA
AATQTTTPENTSLVELRVTTPKSTVVIRLHLAAATTRYPLLSLLNSYSTPP
HRIPAPCPWAPQRPAAAPIPKPSPWAPAAARIPAPCPWAPAAAPRPPHCPW
VPAAAPPPPPRPWAPAAACFLLCFCVLLCVCLLIRPLLLSVSTYAAALRPL
LLSISVYAQVLVLVLLLWVSIGSAAALLPSVCMCAYAWVLVFVYIVVITSP
ATAAAIVYRDGNPYAVCDKCLKFYSKISEYRHYCYSLYGTTLEQQYNKPLC
DLLIRCINAAAVVYRDSIPHAACHKCIDFYSRIRELRHYSDSVYGDTLEKL
TNTGLYNLLIRCLRAAAVFCKKALTASEVYNFAYTDLRVVYRDAAASKVRK
LRYYNCSVYGASLAAAVYCKGQLTETEVLDFAFTDLTIVYRDAAASKVSEF
RWYRYSVYGTTLAAACVECKKTLQRSEVYDAAACQRPLCPQEKKRHVDLNK
RFHAAATLHEYMLDLQPETTDLYCYEQAAAPETTDLHCYEQLGDSSDEEDT
GGLDAAAGDEDEDEVDHLQEQPQQARRDEQHPCYLIETQCCRCESLVAAAE
ENDEIDGVNHQHLPARRAEPQRHTMLCMCCKCEARIAGSGPGASGKPIPNP
LLGLDSTRT**

TABLE 9

Figure 3:
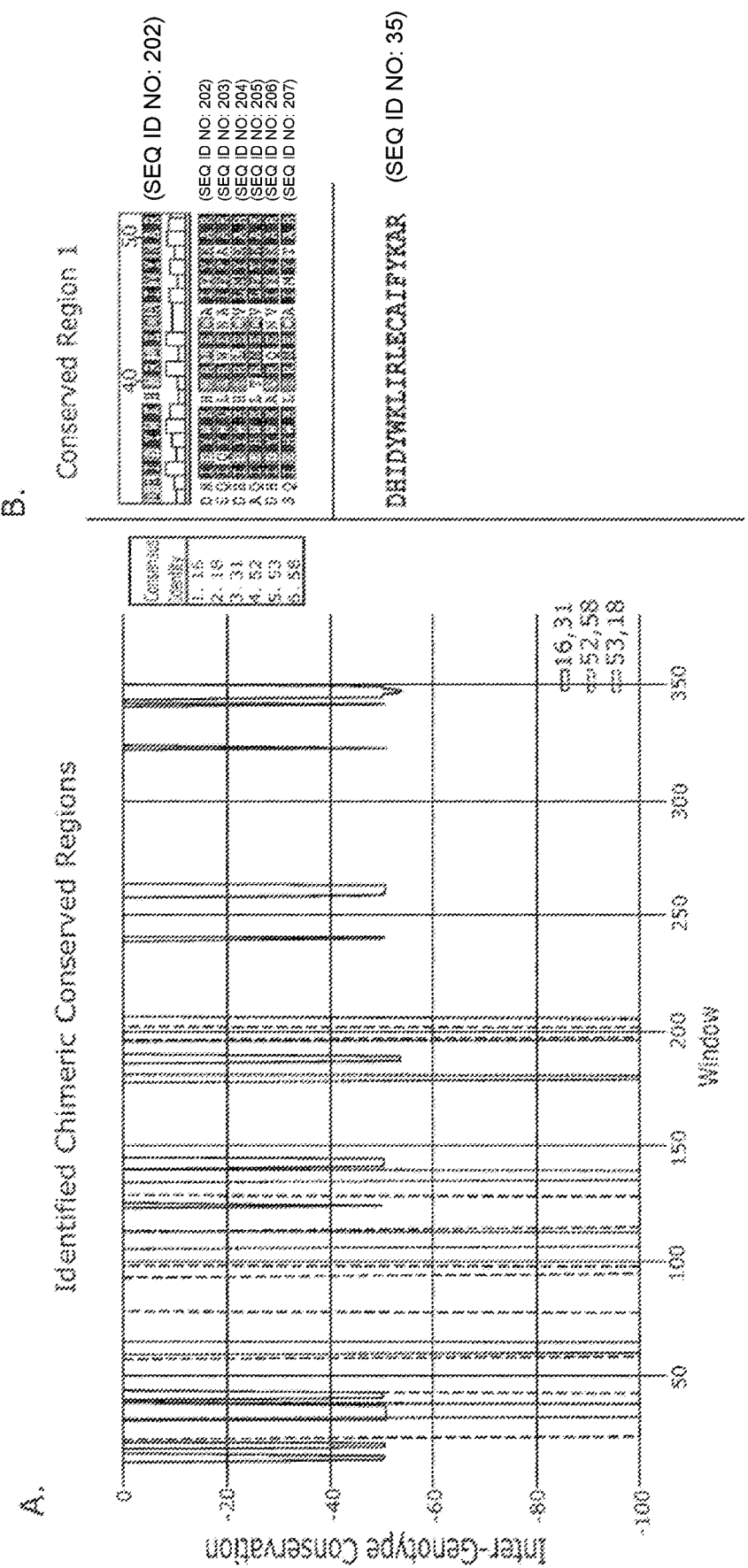
Figure 4:
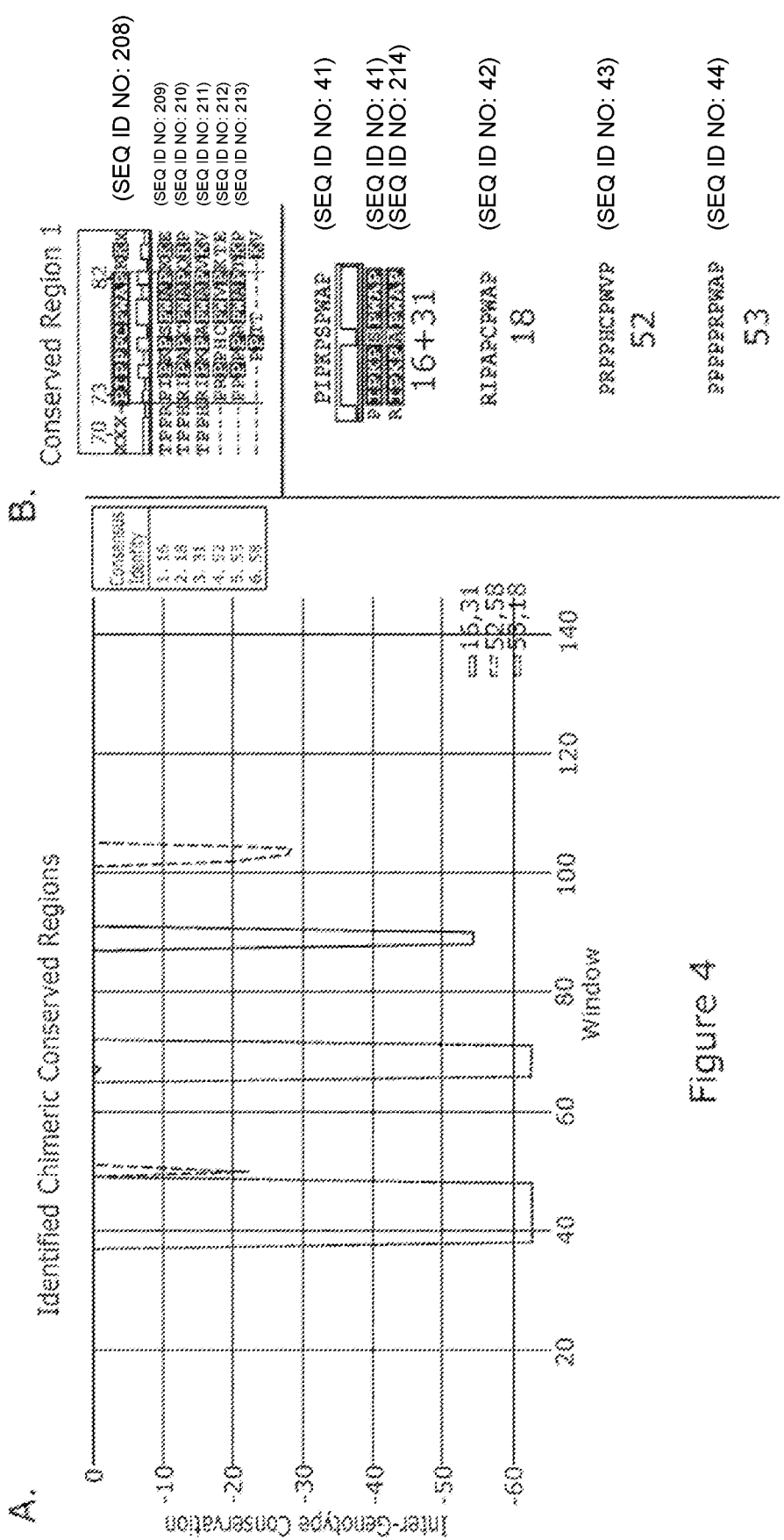
Figure 5:
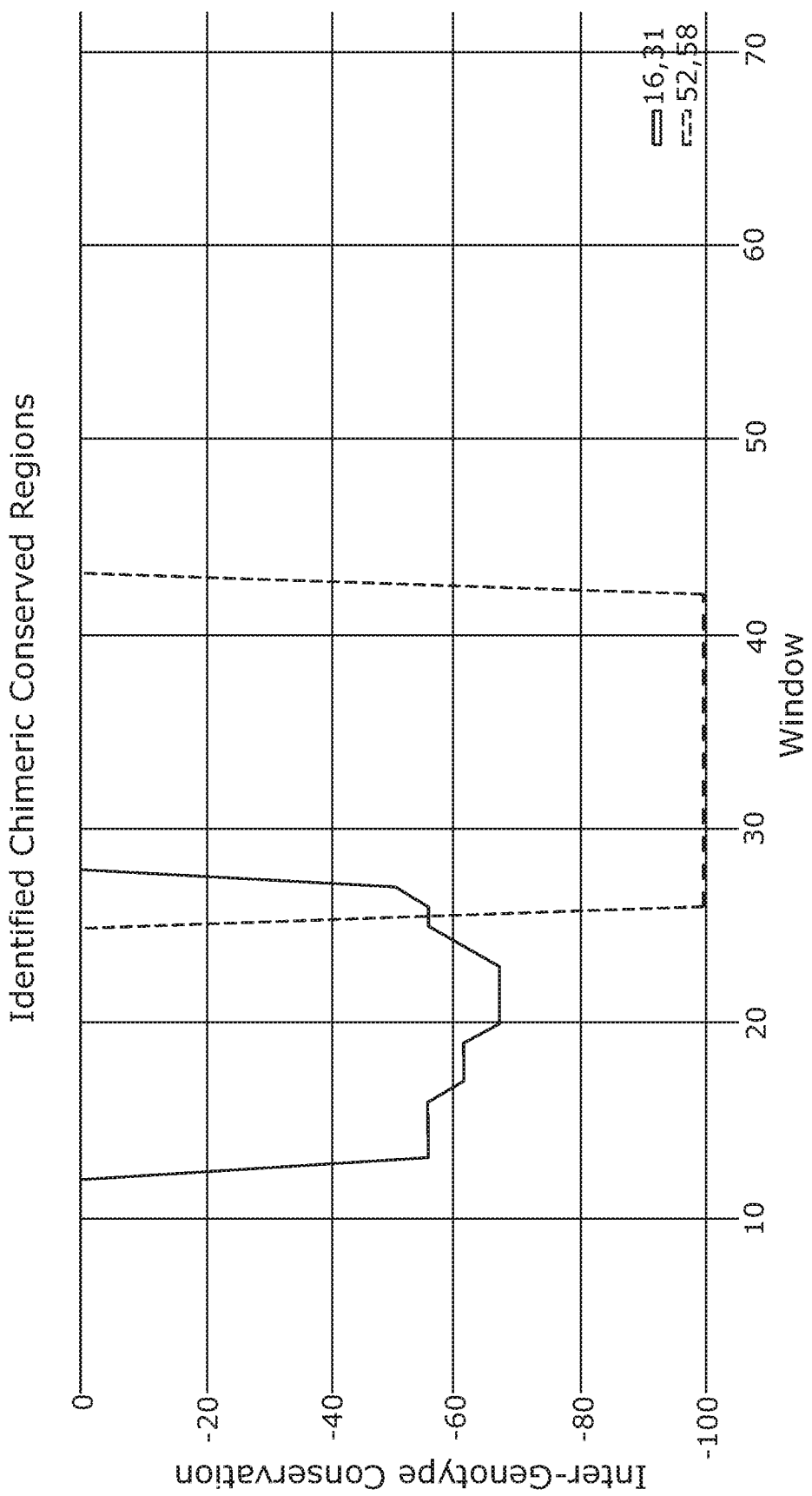

Summary of Fragment Variants with SEQ ID NOs. (FIGS. 2-4)

| SEQ ID NO: | Protein | Fragment |
|---|---|---|
| 160 | conserved region 1 | DEDENASDTGXDLVDFIDNS |
| 161 | conserved region 1 | DENENDSDTGEDLVDFIVND |
| 162 | conserved region 1 | DEDENATDTGSDMVDFIDTQ |
| 163 | conserved region 1 | DENEDSSDTGEDMVDFIDNC |

TABLE 9-continued

Summary of Fragment Variants with SEQ ID NOs. (FIGS. 2-4)

| SEQ ID NO: | Protein | Fragment |
|---|---|---|
| 164 | conserved region 1 | DEDENAYDSGTDLIDFIDDS |
| 3 | conserved region 1 | DETDEESTESDLDGFIDNS |
| 165 | conserved region 1 | DEDETADDSGTDLIEFIDDS |
| 166 | conserved region 1 | DEDEXAXDSGTDLIXFIDDS |
| 167 | conserved region 1 | DEDENAYDSGTDLIDFIDDS |
| 168 | conserved region 1 | DEDETADDSGTDLIEFIDDS |
| 169 | conserved region 1 | DENENXSDTGEDMVDFIDN |
| 170 | conserved region 1 | DENEDSSDTGEDMVDFIDN |
| 171 | conserved region 1 | DENENDSDTGEDLVDFIVN |
| 172 | conserved region 1 | DEDENATDTGSDMVDFIDT |
| 3 | conserved region 1 | DETDEESTESDLDGFIDNS |
| 5 | conserved region 2 | AQLADVNSNAAAFLK |
| 173 | conserved region 2 | AQLADTNSNASAFLK |
| 174 | conserved region 2 | ALLADSNSNAAAFLK |
| 175 | conserved region 2 | AQLADSDSNACAFLK |
| 5 | conserved region 2 | AQLADVNSNAAAFLK |
| 176 | conserved region 2 | AQLADVDSNAQAFLK |
| 177 | conserved region 2 | AQLADVNSNAAAFLR |
| 4 | conserved region 2 | AQLADSDSNACAFLK |
| 4 | conserved region 2 | AQLADSDSNACAFLK |
| 178 | conserved region 2 | AQLADVDSNAQAFLK |
| 5 | conserved region 2 | AQLADVNSNAAAFLK |
| 5 | conserved region 2 | AQLADVNSNAAAFLK |
| 179 | conserved region 2 | AQLADVNSNAAAFLR |
| 180 | conserved region 2 | ALLADSNSNAAAFLK |
| 181 | conserved region 2 | AQLADTNSNASAFLK |
| 182 | conserved region 3 | NCLXLYGPANTGKSYFGMSL |
| 6 | conserved region 3 | NCILLYGAANTGKSLFGMSL |
| 183 | conserved region 3 | NCLVFCGPANTGKSYFGMSF |
| 184 | conserved region 3 | NCILIHGAPNTGKSYFGMSL |
| 185 | conserved region 3 | NCLVLYGPANTGKSYFGMSL |
| 8 | conserved region 3 | NCLVIYGPPNTGKSCFAMSL |
| 186 | conserved region 3 | SCMLLCGPANTGKSYFGMSL |
| 187 | conserved region 3 | NCILJYGAANTGKSLFGMSL |
| 6 | conserved region 3 | NCILLYGAANTGKSLFGMSL |
| 188 | conserved region 3 | NCILIHGAPNTGKSYFGMSL |
| 7 | conserved region 3 | NCLVLCGPANTGKSYFGMSL |
| 189 | conserved region 3 | NCLVFCGPANTGKSYFGMSF |
| 190 | conserved region 3 | NCLVLYGPANTGKSYFGMSL |
| 191 | conserved region 3 | SCMLLCGPANTGKSYFGMSL |
| 8 | conserved region 3 | NCLVIYGPPNTGKSCFAMSL |
| 192 | conserved region 4 | DEDENASDTGXDLVDFIDNS |
| 193 | conserved region 4 | DENENDSDTGEDLVDFIVND |
| 194 | conserved region 4 | DEDENATDTGSDMVDFIDTQ |
| 195 | conserved region 4 | DENEDSSDTGEDMVDFIDNC |
| 196 | conserved region 4 | DEDENAYDSGTDLIDFIDDS |
| 3 | conserved region 4 | DETDEESTESDLDGFIDNS |
| 197 | conserved region 4 | DEDETADDSGTDLIEFIDDS |
| 9 | conserved region 4 | WPYLHSRLVVFTFPNPF |
| 198 | conserved region 4 | WPYLHNRLVVFTFPNEF |
| 9 | conserved region 4 | WPYLHSRLVVFTFPNPF |
| 199 | conserved region 4 | WPYLHSRLVVFHFKNPF |
| 200 | conserved region 4 | WPYLESRJTVFEFPNAF |
| 10 | conserved region 4 | WPYLESRITVFEFPNAF |
| 201 | conserved region 4 | WPYLHSRLTVFEFNNPF |
| 11 | conserved region 4 | LRYLHSRIHVLQFLNPF |
| 202 | conserved region 1 | DHIDYWKHMRLECAIYYKAR |
| 202 | conserved region 1 | DHIDYWKHMRLECAIYYKAR |
| 203 | conserved region 1 | SQIQYWQLIRWENAIFFAAR |
| 204 | conserved region 1 | DHIDYWKHIRLECVLMYKAR |
| 205 | conserved region 1 | AQIEHWKLTRMECVLFYKAK |
| 206 | conserved region 1 | DHIDYWKAVRQENVIYYKAR |
| 207 | conserved region 1 | SQIEHWKLIRMECAIMYTAR |
| 35 | conserved region 1 | DHIDYWKLIRLECAIFYKAR |
| 208 | conserved region 1 | PIPPPCPWAPKK |
| 209 | conserved region 1 | TPPHRPIPKPSPWAPKKE |
| 210 | conserved region 1 | TPPHRIPAPCPWAPQRP |
| 211 | conserved region 1 | TPPHRIPKPAPWAPVKV |
| 212 | conserved region 1 | PRPPHCPWVPKTE |
| 213 | conserved region 1 | PPPPPRPWAPTKP |
| 41 | conserved region 1 | PIPKPSPWAP |
| 41 | conserved region 1 | PIPKPSPWAP |

TABLE 9-continued

Summary of Fragment Variants with SEQ ID NOs. (FIGS. 2-4)

| SEQ ID NO: | Protein | Fragment |
|---|---|---|
| 214 | conserved region 1 | RIPKPAPWAP |
| 42 | conserved region 1 | RIPAPCPWAP |
| 43 | conserved region 1 | PRPPHCPWVP |
| 44 | conserved region 1 | PPPPPRPWAP |

The invention claimed is:

1. A nucleic acid encoding a polypeptide comprising a plurality of conserved peptide sequences,
   wherein the conserved sequences are conserved across one or more HPV genotypes 16, 18, 31, 52, 53, and 58; and
   wherein the polypeptide comprises a conserved peptide sequence of each of the HPV proteins E1, E2, E4, E5, E6, and E7
   wherein the polypeptide comprises:
   one or more conserved E1 sequence(s) selected from any one of SEQ ID NOs: 1-11, wherein each of the genotypes 16, 18, 31, 52, 53, and 58 are represented by at least one conserved E1 sequence;
   one or more conserved E2 sequence(s) selected from any one of SEQ ID NOs: 12-35, wherein each of the genotypes 16, 18, 31, 52, 53, and 58 are represented by at least one conserved E2 sequence;
   one or more conserved E4 sequence(s) selected from any one of SEQ ID NOs: 36-44, wherein each of the genotypes 16, 18, 31, 52, 53, and 58 are represented by at least one conserved E4 sequence;
   one or more conserved E5 sequence(s) selected from any one of SEQ ID NOs: 45-47, wherein each of the genotypes 16, 18, 31, 52, 53, and 58 are represented by at least one conserved E5 sequence;
   one or more conserved E6 sequence(s) selected from any one of SEQ ID NOs: 48-55, wherein each of the genotypes 16, 18, 31, 52, 53, and 58 are represented by at least one conserved E6 sequence; and
   one or more conserved E7 sequence(s) selected from any one of SEQ ID NOs: 56-59, wherein each of the genotypes 16, 18, 31, 52, 53, and 58 are represented by at least one conserved E7 sequence.

2. A nucleic acid encoding a polypeptide comprising a plurality of conserved peptide sequences,
   wherein the conserved sequences are conserved across one or more HPV genotypes 16, 18, 31, 52, 53, and 58; and
   wherein the polypeptide comprises a conserved peptide sequence of each of the HPV proteins E1, E2, E4, E5, E6, and E7,
   wherein the polypeptide comprises:
   one or more conserved E1 sequence(s) selected from any one of SEQ ID NOs: 1-11, wherein each of the genotypes 16, 18, 31, 52 and 58 are represented by at least one conserved E1 sequence;
   one or more conserved E2 sequence(s) selected from any one of SEQ ID NOs: 12-35, wherein each of the genotypes 16, 18, 31, 52 and 58 are represented by at least one conserved E2 sequence;
   one or more conserved E4 sequence(s) selected from any one of SEQ ID NOs: 36-44, wherein each of the genotypes 16, 18, 31, 52 and 58 are represented by at least one conserved E4 sequence;
   one or more conserved E5 sequence(s) selected from any one of SEQ ID NOs: 45-47, wherein each of the genotypes 16, 18, 31, 52 and 58 are represented by at least one conserved E5 sequence;

one or more conserved E6 sequence(s) selected from any one of SEQ ID NOs: 48-55, wherein each of the genotypes 16, 18, 31, 52 and 58 are represented by at least one conserved E6 sequence; and one or more conserved E7 sequence(s) selected from any one of SEQ ID NOs: 56-59, wherein each of the genotypes 16, 18, 31, 52 and 58 are represented by at least one conserved E7 sequence.

3. A nucleic acid encoding a polypeptide comprising a plurality of conserved peptide sequences, wherein the conserved sequences are conserved across one or more HPV genotypes 16, 18, 31, 52, 53, and 58; and wherein the polypeptide comprises a conserved peptide sequence of each of the HPV proteins E1, E2, E4, E5, E6, and E7, wherein the nucleic acid comprises or consists of the sequence of SEQ ID NO: 60, comprises or consists of the sequence of SEQ ID NO: 65, or comprises or consists of the sequence of SEQ ID NO: 60, without encoding the TPA lead sequence.

4. A nucleic acid encoding a polypeptide comprising a plurality of conserved peptide sequences, wherein the conserved sequences are conserved across one or more HPV genotypes 16, 18, 31, 52, 53, and 58; and wherein the polypeptide comprises a conserved peptide sequence of each of the HPV proteins E1, E2, E4, E5, E6, and E7, wherein the nucleic acid comprises or consists of the sequence of SEQ ID NO: 62, or comprises or consists of the sequence of SEQ ID NO: 62, without encoding the TPA lead sequence.

5. A nucleic acid encoding a polypeptide comprising a plurality of conserved peptide sequences, wherein the conserved sequences are conserved across one or more HPV genotypes 16, 18, 31, 52, 53, and 58; and wherein the polypeptide comprises a conserved peptide sequence of each of the HPV proteins E1, E2, E4, E5, E6, and E7, wherein the nucleic acid comprises or consists of the sequence of SEQ ID NO: 71, 73 or 75; or the nucleic acid comprises or consists of the sequence of SEQ ID NO: 71, 73 or 75, and without encoding the TPA lead sequence.

6. A nucleic acid encoding a polypeptide comprising a plurality of conserved peptide sequences, wherein the conserved sequences are conserved across one or more HPV genotypes 16, 18, 31, 52, 53, and 58; and wherein the polypeptide comprises a conserved peptide sequence of each of the HPV proteins E1, E2, E4, E5, E6, and E7, wherein the polypeptide comprises or consists of the sequence of SEQ ID NO: 61, comprises or consists of the sequence of SEQ ID NO: 61 without the TPA lead sequence, or comprises or consists of the sequence of SEQ ID NO: 66.

7. A nucleic acid encoding a polypeptide comprising a plurality of conserved peptide sequences, wherein the conserved sequences are conserved across one or more HPV genotypes 16, 18, 31, 52, 53, and 58; and wherein the polypeptide comprises a conserved peptide sequence of each of the HPV proteins E1, E2, E4, E5, E6, and E7, wherein the polypeptide comprises or consists of the sequence of SEQ ID NO: 72, 74 or 76, or comprises or consists of the sequence of SEQ ID NO: 72, 74 or 76, without the TPA lead sequence.

\* \* \* \* \*